(12) United States Patent
Cha et al.

(10) Patent No.: US 10,230,056 B2
(45) Date of Patent: Mar. 12, 2019

(54) HETEROCYCLIC COMPOUND AND ORGANIC LIGHT EMITTING ELEMENT COMPRISING SAME

(71) Applicant: LG Chem, Ltd., Seoul (KR)

(72) Inventors: Yongbum Cha, Daejeon (KR); Seongmi Cho, Daejeon (KR); Jin Joo Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/556,192

(22) PCT Filed: Aug. 23, 2016

(86) PCT No.: PCT/KR2016/009329
§ 371 (c)(1),
(2) Date: Sep. 6, 2017

(87) PCT Pub. No.: WO2017/034303
PCT Pub. Date: Mar. 2, 2017

(65) Prior Publication Data
US 2018/0047914 A1    Feb. 15, 2018

(30) Foreign Application Priority Data

Aug. 27, 2015  (KR) .................. 10-2015-0121167

(51) Int. Cl.
| | | |
|---|---|---|
| *C07D 491/048* | (2006.01) | |
| *H01L 51/00* | (2006.01) | |
| *C09K 11/06* | (2006.01) | |
| *H01L 51/50* | (2006.01) | |
| *C09K 11/02* | (2006.01) | |

(52) U.S. Cl.
CPC ...... *H01L 51/0072* (2013.01); *C07D 491/048* (2013.01); *C09K 11/02* (2013.01); *C09K 11/06* (2013.01); *H01L 51/006* (2013.01); *H01L 51/0052* (2013.01); *H01L 51/0061* (2013.01); *H01L 51/0067* (2013.01); *H01L 51/0071* (2013.01); *H01L 51/0073* (2013.01); *H01L 51/0074* (2013.01); *H01L 51/0077* (2013.01); *H01L 51/0085* (2013.01); *H01L 51/50* (2013.01); *C09K 2211/1011* (2013.01); *C09K 2211/1018* (2013.01); *H01L 51/0054* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC .................. H01L 51/0072; C07D 491/048
See application file for complete search history.

(56) References Cited

U.S. PATENT DOCUMENTS

| | | | |
|---|---|---|---|
| 10,032,996 B2 * | 7/2018 | Cho | .......... H01L 51/0072 |
| 2014/0319507 A1 | 10/2014 | Yamamoto et al. | |
| 2014/0332793 A1 | 11/2014 | Park et al. | |
| 2018/0141957 A1 | 5/2018 | Park et al. | |

FOREIGN PATENT DOCUMENTS

| | | |
|---|---|---|
| KR | 20130093195 A | 8/2013 |
| KR | 20140049186 A | 4/2014 |
| KR | 20140101807 A | 8/2014 |
| KR | 20150010016 A | 1/2015 |
| KR | 10-1555680 B1 | 9/2015 |
| WO | 2013105747 A1 | 7/2013 |
| WO | 2014061963 A1 | 4/2014 |
| WO | 2015009076 A1 | 1/2015 |
| WO | 2016140497 A2 | 9/2016 |

OTHER PUBLICATIONS

Search report from International Application No. PCT/KR2016/009329, dated Dec. 5, 2016.

* cited by examiner

*Primary Examiner* — Golam M Shameem
(74) *Attorney, Agent, or Firm* — Lerner, David, Littenberg, Krumholz & Mentlik, LLP

(57) ABSTRACT

The present specification provides a heterocyclic compound and an organic light emitting device including the same.

20 Claims, 2 Drawing Sheets

【Fig. 1】
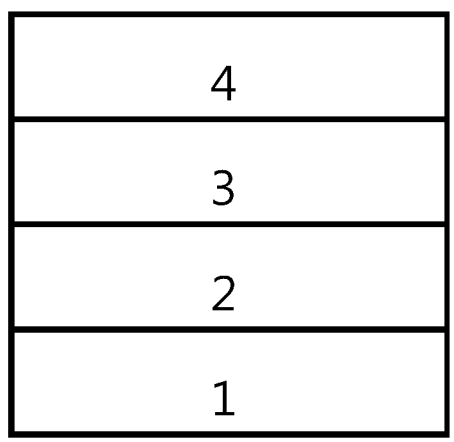

【Fig. 2】
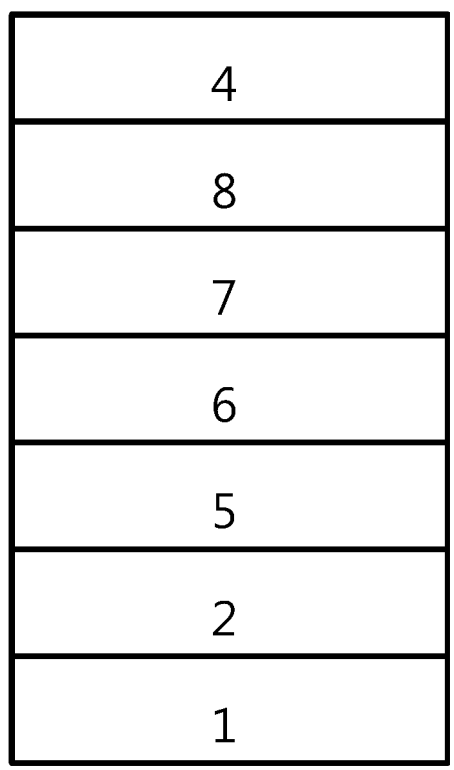

HETEROCYCLIC COMPOUND AND ORGANIC LIGHT EMITTING ELEMENT COMPRISING SAME

CROSS-REFERENCED TO RELATED APPLICATIONS

The present application is a national phase entry under 35 U.S.C. § 371 of International Application No. PCT/KR2016/009329, filed Aug. 23, 2016, which claims priority from Korean Patent Application No. 10-2015-0121167, filed Aug. 27, 2015, all of which are incorporated herein by reference.

TECHNICAL FIELD

The present specification relates to a heterocyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween.

Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a heterocyclic compound and an organic light emitting device comprising the same.

Technical Solution

One embodiment of the present specification provides a compound represented by the following Chemical Formula 1:

[Chemical Formula 1]

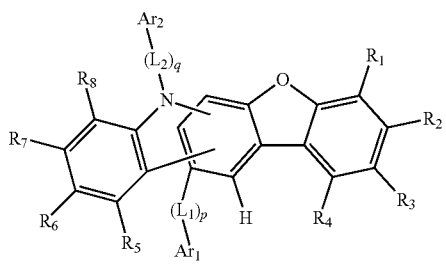

wherein, in Chemical Formula 1, $Ar_1$ is a substituted or unsubstituted biphenyl group; a substituted or unsubstituted terphenyl group; a substituted or unsubstituted quaterphenyl group; a substituted or unsubstituted multicyclic aryl group; a substituted or unsubstituted arylamine group; or a substituted or unsubstituted heterocyclic group, $L_1$ and $L_2$ are the same as or different from each other, and each independently a direct bond; a substituted or unsubstituted arylene group; or a substituted or unsubstituted heteroarylene group, p and q are the same as or different from each other, and each independently an integer of 0 to 5, when p and q are 2 or greater, the structures in the parentheses are the same as or different from each other, $Ar_2$ is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, and $R_1$ to $R_8$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or adjacent groups may bond to each other to form a substituted or unsubstituted ring.

Another embodiment of the present specification provides an organic light emitting device comprising a first electrode; a second electrode; and one or more organic material layers disposed between the first electrode and the second electrode, wherein one or more layers of the organic material layers include the compound of Chemical Formula 1.

Advantageous Effects

Compounds described in the present specification can be used as a material of an organic material layer of an organic light emitting device. Compounds according to at least one embodiment are capable of enhancing efficiency, low driving voltage and/or enhancing lifespan properties in an organic light emitting device. Particularly, compounds described in the present specification can be used as material of hole injection, hole transfer, hole injection and hole transfer, electron blocking, light emitting, hole suppression, electron transfer or electron injection.

DESCRIPTION OF DRAWINGS

FIG. 1 illustrates an organic light emitting device formed with a substrate (1), an anode (2), a light emitting layer (3) and a cathode (4).

FIG. 2 illustrates an organic light emitting device formed with a substrate (1), an anode (2), a hole injection layer (5), a hole transfer layer (6), a light emitting layer (7), an electron transfer layer (8) and a cathode (4).

REFERENCE NUMERAL

1: Substrate
2: Anode
3: Light Emitting Layer
4: Cathode
5: Hole Injection Layer
6: Hole Transfer Layer
7: Light Emitting Layer
8: Electron Transfer Layer

MODE FOR DISCLOSURE

Hereinafter, the present specification will be described in more detail.

One embodiment of the present specification provides a compound represented by Chemical Formula 1.

Examples of the substituents are described below, however, the substituents are not limited thereto.

In the present specification, the term "substituted or unsubstituted" means being substituted with one or more substituents selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, examples of the halogen group may include fluorine, chlorine, bromine or iodine.

In the present specification, the number of carbon atoms of the carbonyl group is not particularly limited, but is preferably from 1 to 40. Specifically, compounds having structures such as below may be included, but the carbonyl group is not limited thereto.

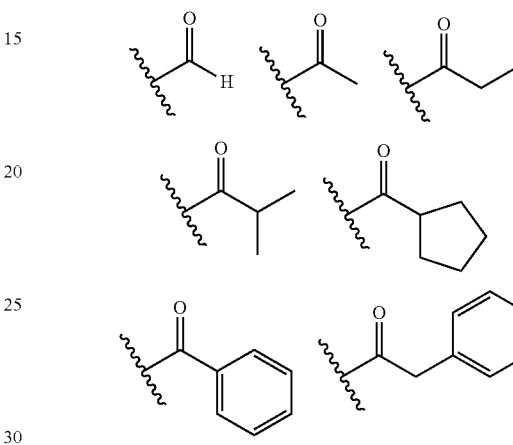

In the present specification, the oxygen of the ester group may be substituted with a linear, branched or cyclic alkyl group having 1 to 25 carbon atoms or an aryl group having 6 to 25 carbon atoms. Specifically, compounds having the following structural formulae may be included, but the ester group is not limited thereto.

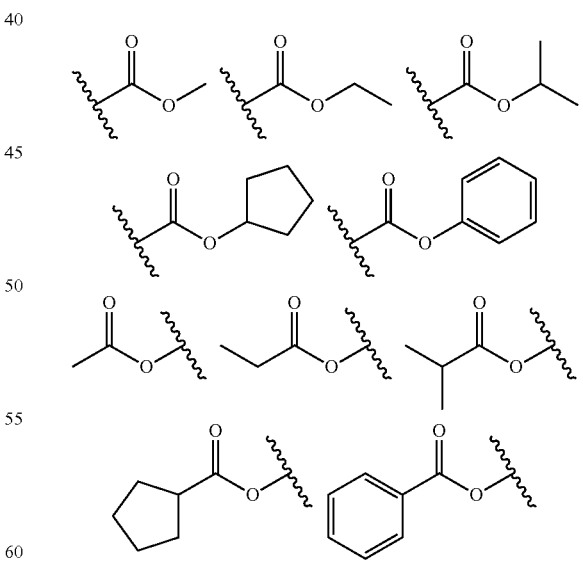

In the present specification, the number of carbon atoms of the imide group is not particularly limited, but is preferably from 1 to 25. Specifically, compounds having structures such as below may be included, but the imide group is not limited thereto.

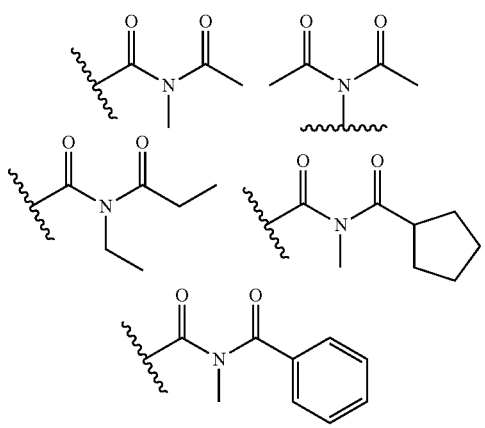

In the present specification, the silyl group may be represented by the chemical formula of —SiRR'R", and R, R' and R" may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of —BRR', and R and R' may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and the number of carbon atoms is not particularly limited, but is preferably from 1 to 40. According to one embodiment, the number of carbon atoms of the alkyl group is from 1 to 20. According to another embodiment, the number of carbon atoms of the alkyl group is from 1 to 10. According to still another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to still another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

The alkyl group, the alkoxy group and other substituents including an alkyl group part described in the present specification include all of linear or branched forms.

In the present specification, the aryloxy group is not particularly limited, but preferably has 6 to 60 carbon atoms. Specific examples thereof may include a phenoxy group, a biphenoxy group, a naphthoxy group, a binaphthoxy group, an anthracenoxy group, a phenanthrenoxy group, a fluorenoxy group and the like, but are not limited thereto.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to still another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, examples of the arylamine group may include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both a monocyclic aryl group and a multicyclic aryl group.

In the present specification, specific examples of the arylamine group may include a phenylamine group, a biphenylamine group, a naphthylamine group, an anthracenylamine group, a 3-methylphenylamine group, a 4-methylnaphthylamine group, a 2-methylbiphenylamine group, a 9-methylanthracenylamine group, a diphenylamine group, a phenylbiphenylamine group, a dibiphenylamine group, a phenylterphenylamine group, a biphenyl-terphenylamine group, a phenylnaphthylamine group, a biphenylnaphthylamine group; a dinaphthylamine group, a ditolylamine group, a phenyltolylamine group, a fluoreneamine group, a phenyl-fluoreneamine group, a biphenyl-fluoreneamine group, a naphthyl-fluoreneamine group, a terphenyl-fluoreneamine group, a carbazolyl group, a triphenylamine group, a diphenyl-biphenylamine group, a phenyldibiphenylamine group; a diphenylnaphthylamine group, a naphthylphenylbiphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including two or more heterocyclic groups may include monocyclic heterocyclic groups, multicyclic heterocyclic groups, or both a monocyclic heterocyclic group and a multicyclic heterocyclic group.

In the present specification, the arylheteroarylamine group means an amine group substituted with an aryl group and a heterocyclic group.

In the present specification, the number of carbon atoms of the amine group is not particularly limited, but is preferably from 1 to 60. In the amine group, the N atom may be substituted with an aryl group, an alkyl group, an arylalkyl group, a heterocyclic group and the like, and specific examples of the amine group may include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, a phenylnaphthylamine group, a ditolylamine group, a phenyltolylamine group, a triphenylamine group and the like, but are not limited thereto.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or both a monocyclic aryl group and a multicyclic aryl group.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 40. According to another embodiment, the number of carbon atoms of the aryl group is from 6 to 20. Examples of the monocyclic aryl group may include a phenyl group, a biphenyl group, a terphenyl group, a quaterphenyl group and the like, but are not limited thereto. Examples of the multicyclic aryl group may include a naphthyl group, an anthracenyl group, a phenanthrenyl group, a perylenyl group, a fluoranthenyl group, a triphenylenyl group, a phenalenyl group, a pyrenyl group, a tetracenyl group, a chrysenyl group, a pentacenyl group, a fluorenyl group, an indenyl group, an acenaphthylenyl group, a benzofluorenyl group, a spirofluorenyl group and the like, but are not limited thereto.

In the present specification, the fluorenyl group may be substituted, and two of the substituents may bond to each other to form a spiro structure.

When the fluorenyl group is substituted, spirofluorenyl groups such as

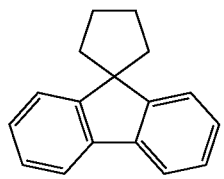 [SMILES: c1ccc2c(c1)-c1ccccc1C21CCCC1]

(spiro[cyclopentane-1,9'-fluorene]) and

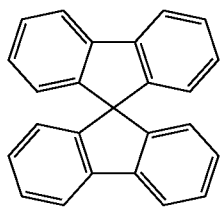 [SMILES: c1ccc2c(c1)-c1ccccc1C21c2ccccc2-c2ccccc21]

(9,9'-spirobi[fluorene]), and substituted fluorenyl groups such as

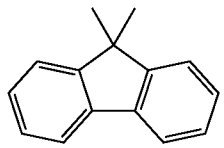

(9,9-dimethylfluorenyl group) and

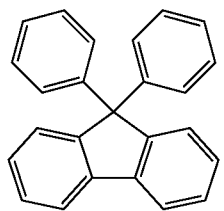 [SMILES: c1ccc(C2(c3ccccc3)c3ccccc3-c3ccccc32)cc1]

(9,9-diphenylfluorenyl group) may be included. However, the compounds are not limited thereto.

In the present specification, the heterocyclic group is a heterocyclic group including one or more of N, O and S as a heteroatom, and although not particularly limited thereto, the number of carbon atoms is preferably from 2 to 60. According to one embodiment, the number of carbon atoms of the heterocyclic group is from 2 to 40. Examples of the heterocyclic group may include a pyridyl group, a pyrrole group, a pyrimidyl group, a pyridazinyl group, a furanyl group, a thiophenyl group, an imidazole group, a pyrazole group, an oxazole group, an isoxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophene group, a dibenzofuranyl group, a carbazolyl group, a benzocarbazolyl group, a dibenzocarbazolyl group, an indolocarbazolyl group, an indenocarbazolyl group, a phenazinyl group, a phenoxazinyl group, a phenanthridine group, a phenanthroline group, a phenothiazine group, an imidazopyridine group, an imidazophenanthridine group, a benzimidazoquinazoline group, a benzimidazophenanthridine group or the like, but are not limited thereto.

In the present specification, the descriptions on the heterocyclic group may be used on the heteroaryl group except that the heteroaryl group is an aromatic group.

In the present specification, the descriptions on the aryl group provided above may be used on the aryl group in the aryloxy group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, the descriptions on the alkyl group provided above may be used on the alkyl group in the alkylthioxy group, the alkylsulfoxy group, the aralkyl group, the aralkylamine group, the alkylaryl group and the alkylamine group.

In the present specification, the descriptions on the heterocyclic group provided above may be used on the heteroaryl group in the heteroaryl group, the heteroarylamine group and the arylheteroarylamine group.

In the present specification, the descriptions on the alkenyl group provided above may be used on the alkenyl group in the aralkenyl group.

In the present specification, the descriptions on the aryl group provided above may be used on the arylene group except that the arylene group is divalent. According to one embodiment, the number of carbon atoms of the arylene group is from 6 to 30.

In the present specification, the descriptions on the heterocyclic group provided above may be used on the heteroarylene group except that the heteroarylene group is divalent. According to one embodiment, the number of carbon atoms of the heteroarylene group is from 2 to 30.

In the present specification, the meaning of bonding with an adjacent group to form a ring is bonding with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a fused ring thereof.

In the present specification, the aliphatic hydrocarbon ring means, as a ring that is not aromatic, a ring formed with only carbon and hydrogen atoms. Specific examples of the aliphatic hydrocarbon ring may include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene and the like, but are not limited thereto.

In the present specification, the aromatic hydrocarbon ring means an aromatic ring formed with only carbon and hydrogen atoms. Specific examples of the aromatic hydrocarbon ring may include benzene, naphthalene, anthracene, phenanthrene, perylene, fluoranthene, triphenylene, phenalene, pyrene, tetracene, chrysene, pentacene, fluorene, indene, acenaphthylene, benzofluorene, spirofluorene and the like, but are not limited thereto.

In the present specification, the aliphatic hetero ring means an aliphatic ring including one or more of heteroatoms. Specific examples of the aliphatic hetero ring may include oxirane, tetrahydrofuran, 1,4-dioxane, pyrrolidine, piperidine, morpholine, oxepane, azocane, thiocane and the like, but are not limited thereto.

In the present specification, the aromatic hetero ring means an aromatic ring including one or more of heteroatoms. Specific examples of the aromatic hetero ring may include pyridine, pyrrole, pyrimidine, pyridazine, furan, thiophene, imidazole, pyrazole, oxazole, isoxazole, triazole, isothiazole, triazole, oxadiazole, thiadiazole, dithiazole, tetrazole, pyran, thiopyran, diazine, oxazine, triazine, dioxine, triazine, tetrazine, isoquinoline, quinoline, quinole, quinazoline, quinoxaline, naphthyridine, acridine, phenanthridine, diazanaphthalene, triazaindene, indole, indolizine, benzothiazole, benzoxazole, benzimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole, indenocarbazole and the like, but are not limited thereto.

According to one embodiment of the present specification, Chemical Formula 1 may be represented by the following Chemical Formula 2 or Chemical Formula 3.

[Chemical Formula 2]

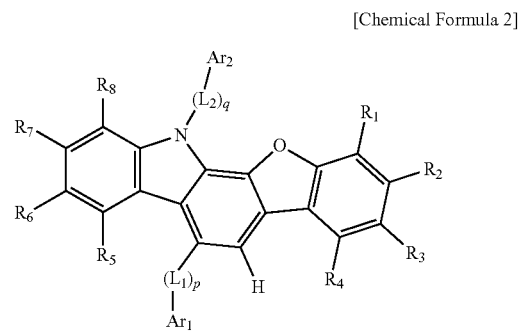

[Chemical Formula 3]

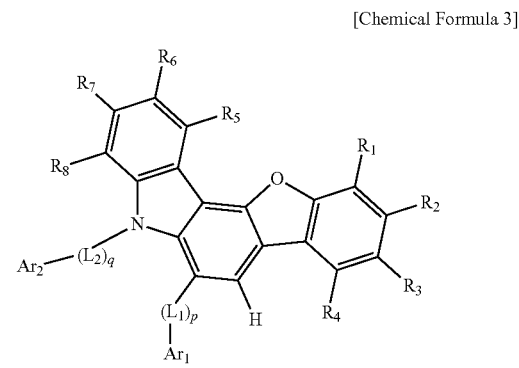

wherein, in Chemical Formula 2 and Chemical Formula 3, definitions of p, q, $L_1$, $L_2$, $Ar_1$, $Ar_2$ and $R_1$ to $R_8$ are the same as in Chemical Formula 1.

According to one embodiment of the present specification, Chemical Formula 1 may be represented by the following Chemical Formula 4 to Chemical Formula 9.

[Chemical Formula 4]

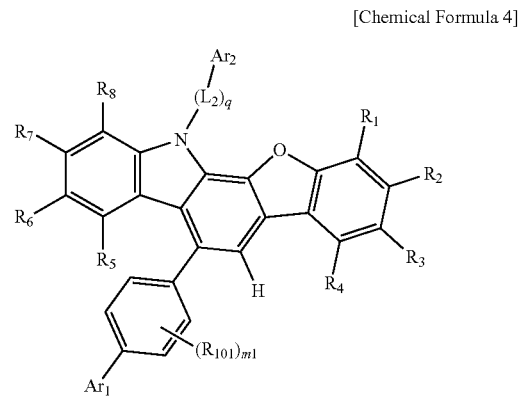

[Chemical Formula 5]

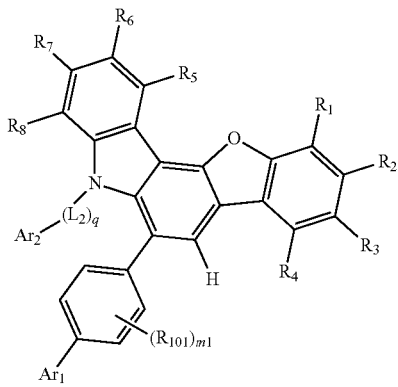

[Chemical Formula 6]

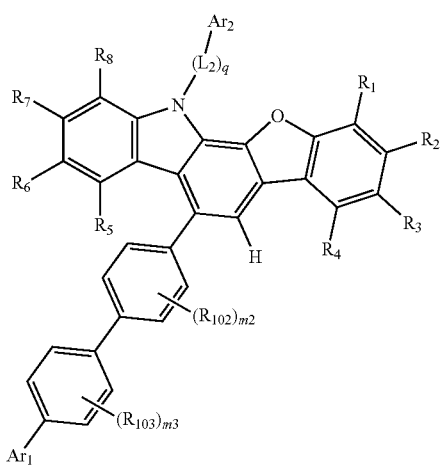

[Chemical Formula 7]

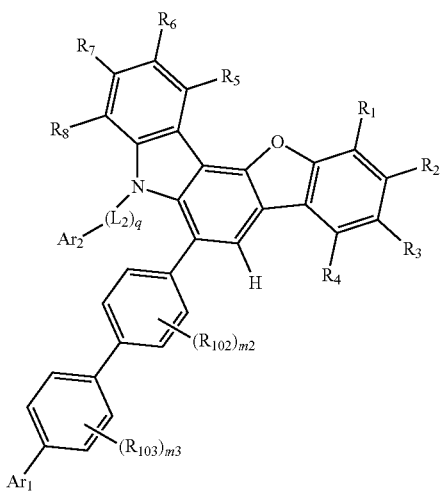

[Chemical Formula 8]

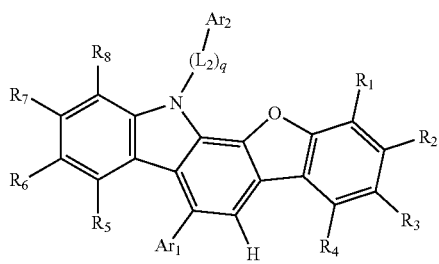

[Chemical Formula 9]

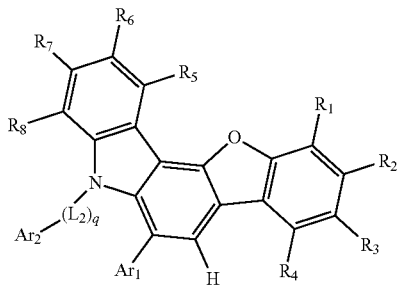

wherein, in Chemical Formula 4 to Chemical Formula 9, definitions of q, $L_2$, $Ar_1$, $Ar_2$ and $R_1$ to $R_8$ are the same as in Chemical Formula 1, m1 to m3 are each independently an integer of 0 to 4, when m1 to m3 are 2 or greater, the structures in the parentheses are the same as or different from each other, and $R_{101}$ to $R_{103}$ are the same as or different from each other, and each independently have the same definitions as $R_1$ to $R_8$ in Chemical Formula 1.

According to one embodiment of the present specification, Chemical Formula 1 may be represented by the following Chemical Formula 10 or Chemical Formula 11.

[Chemical Formula 10]

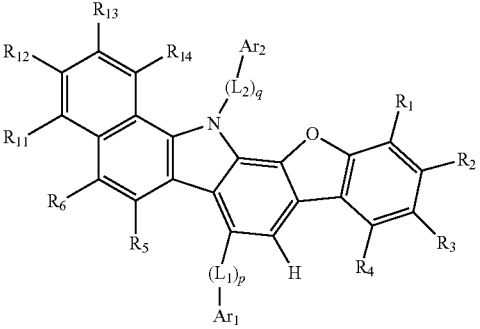

[Chemical Formula 11]

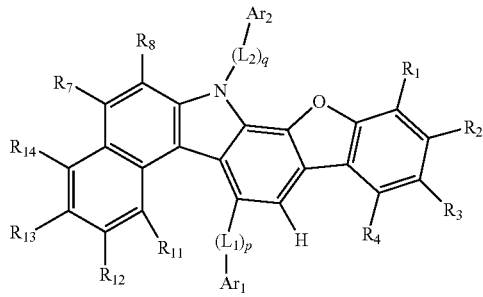

wherein, in Chemical Formula 10 and Chemical Formula 11, definitions of p, q, $L_1$, $L_2$, $Ar_1$, $Ar_2$ and $R_1$ to $R_8$ are the same as in Chemical Formula 1, and $R_{11}$ to $R_{14}$ are the same as or different from each other, and each independently have the same definitions as $R_1$ to $R_8$.

In one embodiment of the present specification, $L_1$ and $L_2$ are the same as or different from each other, and each independently a direct bond; a substituted or unsubstituted arylene group having 6 to 30 carbon atoms; or a substituted or unsubstituted heteroarylene group having 2 to 30 carbon atoms.

In another embodiment of the present specification, $L_1$ and $L_2$ are the same as or different from each other, and each independently preferably a direct bond; or may be linked with one or more linking groups selected from the group consisting of a substituted or unsubstituted phenylene group; a substituted or unsubstituted biphenylylene group; a substituted or unsubstituted terphenylene group; a substituted or unsubstituted quaterphenylene group; a substituted or unsubstituted naphthylene group; a substituted or unsubstituted pyrenylene group; a substituted or unsubstituted phenanthrenylene group; a substituted or unsubstituted perylenylene group; a substituted or unsubstituted tetracenylene group; a substituted or unsubstituted triphenylene group; a substituted or unsubstituted fluoranthenylene group; a substituted or unsubstituted fluorenylene group; a substituted or unsubstituted pyrrolylene group; a substituted or unsubstituted furanylene group; a substituted or unsubstituted divalent thiophene group; a substituted or unsubstituted pyridinylene group; a substituted or unsubstituted pyrazolylene group; a substituted or unsubstituted imidazolylene group; a substituted or unsubstituted oxazolylene group; a substituted or unsubstituted isoxazolylene group; a substituted or unsubstituted thiazolylene group; a substituted or unsubstituted isothiazolylene group; a substituted or unsubstituted pyridazinylene group; a substituted or unsubstituted pyrimidinylene group; a substituted or unsubstituted indolylene group; a substituted or unsubstituted isoindolylene group; a substituted or unsubstituted indolizinylene group; a substituted or unsubstituted quinolinylene group; a substituted or unsubstituted quinazolinylene group; a substituted or unsubstituted isoquinolinylene group; a substituted or unsubstituted quinoxalinylene group; a substituted or unsubstituted naphthyridinylene group; a substituted or unsubstituted acridinylene group; a substituted or unsubstituted xanthenylene group; a substituted or unsubstituted dibenzofuranylene group; a substituted or unsubstituted phenanthrolylene group; a substituted or unsubstituted divalent dibenzothiophene group; and a substituted or unsubstituted carbazolylene group, or two or more substituents of the linking groups illustrated above may be the linking group.

According to one embodiment of the present specification, $L_1$ and $L_2$ are the same as or different from each other, and may be each independently a direct bond; a phenylene group, a biphenylylene group, a terphenylene group, a quaterphenylene group, a naphthylene group, an anthracenylene group, a 9,9-dimethylfluorenylene group, a phenanthrenylene group, a pyridinylene group, a pyrimidinylene group, a triazinylene group, a quinolinylene group, a quinazolinylene group, a carbazolylene group, a dibenzofuranylene group, or a divalent dibenzothiophene group, and these may be further substituted.

According to one embodiment of the present specification, $L_1$ and $L_2$ are the same as or different from each other, and each independently a direct bond; a substituted or unsubstituted phenylene group; a substituted or unsubstituted biphenylylene group; a substituted or unsubstituted naphthylene group; a substituted or unsubstituted anthracenylene group; a substituted or unsubstituted fluorenylene group; a substituted or unsubstituted quinazolinylene group; or a substituted or unsubstituted carbazolylene group.

In addition, according to one embodiment of the present specification, $L_1$ and $L_2$ are the same as or different from each other, and each independently preferably a direct bond or any one linking group selected from among the following groups, however, $L_1$ and $L_2$ are not limited thereto.

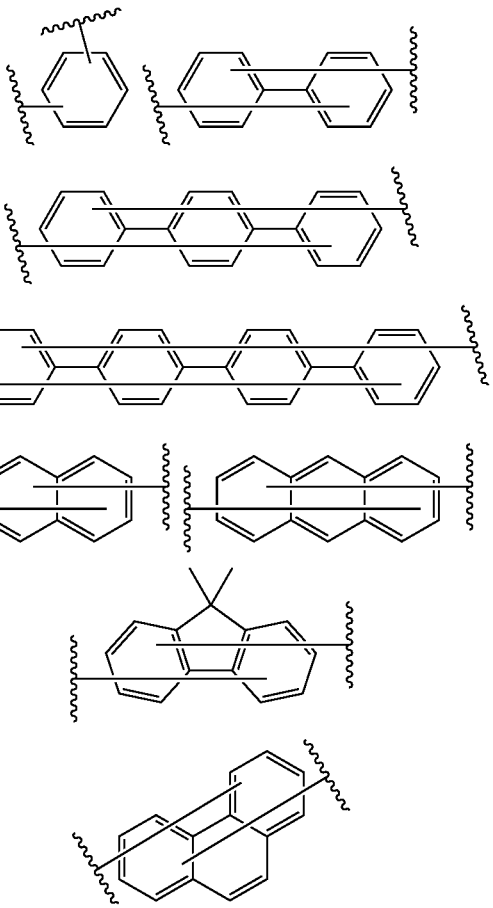

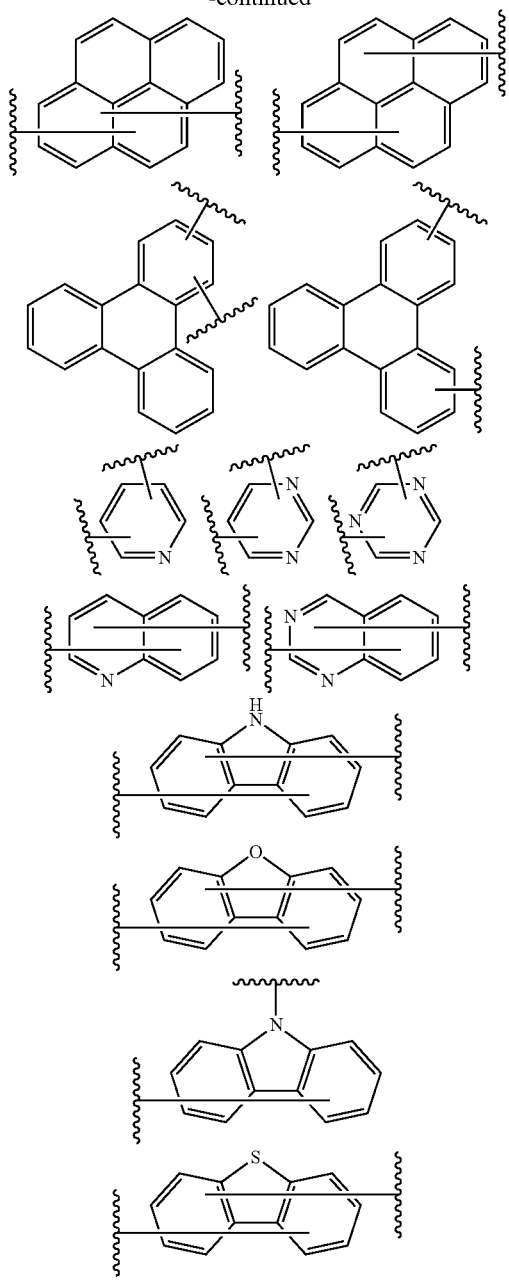

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group. More specifically, the structures may be unsubstituted or substituted with one or more phenyl groups.

According to one embodiment of the present specification, $Ar_1$ is a substituted or unsubstituted biphenyl group; a substituted or unsubstituted terphenyl group; a substituted or unsubstituted quaterphenyl group; a substituted or unsubstituted multicyclic aryl group; a substituted or unsubstituted arylamine group; or a substituted or unsubstituted heterocyclic group.

According to one embodiment of the present specification, $Ar_1$ is a substituted or unsubstituted biphenyl group; a substituted or unsubstituted terphenyl group; a substituted or unsubstituted quaterphenyl group; a multicyclic substituted or unsubstituted aryl group having 6 to 60 carbon atoms; a monocyclic or multicyclic substituted or unsubstituted arylamine group having 6 to 60 carbon atoms; or a monocyclic or multicyclic substituted or unsubstituted heterocyclic group having 2 to 60 carbon atoms.

According to one embodiment of the present specification, $Ar_1$ is a substituted or unsubstituted biphenyl group; a substituted or unsubstituted terphenyl group; a substituted or unsubstituted quaterphenyl group; a substituted or unsubstituted aryl group having 6 to 40 carbon atoms; a substituted or unsubstituted arylamine group having 6 to 40 carbon atoms; or a substituted or unsubstituted heterocyclic group having 2 to 40 carbon atoms.

According to one embodiment of the present specification, $Ar_1$ is a substituted or unsubstituted biphenyl group; a substituted or unsubstituted terphenyl group; a substituted or unsubstituted quaterphenyl group; a dicyclic to tricyclic substituted or unsubstituted aryl group having 6 to 40 carbon atoms; a primary, secondary or tertiary substituted or unsubstituted arylamine group having 6 to 40 carbon atoms; or a monocyclic to tricyclic substituted or unsubstituted heterocyclic group having 2 to 40 carbon atoms.

According to one embodiment of the present specification, $Ar_1$ is a substituted or unsubstituted biphenyl group; a substituted or unsubstituted naphthyl group; a substituted or unsubstituted terphenyl group; a substituted or unsubstituted phenylamine group; a substituted or unsubstituted biphenylamine group; a substituted or unsubstituted naphthylamine group; a substituted or unsubstituted anthracenylamine group; a substituted or unsubstituted diphenylamine group; a substituted or unsubstituted phenylbiphenylamine group; a substituted or unsubstituted dibiphenylamine group; a substituted or unsubstituted phenylterphenylamine group; a substituted or unsubstituted biphenylterphenylamine group; a substituted or unsubstituted phenylnaphthylamine group; a substituted or unsubstituted ditolylamine group; a substituted or unsubstituted phenyltolylamine group; a substituted or unsubstituted fluoreneamine group; a substituted or unsubstituted N-phenylfluoreneamine group; a substituted or unsubstituted N-biphenylfluoreneamine group; a substituted or unsubstituted triphenylamine group; a substituted or unsubstituted diphenylbiphenylamine group; a substituted or unsubstituted phenyldibiphenylamine group; a substituted or unsubstituted naphthylphenylbiphenylamine group; a substituted or unsubstituted tribiphenylamine group; a substituted or unsubstituted diphenylnaphthylamine group; a substituted or unsubstituted diphenylfluoreneamine group; a substituted or unsubstituted phenylbiphenylfluoreneamine group; a substituted or unsubstituted pyrimidyl group; a substituted or unsubstituted pyrimidinyl group; a substituted or unsubstituted triazinyl group; a substituted or unsubstituted quinolinyl group; a substituted or unsubstituted isoquinolinyl group; a substituted or unsubstituted quinazolinyl group; a substituted or unsubstituted quinoxalinyl group; a substituted or unsubstituted naphthyridinyl group; a substituted or unsubstituted acridyl group; a substituted or unsubstituted xanthenyl group; a substituted or unsubstituted phenanthridinyl group; a substituted or unsubstituted diazanaphthalenyl group; a substituted or unsubstituted triazaindenyl group; a substituted or unsubstituted indole group; a substituted or unsubstituted indolinyl group; a substituted or unsubstituted indolizinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted carbazolyl group; a substituted or unsubstituted benzothiophene group; a substituted or unsubstituted dibenzothiophene group; a substituted or unsubstituted benzofuranyl group; a substituted or unsubstituted benzocarbazolyl group; a substituted or unsubstituted naphthobenzothiophene group; a substituted or unsubstituted naphthobenzofuranyl group; a substituted or unsubstituted dibenzocarbazolyl group; a substituted or unsubstituted indolocarbazolyl group; a substituted or unsubstituted indenocarbazolyl group; a substituted or unsubstituted phenanthroline group; a substituted or unsubstituted phenazinyl group; a substituted or unsubstituted phenoxazinyl group; a substituted or unsubstituted phenothiazinyl group; a substituted or unsubstituted imidazopyridinyl group; a substituted or unsubstituted imidazophenanthridine group; a substituted or unsubstituted benzimidazoquinazolinyl group; or a substituted or unsubstituted benzimidazophenanthridinyl group.

According to one embodiment of the present specification, $Ar_1$ is a biphenyl group unsubstituted or substituted with one or more types of substituents selected from the group consisting of an aryl group and an arylamine group; a naphthyl group; a diphenylamine group unsubstituted or substituted with an aryl group; a phenylbiphenylamine group unsubstituted or substituted with an aryl group; a dibiphenylamine group unsubstituted or substituted with an aryl group; a phenylterphenylamine group unsubstituted or substituted with an aryl group; a biphenyl-terphenylamine group unsubstituted or substituted with an aryl group; a phenylnaphthylamine group unsubstituted or substituted with an aryl group; a fluoreneamine group unsubstituted or substituted with an aryl group; a N-phenylfluoreneamine group unsubstituted or substituted with an aryl group; a N-biphenyl-fluoreneamine group unsubstituted or substituted with an aryl group; a triphenylamine group unsubstituted or substituted with an aryl group; a carbazolyl group unsubstituted or substituted with an aryl group; a dibenzofuranyl group unsubstituted or substituted with an aryl group; a dibenzothiophene group unsubstituted or substituted with an aryl group; or a substituted or unsubstituted fluorenyl group, and the aryl group may be one or more types selected from the group consisting of a phenyl group, a biphenyl group, a naphthyl group and a fluorenyl group.

According to one embodiment of the present specification, the -$(L_1)p$-$Ar_1$ may be any one selected from among the following structures.

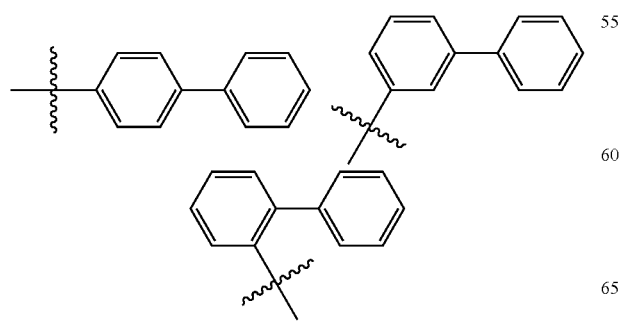

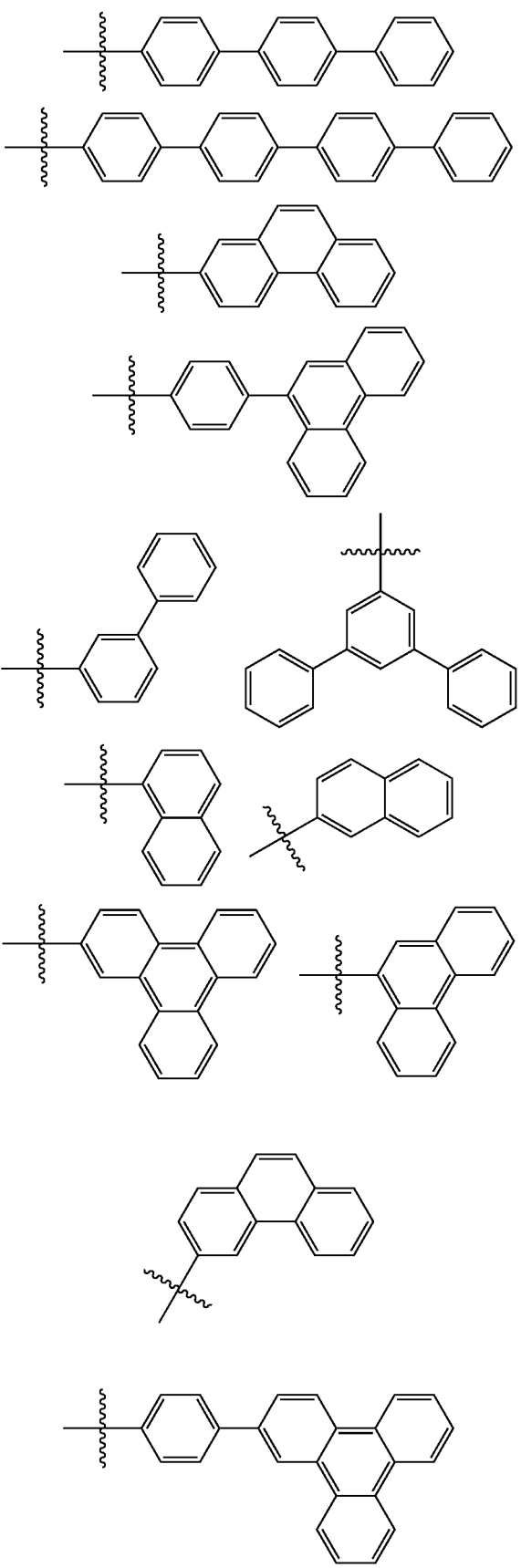

-continued
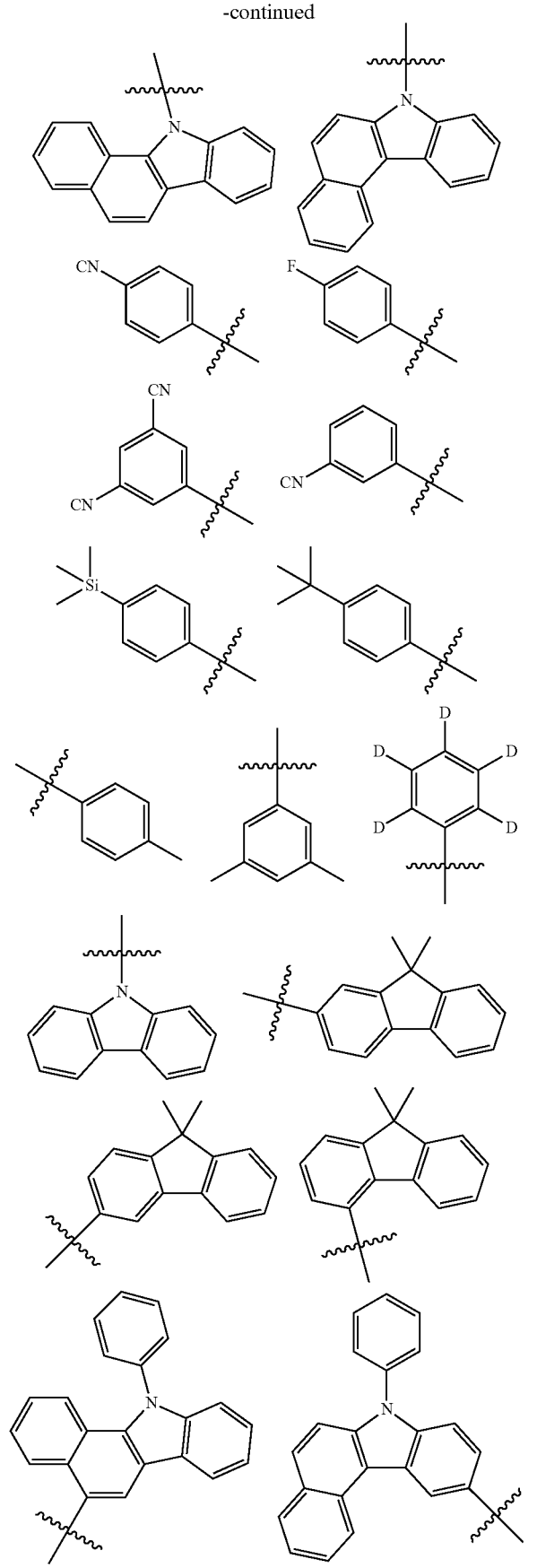
-continued
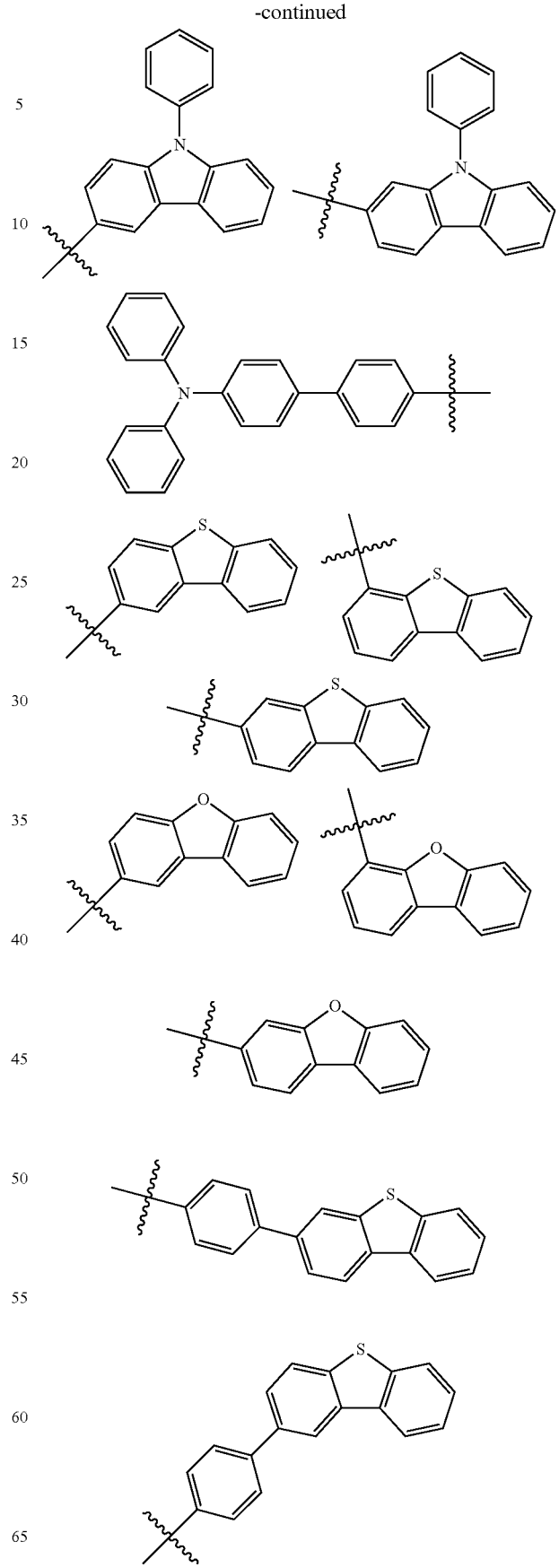

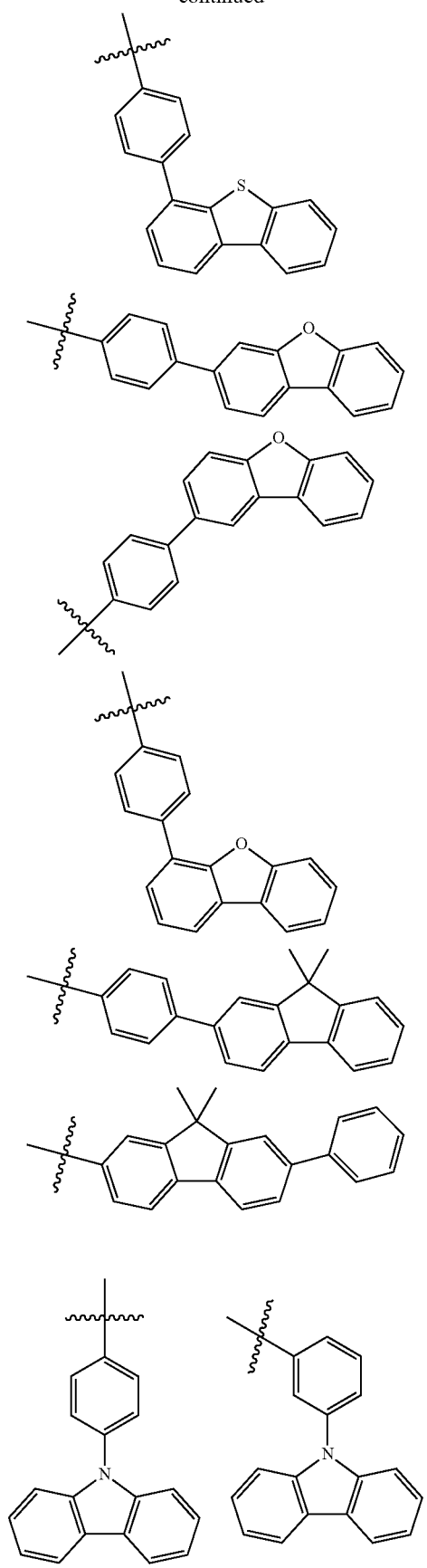

-continued
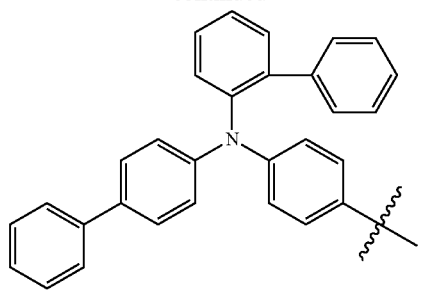
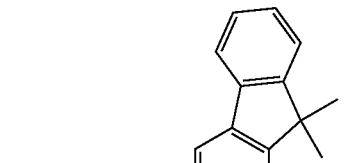
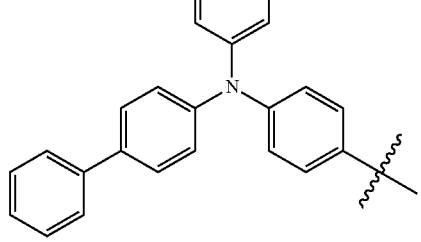
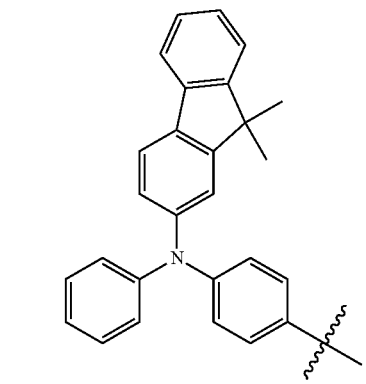
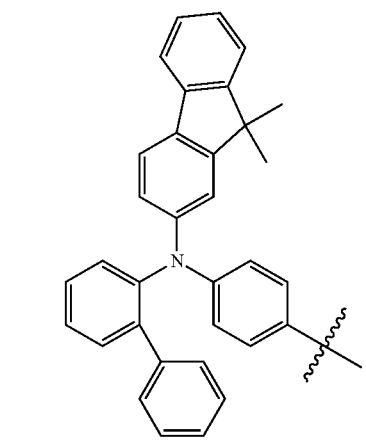
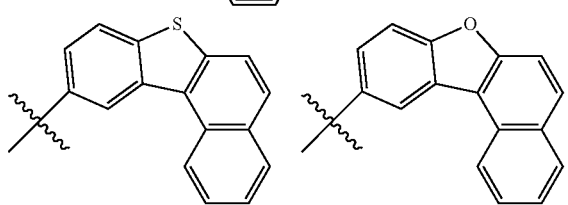
-continued
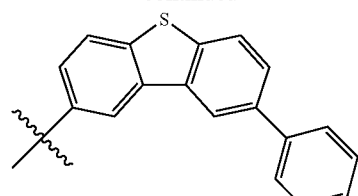
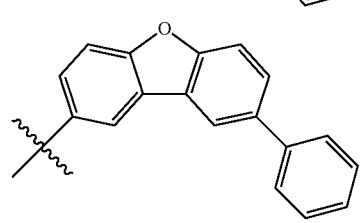
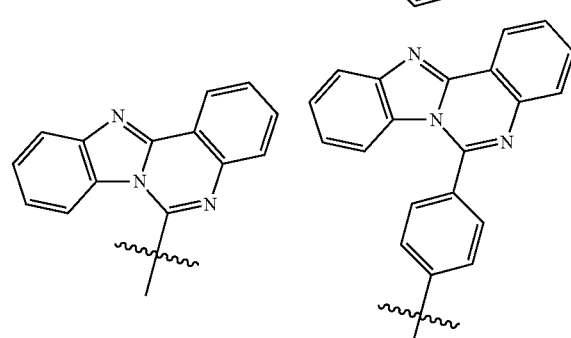
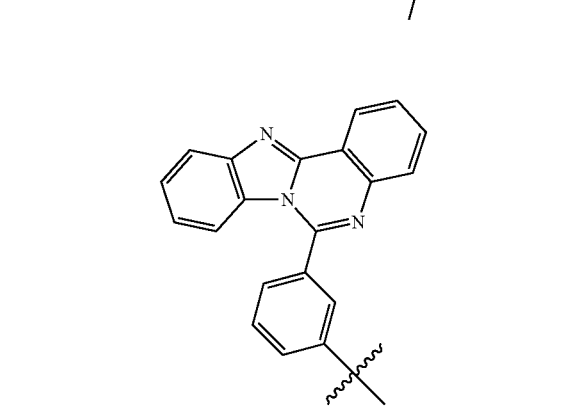
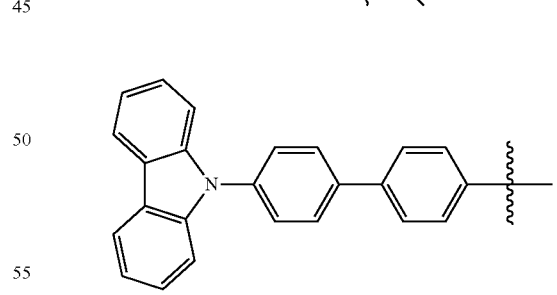
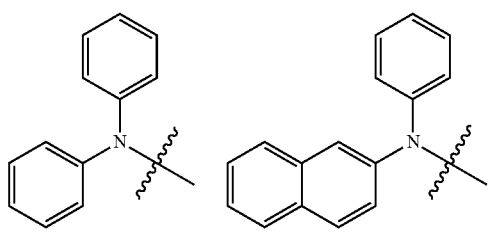

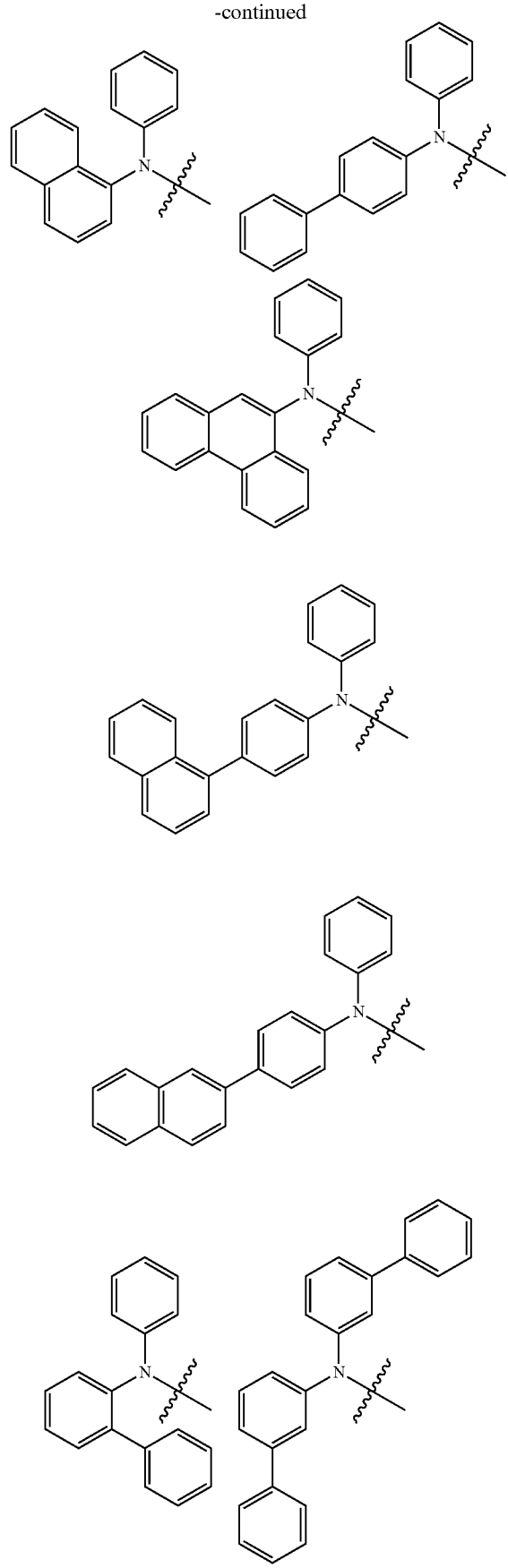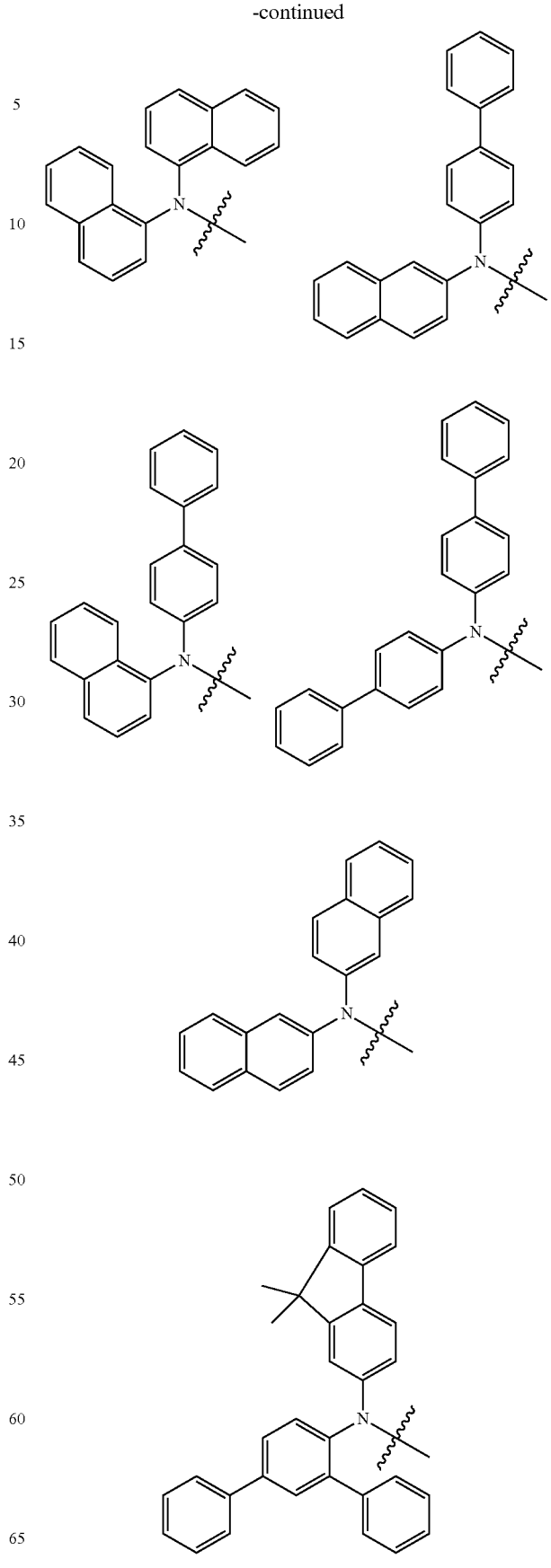

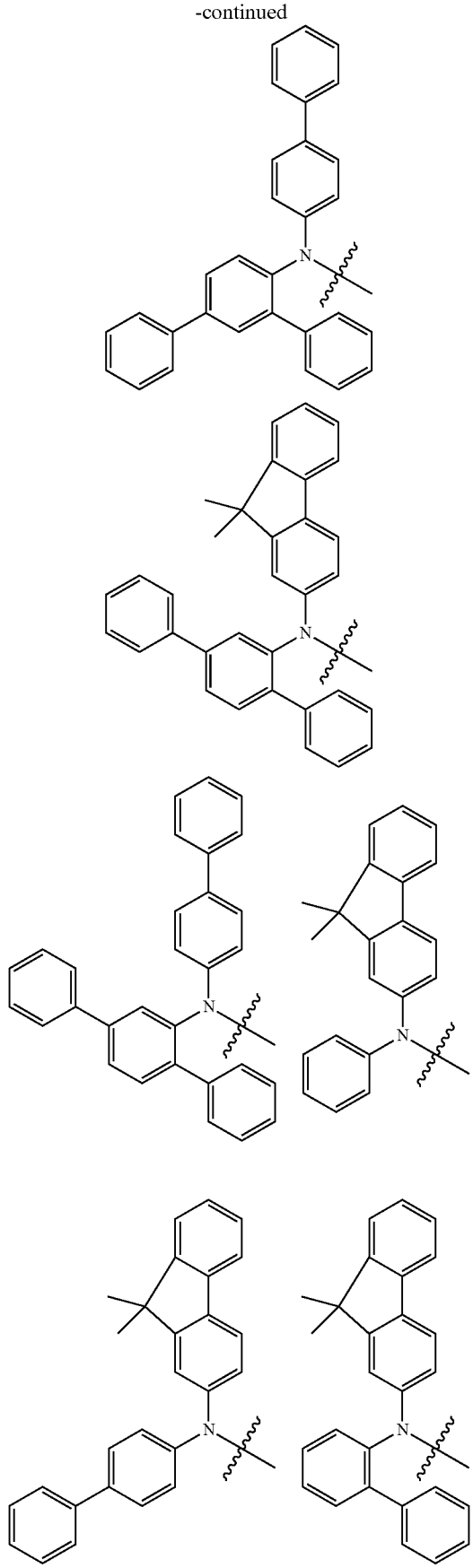
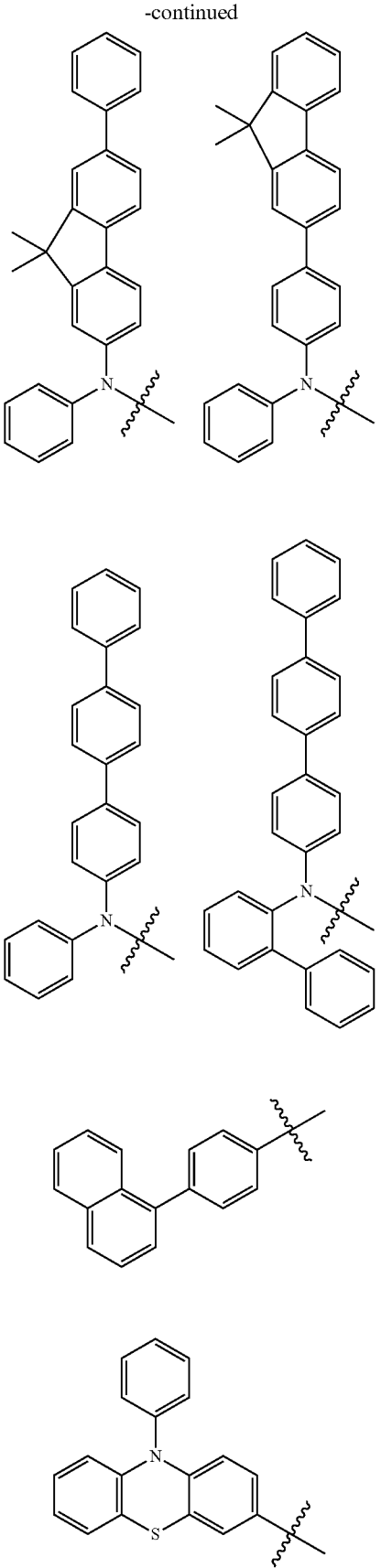

-continued

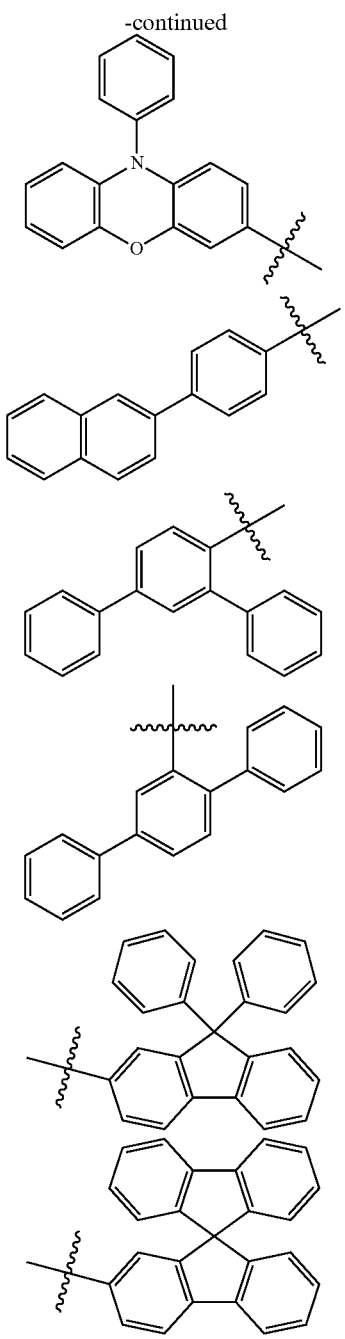

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present specification, $Ar_2$ is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

According to one embodiment of the present specification, $Ar_2$ is selected from the group consisting of hydrogen; deuterium; a halogen group; a linear or branched substituted or unsubstituted alkyl group having 1 to 60 carbon atoms; a linear or branched substituted or unsubstituted alkenyl group having 2 to 60 carbon atoms; a linear or branched substituted or unsubstituted alkynyl group having 2 to 60 carbon atoms; a monocyclic or multicyclic substituted or unsubstituted cycloalkyl group having 3 to 60 carbon atoms; a monocyclic or multicyclic substituted or unsubstituted heterocycloalkyl group having 2 to 60 carbon atoms; a monocyclic or multicyclic substituted or unsubstituted aryl group having 6 to 60 carbon atoms; and a monocyclic or multicyclic substituted or unsubstituted heterocyclic group having 2 to 60 carbon atoms.

According to one embodiment of the present specification, $Ar_2$ is selected from the group consisting of hydrogen; a monocyclic or multicyclic substituted or unsubstituted aryl group having 6 to 40 carbon atoms; and a monocyclic or multicyclic substituted or unsubstituted heterocyclic group having 2 to 40 carbon atoms.

According to one embodiment of the present specification, $Ar_2$ may be hydrogen; deuterium; an aryl group such as a phenyl group, a biphenyl group, a terphenyl group, a quaterphenyl group, a naphthyl group, an anthracenyl group, a chrysenyl group, a phenanthrenyl group, a triphenylenyl group, a pyrenyl group, a tetracenyl group, a pentacenyl group or a fluorenyl group; an amine group such as a phenylamine group, a biphenylamine group, a naphthylamine group, an anthracelamine group, a diphenylamine group, a phenyl biphenylamine group, a diphenyl terphenylamine group, a phenyl phenanthreneamine group, a dinaphthylamine group, a phenyl fluoreneamine group, a biphenyl fluoreneamine group, a triphenylamine group, a diphenyl biphenylamine group, a phenyl dibiphenylamine group, a naphthyl phenyl biphenylamine group, a tribiphenylamine group, a diphenyl naphthylamine group, a diphenyl fluoreneamine group or a phenyl biphenyl fluoreneamine group; or a heterocyclic group such as a pyridinyl group, a pyrrole group, a pyrimidinyl group, a pyridazinyl group, a furanyl group, a thiophene group, an imidazole group, a pyrazole group, an oxazole group, an isoxazole group, a triazole group, an isothiazole group, a triazole group, a pyrazinyl group, a triazine group, a quinolinyl group, an isoquinolinyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a carbazolyl group, a benzothiophene group, a benzofuranyl group, a benzimidazole group, a benzothiazole group, a benzoxazole group, a dibenzothiophene group, a dibenzofuranyl group, a benzocarbazolyl group, a naphthobenzothiophene group, a naphthobenzofuranyl group, a dibenzocarbazolyl group, an indolocarbazolyl group, an indenocarbazolyl group, a phenanthroline group, a phenazinyl group, a phenoxazinyl group, a phenothiazinyl group, an imidazopyridinyl group, an imidazophenanthridine group, a benzimidazoquinazolinyl group or a benzimidazophenanthridinyl group, and these may be further substituted.

According to one embodiment of the present specification, specifically, $Ar_2$ may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group. More specifically, $Ar_2$ may be unsubstituted or substituted with one or more aryl groups.

According to one embodiment of the present specification, $Ar_2$ is hydrogen; deuterium; a substituted or unsubstituted phenyl group; a substituted or unsubstituted biphenyl group; a substituted or unsubstituted terphenyl group; a substituted or unsubstituted quaterphenyl group; a substituted or unsubstituted naphthyl group; a substituted or unsubstituted phenanthrenyl group; a substituted or unsubstituted triphenylenyl group; a substituted or unsubstituted fluorenyl group; a substituted or unsubstituted diphenylamine group; a substituted or unsubstituted phenyl biphenylamine group; a substituted or unsubstituted phenyl terphenylamine group; a substituted or unsubstituted phenyl naphthylamine group; a substituted or unsubstituted phenyl phenanthreneamine group; a substituted or unsubstituted dibiphenylamine group; a substituted or unsubstituted biphenyl terphenylamine group; a substituted or unsubstituted biphenyl naphthylamine group; a substituted or unsubstituted phenyl fluoreneamine group; a substituted or unsubstituted biphenyl fluoreneamine group; a substituted or unsubstituted terphenyl fluoreneamine group; a substituted or unsubstituted triphenylamine group; a substituted or unsubstituted diphenyl biphenylamine group; a substituted or unsubstituted phenyl dibiphenylamine group; a substituted or unsubstituted carbazolyl group; a substituted or unsubstituted dibenzothiophene group; a substituted or unsubstituted dibenzofuranyl group; a substituted or unsubstituted benzocarbazolyl group; a substituted or unsubstituted naphthobenzothiophene group; a substituted or unsubstituted naphthobenzofuranyl group; a substituted or unsubstituted benzimidazoquinazolinyl group; a substituted or unsubstituted phenothiazinyl group; or a substituted or unsubstituted phenoxazinyl group.

According to one embodiment of the present specification, $Ar_2$ is a phenyl group unsubstituted or substituted with hydrogen, deuterium, a halogen group, a nitrile group, an alkyl group, an arylamine group, an aryl group or a heterocyclic group; a biphenyl group unsubstituted or substituted with an aryl group; a naphthyl group unsubstituted or substituted with an aryl group; a phenanthrenyl group unsubstituted or substituted with an aryl group; a triphenylenyl group unsubstituted or substituted with an aryl group; a fluorenyl group unsubstituted or substituted with an alkyl group or an aryl group; a diphenylamine group unsubstituted or substituted with an aryl group; a phenyl biphenylamine group unsubstituted or substituted with an aryl group; a phenylnaphthylamine group unsubstituted or substituted with an aryl group; a phenyl-phenanthreneamine group unsubstituted or substituted with an aryl group; a dibiphenylamine group unsubstituted or substituted with an aryl group; a phenyl-fluoreneamine group unsubstituted or substituted with an aryl group; a biphenyl-fluoreneamine group unsubstituted or substituted with an aryl group; a triphenylamine group unsubstituted or substituted with an aryl group; a diphenyl biphenylamine group unsubstituted or substituted with an aryl group; a phenyl dibiphenylamine group unsubstituted or substituted with an aryl group; a carbazolyl group unsubstituted or substituted with an aryl group; a dibenzothiophene group unsubstituted or substituted with an aryl group; a dibenzofuranyl group unsubstituted or substituted with an aryl group; a benzocarbazolyl group unsubstituted or substituted with an aryl group; a naphthobenzothiophene group; a naphthobenzofuranyl group; a substituted or unsubstituted benzimidazoquinazolinyl group; a phenothiazinyl group unsubstituted or substituted with an aryl group; or a phenoxazinyl group unsubstituted or substituted with an aryl group.

According to one embodiment of the present specification, $Ar_2$ may be hydrogen or any one selected from among the following structures.

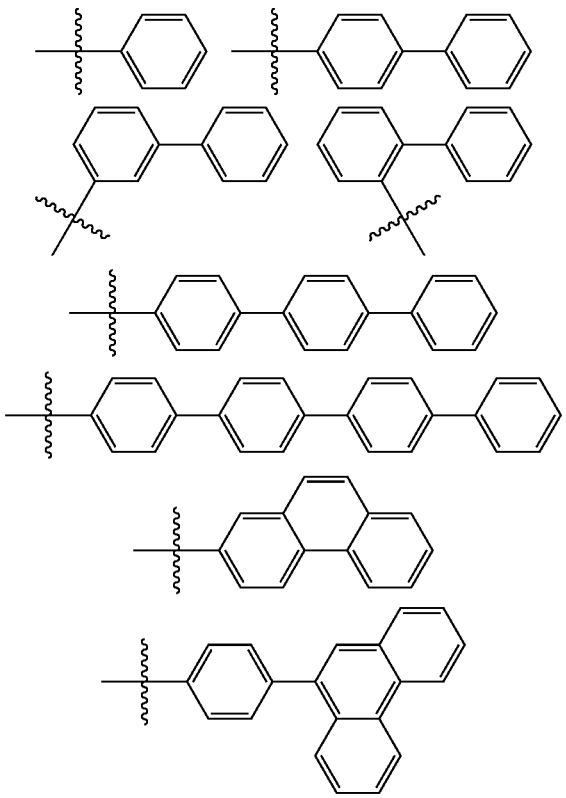

-continued
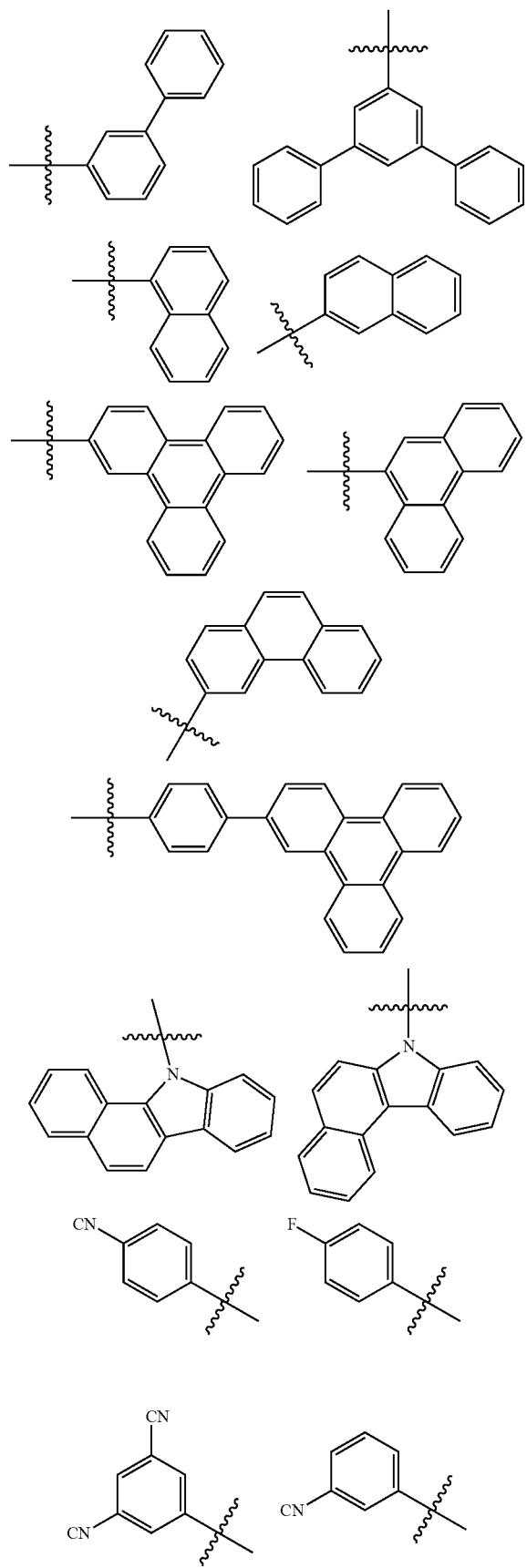
-continued
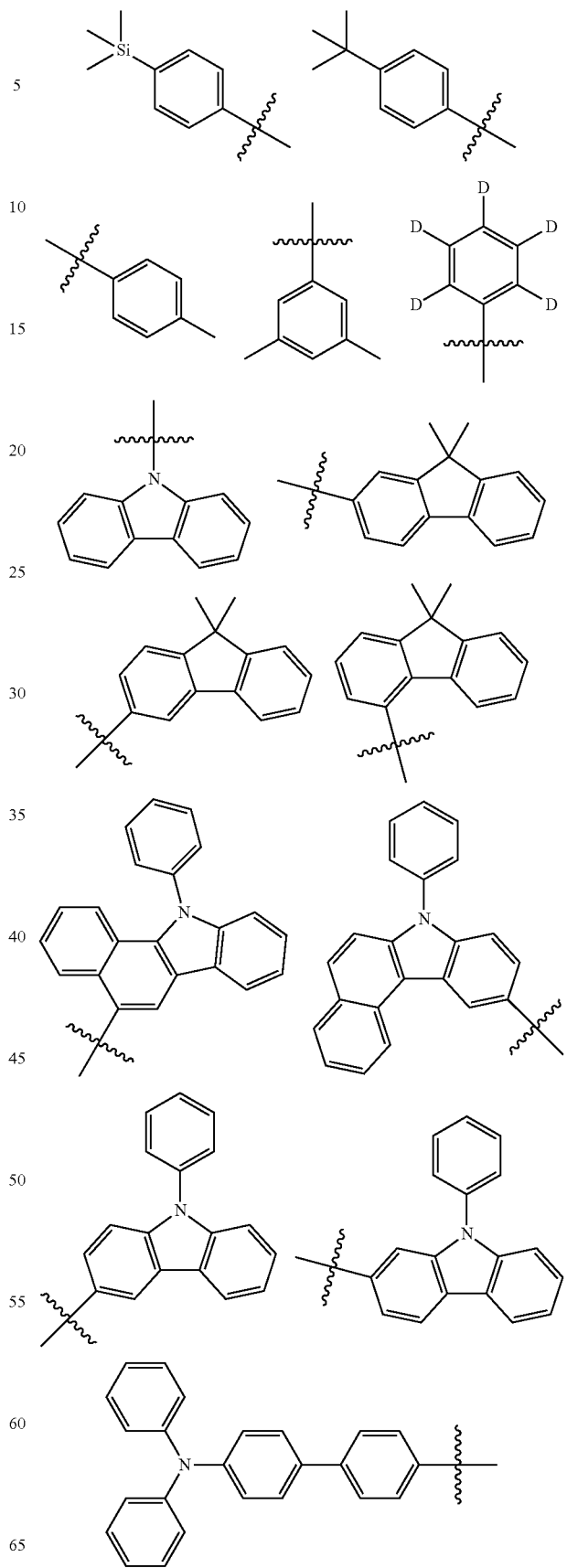

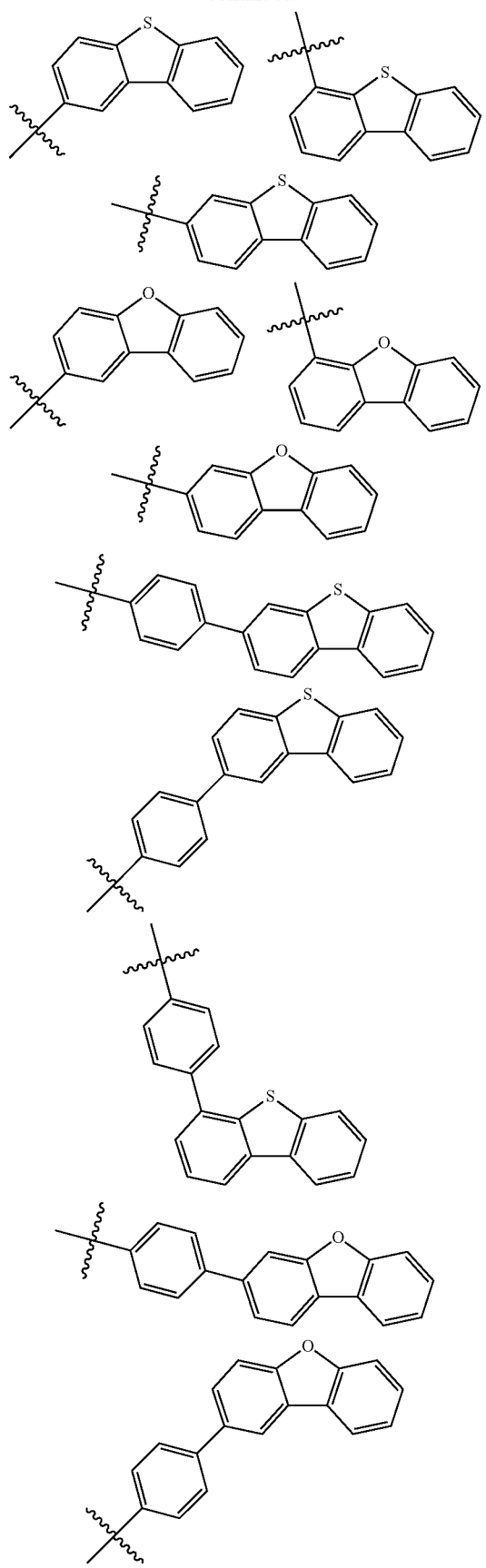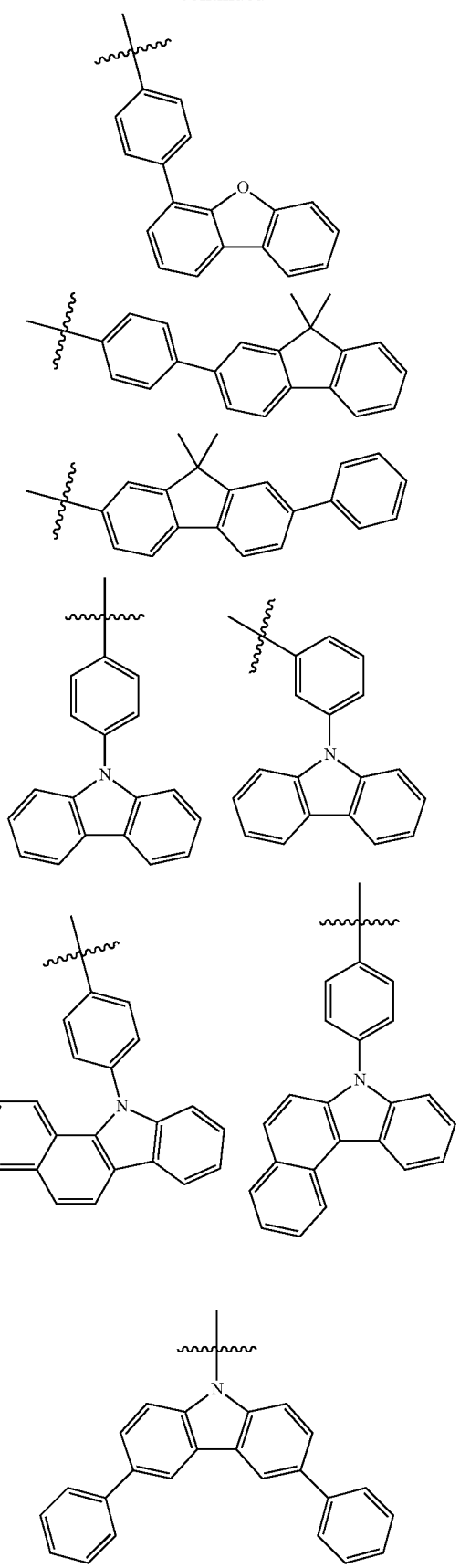

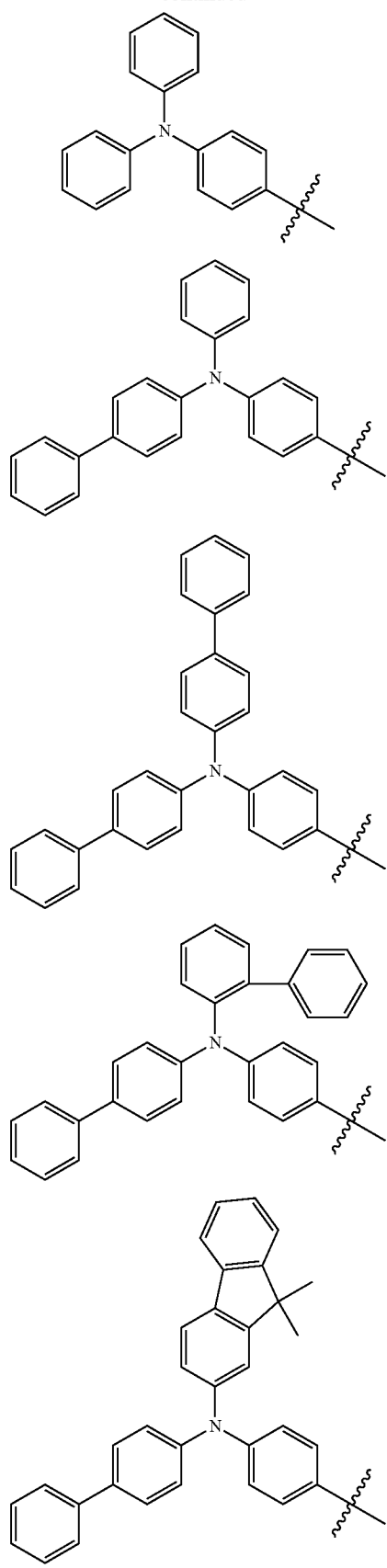
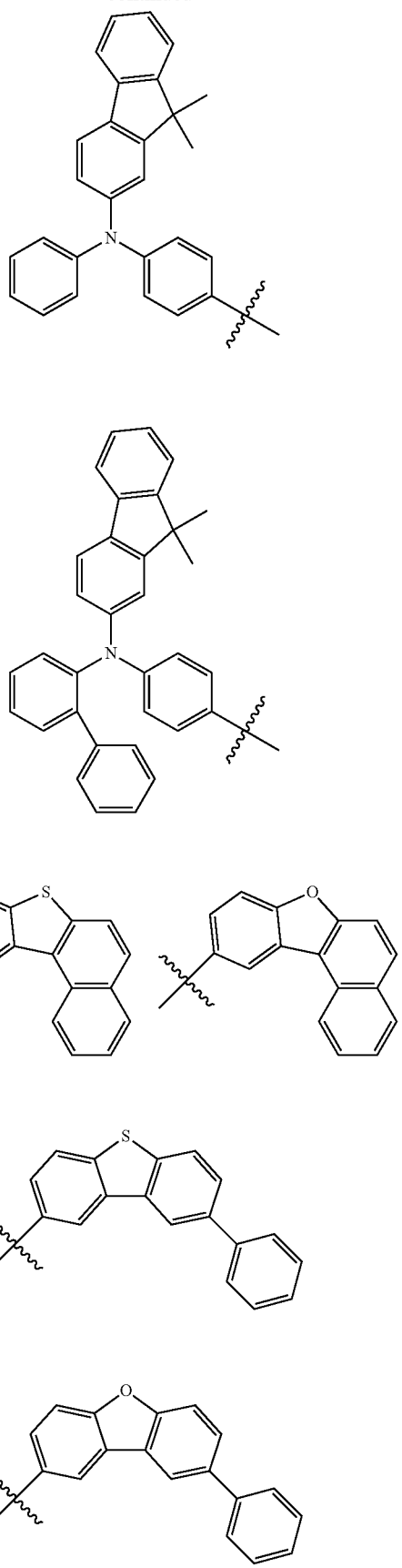

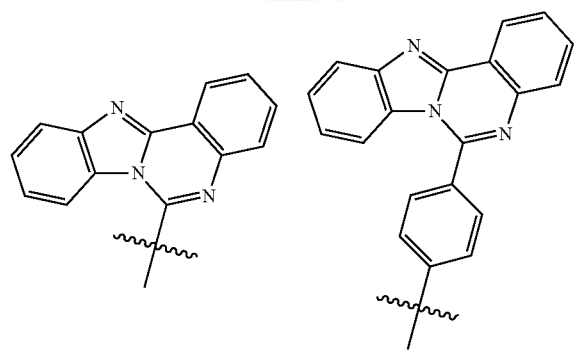
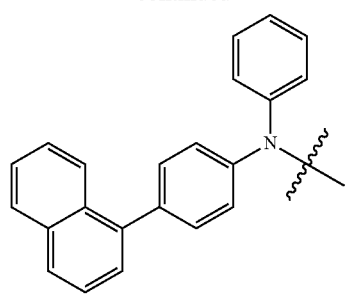
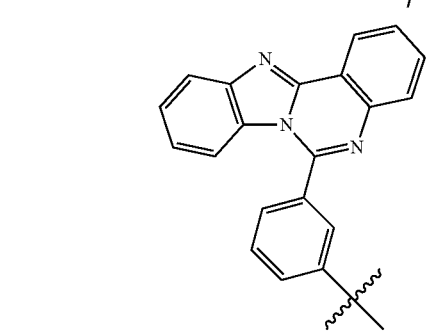
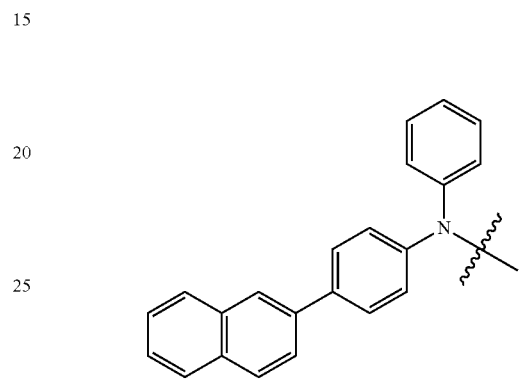
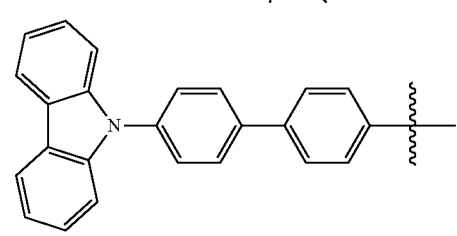
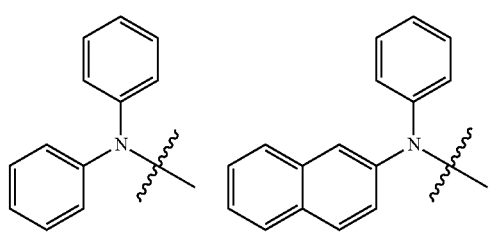
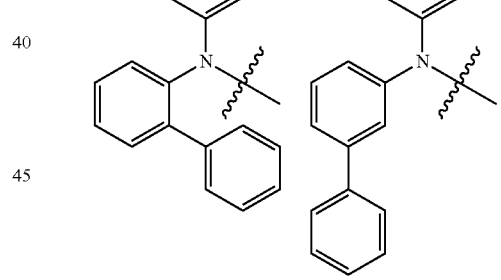
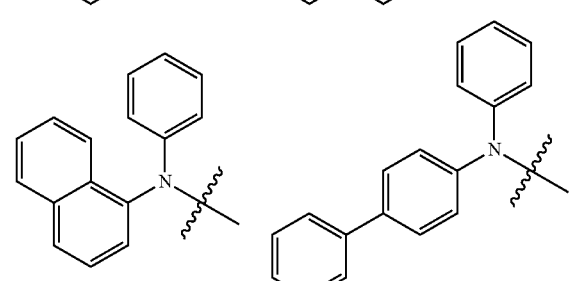
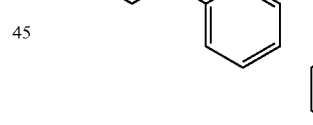
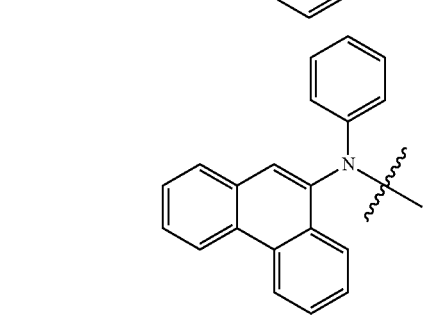
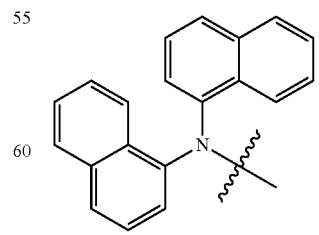
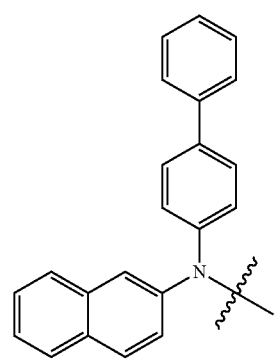

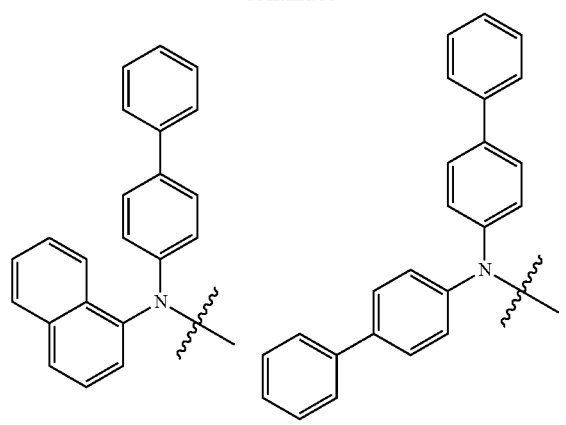
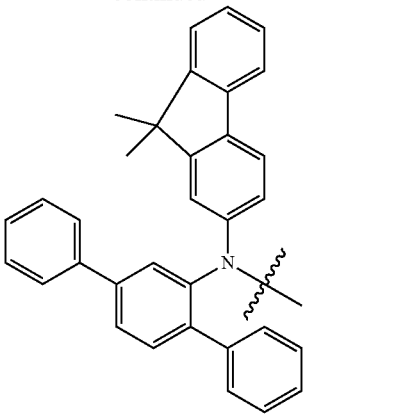
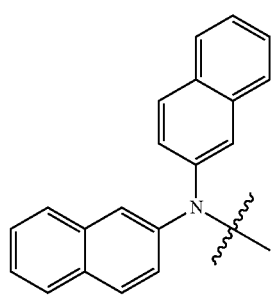
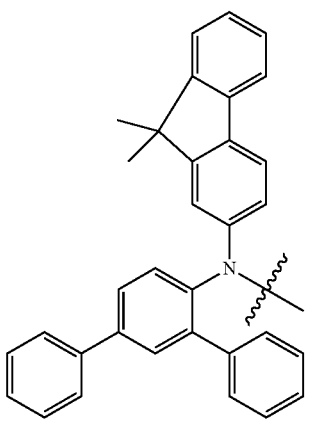

-continued
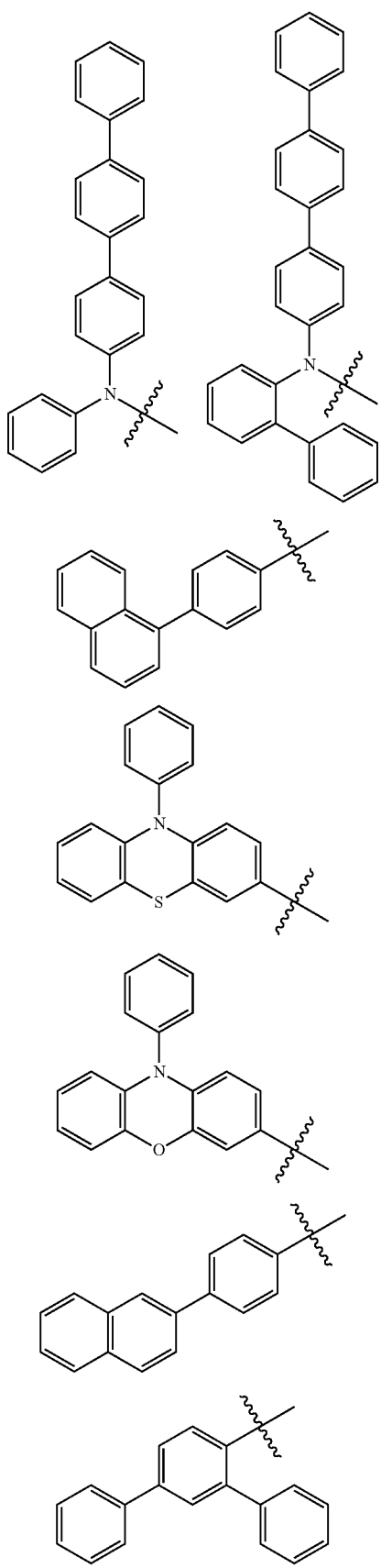
-continued
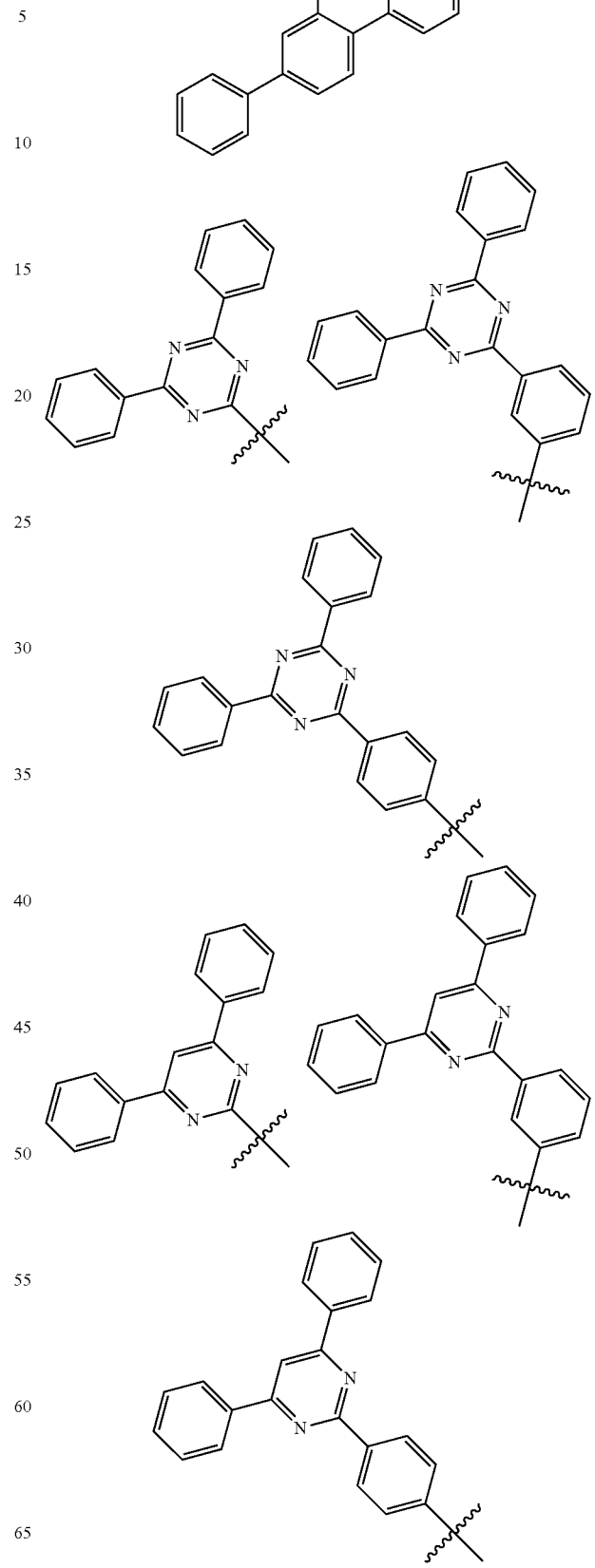

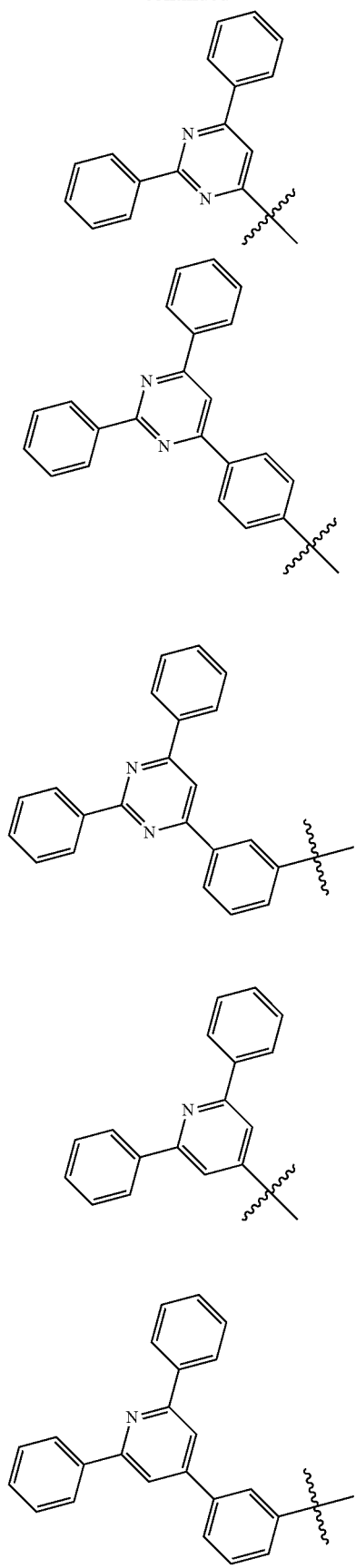
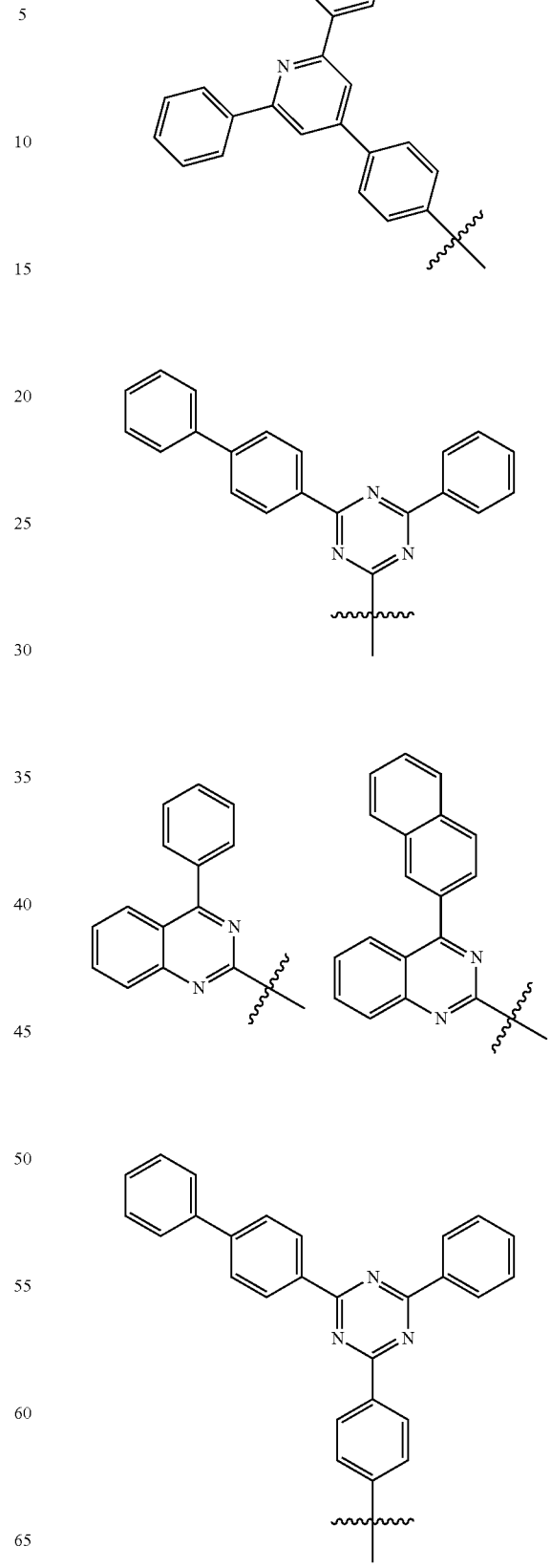

-continued
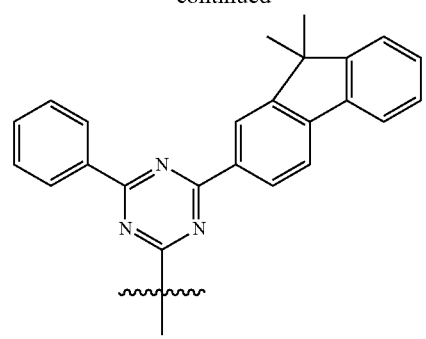
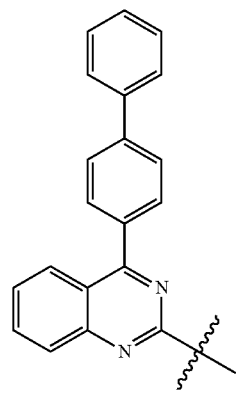
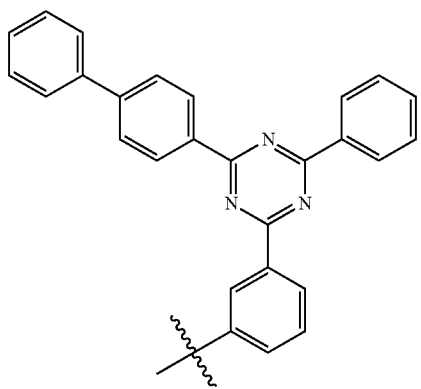
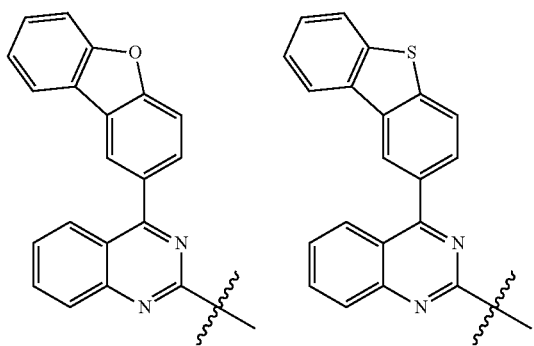
-continued
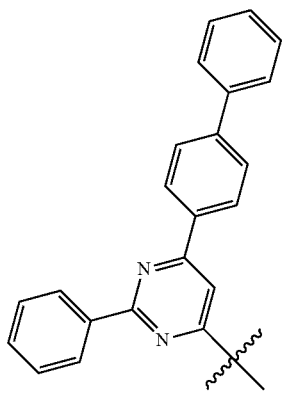
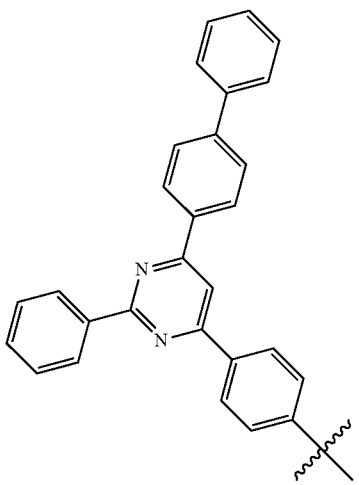
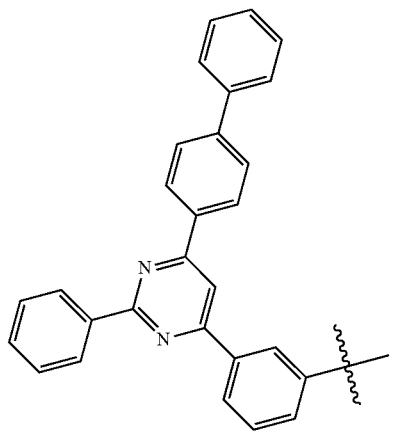
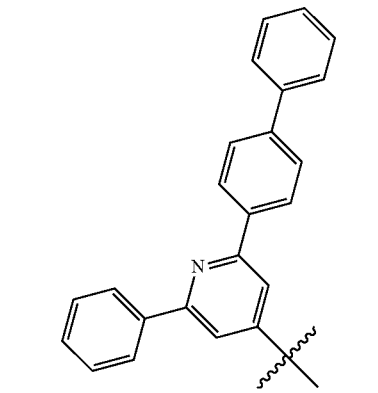

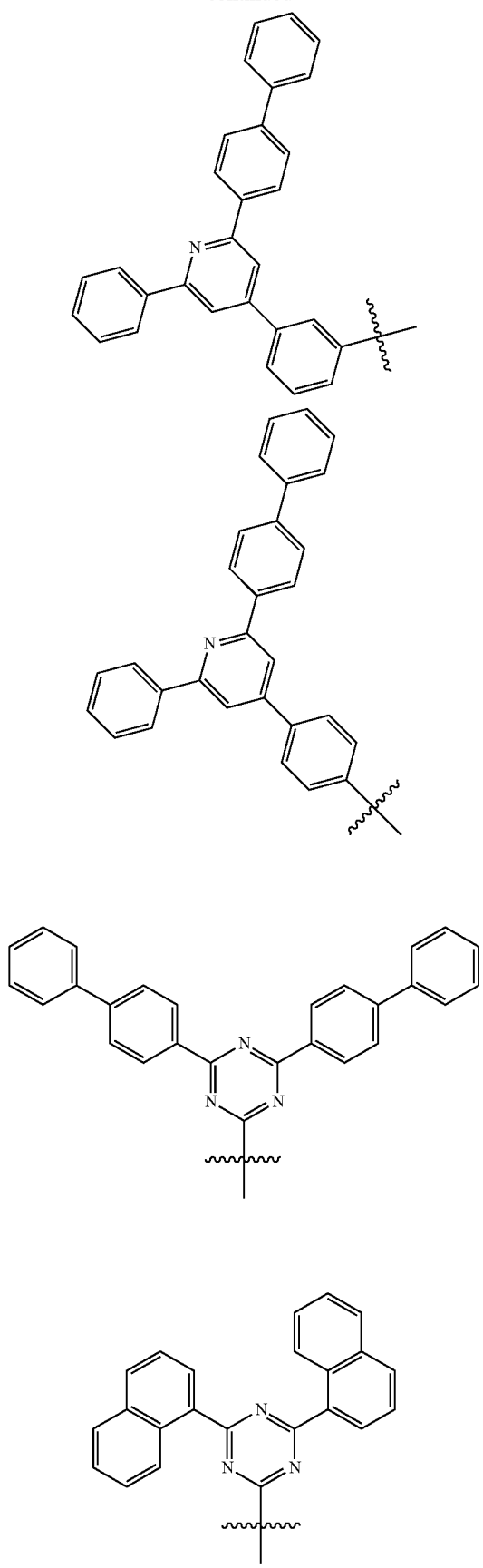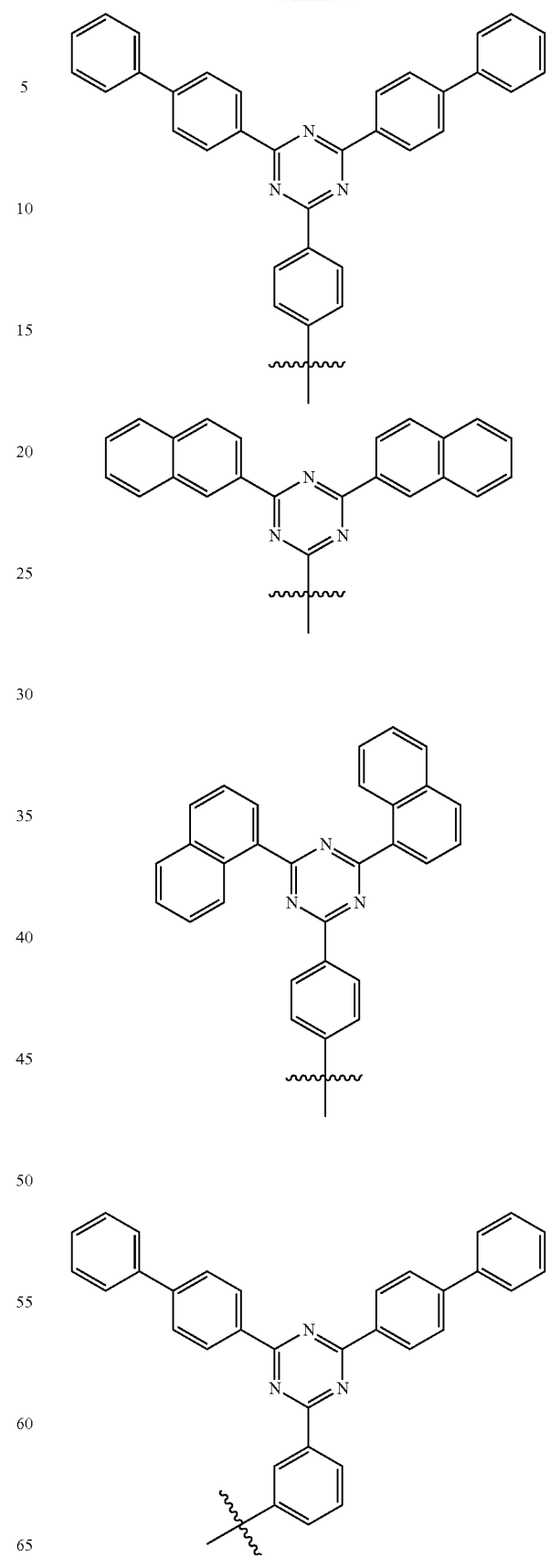

-continued

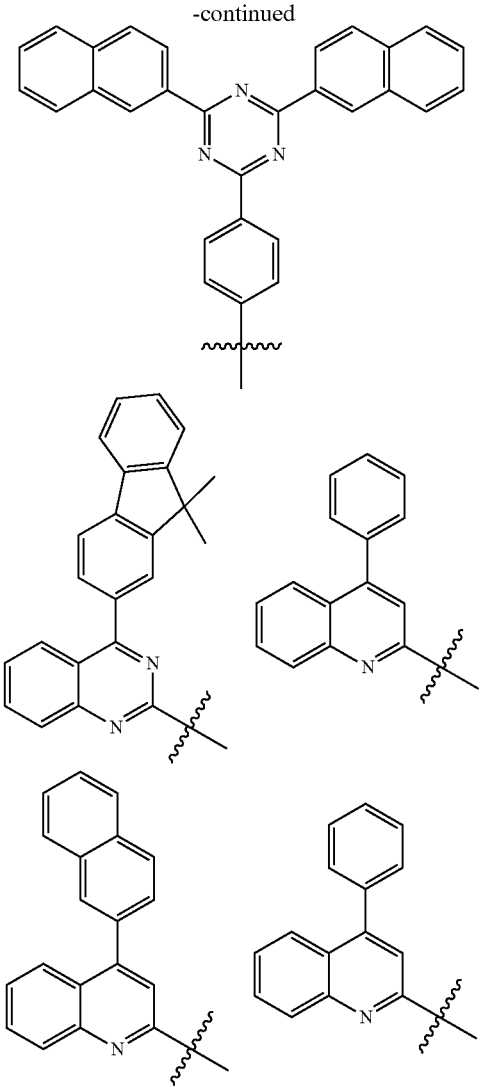

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present specification, $Ar_2$ is a phenyl group unsubstituted or substituted with an arylamine group, an aryl group or a heterocyclic group; a biphenyl group unsubstituted or substituted with an aryl group; a triphenylenyl group unsubstituted or substituted with an aryl group; a fluorenyl group unsubstituted or substituted with an alkyl group or an aryl group; a diphenylamine group unsubstituted or substituted with an aryl group; a phenylbiphenylamine group unsubstituted or substituted with an aryl group; a phenyl naphthylamine group unsubstituted or substituted with an aryl group; a phenyl phenanthreneamine group unsubstituted or substituted with an aryl group; a dibiphenylamine group unsubstituted or substituted with an aryl group; a phenyl fluoreneamine group unsubstituted or substituted with an aryl group; a biphenyl fluoreneamine group unsubstituted or substituted with an aryl group; a triphenylamine group unsubstituted or substituted with an aryl group; a diphenyl biphenylamine group unsubstituted or substituted with an aryl group; a phenyl dibiphenylamine group unsubstituted or substituted with an aryl group; a pyrimidyl group unsubstituted or substituted with an aryl group; a pyrimidinyl group unsubstituted or substituted with an aryl group; a triazinyl group unsubstituted or substituted with an aryl group; a quinazolinyl group unsubstituted or substituted with an aryl group; a carbazolyl group unsubstituted or substituted with an aryl group; a dibenzothiophene group unsubstituted or substituted with an aryl group; a dibenzofuranyl group unsubstituted or substituted with an aryl group; a benzocarbazolyl group unsubstituted or substituted with an aryl group; a naphthobenzothiophene group; a naphthobenzofuranyl group; a substituted or unsubstituted benzimidazoquinazolinyl group; a phenothiazinyl group unsubstituted or substituted with an aryl group; or a phenoxazinyl group unsubstituted or substituted with an aryl group, and the aryl group may be one or more types selected from the group consisting of a phenyl group, a biphenyl group, a naphthyl group and a fluorenyl group.

According to one embodiment of the present specification, when $L_2$ is a phenylene group, $Ar_2$ may be hydrogen, deuterium, a phenyl group, a nitrile group, a trimethylsilyl group, a naphthyl group, a triphenylamine group, a pyrrolyl group, a pyridyl group, a pyrimidinyl group, a triazinyl group, a quinolinyl group, a quinazolinyl group, a benzimidazole group, a benzoxazole group, a benzothiazole group, a carbazolyl group, a dibenzofuranyl group, a phenanthrolyl group; a dibenzothiophene group, a 9,9-dimethylfluorenyl group, a diphenylphosphine oxide group, an imidazophenanthridinyl group, a benzimidazoquinazolinyl group or a benzimidazophenanthridyl group, and these may be further substituted.

According to one embodiment of the present specification, when $L_2$ is a quinolinyl group, $Ar_2$ may be hydrogen, a phenyl group, a biphenyl group, a naphthyl group or a triphenylene group.

According to one embodiment of the present specification, when $L_2$ is a quinazolinyl group, $Ar_2$ may be hydrogen, a phenyl group, a biphenyl group, a naphthyl group or a triphenylene group.

According to one embodiment of the present specification, when $L_2$ is a phenylene group, $Ar_2$ may be hydrogen, deuterium, a phenyl group, a nitrile group, a trimethylsilyl group, a naphthyl group, a triphenylamine group, a pyrrolyl group, a pyridyl group, a pyrimidinyl group, a triazinyl group, a quinolinyl group, a quinazolinyl group, a benzimidazole group, a benzoxazole group, a benzothiazole group, a carbazolyl group, a 9,9-dimethylfluorenyl group, a dibenzofuranyl group, a dibenzothiophene group, a phenanthrolyl group, a phosphine oxide group, an imidazophenanthridinyl group, a benzimidazoquinazolinyl group or a benzimidazophenanthridyl group, and these may be further substituted.

According to one embodiment of the present specification, $R_1$ to $R_8$ and $R_{101}$ to $R_{103}$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or adjacent groups may bond to each other to form a substituted or unsubstituted ring.

According to one embodiment, $R_1$ to $R_8$ and $R_{101}$ to $R_{103}$ are the same as or different from each other, and each independently hydrogen; deuterium; a halogen group; a linear or branched substituted or unsubstituted alkyl group having 1 to 60 carbon atoms; a linear or branched substituted or unsubstituted alkenyl group having 2 to 60 carbon atoms; a linear or branched substituted or unsubstituted alkynyl group having 2 to 60 carbon atoms; a monocyclic or multicyclic substituted or unsubstituted cycloalkyl group having 3 to 60 carbon atoms; a monocyclic or multicyclic substituted or unsubstituted heterocycloalkyl group having 2 to 60 carbon atoms; a monocyclic or multicyclic substituted or unsubstituted aryl group having 6 to 60 carbon atoms; and a monocyclic or multicyclic substituted or unsubstituted heterocyclic group having 2 to 60 carbon atoms.

According to one embodiment, $R_1$ to $R_8$ and $R_{101}$ to $R_{103}$ are the same as or different from each other, and each independently hydrogen; deuterium; a monocyclic or multicyclic substituted or unsubstituted aryl group having 6 to 40 carbon atoms; and a monocyclic or multicyclic substituted or unsubstituted heterocyclic group having 2 to 40 carbon atoms.

According to one embodiment, $R_1$ to $R_8$ and $R_{101}$ to $R_{103}$ are the same as or different from each other, and each independently hydrogen; deuterium; an aryl group such as a phenyl group, a biphenyl group, a naphthyl group, an anthryl group, a chrysenyl group, a phenanthrenyl group, a triphenylenyl group, a pyrenyl group, a tetracenyl group, a pentacenyl group or a fluorenyl group; or a heterocyclic group such as a pyridyl group, a pyrrole group, a pyrimidyl group, a pyridazinyl group, a furanyl group, a thiophene group, an imidazole group, a pyrazole group, an oxazole group, an isoxazole group, a triazole group, an isothiazole group, a triazole group, a pyrazinyl group, a triazine group, a quinolinyl group, an isoquinolinyl group, a quinazoline group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a carbazole group, a benzothiophene group, a benzofuranyl group, a benzimidazole group, a benzothiazole group, a benzoxazole group, a benzocarbazole group, a dibenzothiophene group, a dibenzofuranyl group, a dibenzocarbazole group, an indolocarbazole group, an indenocarbazole group, a phenanthroline group, a phenazinyl group, a phenoxazinyl group, a phenothiazinyl group, an imidazopyridinyl group, an imidazophenanthridine group, a benzimidazoquinazolinyl group or a benzimidazophenanthridinyl group, and these may be further substituted.

Specifically, $R_1$ to $R_8$ and $R_{101}$ to $R_{103}$ may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment, $R_1$ to $R_8$ and $R_{101}$ to $R_{103}$ are the same as or different from each other, and may be each independently hydrogen; deuterium; a substituted or unsubstituted phenyl group; a substituted or unsubstituted biphenyl group; a substituted or unsubstituted naphthyl group; a substituted or unsubstituted anthracenyl group; a substituted or unsubstituted phenanthrenyl group; a substituted or unsubstituted fluorenyl group; a substituted or unsubstituted pyridinyl group; a substituted or unsubstituted phenanthridinyl group; a substituted or unsubstituted dibenzothiophene group; or a substituted or unsubstituted carbazolyl group.

According to one embodiment, $R_1$ to $R_8$ and $R_{101}$ to $R_{103}$ are the same as or different from each other, and may be each independently hydrogen; a phenyl group; a biphenyl group; a naphthyl group; an anthracenyl group; a phenanthrenyl group; a fluorenyl group; a pyridinyl group; a phenanthridinyl group; a dibenzothiophene group; or a carbazolyl group.

According to one embodiment, $R_1$ to $R_8$ and $R_{101}$ to $R_{103}$ are hydrogen.

In one embodiment, adjacent groups among $R_1$ to $R_8$ and $R_{101}$ to $R_{103}$ bond to each other to form a substituted or unsubstituted aromatic ring.

In one embodiment, adjacent groups among $R_1$ to $R_8$ and $R_{101}$ to $R_{103}$ bond to each other to form a substituted or unsubstituted benzene ring; or a substituted or unsubstituted naphthalene ring.

According to one embodiment of the present specification, the compound of Chemical Formula 1 may be any one selected from among the following compounds.

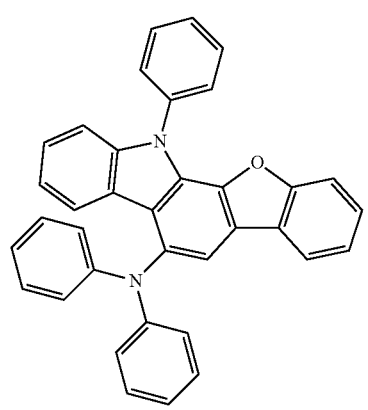

1

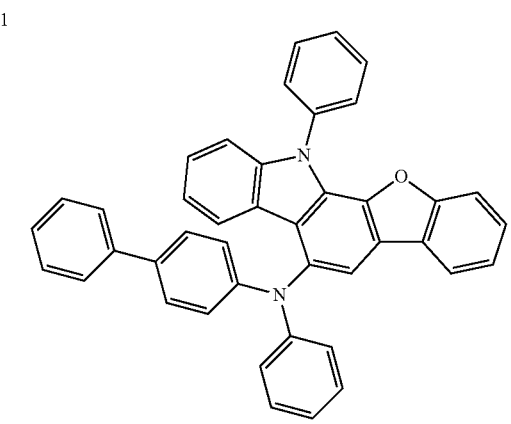

2

-continued
3
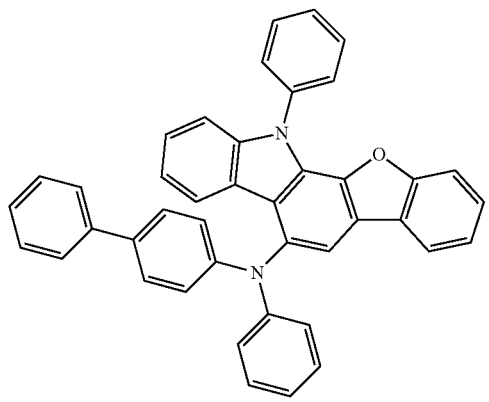
4
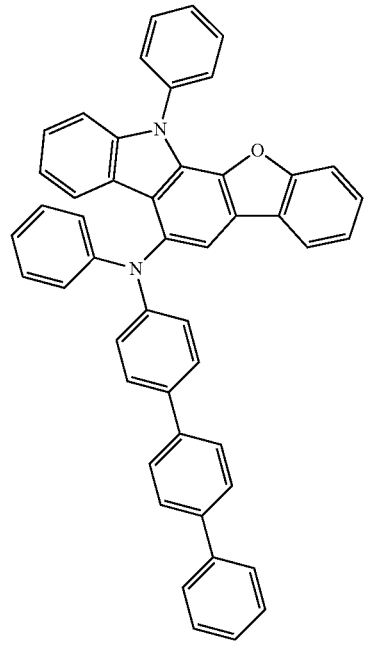
5
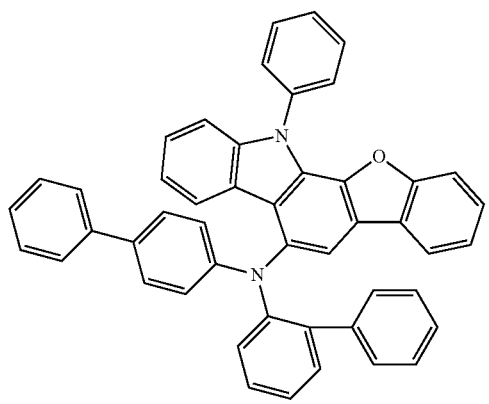
6
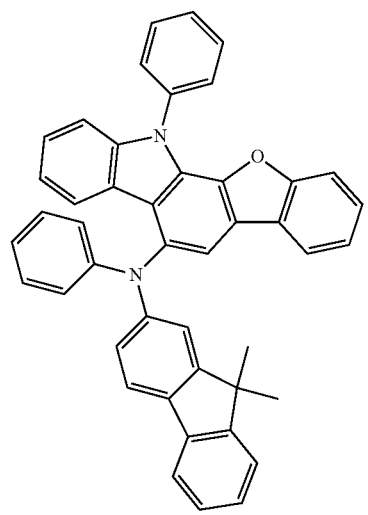
7
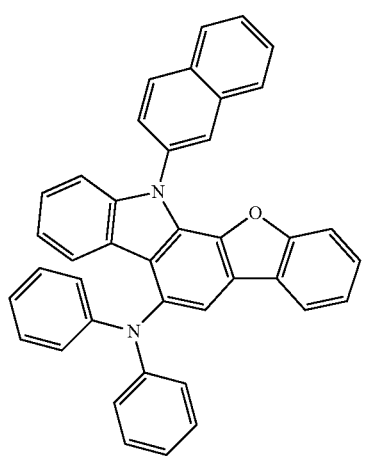
8
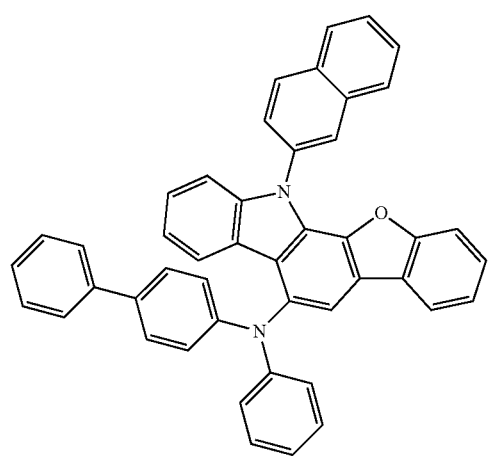

-continued
9
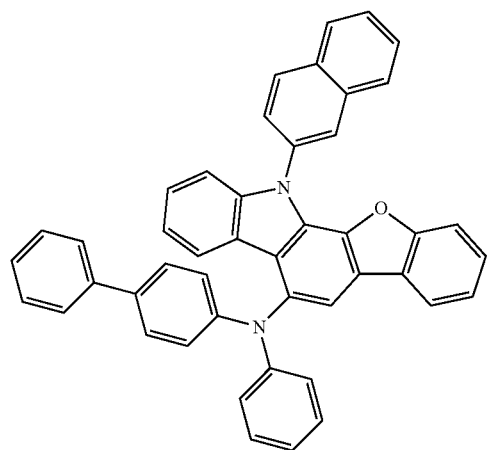
10
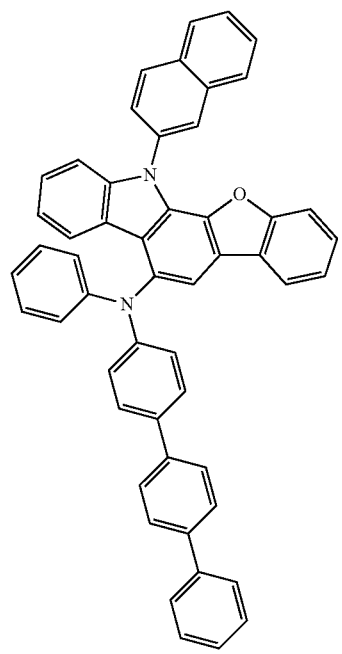
11
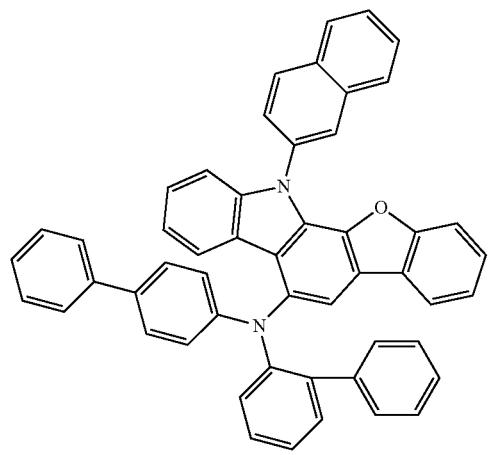
12
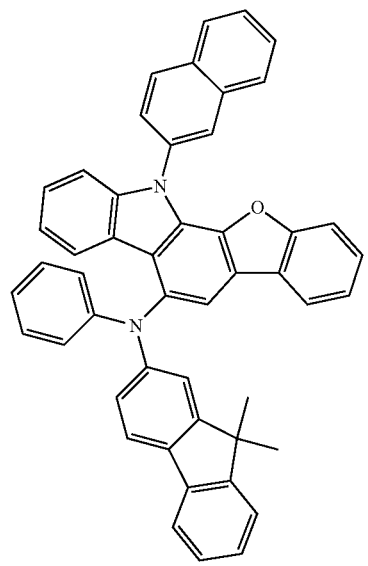

13
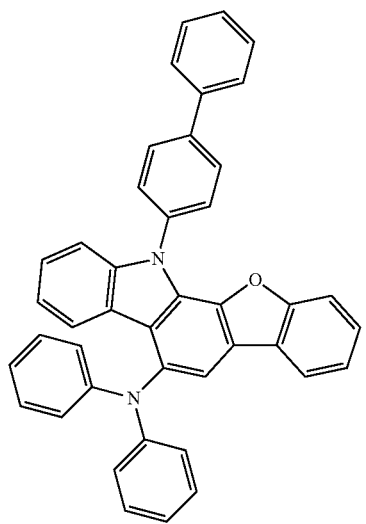
14
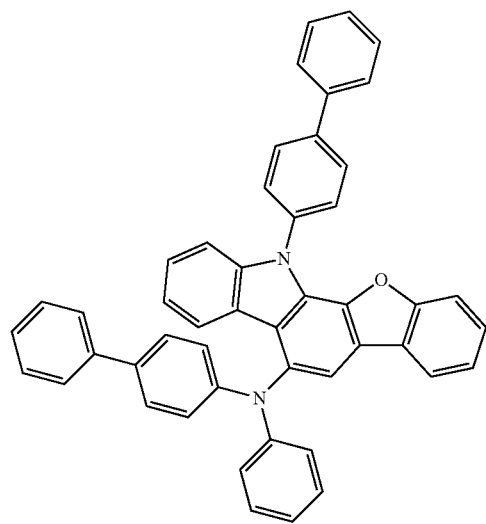
15
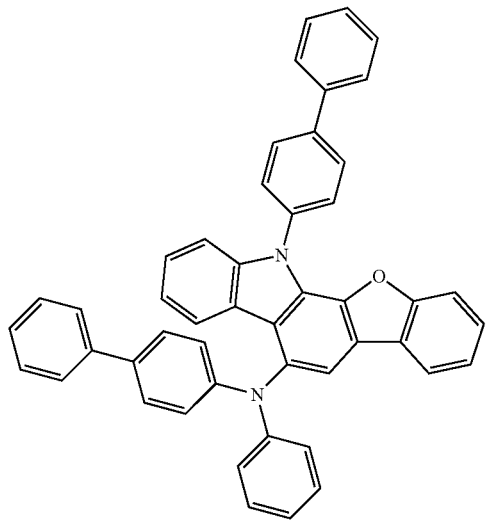
16
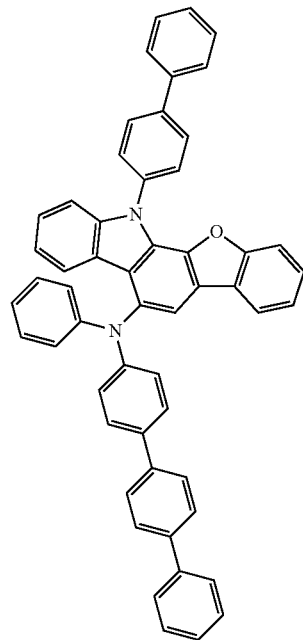

17
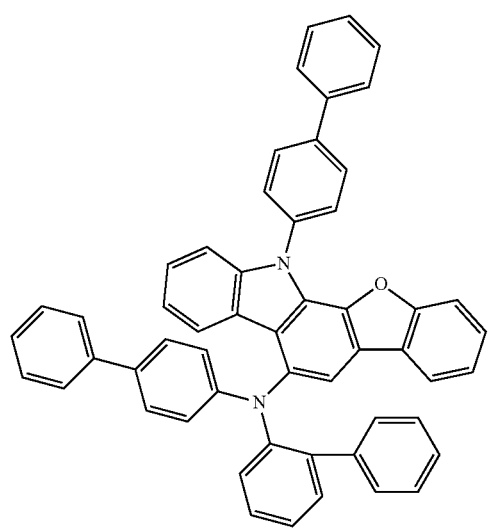
18
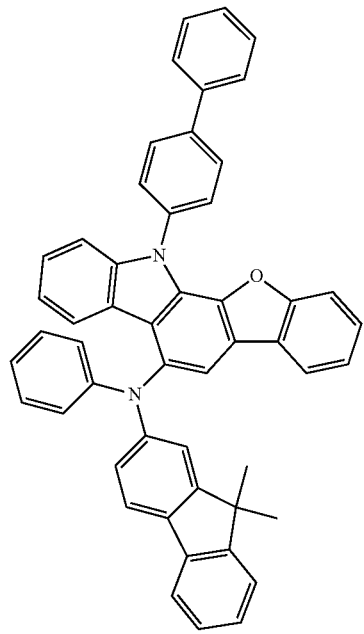
19
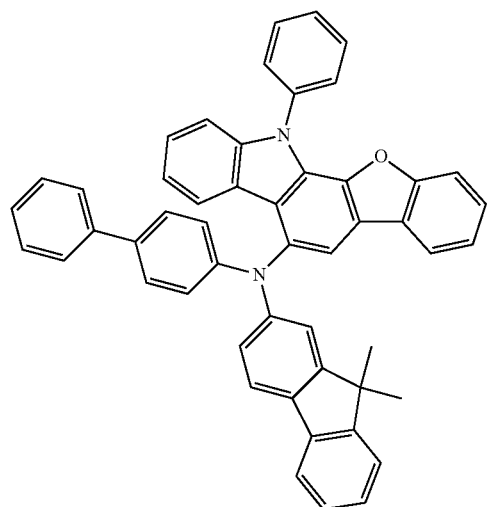
20
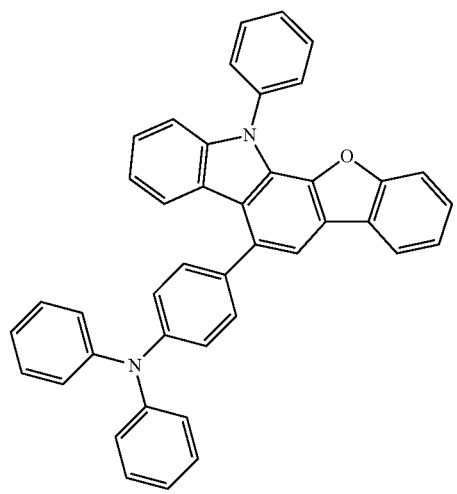

-continued
21
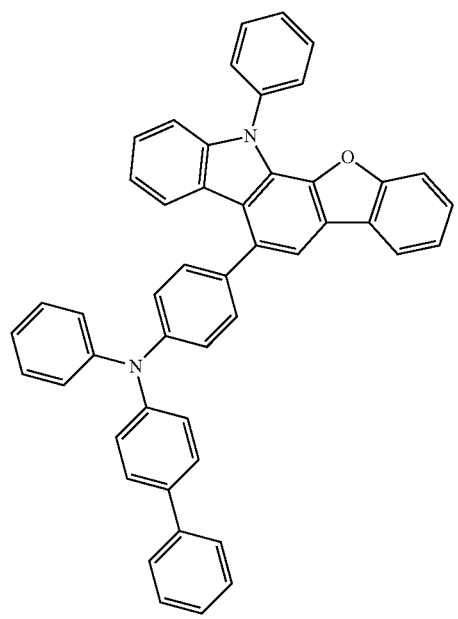
22
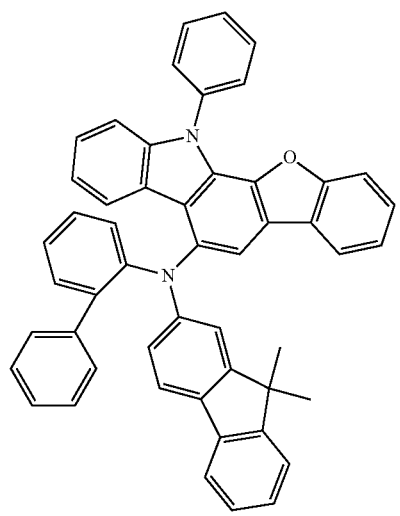
23
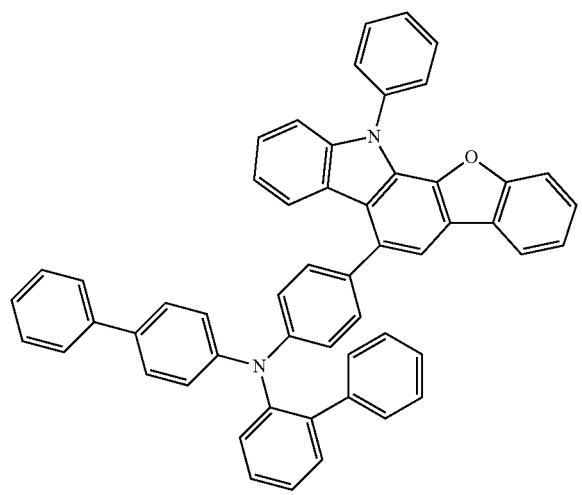
24
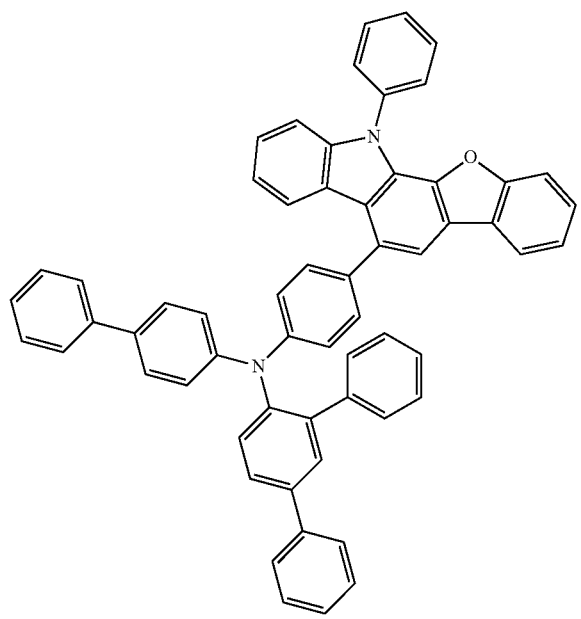

-continued
25
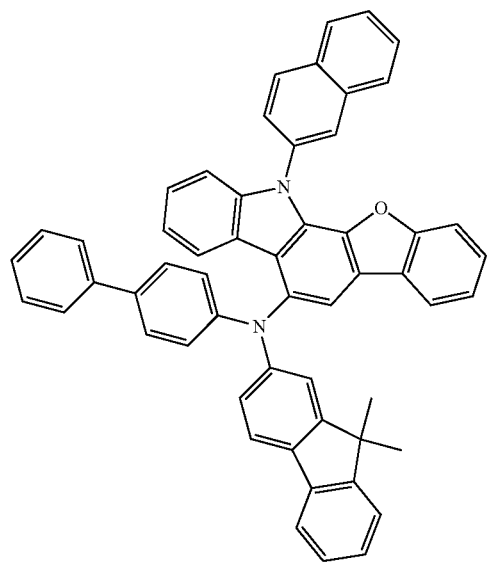
26
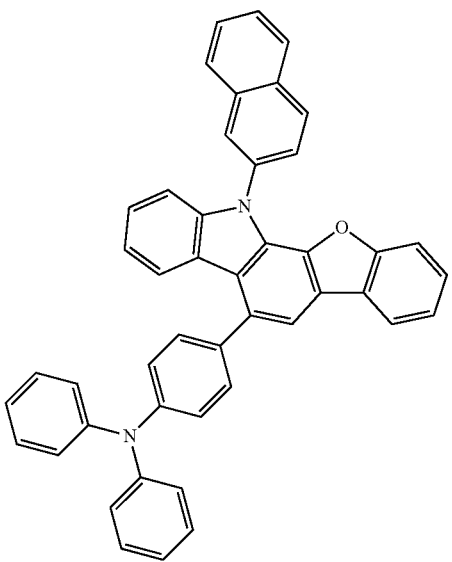
27
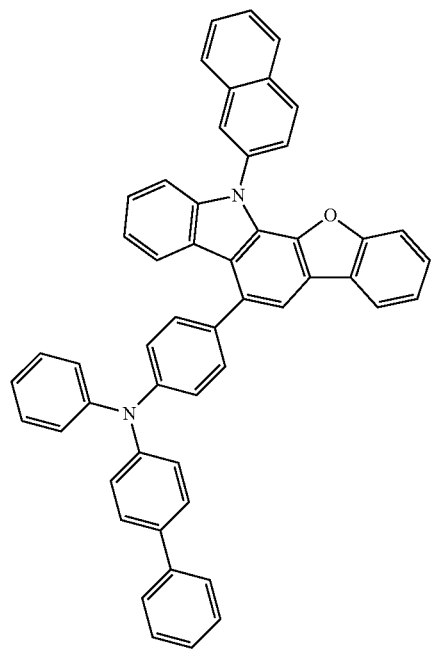
28
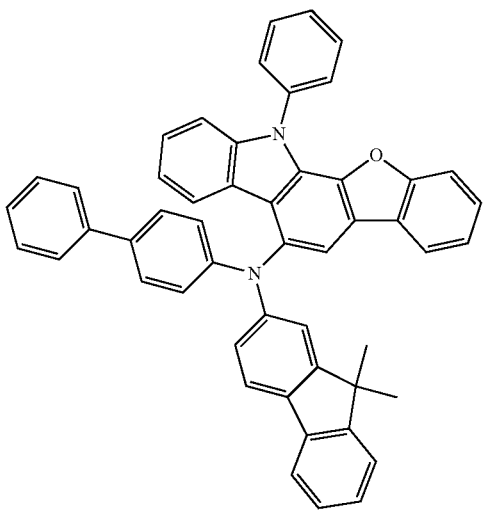

-continued
29
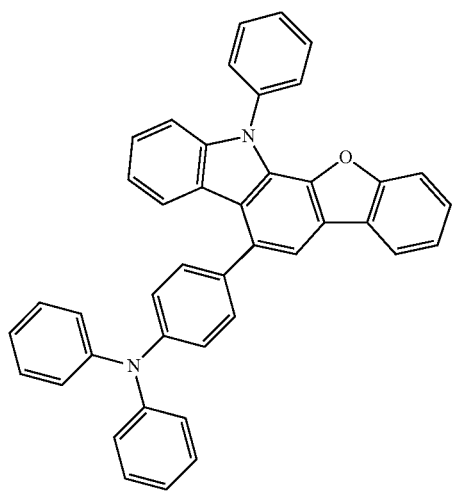
30
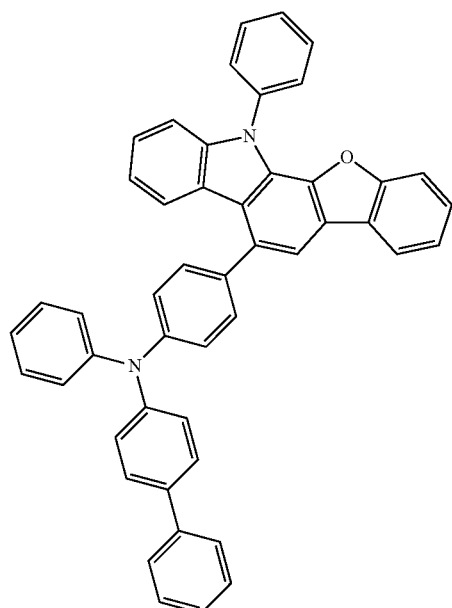
31
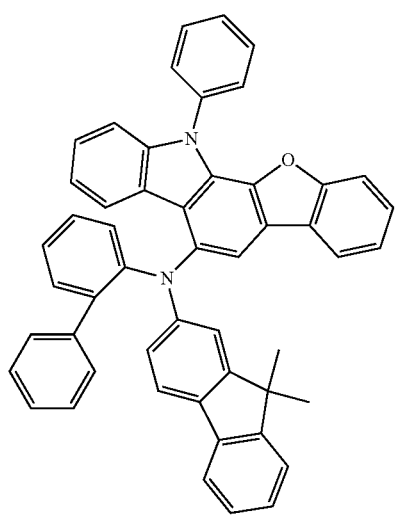
32
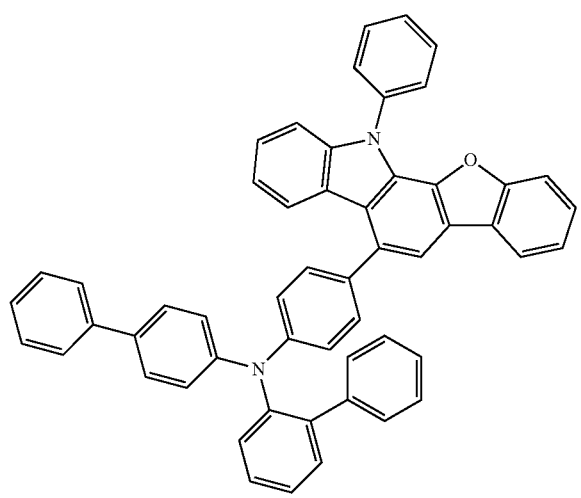

-continued
33
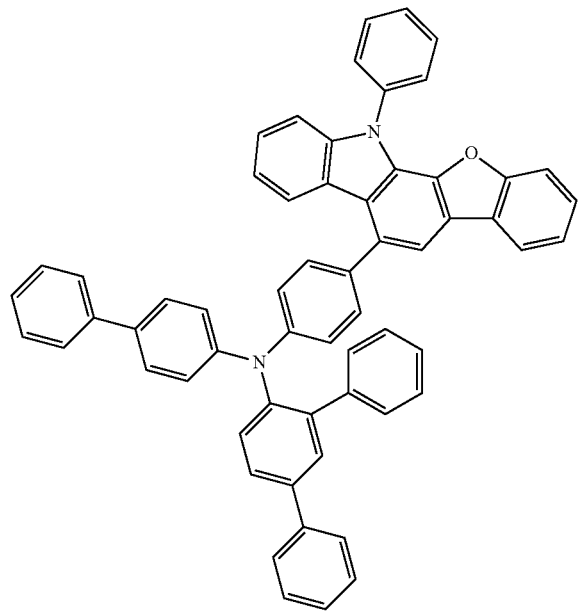
34
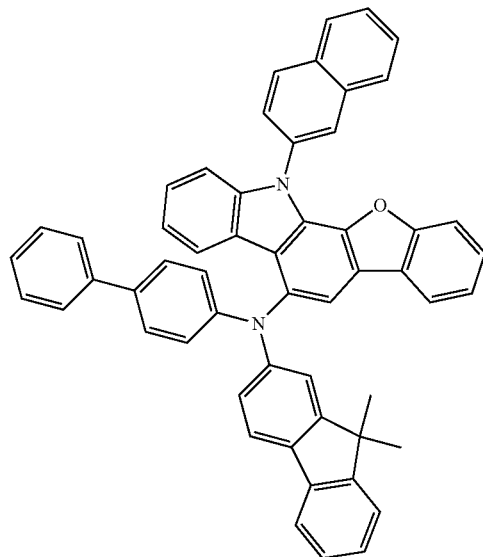
35
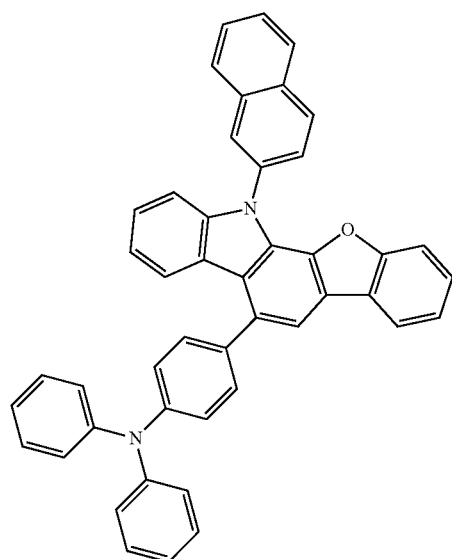
36
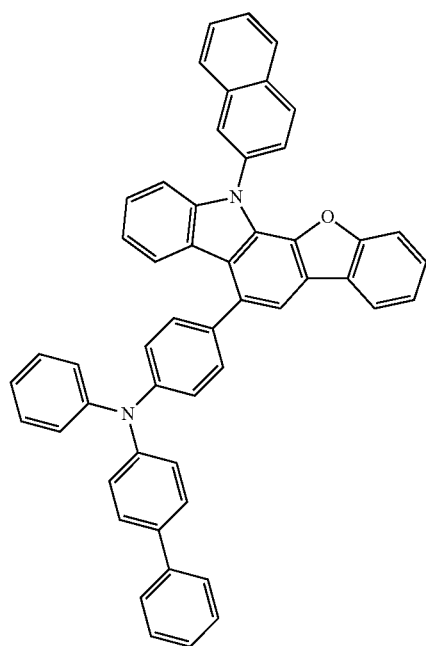

37
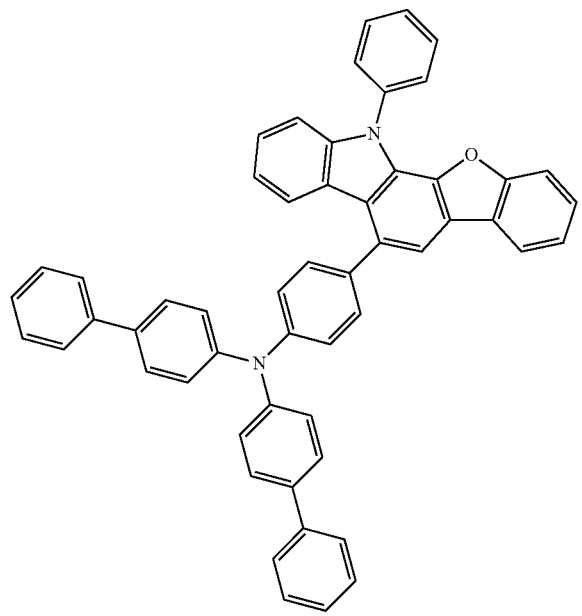
38
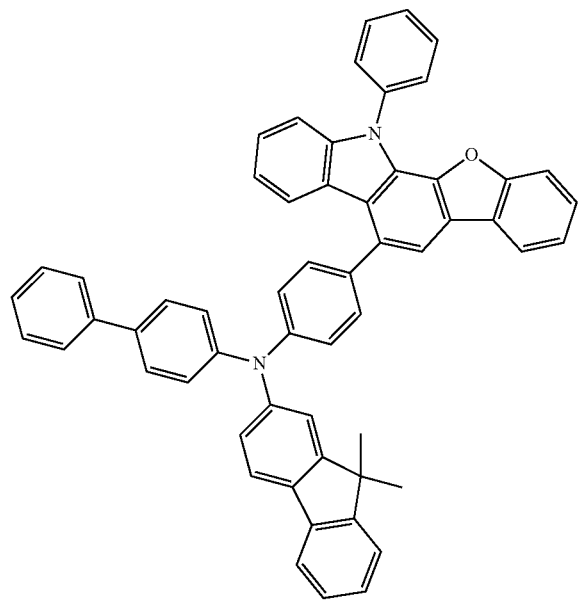
39
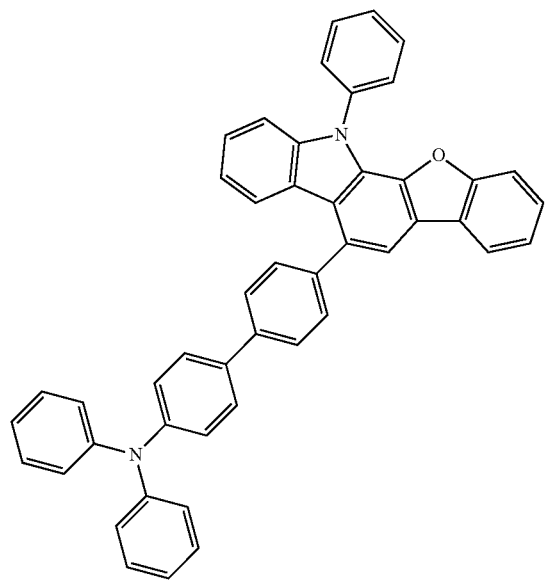
40
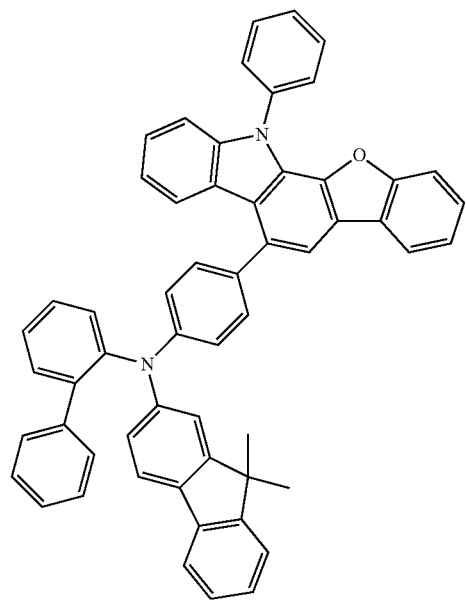

-continued
41
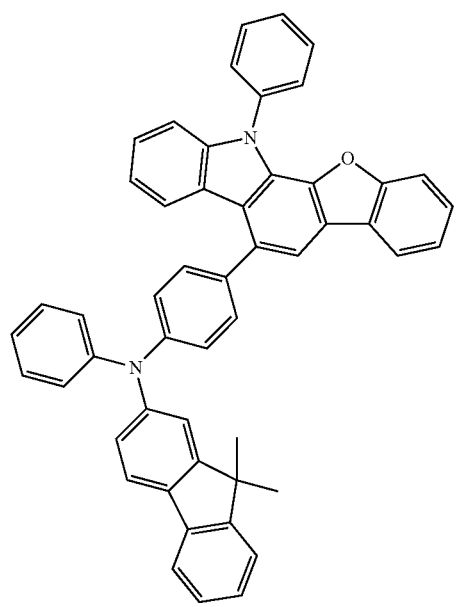
42
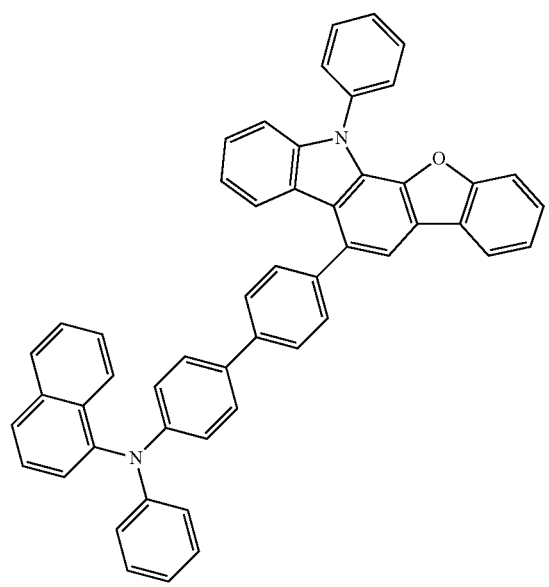
43
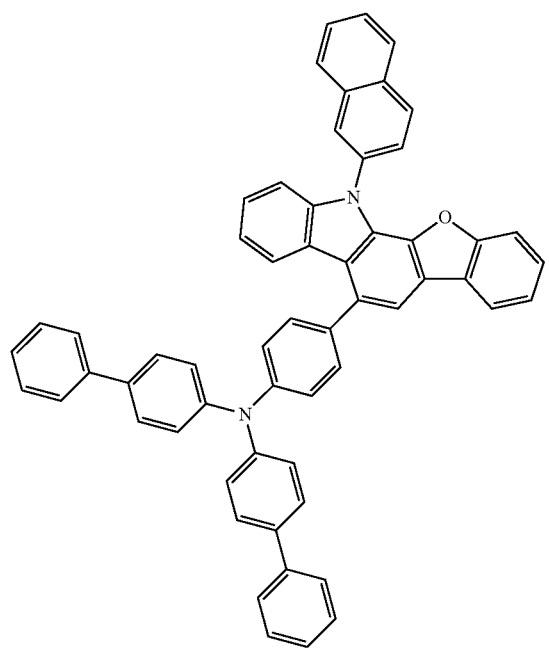
44
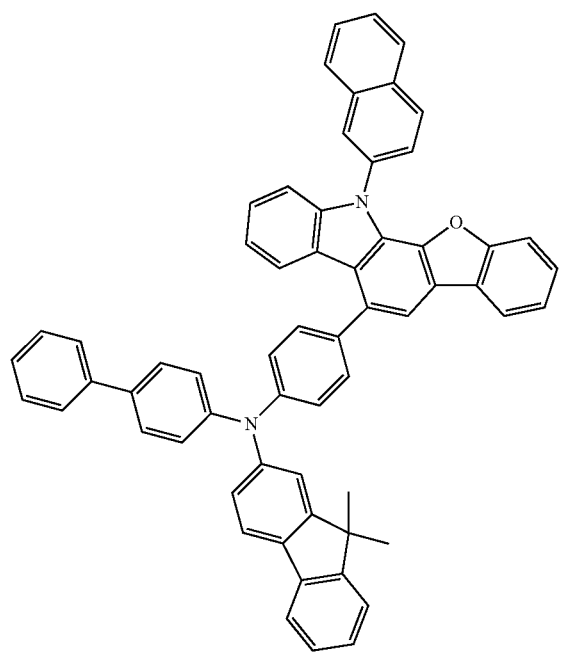

45
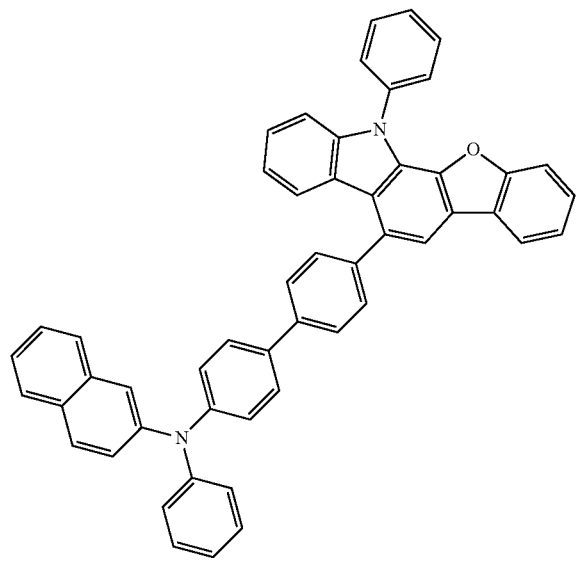
46
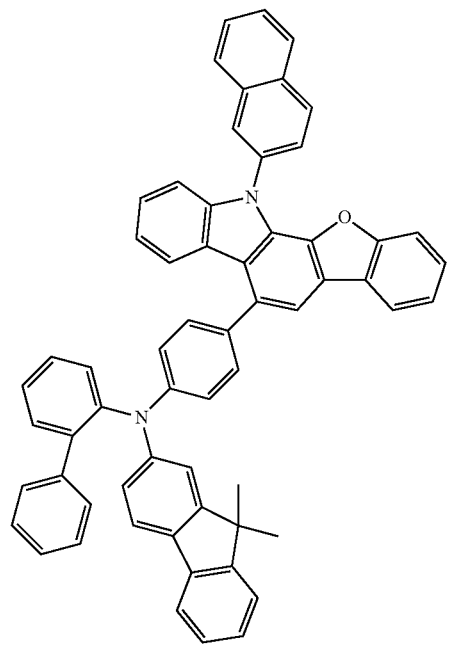
47
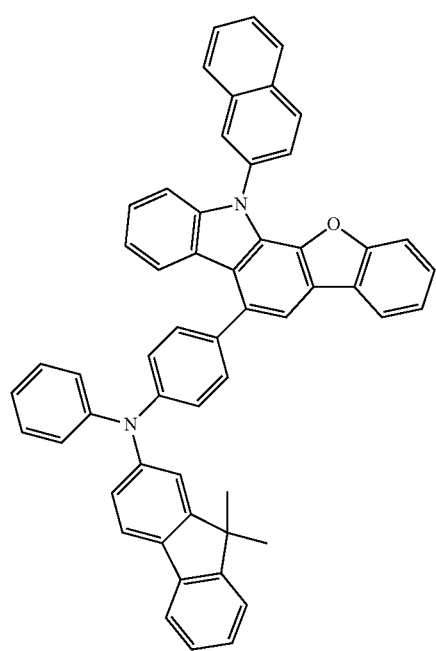
48
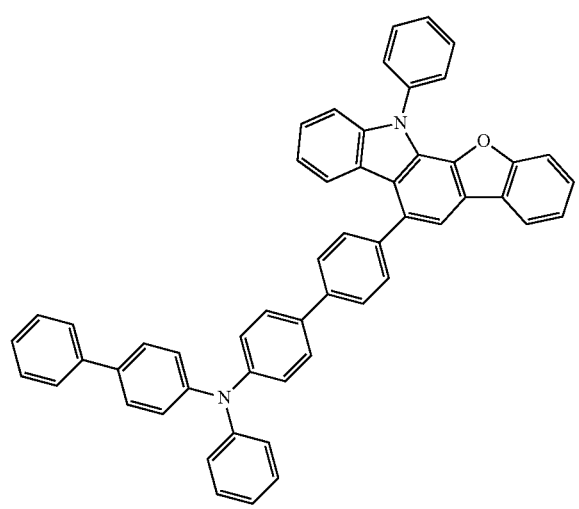

49
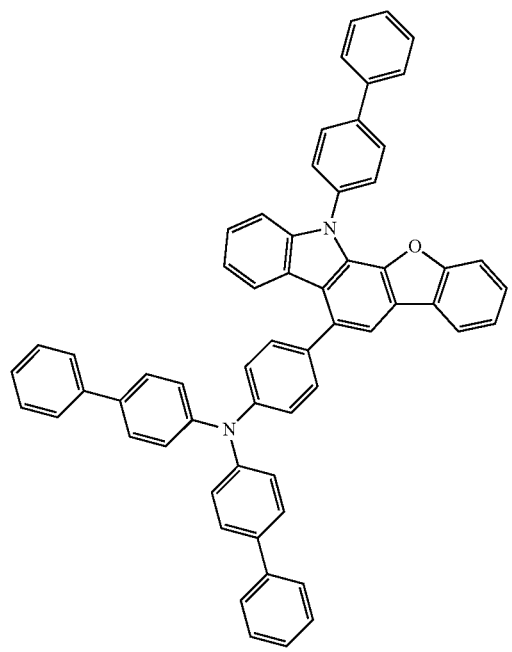
50
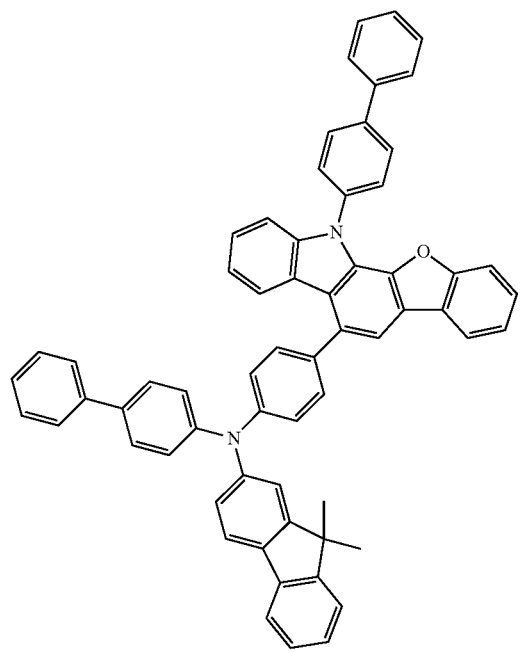
51
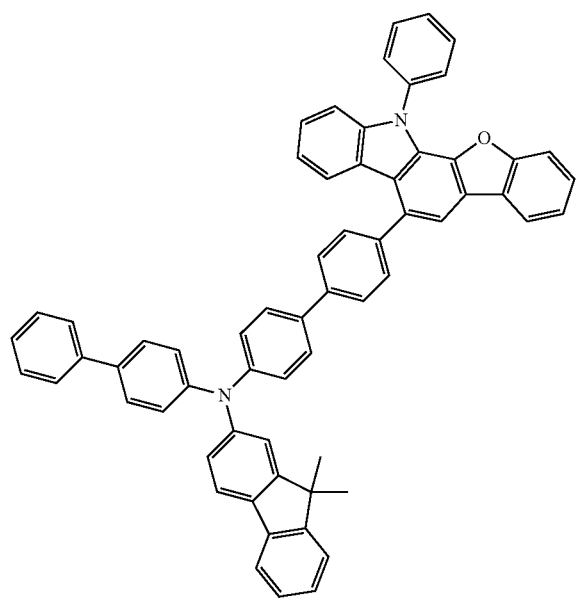
52
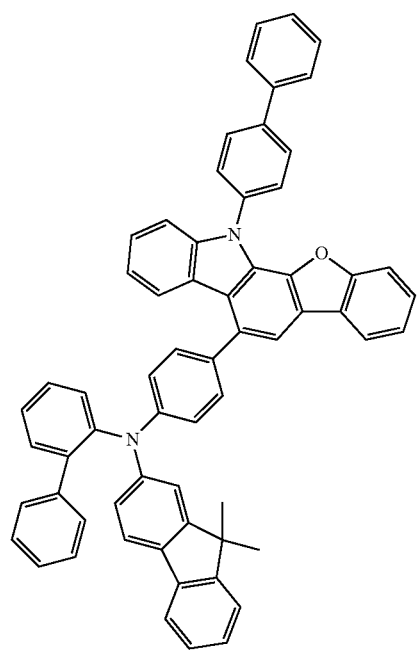

-continued
53
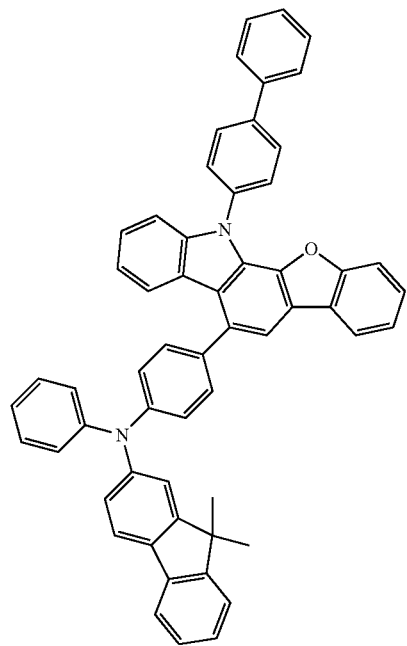
54
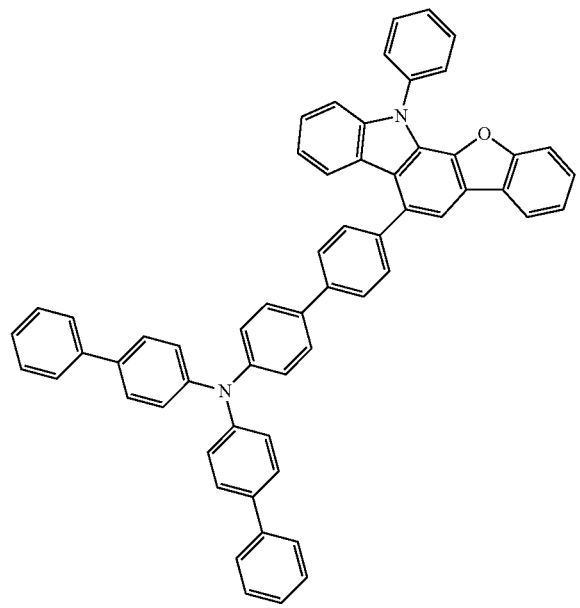
55
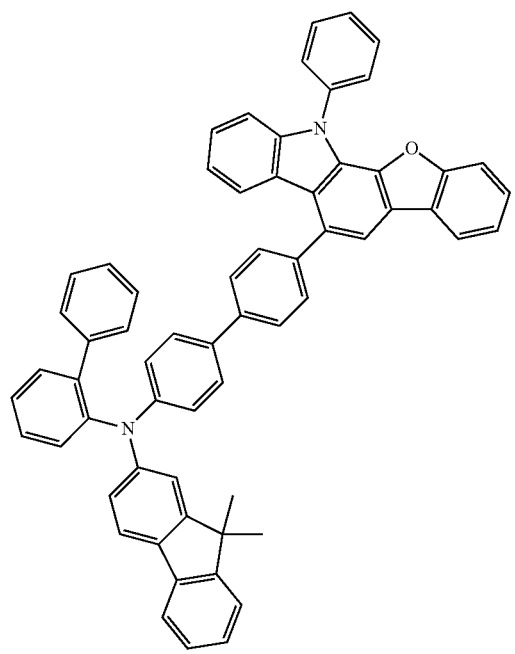
56
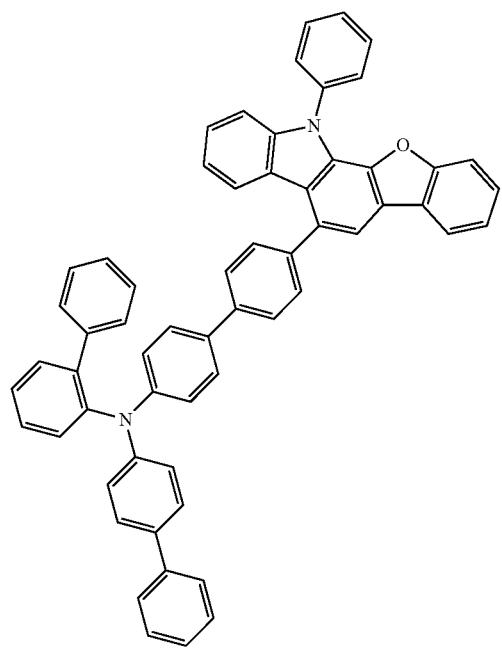

57
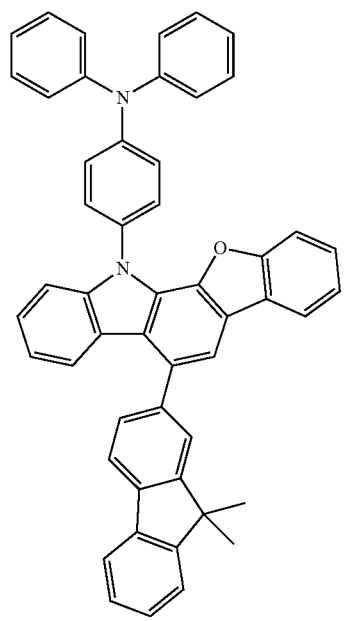
58
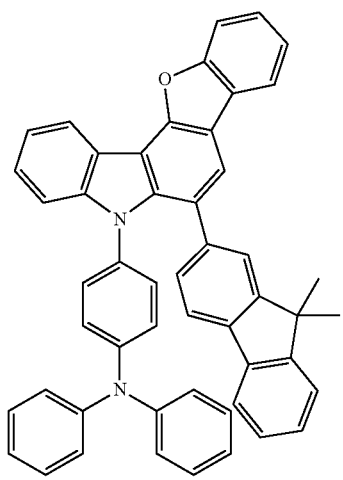
59
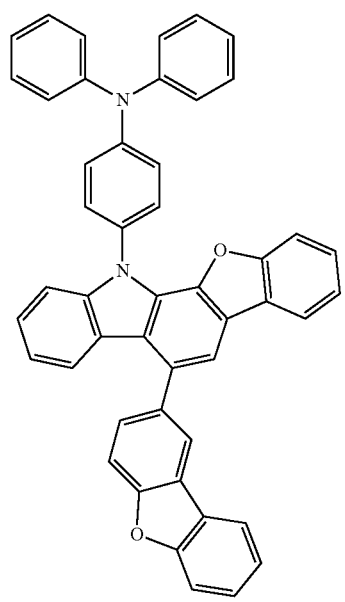
60
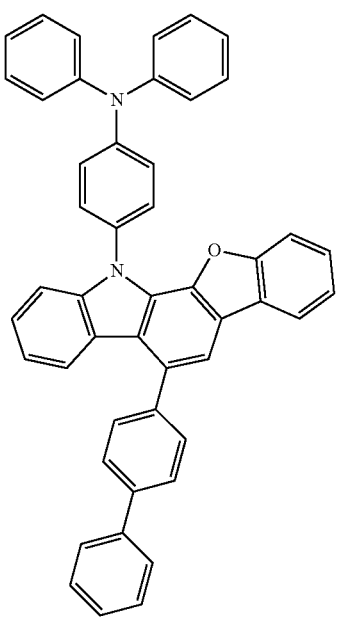

-continued
61
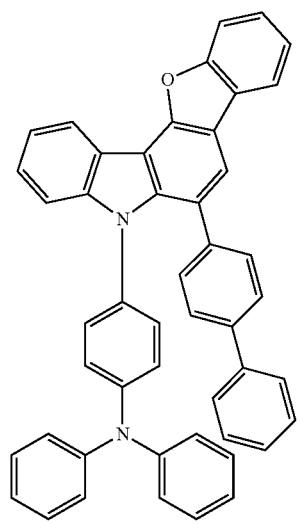
62
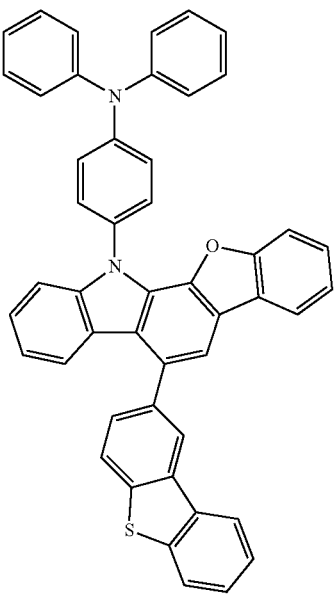
63
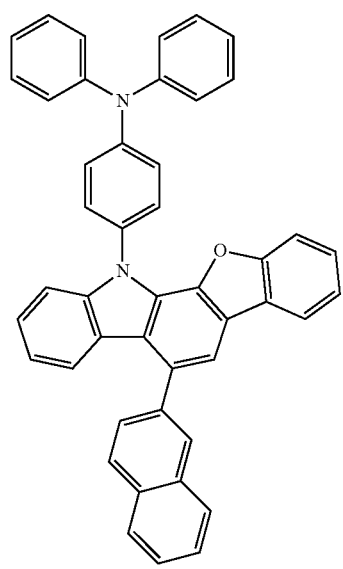
64
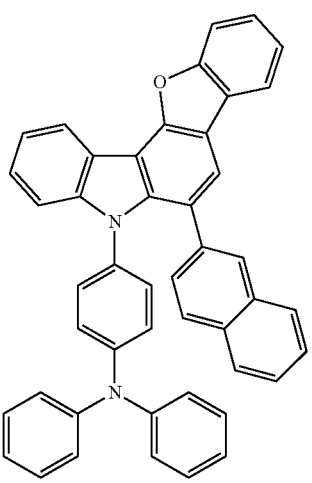

65
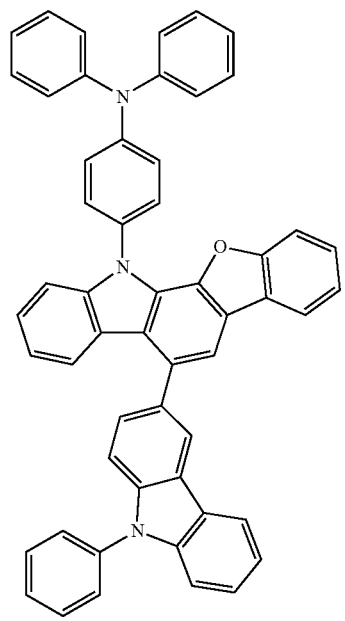
66
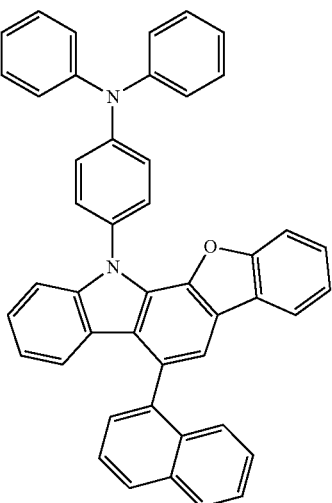
-continued
67
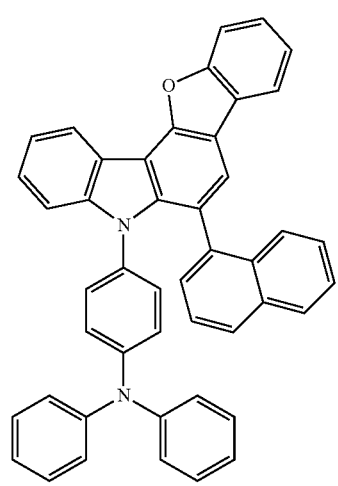
68
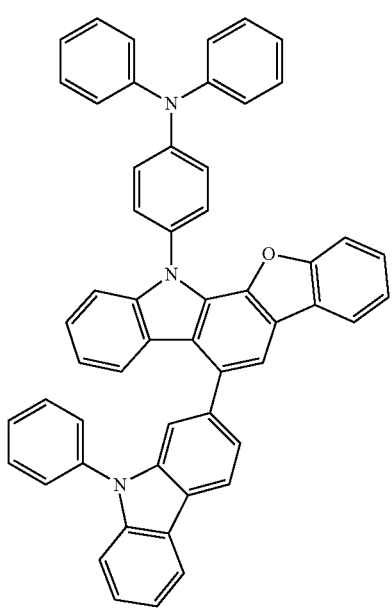

-continued
69
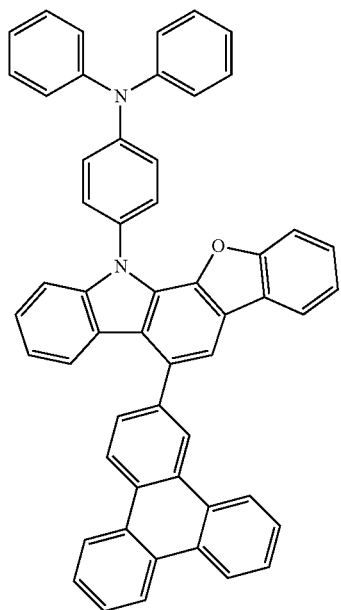
70
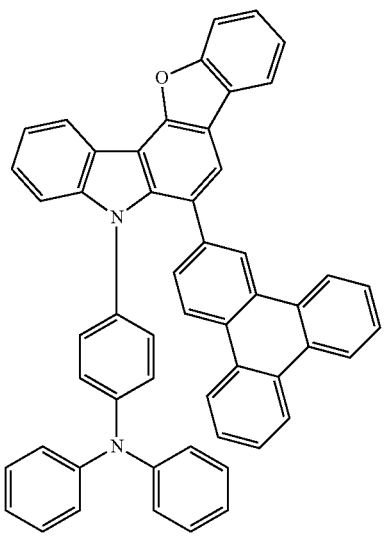
71
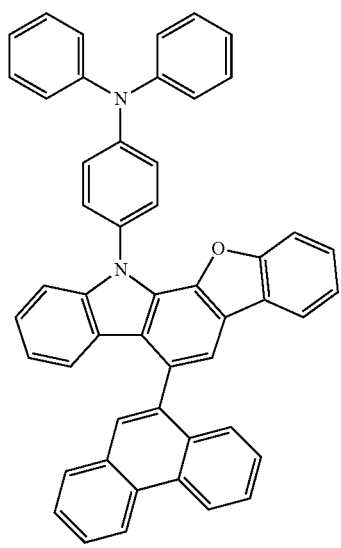
72
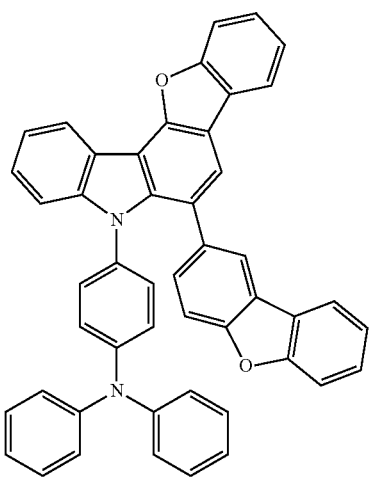
73
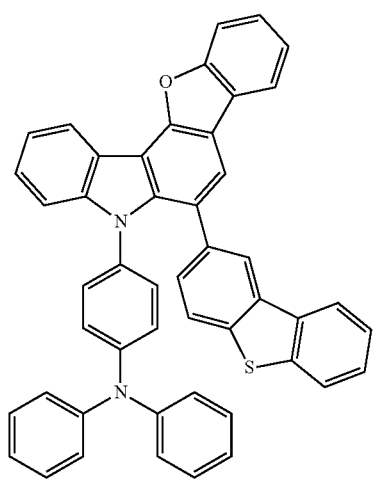
74
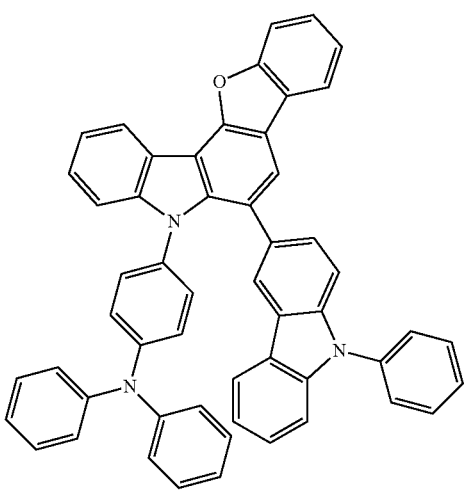

75
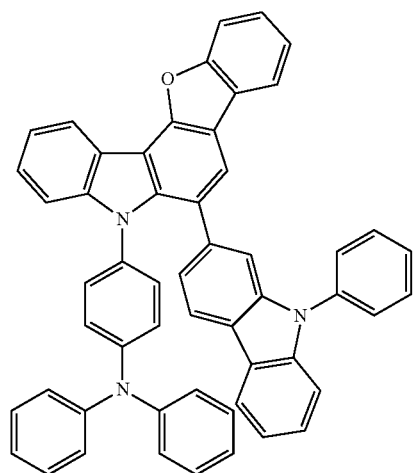
76
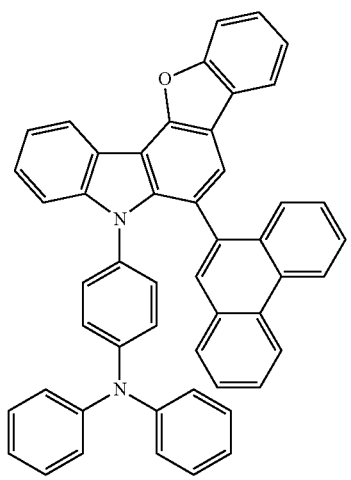
77
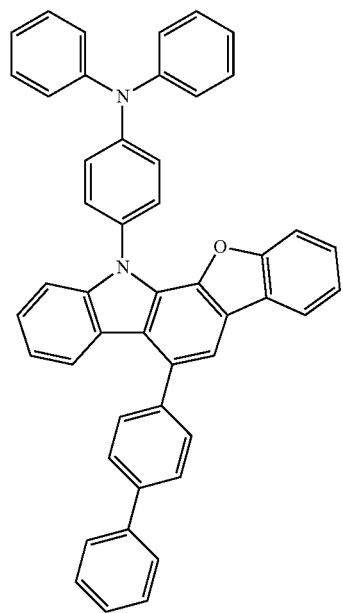
78
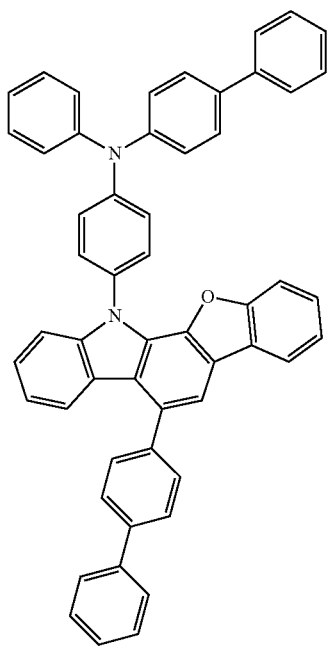

-continued
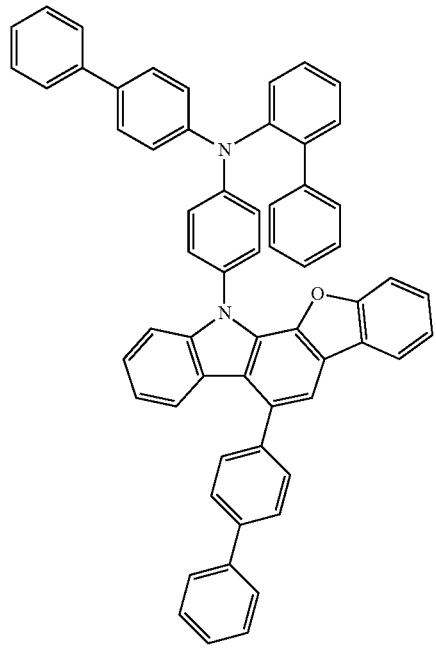
79
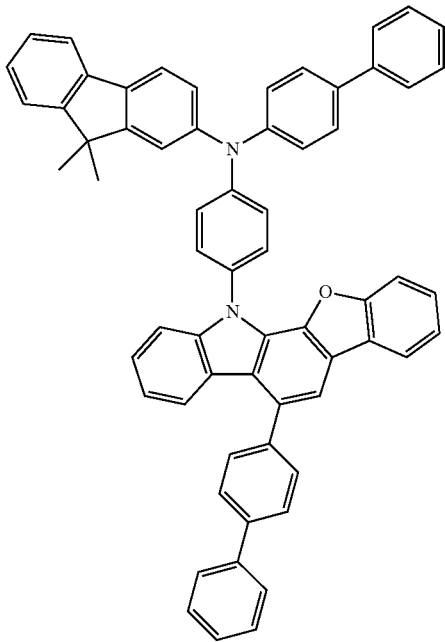
80
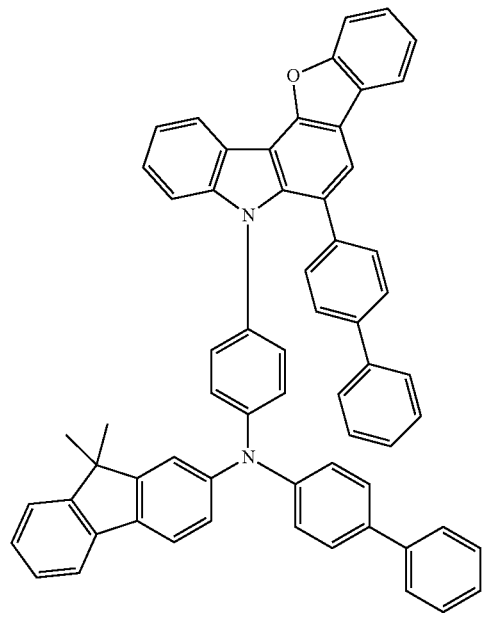
81
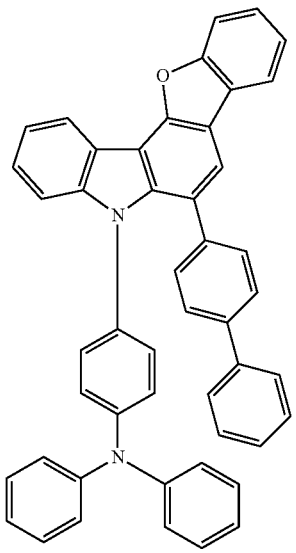
82

83
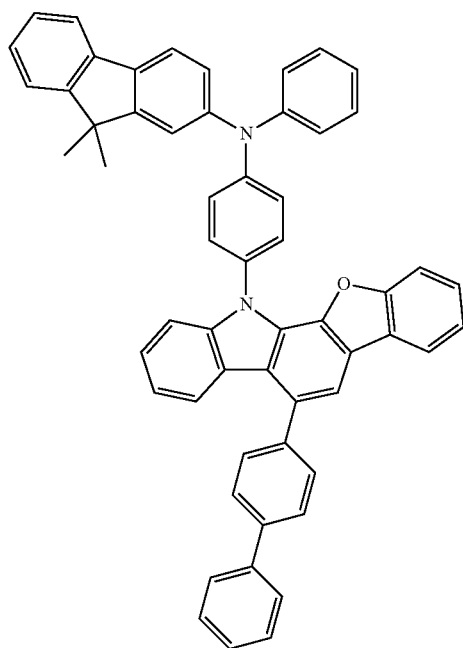
84
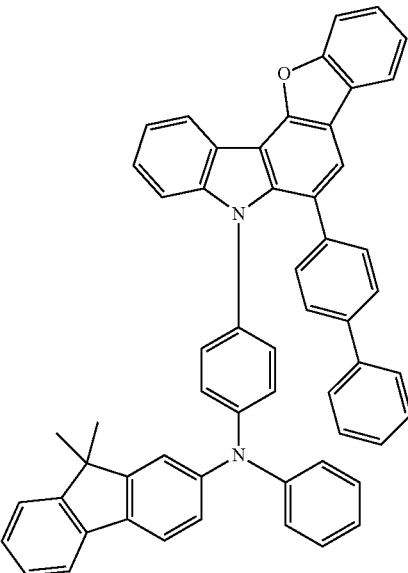
85
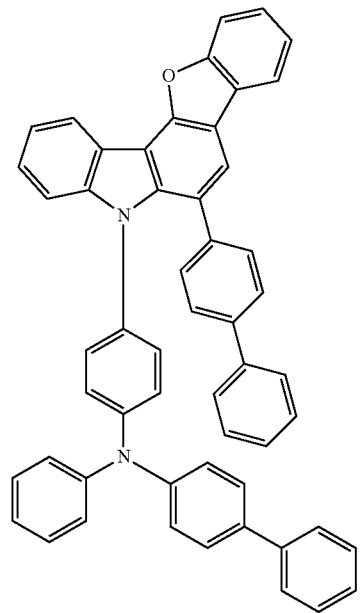
86
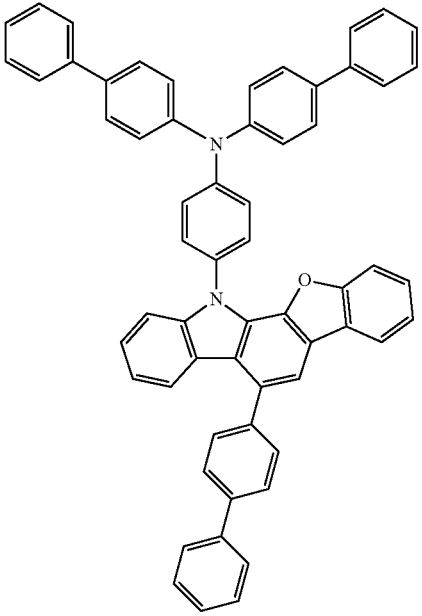

-continued
87
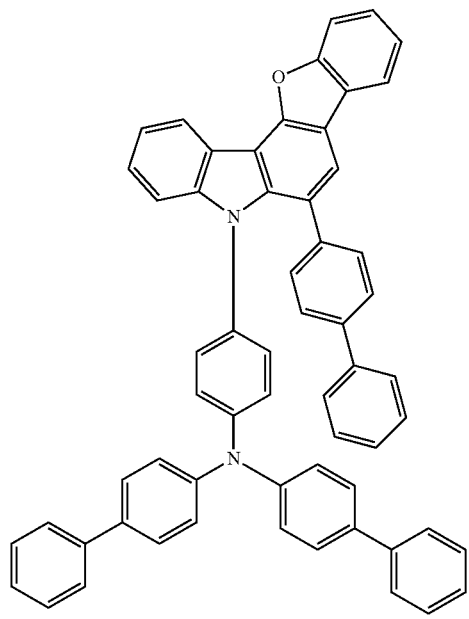
88
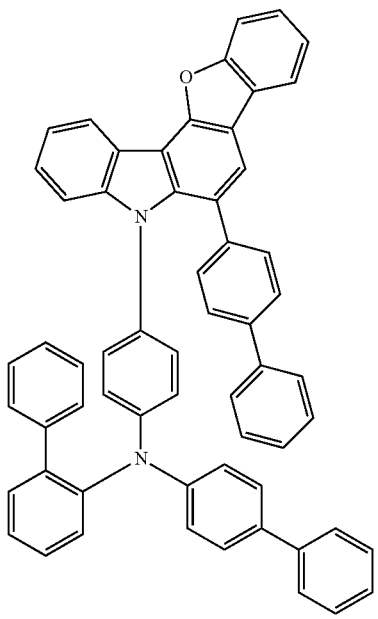
89
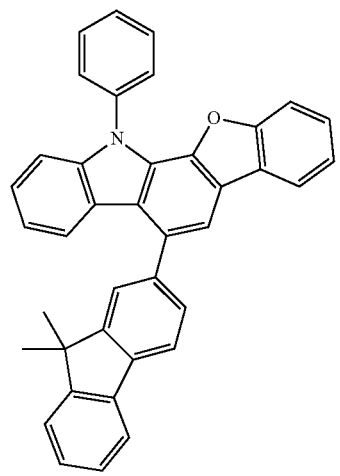
90
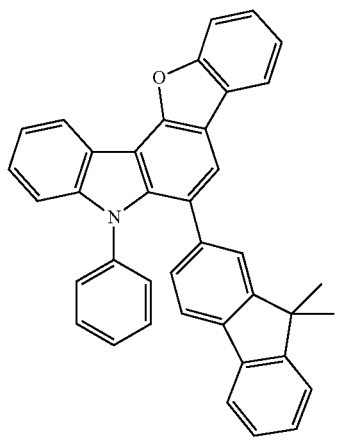
91
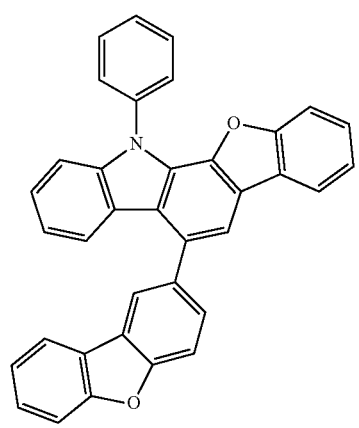
92
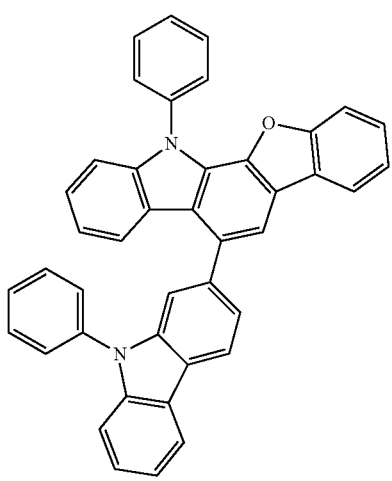

-continued
93
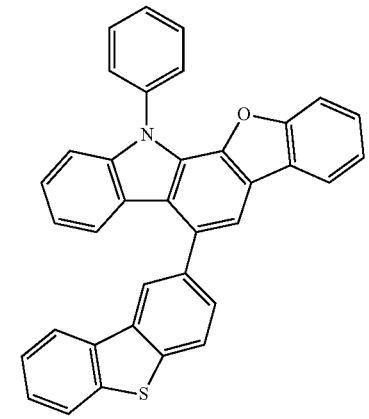
94
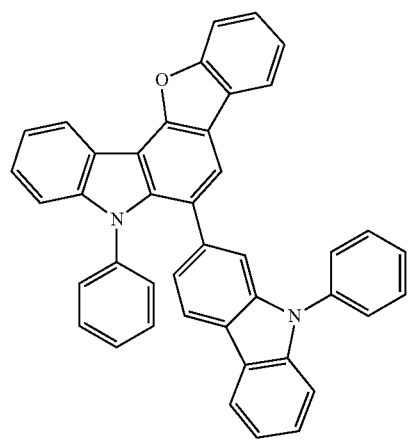
95
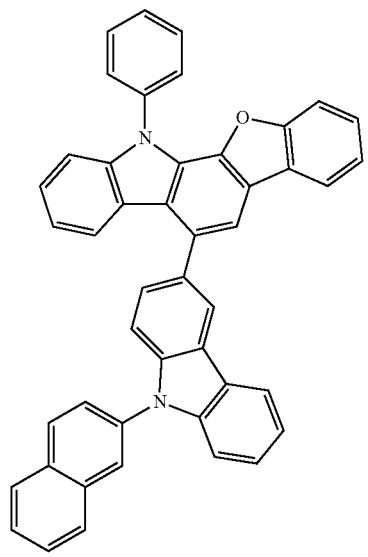
96
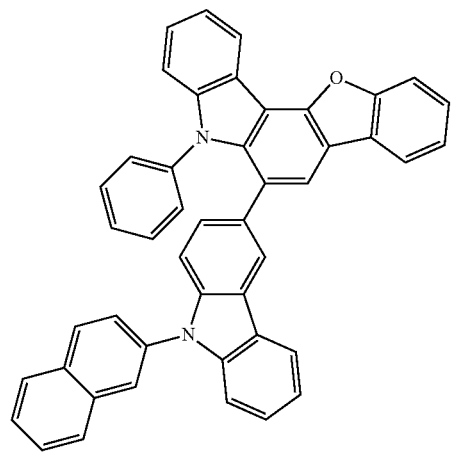
97
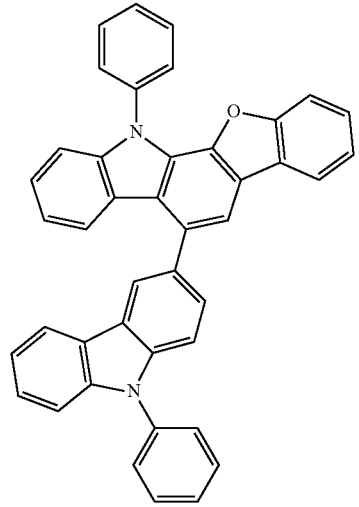
98
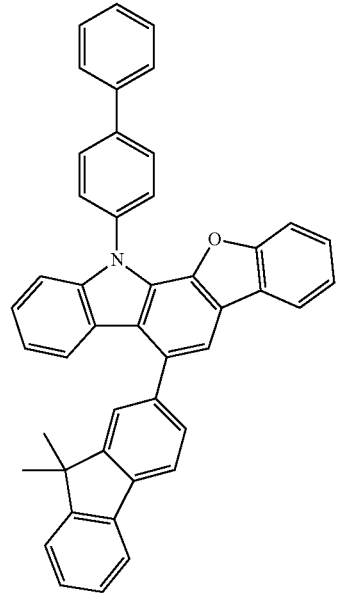

-continued
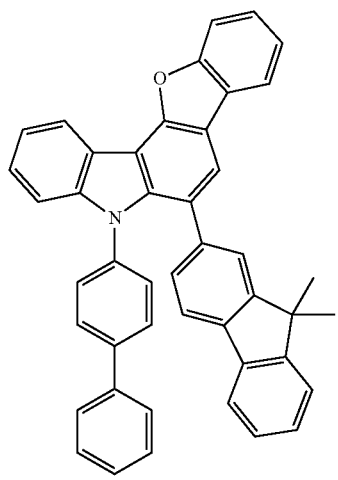
99
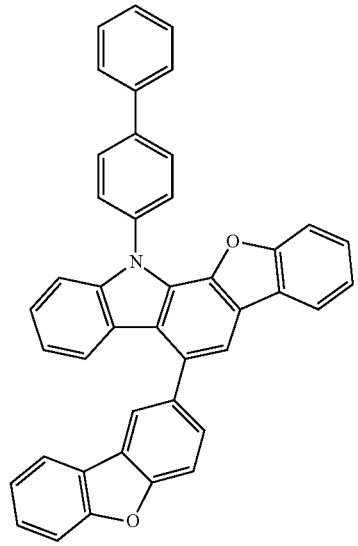
100
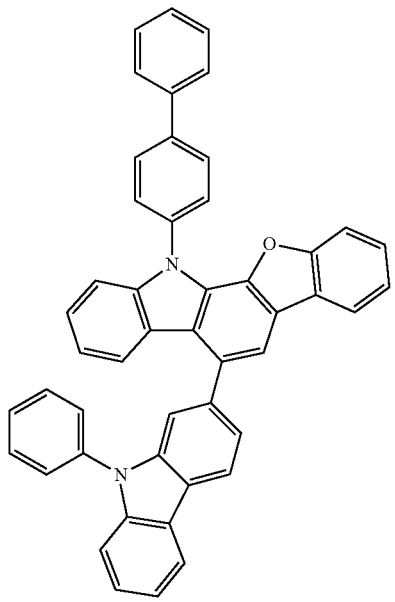
101
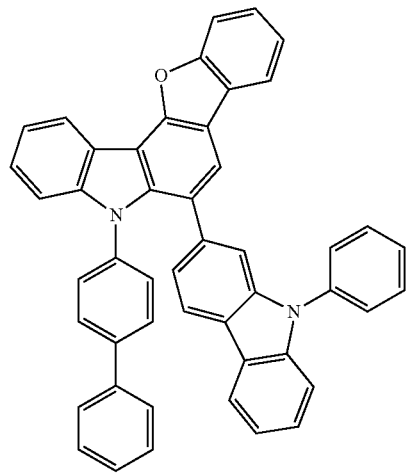
102

101                               102
-continued
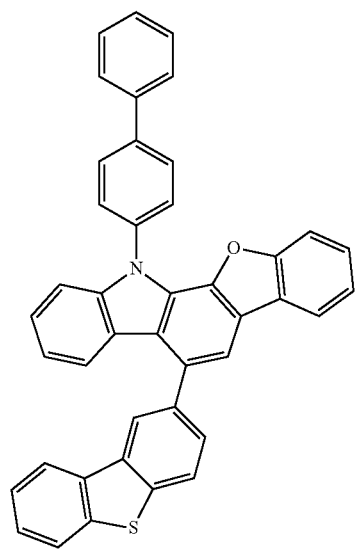
103
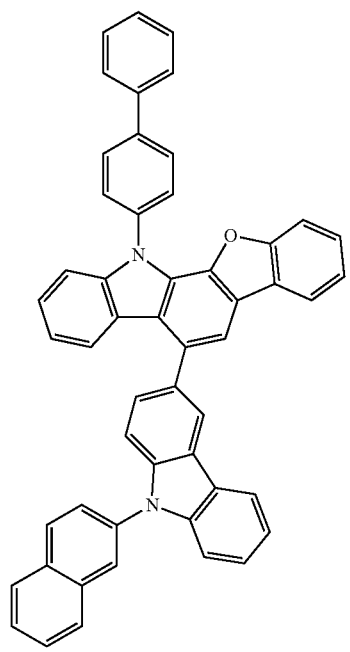
104
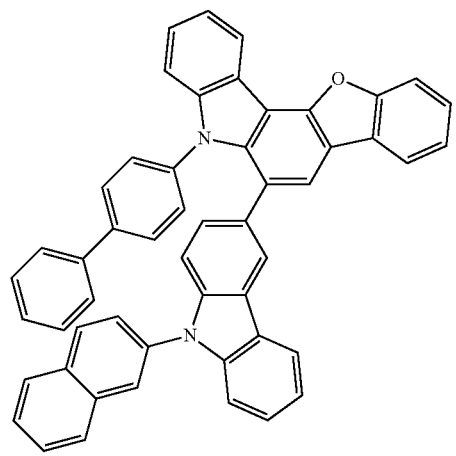
105
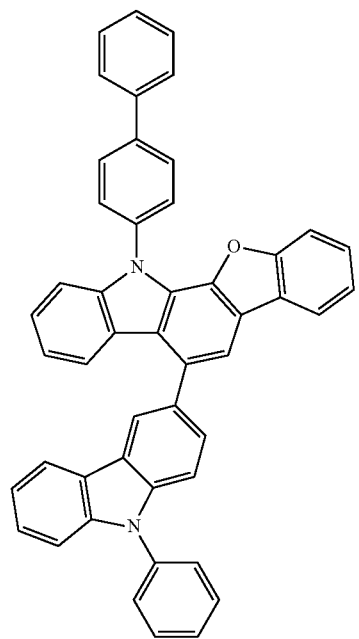
106

-continued
107
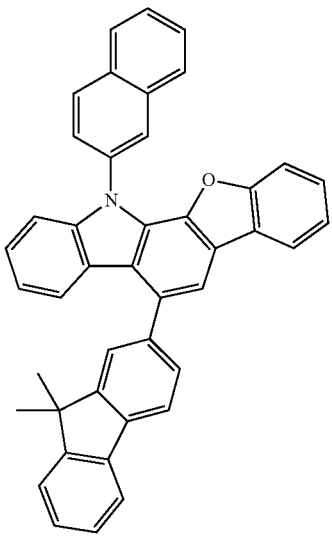
108
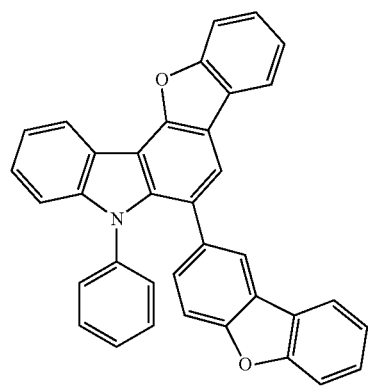
109
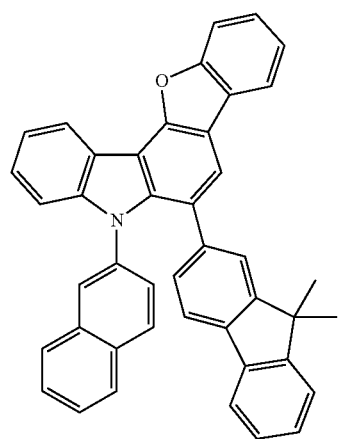
110
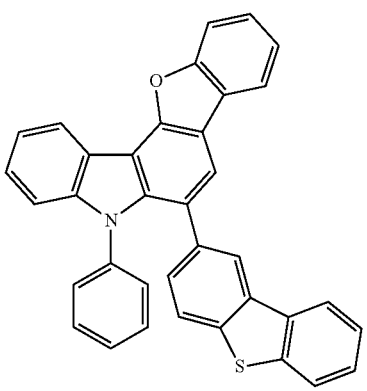
111
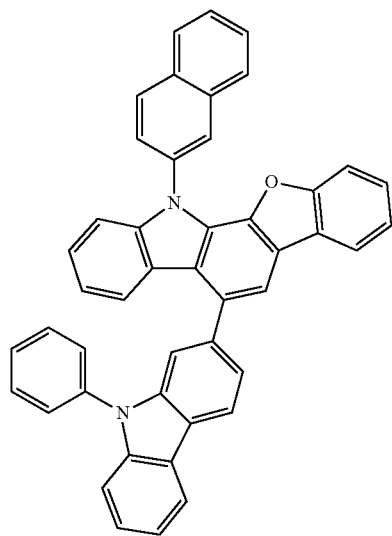
112
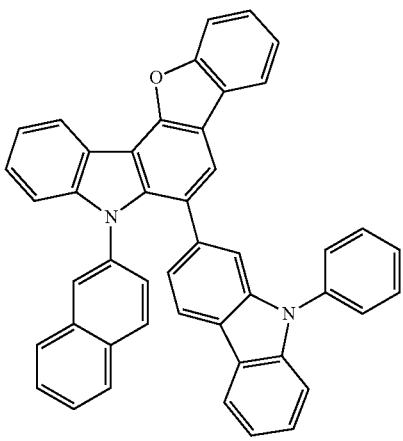

-continued
113 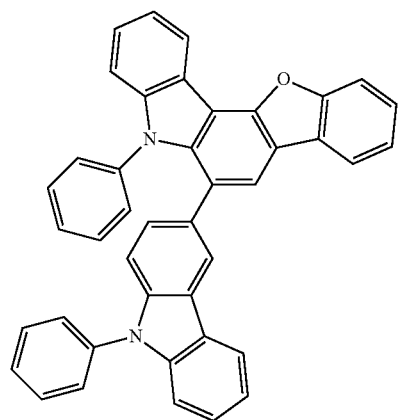
114 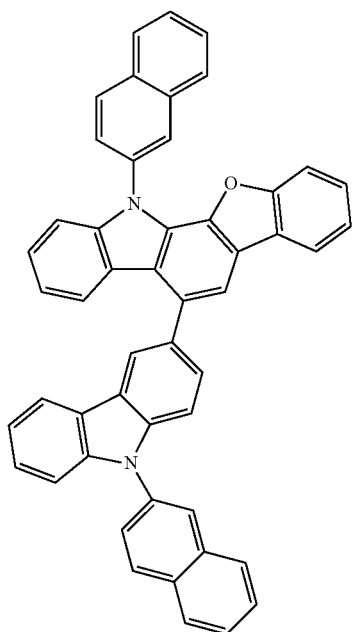
115 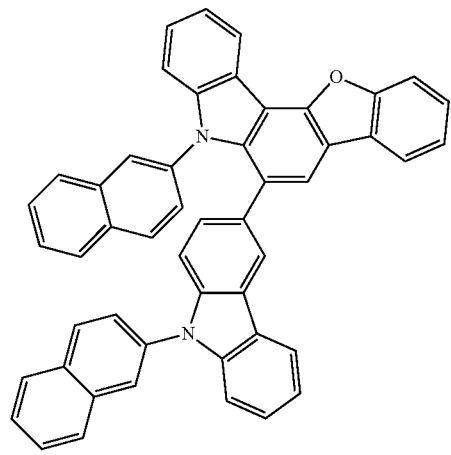
116 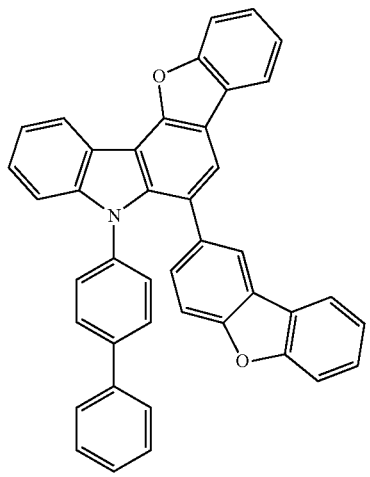

-continued
117 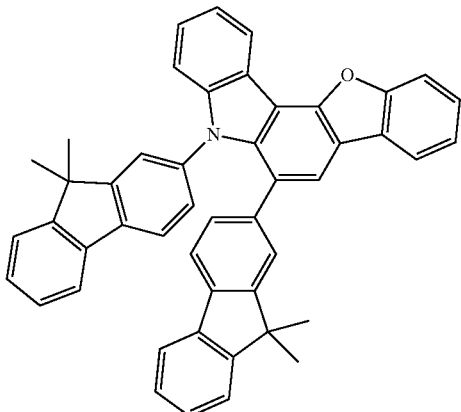
118 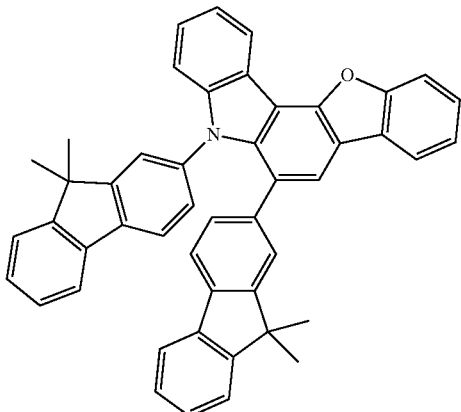
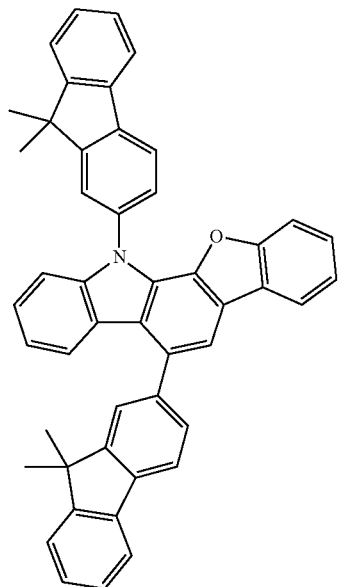
119 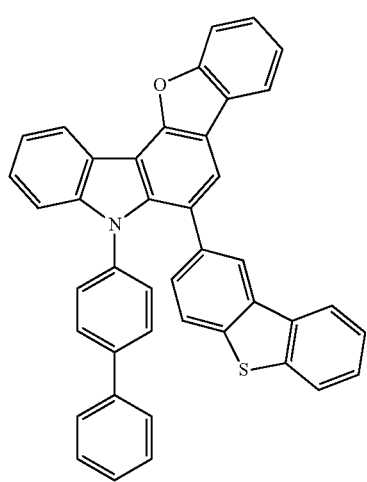
120 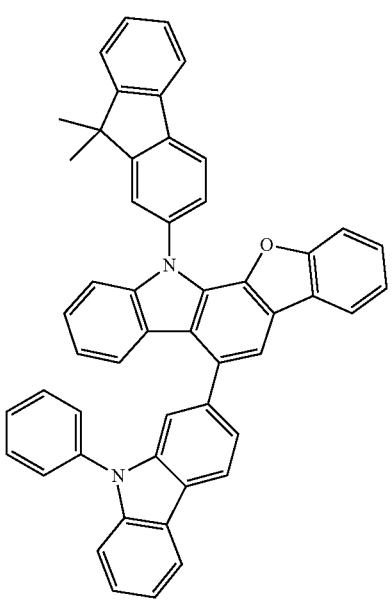
121 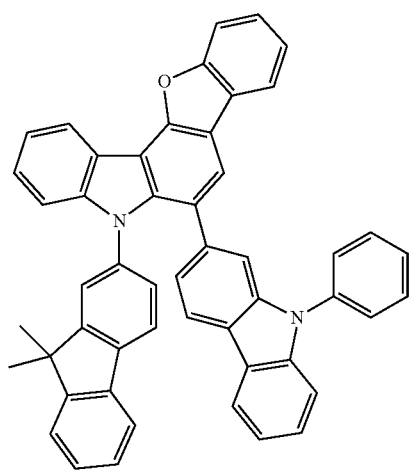
122 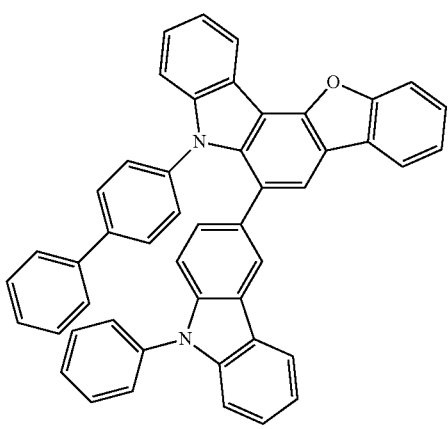

-continued
123
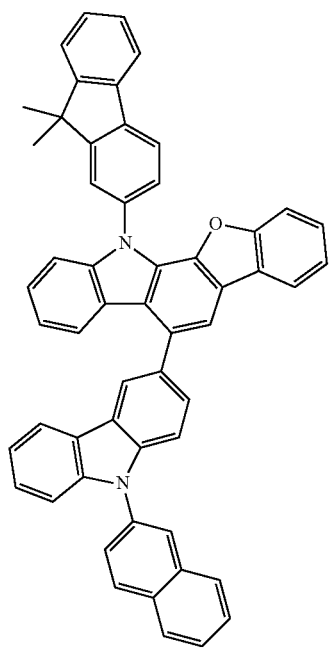
124
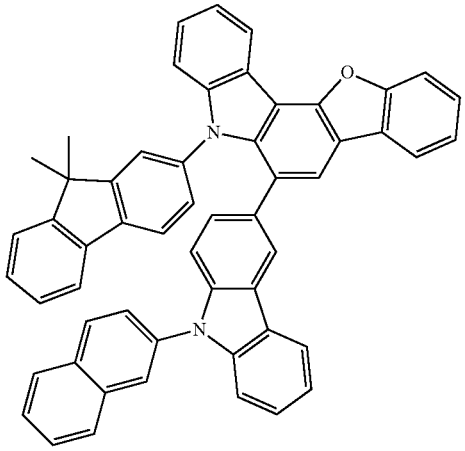
125
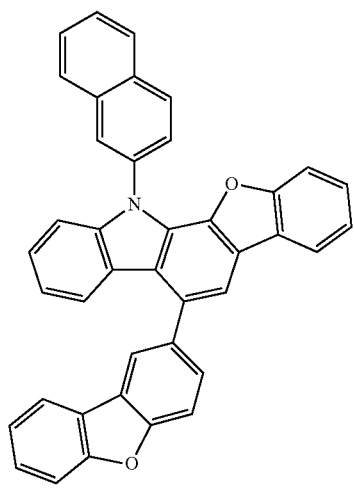
126
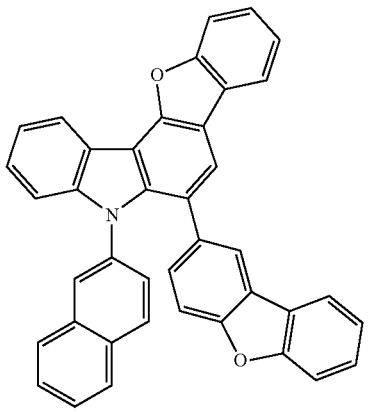
127
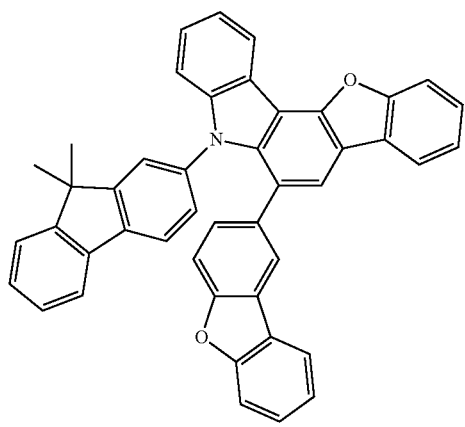
128
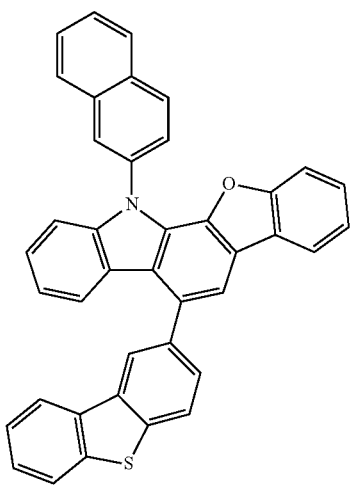

-continued
129
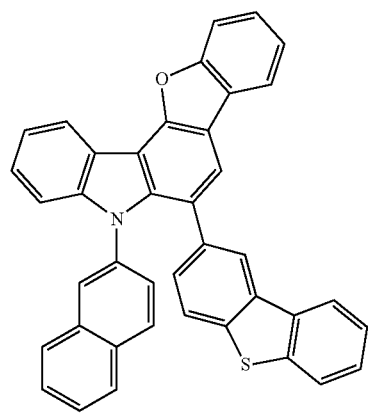
130
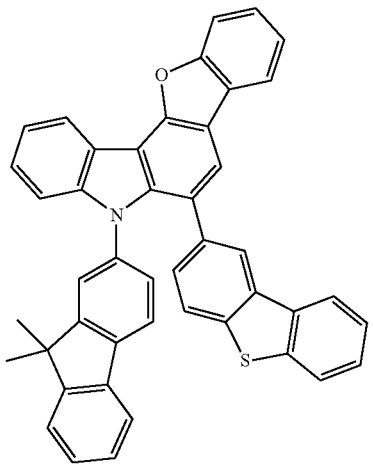
131
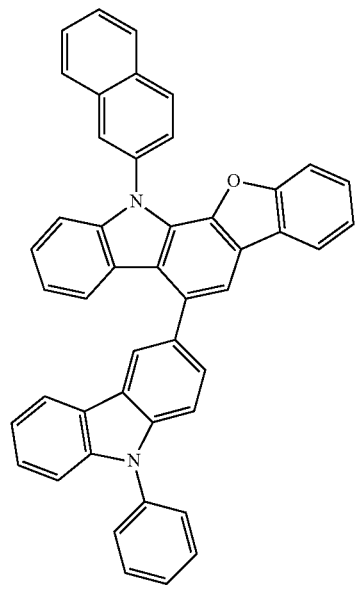
132
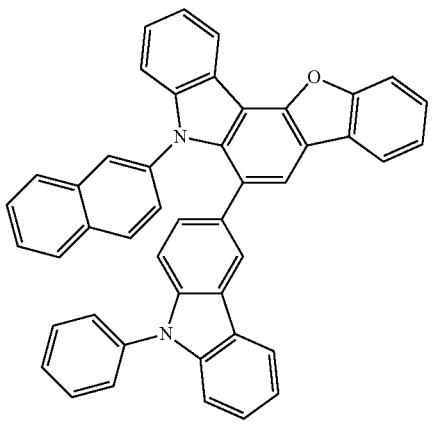
133
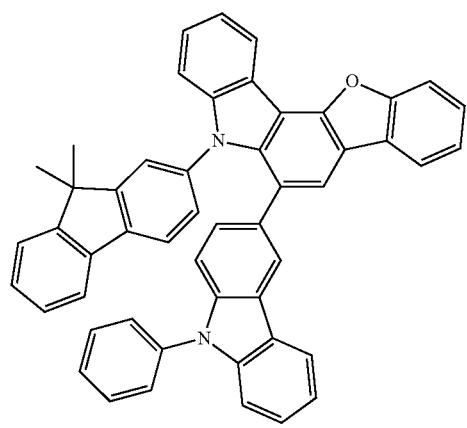
134
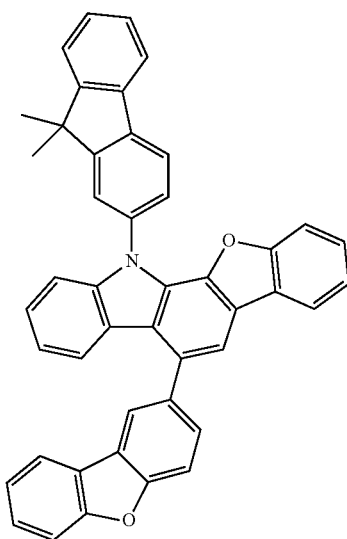

-continued
135
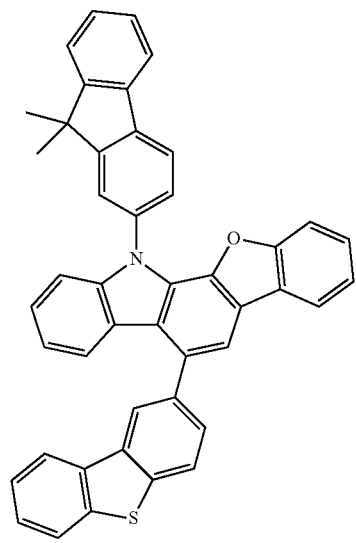
136
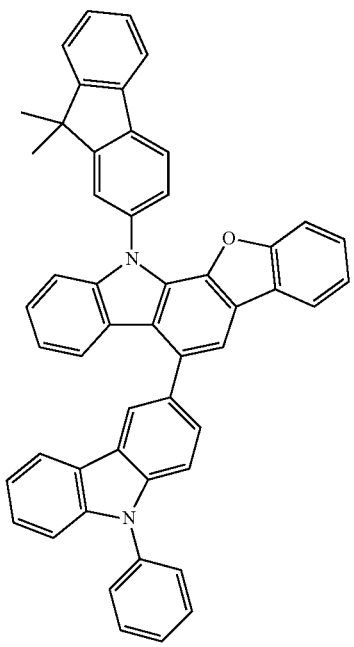
137
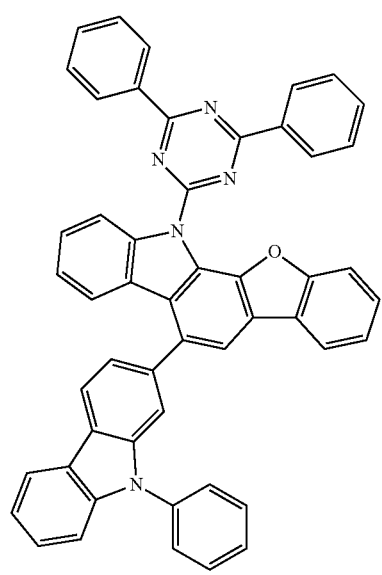
138
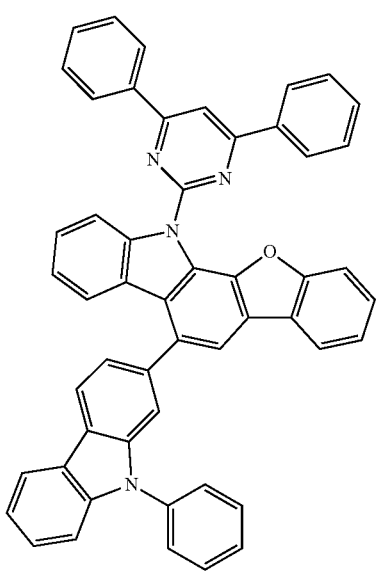

-continued
139 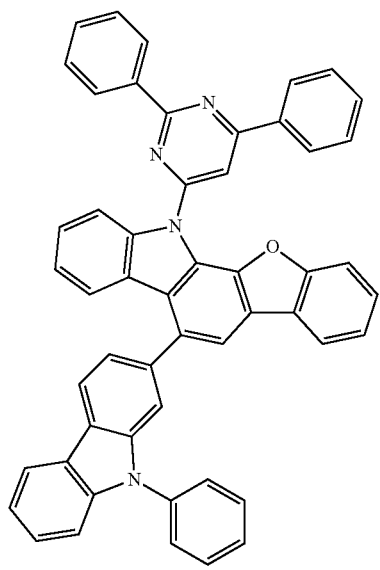
140 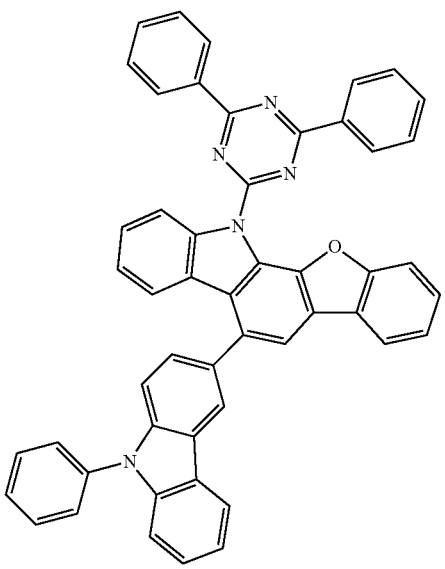
141 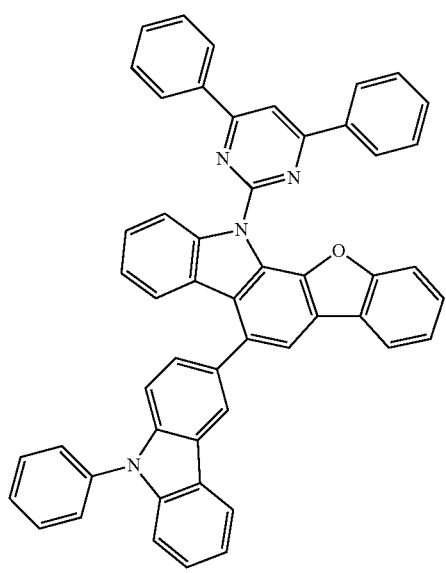
142 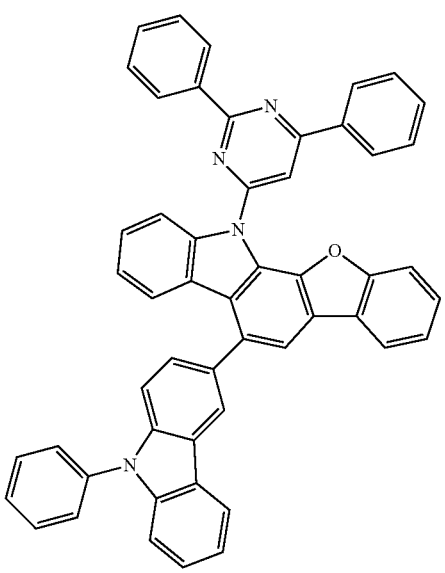

-continued
143
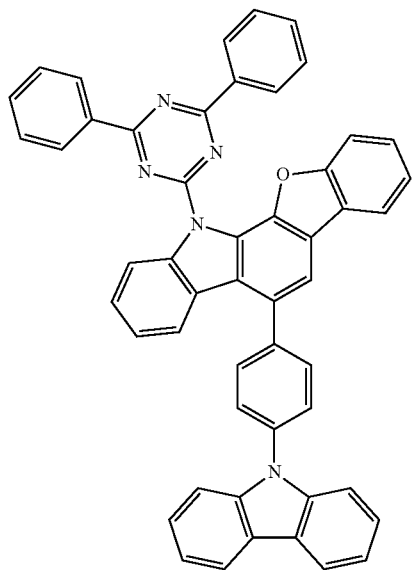
144
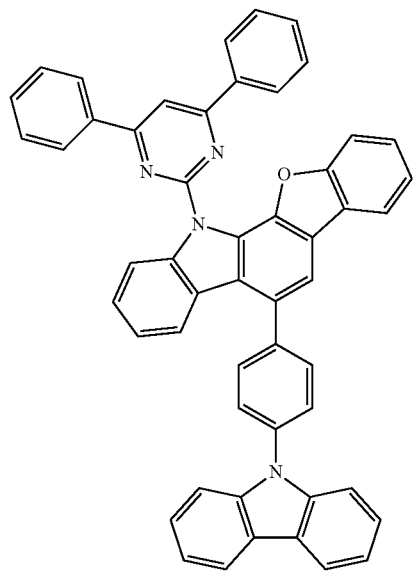
145
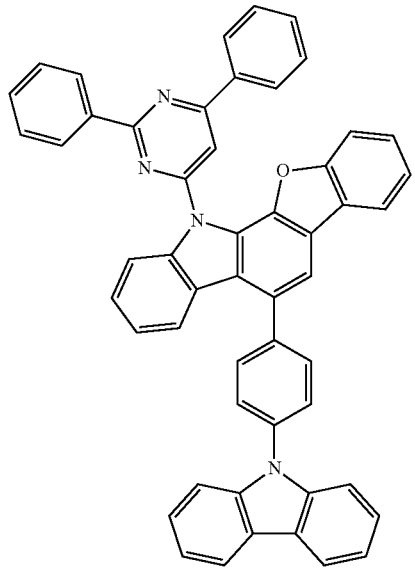
146
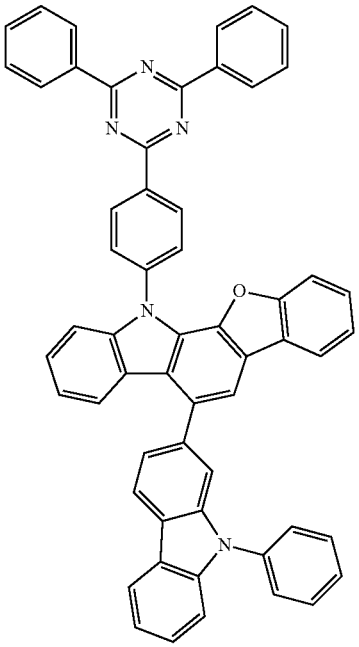

-continued
147 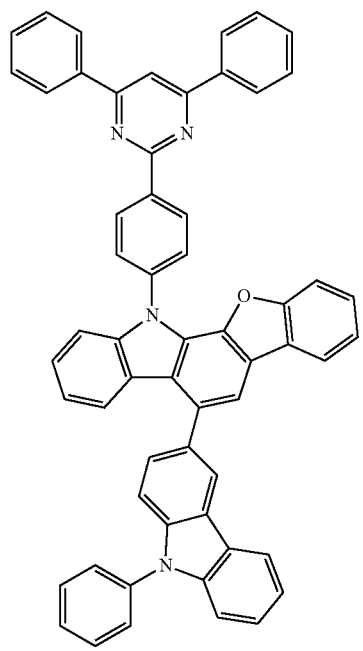
148 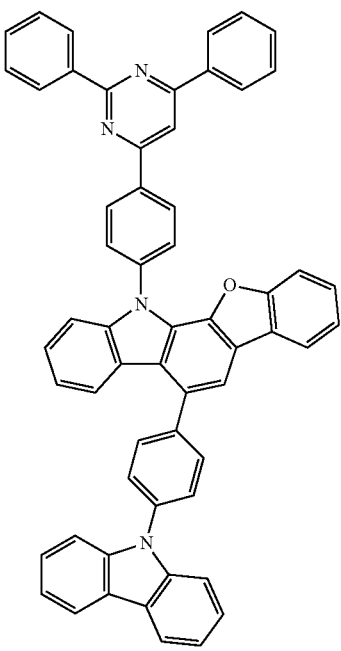
149 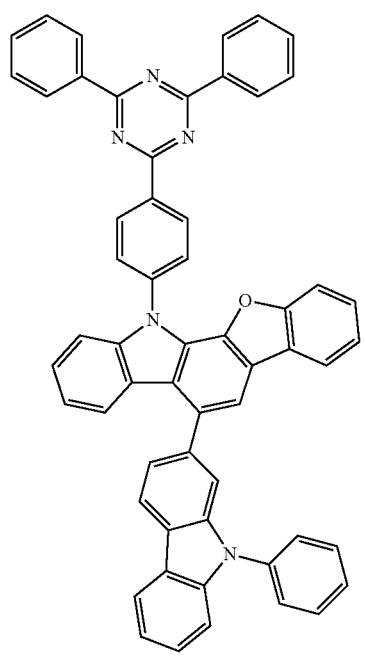
150 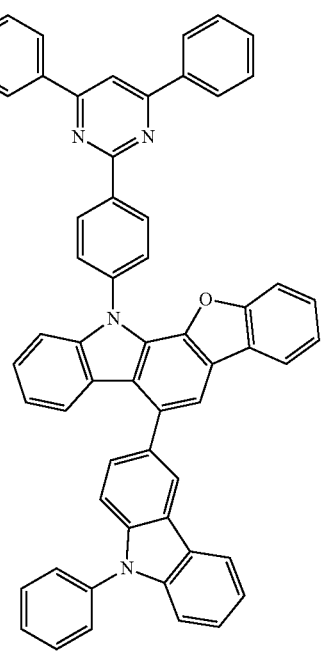

-continued
151
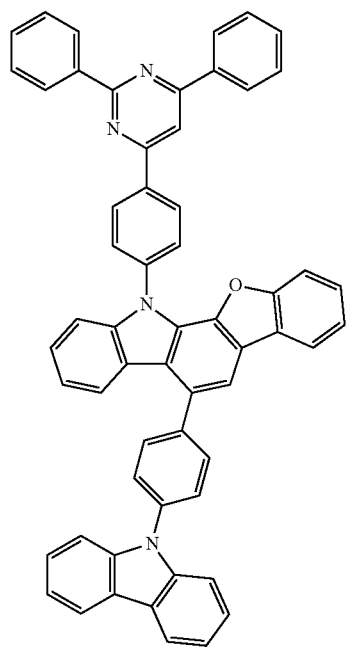
152
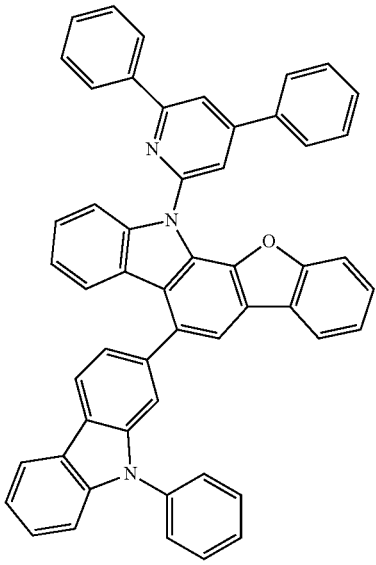
153
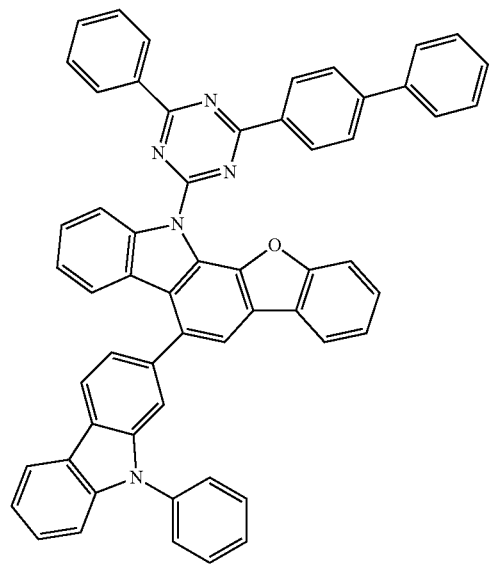
154
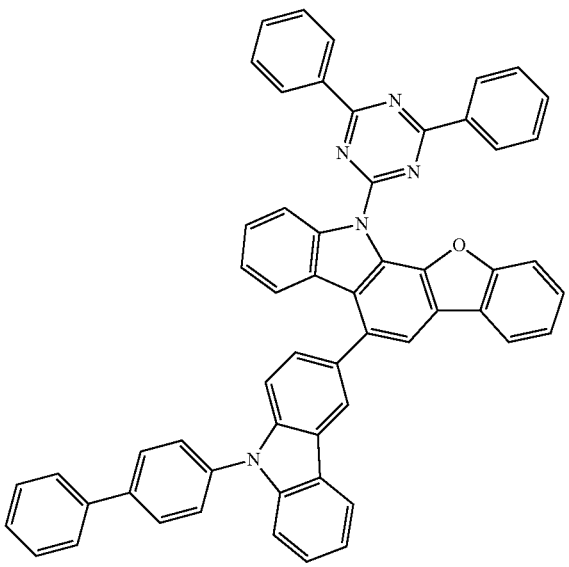

-continued
155
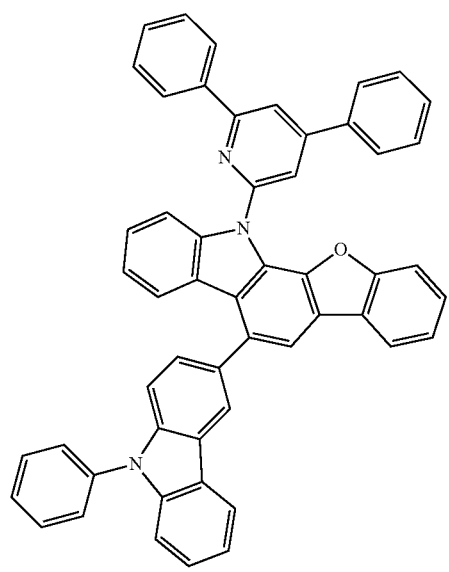
156
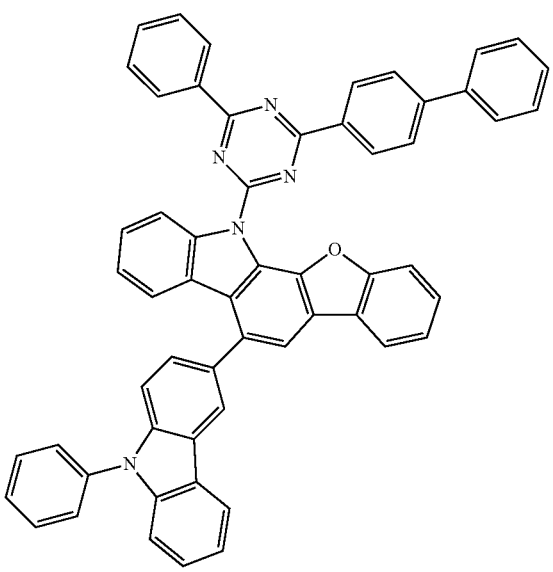
157
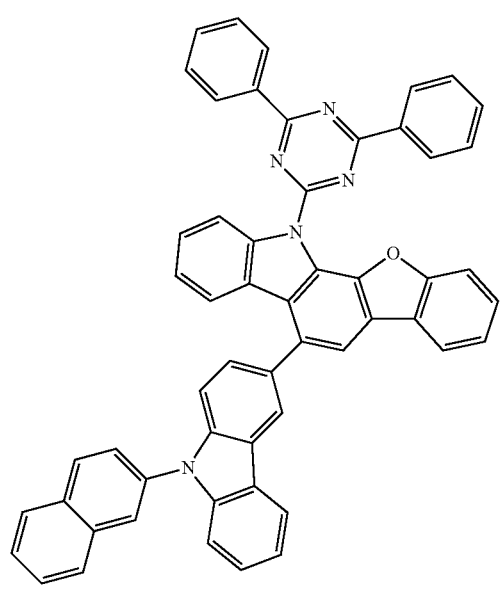
158
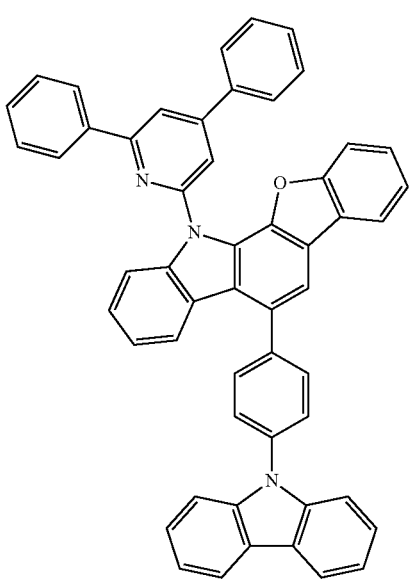

-continued
159 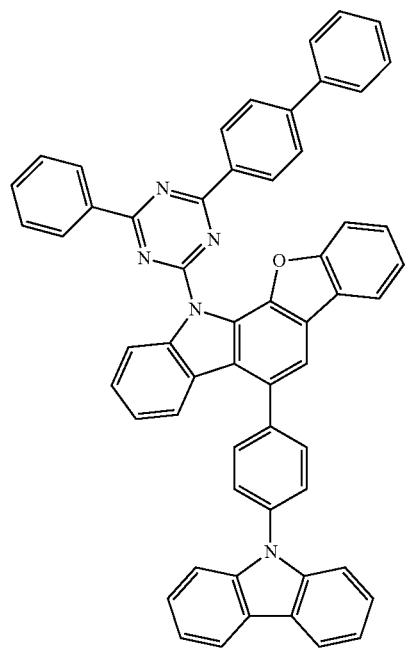
160 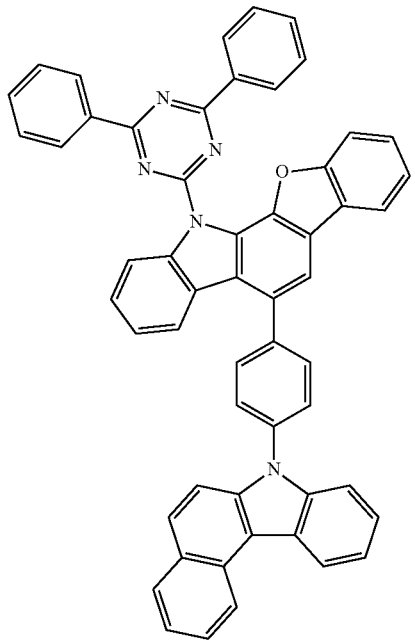
161 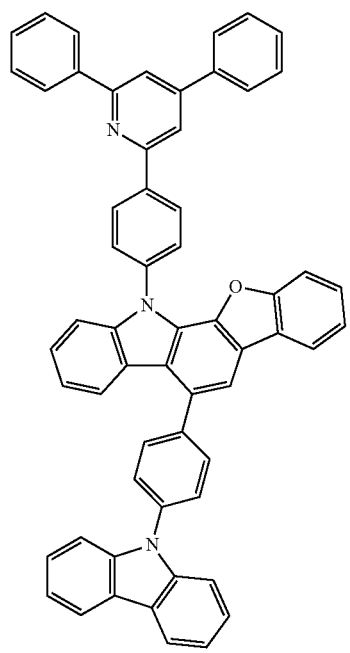
162 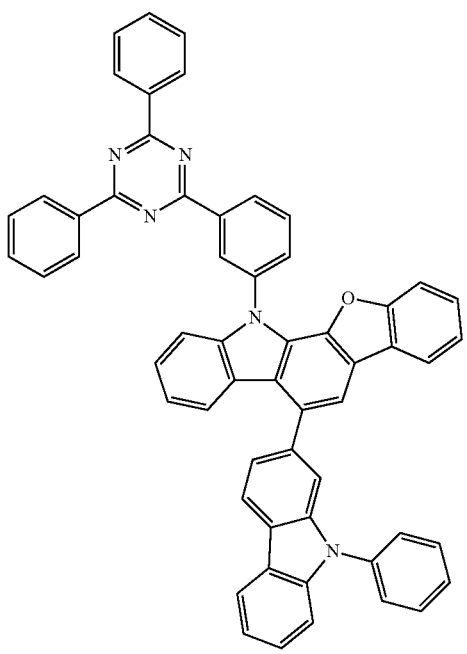

-continued
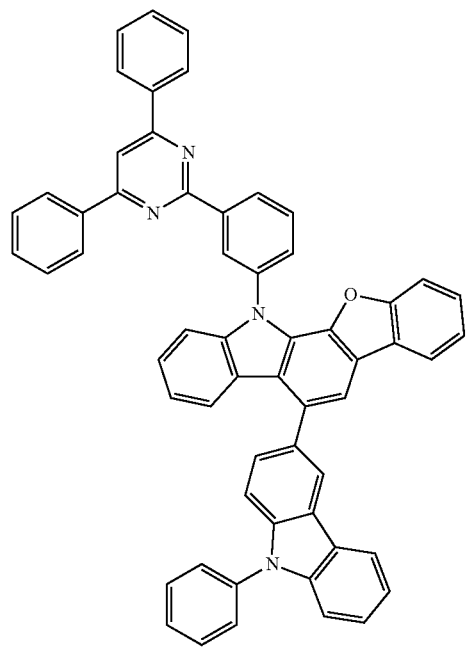
163
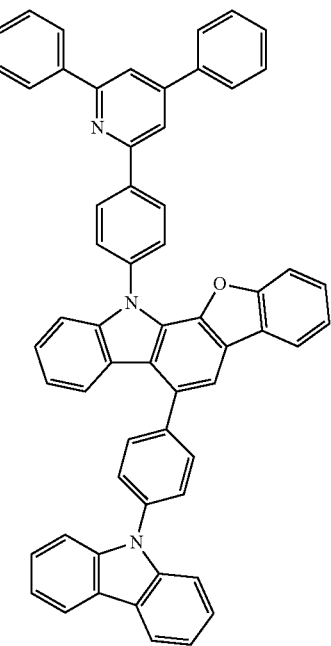
164
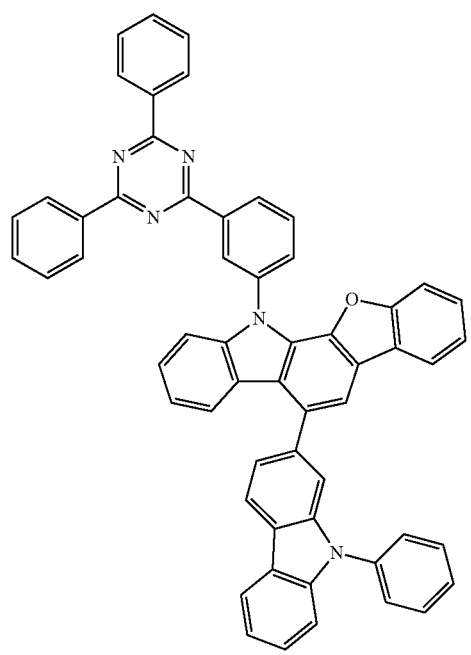
165
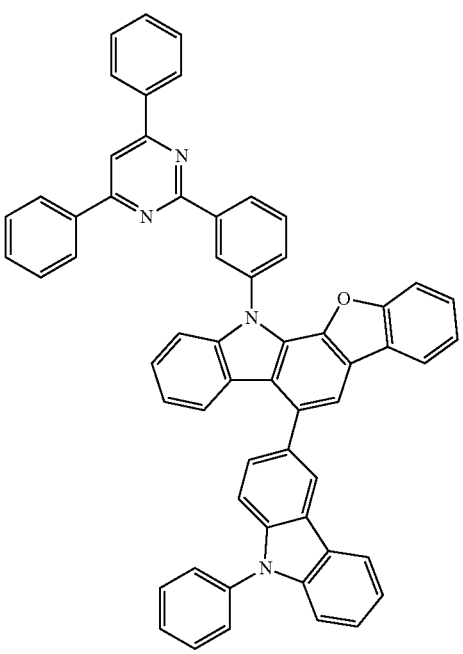
166

167
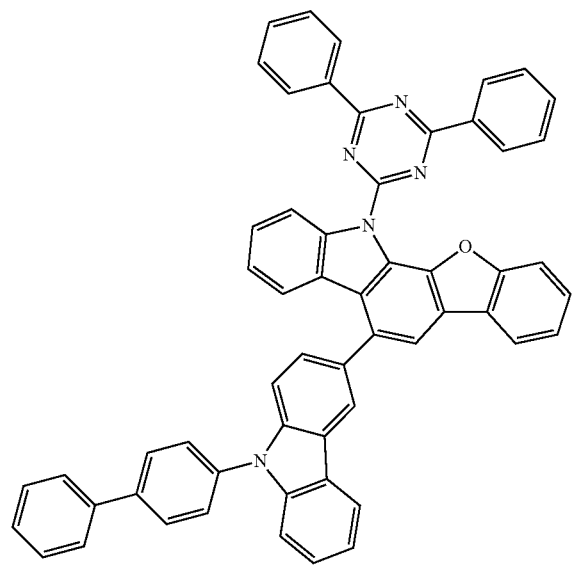
168
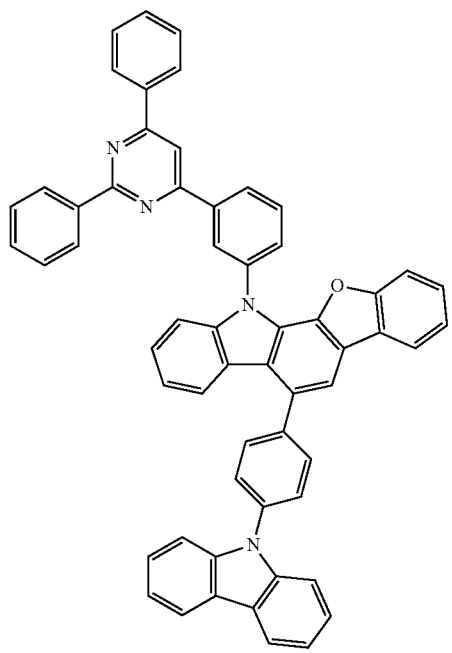
169
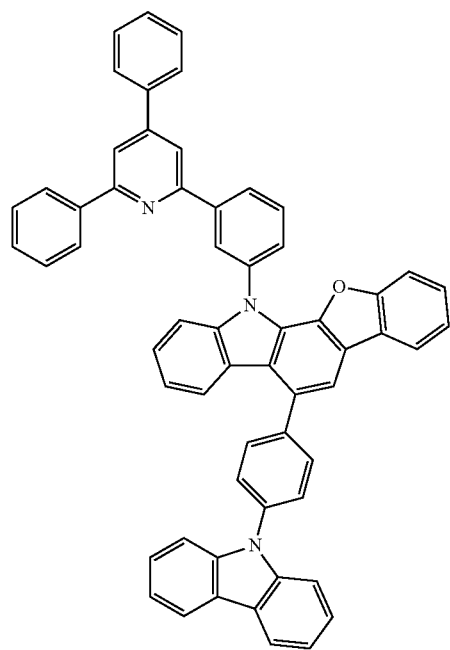
170
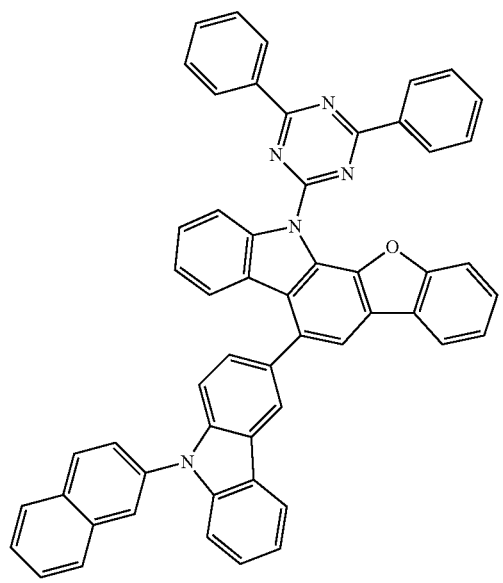

171
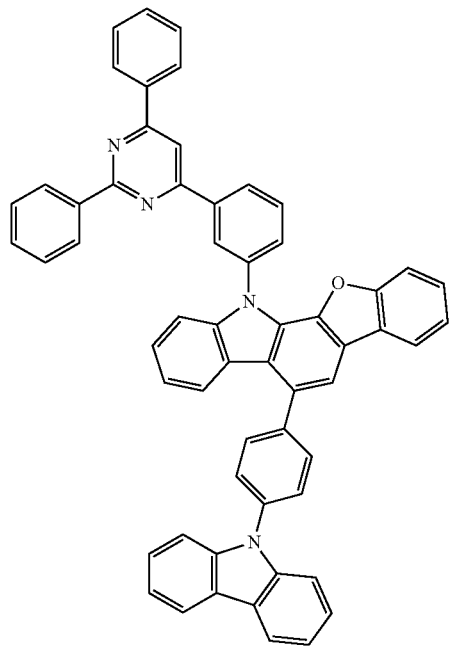
172
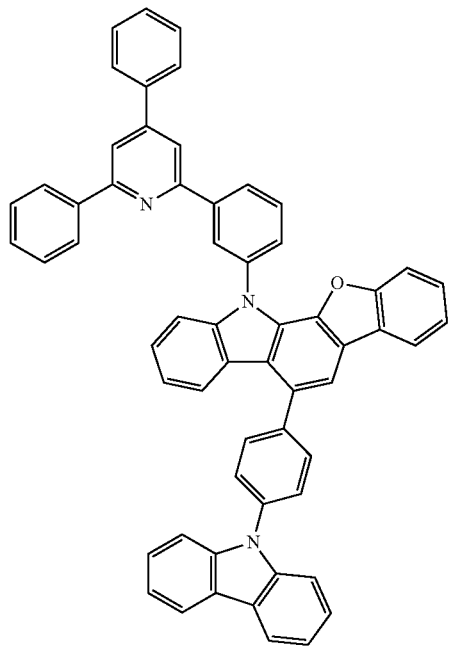
173
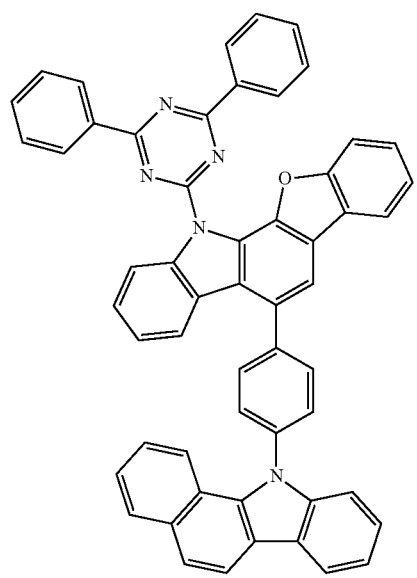
174
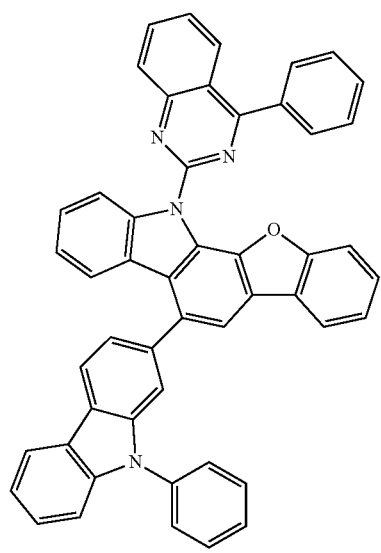

-continued
175
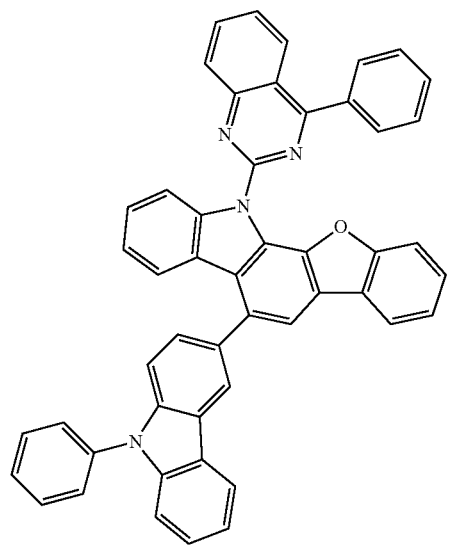
176
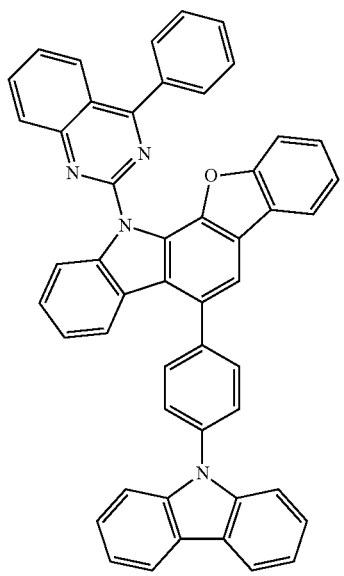
177
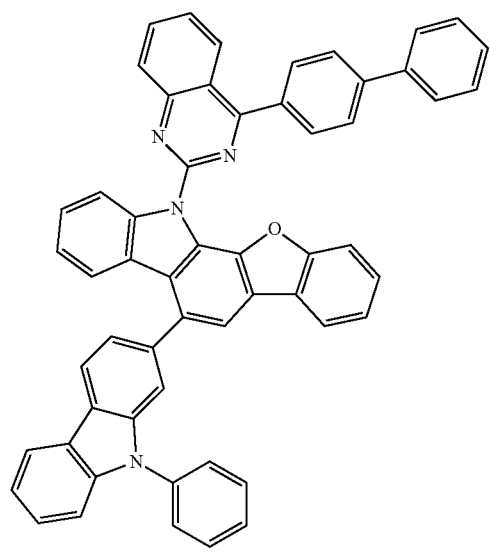
178
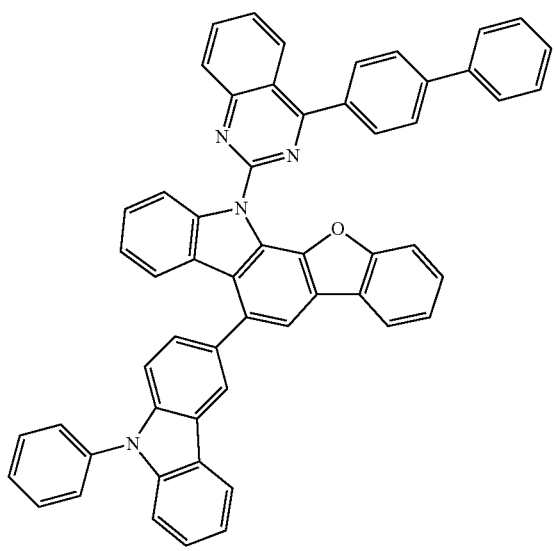

-continued
179 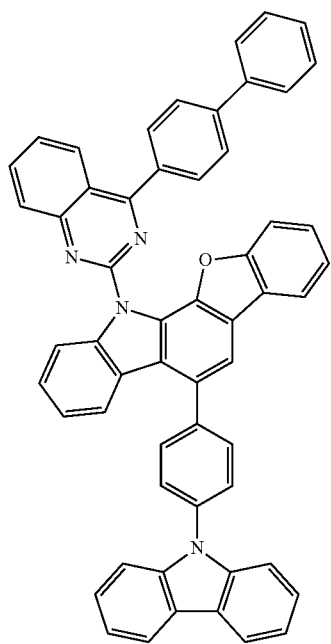
180 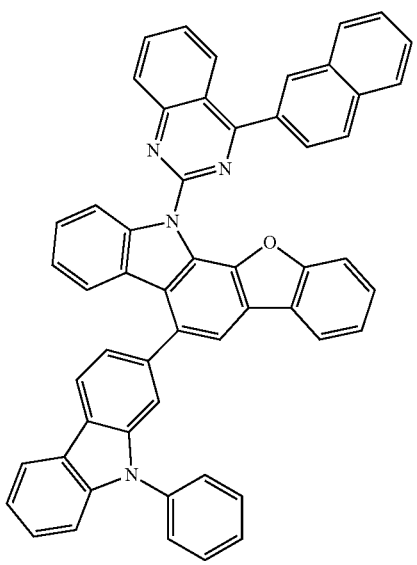
181 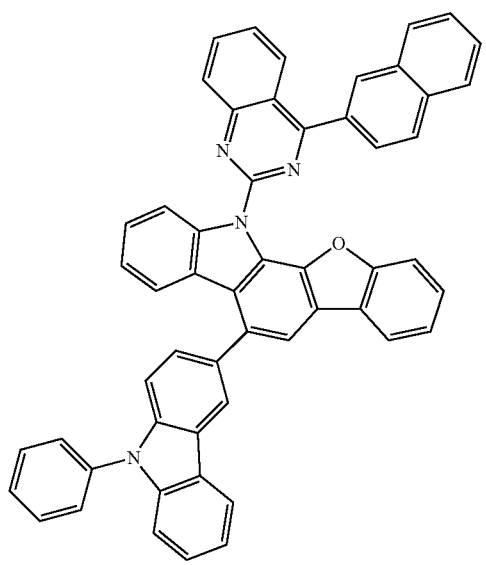
182 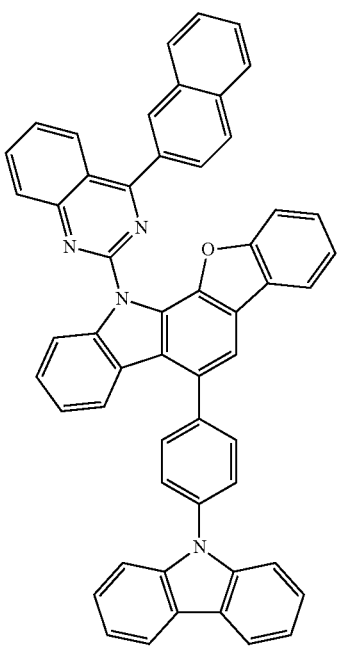

-continued
183
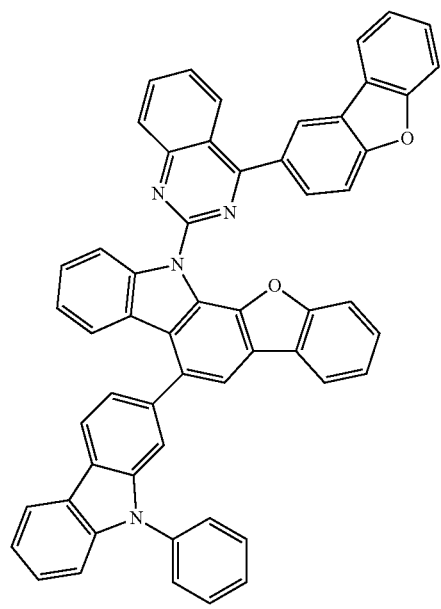
184
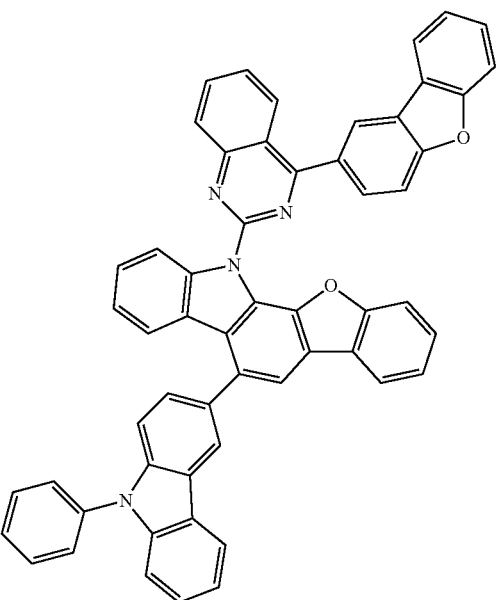
185
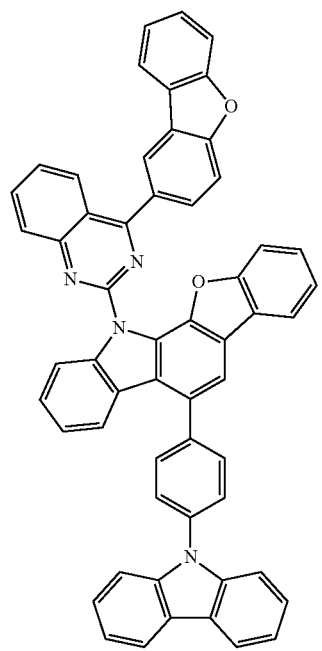
186
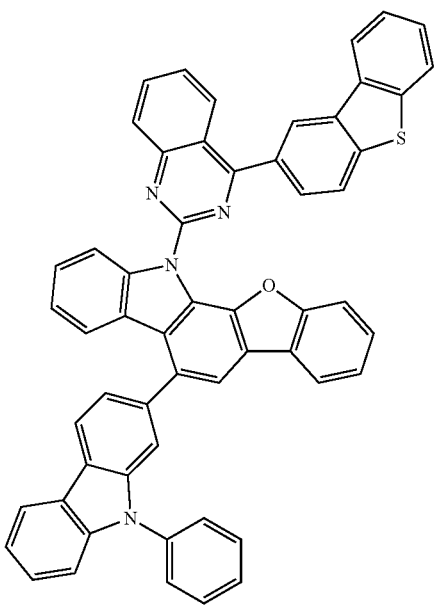

-continued
187
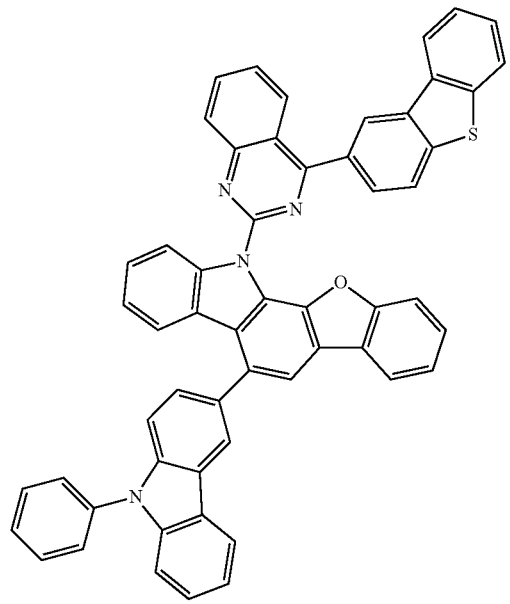
188
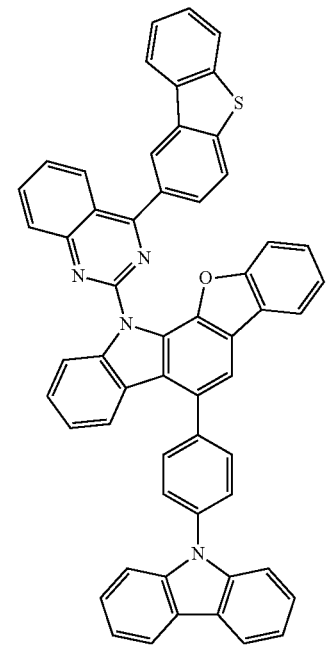
189
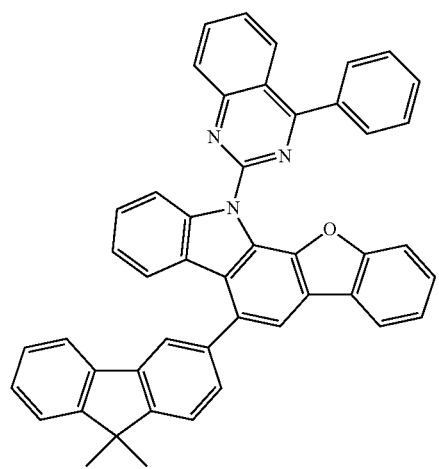
190
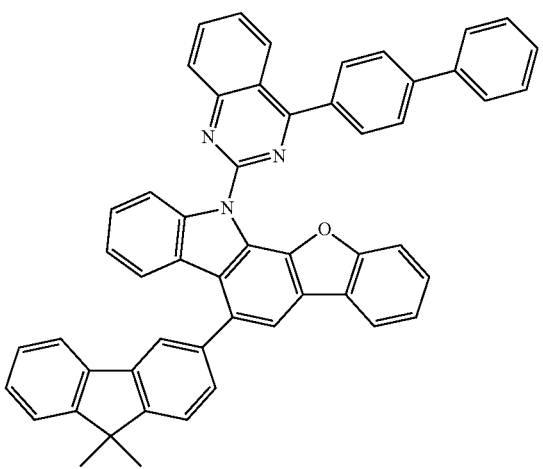
191
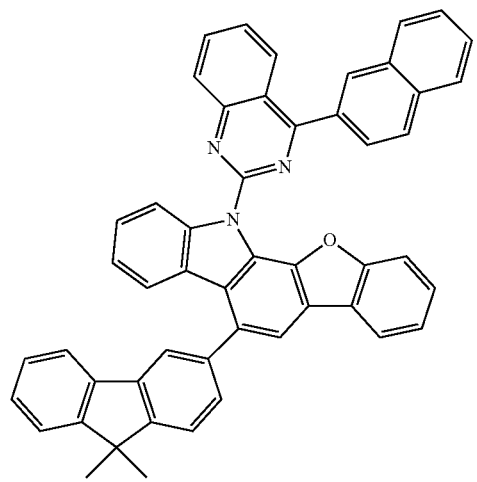
192
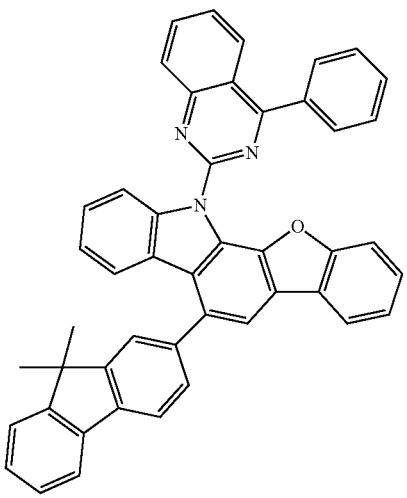

-continued
193
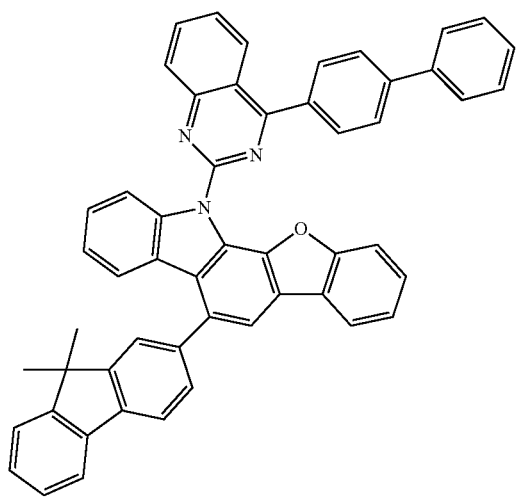
194
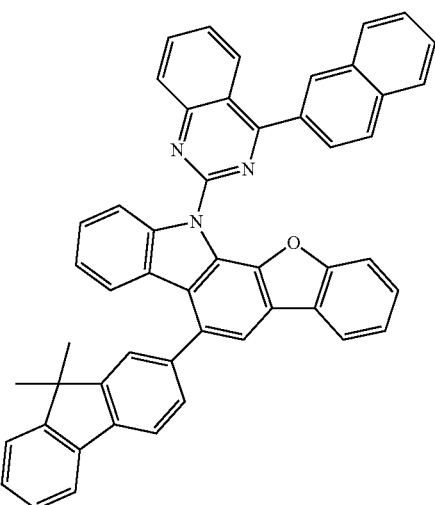
195
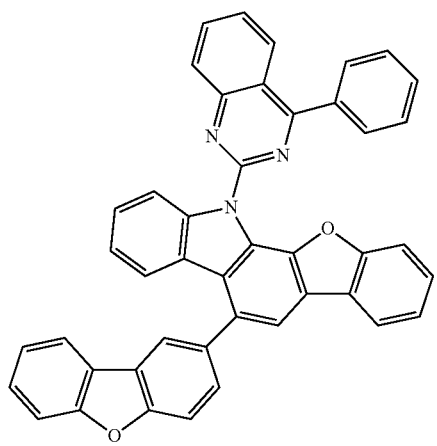
196
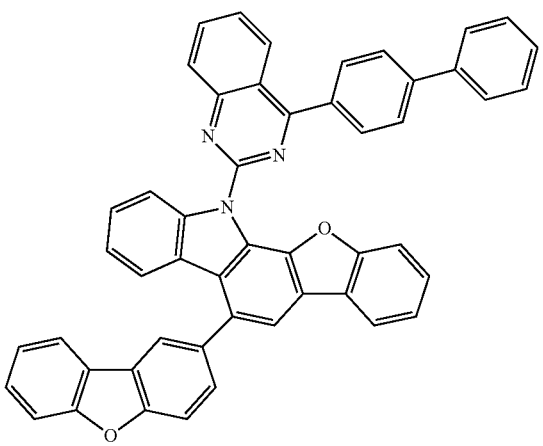
197
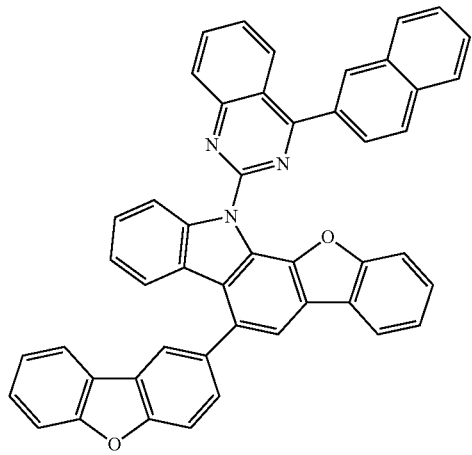
198
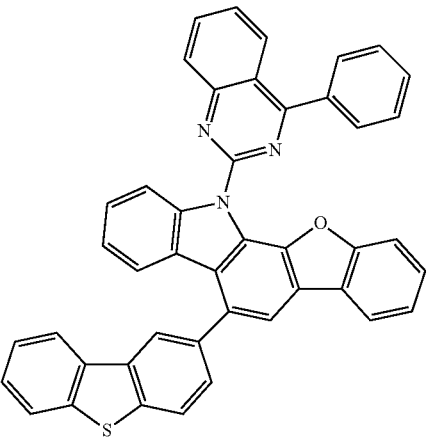

-continued
199
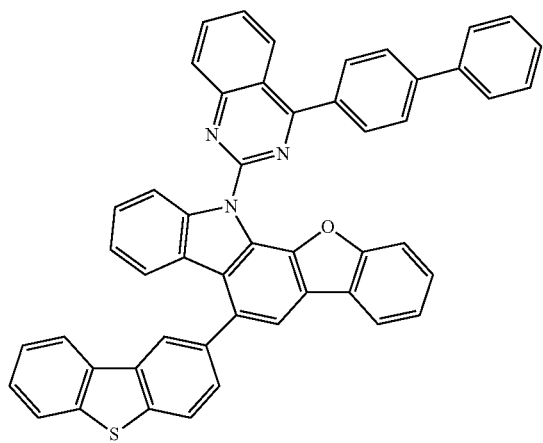
200
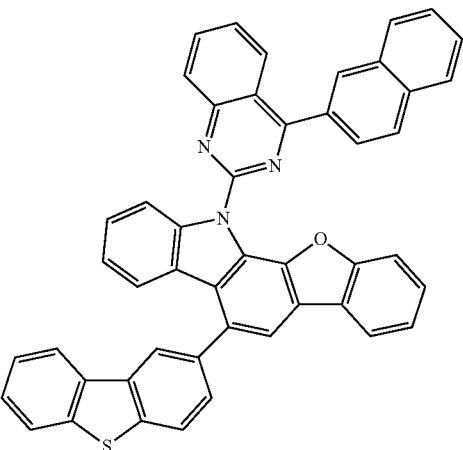
201
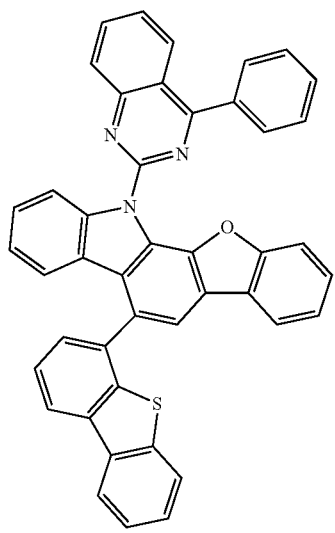
202
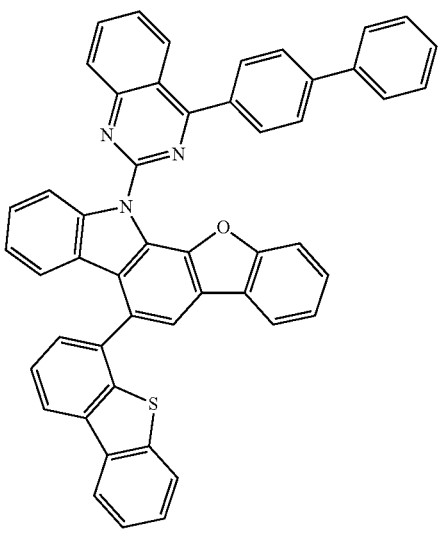
203
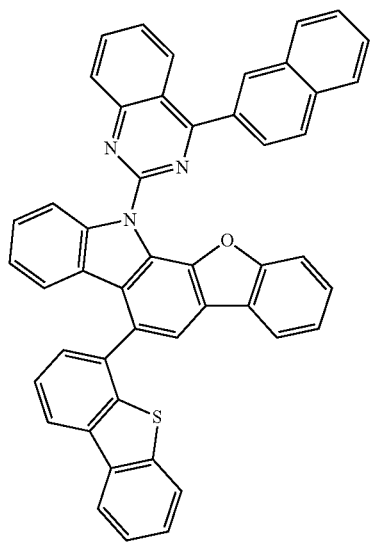
204
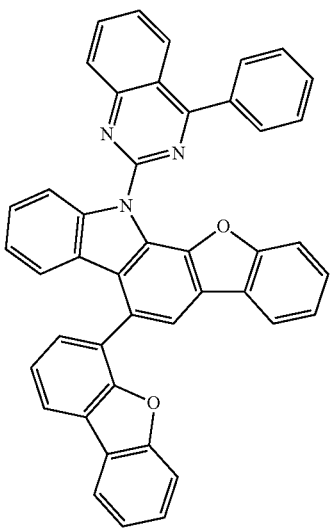

-continued
205
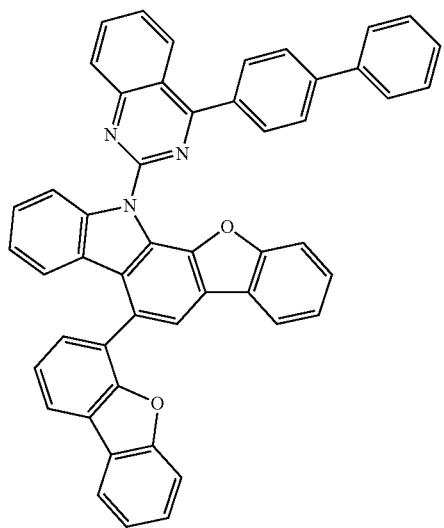
206
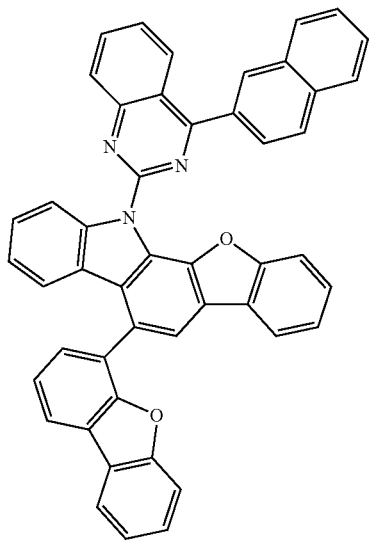
207
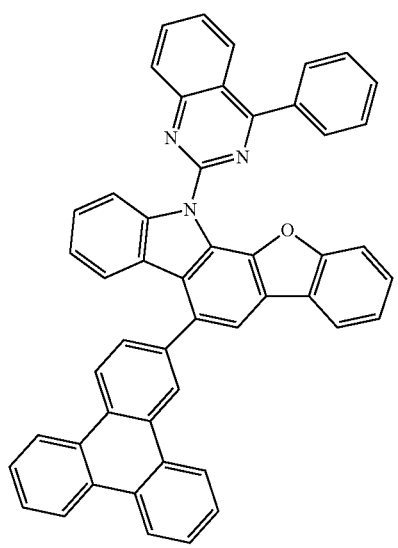
208
209
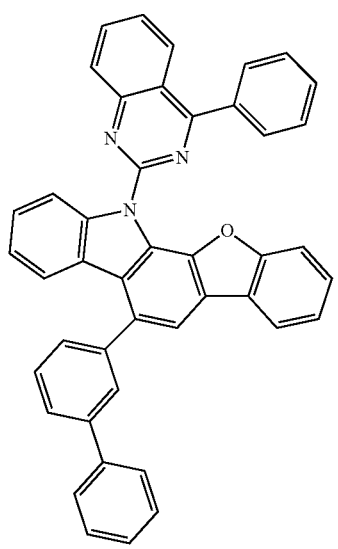
210
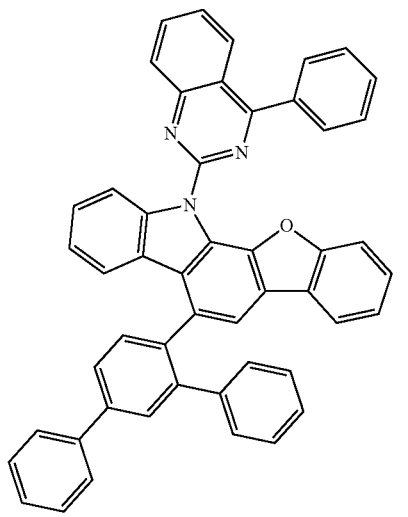

-continued
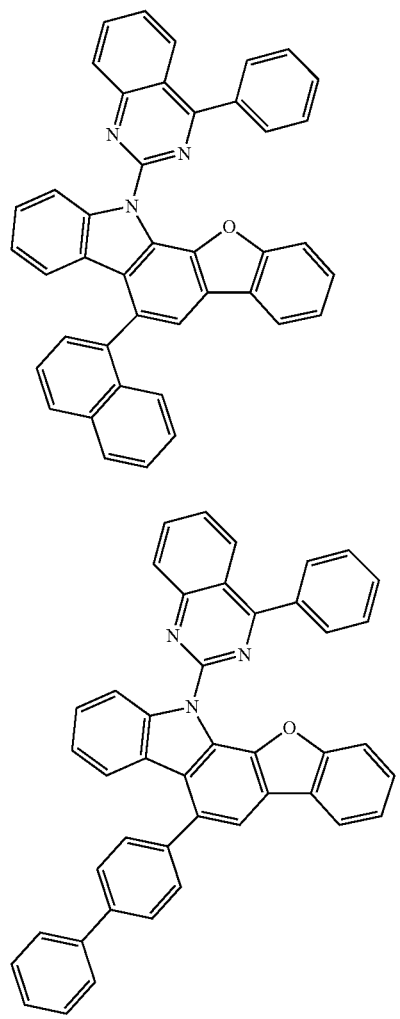
211
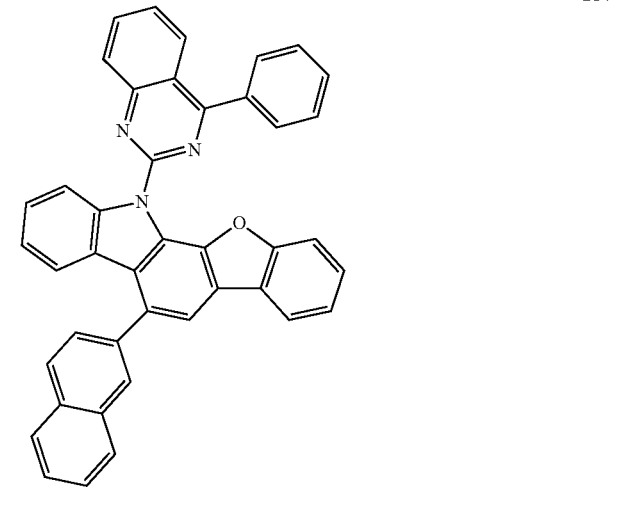
212
213
214
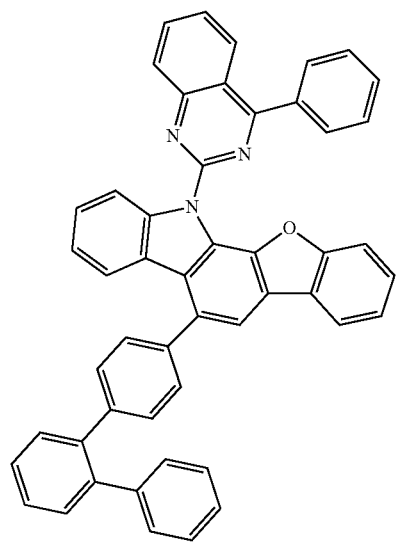
215
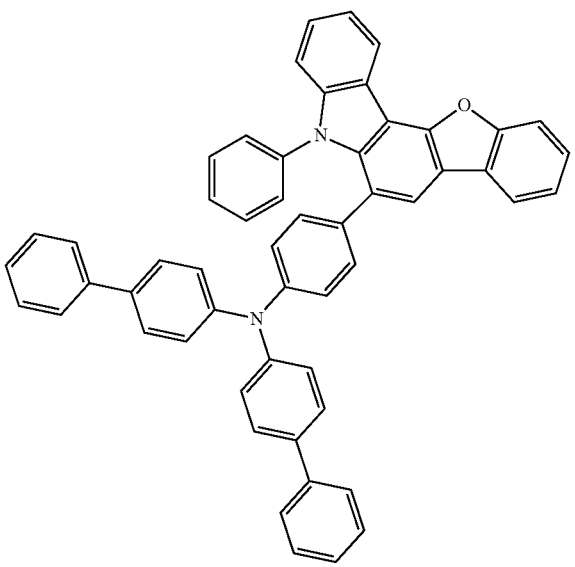
216

-continued
217
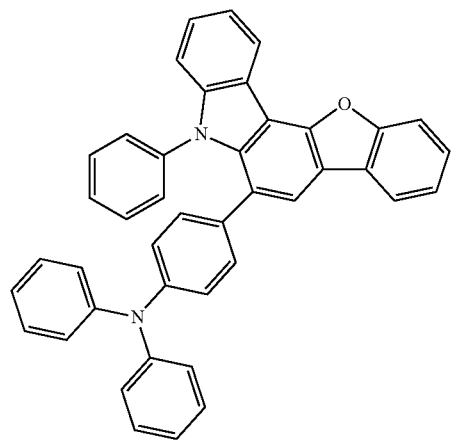
218
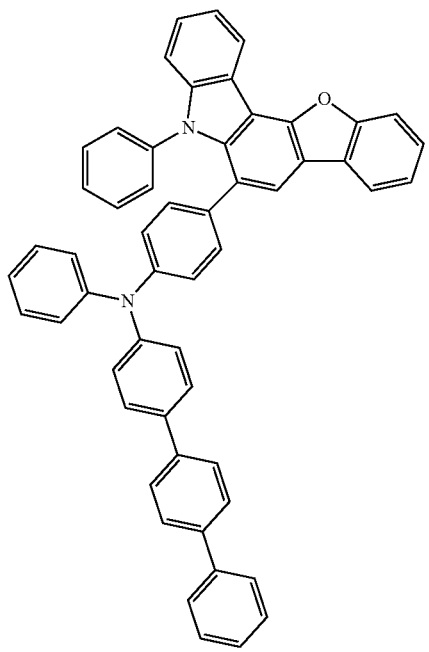
219
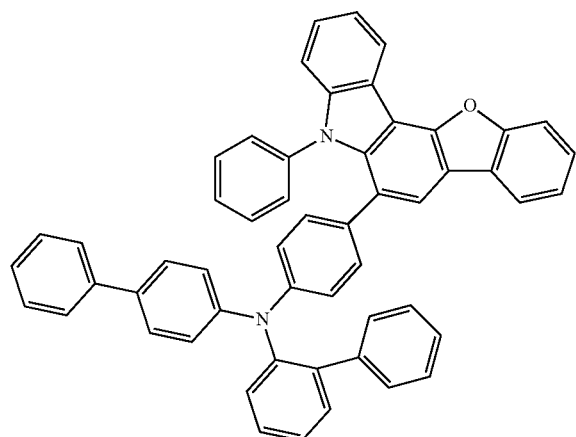
220
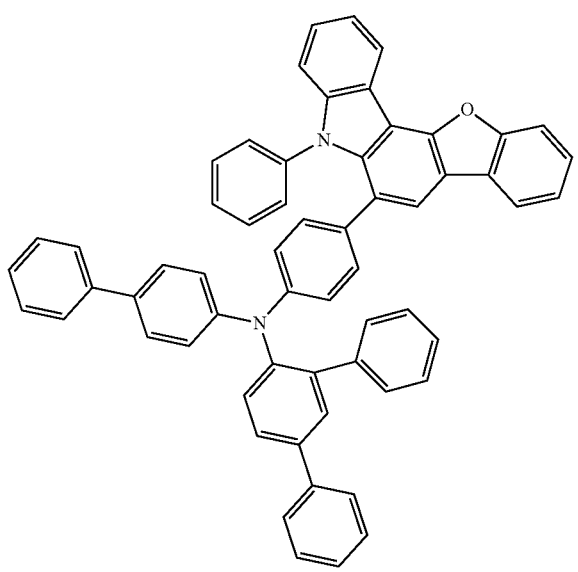

-continued
221 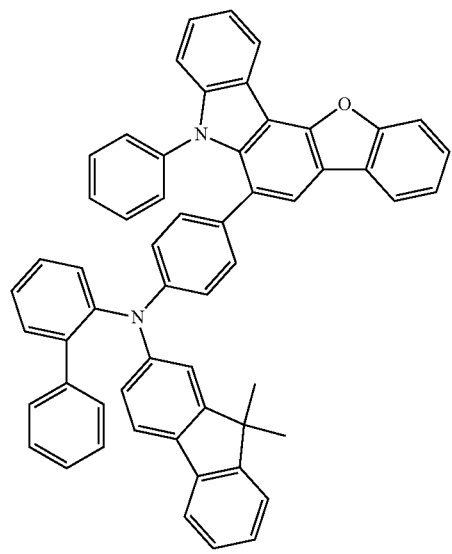
222 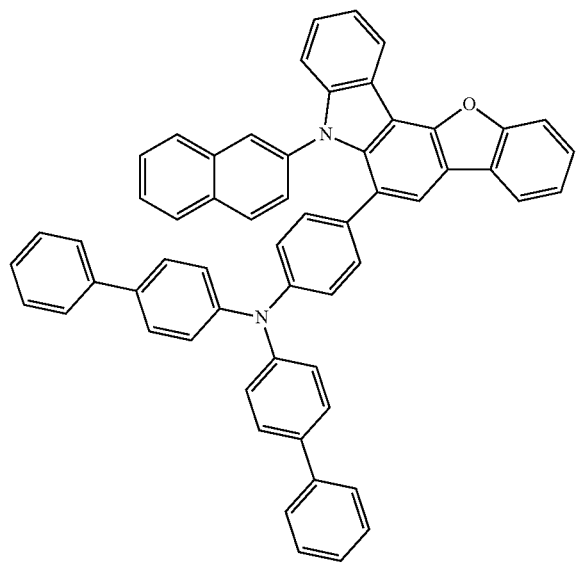
223 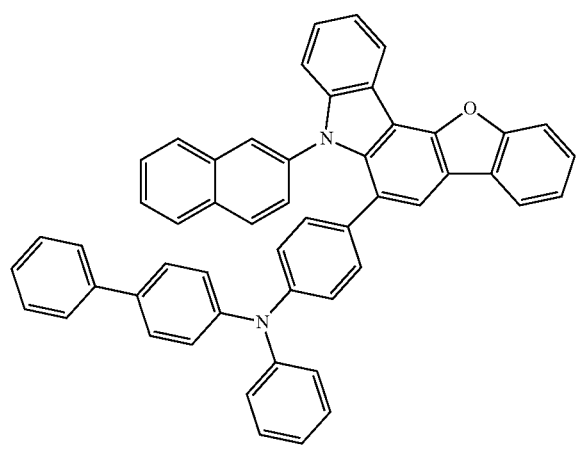
224 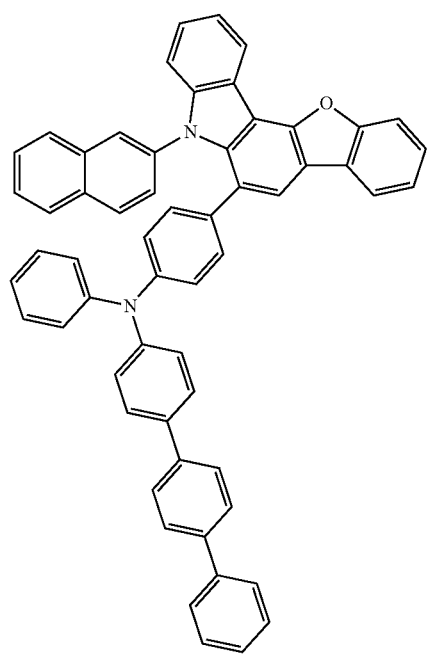

153 154
225
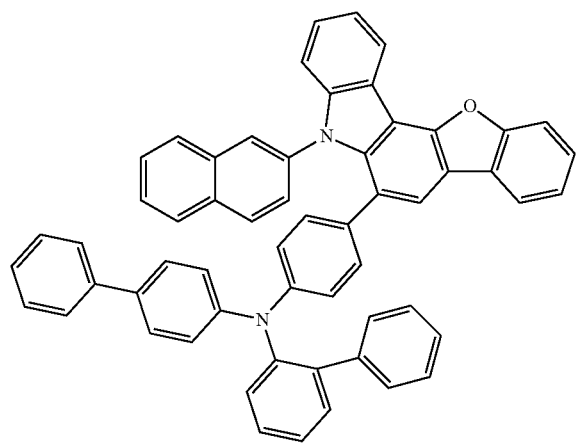
226
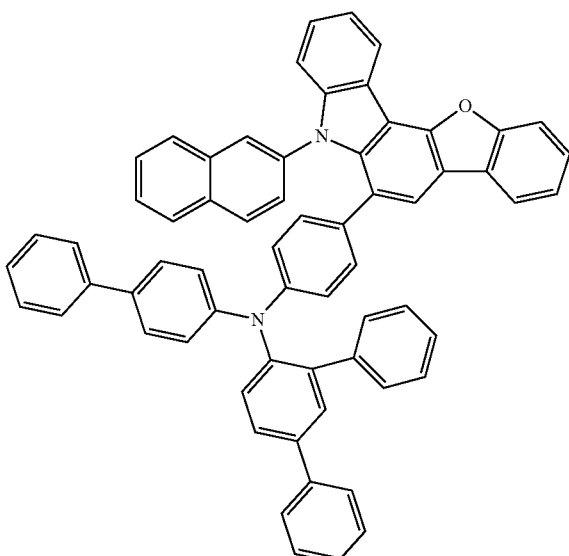
227
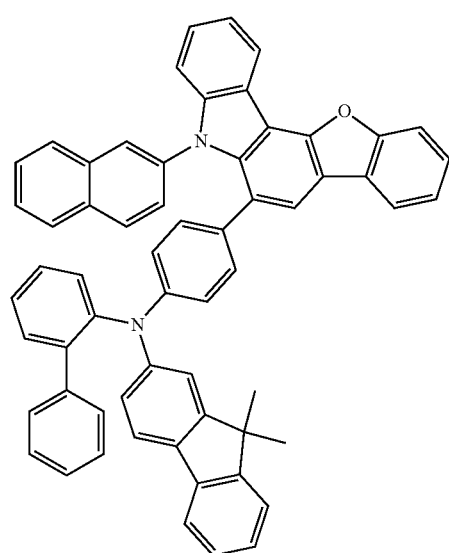
228
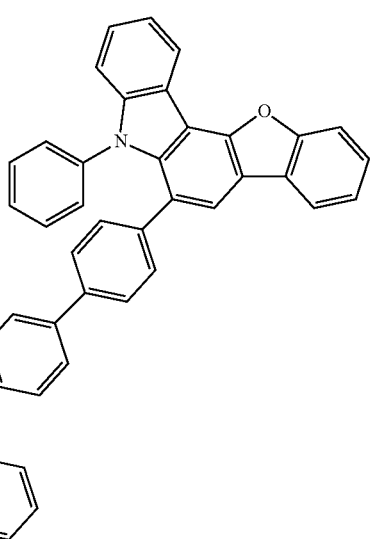
229
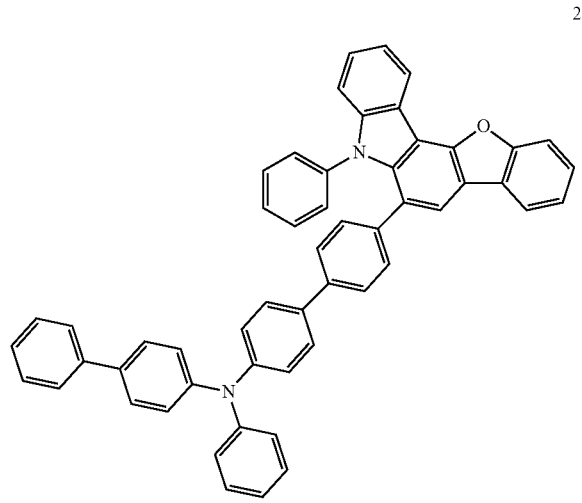
230
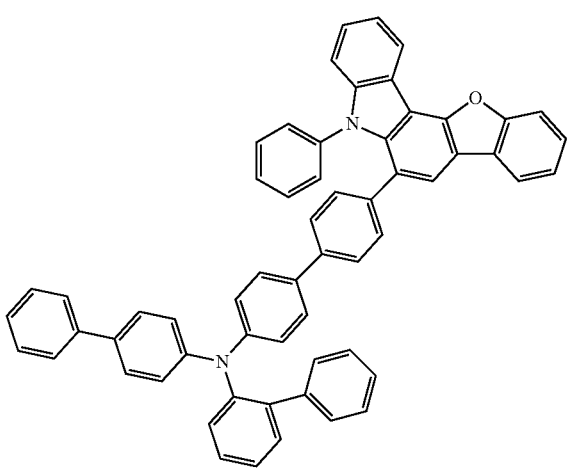

231
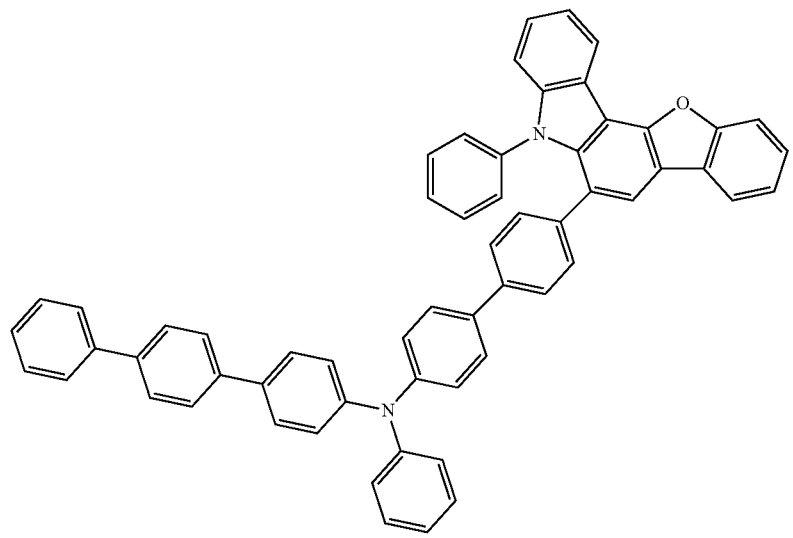
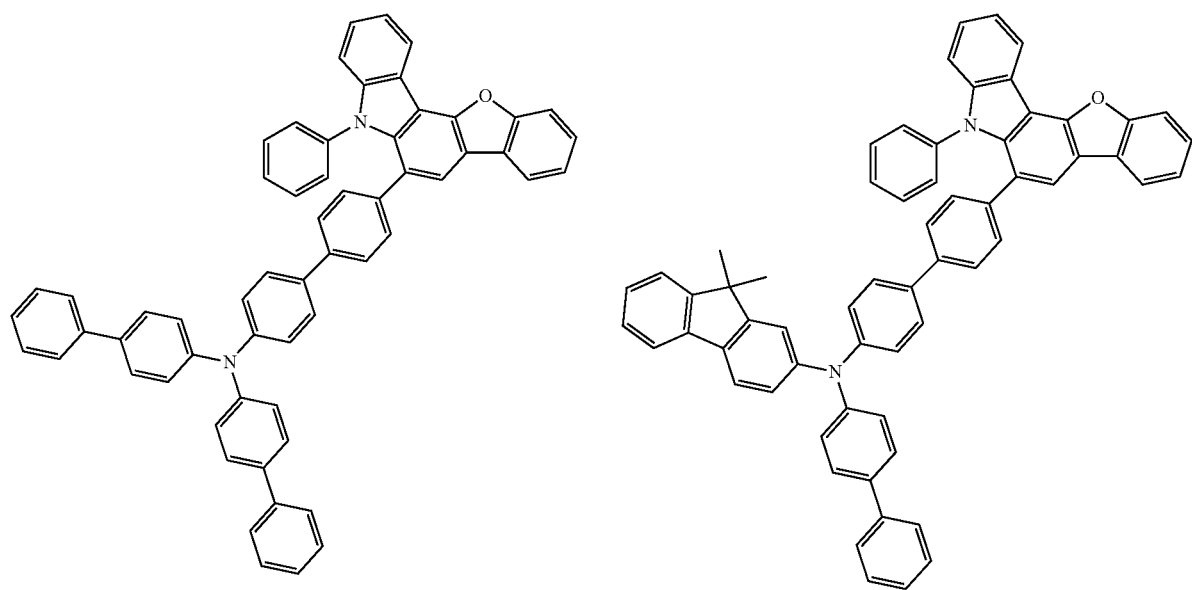

-continued
234 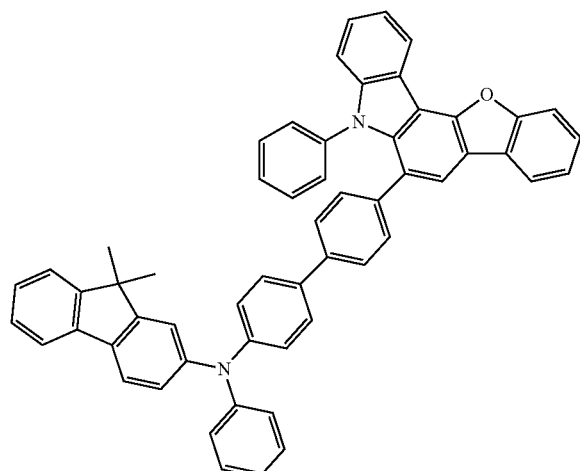
235 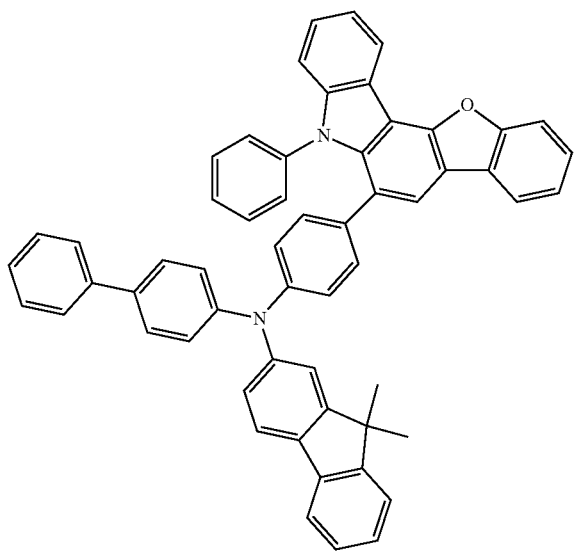
236 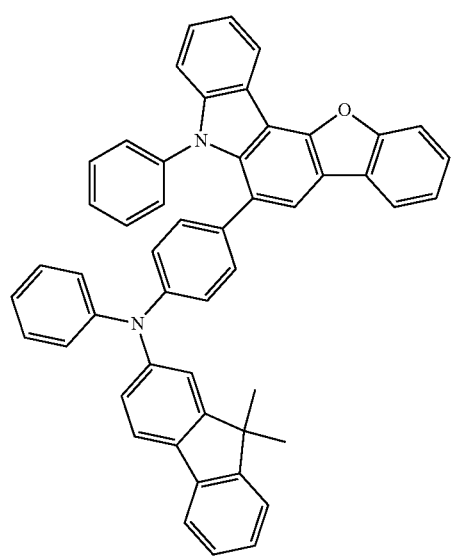
237 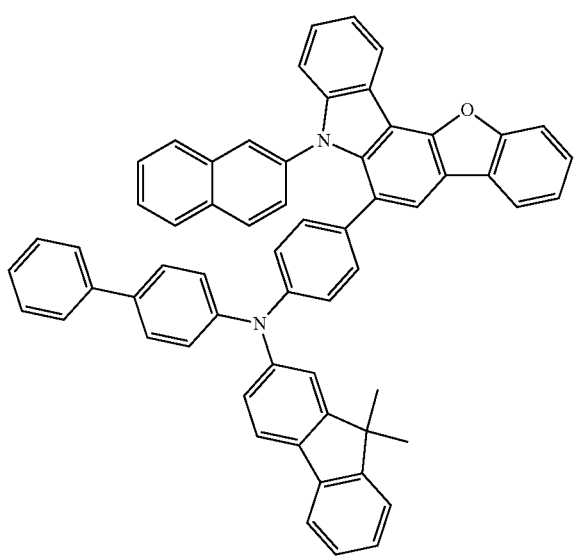

238
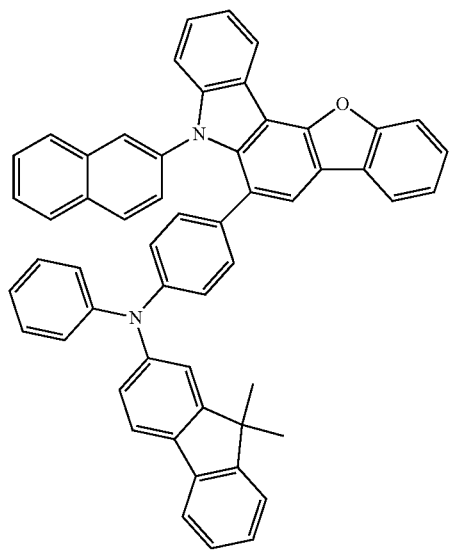
239
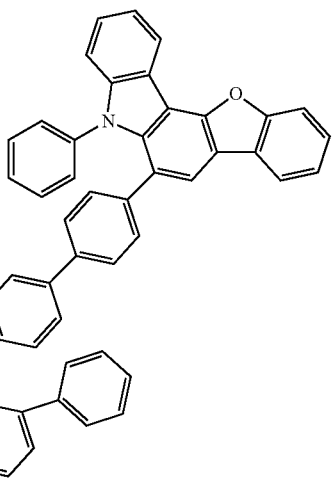
240
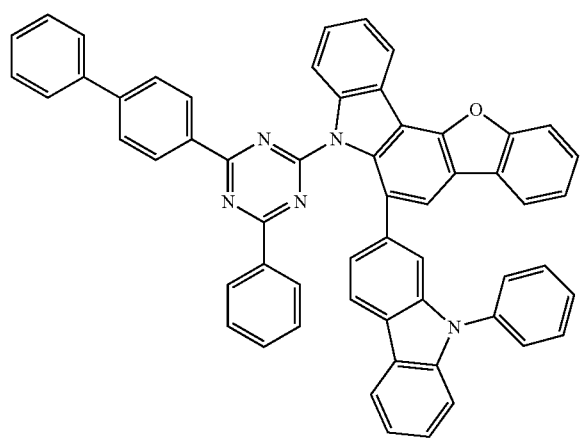
241
242
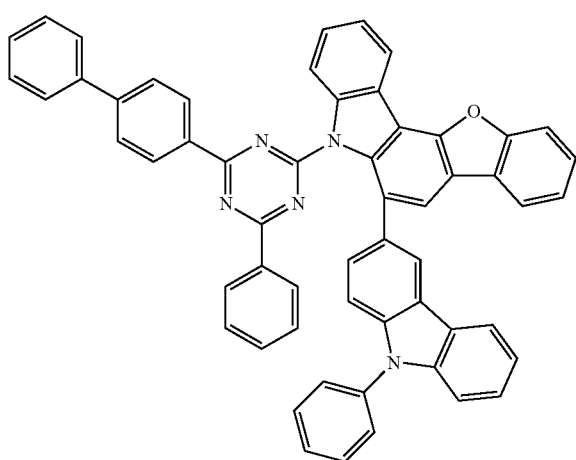
243
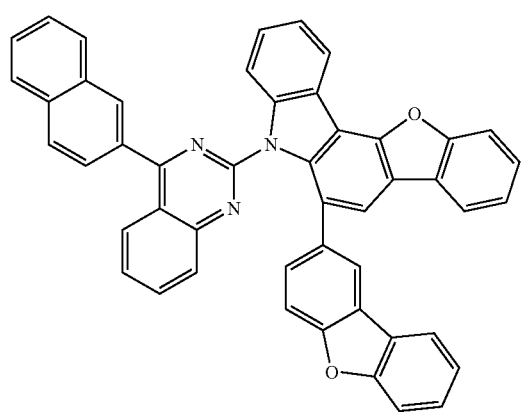

-continued
244
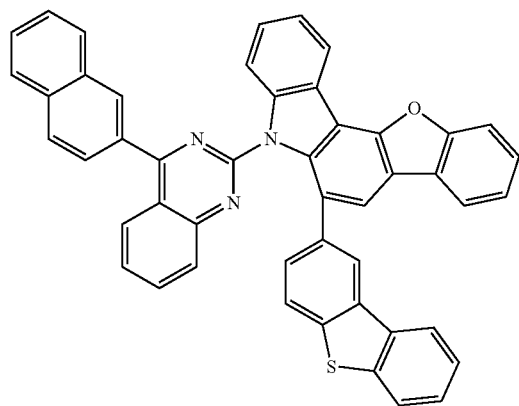
245
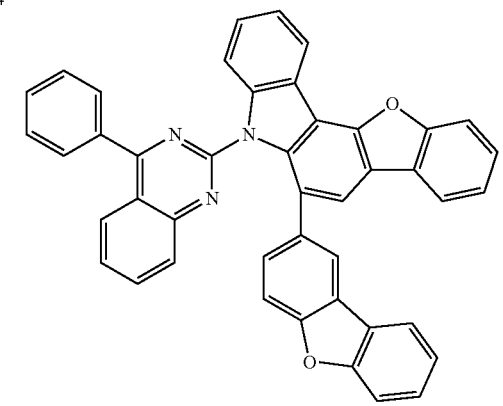
246
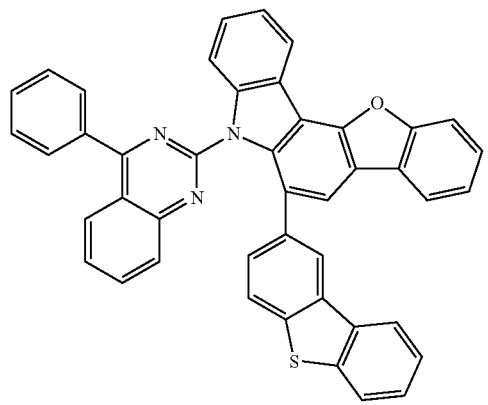
247
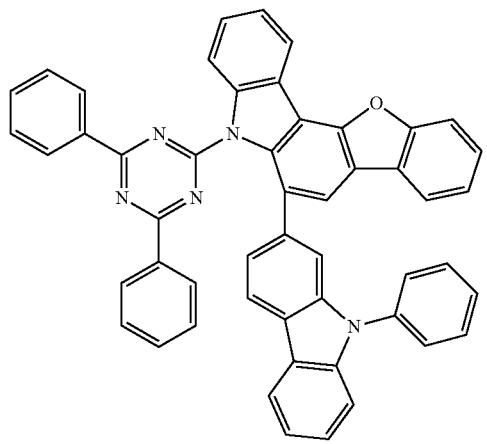
248
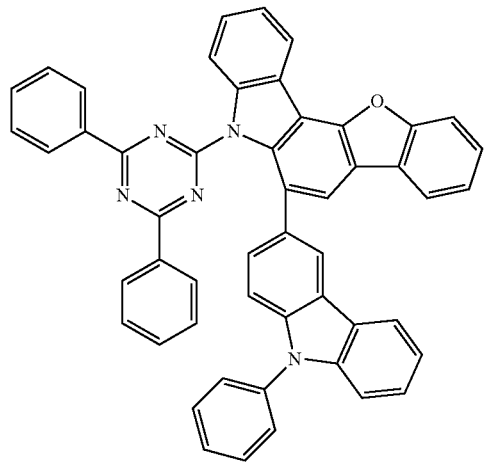
249
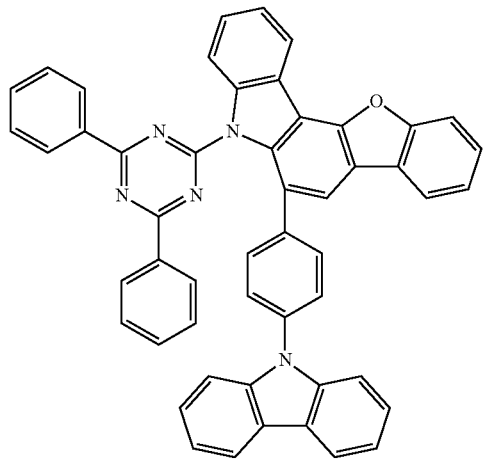

163 164
-continued
250 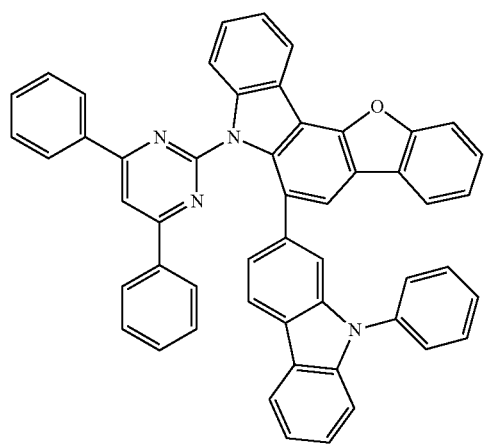 251 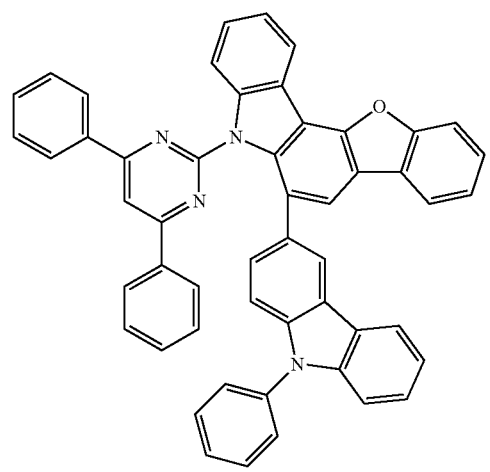
252 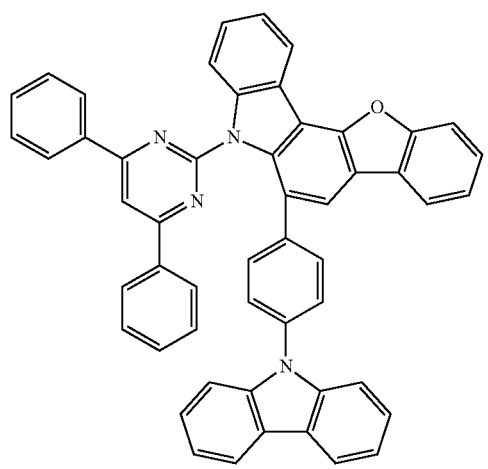 253 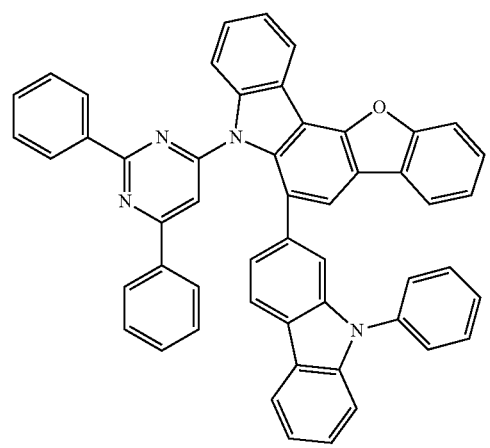
254 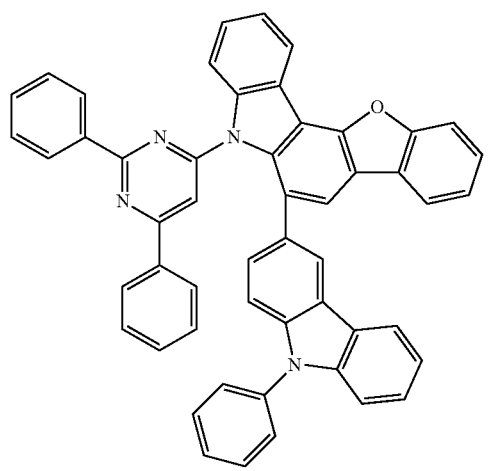 255 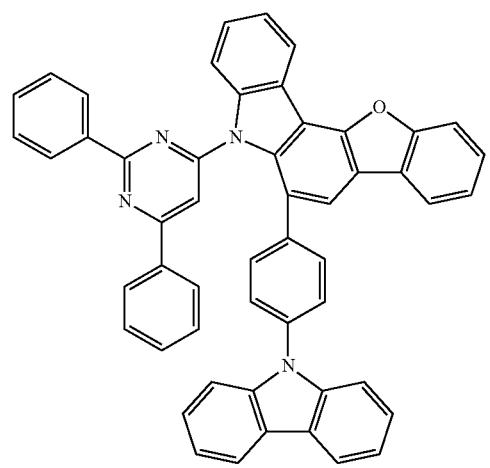

-continued
256
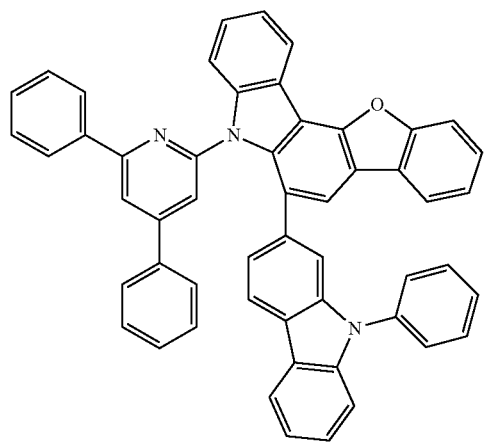
257
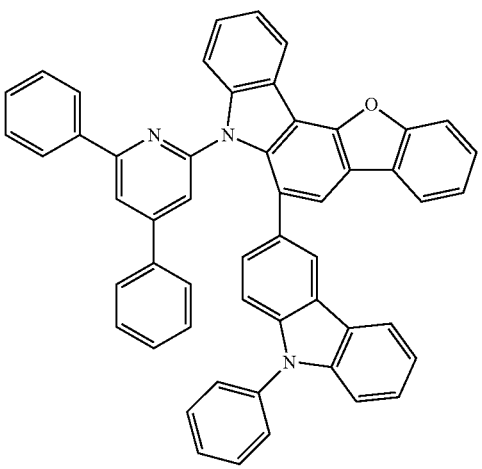
258
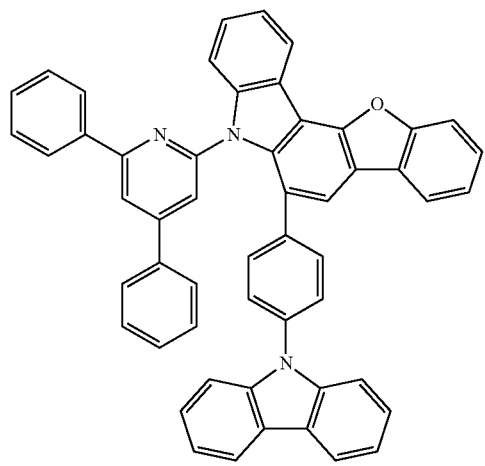
259
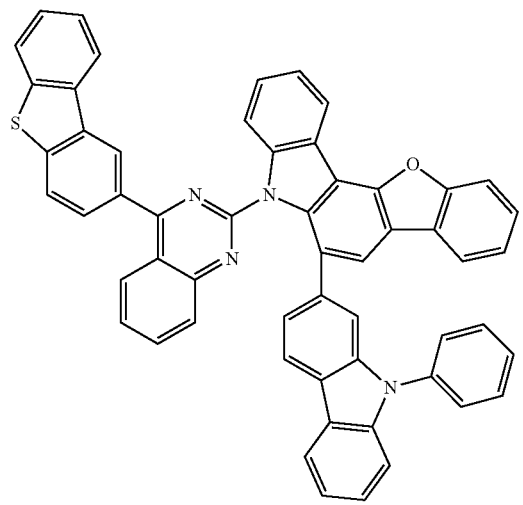
260
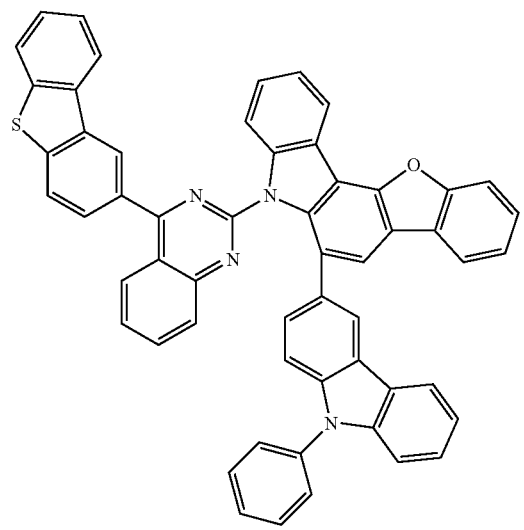
261
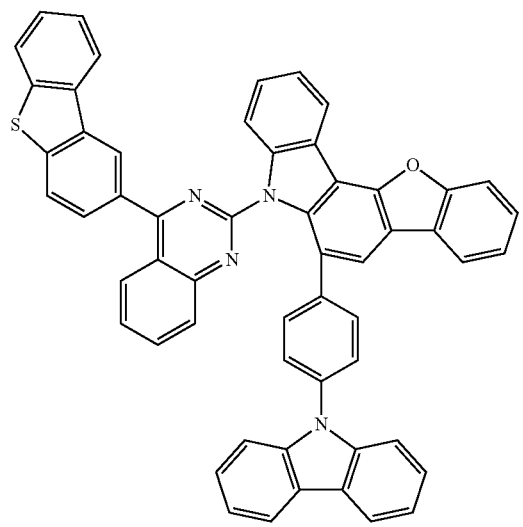

-continued
262
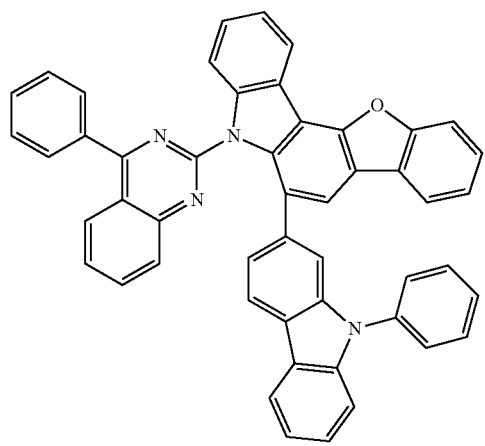
263
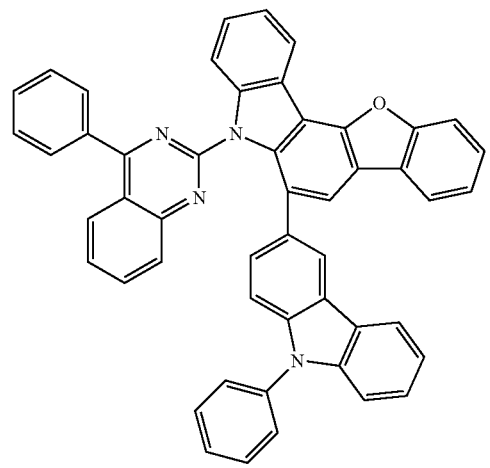
264
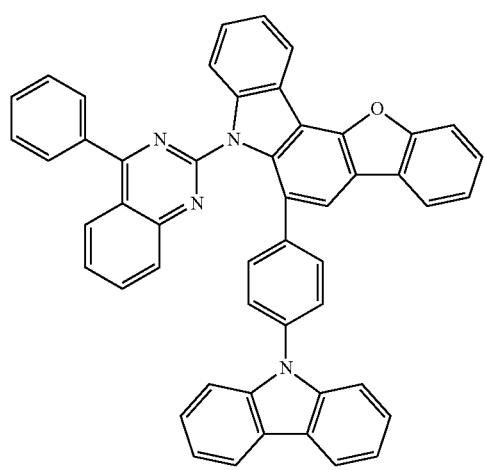
265
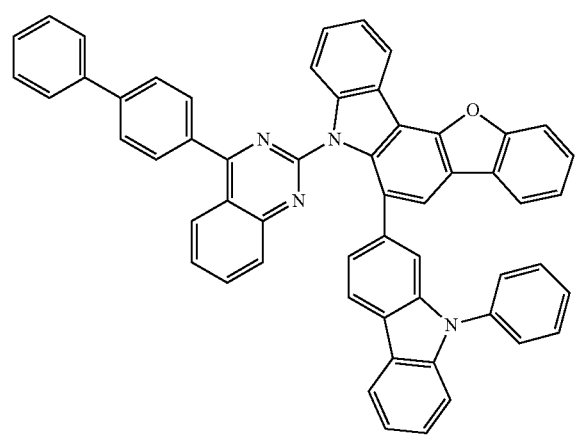
266
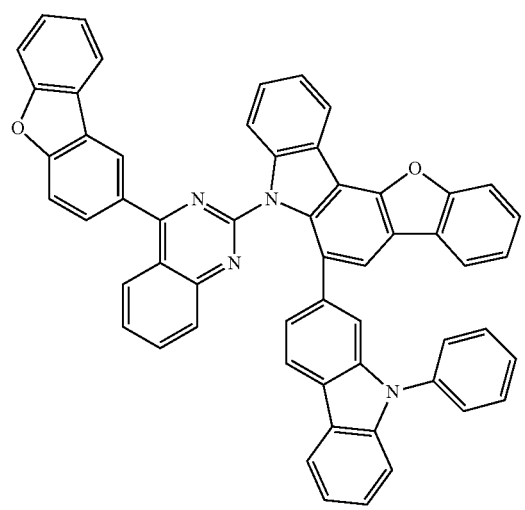
267
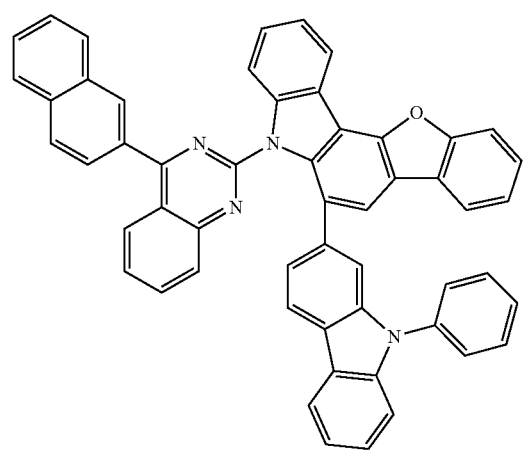

268
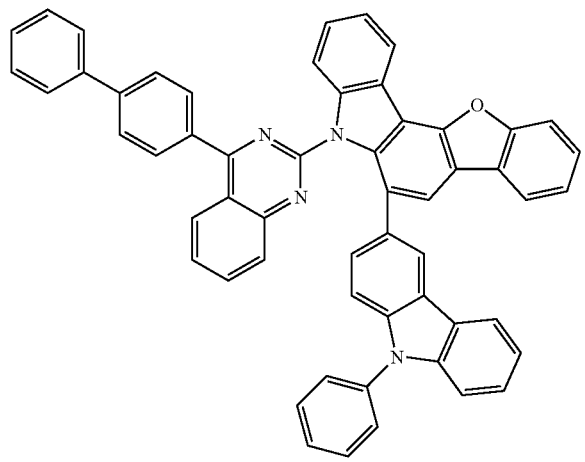
269
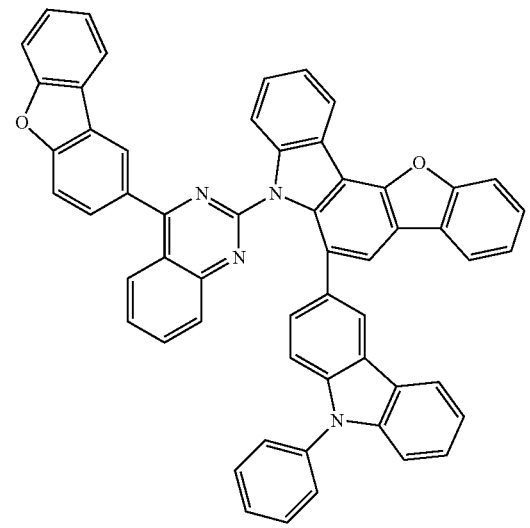
270
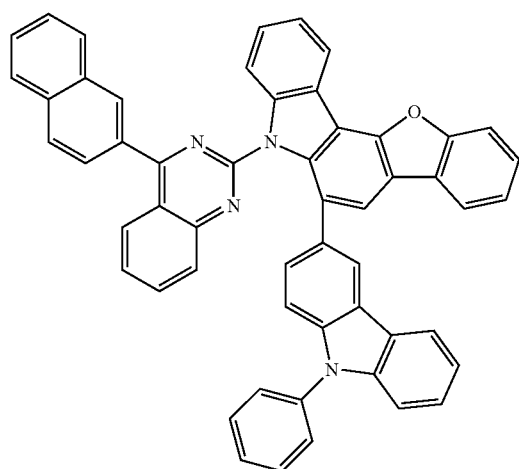
271
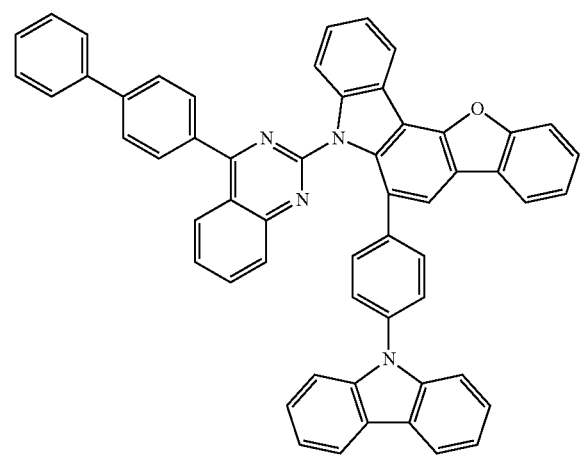
272
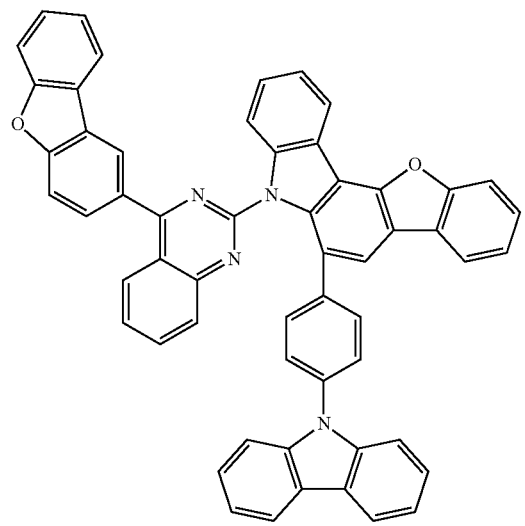
273
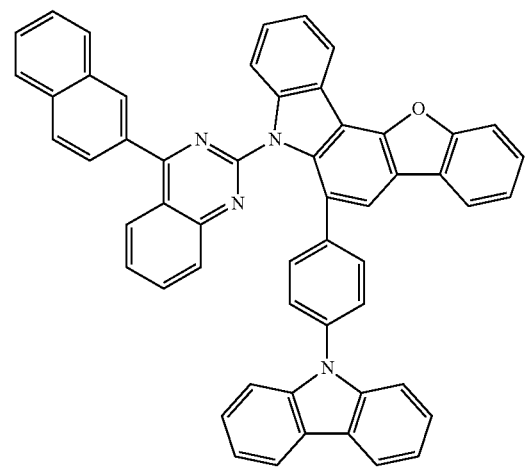

-continued
171
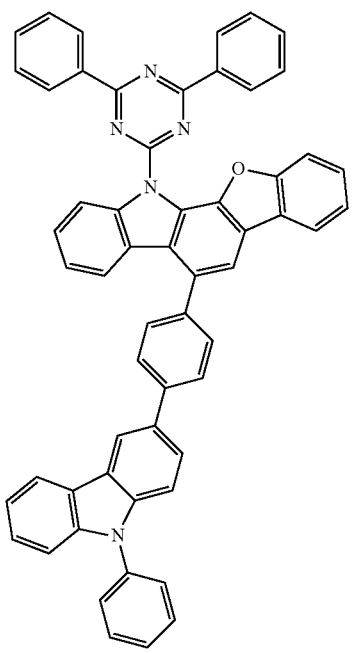
172
274
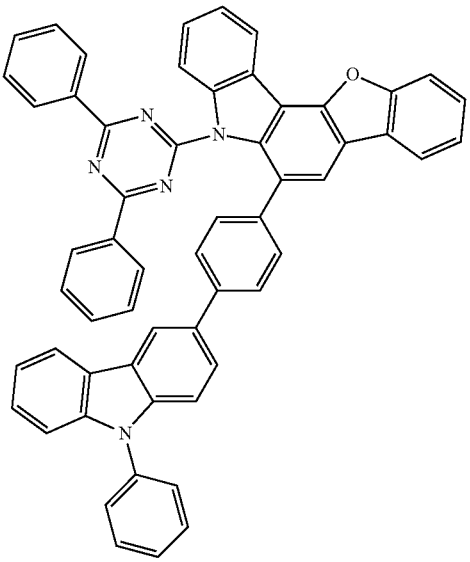
275
276
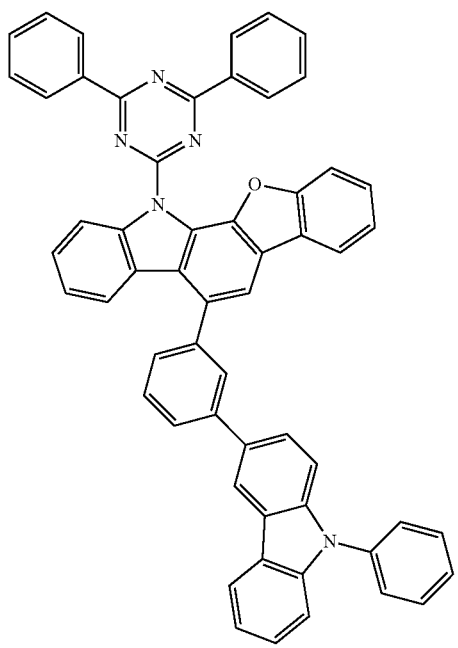
277
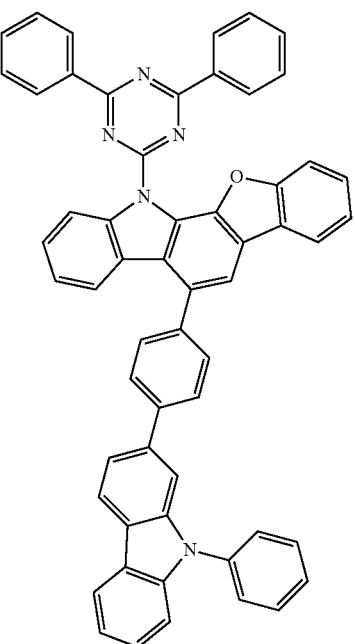

-continued
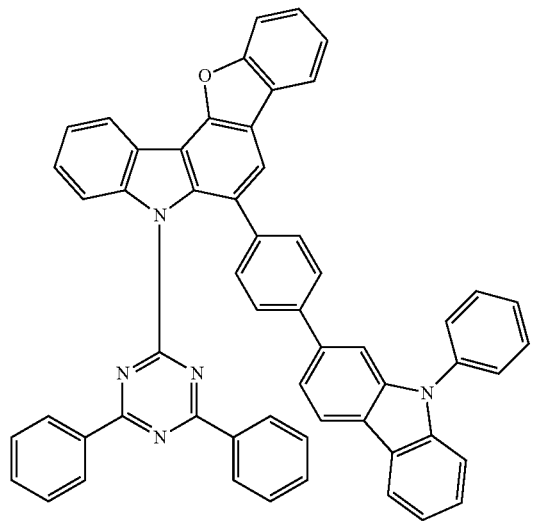
278
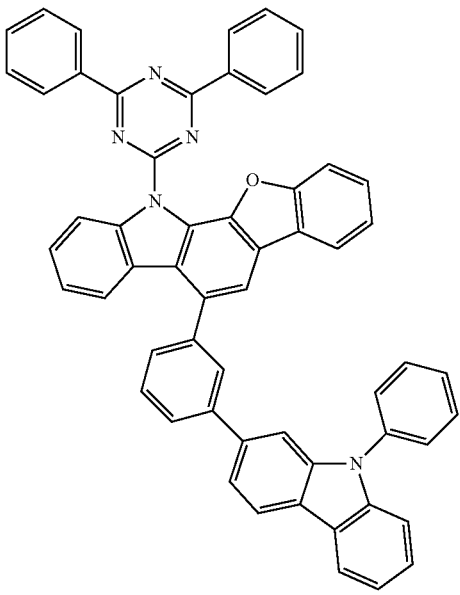
279
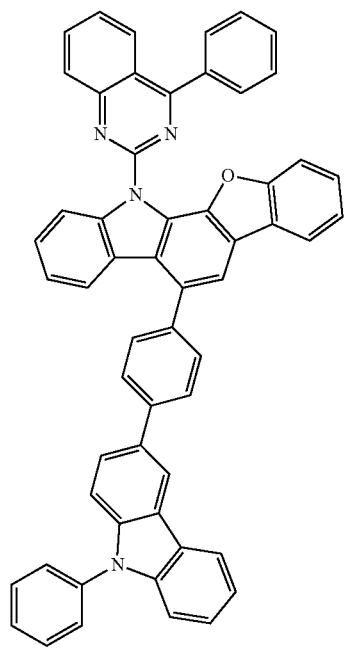
280
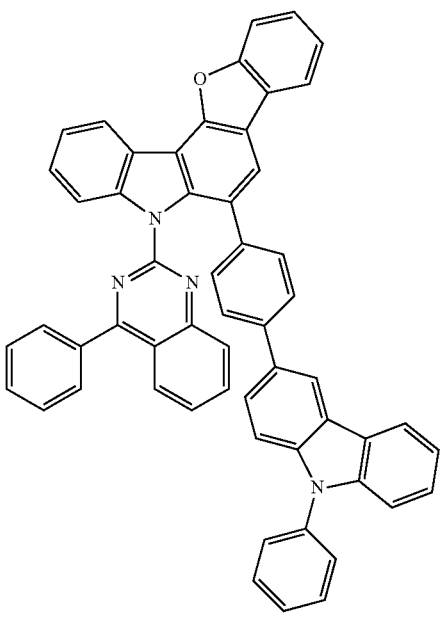
281

-continued
175
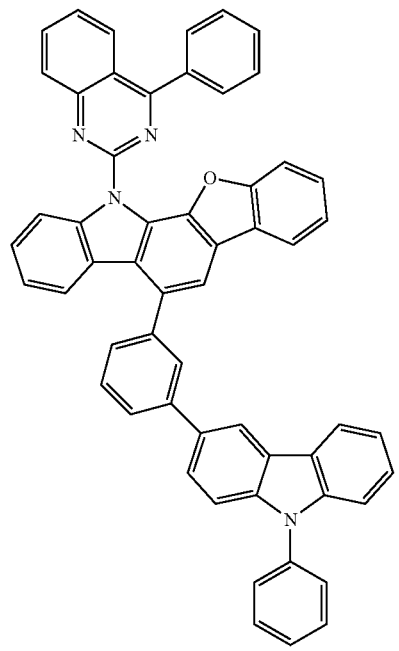
282
176
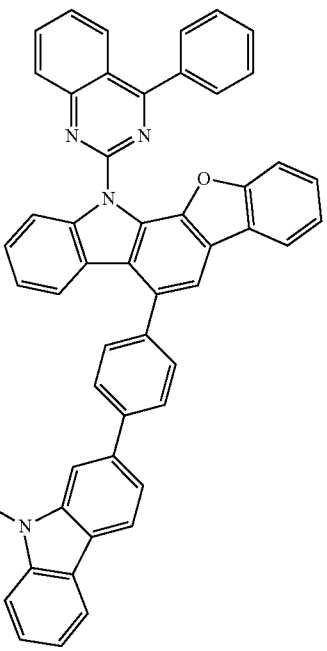
283
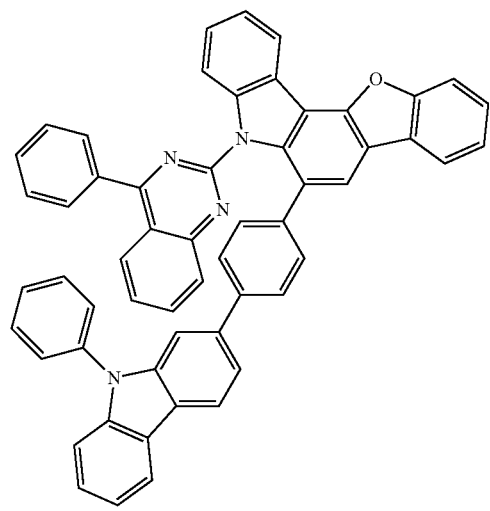
284
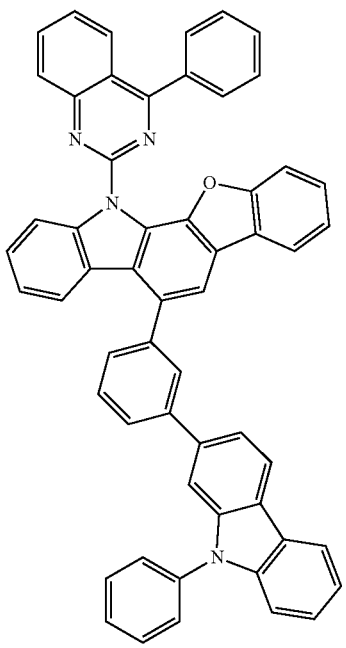
285

-continued
286
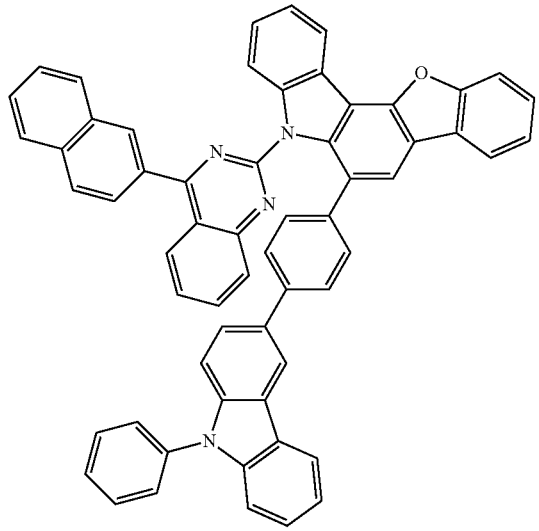
287
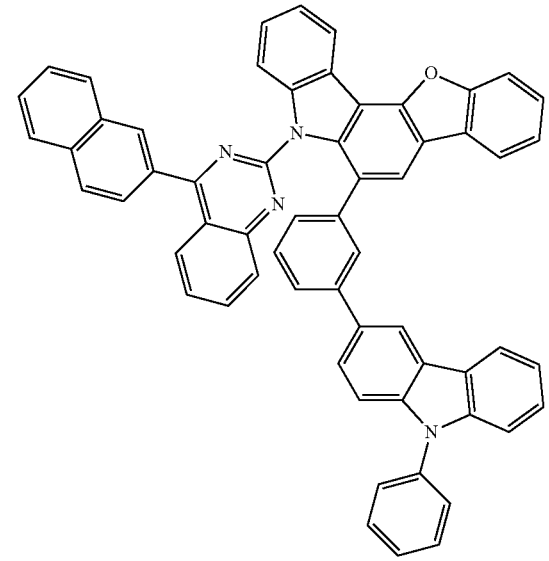
288
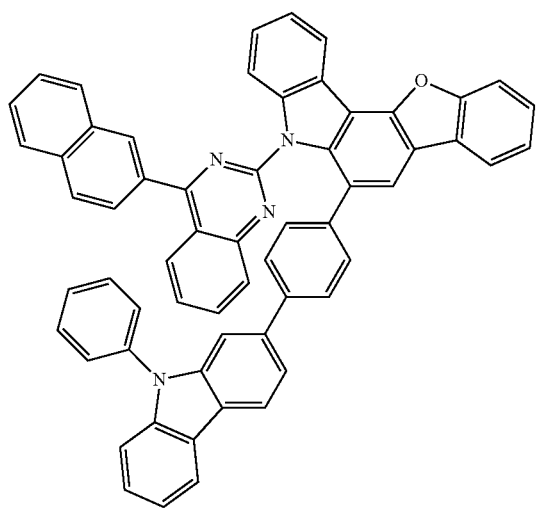
289
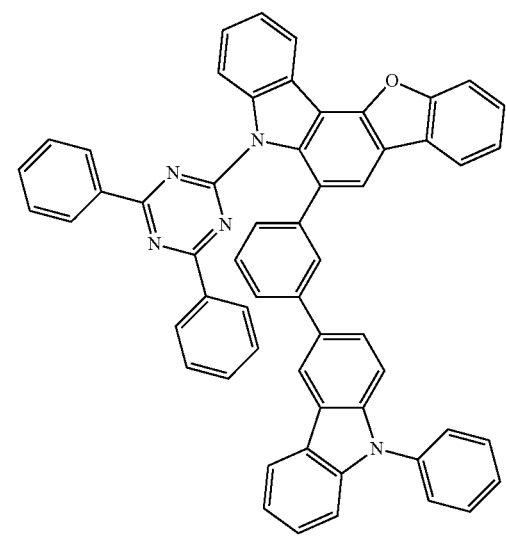
290
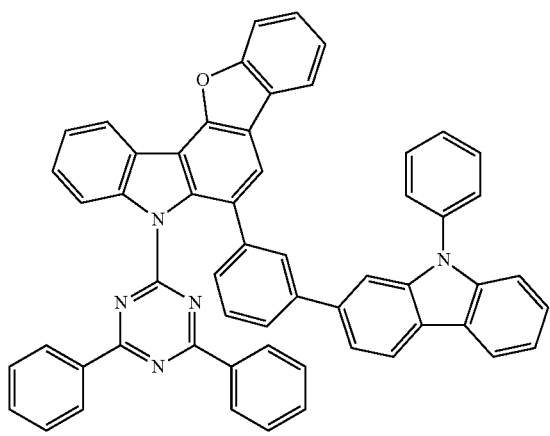
291
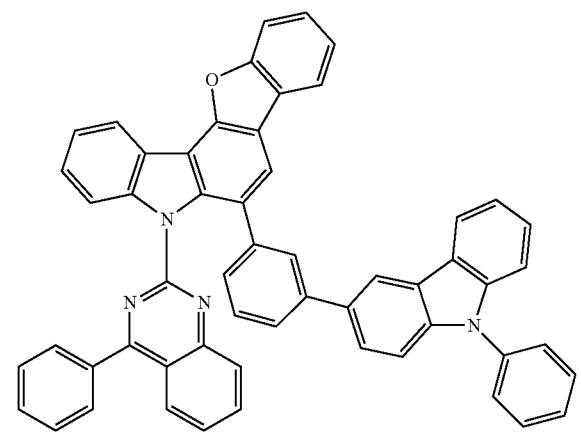

-continued
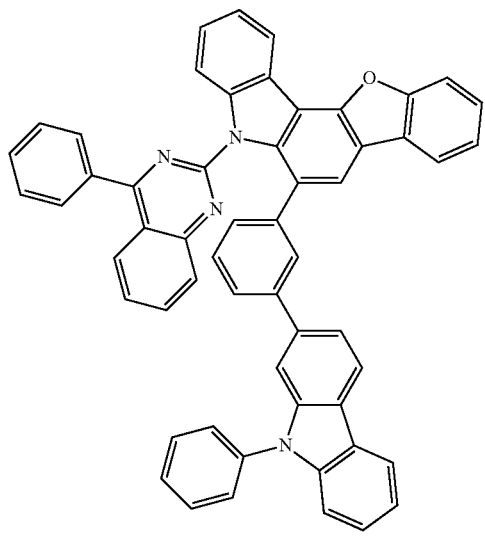
292
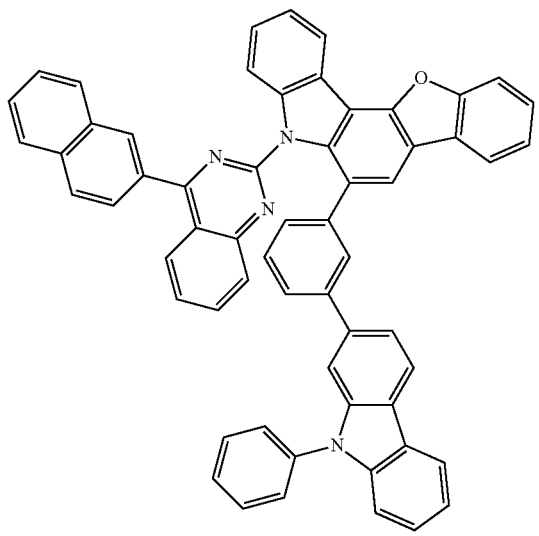
293
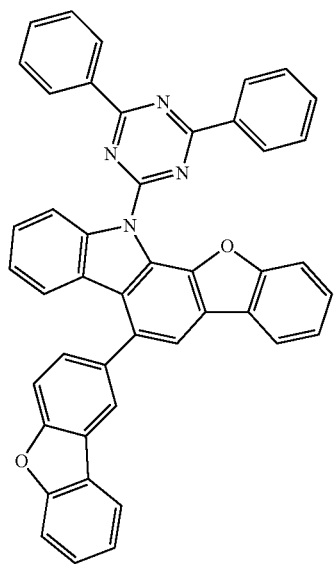
294
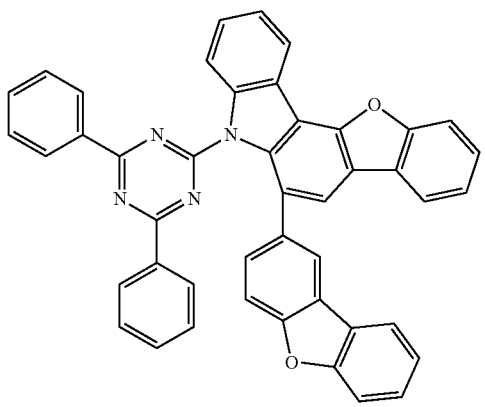
295
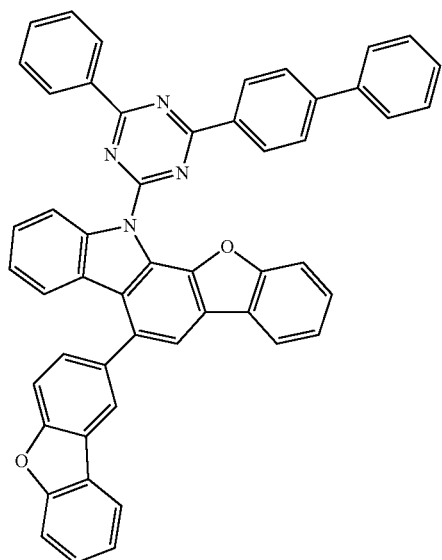
296
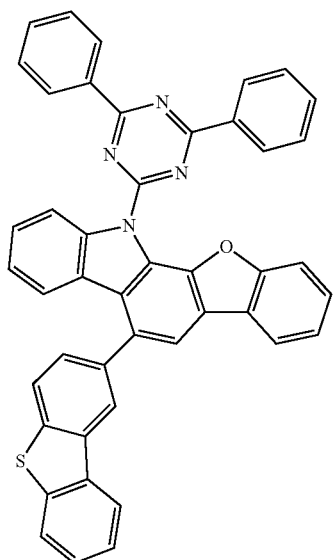
297

-continued
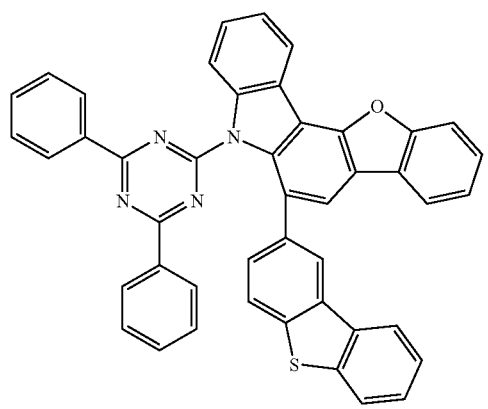
298
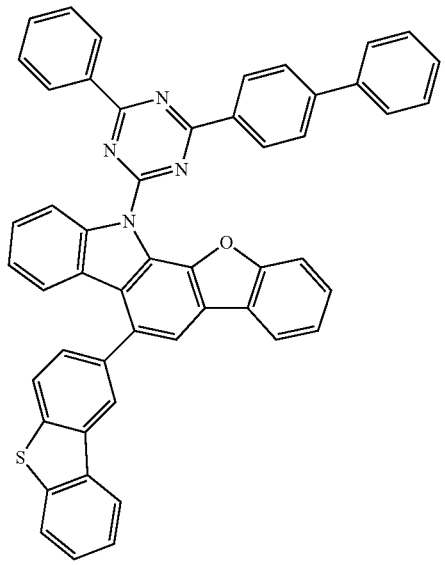
299
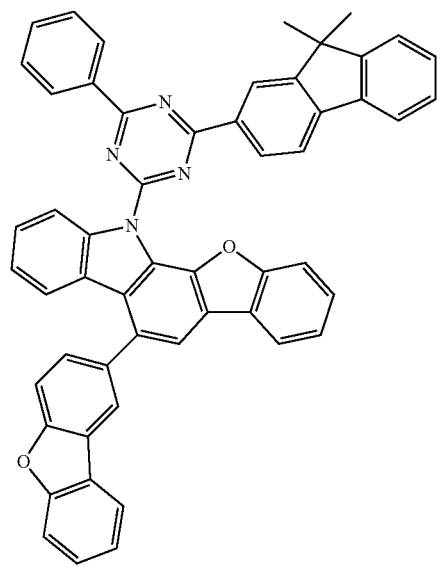
300
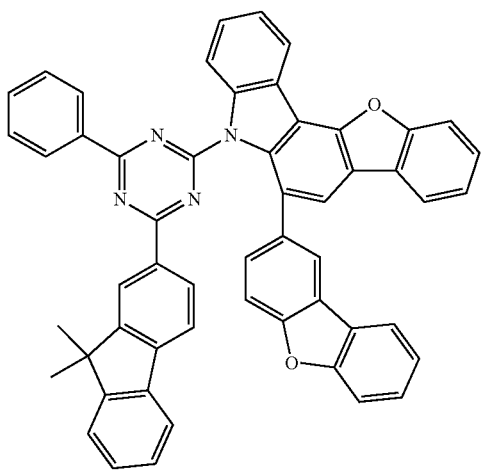
301

183
184
-continued
| 302 | 303 |
|---|---|
| 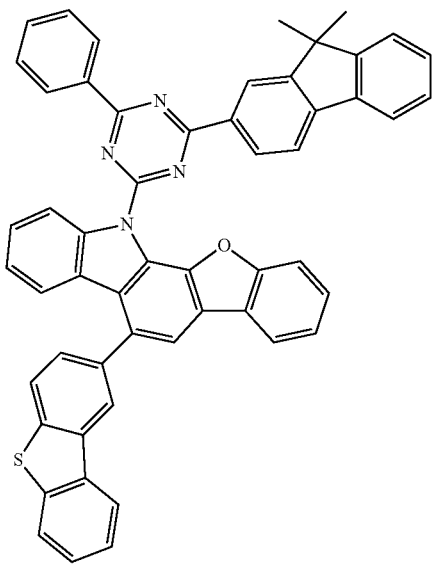 | 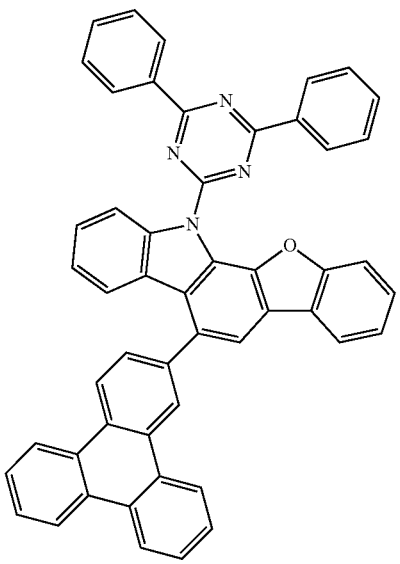 |
| 304 | 305 |
| 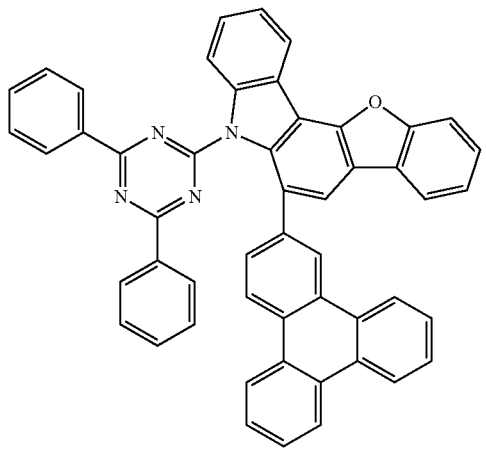 | 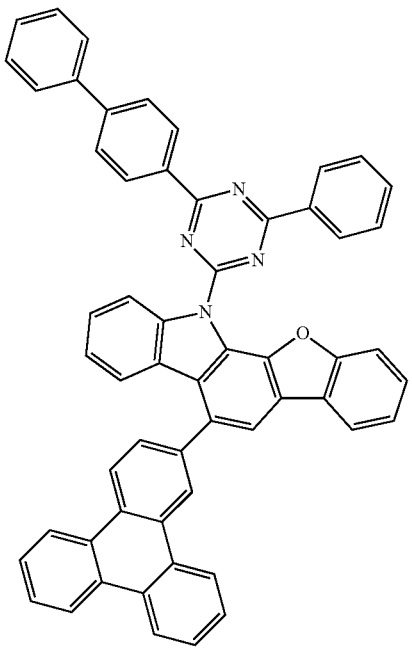 |

-continued
305
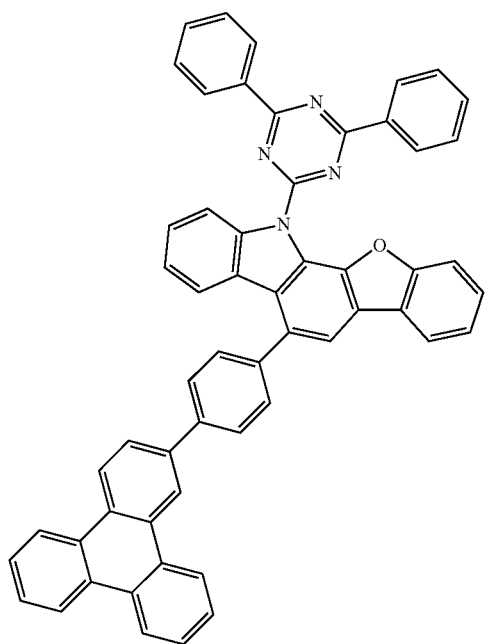
306
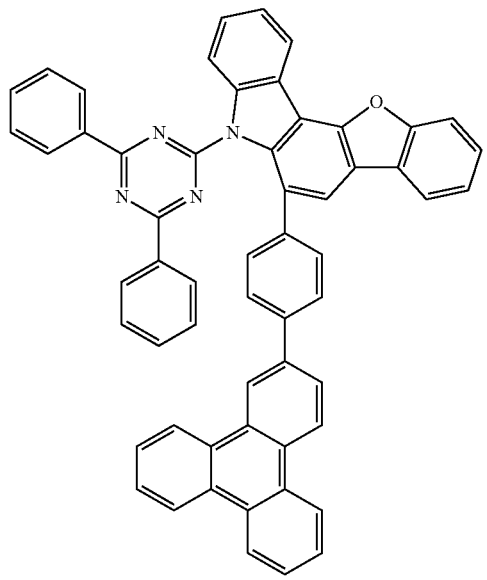
307
308
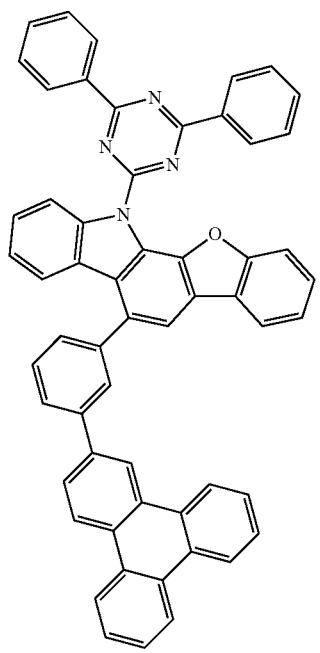
309
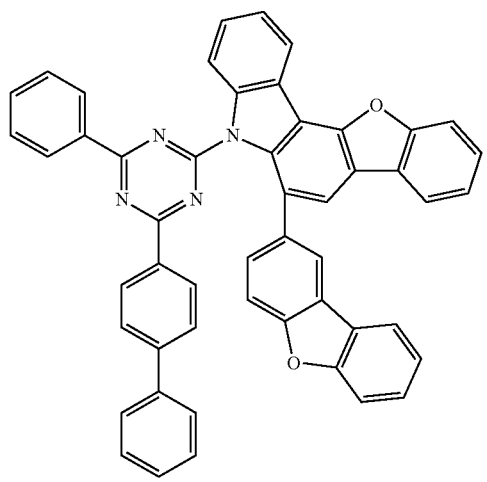

-continued
187
310
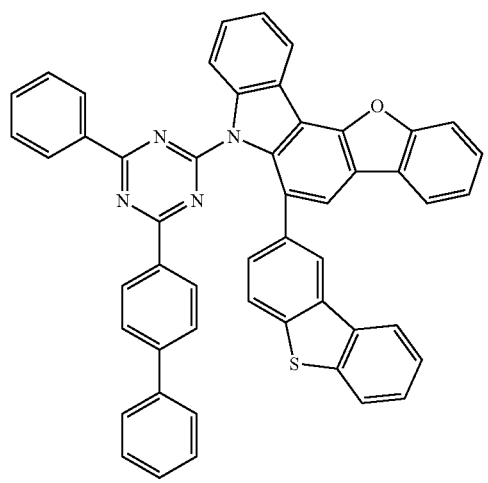
311
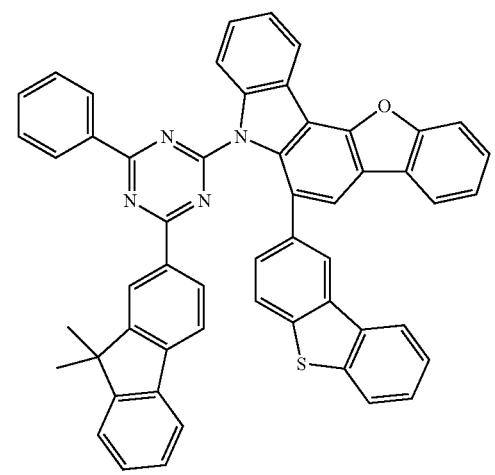
312
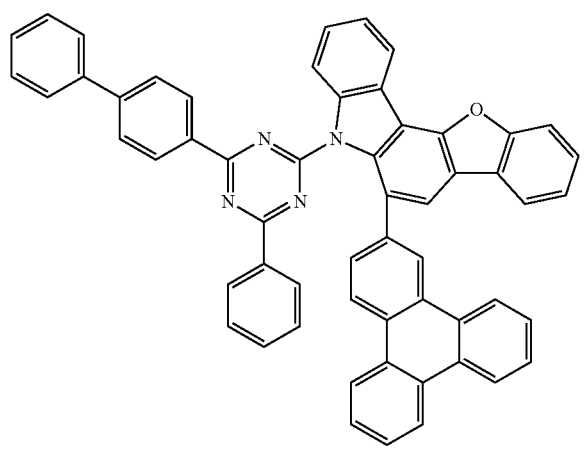
188
313
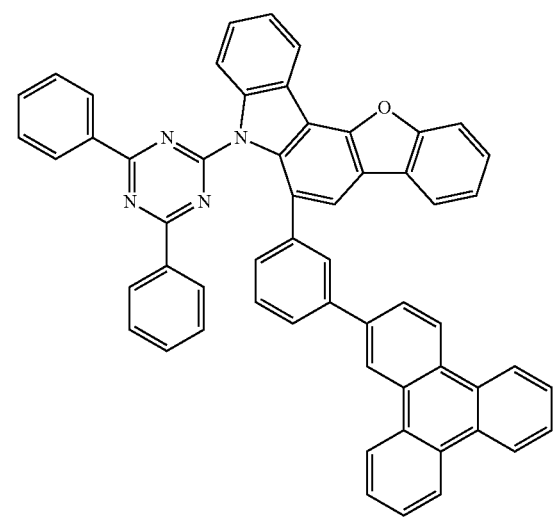
314
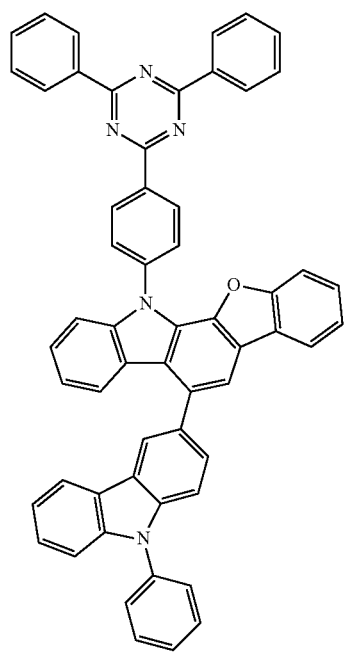
315
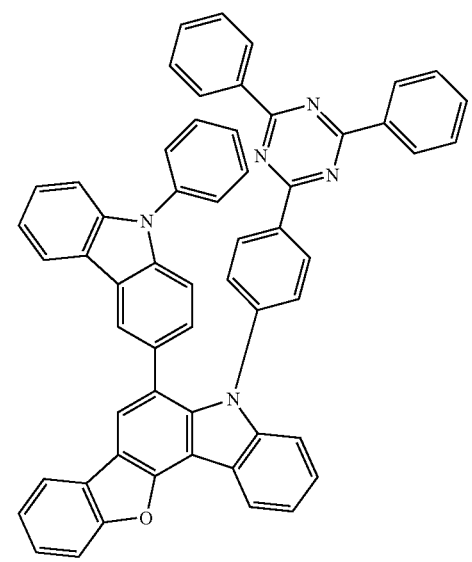

-continued
189
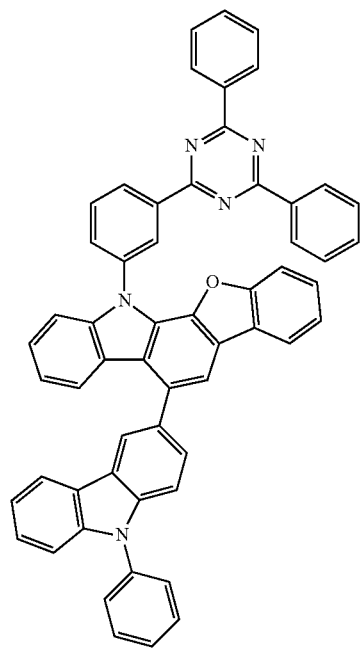
316
190
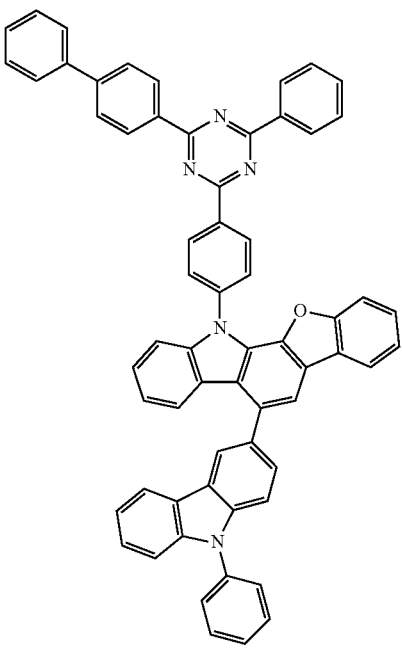
317
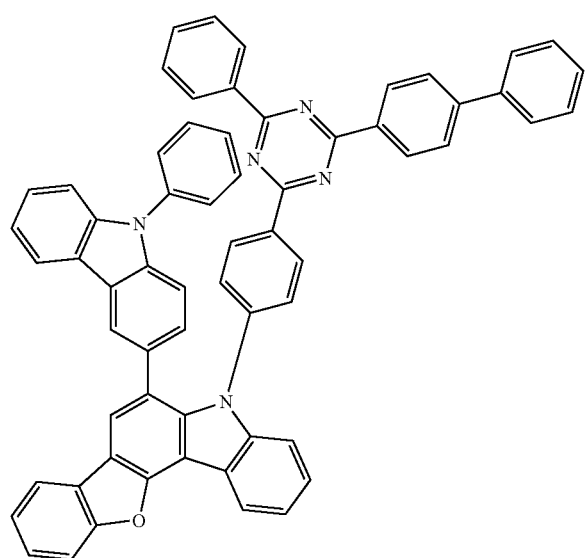
318
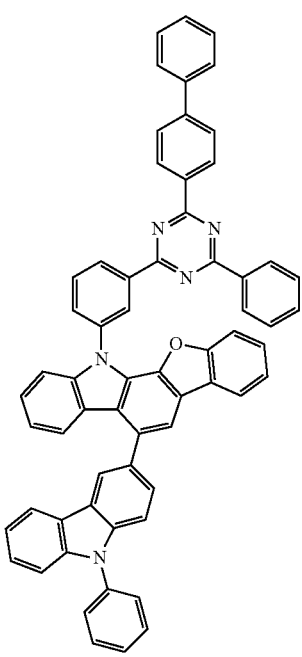
319

191
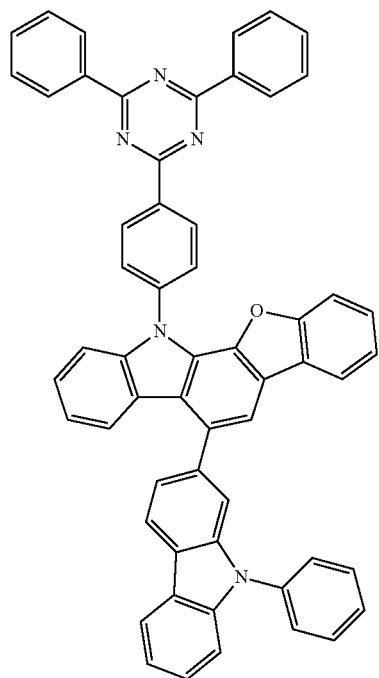
192
-continued
320
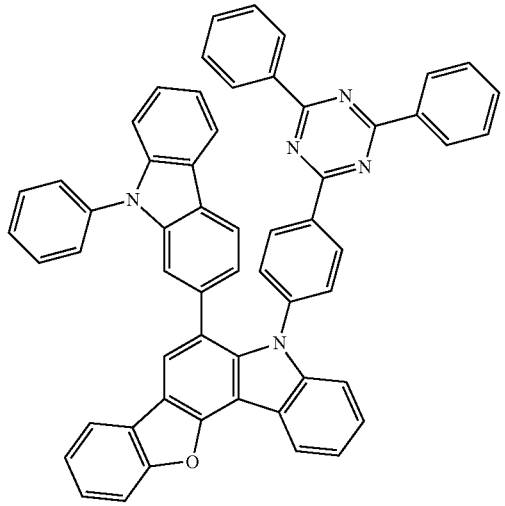
321
322
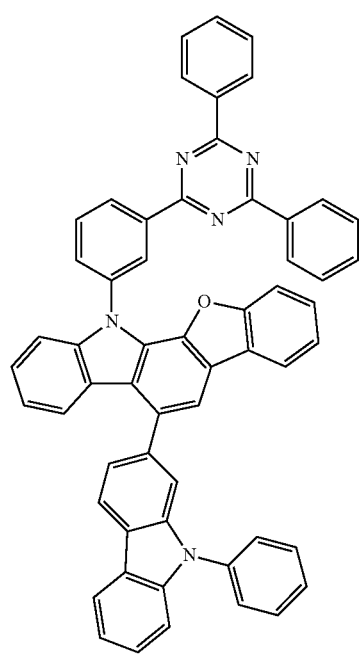
323
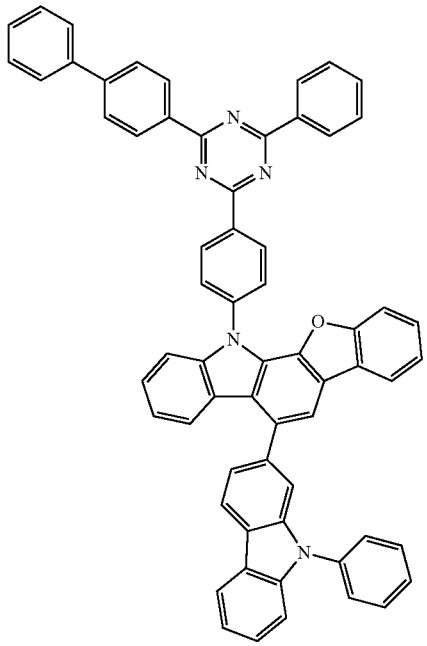

-continued
324
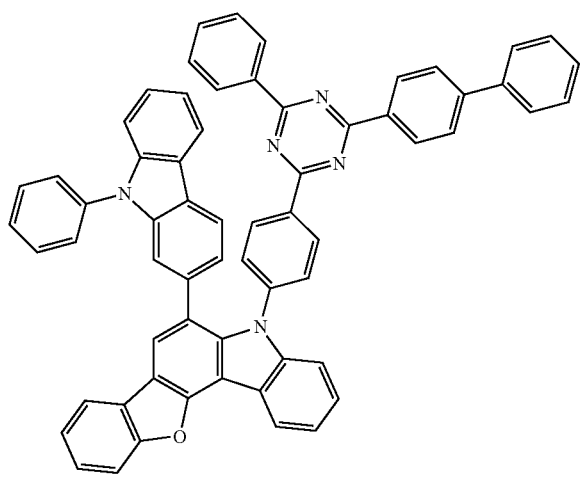
325
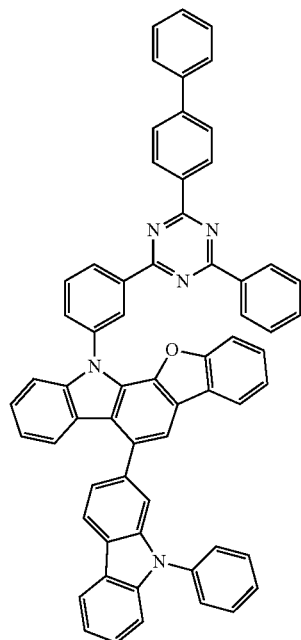
326
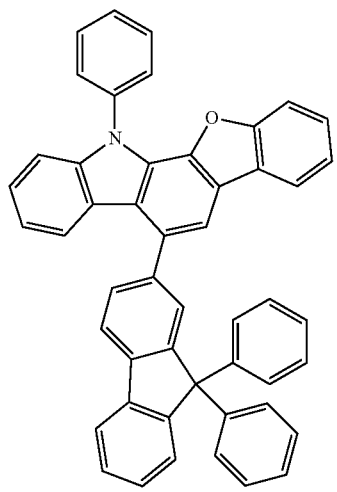
327
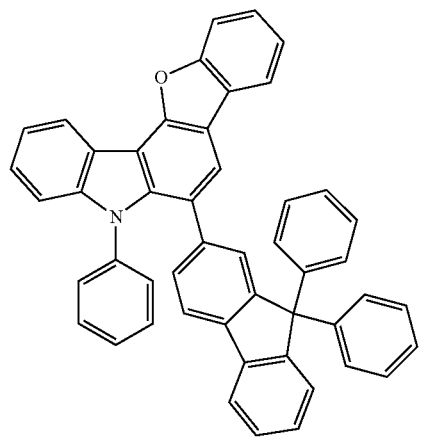

328
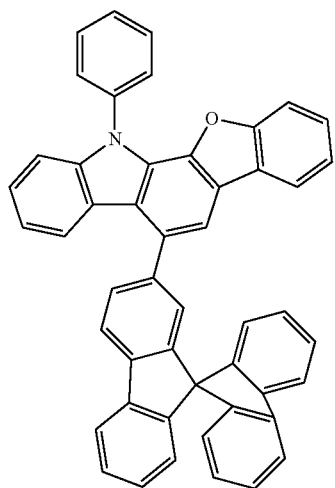
329
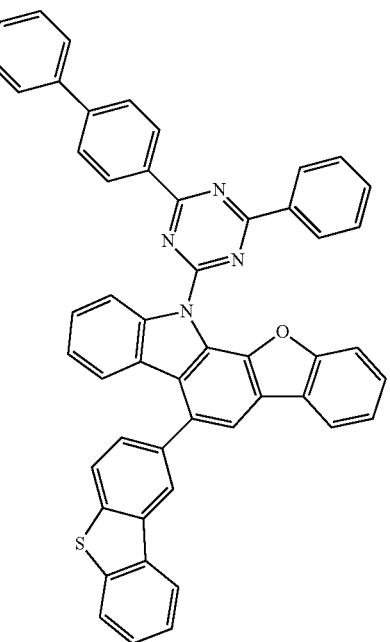
330
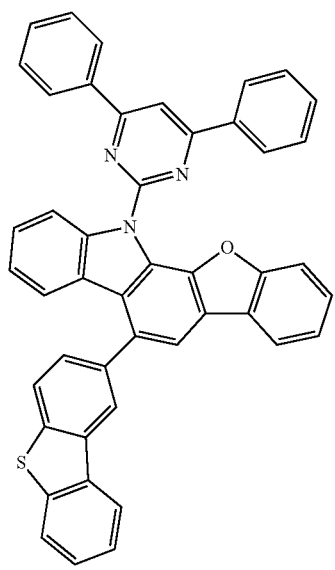
331
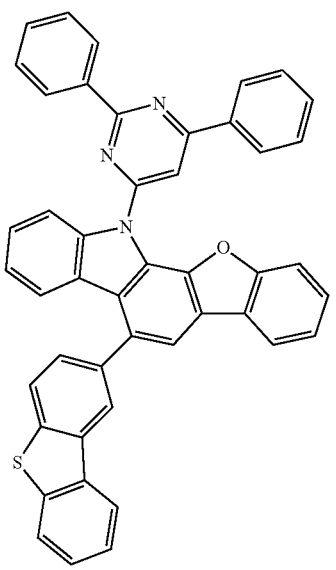

-continued
332
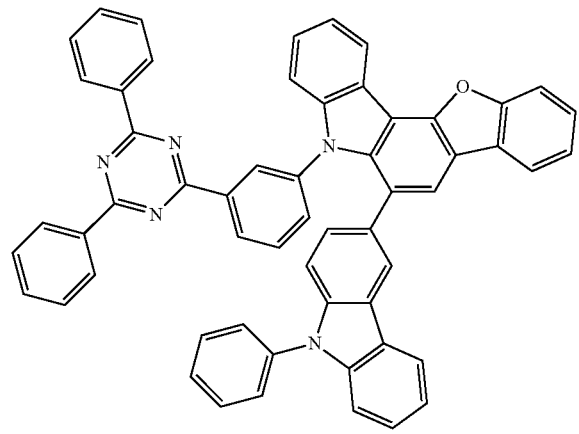
333
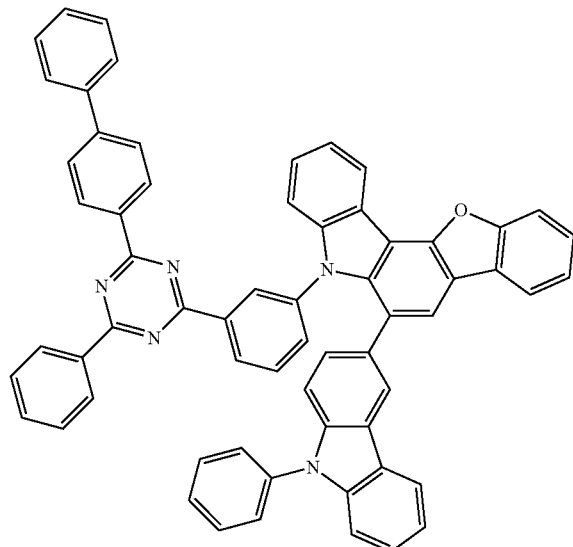
334
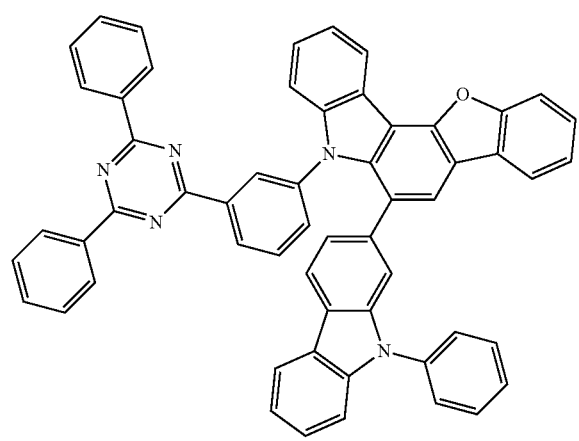
335
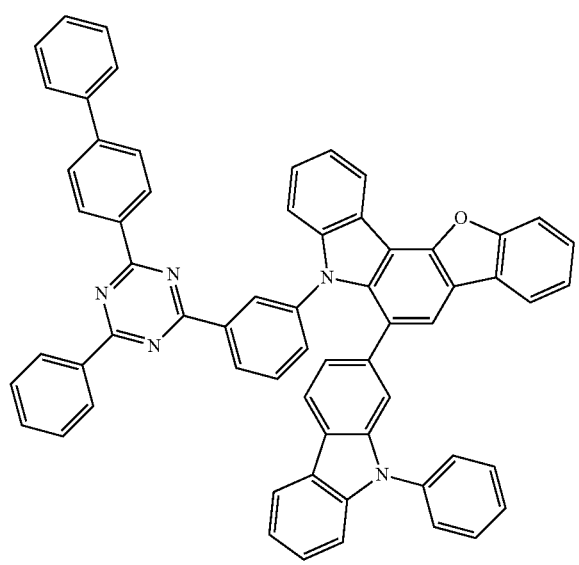

-continued
336 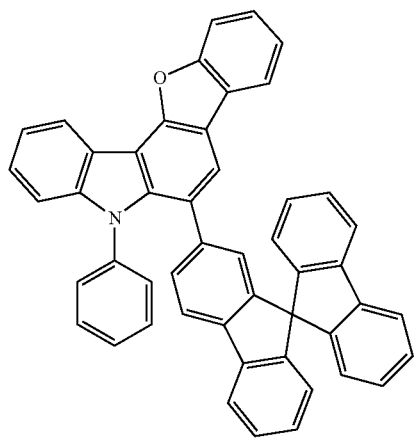
337 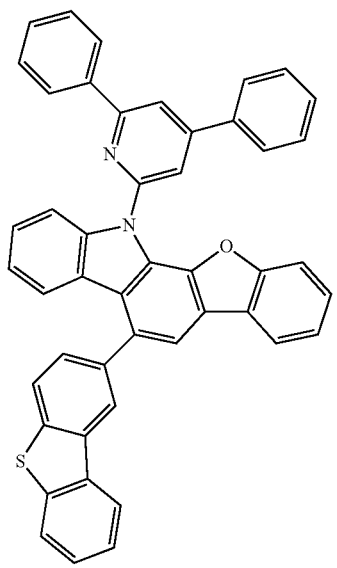
338 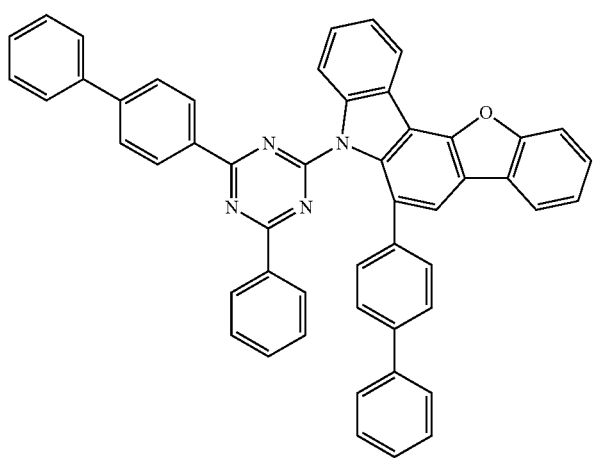
339 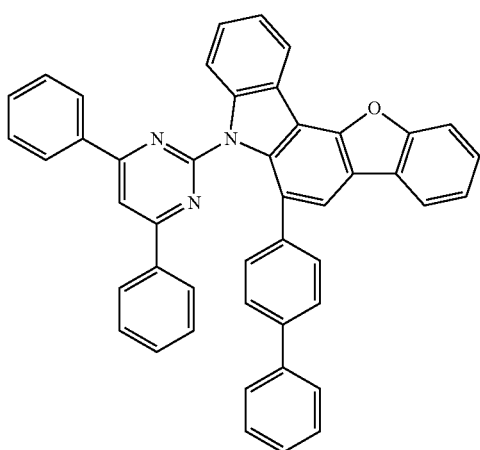
340 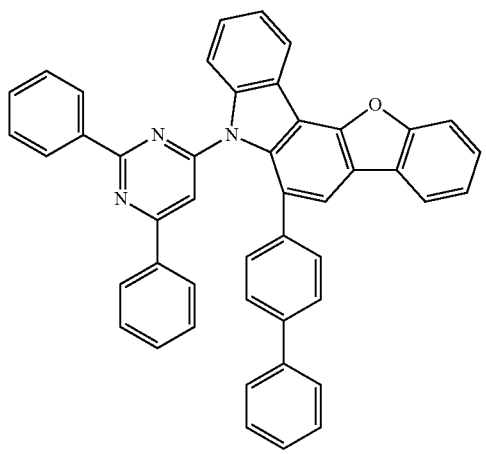
341 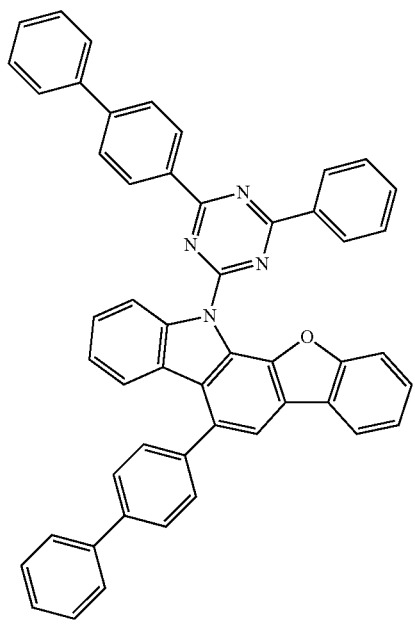

-continued
| 342 | 343 |
|---|---|
| 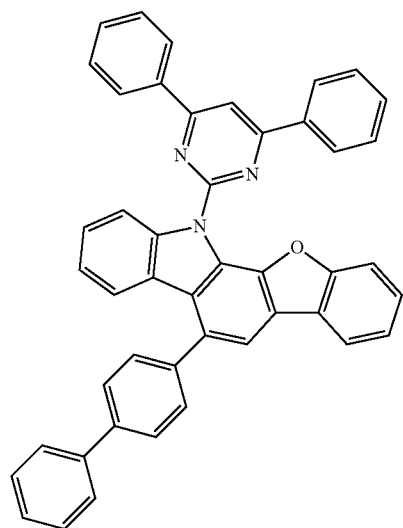 | 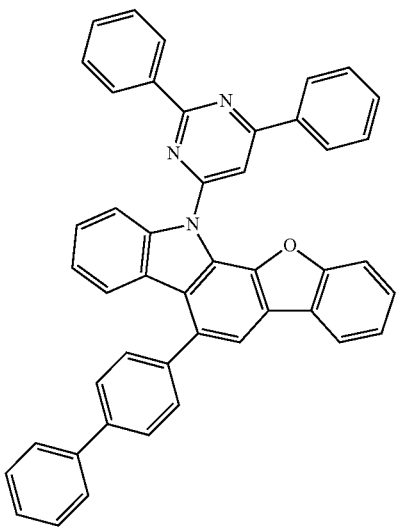 |
| 344 | 345 |
|---|---|
| 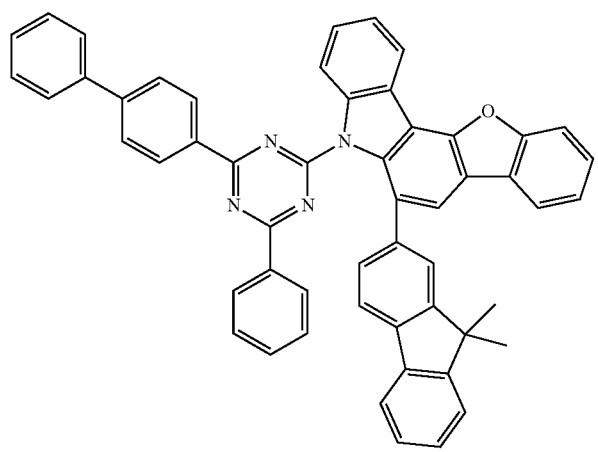 | 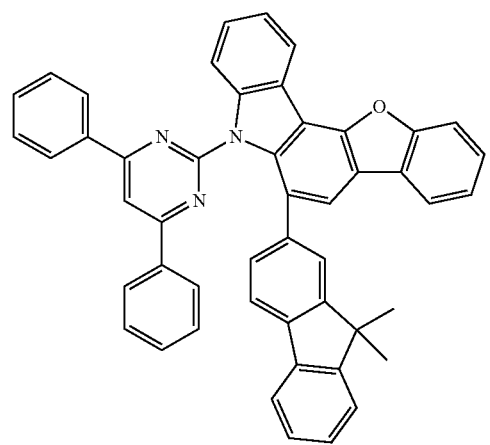 |
| 346 | 347 |
|---|---|
| 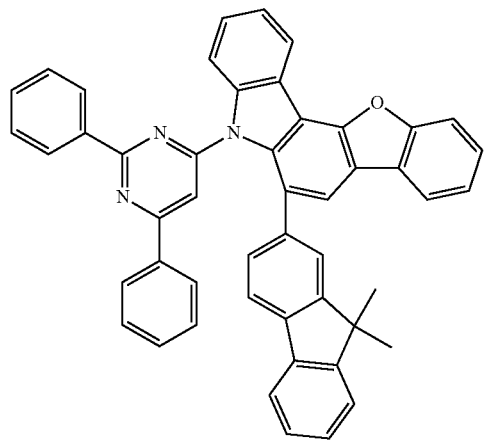 | 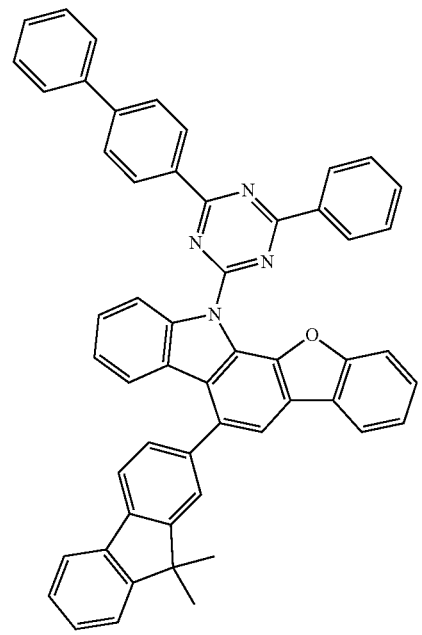 |

-continued
348
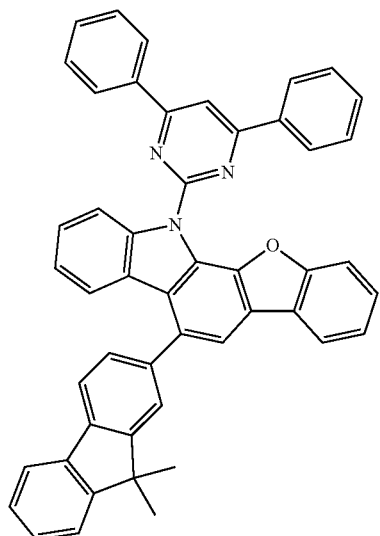
349
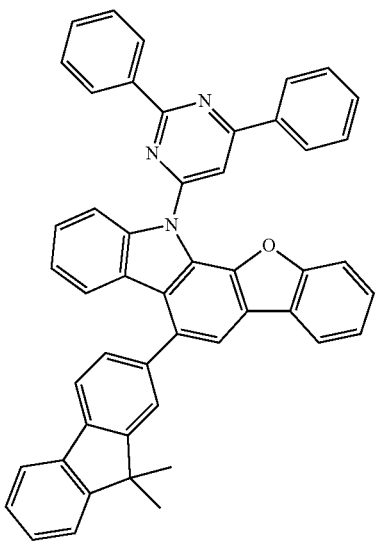
350
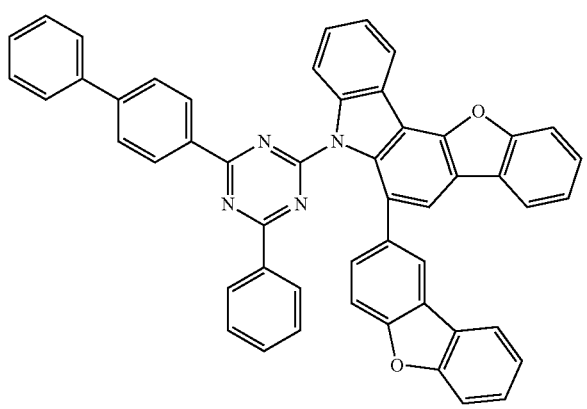
351
352
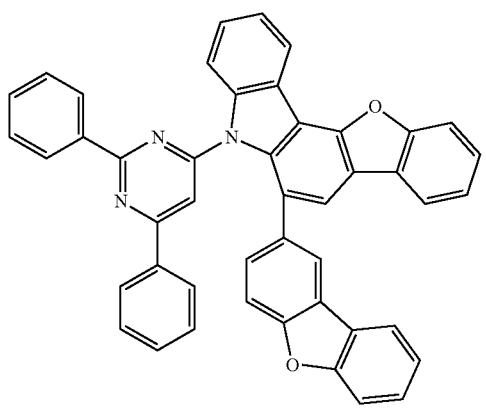
353
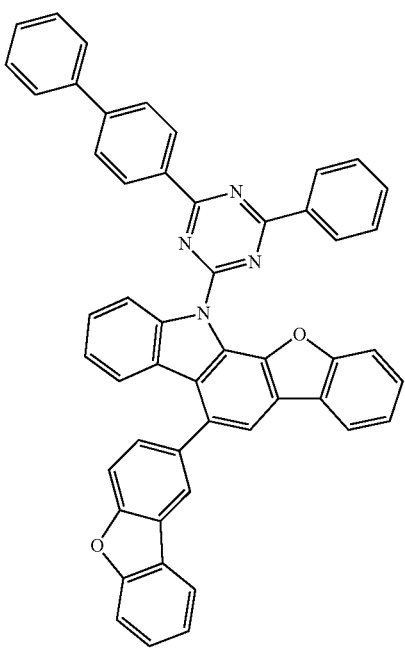

205
-continued
354
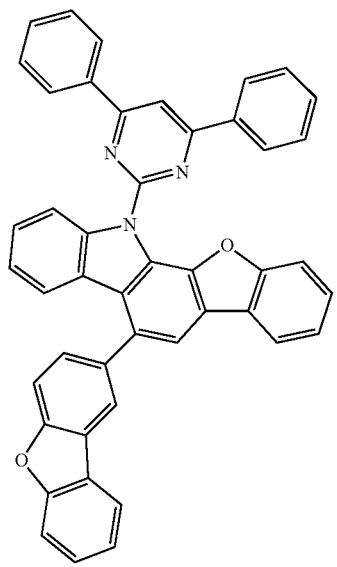
355
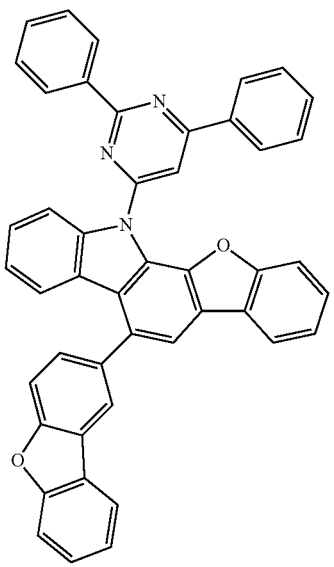
356
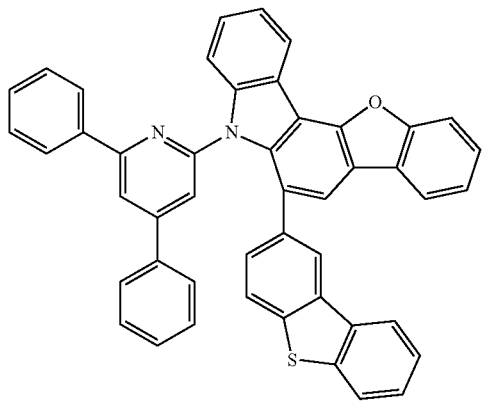
357
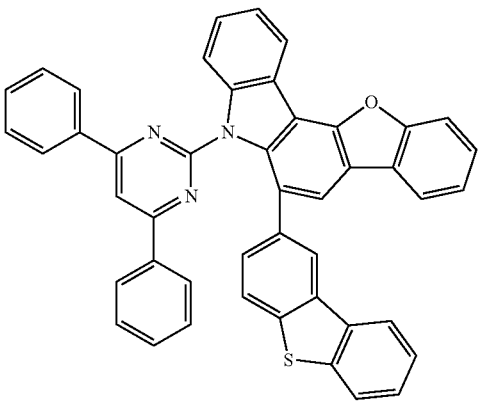
358
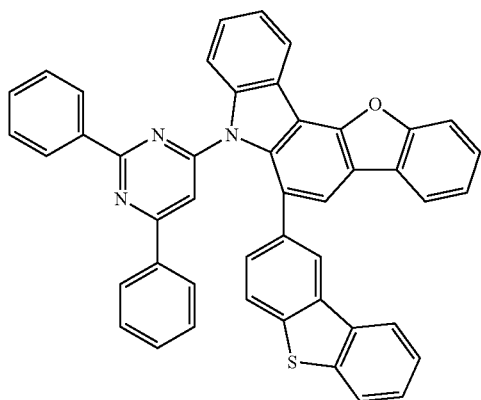
359
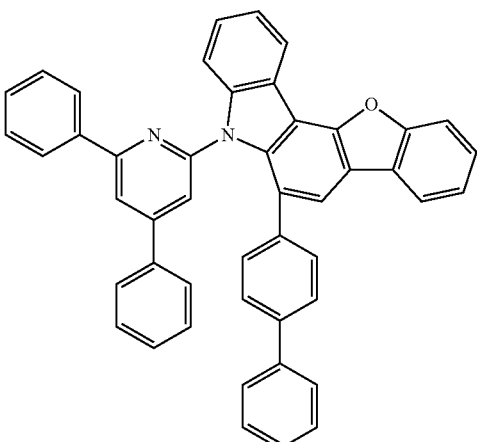

-continued
360
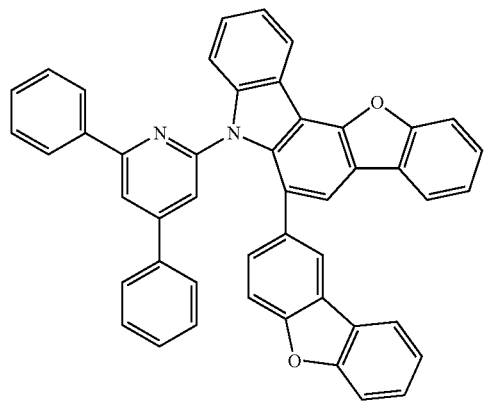
361
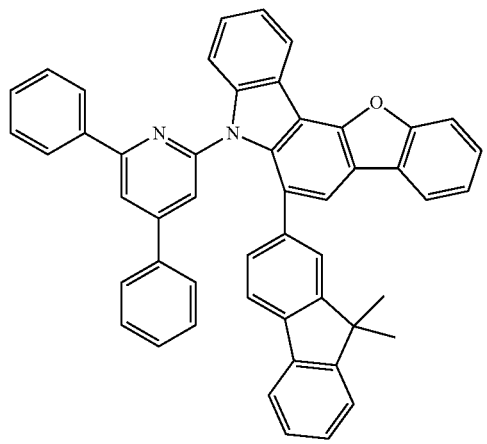
362
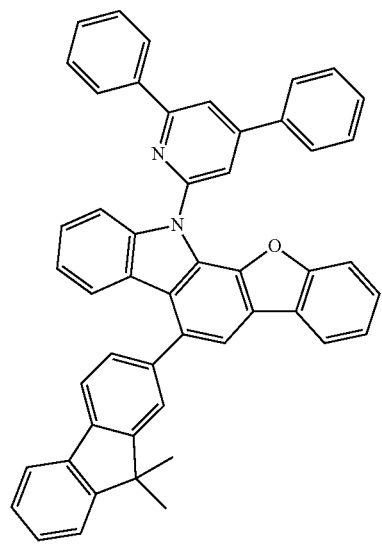
363
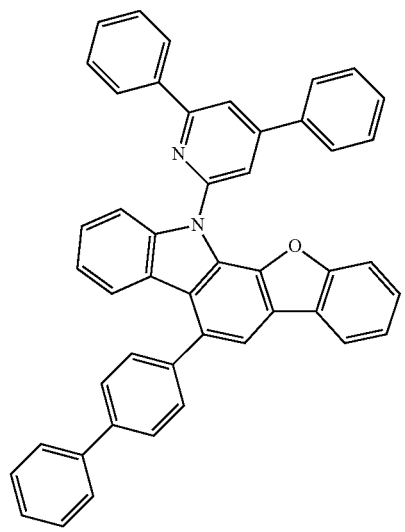
364
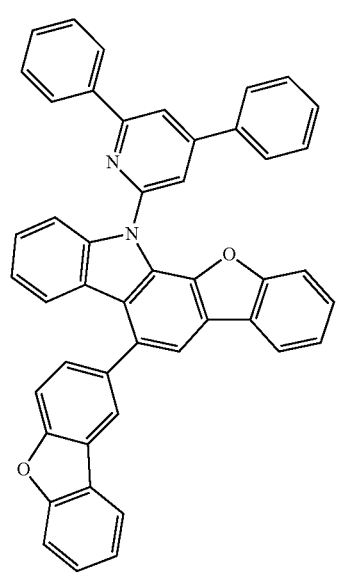
365
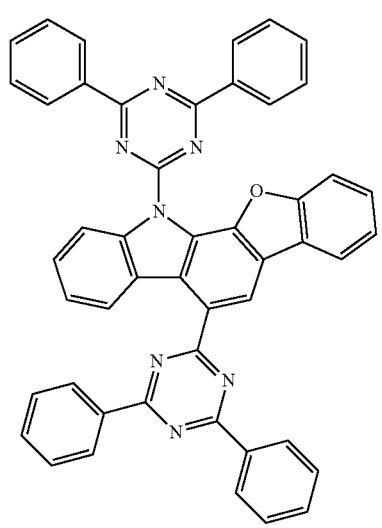

-continued
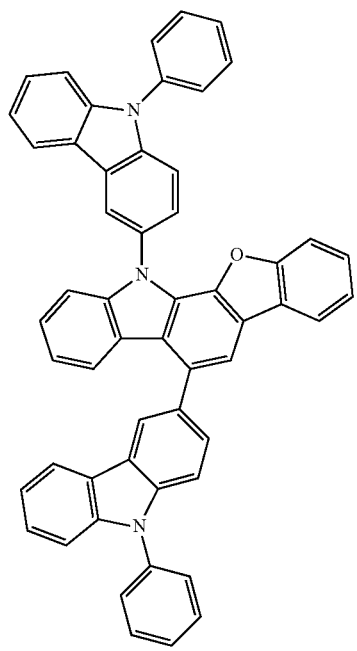
366
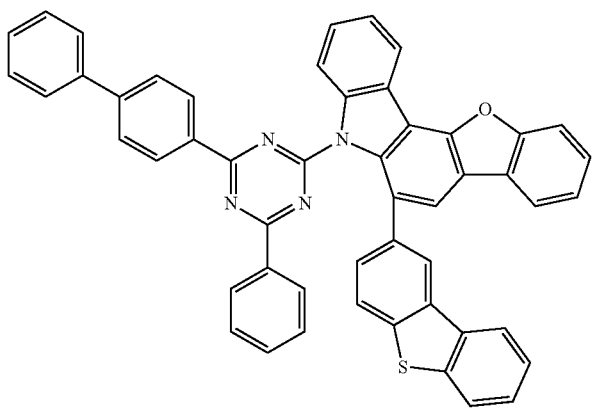
367
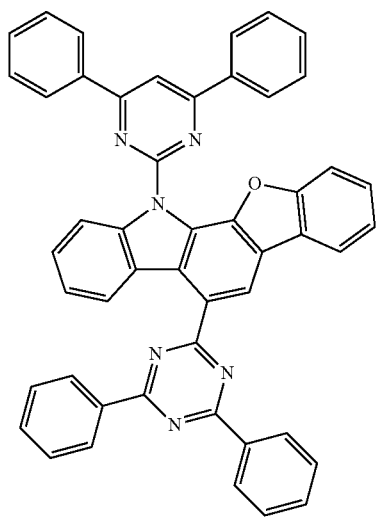
368
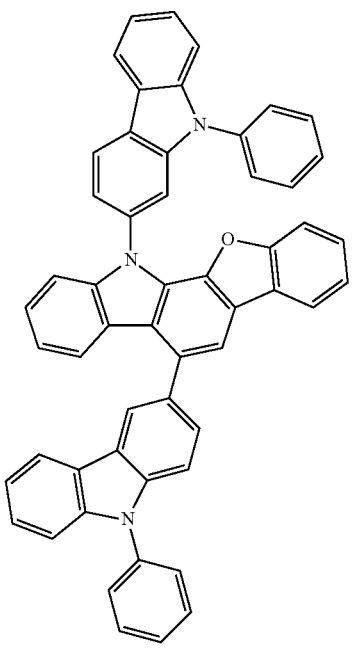
369

-continued
370
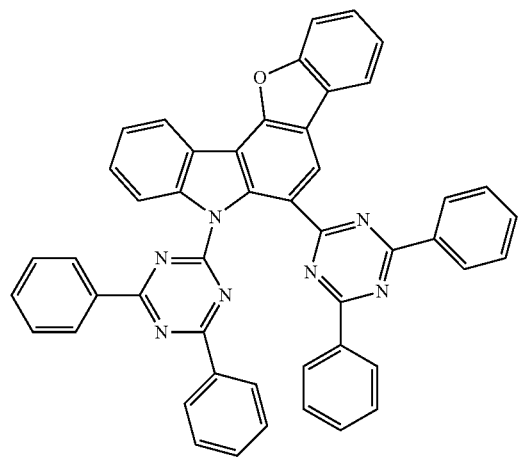
371
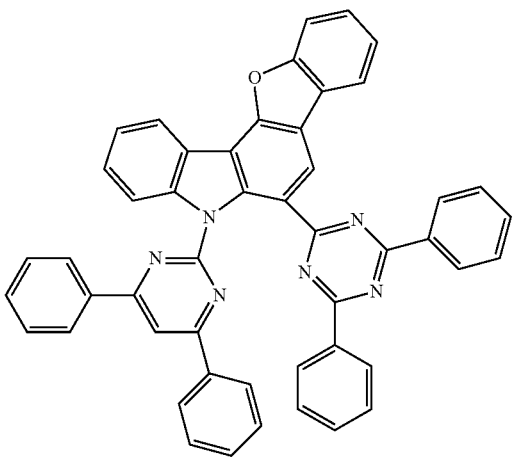
372
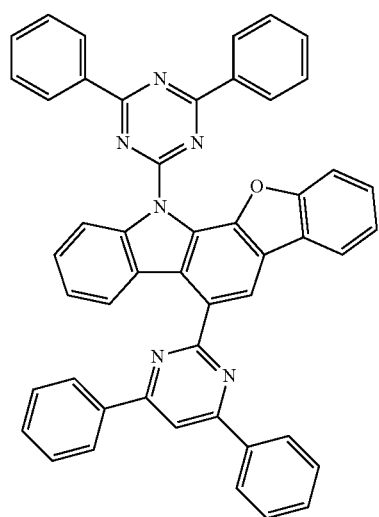
373
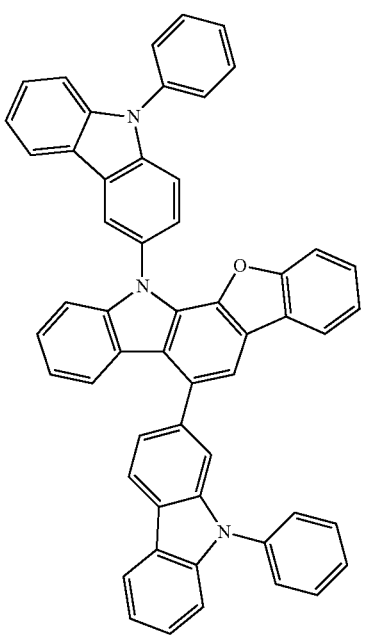
374
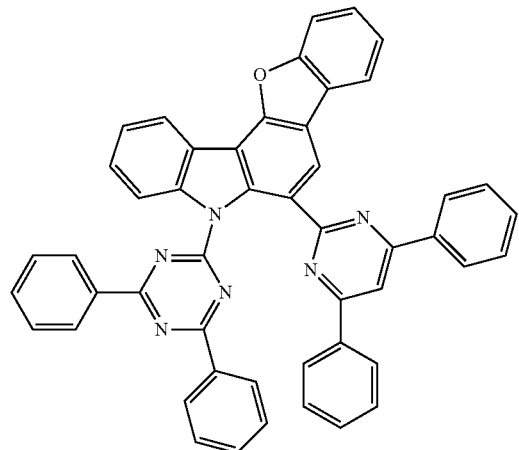
375
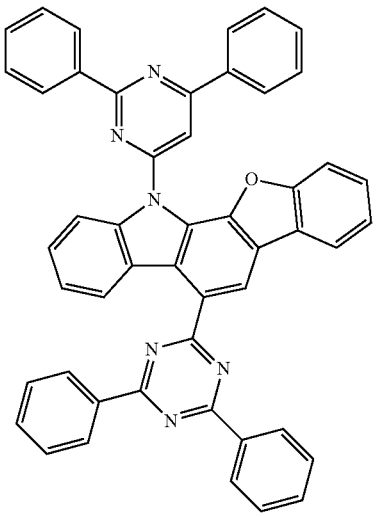

-continued
213 376
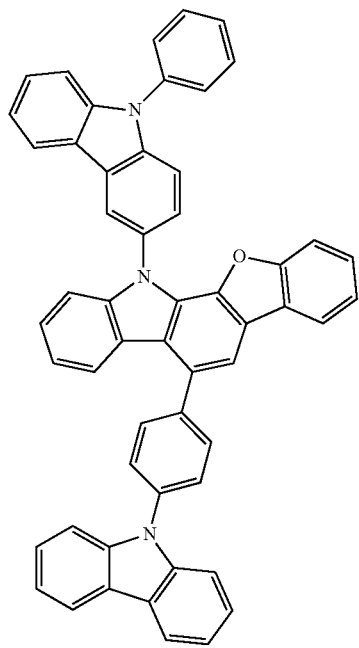
214 377
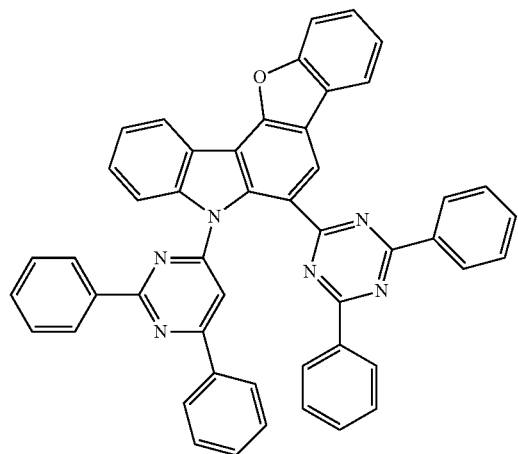
378
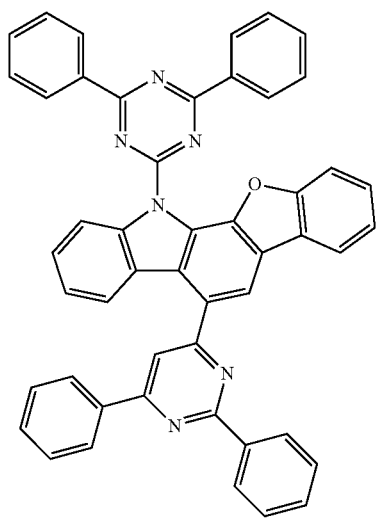
379
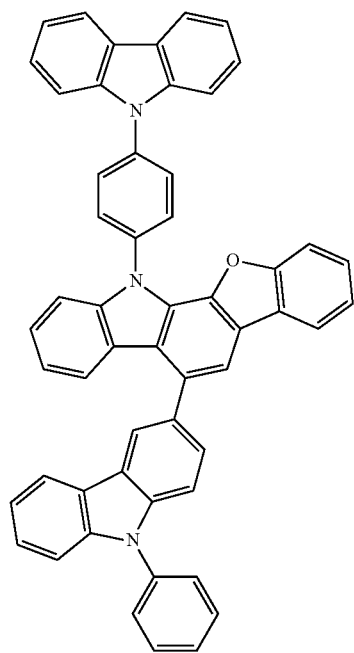

-continued
380
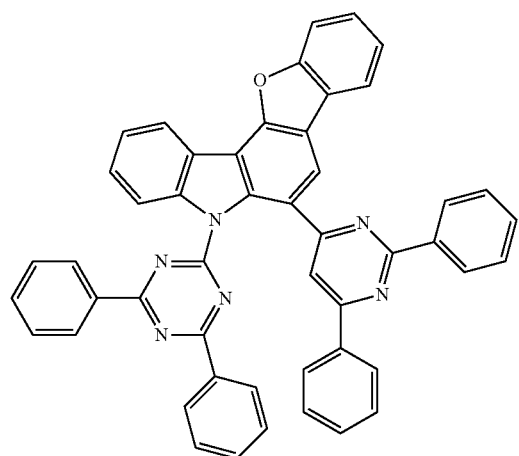
381
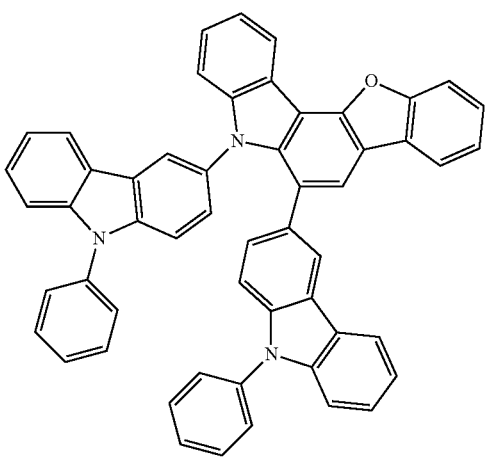
382
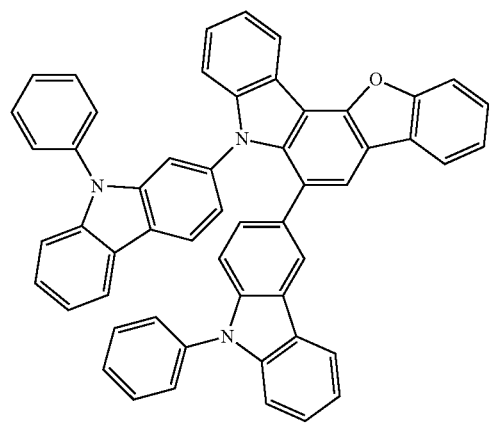
383
384
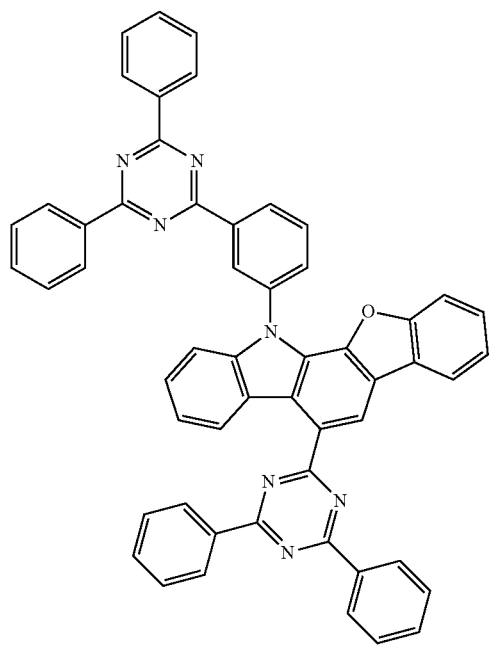
385
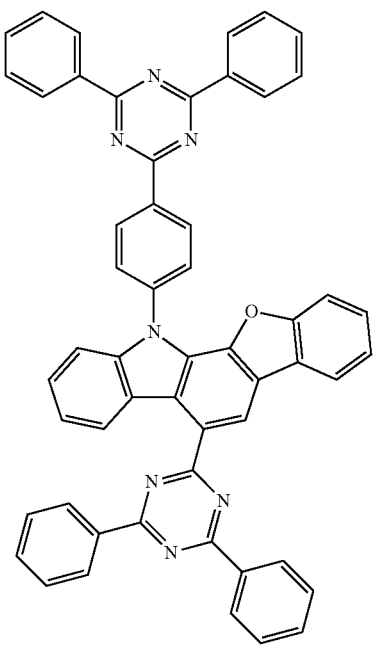

-continued
217
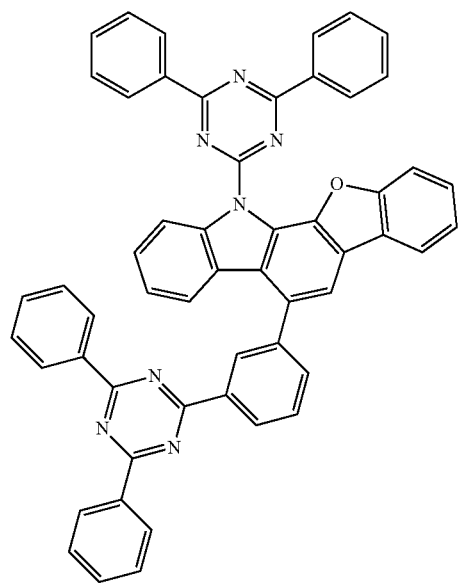
386
218
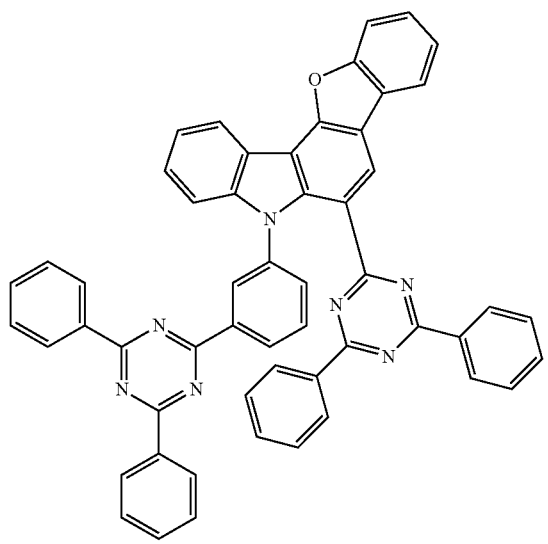
387
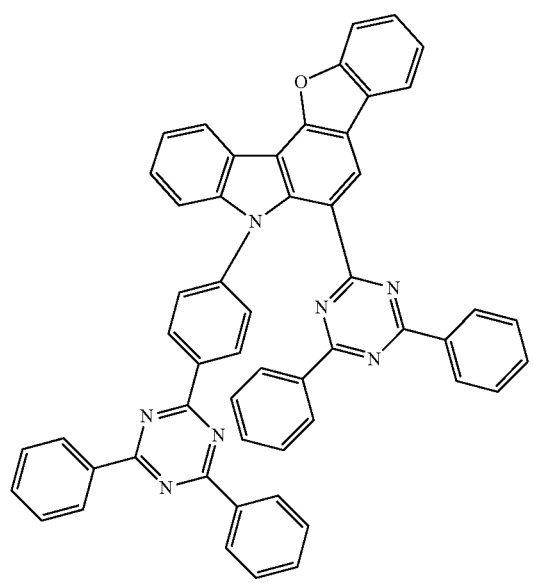
388
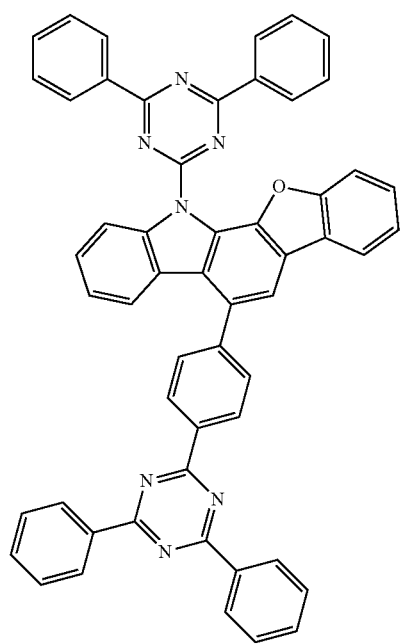
389

-continued
219
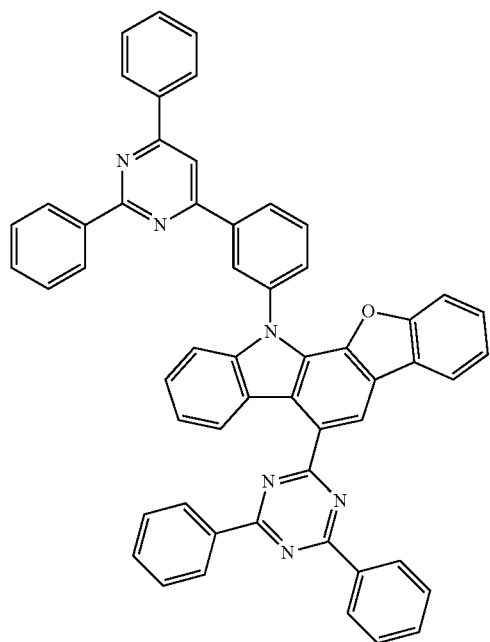
220
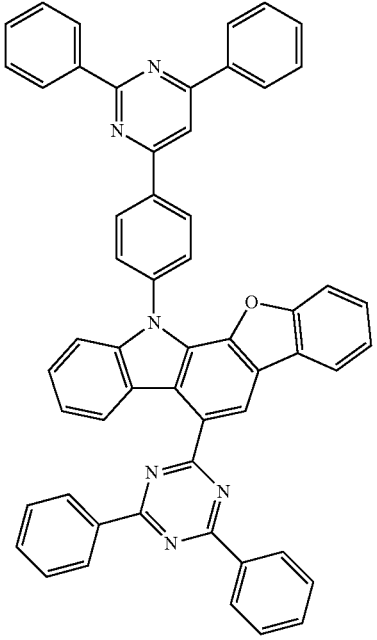
390
392
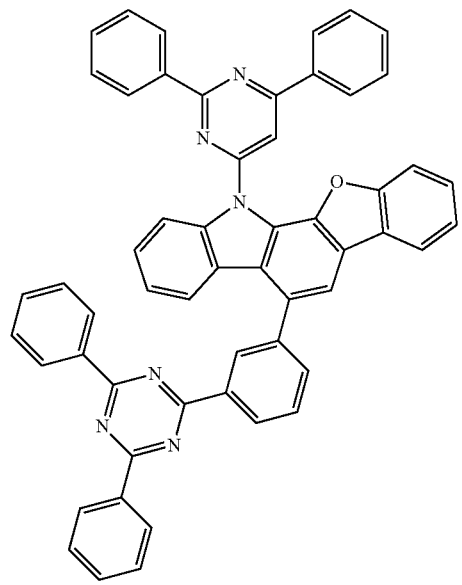
391
393
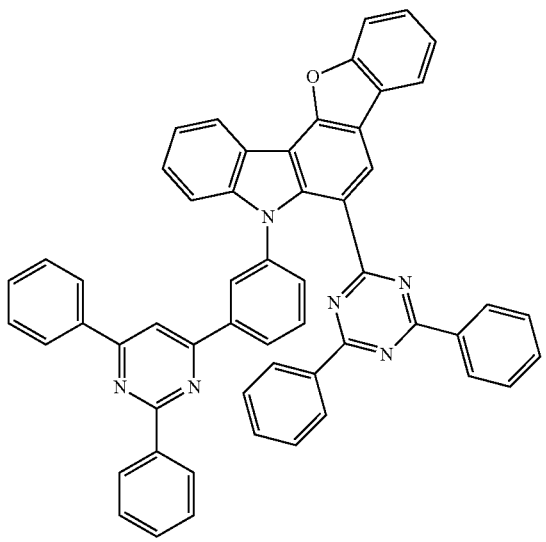

-continued
394
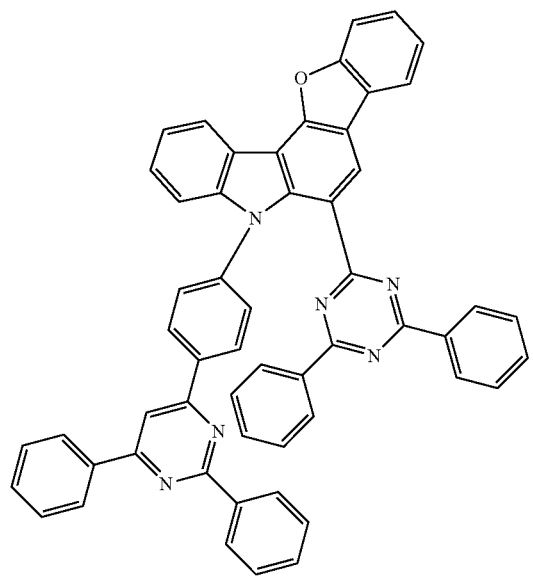
395
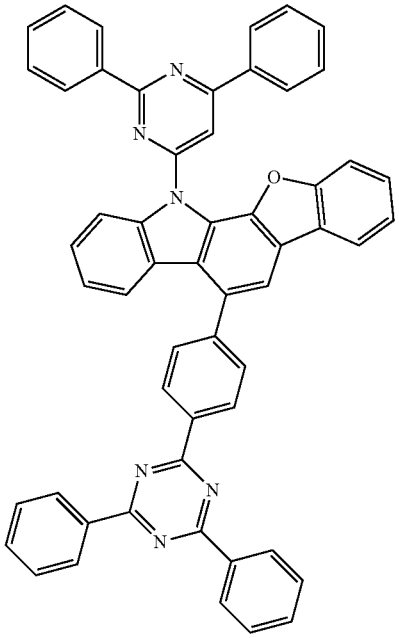
396
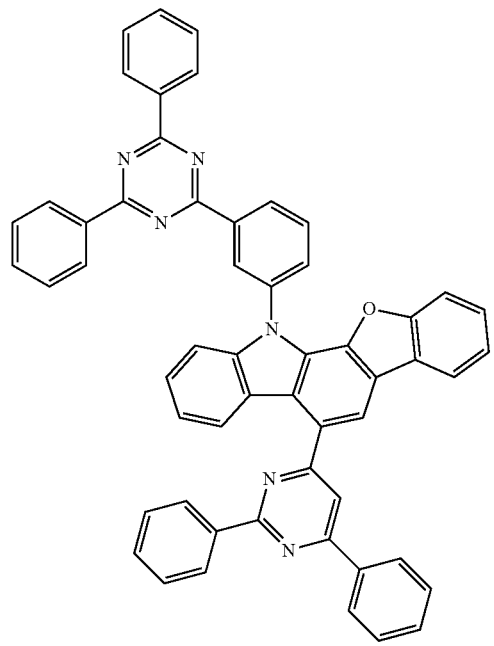
397
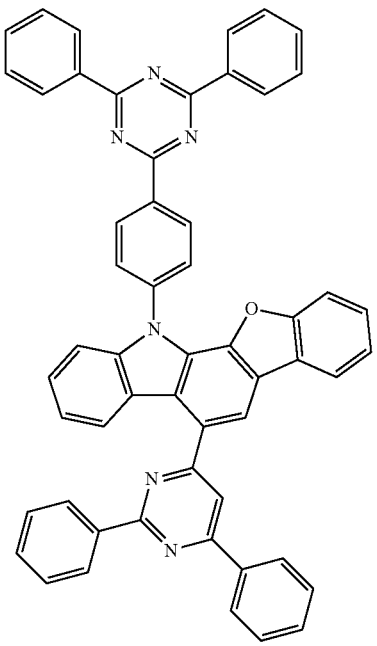

-continued
398
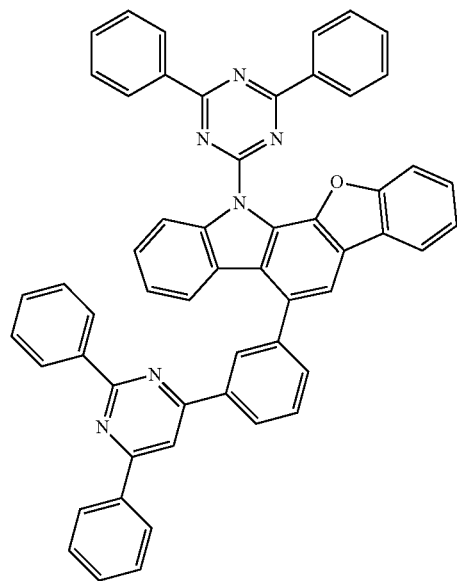
399
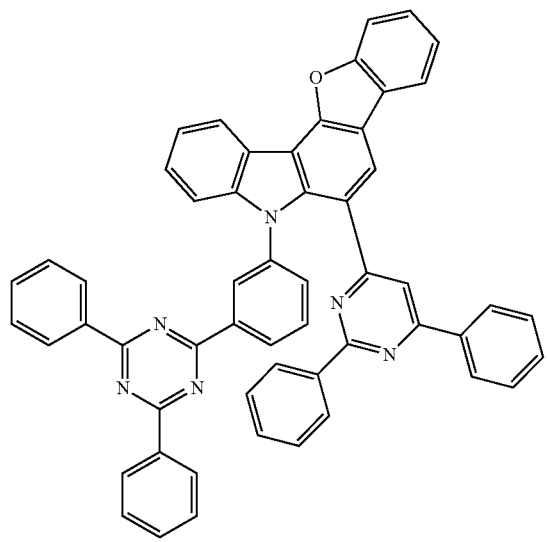
400
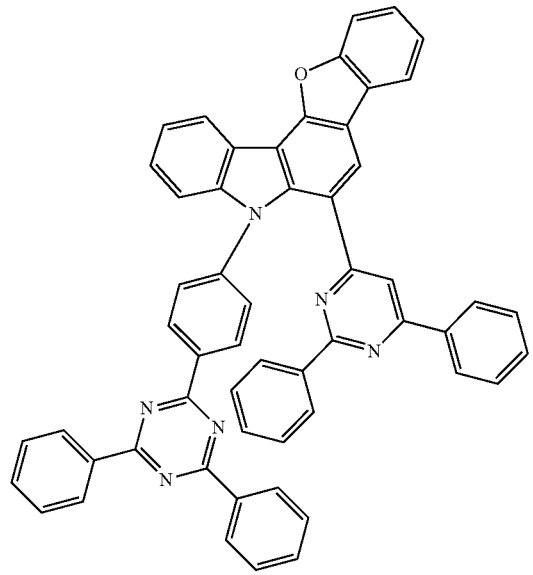
401
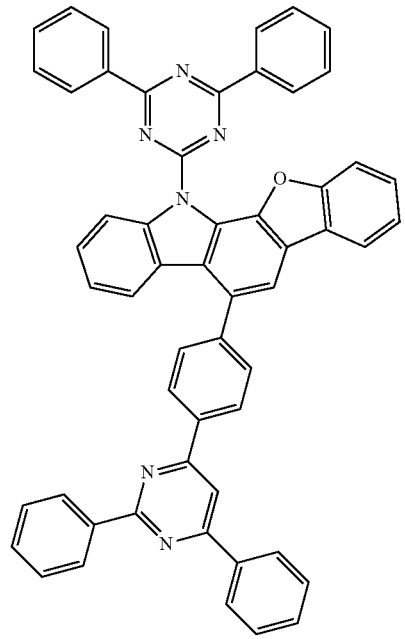

-continued
402
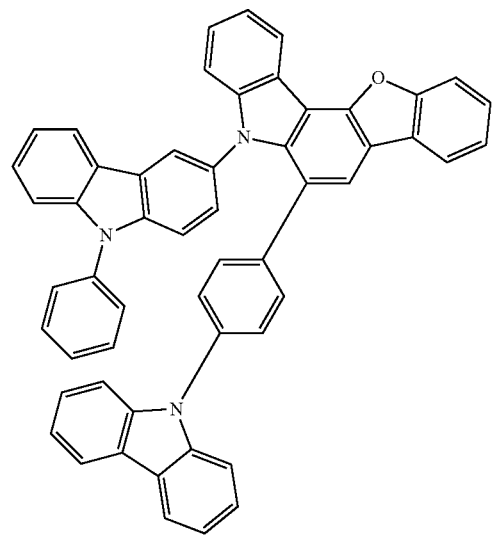
403
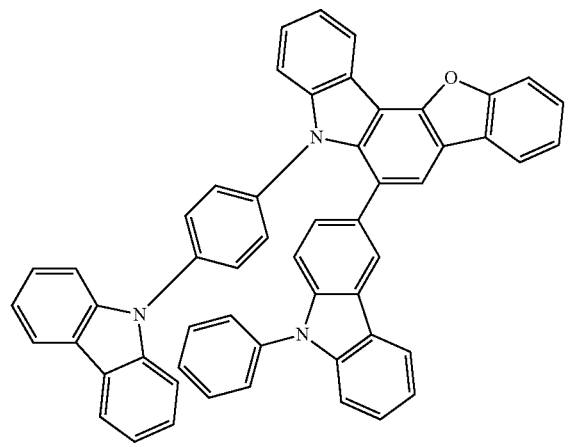
404
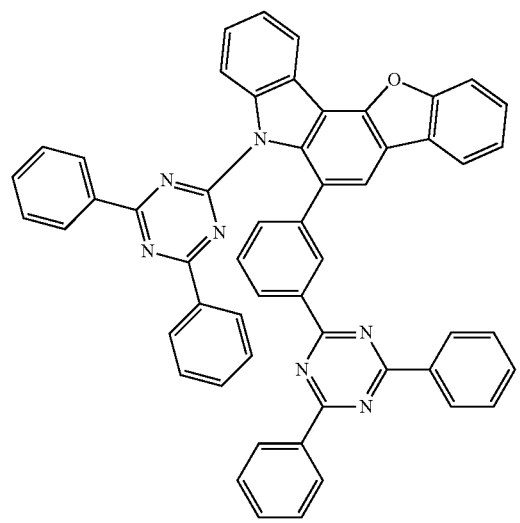
405
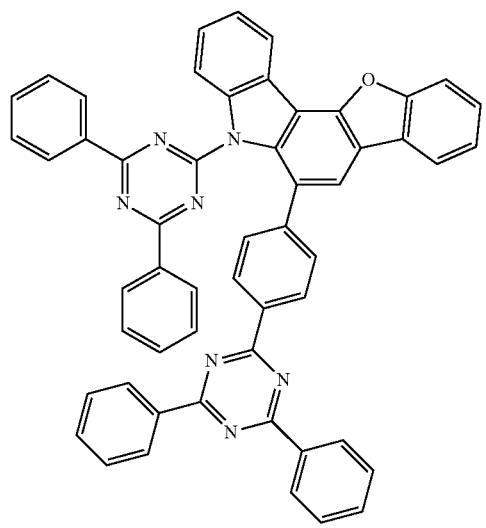
406
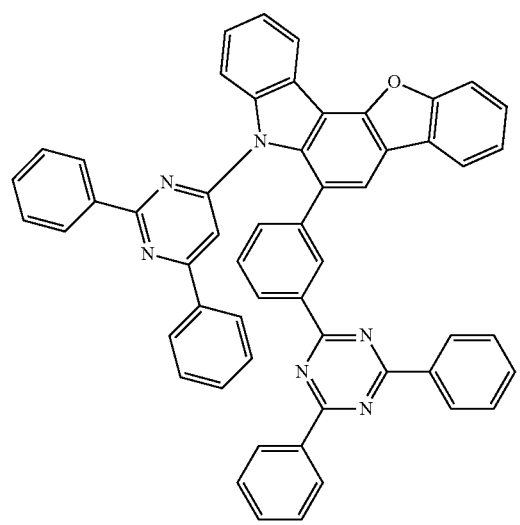
407
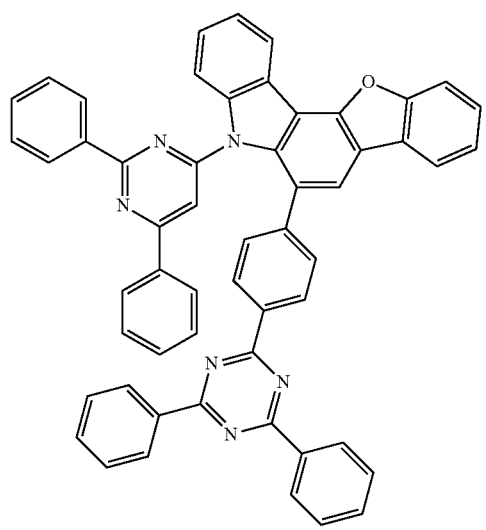

-continued
408
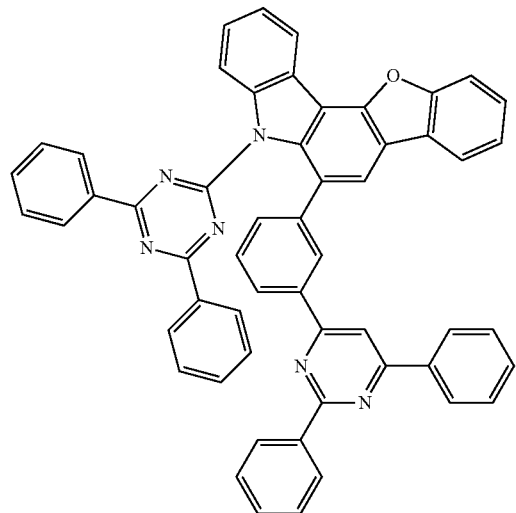
409
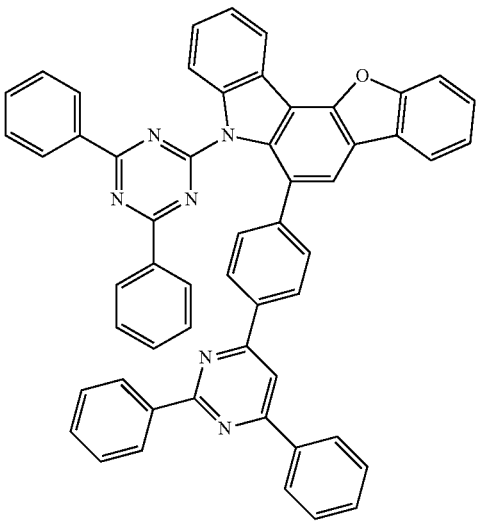
410
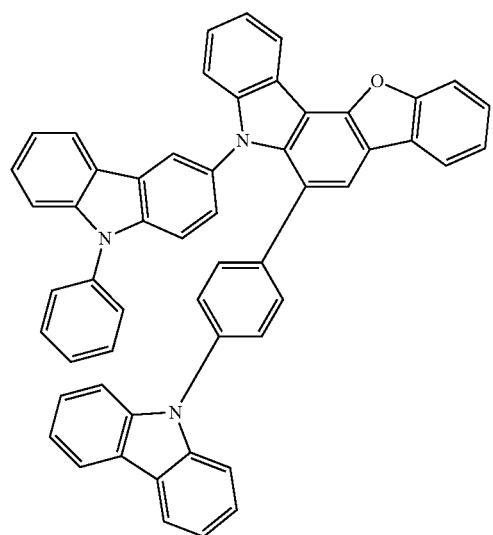
411
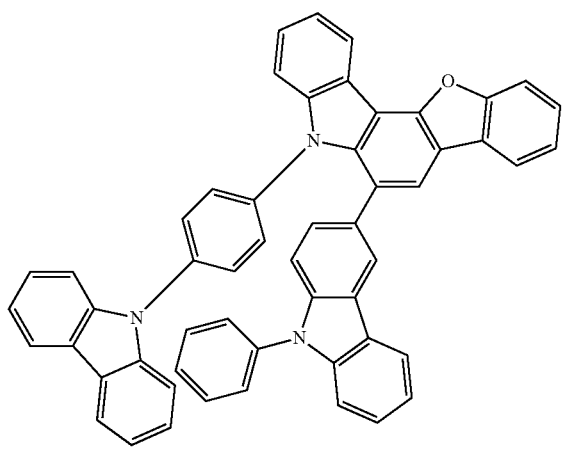
412
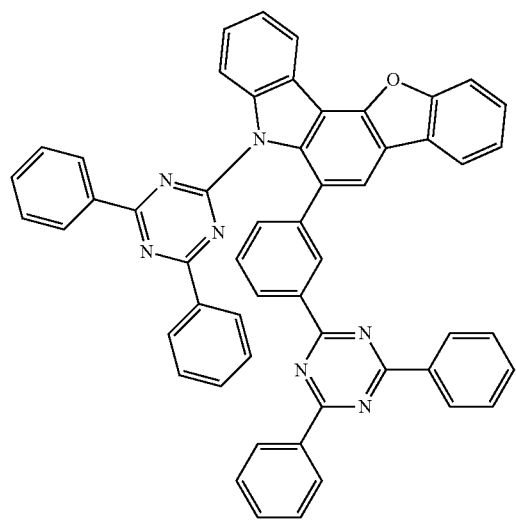
413
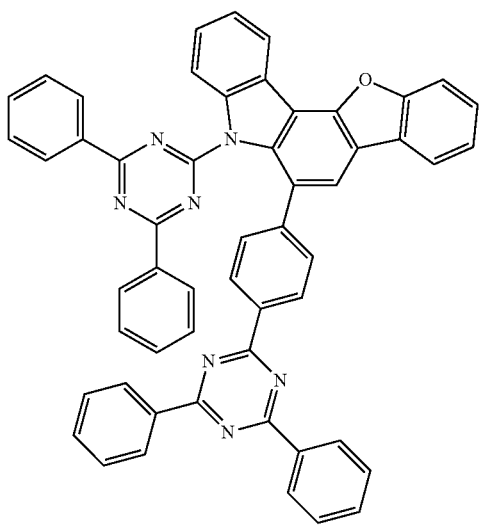

414
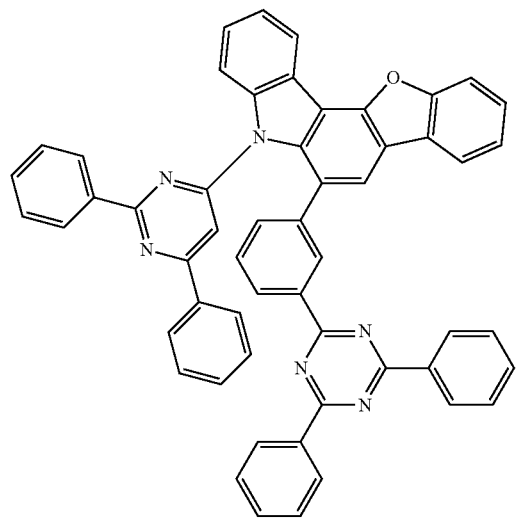
415
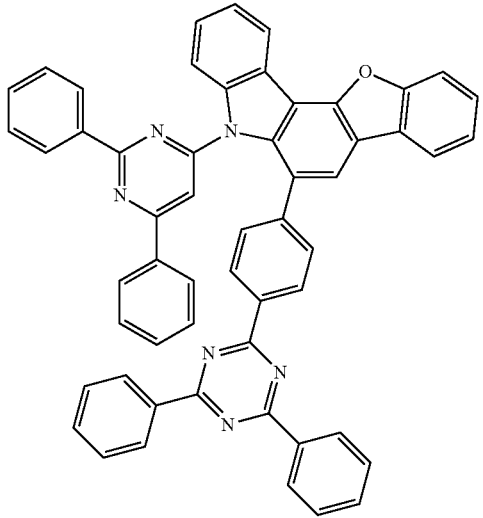
416
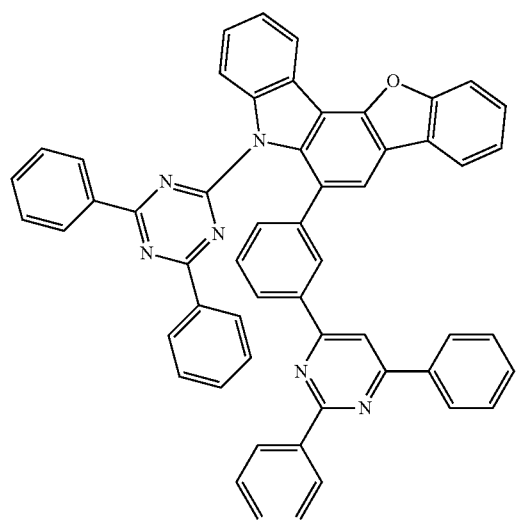
417
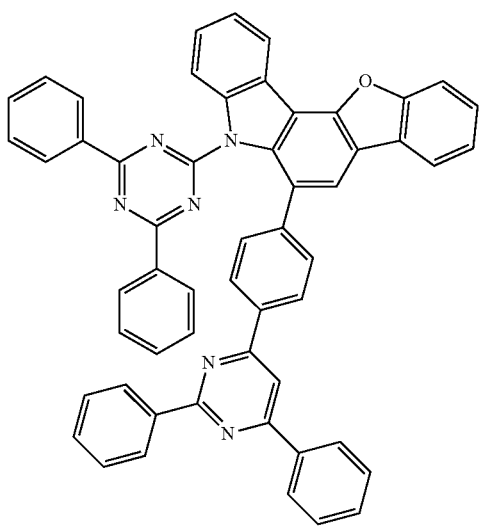
418
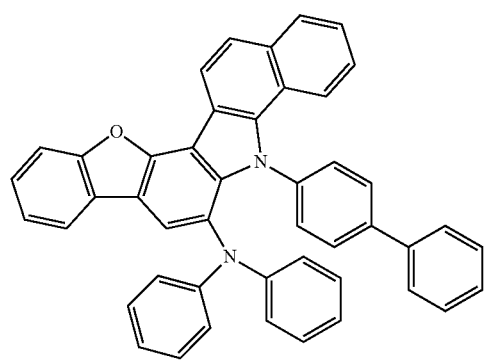
419
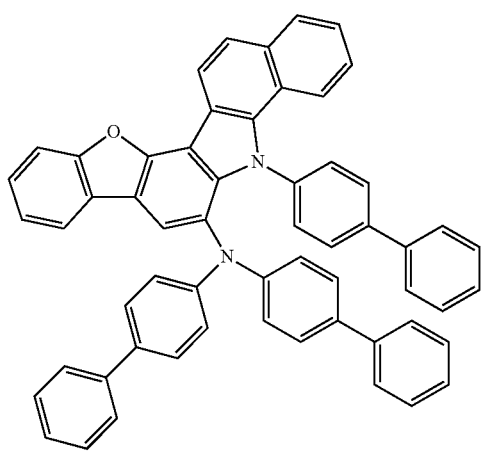

-continued
420
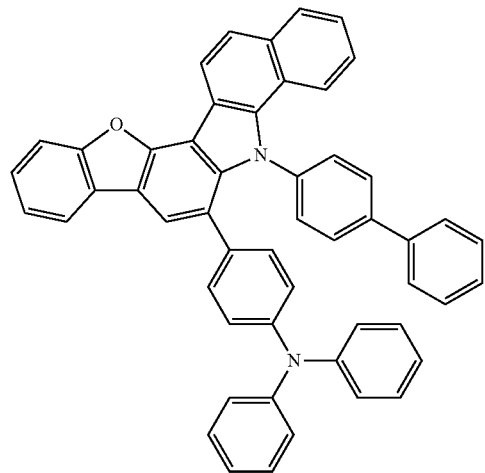
421
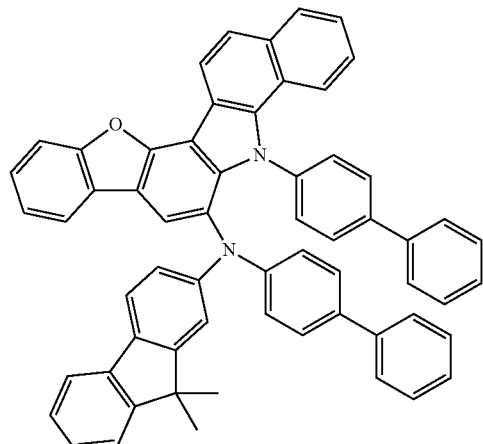
422
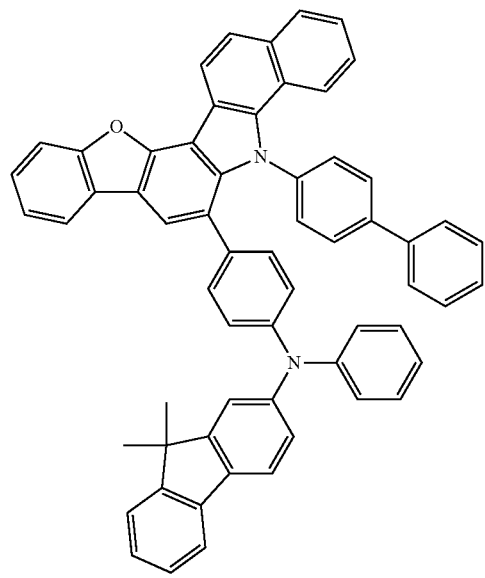
423
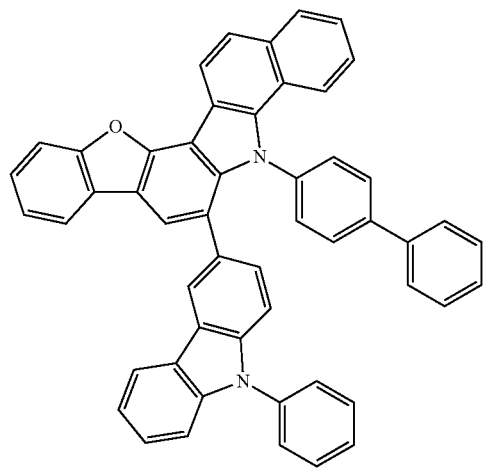
424
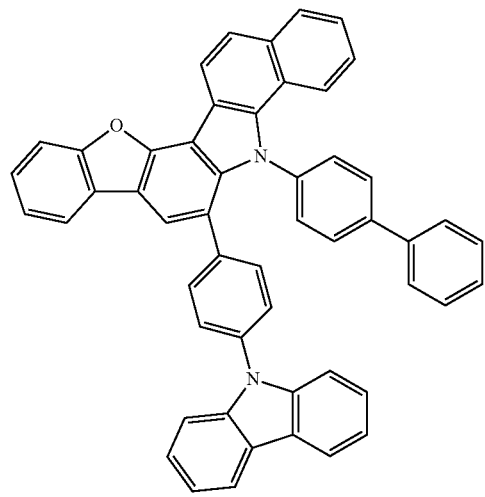
425
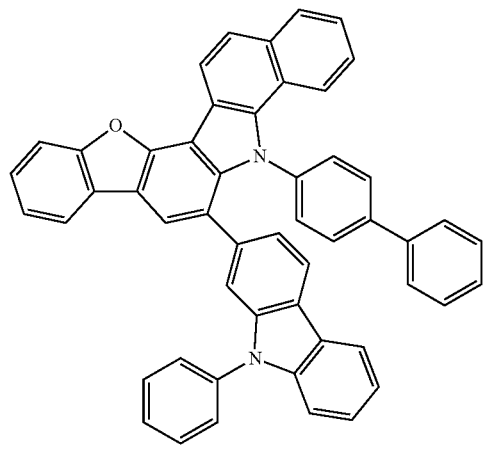

-continued
426
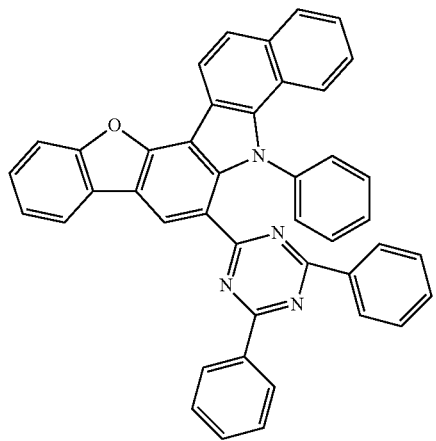
427
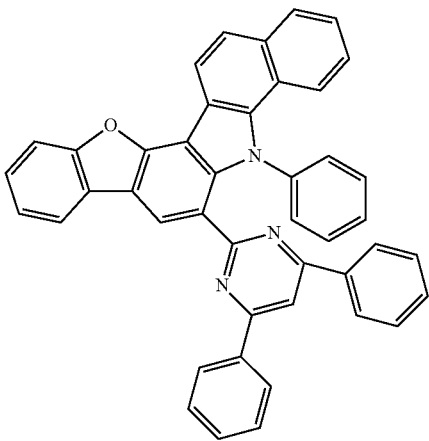
428
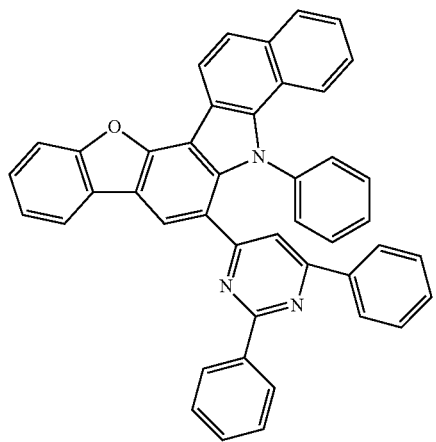
429
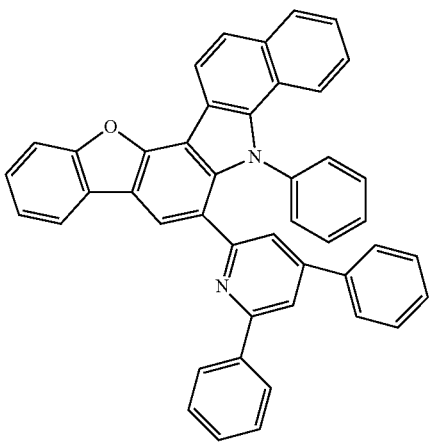
430
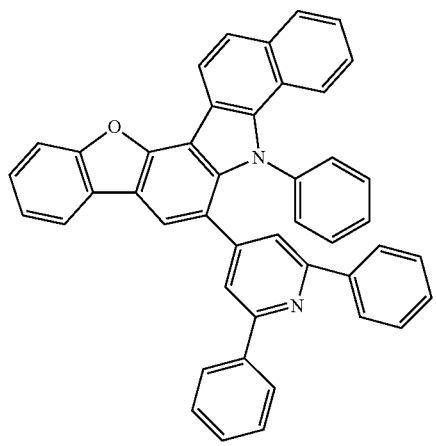
431
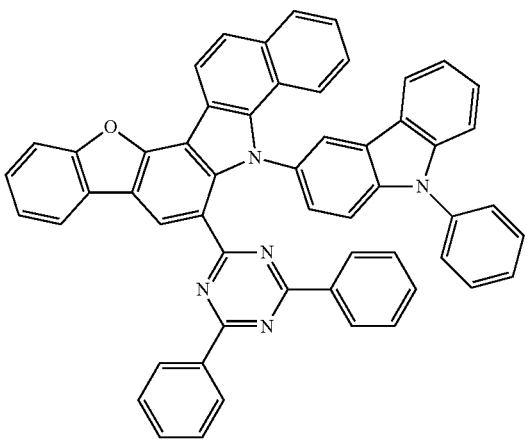

-continued
432
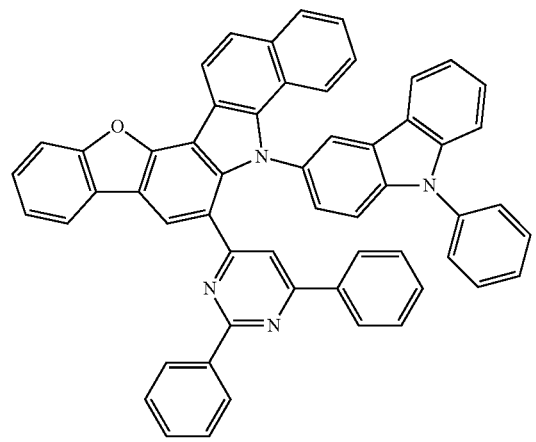
433
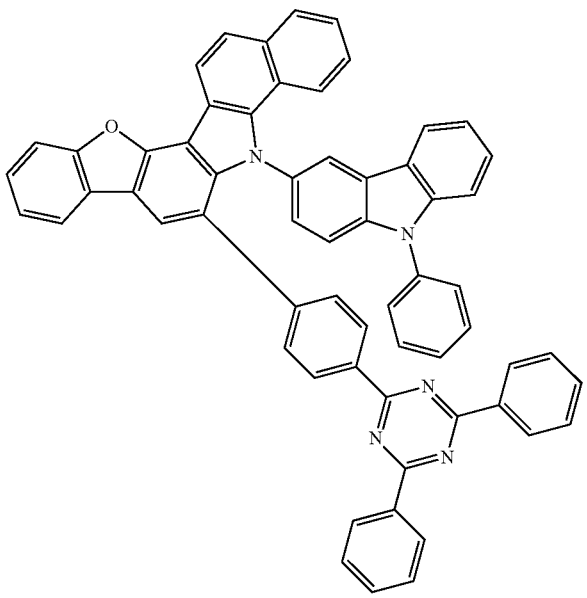
434
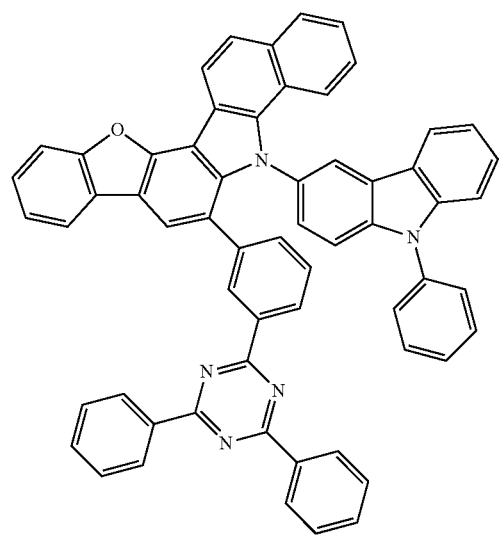
435
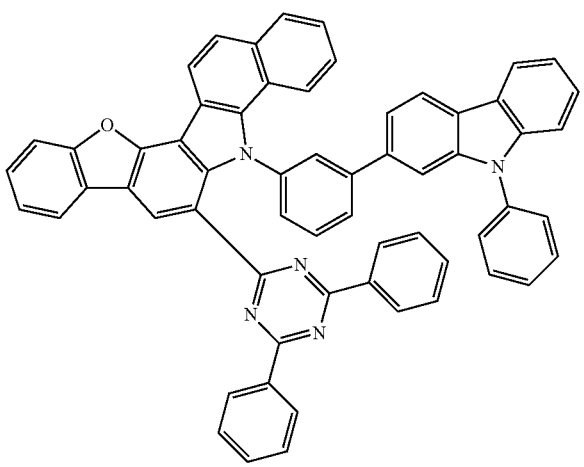
436
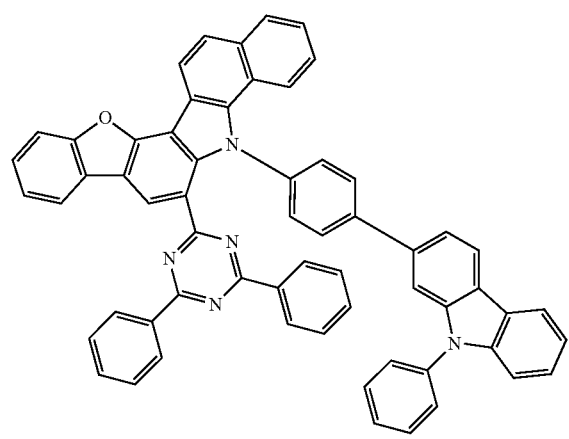
437
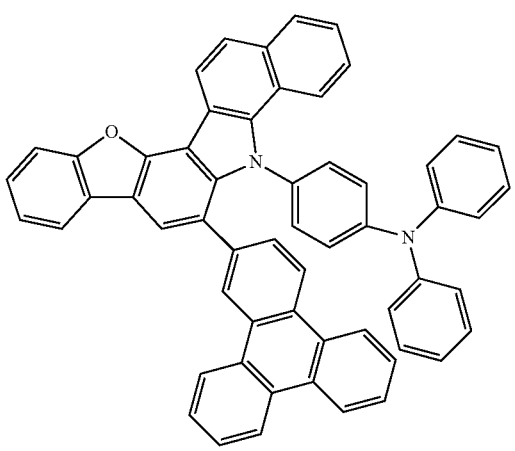

-continued
| 438 | 439 |
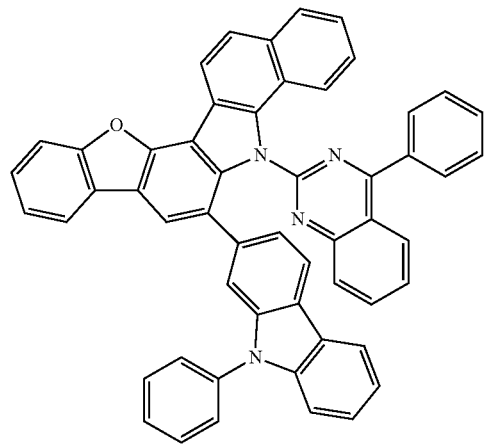 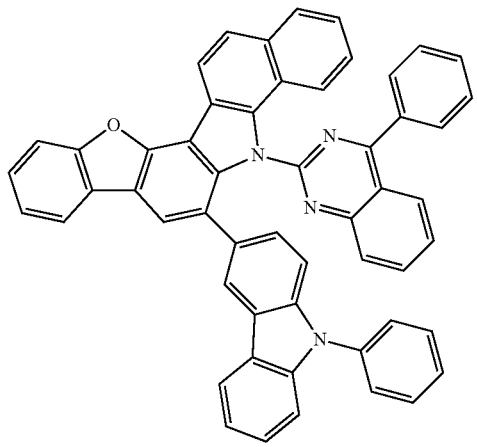
| 440 | 441 |
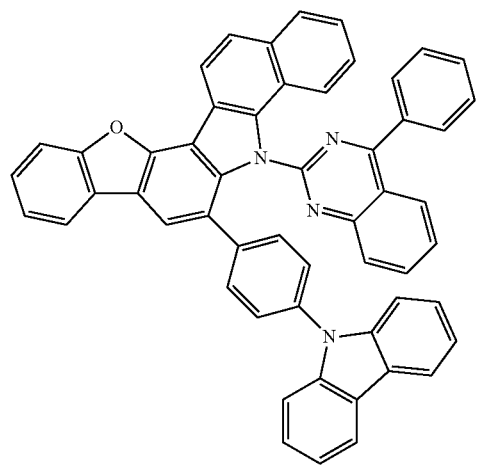 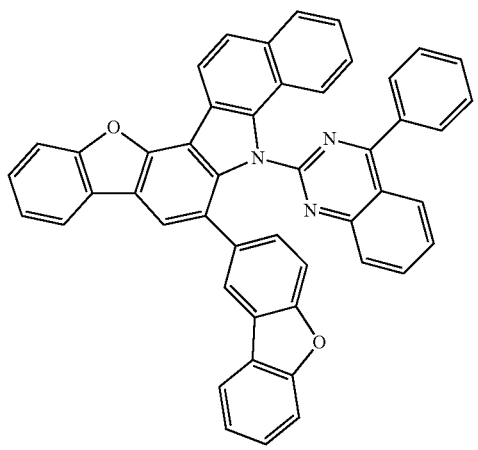
| 442 | 443 |
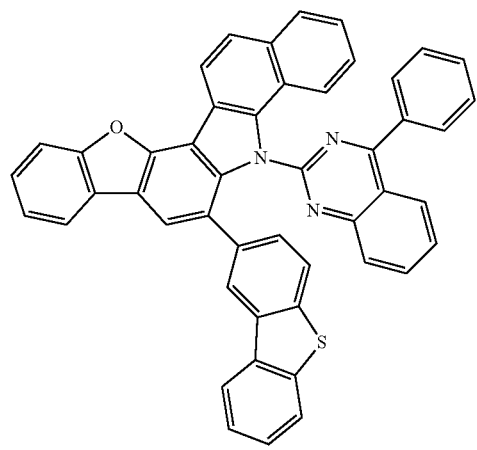 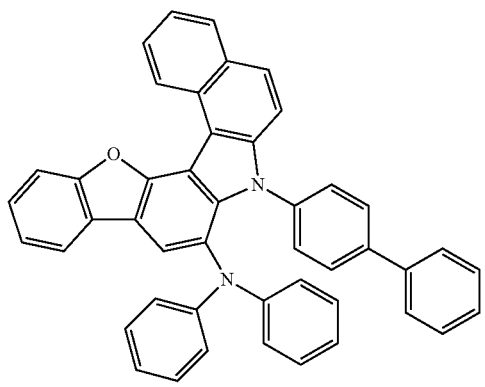

-continued
444
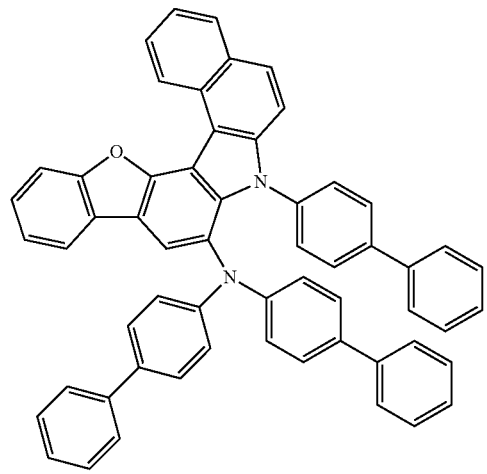
445
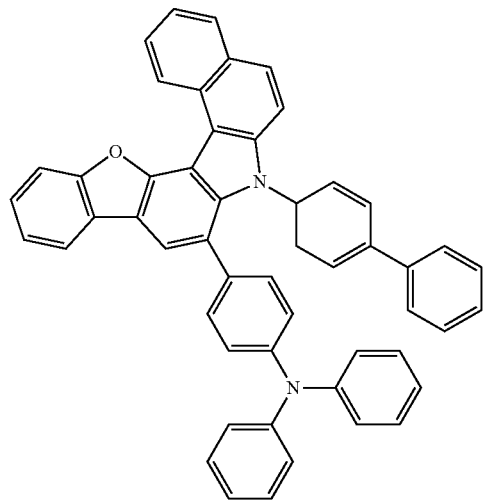
446
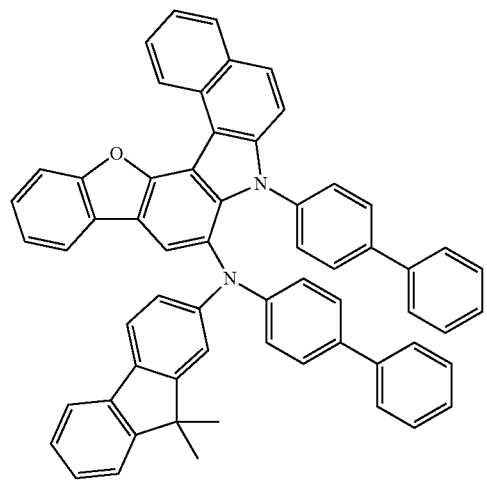
447
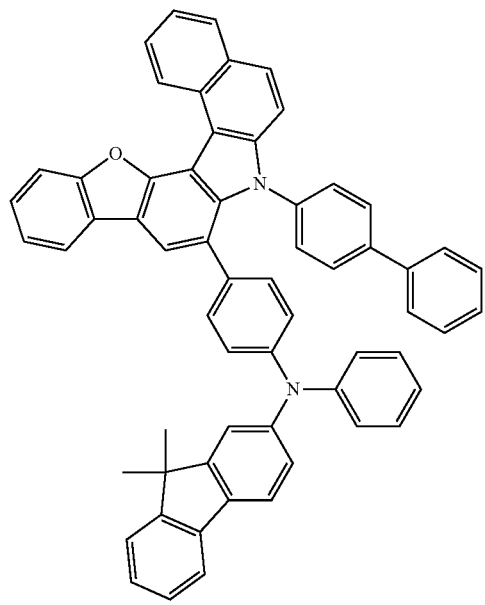
448
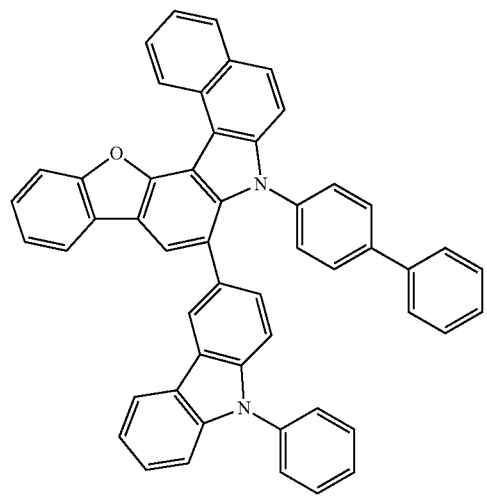
449
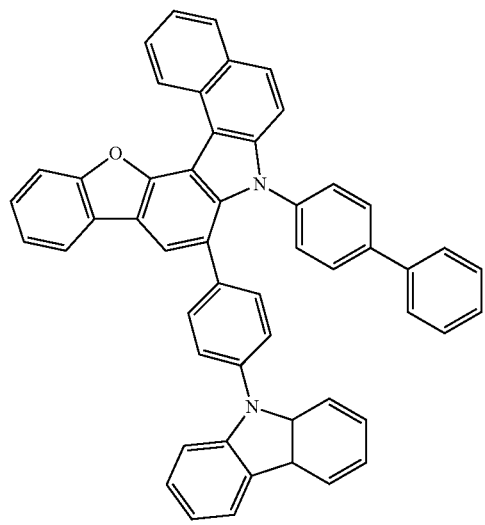

-continued
450
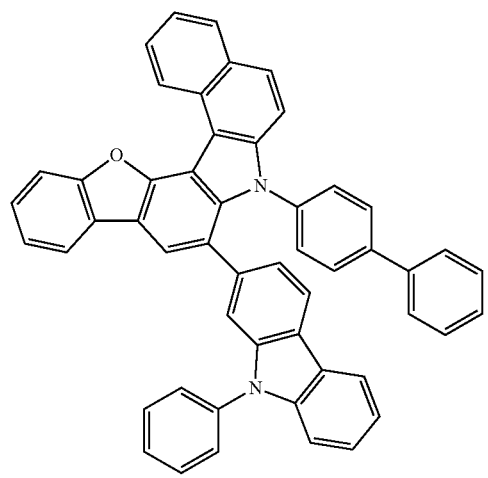
451
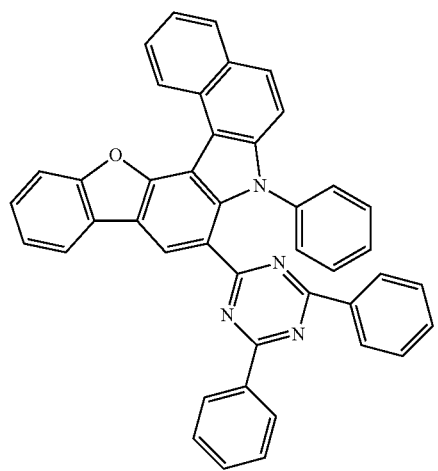
452
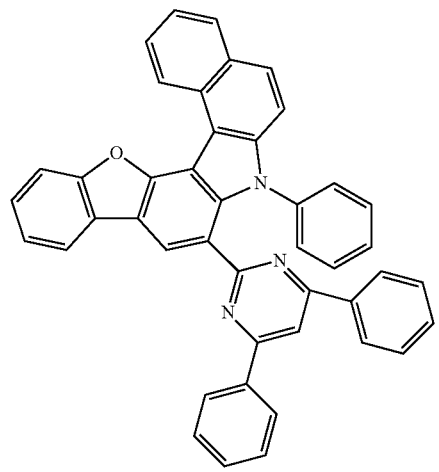
453
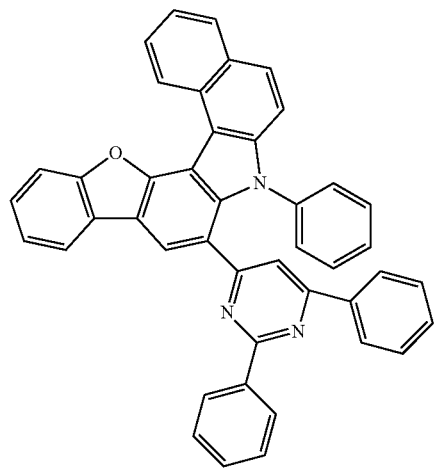
454
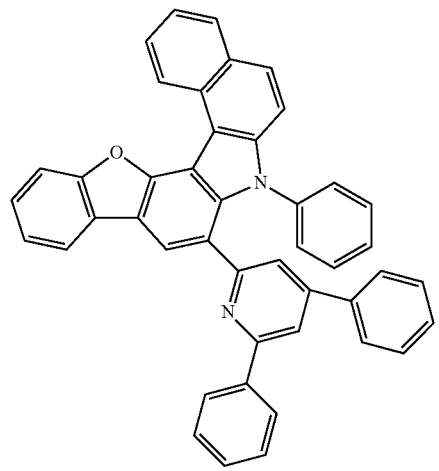
455
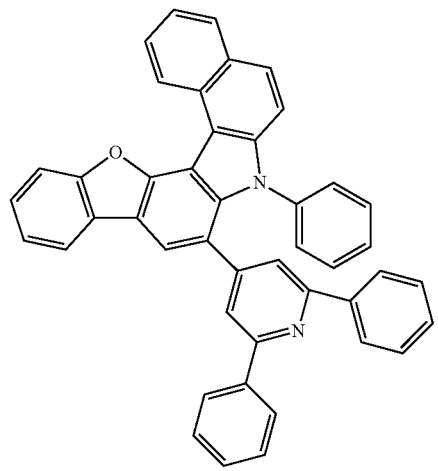

-continued
456
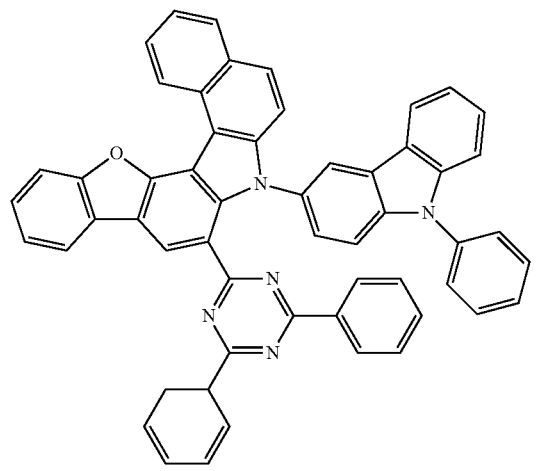
457
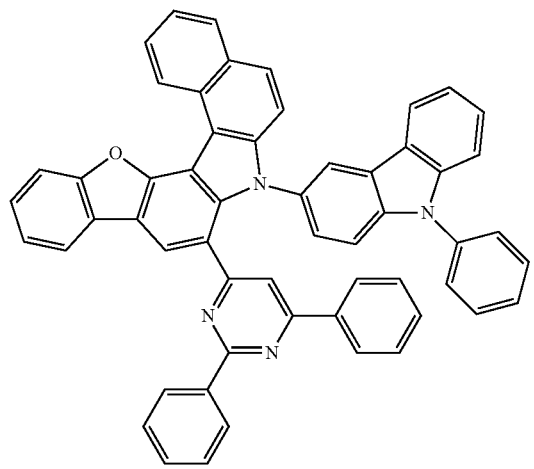
458
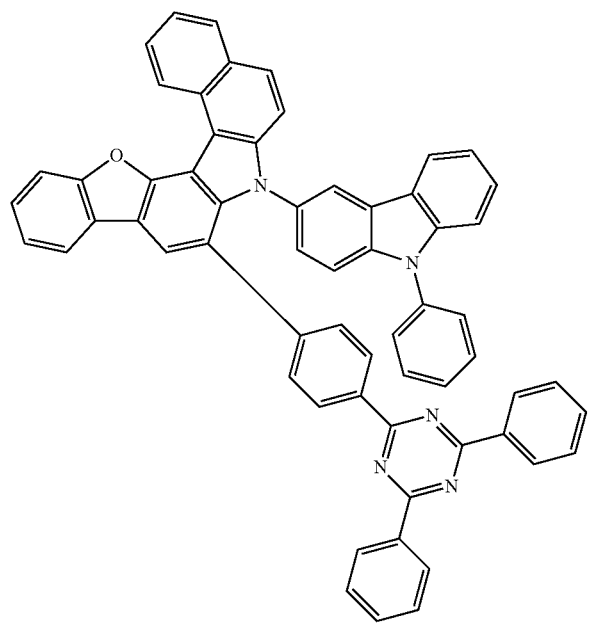
459
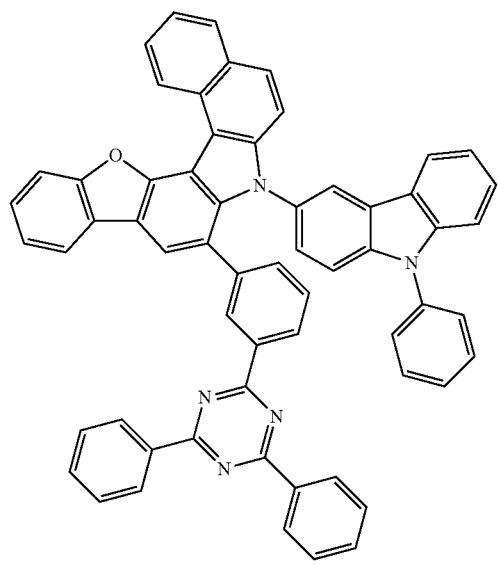
460
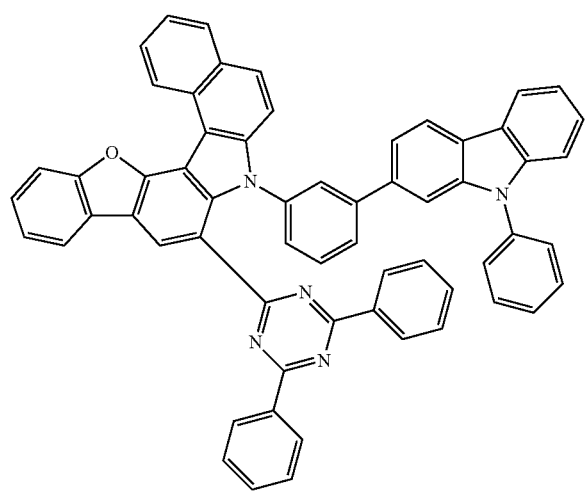

245                                           246
461                                            462
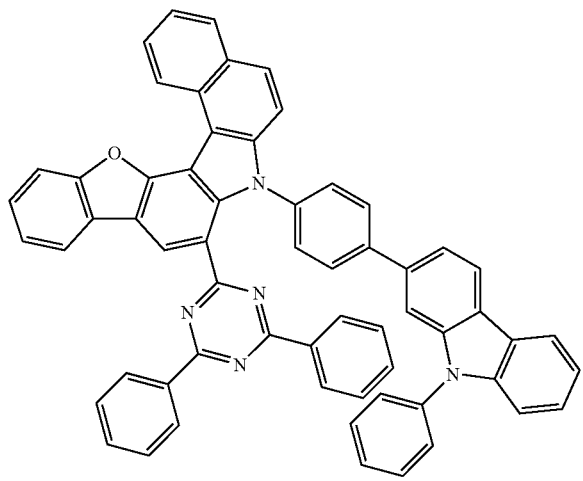 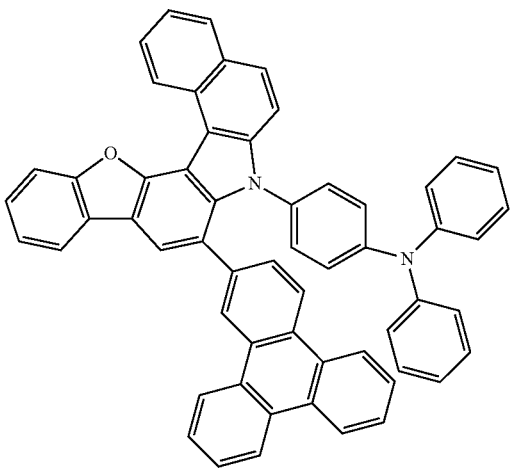
463                                            464
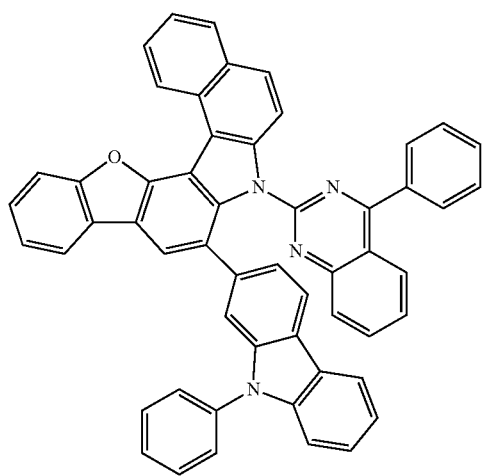 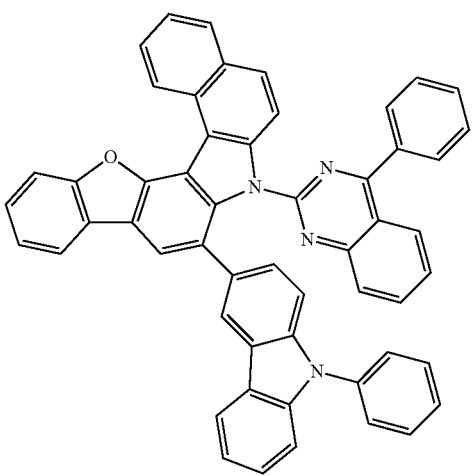
465                                            466
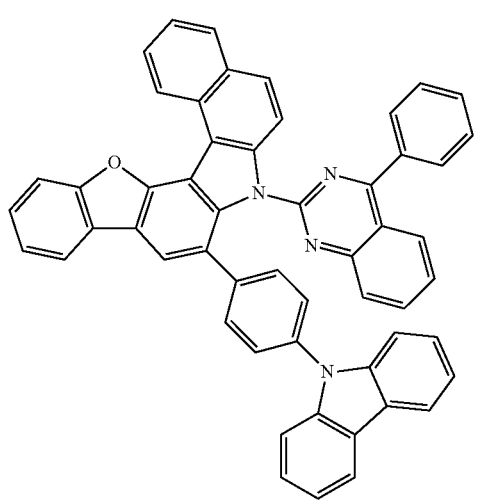 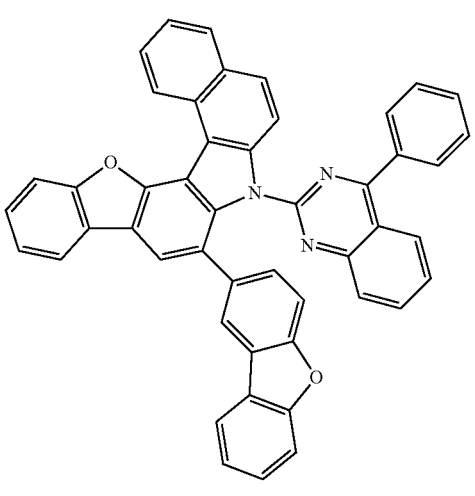

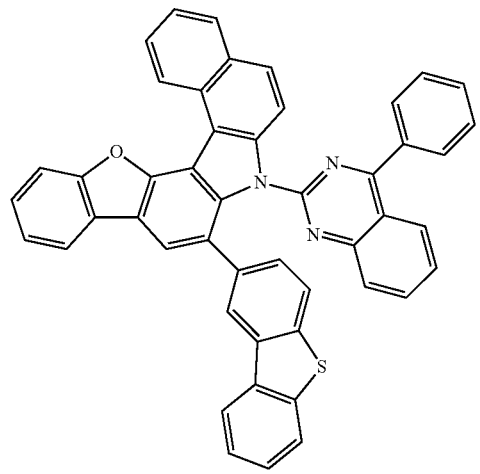

A conjugation length of a compound and an energy band gap are closely related. Specifically, as a conjugation length of a compound increases, an energy band gap decreases.

In the present specification, compounds having various energy band gaps may be synthesized by introducing various substituents at positions of $Ar_1$, $Ar_2$ and $R_1$ to $R_8$ of a core structure as above. In addition, in the present specification, HOMO and LUMO energy levels may be controlled as well by introducing various substituents at positions of $Ar_1$, $Ar_2$ and $R_1$ to $R_8$ of a core structure having a structure as above.

Furthermore, by introducing various substituents to a core structure having a structure as above, compounds having unique properties of the introduced substituents may be synthesized. For example, by introducing substituents normally used in hole injection layer materials, hole transfer layer materials, light emitting layer materials and electron transfer layer materials used for manufacturing an organic light emitting device to the core structure, materials satisfying needs required for each organic material layer may be synthesized.

In addition, an organic light emitting device according to the present specification includes a first electrode, a second electrode, and one or more organic material layers disposed between the first electrode and the second electrode, wherein one or more layers of the organic material layers include the above-mentioned compound.

The organic light emitting device of the present specification may be manufactured using common methods and materials for manufacturing organic light emitting devices, except that one or more layers of the organic material layers are formed using the compound described above.

The compound may be formed into the organic material layer using a solution coating method as well as a vacuum deposition method when manufacturing an organic light emitting device. Herein, the solution coating method means spin coating, dip coating, ink jet printing, screen printing, a spray method, roll coating and the like, but is not limited thereto.

The organic material layer of the organic light emitting device of the present specification may be formed in a single layer structure, but may be formed in a multilayer structure in which two or more organic material layers are laminated. For example, the organic light emitting device of the present specification may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

Accordingly, in the organic light emitting device of the present specification, the organic material layer may include one or more layers of a hole injection layer; a hole transfer layer; and a layer carrying out hole injection and hole transfer at the same time, and one or more layers of the layers may include the compound represented by Chemical Formula 1.

In another embodiment, the organic material layer includes a light emitting layer, and the light emitting layer includes the compound represented by Chemical Formula 1. As one example, the compound represented by Chemical Formula 1 may be included as a phosphorescent host material of the light emitting layer.

As another example, the organic material layer including the compound represented by Chemical Formula 1 includes the compound represented by Chemical Formula 1 as a host, and includes other organic compounds, metals or metal compounds as a dopant.

As still another example, the organic material layer including the compound represented by Chemical Formula 1 includes the compound represented by Chemical Formula 1 as a host, and the compound may be used together with an iridium (Ir)-based dopant.

In addition, the organic material layer may include one or more layers of an electron transfer layer; an electron injection layer; and a layer carrying out electron transfer and electron injection at the same time, and one or more layers of the layers may include the compound.

In another embodiment, the organic material layer of the organic light emitting device includes a hole transfer layer, and the hole transfer layer includes the compound represented by Chemical Formula 1.

In addition, the organic material layer may include a hole transfer layer; an electron blocking layer; and a layer carrying out hole transfer and electron blocking at the same time, and one or more layers of the layers may include the compound.

In such an organic material layer having a multilayer structure, the compound may be included in a light emitting layer; a layer carrying out hole injection/hole transfer and light emitting at the same time; a layer carrying out hole transfer and light emitting at the same time; or a layer carrying out electron transfer and light emitting at the same time, and the like.

According to one embodiment of the present specification, the organic material layer includes a light emitting layer, and the light emitting layer may include a compound represented by the following Chemical Formula 1-A:

[Chemical Formula 1-A]

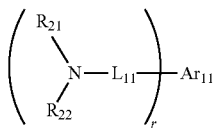

wherein, in Chemical Formula 1-A, r is an integer of 1 or greater, and when r is 2 or greater, the structures in the parentheses are the same as or different from each other, $Ar_{11}$ is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group, $L_{11}$ is a direct bond; a substituted or unsubstituted arylene group; or a substituted or unsubstituted heteroarylene group, and $R_{21}$ and $R_{22}$ are the same as or different from each other, and each independently a substituted or unsubstituted aryl group; a substituted or unsubstituted alkyl group; a substituted or unsubstituted silyl group; a substituted or unsubstituted arylalkyl group; or a substituted or unsubstituted heteroaryl group, or may bond to each other to form a substituted or unsubstituted ring.

According to one embodiment of the present specification, the light emitting layer includes the compound represented by Chemical Formula 1-A as a dopant of the light emitting layer.

According to one embodiment of the present specification, $L_{11}$ is a direct bond.

According to one embodiment of the present specification, r is 2.

According to one embodiment of the present specification, $Ar_{11}$ is a divalent pyrene group unsubstituted or substituted with deuterium, a methyl group, an ethyl group, an iso-propyl group or a tert-butyl group; or a divalent chrysene group unsubstituted or substituted with deuterium, a methyl group, an ethyl group, an iso-propyl group or a tert-butyl group.

According to one embodiment of the present specification, $Ar_{11}$ is a divalent pyrene group unsubstituted or substituted with deuterium, a methyl group, an ethyl group, an iso-propyl group or a tert-butyl group.

According to one embodiment of the present specification, $R_{21}$ and $R_{22}$ are the same as or different from each other, and each independently a substituted or unsubstituted aryl group having 6 to 60 carbon atoms; or a substituted or unsubstituted heteroaryl group having 2 to 60 carbon atoms.

According to one embodiment of the present specification, $R_{21}$ and $R_{22}$ are the same as or different from each other, and each independently an aryl group having 6 to 60 carbon atoms unsubstituted or substituted with deuterium, an alkyl group, a nitrile group, an aryl group, an alkylsilyl group or an alkylgermanium group; or a heteroaryl group having 2 to 60 carbon atoms unsubstituted or substituted with deuterium, an alkyl group, a nitrile group, an aryl group, an alkylsilyl group or an alkylgermanium group.

According to one embodiment of the present specification, $R_{21}$ and $R_{22}$ are the same as or different from each other, and each independently an aryl group having 6 to 60 carbon atoms unsubstituted or substituted with deuterium, a methyl group, an ethyl group, an iso-propyl group, a tert-butyl group, a nitrile group, a phenyl group, a trimethylsilyl group or a trimethylgermanium group; or a heteroaryl group having 2 to 60 carbon atoms unsubstituted or substituted with deuterium, a methyl group, an ethyl group, an iso-propyl group, a tert-butyl group, a nitrile group, a phenyl group, a trimethylsilyl group or a trimethylgermanium group.

According to one embodiment of the present specification, $R_{21}$ and $R_{22}$ are the same as or different from each other, and each independently a phenyl group unsubstituted or substituted with deuterium, a methyl group, an ethyl group, an iso-propyl group, a tert-butyl group, a nitrile group, a phenyl group, a trimethylsilyl group or a trimethylgermanium group; a biphenyl group unsubstituted or substituted with deuterium, a methyl group, an ethyl group, an iso-propyl group, a tert-butyl group, a nitrile group, a phenyl group, a trimethylsilyl group or a trimethylgermanium group; a terphenyl group unsubstituted or substituted with deuterium, a methyl group, an ethyl group, an iso-propyl group, a tert-butyl group, a nitrile group, a phenyl group, a trimethylsilyl group or a trimethylgermanium group; or a dibenzofuran group unsubstituted or substituted with deuterium, a methyl group, an ethyl group, an iso-propyl group, a tert-butyl group, a nitrile group, a phenyl group, a trimethylsilyl group or a trimethylgermanium group.

According to one embodiment of the present specification, $R_{21}$ and $R_{22}$ are the same as or different from each other, and each independently a phenyl group unsubstituted or substituted with a trimethylgermanium group.

According to one embodiment of the present specification, Chemical Formula 1-A may be selected from among the following compounds.

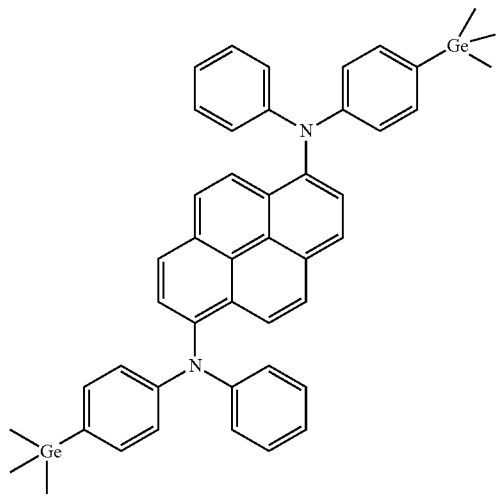

251
-continued
252
-continued
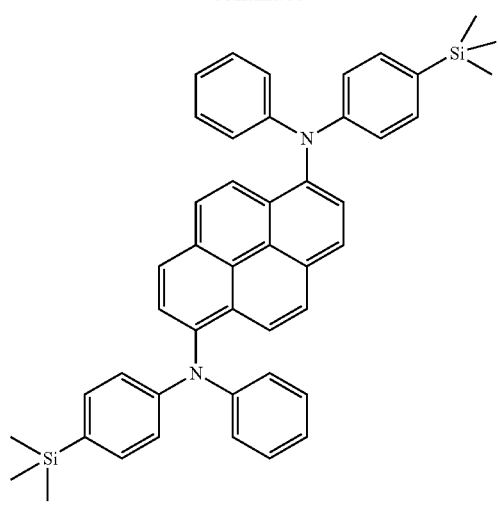
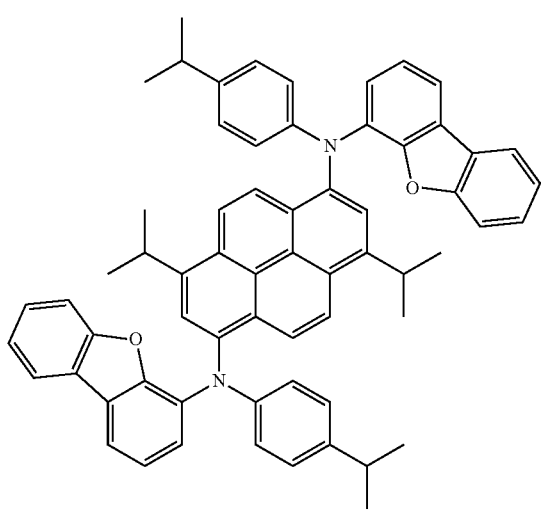
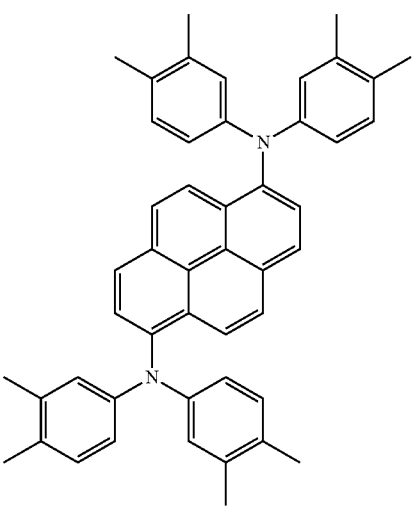
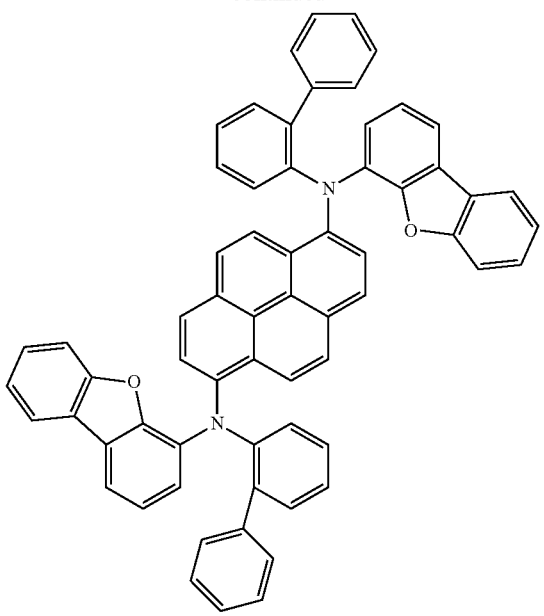
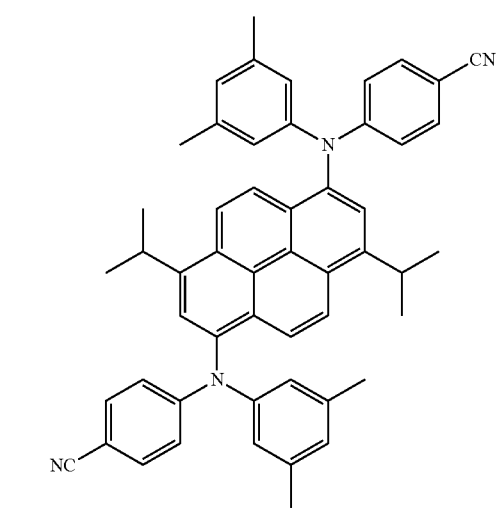
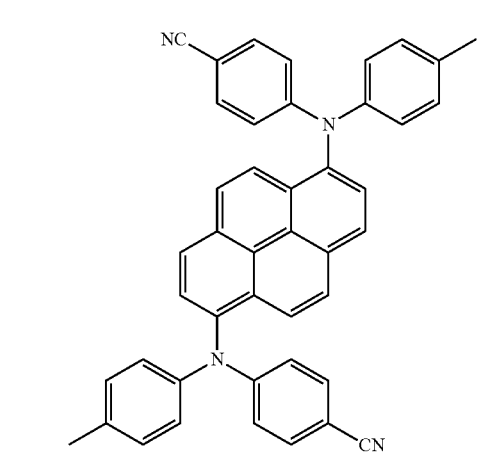

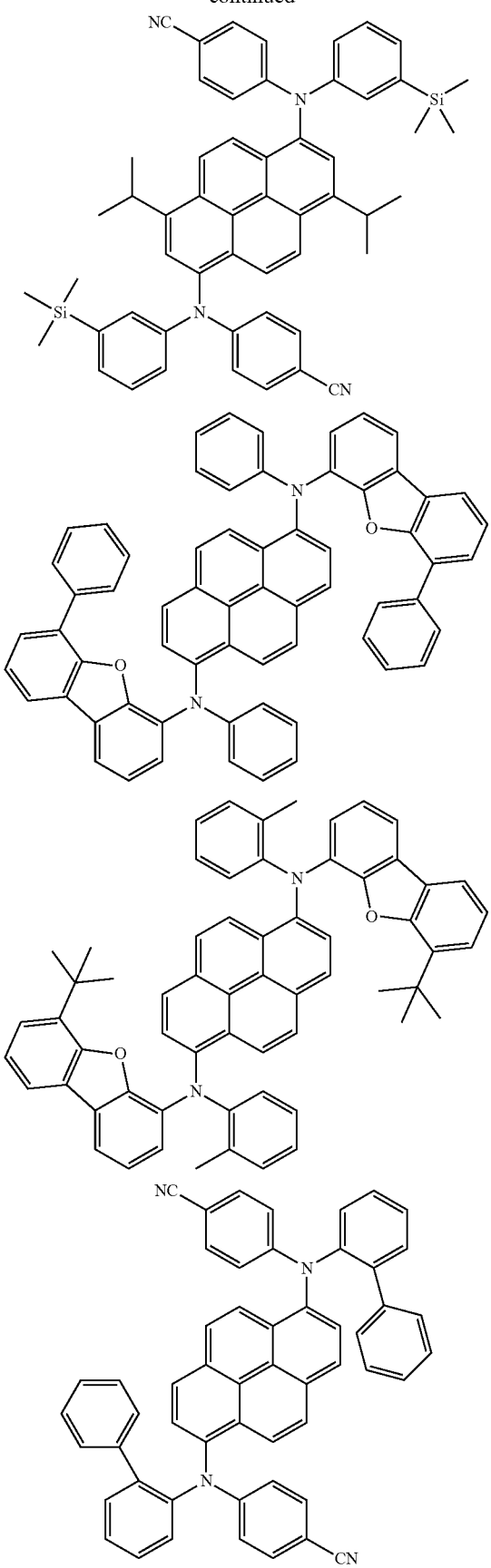

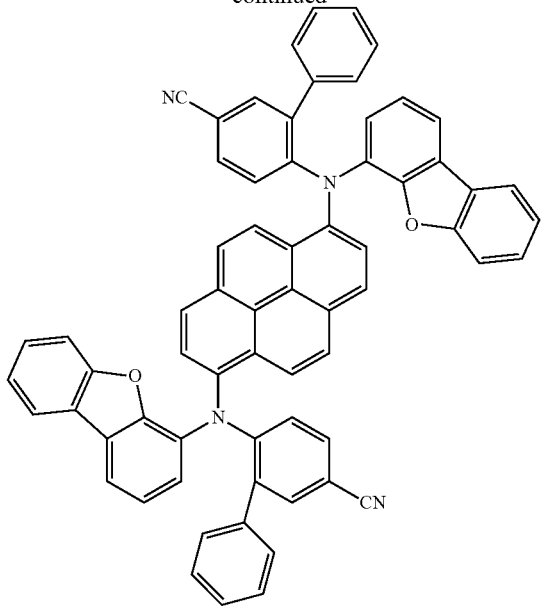

According to one embodiment of the present specification, the organic material layer includes a light emitting layer, and the light emitting layer may include a compound represented by the following Chemical Formula 1-B:

[Chemical Formula 1-B]

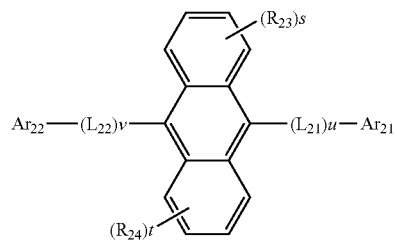

wherein, in Chemical Formula 1-B, $Ar_{21}$ and $Ar_{22}$ are the same as or different from each other, and each independently a substituted or unsubstituted aryl group; or a substituted or unsubstituted heteroaryl group, $L_{21}$ and $L_{22}$ are the same as or different from each other, and each independently a direct bond; a substituted or unsubstituted arylene group; or a substituted or unsubstituted heteroarylene group, u and v are each independently an integer of 1 or 2, and when u and v are 2, the substituents in the parentheses are the same as or different from each other, $R_{23}$ and $R_{24}$ are the same as or different from each other, and each independently hydrogen; deuterium; a halogen group; a nitrile group; a hydroxyl group; a substituted or unsubstituted alkyl group; a substituted or unsubstituted silyl group; a substituted or unsubstituted cycloalkyl group; a substituted or unsubstituted alkoxy group; a substituted or unsubstituted aryloxy group; a substituted or unsubstituted amine group; a substituted or unsubstituted aryl group; or a substituted or unsubstituted heteroaryl group, and t and s are each an integer of 0 to 4, and when t and s are 2 or greater, the substituents in the parentheses are the same as or different from each other.

According to one embodiment of the present specification, the light emitting layer includes the compound represented by Chemical Formula 1-B as a host of the light emitting layer.

According to one embodiment of the present specification, $Ar_{21}$ and $Ar_{22}$ are the same as or different from each other, and each independently a substituted or unsubstituted aryl group having 6 to 60 carbon atoms; or a substituted or unsubstituted heteroaryl group having 2 to 60 carbon atoms.

According to one embodiment of the present specification, $Ar_{21}$ and $Ar_{22}$ are the same as or different from each other, and each independently an aryl group having 6 to 60 carbon atoms unsubstituted or substituted with an aryl group or a heteroaryl group; or a heteroaryl group having 2 to 60 carbon atoms unsubstituted or substituted with an aryl group or a heteroaryl group.

According to one embodiment of the present specification, $Ar_{21}$ and $Ar_{22}$ are the same as or different from each other, and each independently a phenyl group unsubstituted or substituted with an aryl group or a heteroaryl group; a biphenyl group unsubstituted or substituted with an aryl group or a heteroaryl group; a naphthyl group unsubstituted or substituted with an aryl group or a heteroaryl group; a thiophene group unsubstituted or substituted with an aryl group or a heteroaryl group; a naphthobenzofuran group unsubstituted or substituted with an aryl group or a heteroaryl group; or an indolocarbazole group unsubstituted or substituted with an aryl group or a heteroaryl group.

According to one embodiment of the present specification, $L_{21}$ and $L_{22}$ are the same as or different from each other, and each independently a direct bond; a phenylene group; or a naphthylene group.

According to one embodiment of the present specification, $Ar_{21}$ is a 2-naphthyl group.

According to one embodiment of the present specification, $Ar_{22}$ is a 1-naphthyl group.

According to one embodiment of the present specification, $L_{21}$ is a phenylene group.

According to one embodiment of the present specification, $L_{22}$ is a direct bond.

According to one embodiment of the present specification, u is 1.

According to one embodiment of the present specification, v is 1.

According to one embodiment of the present specification, $R_{23}$ and $R_{24}$ are each hydrogen.

According to one embodiment of the present specification, Chemical Formula 1-B may be selected from among the following compounds.

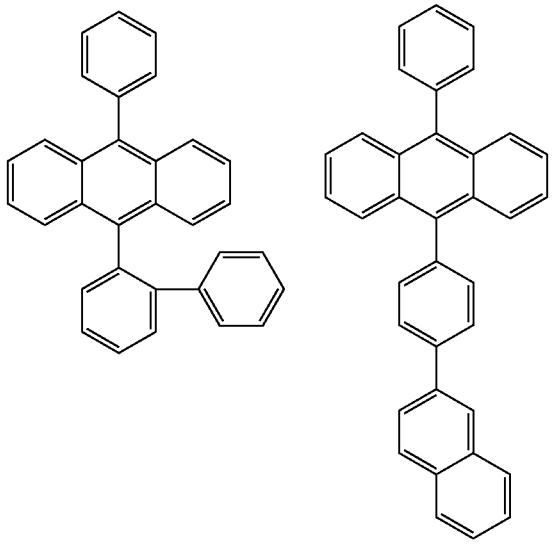

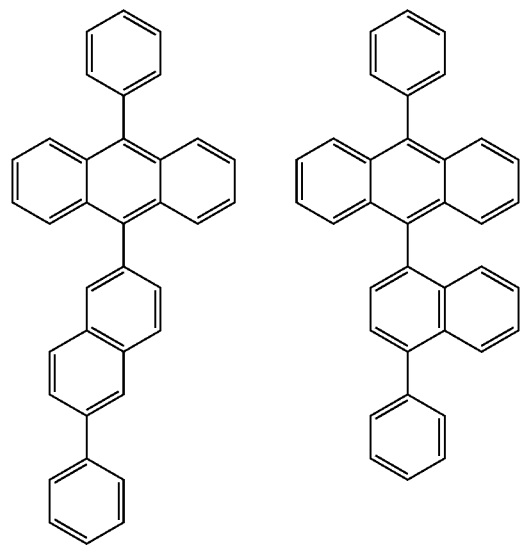

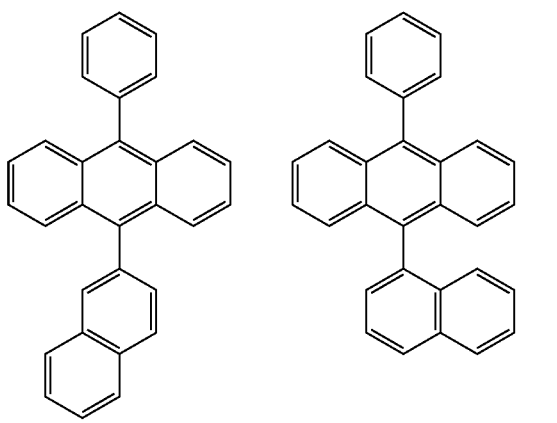

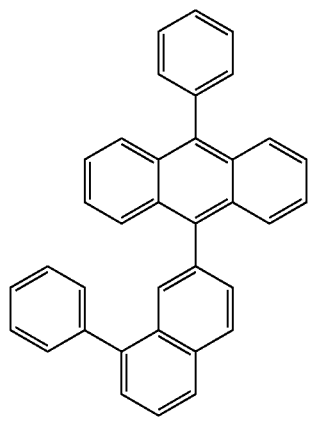

257
-continued
258
-continued
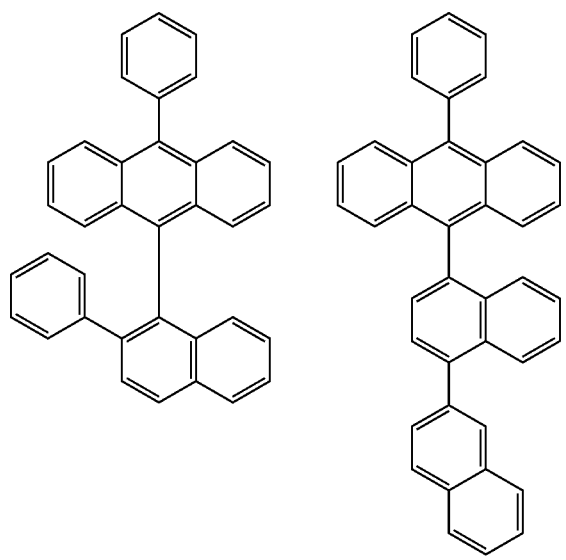
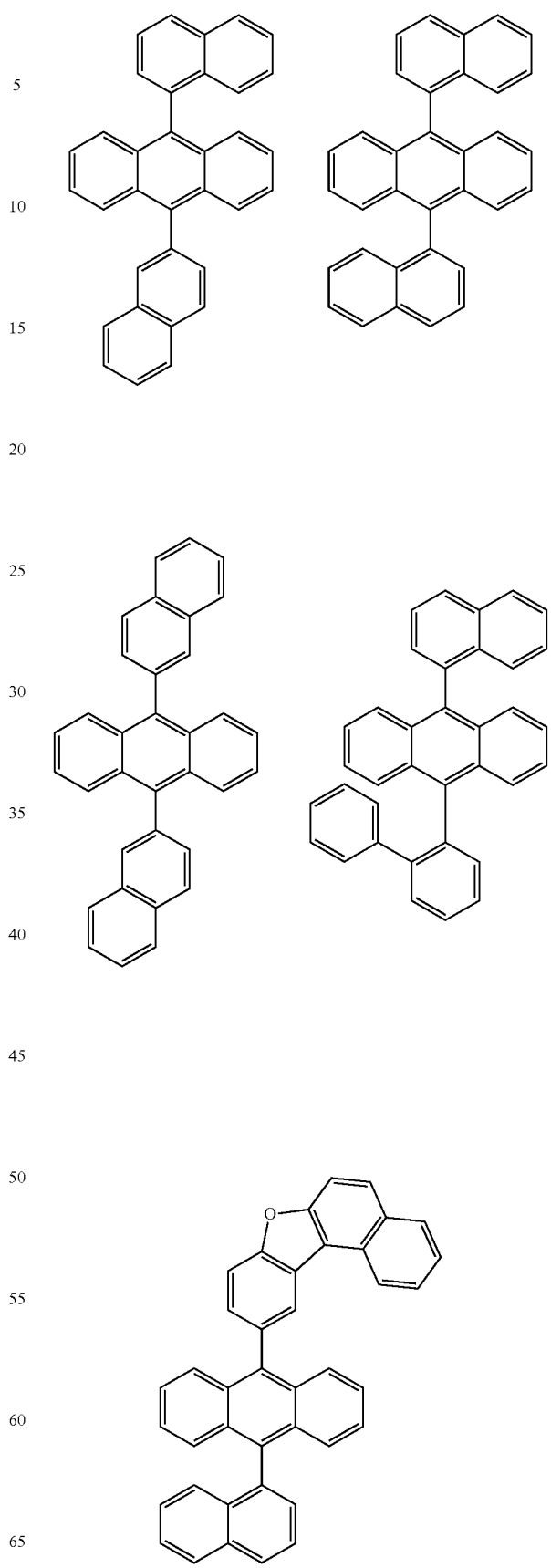

259
-continued
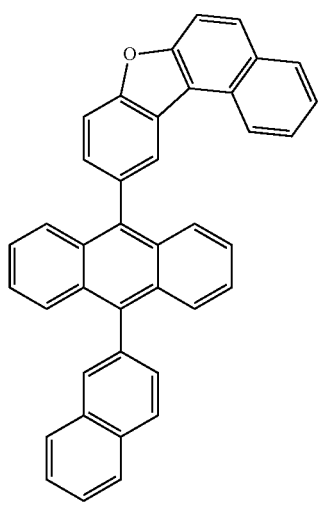
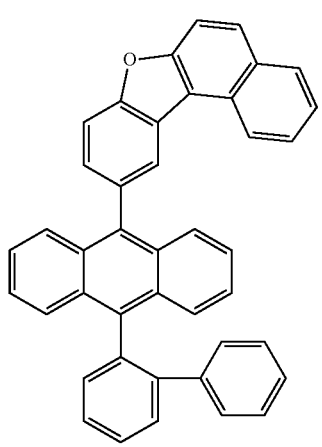
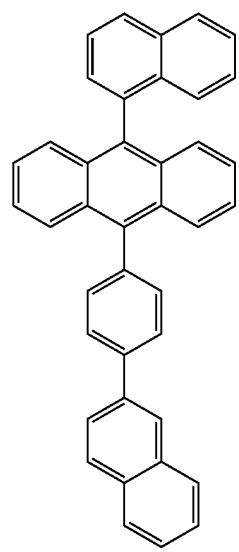
260
-continued
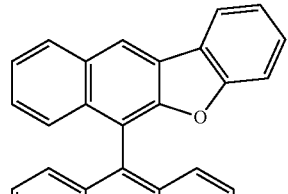
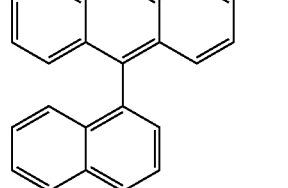
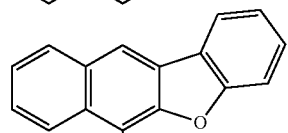
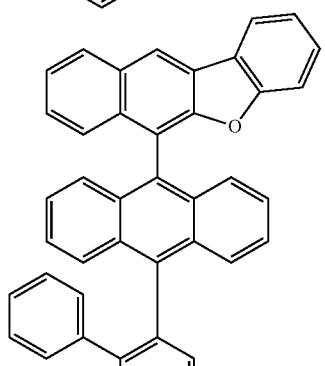
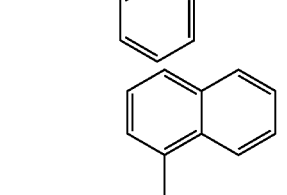

261
-continued
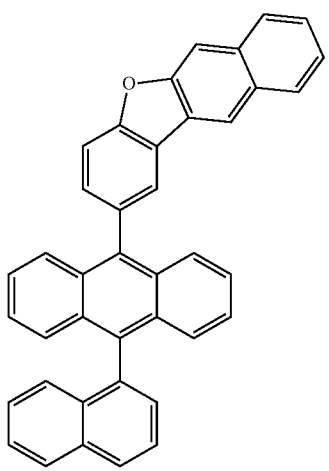
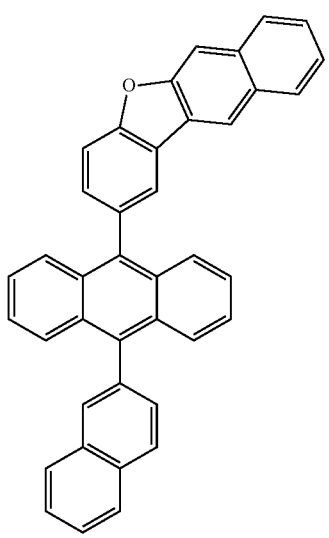
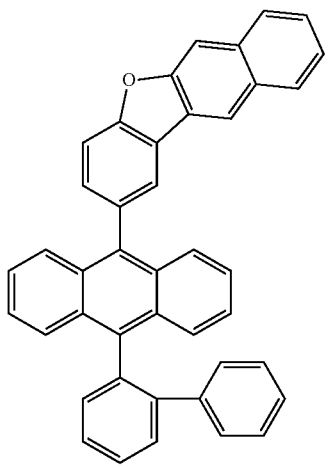
262
-continued
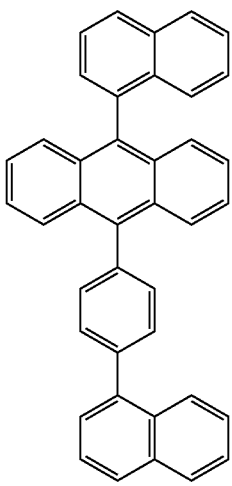
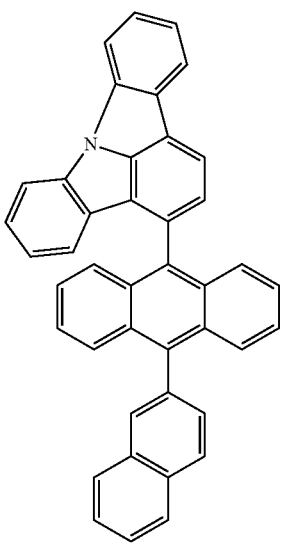
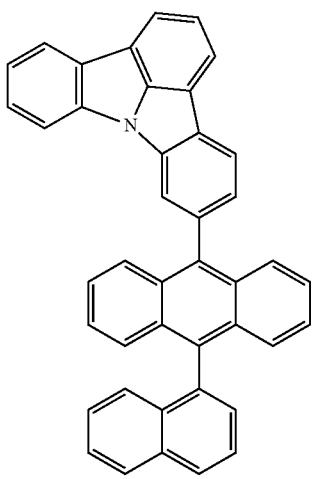

263
-continued
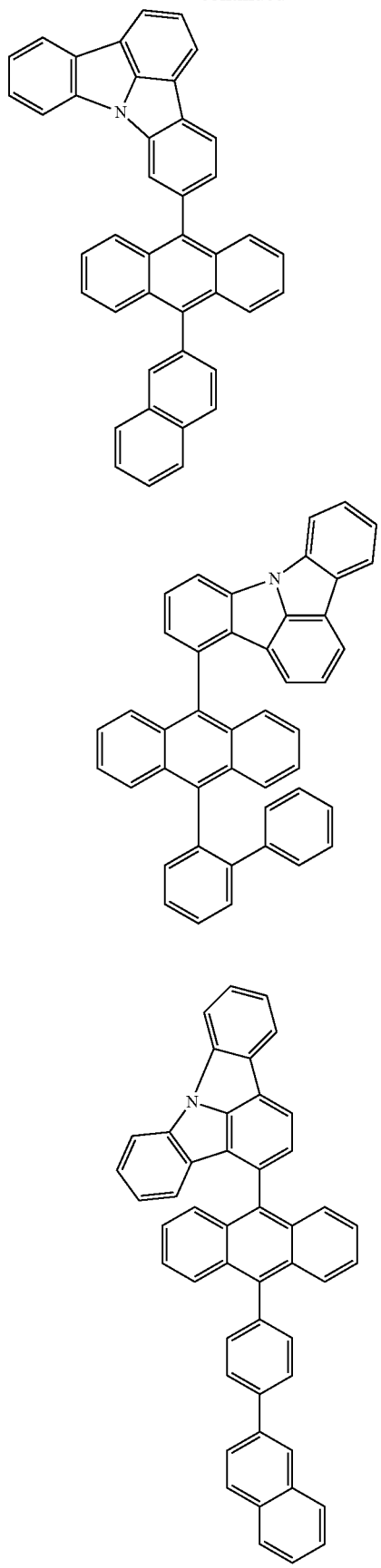
264
-continued
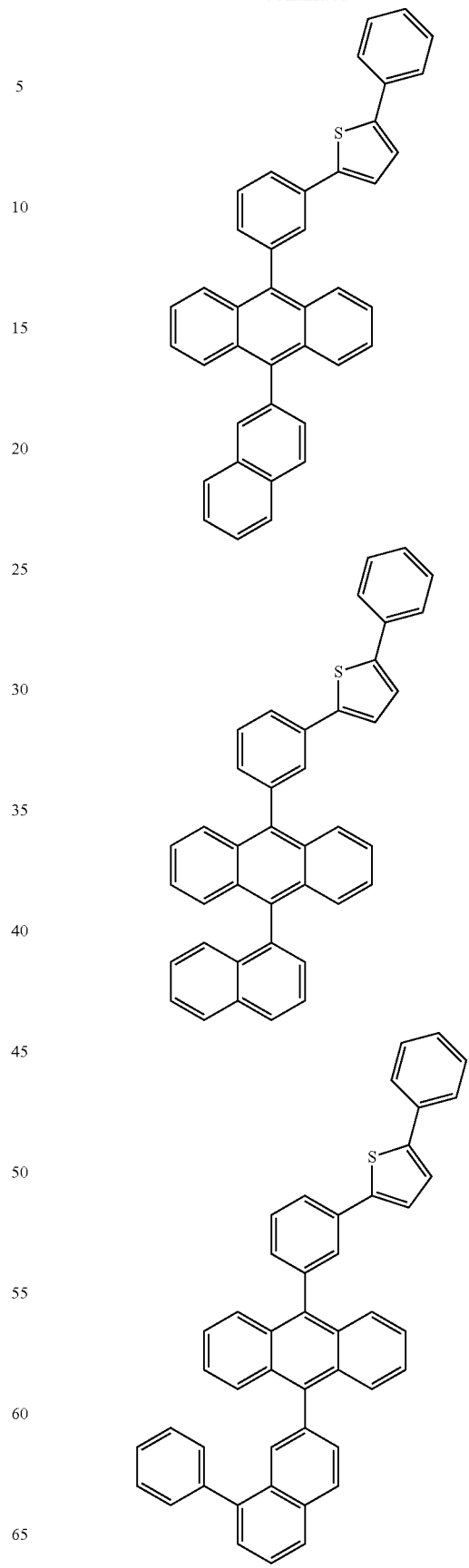

265
-continued
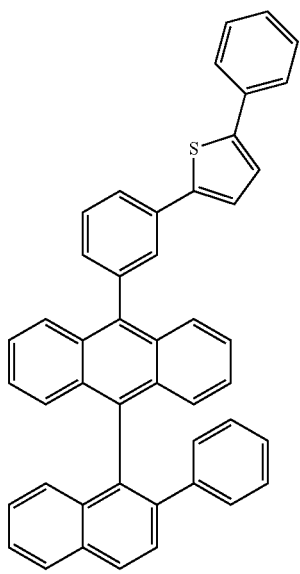
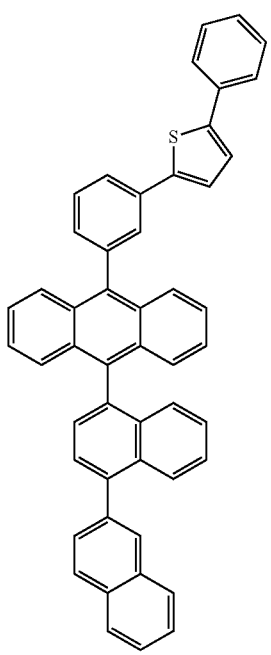
266
-continued
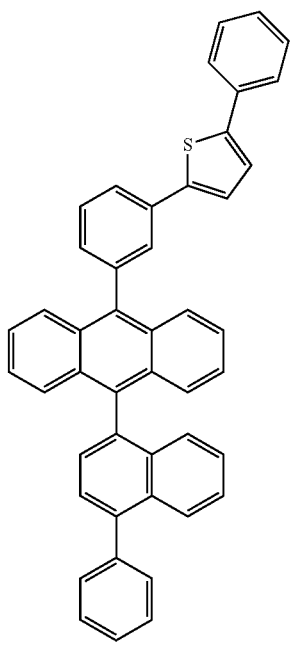
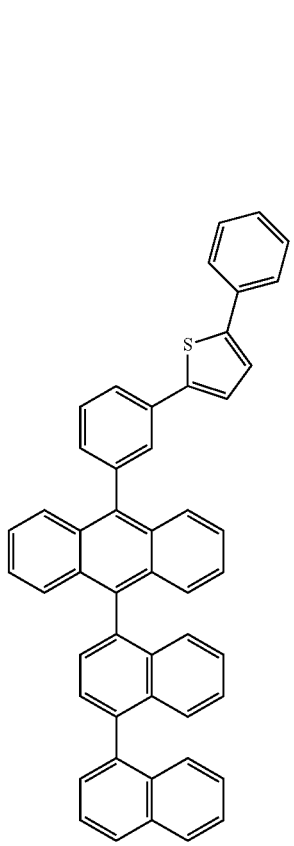

-continued

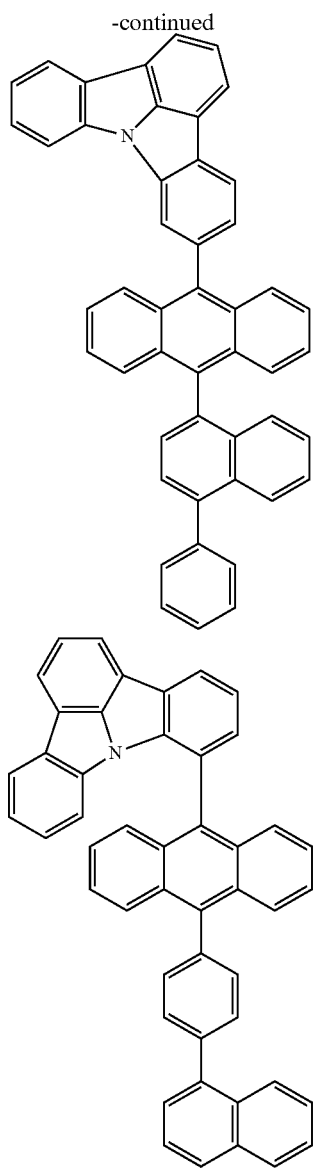

For example, the structure of the organic light emitting device of the present specification may have structures as shown in FIG. 1 and FIG. 2, however, the structure is not limited thereto.

FIG. 1 illustrates a structure of an organic light emitting device in which an anode (2), a light emitting layer (3) and a cathode (4) are consecutively laminated on a substrate (1). In such a structure, the compound may be included in the light emitting layer (3).

FIG. 2 illustrates a structure of an organic light emitting device in which an anode (2), a hole injection layer (5), a hole transfer layer (6), a light emitting layer (7), an electron transfer layer (8) and a cathode (4) are consecutively laminated on a substrate (1). In such a structure, the compound may be included in the hole injection layer (5), the hole transfer layer (6), the light emitting layer (7) or the electron transfer layer (8).

For example, the organic light emitting device according to the present specification may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer, and an anode material on a substrate.

The organic material layer may have a multilayer structure including a hole injection layer, a hole transfer layer, a light emitting layer, an electron transfer layer and the like, but is not limited thereto, and may have a single layer structure. In addition, the organic material layer may be prepared into less numbers of layers using various polymer materials through a solvent process such as spin coating, dip coating, doctor blading, screen printing, ink jet printing or a thermal transfer method instead of a deposition method.

As the anode material, materials having large work function are normally preferable so that hole injection to an organic material layer is smooth. Specific examples of the anode material capable of being used in the present specification include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methyl compound), poly[3,4-(ethylene-1,2-dioxy)compound] (PEDOT), polypyrrole and polyaniline, but are not limited thereto.

As the cathode material, materials having small work function are normally preferable so that electron injection to an organic material layer is smooth. Specific examples of the cathode material capable of being used in the present specification include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, materials having a highest occupied molecular orbital (HOMO) between the work function of an anode material and the HOMO of surrounding organic material layers are preferable as a material favorably receiving holes from an anode at a low voltage. Specific examples of the hole injection material include a metal porphyrin, oligothiophene, an arylamine-based organic material, a hexanitrile hexaazatriphenylene-based organic material, a quinacridone-based organic material, a perylene-based organic material, anthraquinone, and a polyaniline- and a polythiophene-based conductive polymer, and the like, but are not limited thereto.

As the hole transfer material, materials having high mobility for the holes are suitable as a material receiving holes from an anode or a hole injection layer and transfers the holes to a light emitting layer. Specific examples thereof include an arylamine-based organic material, a conductive polymer, a block copolymer having conjugated parts and non-conjugated parts together, and the like, but are not limited thereto.

As the light emitting material, materials having favorable quantum efficiency for fluorescence or phosphorescence are preferable as a material capable of emitting light in a visible light region by receiving holes and electrons from a hole transfer layer and an electron transfer layer, respectively, and binding the holes and the electrons. Specific examples thereof include a 8-hydroxyquinoline aluminum complex ($Alq_3$); a carbazole-based compound; a dimerized styryl compound; BAlq; a 10-hydroxybenzo quinoline-metal compound; a benzoxazole-, a benzothiazole- and a benzimidazole-based compound; a poly(p-phenylenevinylene) (PPV)-based polymer; a spiro compound; polyfluorene, rubrene, and the like, but are not limited thereto.

The organic material layer including the compound represented by Chemical Formula 1 includes the compound represented by Chemical Formula 1 as a host, and the compound may be used together with an iridium (Ir)-based dopant.

The iridium-based complexes used as the dopant are as follows.

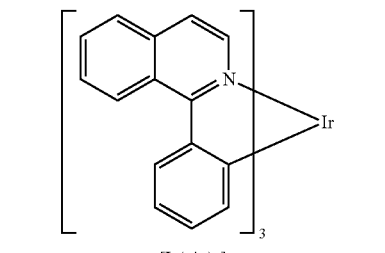

[Ir(piq)₃]

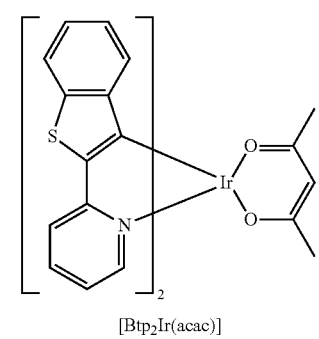

[Btp₂Ir(acac)]

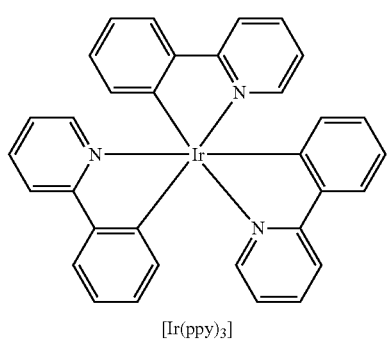

[Ir(ppy)₃]

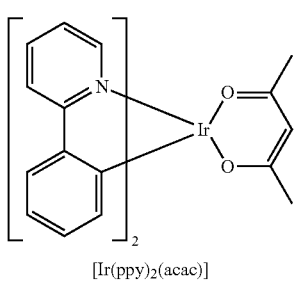

[Ir(ppy)₂(acac)]

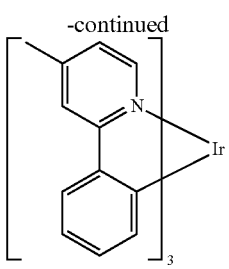

[Ir(mpyp)₃]

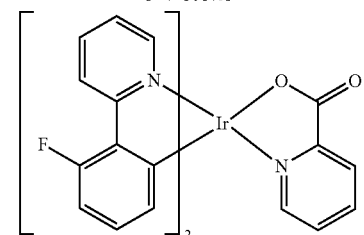

[F₂Irpic]

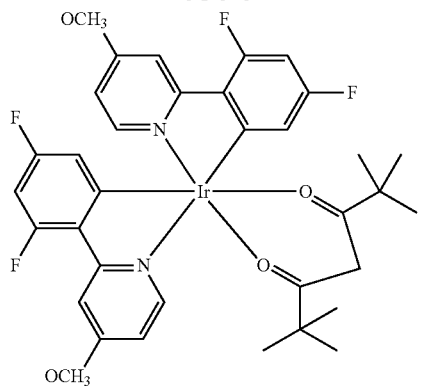

[F₂ppy)₂Ir(tmd)]

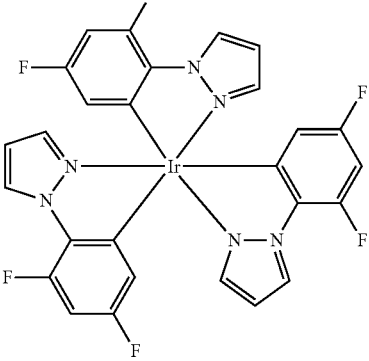

[Ir(dfppz)₃]

As the electron transfer material, materials having high mobility for electrons are suitable as a material favorably receiving electrons from a cathode and transferring the electrons to a light emitting layer. Specific examples thereof include an Al complex of 8-hydroxyquinoline; a complex including Alq₃; an organic radical compound; a hydroxyflavon-metal complex and the like, but are not limited thereto.

The organic light emitting device according to the present specification may be a top-emission type, a bottom-emission type or a dual-emission type depending on the materials used.

The compound according to the present specification may be also used in organic electronic devices including organic solar cells, organic photoconductors, organic transistors and the like using a similar principle as in the organic light emitting device.

Hereinafter, methods for preparing the compound of Chemical Formula 1 and manufacturing an organic light emitting device using the same will be specifically described with reference to the following examples. However, the following examples are for illustrative purposes only, and the scope of the present disclosure is not limited thereto.

PREPARATION EXAMPLE

<Preparation Example A> Synthesis of Intermediate A

Intermediate A was synthesized as in the following reaction formula.

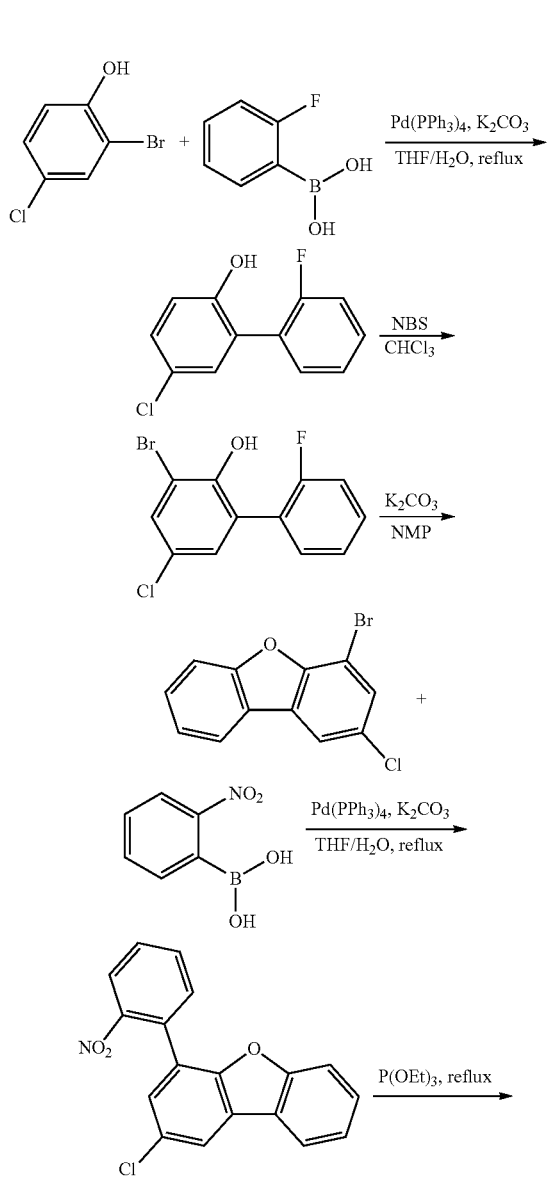

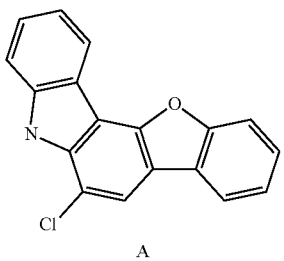

A

<Preparation Example B> Syntheses of Intermediate B to Intermediate D

Intermediate B to Intermediate D were synthesized as in the following reaction formulae.

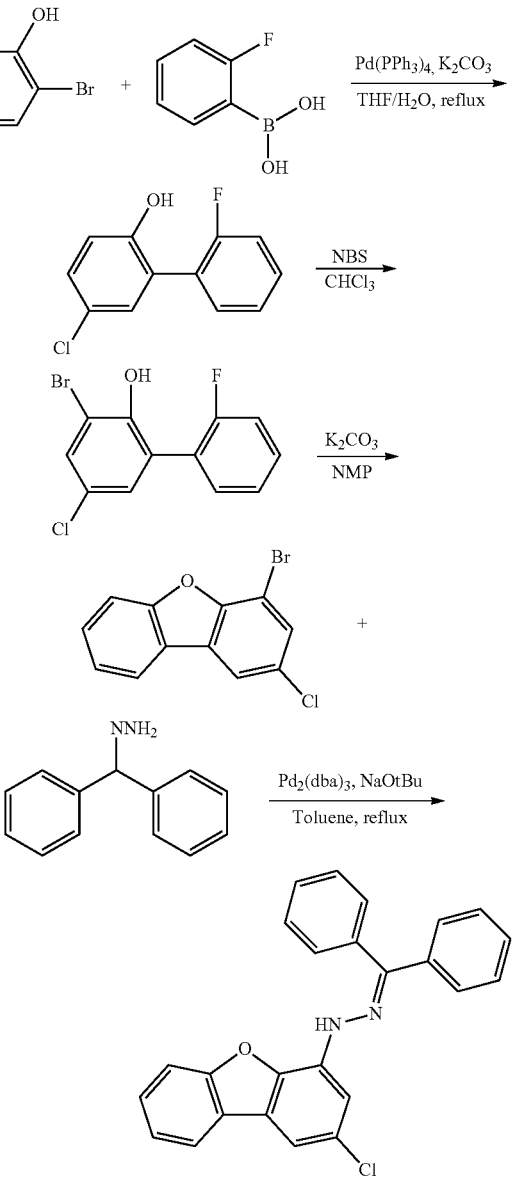

273
-continued
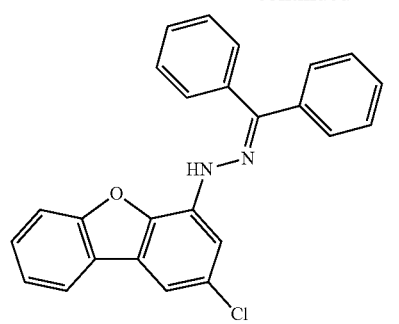
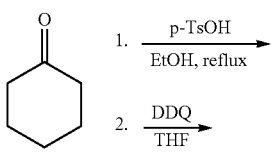
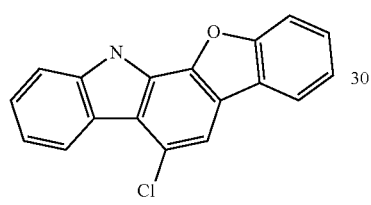
B
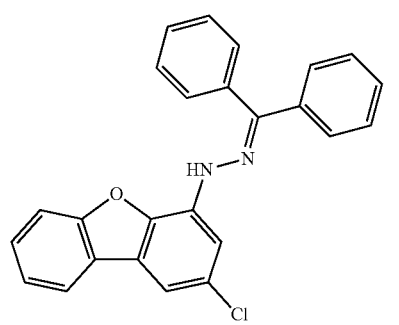
+
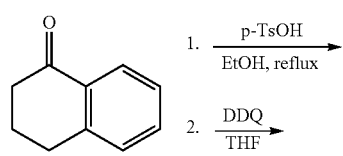
274
-continued
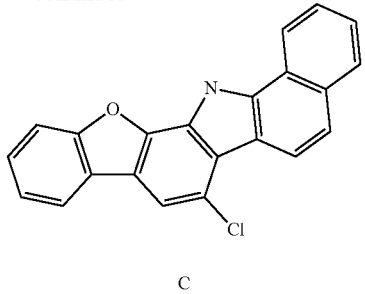
C
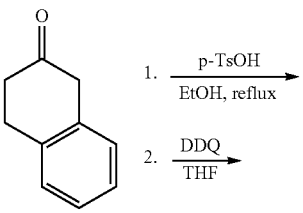
+
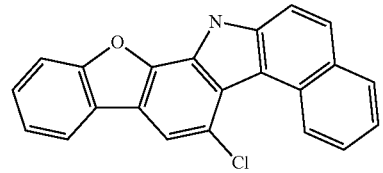
D
<Preparation Example C> Syntheses of Intermediate E to Intermediate H
Intermediate E to Intermediate H were synthesized as in the following reaction formula.

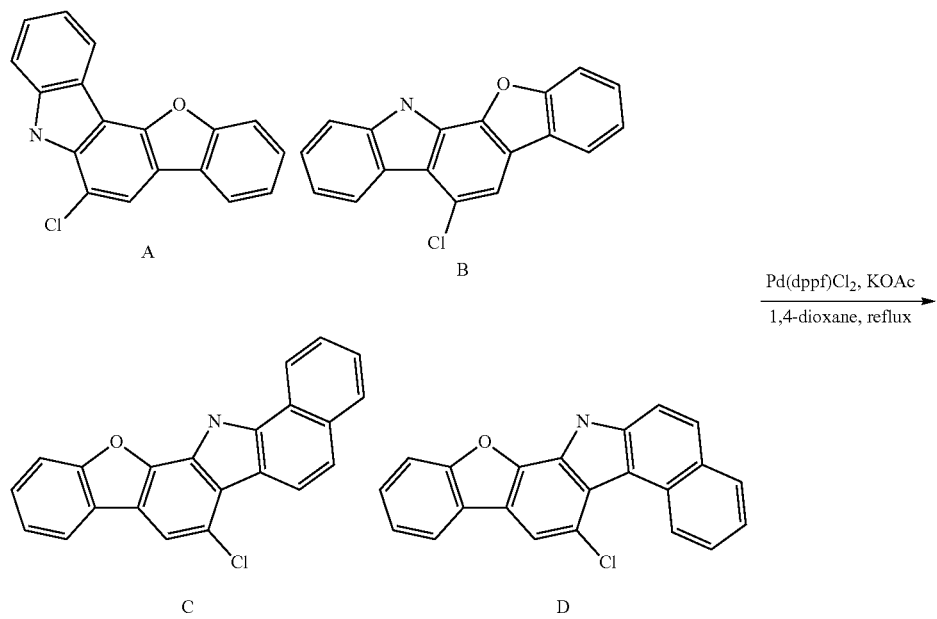
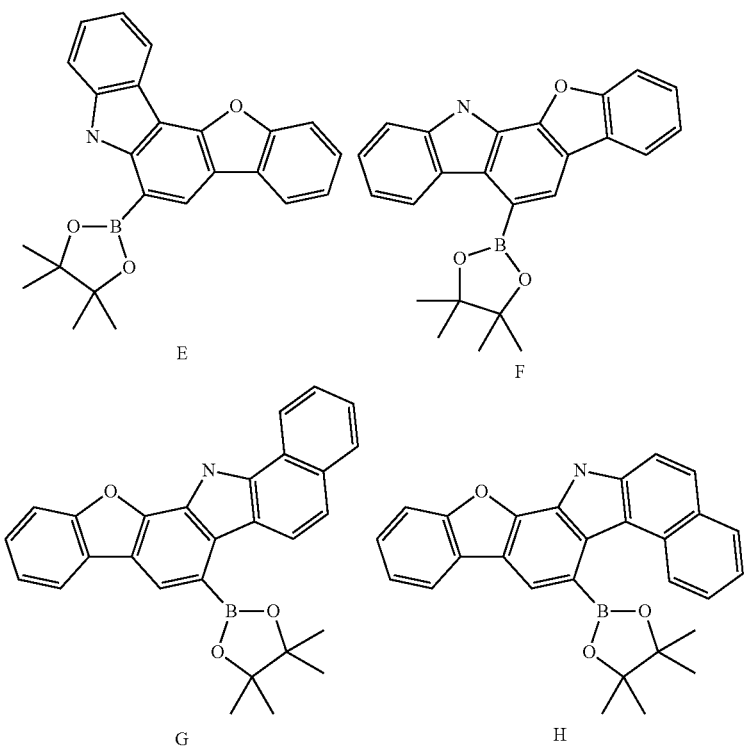

<Preparation Example 1> Syntheses of Compound 1-A and Compound 1-1

1) Synthesis of Compound 1-A

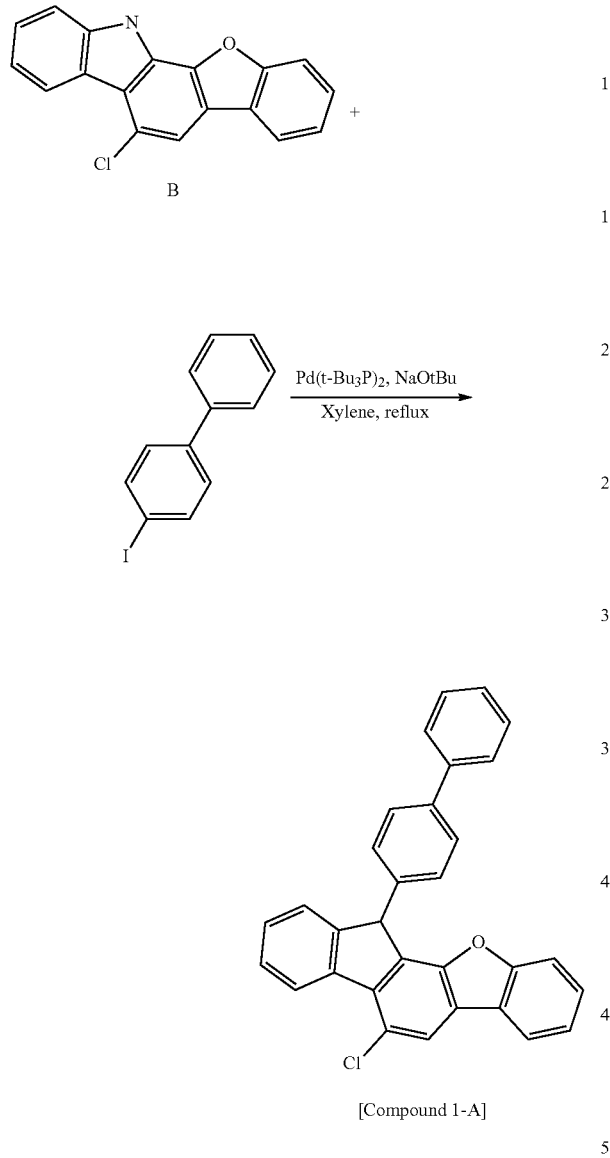

2) Synthesis of Compound 1-1

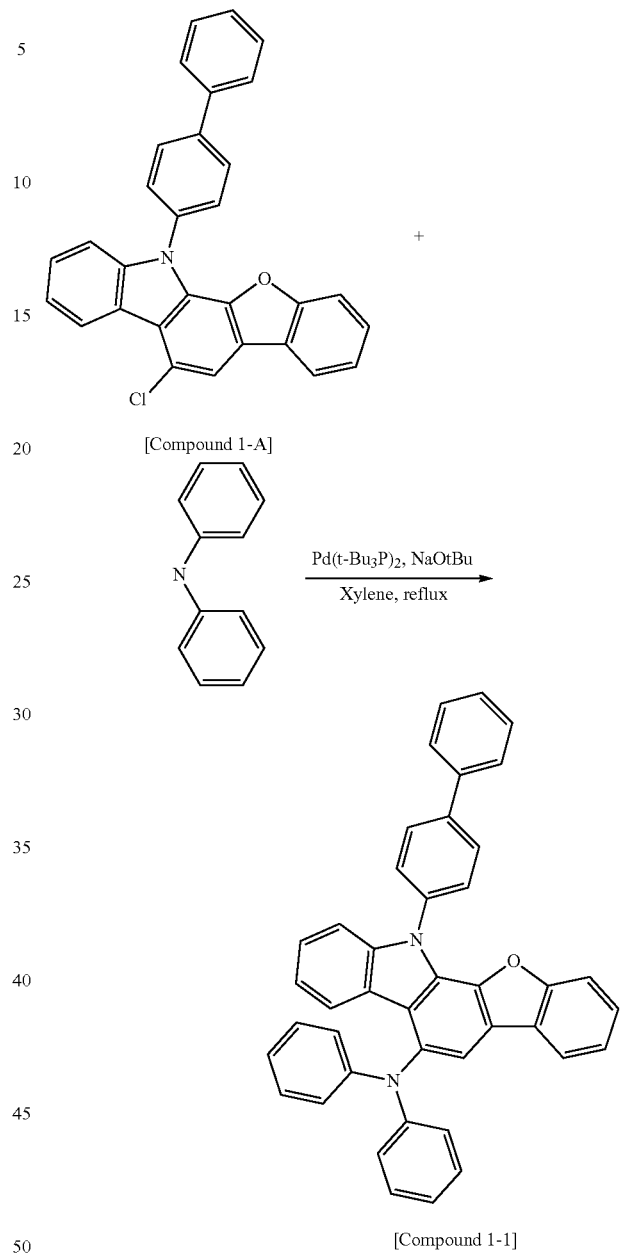

After completely dissolving Intermediate B (10.0 g, 34.48 mmol) and 4-iodo-1,1'-biphenyl (10.62 g, 37.93 mmol) in 150 ml of xylene in a 500 ml round bottom flask under nitrogen atmosphere, sodium tert-butoxide (4.31 g, 44.82 mmol) and then bis(tri-tert-butylphosphine) palladium (0) (0.17 g, 0.34 mmol) were added thereto, and the result was heated and stirred for 3 hours. After lowering the temperature to room temperature, the result was filtered to remove the salt and the xylene was vacuum concentrated, and the result was recrystallized with 250 ml of ethyl acetate to prepare Compound 1-A (12.44 g, yield: 81%).

MS[M+H]$^+$=444

After completely dissolving Compound 1-A (12.44 g, 28.02 mmol) and diphenylamine (5.21 g, 30.82 mmol) in 210 ml of xylene in a 500 ml round bottom flask under nitrogen atmosphere, sodium tert-butoxide (3.51 g, 36.43 mmol) and then bis(tri-tert-butylphosphine) palladium(0) (0.14 g, 0.28 mmol) were added thereto, and the result was heated and stirred for 5 hours. After lowering the temperature to room temperature, the result was filtered to remove the salt and the xylene was vacuum concentrated, and the result was columned using tetrahydrofuran:hexane=1:20 to prepare Compound 1-1 (12.36 g, yield: 76%).

MS[M+H]$^+$=577

<Preparation Example 2> Synthesis of Compound 1-2

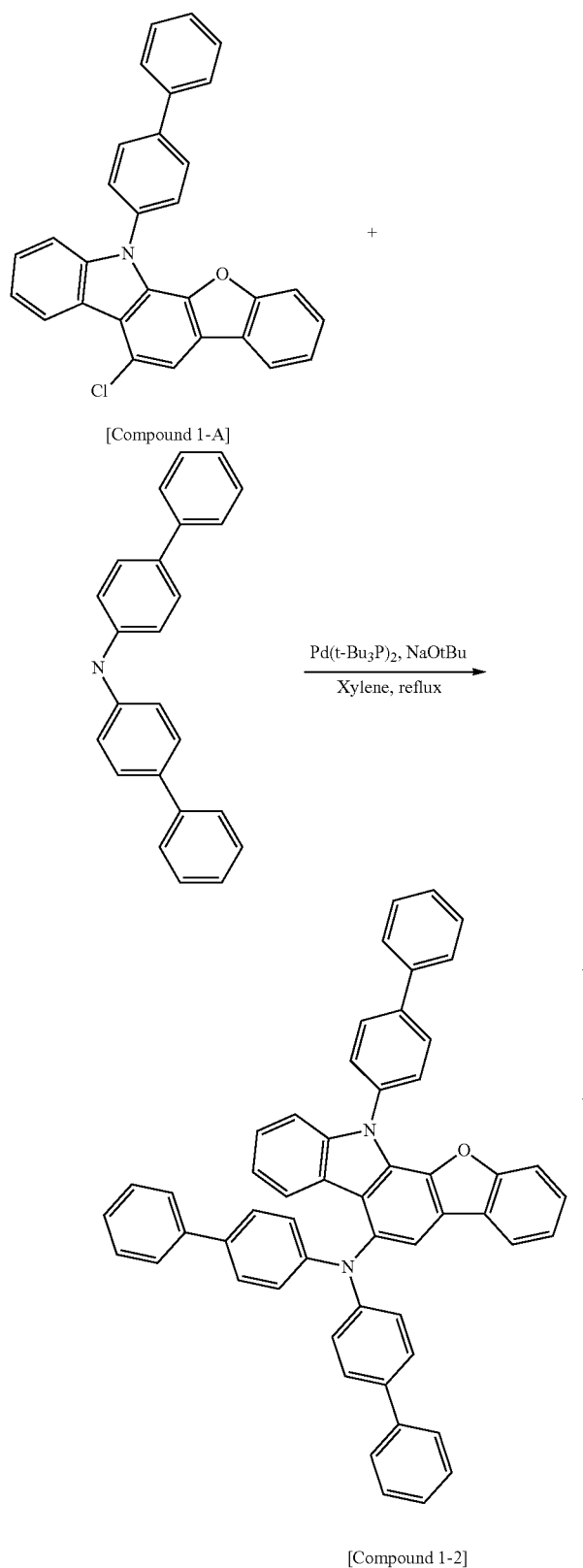

[Compound 1-2]

After completely dissolving Compound 1-A (8.0 g, 18.02 mmol) and di([1,1'-biphenyl]-4-yl)amine (6.36 g, 19.82 mmol) in 160 ml of xylene in a 500 ml round bottom flask under nitrogen atmosphere, sodium tert-butoxide (3.51 g, 36.43 mmol) and then bis(tri-tert-butylphosphine) palladium (0) (0.14 g, 0.28 mmol) were added thereto, and the result was heated and stirred for 5 hours. After lowering the temperature to room temperature, the result was filtered to remove the salt and the xylene was vacuum concentrated, and the result was columned using tetrahydrofuran:hexane=1:20 to prepare Compound 1-2 (10.25 g, yield: 78%).

MS[M+H]$^+$=729

<Preparation Example 3> Synthesis of Compound 1-3

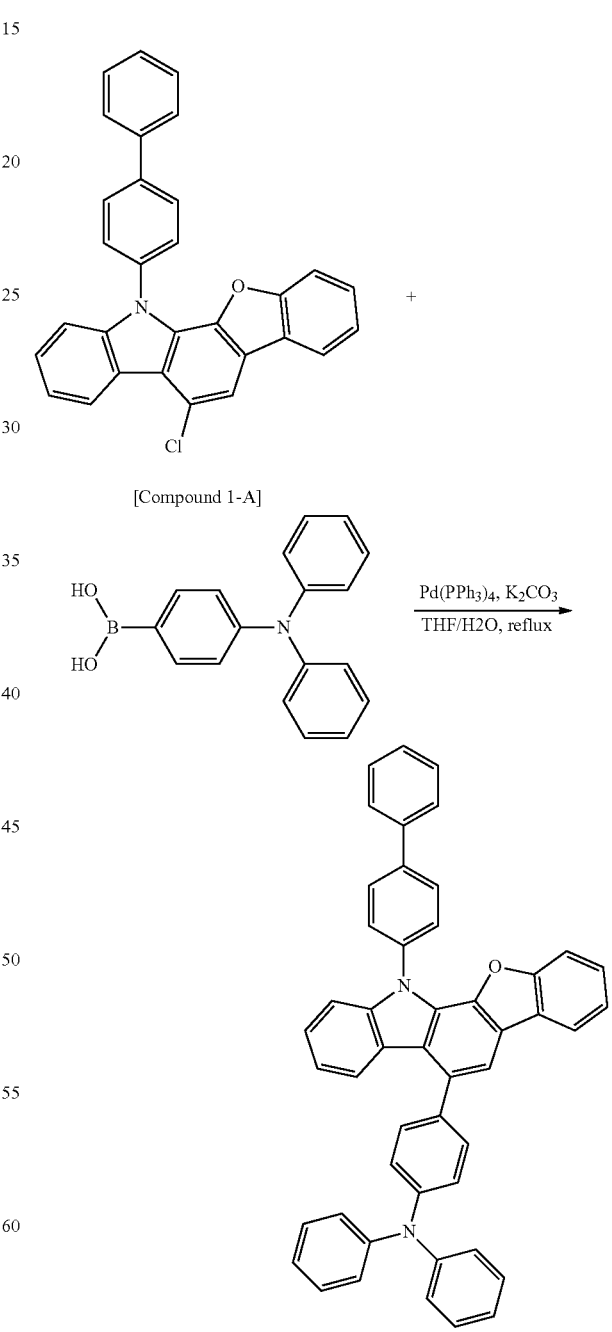

[Compound 1-3]

After completely dissolving Compound 1-A (11.0 g, 24.77 mmol) and (4-(diphenylamino)phenyl)boronic acid (7.88 g, 27.25 mmol) in 320 ml of tetrahydrofuran in a 500 ml round bottom flask under nitrogen atmosphere, a 2 M aqueous potassium carbonate solution (160 ml) and then tetrakis-(triphenylphosphine)palladium (0.86 g, 0.74 mmol) were added thereto, and the result was heated and stirred for 5 hours. After lowering the temperature to room temperature, the water layer was removed, and the result was dried with anhydrous magnesium sulfate, vacuum concentrated, and then recrystallized with 220 ml of ethyl acetate to prepare Compound 1-3 (13.75 g, yield: 85%).

MS[M+H]$^+$=653

<Preparation Example 4> Synthesis of Compound 1-4

[Compound 1-4]

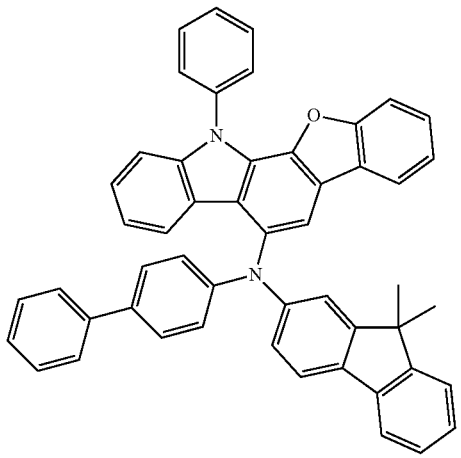

Compound 1-4 was prepared using the same method as the method preparing Compound 1-1, except that iodobenzene was used instead of 4-iodo-1,1'-biphenyl and N-([1,1'-biphenyl]-4-yl)-9,9-dimethyl-9H-fluoren-2-amine was used instead of diphenylamine in Preparation Example 1.

MS[M+H]$^+$=693

<Preparation Example 5> Synthesis of Compound 1-5

[Compound 1-5]

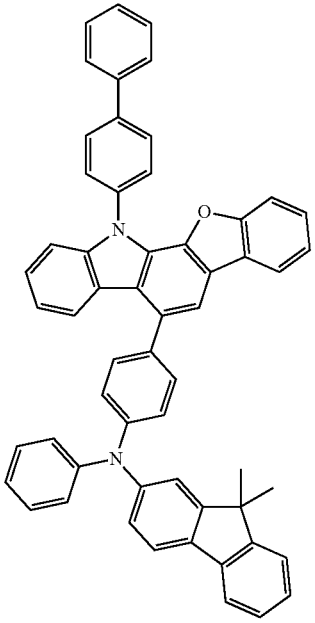

Compound 1-5 was prepared using the same method as the method preparing Compound 1-3, except that (4-((9,9-dimethyl-9H-fluoren-2-yl)(phenyl)amino)phenyl)boronic acid was used instead of (4-(diphenylamino)phenyl)boronic acid in Preparation Example 3.

MS[M+H]$^+$=769

<Preparation Example 6> Synthesis of Compound 1-6

[Compound 1-6]

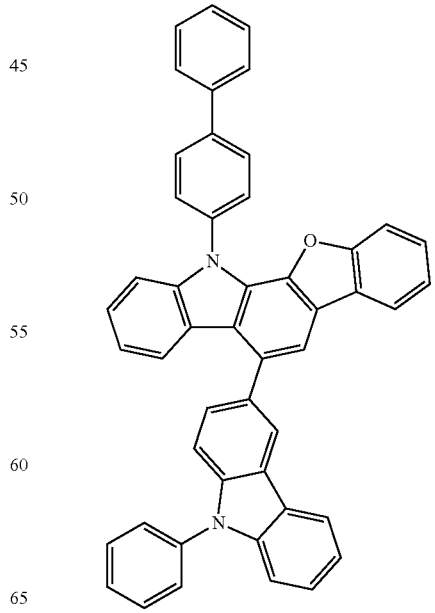

Compound 1-6 was prepared using the same method as the method preparing Compound 1-3, except that (9-phenyl-9H-carbazol-3-yl)boronic acid was used instead of (4-(diphenylamino)phenyl)boronic acid in Preparation Example 3.

MS[M+H]$^+$=651

<Preparation Example 7> Synthesis of Compound 1-7

[Compound 1-7]

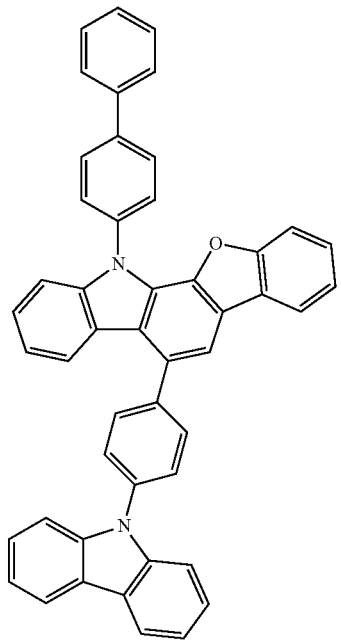

Compound 1-7 was prepared using the same method as the method preparing Compound 1-3, except that 4-(9H-carbazol-9-yl)phenyl)boronic acid was used instead of (4-(diphenylamino)phenyl)boronic acid in Preparation Example 3.

MS[M+H]$^+$=651

<Preparation Example 8> Synthesis of Compound 1-8

[Compound 1-8]

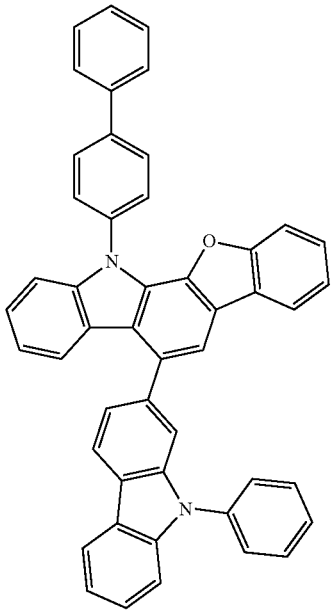

Compound 1-8 was prepared using the same method as the method preparing Compound 1-3, except that (9-phenyl-9H-carbazol-2-yl)boronic acid was used instead of (4-(diphenylamino)phenyl)boronic acid in Preparation Example 3.

MS[M+H]$^+$=651

<Preparation Example 9> Syntheses of Compound 1-B, Compound 1-C and Compound 1-9

1) Synthesis of Compound 1-B

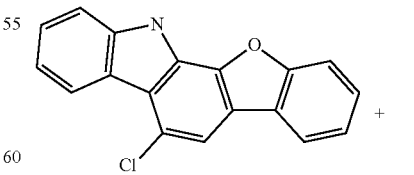

3) Synthesis of Compound 1-9

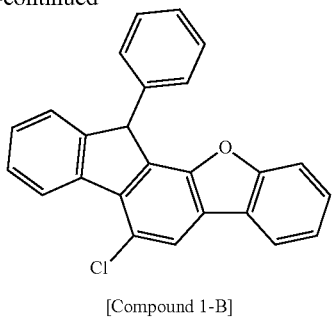

[Compound 1-B]

After completely dissolving Intermediate B (10.0 g, 34.48 mmol) and iodobenzene (7.74 g, 37.93 mmol) in 120 ml of xylene in a 500 ml round bottom flask under nitrogen atmosphere, sodium tert-butoxide (4.31 g, 44.82 mmol) and then bis(tri-tert-butylphosphine) palladium(0) (0.17 g, 0.34 mmol) were added thereto, and the result was heated and stirred for 2 hours. After lowering the temperature to room temperature, the result was filtered to remove the salt and the xylene was vacuum concentrated, and the result was recrystallized with 200 ml of ethyl acetate to prepare Compound 1-B (9.75 g, yield: 77%).

MS[M+H]$^+$=368

2) Synthesis of Compound 1-C

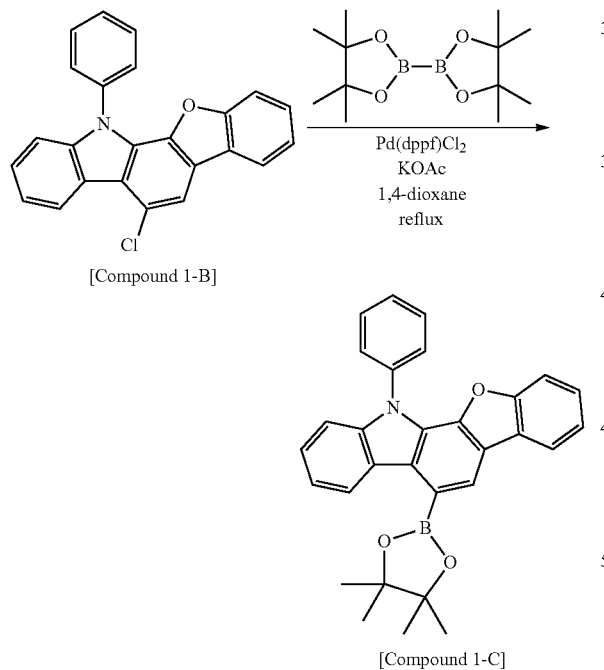

After completely dissolving Compound 1-B (9.75 g, 28.02 mmol) and bis(pinacolato)diboron (5.21 g, 30.82 mmol) in 210 ml of 1,4-dioxane in a 500 ml round bottom flask under nitrogen atmosphere, potassium acetate (3.91 g, 39.86 mmol) and then bis(tri-tert-butylphosphine) palladium (0) (0.14 g, 0.28 mmol) were added thereto, and the result was heated and stirred for 3 hours. After lowering the temperature to room temperature, the result was filtered to remove the salt and the xylene was vacuum concentrated, and the result was recrystallized with 300 ml of ethyl alcohol to prepare Compound 1-C (8.36 g, yield: 83%).

MS[M+H]$^+$=460

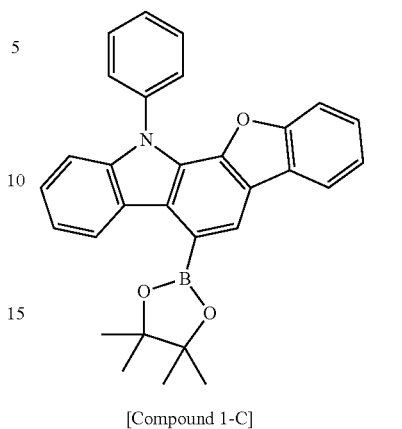

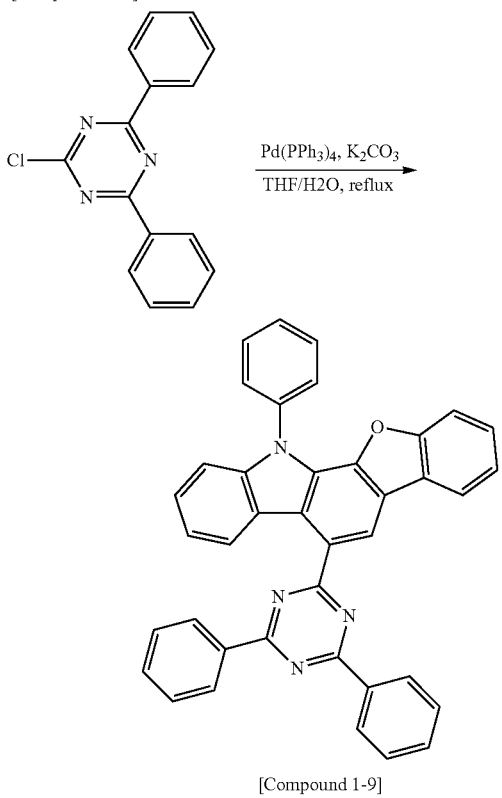

[Compound 1-9]

After completely dissolving Compound 1-C (8.36 g, 24.77 mmol) and 2-chloro-4,6-diphenyl-1,3,5-triazine (7.88 g, 27.25 mmol) in 260 ml of tetrahydrofuran in a 500 ml round bottom flask under nitrogen atmosphere, a 2 M aqueous potassium carbonate solution (130 ml) and then tetrakis-(triphenylphosphine)palladium (0.57 g, 0.49 mmol) were added thereto, and the result was heated and stirred for 5 hours. After lowering the temperature to room temperature, the water layer was removed, and the result was dried with anhydrous magnesium sulfate, vacuum concentrated, and then recrystallized with 280 ml of ethyl acetate to prepare Compound 1-9 (9.04 g, yield: 85%).

MS[M+H]$^+$=565

\<Preparation Example 10\> Synthesis of Compound 1-10

[Compound 1-10]

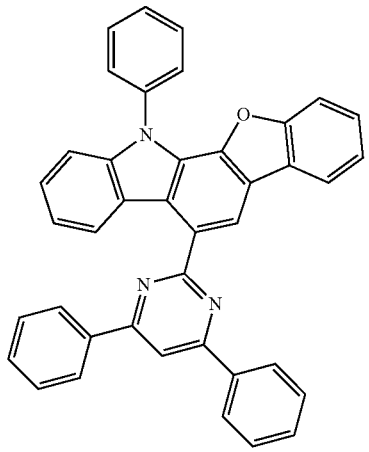

Compound 1-10 was prepared using the same method as the method preparing Compound 1-9, except that 2-chloro-4,6-diphenylpyrimidine was used instead of 2-chloro-4,6-diphenyl-1,3,5-triazine in Preparation Example 9.

MS[M+H]$^+$=564

\<Preparation Example 11\> Synthesis of Compound 1-11

[Compound 1-11]

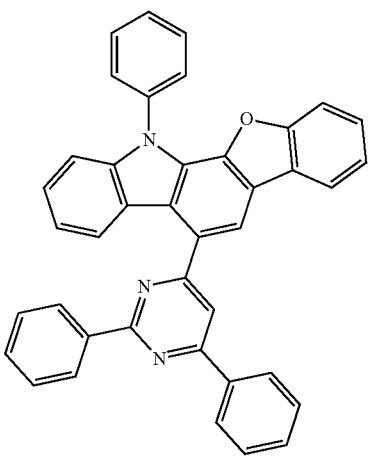

Compound 1-11 was prepared using the same method as the method preparing Compound 1-9, except that 4-chloro-2,6-diphenylpyrimidine was used instead of 2-chloro-4,6-diphenyl-1,3,5-triazine in Preparation Example 9.

MS[M+H]$^+$=564

\<Preparation Example 12\> Synthesis of Compound 1-12

[Compound 1-12]

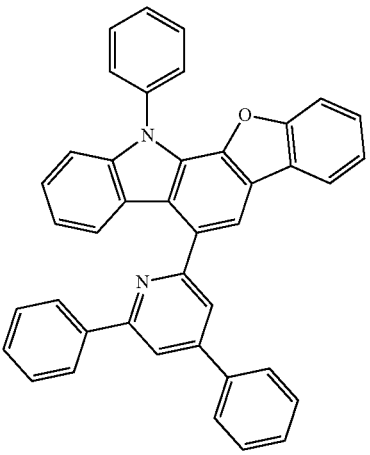

Compound 1-12 was prepared using the same method as the method preparing Compound 1-9, except that 2-chloro-4,6-diphenylpyridine was used instead of 2-chloro-4,6-diphenyl-1,3,5-triazine in Preparation Example 9.

MS[M+H]$^+$=563

\<Preparation Example 13\> Synthesis of Compound 1-13

[Compound 1-13]

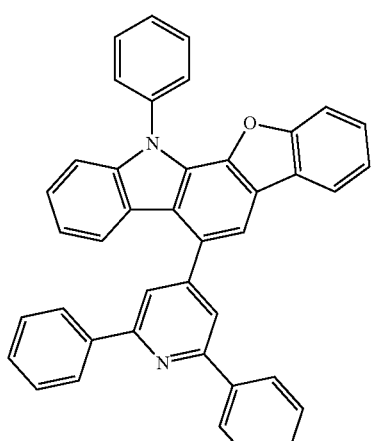

Compound 1-13 was prepared using the same method as the method preparing Compound 1-9, except that 4-chloro-2,6-diphenylpyridine was used instead of 2-chloro-4,6-diphenyl-1,3,5-triazine in Preparation Example 9.

MS[M+H]$^+$=563

<Preparation Example 14> Synthesis of Compound 1-14

[Compound 1-14]

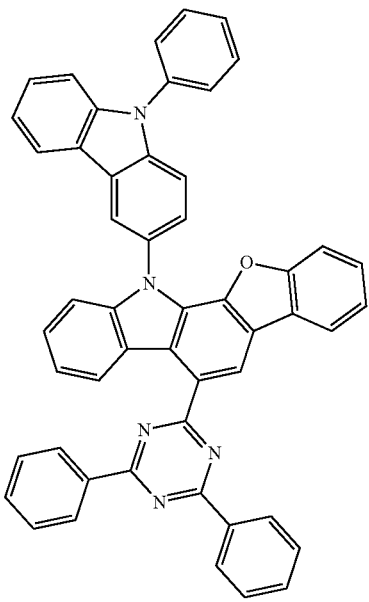

Compound 1-14 was prepared using the same method as the method preparing Compound 1-9, except that 3-bromo-9-phenyl-9H-carbazole was used instead of iodobenzene in Preparation Example 9.
MS[M+H]$^+$=730

<Preparation Example 15> Synthesis of Compound 1-15

[Compound 1-15]

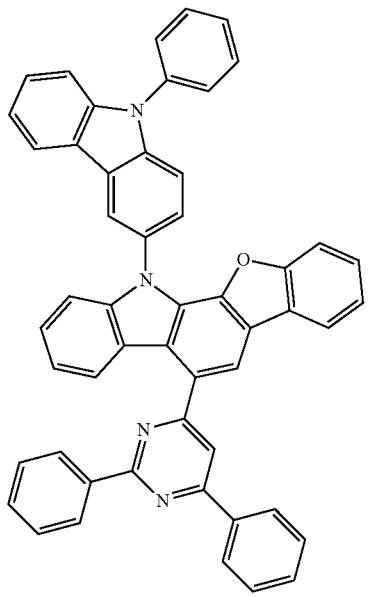

Compound 1-15 was prepared using the same method as the method preparing Compound 1-9, except that 3-bromo-9-phenyl-9H-carbazole was used instead of iodobenzene, and 4-chloro-2,6-diphenylpyrimidine was used instead of 2-chloro-4,6-diphenyl-1,3,5-triazine in Preparation Example 9.
MS[M+H]$^+$=729

<Preparation Example 16> Synthesis of Compound 1-16

[Compound 1-16]

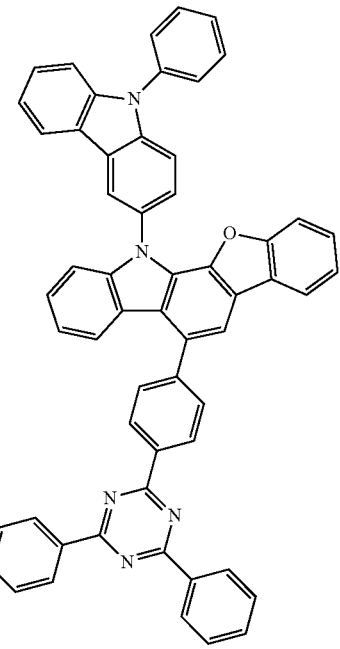

Compound 1-16 was prepared using the same method as the method preparing Compound 1-9, except that 3-bromo-9-phenyl-9H-carbazole was used instead of iodobenzene, and 2-(4-bromophenyl)-4,6-diphenyl-1,3,5-triazine was used instead of 2-chloro-4,6-diphenyl-1,3,5-triazine in Preparation Example 9.
MS[M+H]$^+$=806

<Preparation Example 17> Synthesis of Compound 1-17

[Compound 1-17]

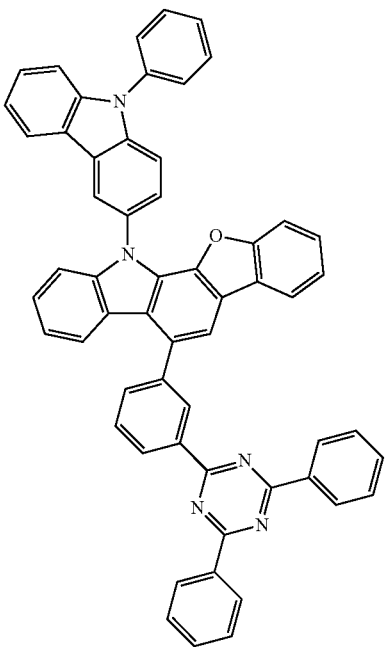

Compound 1-17 was prepared using the same method as the method preparing Compound 1-9, except that 3-bromo-9-phenyl-9H-carbazole was used instead of iodobenzene, and 2-(3-bromophenyl)-4,6-diphenyl-1,3,5-triazine was used instead of 2-chloro-4,6-diphenyl-1,3,5-triazine in Preparation Example 9.
MS[M+H]$^+$=806

<Preparation Example 18> Synthesis of Compound 1-18

[Compound 1-18]

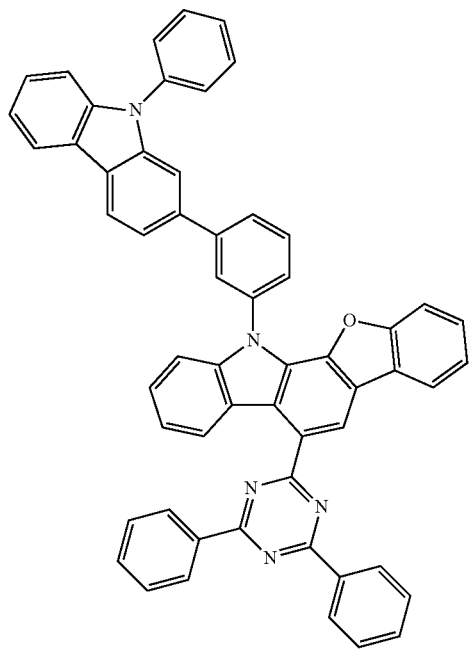

Compound 1-18 was prepared using the same method as the method preparing Compound 1-9, except that 2-(3-bromophenyl)-9-phenyl-9H-carbazole was used instead of iodobenzene in Preparation Example 9.
MS[M+H]$^+$=806

<Preparation Example 19> Synthesis of Compound 1-19

[Compound 1-19]

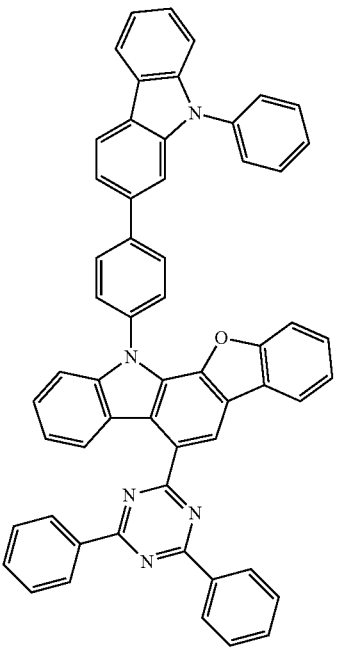

Compound 1-19 was prepared using the same method as the method preparing Compound 1-9, except that 2-(4-bromophenyl)-9-phenyl-9H-carbazole was used instead of iodobenzene in Preparation Example 9.
MS[M+H]$^+$=806

<Preparation Example 20> Synthesis of Compound 1-20

[Compound 1-20]

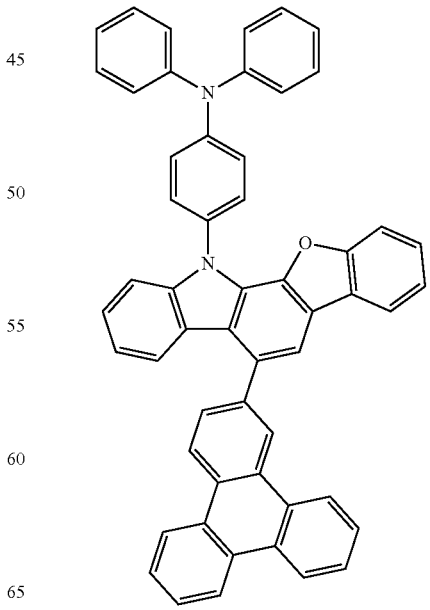

Compound 1-20 was prepared using the same method as the method preparing Compound 1-3, except that 4-bromo-N,N-diphenylaniline was used instead of iodobenzene, and triphenylen-2-ylboronic acid was used instead of (4-(diphenylamino)phenyl)boronic acid in Preparation Example 3.
MS[M+H]$^+$=727

<Preparation Example 21> Synthesis of Compound 1-21

[Compound 1-21]

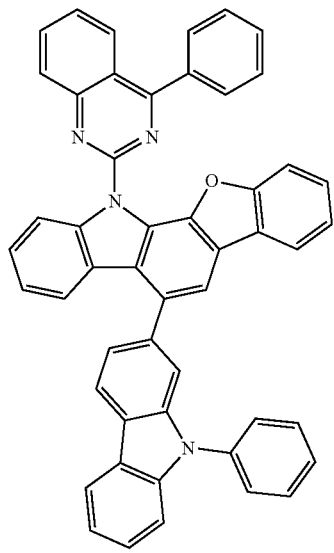

Compound 1-21 was prepared using the same method as the method preparing Compound 1-3, except that 2-chloro-4-phenylquinazoline was used instead of iodobenzene, and (9-phenyl-9H-carbazol-2-yl)boronic acid was used instead of (4-(diphenylamino)phenyl)boronic acid in Preparation Example 3.
MS[M+H]$^+$=703

<Preparation Example 22> Synthesis of Compound 1-22

[Compound 1-22]

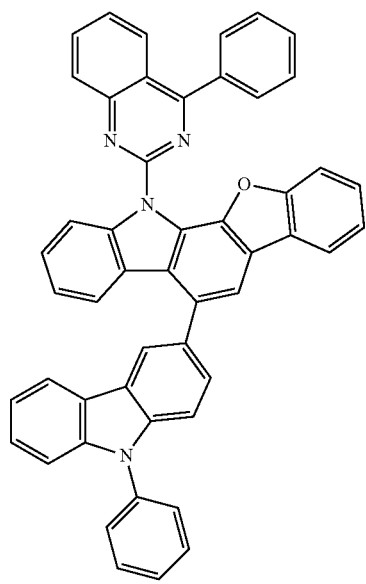

Compound 1-22 was prepared using the same method as the method preparing Compound 1-3, except that 2-chloro-4-phenylquinazoline was used instead of iodobenzene, and (9-phenyl-9H-carbazol-3-yl)boronic acid was used instead of (4-(diphenylamino)phenyl)boronic acid in Preparation Example 3.
MS[M+H]$^+$=703

<Preparation Example 23> Synthesis of Compound 1-23

[Compound 1-23]

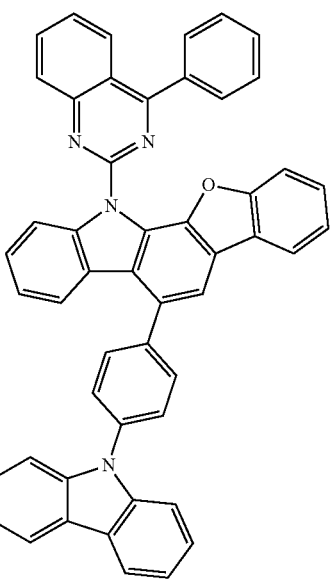

Compound 1-23 was prepared using the same method as the method preparing Compound 1-3, except that 2-chloro-4-phenylquinazoline was used instead of iodobenzene, and 4-(9H-carbazol-9-yl)phenyl)boronic acid was used instead of (4-(diphenylamino)phenyl)boronic acid in Preparation Example 3.
MS[M+H]$^+$=703

<Preparation Example 24> Synthesis of Compound 1-24 \

[Compound 1-24]

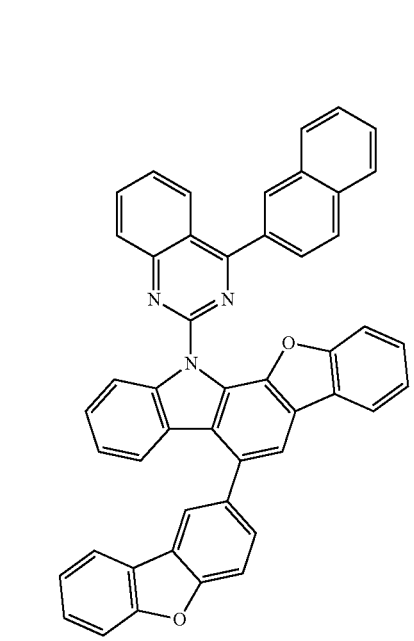

Compound 1-24 was prepared using the same method as the method preparing Compound 1-3, except that 2-chloro-4-(naphthalen-2-yl)quinazoline was used instead of iodobenzene, and dibenzo[b,d]furan-2-ylboronic acid was used instead of (4-(diphenylamino)phenyl)boronic acid in Preparation Example 3.
MS[M+H]$^+$=678

<Preparation Example 25> Synthesis of Compound 1-25

[Compound 1-25]

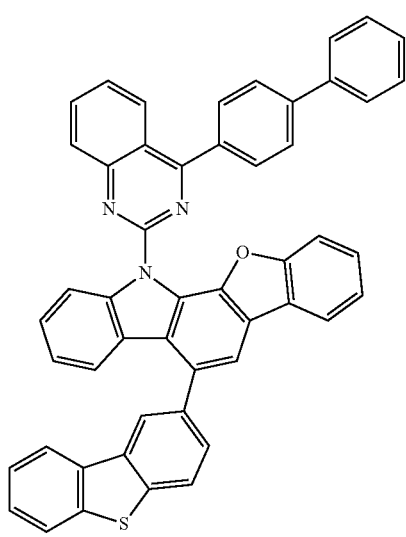

Compound 1-25 was prepared using the same method as the method preparing Compound 1-3, except that 4-([1,1'-biphenyl]-4-yl)-2-chloroquinazoline was used instead of iodobenzene, and dibenzo[b,d]thiophen-2-ylboronic acid was used instead of (4-(diphenylamino)phenyl)boronic acid in Preparation Example 3.
MS[M+H]$^+$=720

<Preparation Example 26> Syntheses of Compound 1-26 to Compound 1-50

The following Compounds 1-26 to 1-50 were prepared using the same methods as the methods preparing Compounds 1-1 to 1-25 except that Intermediate A was used as a starting material instead of Intermediate B in Preparation Examples 1 to 25.

1-26

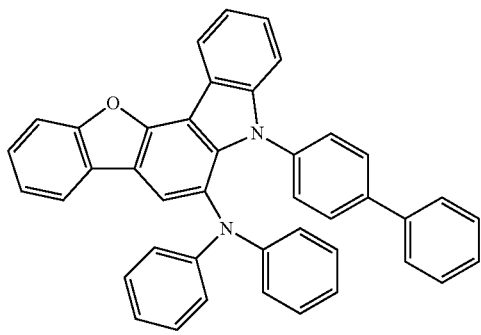

1-27

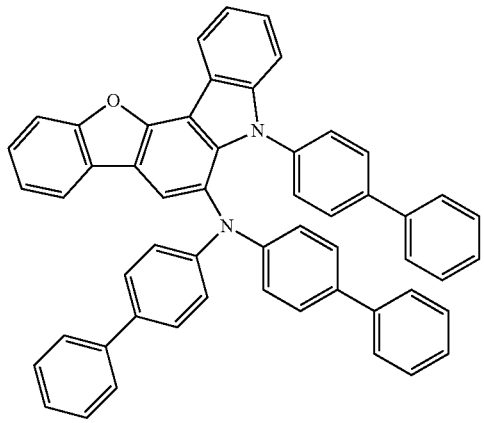

1-28

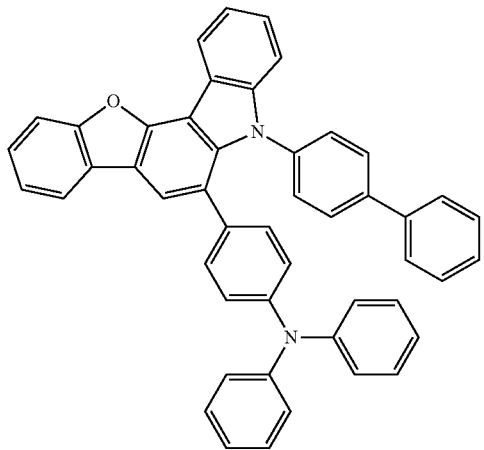

1-29

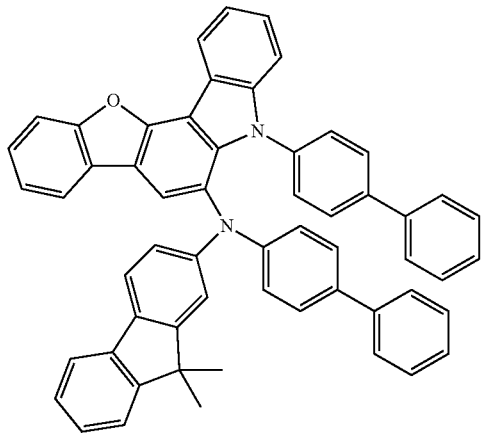

1-30
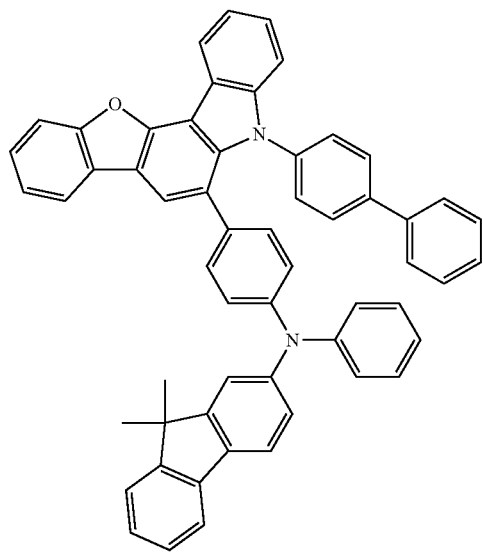
1-31
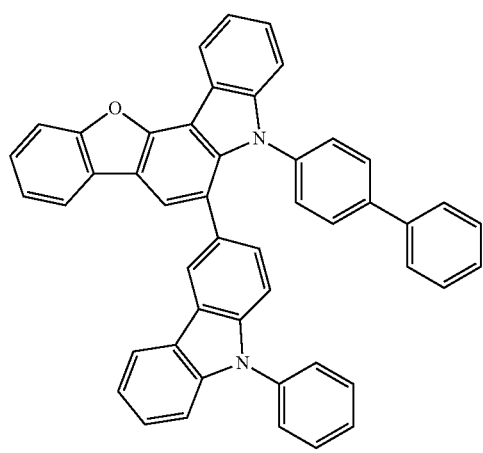
1-32
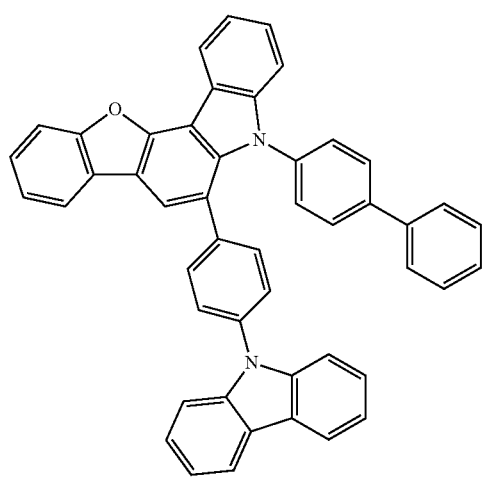
1-33
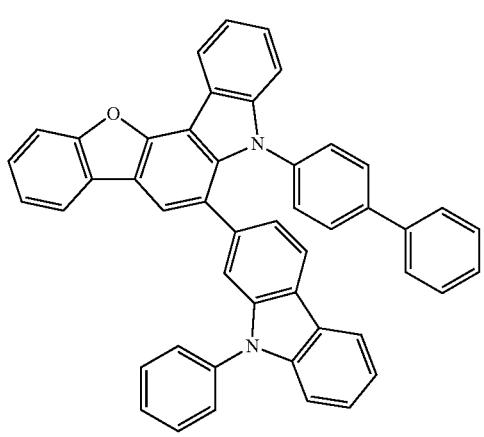
1-34
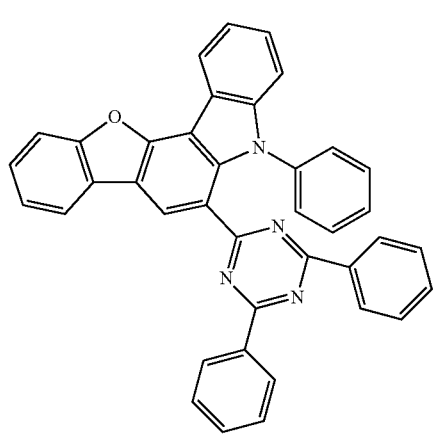
1-35
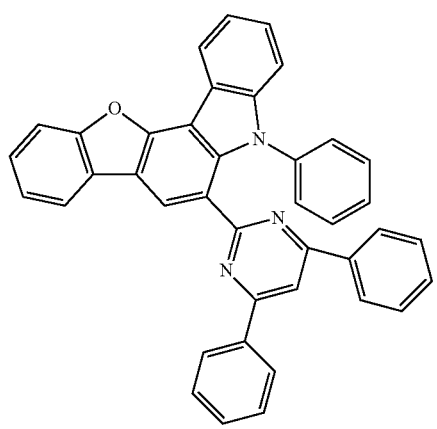

1-36
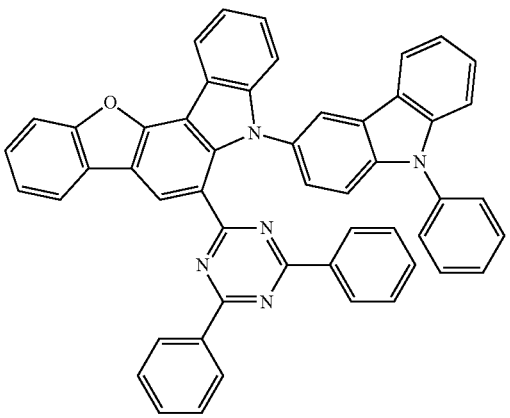
1-37
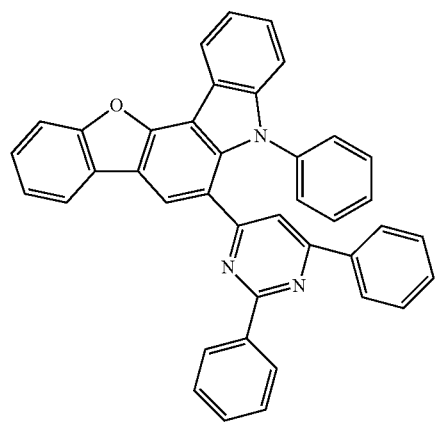
1-38
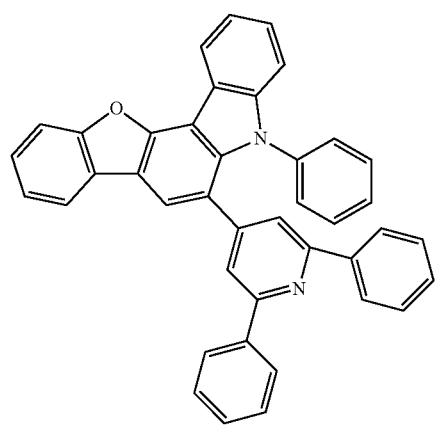
1-39
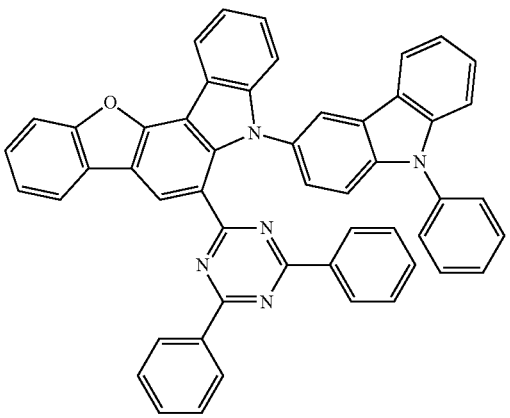
1-40
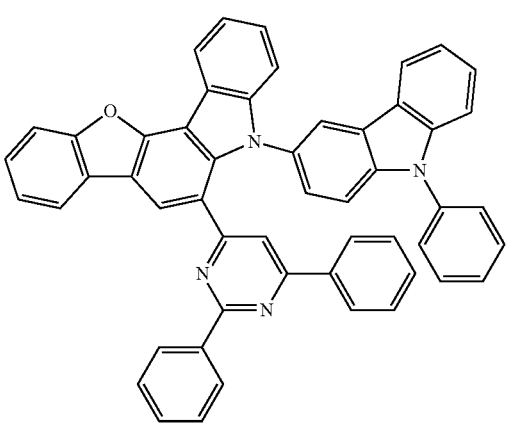
1-41
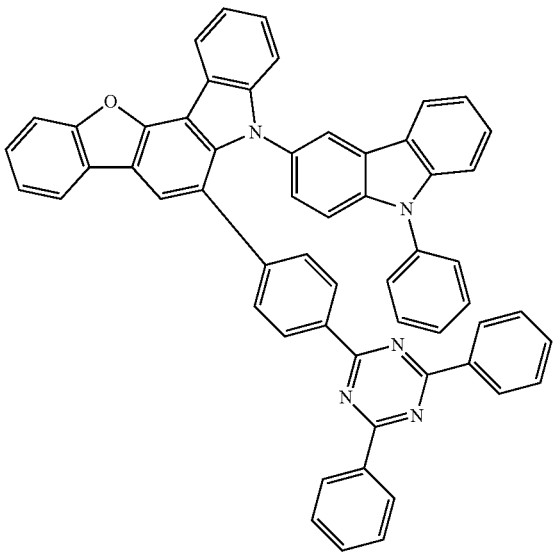

1-42
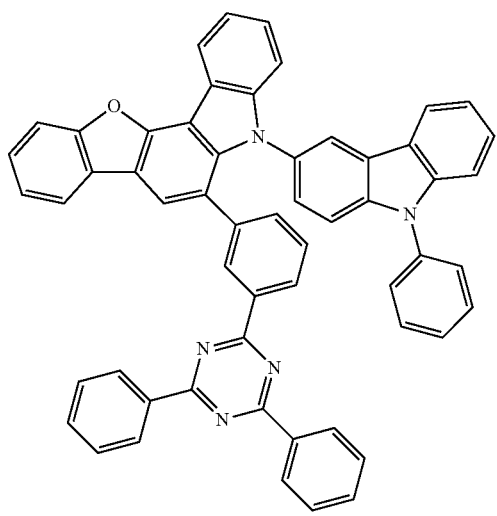
1-45
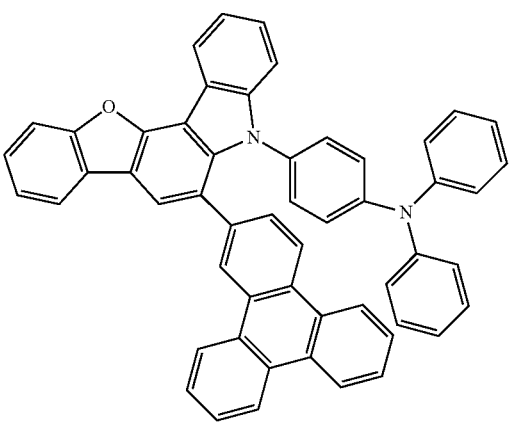
1-43
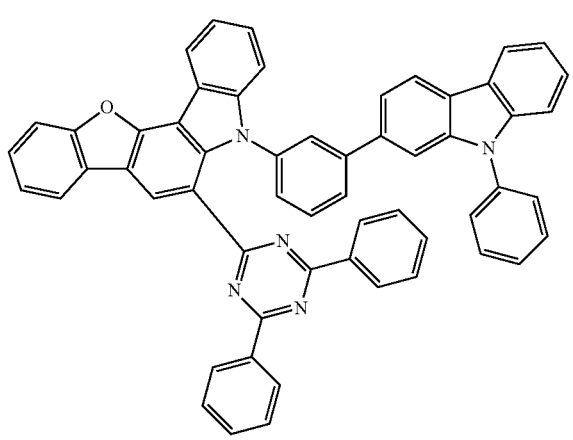
1-46
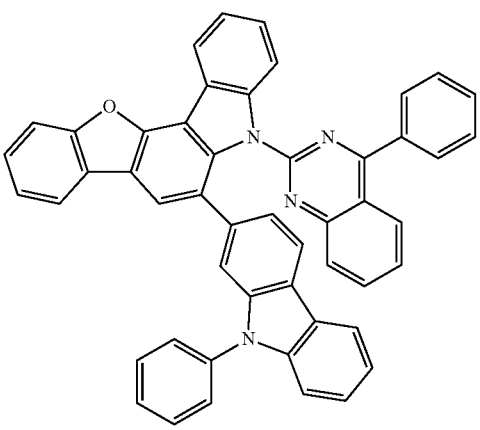
1-44
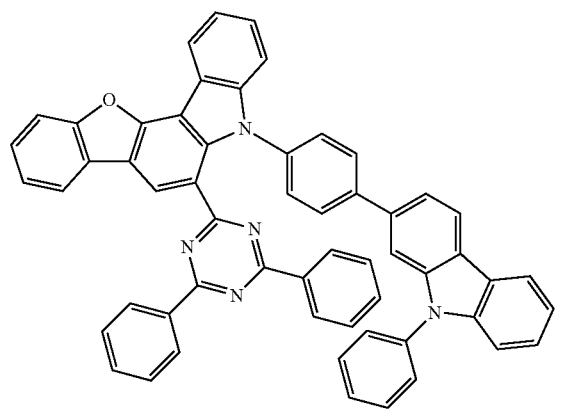
1-47
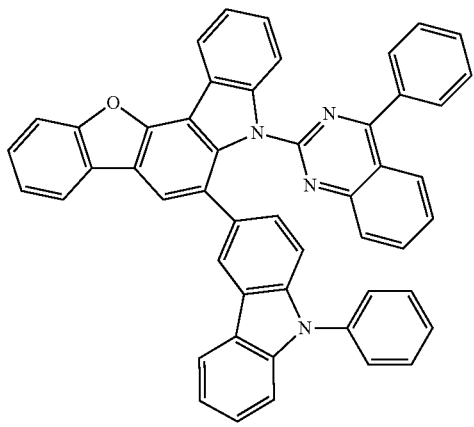

1-48
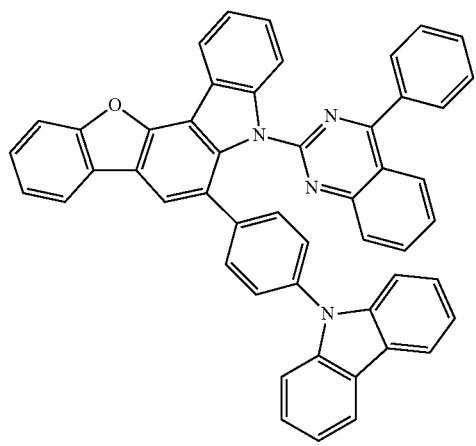
1-49
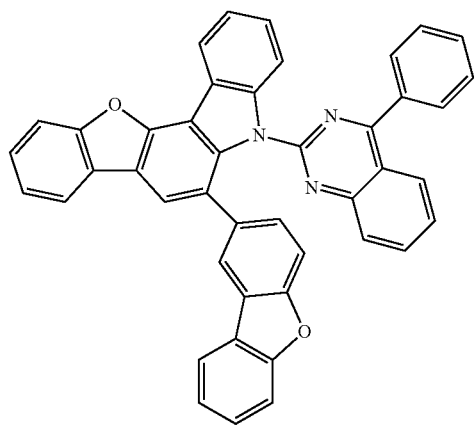
1-50
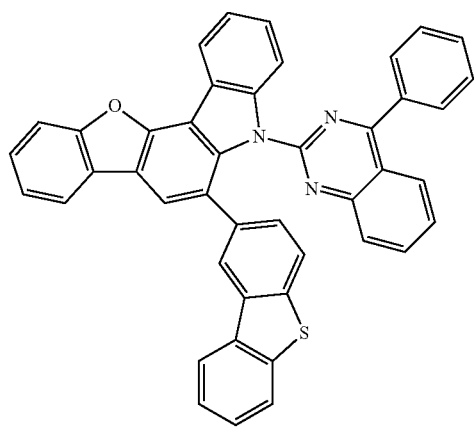
1-51
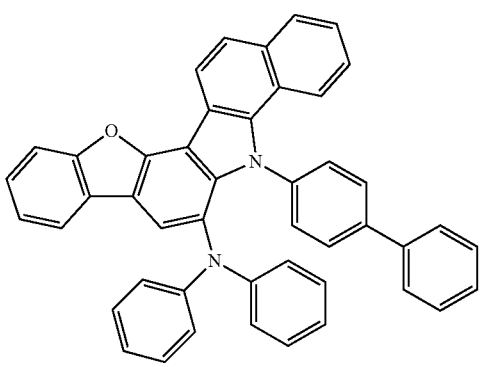
1-52
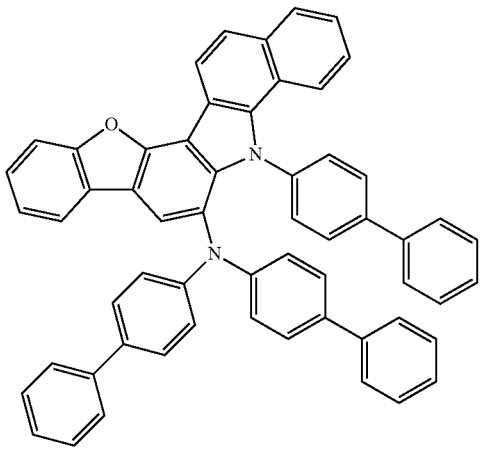
1-53
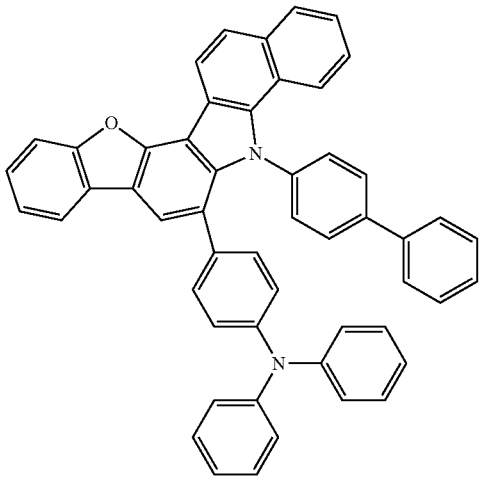
<Preparation Example 27> Syntheses of Compounds 1-51 to Compound 1-75
The following Compounds 1-51 to 1-75 were prepared using the same methods as the methods preparing Compounds 1-1 to 1-25 except that Intermediate C was used as a starting material instead of Intermediate B in Preparation Examples 1 to 25.

1-54
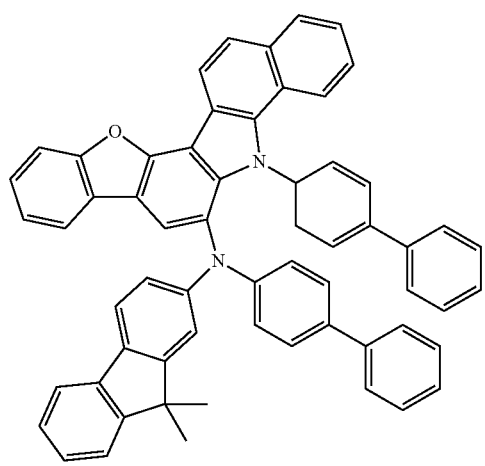
1-55
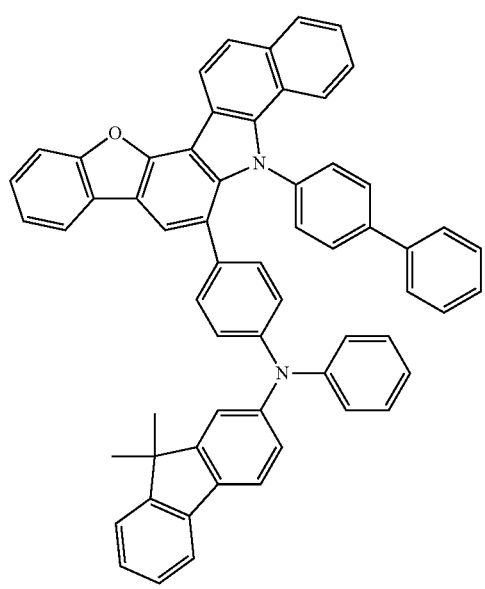
1-56
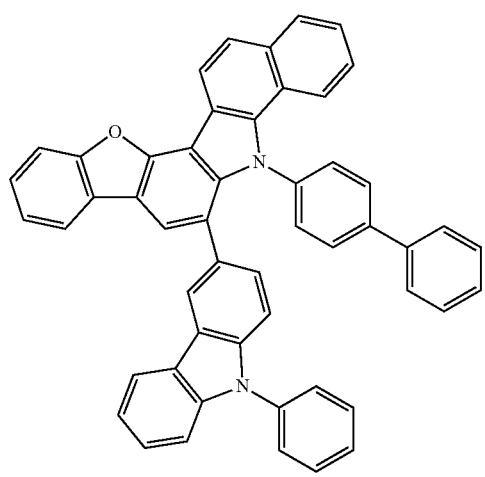
1-57
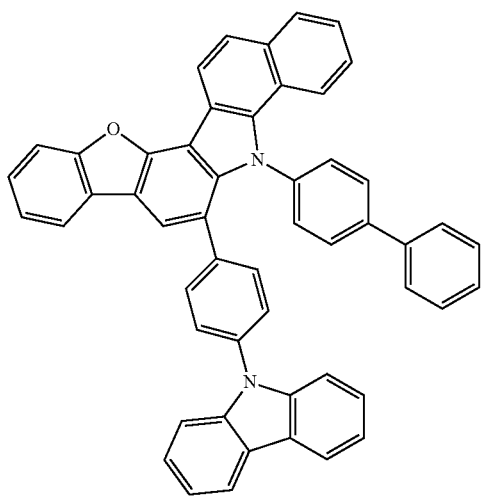
1-58
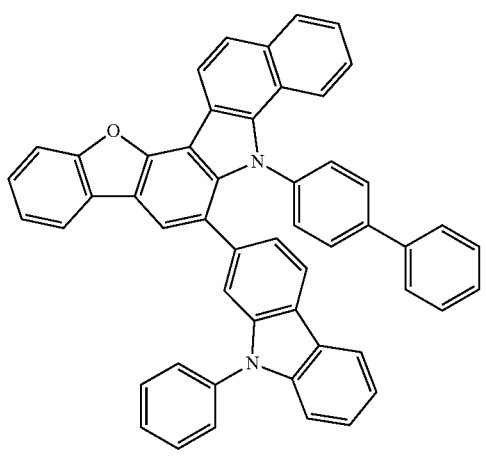
1-59
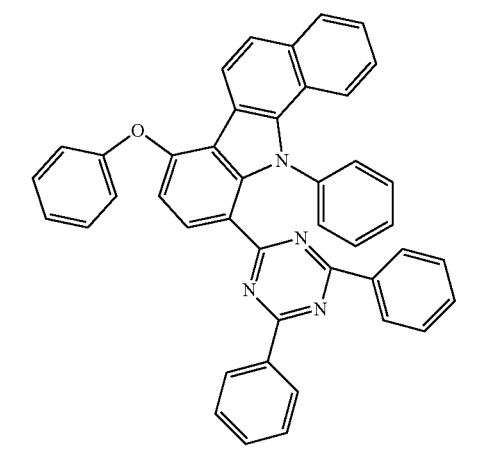

307
-continued
1-60
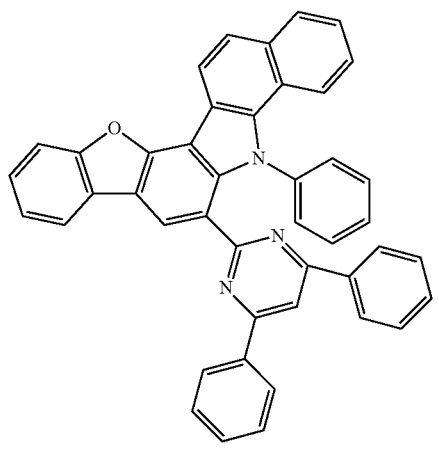
1-61
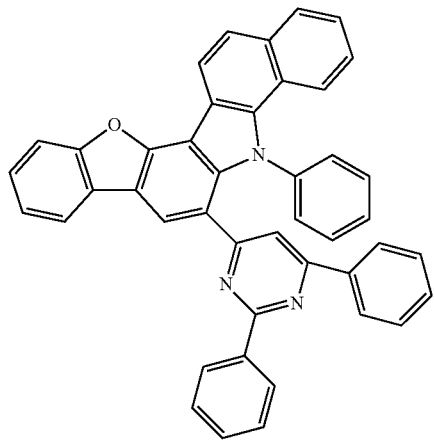
1-62
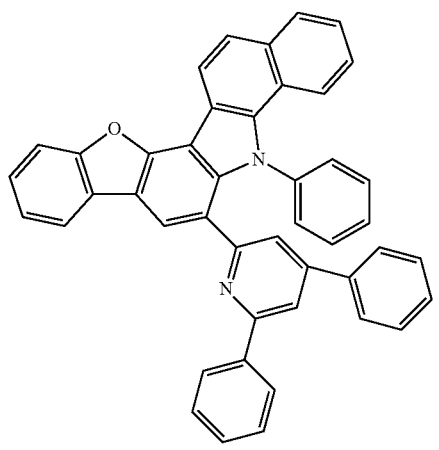
308
-continued
1-63
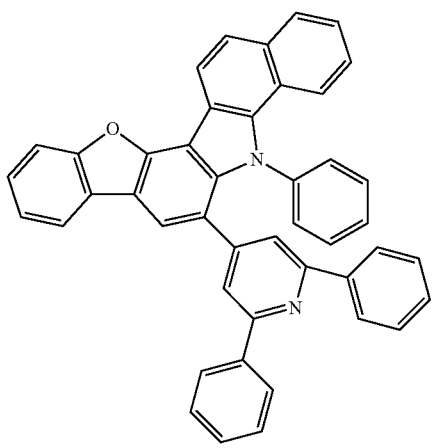
1-64
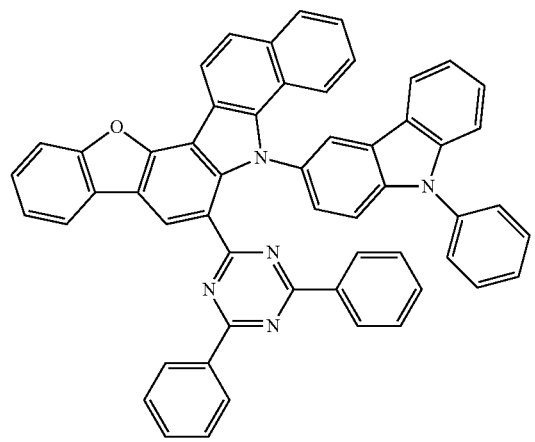
1-65
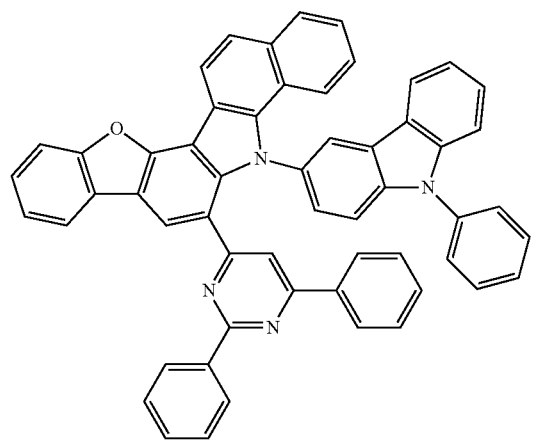

-continued
1-66
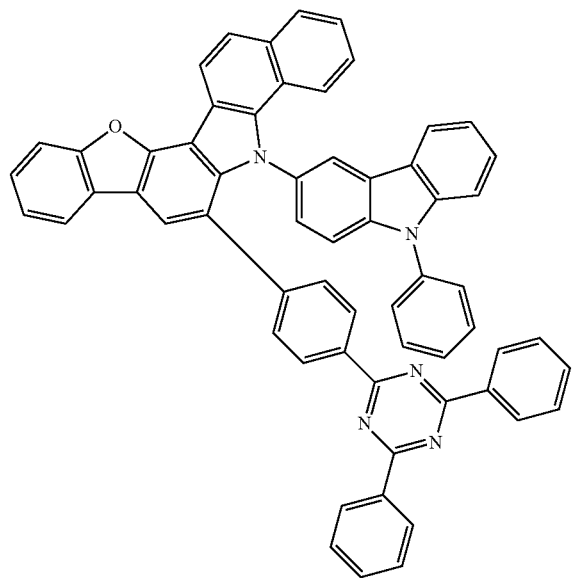
1-67
1-68
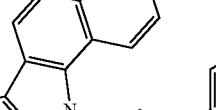
-continued
1-69
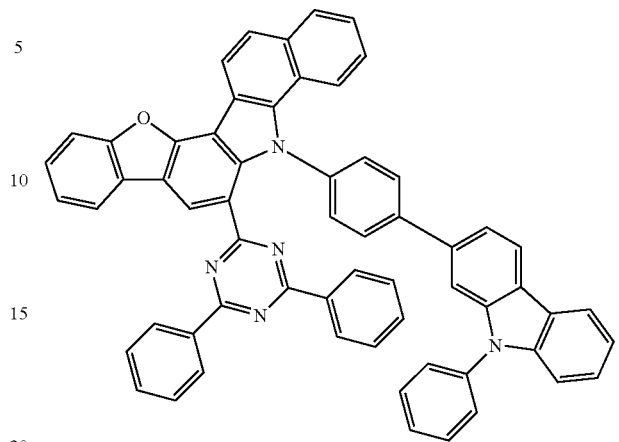
1-70
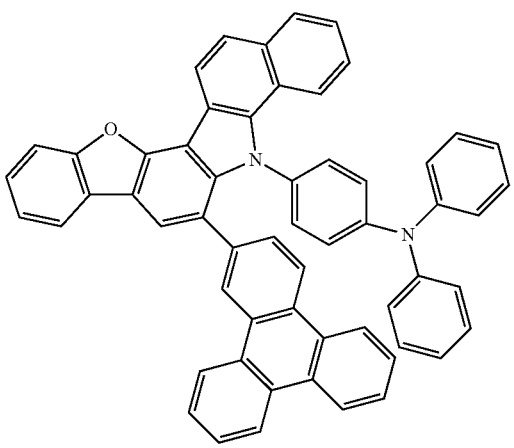
1-71
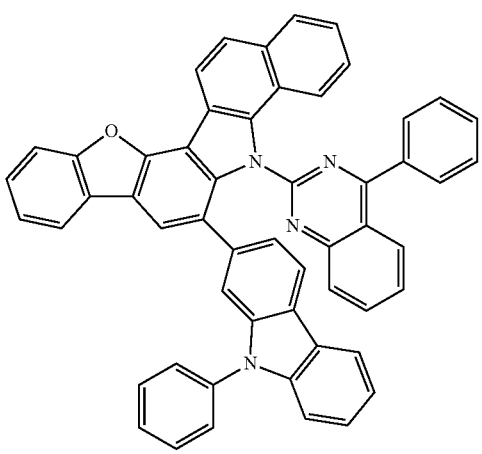

1-72
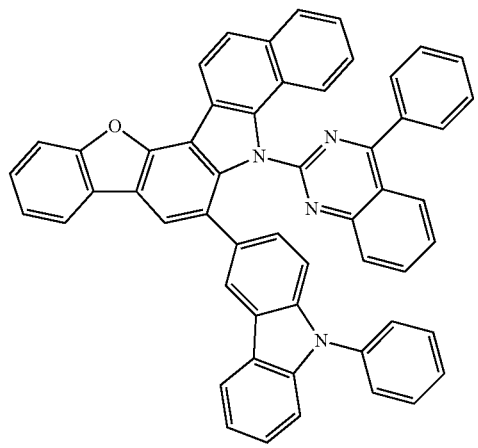
1-73
1-74
1-75
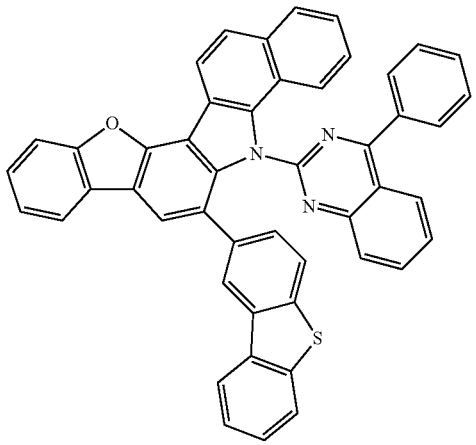
<Preparation Example 28> Syntheses of Compound 1-76 to Compound 1-100
The following Compounds 1-76 to 1-100 were prepared using the same methods as the methods preparing Compounds 1-1 to 1-25 except that Intermediate D was used as a starting material instead of Intermediate B in Preparation Examples 1 to 25.
1-76
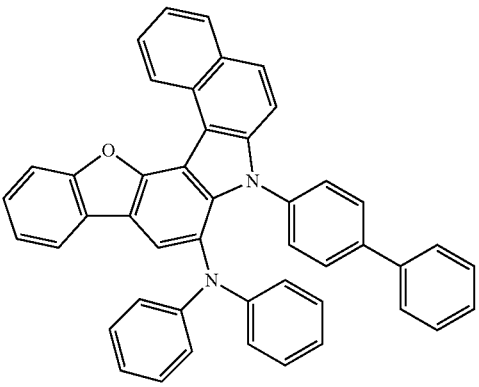
1-77
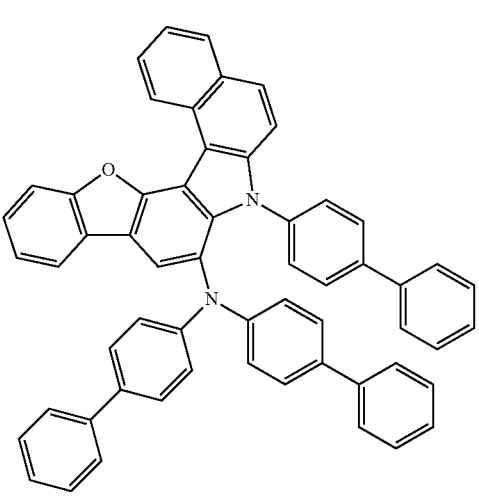

| 1-78 | 1-81 |
|---|---|
| 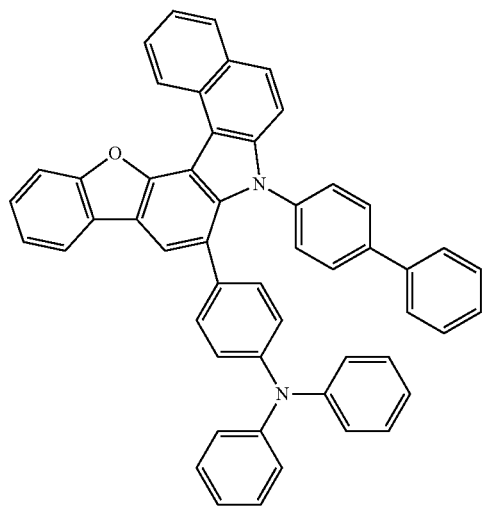 | 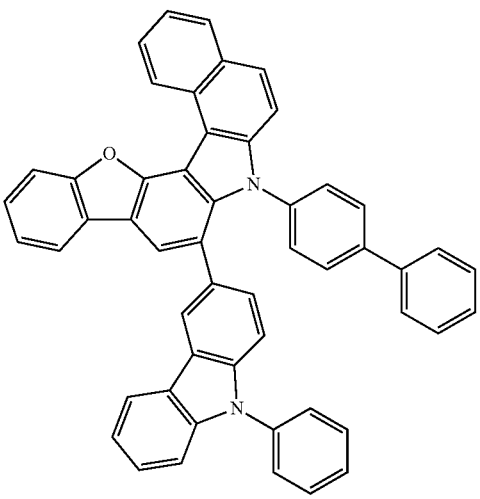 |
| 1-79 | 1-82 |
| 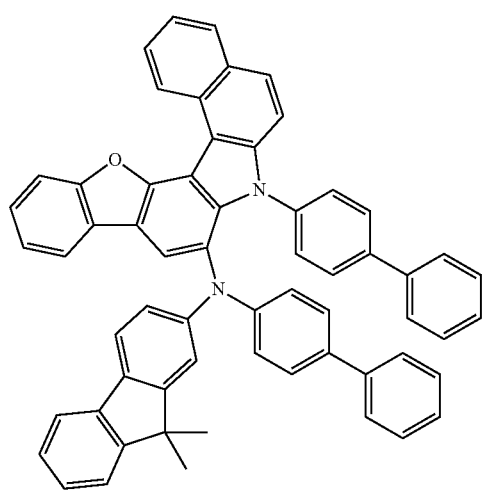 | 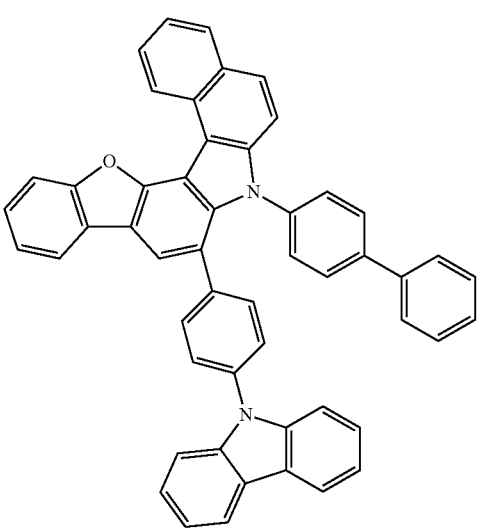 |
| 1-80 | 1-83 |
| 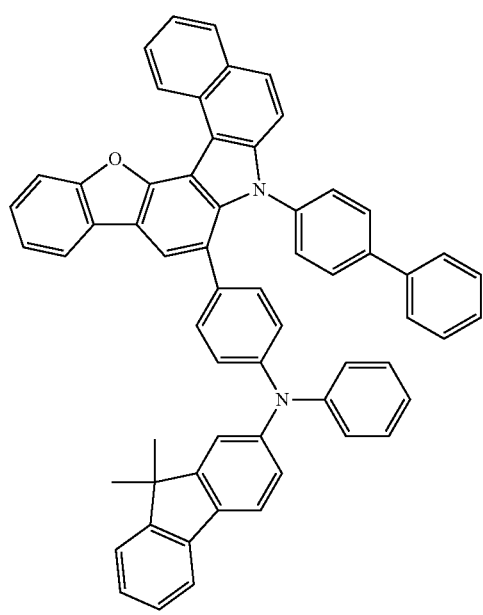 | 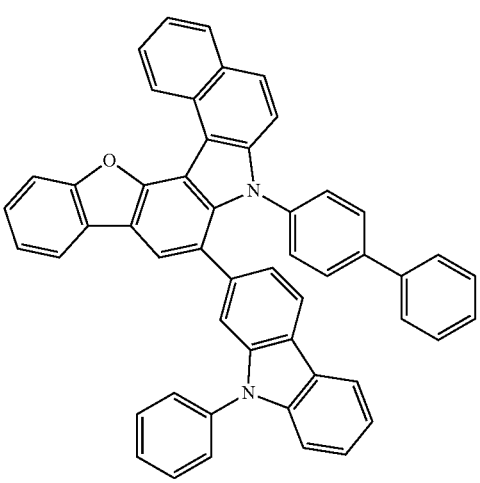 |

1-84
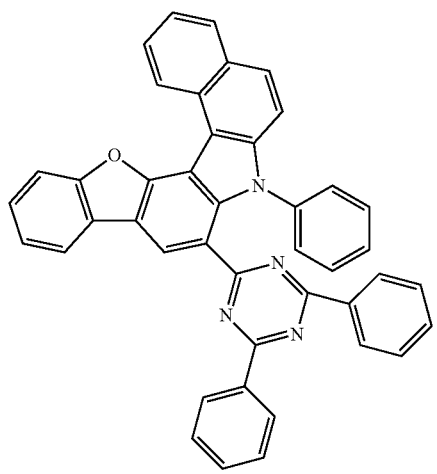
1-87
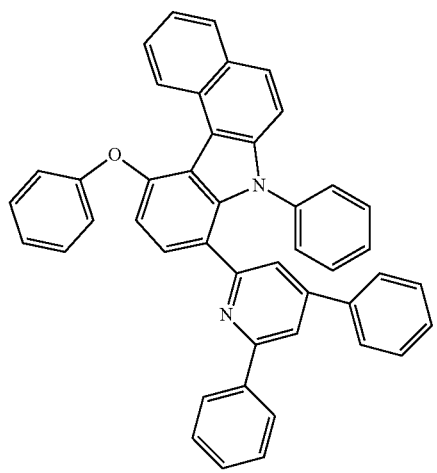
1-85
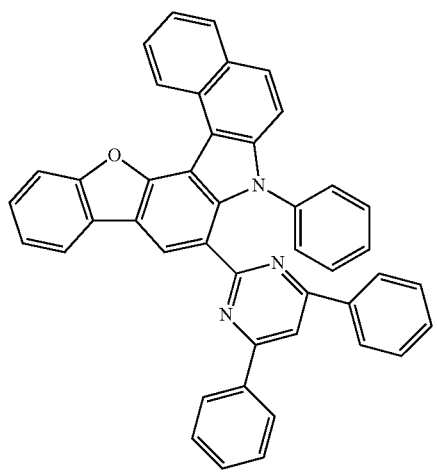
1-88
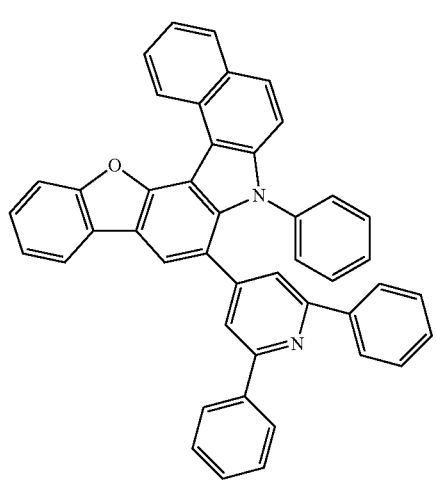
1-86
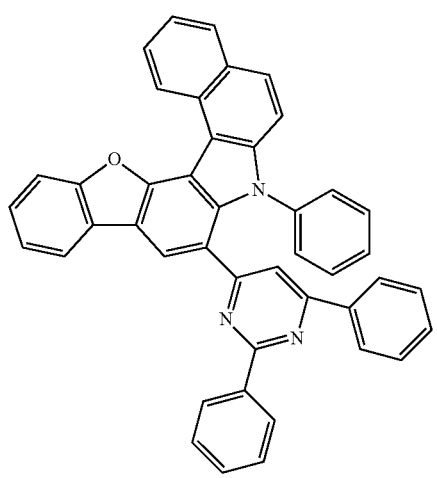
1-89
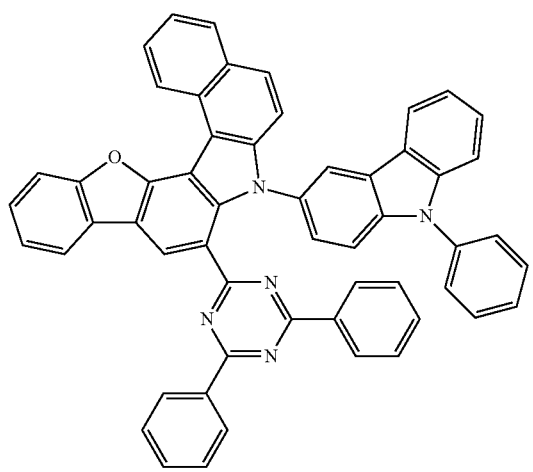

1-90
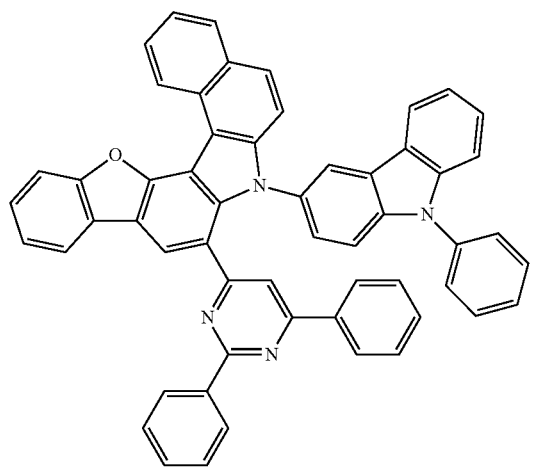
1-91
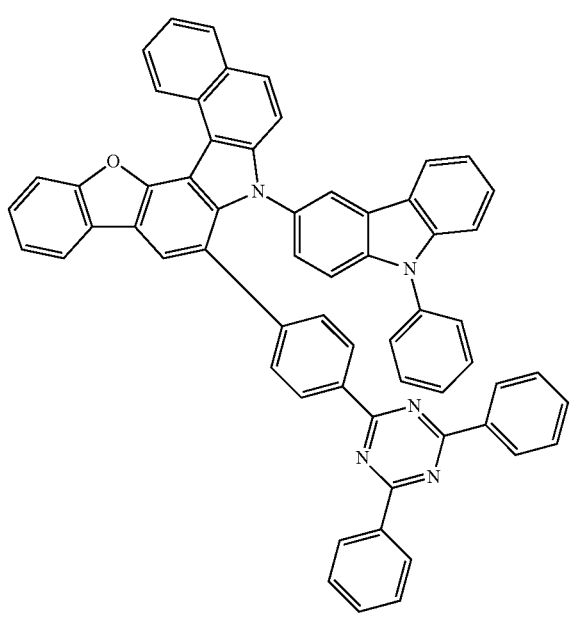
1-92
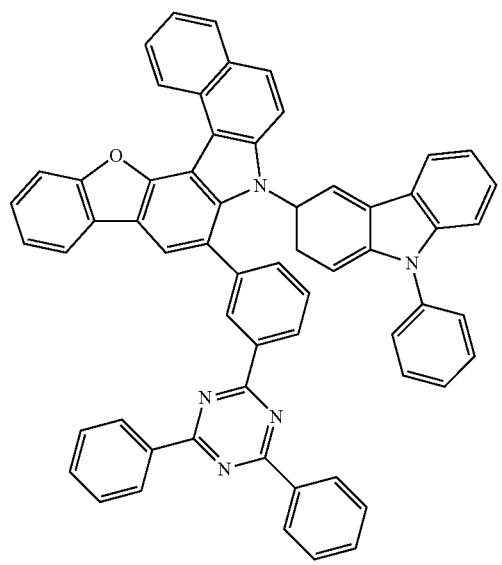
1-93
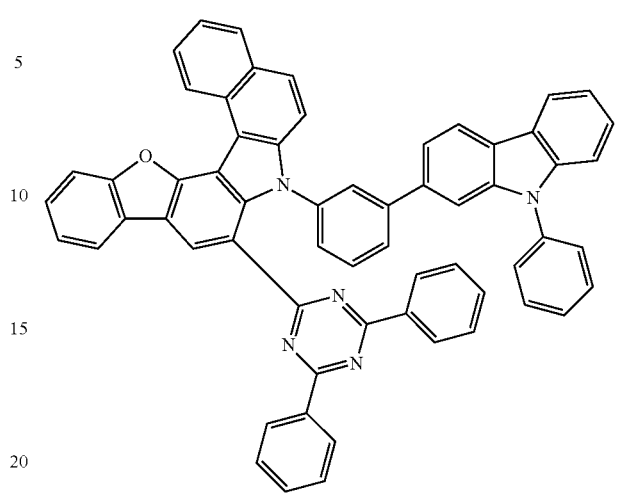
1-94
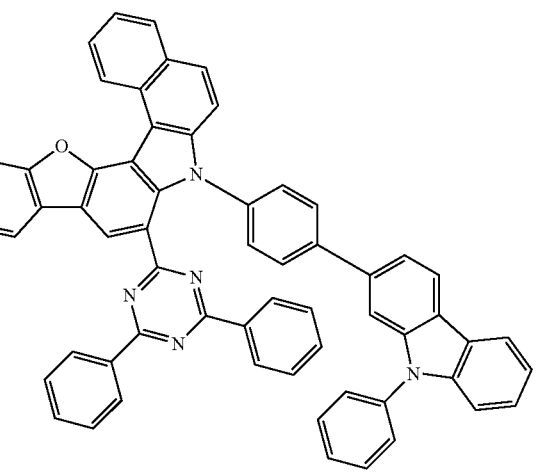
1-95
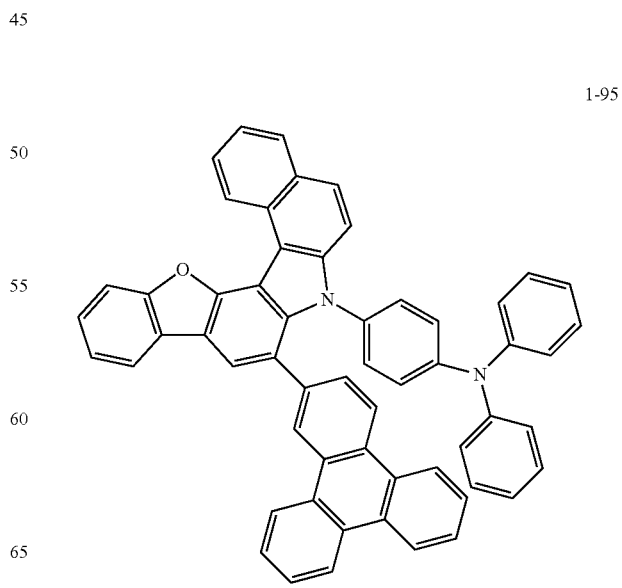

-continued 1-96


1-97

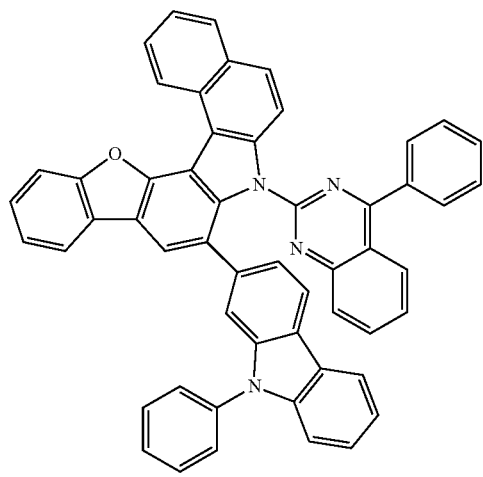

1-98

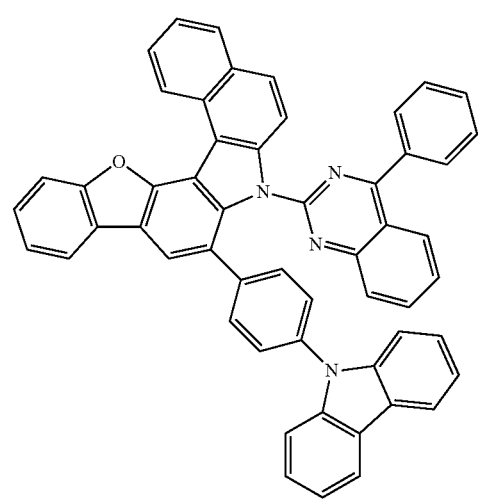

-continued 1-99


1-100

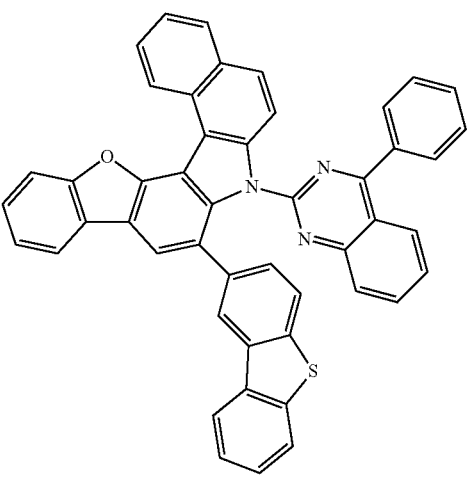

Example 1

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

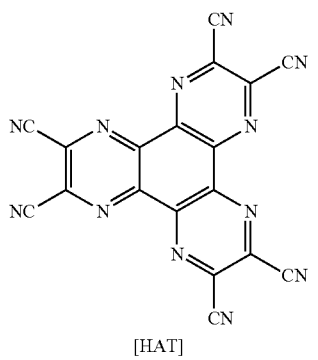

[HAT]

A hole transfer layer was formed on the hole injection layer by vacuum depositing the following compound 4-4'-bis[N-(1-naphthyl)-N-phenylamino]biphenyl (NPB) (300 Å), a material transferring holes.

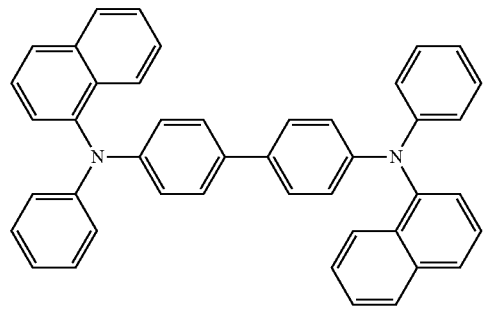

[NPB]

Subsequently, an electron blocking layer was formed on the hole transfer layer to a film thickness of 100 Å by vacuum depositing the following Compound 1-1.

[Compound 1-1]

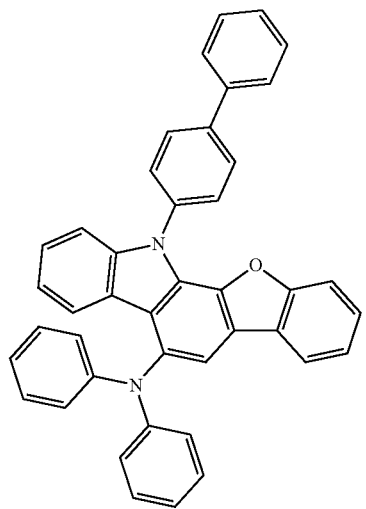

Next, a light emitting layer was formed on the electron blocking layer to a film thickness of 300 Å by vacuum depositing BH and BD shown below in a weight ratio of 25:1.

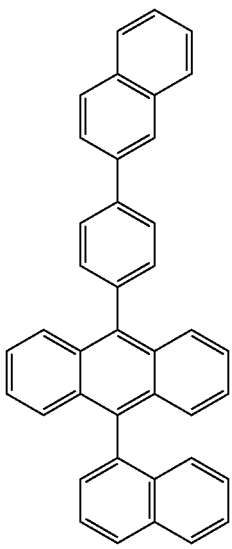

[BH]

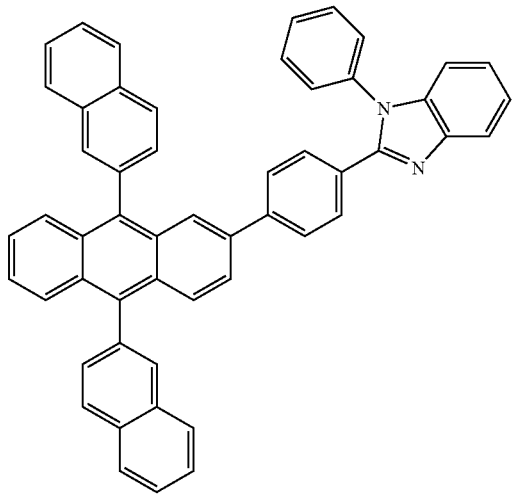

[BD]

[ET1]

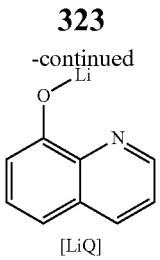

[LiQ]

An electron injection and transfer layer was formed on the light emitting layer to a thickness of 300 Å by vacuum depositing the compound ET1 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 1-2

An organic light emitting device was manufactured in the same manner as in Example 1-1 except that Compound 1-2 was used instead of Compound 1-1.

Example 1-3

An organic light emitting device was manufactured in the same manner as in Example 1-1 except that Compound 1-3 was used instead of Compound 1-1.

Example 1-4

An organic light emitting device was manufactured in the same manner as in Example 1-1 except that Compound 1-4 was used instead of Compound 1-1.

Example 1-5

An organic light emitting device was manufactured in the same manner as in Example 1-1 except that Compound 1-5 was used instead of Compound 1-1.

Example 1-6

An organic light emitting device was manufactured in the same manner as in Example 1-1 except that Compound 1-6 was used instead of Compound 1-1.

Example 1-7

An organic light emitting device was manufactured in the same manner as in Example 1-1 except that Compound 1-7 was used instead of Compound 1-1.

Example 1-8

An organic light emitting device was manufactured in the same manner as in Example 1-1 except that Compound 1-8 was used instead of Compound 1-1.

Example 1-9

An organic light emitting device was manufactured in the same manner as in Example 1-1 except that Compound 1-20 was used instead of Compound 1-1.

Example 1-10

An organic light emitting device was manufactured in the same manner as in Example 1-1 except that Compound 1-26 was used instead of Compound 1-1.

Example 1-11

An organic light emitting device was manufactured in the same manner as in Example 1-1 except that Compound 1-27 was used instead of Compound 1-1.

Example 1-12

An organic light emitting device was manufactured in the same manner as in Example 1-1 except that Compound 1-28 was used instead of Compound 1-1.

Example 1-13

An organic light emitting device was manufactured in the same manner as in Example 1-1 except that Compound 1-29 was used instead of Compound 1-1.

Example 1-14

An organic light emitting device was manufactured in the same manner as in Example 1-1 except that Compound 1-30 was used instead of Compound 1-1.

Example 1-15

An organic light emitting device was manufactured in the same manner as in Example 1-1 except that Compound 1-45 was used instead of Compound 1-1.

Example 1-16

An organic light emitting device was manufactured in the same manner as in Example 1-1 except that Compound 1-51 was used instead of Compound 1-1.

Example 1-17

An organic light emitting device was manufactured in the same manner as in Example 1-1 except that Compound 1-52 was used instead of Compound 1-1.

Example 1-18

An organic light emitting device was manufactured in the same manner as in Example 1-1 except that Compound 1-53 was used instead of Compound 1-1.

Example 1-19

An organic light emitting device was manufactured in the same manner as in Example 1-1 except that Compound 1-54 was used instead of Compound 1-1.

Example 1-20

An organic light emitting device was manufactured in the same manner as in Example 1-1 except that Compound 1-55 was used instead of Compound 1-1.

Example 1-21

An organic light emitting device was manufactured in the same manner as in Example 1-1 except that Compound 1-76 was used instead of Compound 1-1.

Example 1-22

An organic light emitting device was manufactured in the same manner as in Example 1-1 except that Compound 1-77 was used instead of Compound 1-1.

Example 1-23

An organic light emitting device was manufactured in the same manner as in Example 1-1 except that Compound 1-78 was used instead of Compound 1-1.

Example 1-24

An organic light emitting device was manufactured in the same manner as in Example 1-1 except that Compound 1-79 was used instead of Compound 1-1.

Example 1-25

An organic light emitting device was manufactured in the same manner as in Example 1-1 except that Compound 1-80 was used instead of Compound 1-1.

Comparative Example 1-1

An organic light emitting device was manufactured in the same manner as in Example 1-1 except that EB 1 (TCTA) was used instead of Compound 1-1.

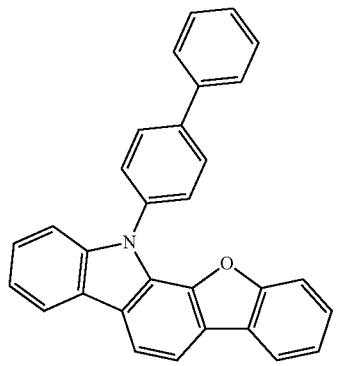

[EB 1]

Comparative Example 1-2

An organic light emitting device was manufactured in the same manner as in Example 1-1 except that EB 2 was used instead of Compound 1-1.

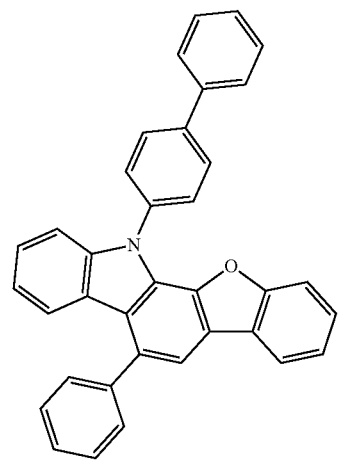

[EB 2]

Comparative Example 1-3

An organic light emitting device was manufactured in the same manner as in Example 1-1 except that EB 3 was used instead of Compound 1-1.

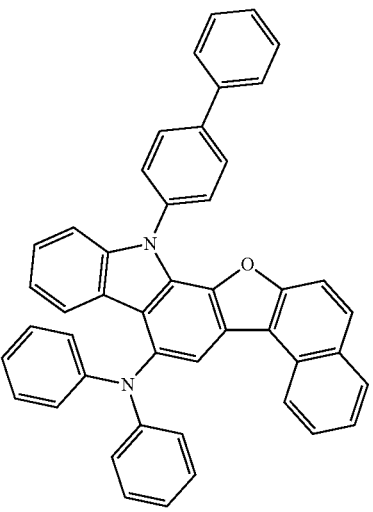

[EB 3]

Comparative Example 1-4

An organic light emitting device was manufactured in the same manner as in Example 1-1 except that EB 4 was used instead of Compound 1-1.

[EB 4]

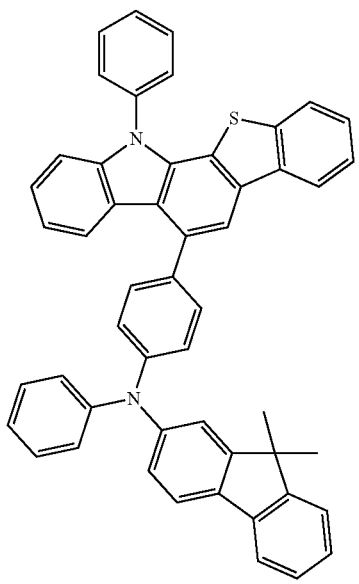

When a current was applied to the organic light emitting devices manufactured in Examples 1-1 to 1-25 and Comparative Examples 1-1 to 1-4, results of Table 1 were obtained.

TABLE 1

| Category | Compound (Electron Blocking Layer) | Voltage (V@10 mA/cm$^2$) | Efficiency (cd/A@10 mA/cm$^2$) | Color Coordinate (x, y) |
|---|---|---|---|---|
| Example 1-1 | Compound 1-1 | 3.75 | 5.25 | (0.137, 0.122) |
| Example 1-2 | Compound 1-2 | 3.82 | 5.58 | (0.138, 0.126) |
| Example 1-3 | Compound 1-3 | 3.67 | 5.41 | (0.138, 0.127) |
| Example 1-4 | Compound 1-4 | 3.68 | 5.62 | (0.137, 0.126) |
| Example 1-5 | Compound 1-5 | 3.69 | 5.73 | (0.136, 0.125) |
| Example 1-6 | Compound 1-6 | 3.64 | 5.67 | (0.136, 0.127) |
| Example 1-7 | Compound 1-7 | 3.63 | 5.78 | (0.136, 0.126) |
| Example 1-8 | Compound 1-8 | 3.64 | 5.61 | (0.137, 0.125) |
| Example 1-9 | Compound 1-20 | 3.73 | 5.58 | (0.138, 0.126) |
| Example 1-10 | Compound 1-26 | 3.78 | 5.42 | (0.136, 0.126) |
| Example 1-11 | Compound 1-27 | 3.65 | 5.57 | (0.137, 0.126) |
| Example 1-12 | Compound 1-28 | 3.73 | 5.45 | (0.136, 0.126) |
| Example 1-13 | Compound 1-29 | 3.81 | 5.58 | (0.138, 0.126) |
| Example 1-14 | Compound 1-30 | 3.87 | 5.61 | (0.137, 0.125) |
| Example 1-15 | Compound 1-45 | 3.80 | 5.42 | (0.136, 0.127) |
| Example 1-16 | Compound 1-51 | 3.81 | 5.53 | (0.135, 0.127) |
| Example 1-17 | Compound 1-52 | 3.60 | 5.57 | (0.138, 0.127) |
| Example 1-18 | Compound 1-53 | 3.73 | 5.58 | (0.137, 0.125) |
| Example 1-19 | Compound 1-54 | 3.64 | 5.61 | (0.137, 0.126) |
| Example 1-20 | Compound 1-55 | 3.73 | 5.58 | (0.136, 0.127) |
| Example 1-21 | Compound 1-76 | 3.64 | 5.52 | (0.135, 0.127) |
| Example 1-22 | Compound 1-77 | 3.71 | 5.57 | (0.137, 0.127) |
| Example 1-23 | Compound 1-78 | 3.67 | 5.55 | (0.137, 0.126) |
| Example 1-24 | Compound 1-79 | 3.75 | 5.68 | (0.137, 0.125) |
| Example 1-25 | Compound 1-80 | 3.57 | 5.81 | (0.136, 0.126) |
| Comparative Example 1-1 | EB 1 | 4.64 | 4.63 | (0.138, 0.127) |
| Comparative Example 1-2 | EB 2 | 4.53 | 4.58 | (0.139, 0.125) |
| Comparative Example 1-3 | EB 3 | 4.48 | 4.42 | (0.139, 0.126) |
| Comparative Example 1-4 | EB 4 | 4.32 | 4.32 | (0.139, 0.127) |

As shown in Table 1, it was seen that using the compounds of Examples 1-1 to 1-25 as the electron blocking layer in the organic light emitting device exhibited low voltage and high efficiency properties compared to the materials of Comparative Examples 1-1 to 1-4.

It was identified that the compound derivatives of the chemical formulae according to the present specification had an excellent electron blocking ability and thereby exhibited low voltage and high efficiency properties, and were capable of being used in organic light emitting devices.

Example 2

Example 2-1 to Example 2-25

Experiments were carried out in the same manner as in Example 1 except that the following compound TCTA was used as the electron blocking layer, and the compounds of Examples 1-1 to 1-25 were used instead of NPB as the hole transfer layer.

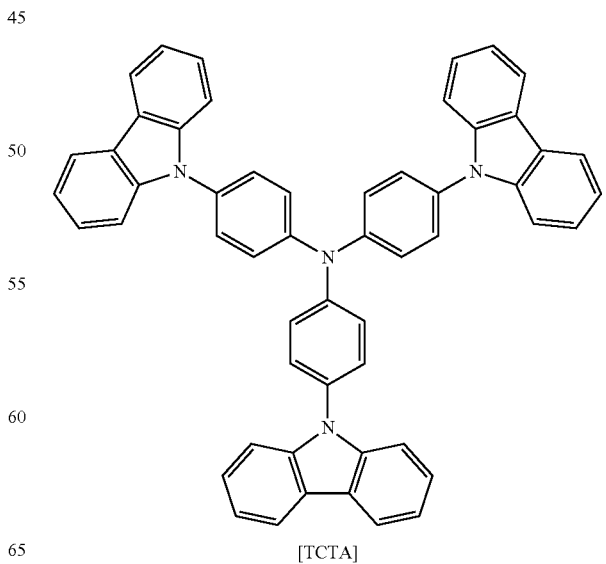

[TCTA]

Comparative Example 2-1

An experiment was carried out in the same manner as in Example 1 except that EB 1 was used as the electron blocking layer, and the following compound HT 1 was used as the hole transfer layer.

[HT 1]

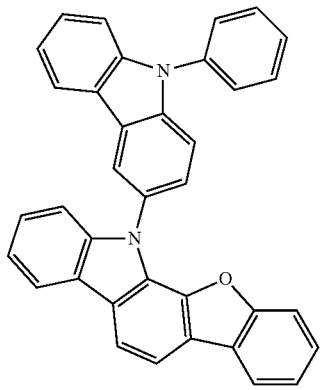

Comparative Example 2-2

An experiment was carried out in the same manner as in Example 1 except that EB 1 was used as the electron blocking layer, and the following compound HT 2 was used as the hole transfer layer.

[HT 2]

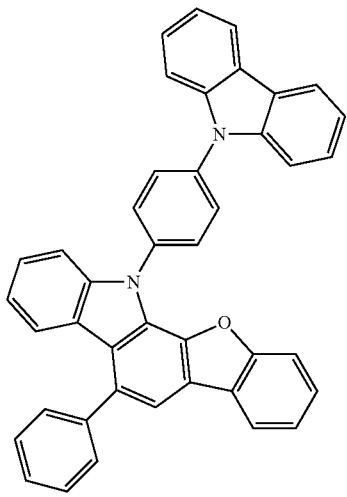

Comparative Example 2-3

An experiment was carried out in the same manner as in Example 1 except that EB 1 was used as the electron blocking layer, and the following compound HT 3 was used as the hole transfer layer.

[HT 3]

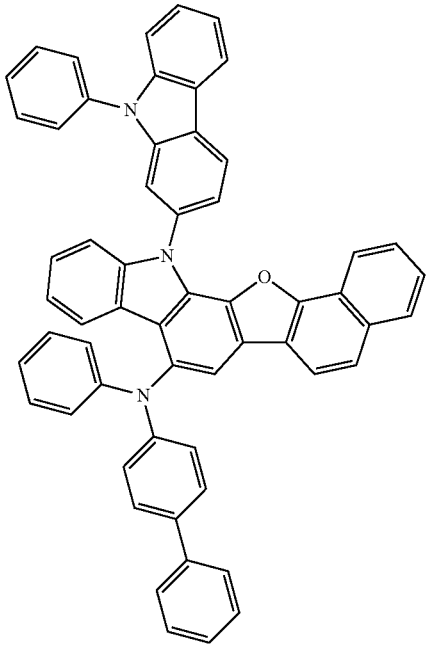

Comparative Example 2-4

An experiment was carried out in the same manner as in Example 1 except that EB 1 was used as the electron blocking layer, and the following compound HT 4 was used as the hole transfer layer.

[HT 4]

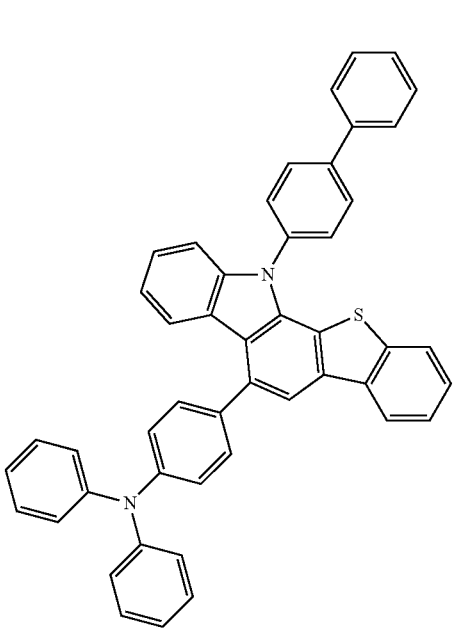

When a current was applied to the organic light emitting devices manufactured in Examples 2-1 to 2-25 and Comparative Examples 2-1 to 2-4, results of Table 2 were obtained.

TABLE 2

| Category | Compound (Hole Transfer Layer) | Voltage (V@10 mA/cm$^2$) | Efficiency (cd/A@10 mA/cm$^2$) | Color Coordinate (x, y) |
|---|---|---|---|---|
| Example 2-1 | Compound 1-1 | 4.15 | 5.55 | (0.139, 0.122) |
| Example 2-2 | Compound 1-2 | 4.02 | 5.68 | (0.138, 0.126) |
| Example 2-3 | Compound 1-3 | 3.87 | 6.05 | (0.138, 0.127) |
| Example 2-4 | Compound 1-4 | 3.88 | 6.04 | (0.137, 0.125) |
| Example 2-5 | Compound 1-5 | 3.89 | 6.02 | (0.136, 0.125) |
| Example 2-6 | Compound 1-6 | 3.84 | 5.93 | (0.136, 0.127) |
| Example 2-7 | Compound 1-7 | 3.83 | 6.00 | (0.136, 0.125) |
| Example 2-8 | Compound 1-8 | 3.84 | 5.90 | (0.137, 0.125) |
| Example 2-9 | Compound 1-20 | 3.93 | 5.81 | (0.138, 0.125) |
| Example 2-10 | Compound 1-26 | 3.98 | 5.72 | (0.136, 0.125) |
| Example 2-11 | Compound 1-27 | 3.93 | 5.85 | (0.137, 0.125) |
| Example 2-12 | Compound 1-28 | 3.95 | 5.75 | (0.136, 0.125) |
| Example 2-13 | Compound 1-29 | 4.02 | 5.88 | (0.138, 0.126) |
| Example 2-14 | Compound 1-30 | 3.97 | 5.81 | (0.137, 0.125) |
| Example 2-15 | Compound 1-45 | 4.00 | 5.72 | (0.136, 0.127) |
| Example 2-16 | Compound 1-51 | 4.01 | 5.82 | (0.135, 0.127) |
| Example 2-17 | Compound 1-52 | 3.84 | 5.95 | (0.138, 0.127) |
| Example 2-18 | Compound 1-53 | 3.93 | 5.83 | (0.137, 0.125) |
| Example 2-19 | Compound 1-54 | 3.84 | 5.93 | (0.137, 0.125) |
| Example 2-20 | Compound 1-55 | 3.93 | 5.85 | (0.136, 0.127) |
| Example 2-21 | Compound 1-76 | 3.84 | 5.96 | (0.135, 0.127) |
| Example 2-22 | Compound 1-77 | 3.93 | 5.87 | (0.138, 0.127) |
| Example 2-23 | Compound 1-78 | 3.89 | 5.95 | (0.137, 0.125) |
| Example 2-24 | Compound 1-79 | 3.98 | 5.98 | (0.137, 0.125) |
| Example 2-25 | Compound 1-80 | 3.75 | 6.21 | (0.136, 0.125) |
| Comparative Example 2-1 | HT 1 | 4.66 | 5.23 | (0.138, 0.127) |
| Comparative Example 2-2 | HT 2 | 4.61 | 5.11 | (0.139, 0.125) |
| Comparative Example 2-3 | HT 3 | 4.79 | 4.98 | (0.139, 0.126) |
| Comparative Example 2-4 | HT 4 | 4.86 | 4.95 | (0.139, 0.127) |

As shown in Table 2, it was seen that using the compounds of Examples 2-1 to 2-25 as the hole transfer layer in the organic light emitting device exhibited low voltage and high efficiency properties compared to the materials of Comparative Examples 2-1 to 2-4.

It was identified that the compound derivatives of the chemical formulae according to the present specification had an excellent hole transfer ability as well and thereby exhibited low voltage and high efficiency properties, and were capable of being used in organic light emitting devices.

Example 3

Example 3-1

The compounds synthesized in the preparation examples were high-purity sublimation purified using commonly known methods, and then a green organic light emitting device was manufactured using a method as below.

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

An organic light emitting device was manufactured by forming a light emitting device in order of m-MTDATA (60 nm)/TCTA (80 nm)/Compound 1-9+10% Ir(ppy)$_3$ (300 nm)/BCP (10 nm)/Alq$_3$ (30 nm)/LiF (1 nm)/Al (200 nm) on the transparent ITO electrode prepared as above using Compound 1-9 as a host.

Structures of the m-MTDATA, the TCTA, the Ir(ppy)$_3$ and the BCP are as follows.

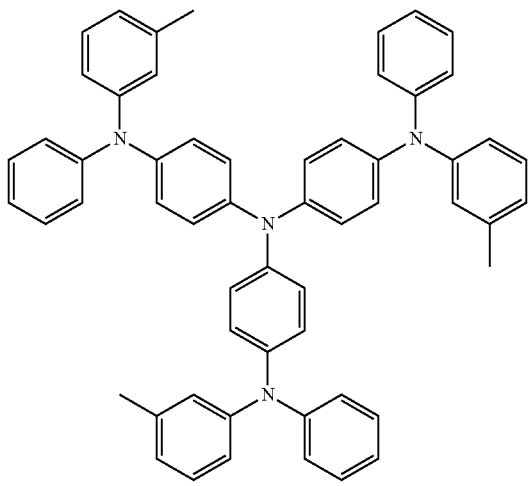

[m-MTDATA]

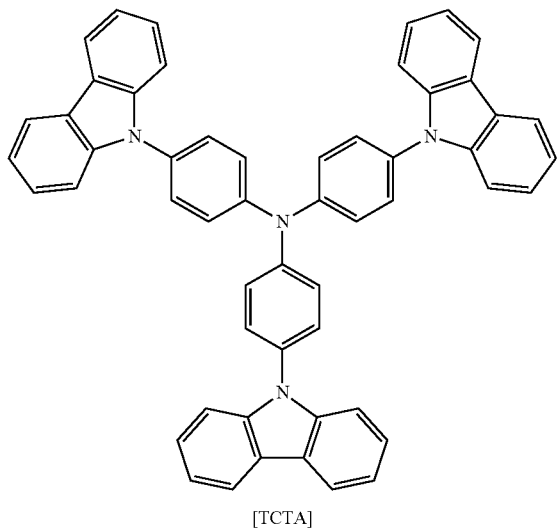 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1]

[TCTA]

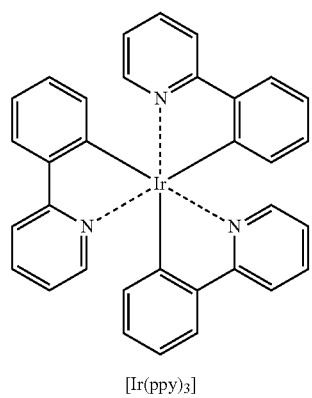

[Ir(ppy)₃]

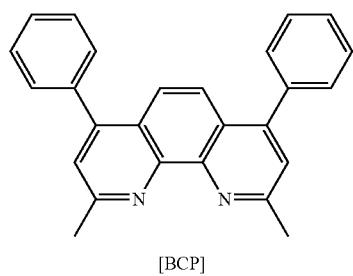

[BCP]

[Compound 1-9]

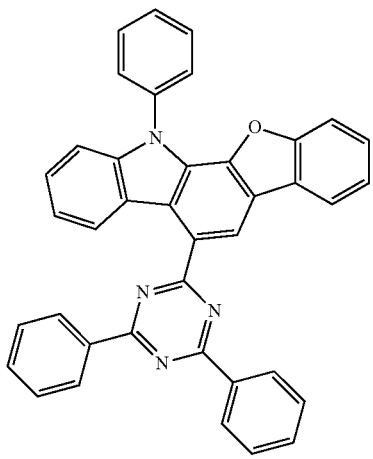

Example 3-2

An organic light emitting device was manufactured in the same manner as in Example 3-1 except that Compound 1-10 was used instead of Compound 1-9.

Example 3-3

An organic light emitting device was manufactured in the same manner as in Example 3-1 except that Compound 1-11 was used instead of Compound 1-9.

Example 3-4

An organic light emitting device was manufactured in the same manner as in Example 3-1 except that Compound 1-12 was used instead of Compound 1-9.

Example 3-5

An organic light emitting device was manufactured in the same manner as in Example 3-1 except that Compound 1-13 was used instead of Compound 1-9.

Example 3-6

An organic light emitting device was manufactured in the same manner as in Example 3-1 except that Compound 1-14 was used instead of Compound 1-9.

Example 3-7

An organic light emitting device was manufactured in the same manner as in Example 3-1 except that Compound 1-15 was used instead of Compound 1-9.

Example 3-8

An organic light emitting device was manufactured in the same manner as in Example 3-1 except that Compound 1-16 was used instead of Compound 1-9.

Example 3-9

An organic light emitting device was manufactured in the same manner as in Example 3-1 except that Compound 1-17 was used instead of Compound 1-9.

Example 3-10

An organic light emitting device was manufactured in the same manner as in Example 3-1 except that Compound 1-18 was used instead of Compound 1-9.

Example 3-11

An organic light emitting device was manufactured in the same manner as in Example 3-1 except that Compound 1-34 was used instead of Compound 1-9.

Example 3-12

An organic light emitting device was manufactured in the same manner as in Example 3-1 except that Compound 1-35 was used instead of Compound 1-9.

Example 3-13

An organic light emitting device was manufactured in the same manner as in Example 3-1 except that Compound 1-36 was used instead of Compound 1-9.

Example 3-14

An organic light emitting device was manufactured in the same manner as in Example 3-1 except that Compound 1-37 was used instead of Compound 1-9.

Example 3-15

An organic light emitting device was manufactured in the same manner as in Example 3-1 except that Compound 1-38 was used instead of Compound 1-9.

Example 3-16

An organic light emitting device was manufactured in the same manner as in Example 3-1 except that Compound 1-39 was used instead of Compound 1-9.

Example 3-17

An organic light emitting device was manufactured in the same manner as in Example 3-1 except that Compound 1-40 was used instead of Compound 1-9.

Example 3-18

An organic light emitting device was manufactured in the same manner as in Example 3-1 except that Compound 1-41 was used instead of Compound 1-9.

Example 3-19

An organic light emitting device was manufactured in the same manner as in Example 3-1 except that Compound 1-42 was used instead of Compound 1-9.

Example 3-20

An organic light emitting device was manufactured in the same manner as in Example 3-1 except that Compound 1-43 was used instead of Compound 1-9.

Example 3-21

An organic light emitting device was manufactured in the same manner as in Example 3-1 except that Compound 1-44 was used instead of Compound 1-9.

Comparative Example 3-1

An organic light emitting device was manufactured in the same manner as in Example 3-1 except that the following compound GH 1 (CBP) was used instead of Compound 1-9.

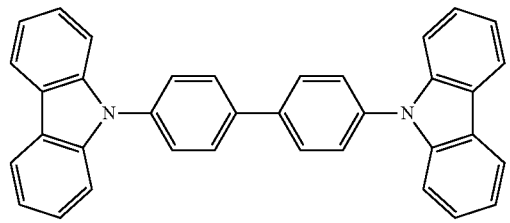

[GH 1]

Comparative Example 3-2

An organic light emitting device was manufactured in the same manner as in Example 3-1 except that the following compound GH 2 was used instead of Compound 1-9.

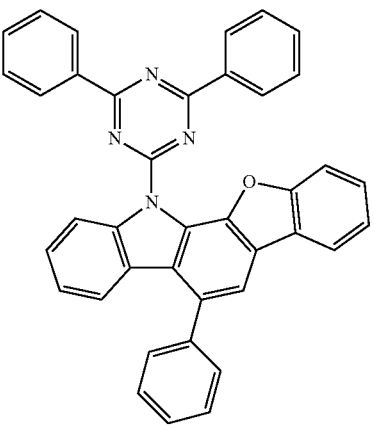

[GH 2]

Comparative Example 3-3

An organic light emitting device was manufactured in the same manner as in Example 3-1 except that the following compound GH 3 was used instead of Compound 1-9.

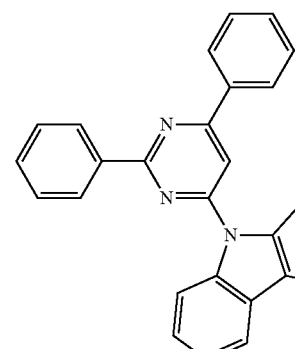

[GH 3]

Comparative Example 3-4

An organic light emitting device was manufactured in the same manner as in Example 3-1 except that the following compound GH 4 was used instead of Compound 1-9.

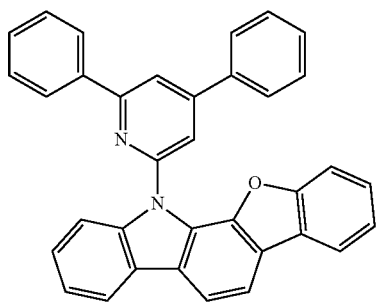

[GH 4]

When a current was applied to the organic light emitting devices manufactured in Examples 3-1 to 3-21 and Comparative Examples 3-1 to 3-4, results of Table 3 were obtained.

TABLE 3

| Category | Compound (Host) | Voltage (V@10 mA/cm$^2$) | Efficiency (cd/A@10 mA/cm$^2$) | EL Peak (nm) |
|---|---|---|---|---|
| Example 3-1 | Compound 1-9 | 6.08 | 47.93 | 517 |
| Example 3-2 | Compound 1-10 | 6.16 | 46.24 | 516 |
| Example 3-3 | Compound 1-11 | 6.05 | 45.78 | 518 |
| Example 3-4 | Compound 1-12 | 6.19 | 47.15 | 517 |
| Example 3-5 | Compound 1-13 | 6.18 | 45.31 | 515 |
| Example 3-6 | Compound 1-14 | 6.03 | 46.63 | 516 |
| Example 3-7 | Compound 1-15 | 6.19 | 46.60 | 516 |
| Example 3-8 | Compound 1-16 | 6.17 | 47.64 | 517 |
| Example 3-9 | Compound 1-17 | 6.14 | 47.68 | 518 |
| Example 3-10 | Compound 1-18 | 6.08 | 44.83 | 517 |
| Example 3-11 | Compound 1-34 | 6.19 | 47.90 | 517 |
| Example 3-12 | Compound 1-35 | 6.18 | 45.31 | 515 |
| Example 3-13 | Compound 1-36 | 6.03 | 46.13 | 516 |
| Example 3-14 | Compound 1-37 | 6.19 | 46.42 | 516 |
| Example 3-15 | Compound 1-38 | 6.17 | 46.61 | 517 |
| Example 3-16 | Compound 1-39 | 6.14 | 47.08 | 518 |
| Example 3-17 | Compound 1-40 | 6.14 | 47.08 | 518 |
| Example 3-18 | Compound 1-41 | 6.03 | 46.13 | 516 |
| Example 3-19 | Compound 1-42 | 6.19 | 46.42 | 516 |
| Example 3-20 | Compound 1-43 | 6.17 | 46.64 | 517 |
| Example 3-21 | Compound 1-44 | 6.14 | 47.01 | 518 |
| Comparative Example 3-1 | GH 1(CBP) | 7.05 | 38.77 | 517 |
| Comparative Example 3-2 | GH 2 | 7.27 | 36.48 | 518 |
| Comparative Example 3-3 | GH 3 | 7.33 | 34.56 | 517 |
| Comparative Example 3-4 | GH 4 | 7.45 | 33.11 | 518 |

As the test results, it was identified that the green organic light emitting devices of Examples 3-1 to 3-21 using the compound represented by Chemical Formula 1 according to the present specification as a host material of a green light emitting layer exhibited superior performance in current efficiency and driving voltage compared to the green organic light emitting device of Comparative Example 3-1 using existing CBP, and the green organic light emitting devices of Comparative Examples 3-2 to 3-4.

Example 4

Example 4-1

The compounds synthesized in the preparation examples were high-purity sublimation purified using commonly known methods, and then a red organic light emitting device was manufactured using a method as below.

An ITO glass was patterned so that a light emitting area became a 2 mm×2 mm size, and then washed. After installing the substrate in a vacuum chamber, the base pressure was set at 1×10$^6$ torr, and as organic materials on the ITO, DNTPD (700 Å), α-NPB (300 Å), Compound 1-21 used as a host (90 wt %), and the following (piq)$_2$Ir(acac) (10 wt %) used as a dopant (300 Å) were vacuum deposited, then Alq$_3$ (350 Å), LiF (5 Å) and Al (1,000 Å) were layered in this order, and measurements were carried out at 0.4 mA.

The structures of the DNTPD, the α-NPB, the (piq)$_2$Ir(acac) and the Alq$_3$ are as follows.

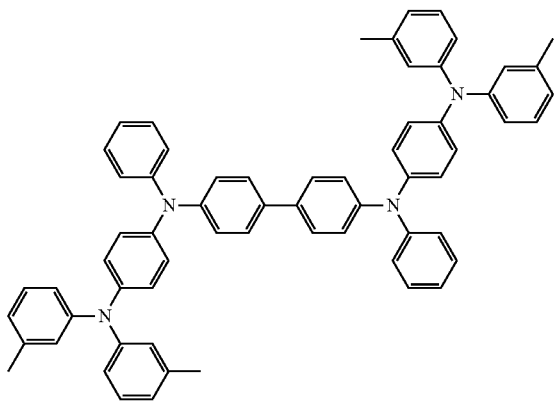

[DNTPD]

-continued

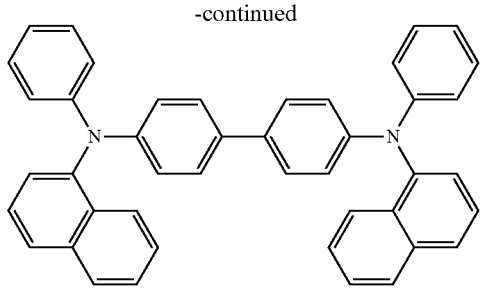
[α-NPB]

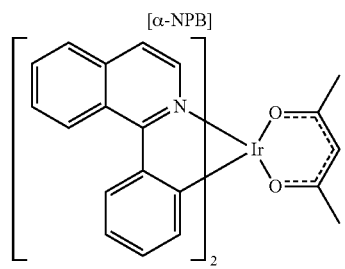
[(piq)₂Ir(acac)]

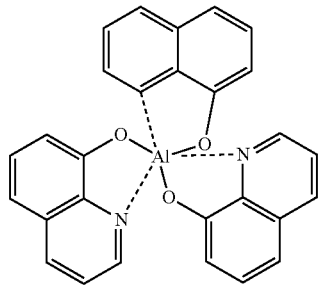
[Alq₃]

Example 4-2

An organic light emitting device was manufactured in the same manner as in Example 4-1 except that Compound 1-22 was used instead of Compound 1-21.

Example 4-3

An organic light emitting device was manufactured in the same manner as in Example 4-1 except that Compound 1-23 was used instead of Compound 1-21.

Example 4-4

An organic light emitting device was manufactured in the same manner as in Example 4-1 except that Compound 1-24 was used instead of Compound 1-21.

Example 4-5

An organic light emitting device was manufactured in the same manner as in Example 4-1 except that Compound 1-25 was used instead of Compound 1-21.

Example 4-6

An organic light emitting device was manufactured in the same manner as in Example 4-1 except that Compound 1-46 was used instead of Compound 1-21.

Example 4-7

An organic light emitting device was manufactured in the same manner as in Example 4-1 except that Compound 1-47 was used instead of Compound 1-21.

Example 4-8

An organic light emitting device was manufactured in the same manner as in Example 4-1 except that Compound 1-48 was used instead of Compound 1-21.

Example 4-9

An organic light emitting device was manufactured in the same manner as in Example 4-1 except that Compound 1-49 was used instead of Compound 1-21.

Example 4-10

An organic light emitting device was manufactured in the same manner as in Example 4-1 except that Compound 1-50 was used instead of Compound 1-21.

Comparative Example 4-1

An organic light emitting device was manufactured in the same manner as in Example 4-1 except that the following Compound RH 1 (CBP) was used instead of Compound 1-21.

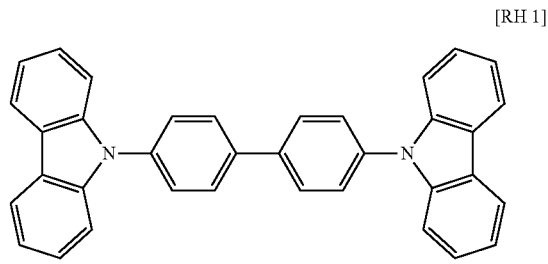 [SMILES: c1ccc2c(c1)c1ccccc1n2-c1ccc(-c2ccc(-n3c4ccccc4c4ccccc43)cc2)cc1]
[RH 1]

Comparative Example 4-2

An organic light emitting device was manufactured in the same manner as in Example 4-1 except that the following Compound RH 2 was used instead of Compound 1-21.

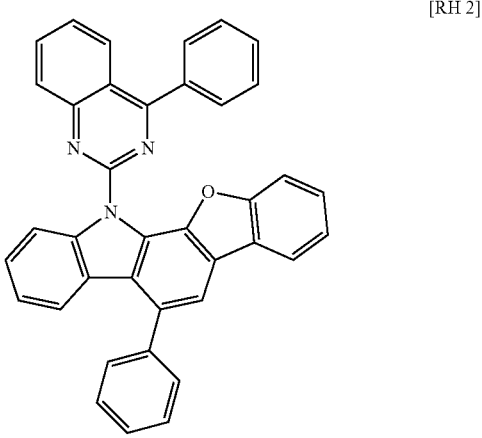 [SMILES: c1ccc(-c2nc(-n3c4ccccc4c4c(-c5ccccc5)cc5c6ccccc6oc5c43)nc3ccccc23)cc1]
[RH 2]

Comparative Example 4-3

An organic light emitting device was manufactured in the same manner as in Example 4-1 except that the following Compound RH 3 was used instead of Compound 1-21.

[RH 3]

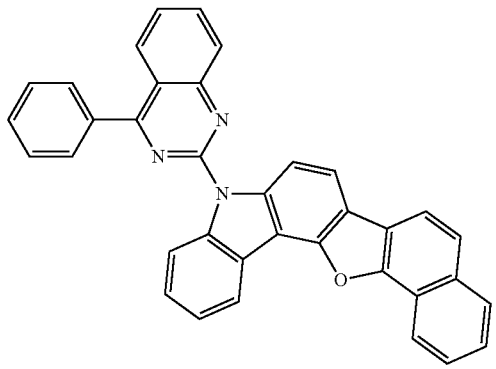

For the organic light emitting devices manufactured according to Examples 4-1 to 4-10 and Comparative Examples 4-1 to 4-3, a voltage, current density, luminance, a color coordinate and a lifespan were measured, and the results are shown in the following Table 4. T95 means time taken for the luminance decreasing to 95% of its initial luminance (5000 nit).

TABLE 4

| Category | Compound (Host) | Voltage (V) | Luminance (cd/m$^2$) | Color Coordinate (x, y) | T95 (hr) |
|---|---|---|---|---|---|
| Example 4-1 | Compound 1-21 | 4.3 | 1860 | (0.670, 0.329) | 465 |
| Example 4-2 | Compound 1-22 | 4.2 | 1850 | (0.674, 0.325) | 415 |
| Example 4-3 | Compound 1-23 | 4.1 | 1900 | (0.672, 0.327) | 440 |
| Example 4-4 | Compound 1-24 | 4.3 | 1840 | (0.673, 0.335) | 435 |
| Example 4-5 | Compound 1-25 | 4.0 | 1790 | (0.675, 0.333) | 405 |
| Example 4-6 | Compound 1-46 | 4.2 | 1810 | (0.670, 0.339) | 420 |
| Example 4-7 | Compound 1-47 | 4.3 | 1970 | (0.671, 0.338) | 445 |
| Example 4-8 | Compound 1-48 | 4.3 | 1860 | (0.668, 0.329) | 465 |
| Example 4-9 | Compound 1-49 | 4.2 | 1950 | (0.673, 0.325) | 415 |
| Example 4-10 | Compound 1-50 | 4.3 | 1860 | (0.670, 0.329) | 465 |
| Comparative Example 4-1 | RH 1(CBP) | 5.7 | 1400 | (0.670, 0.325) | 265 |
| Comparative Example 4-2 | RH 2 | 5.8 | 1350 | (0.671, 0.327) | 275 |
| Comparative Example 4-3 | RH 3 | 6.2 | 1050 | (0.674, 0.329) | 285 |

As the test results, it was identified that the red organic light emitting devices of Examples 4-1 to 4-10 using the compound according to the present specification as a host material of the light emitting layer exhibited superior performance in current efficiency, driving voltage and lifespan compared to the red organic light emitting device of Comparative Example 4-1 using existing CBP and the organic light emitting devices of Comparative Examples 4-2 and 4-3.

Hereinbefore, preferred embodiments of the present disclosure (electron blocking layer, hole transfer layer, green light emitting layer, red light emitting layer) have been described, however, the present disclosure is not limited thereto, and various modifications may be made within the scope of the claims and the detailed descriptions, and the modifications are also included in the scope of the present disclosure.

The invention claimed is:
1. A compound represented by the following Chemical Formula 1:

[Chemical Formula 1]

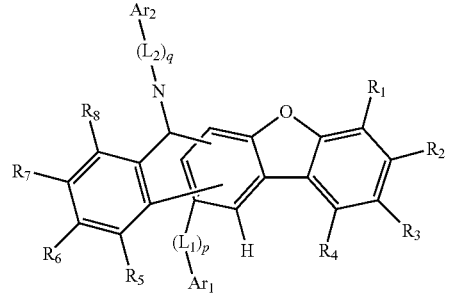

wherein, in Chemical Formula 1,
Ar$_1$ is a substituted or unsubstituted biphenyl group; a substituted or unsubstituted terphenyl group; a substituted or unsubstituted quaterphenyl group; a substituted or unsubstituted multicyclic aryl group; a substituted or unsubstituted arylamine group; or a substituted or unsubstituted heterocyclic group;
L$_1$ and L$_2$ are the same as or different from each other, and each independently a direct bond; a substituted or unsubstituted arylene group; or a substituted or unsubstituted heteroarylene group;
p and q are the same as or different from each other, and each independently an integer of 0 to 5;
when p and q are 2 or greater, structures in the parentheses are the same as or different from each other; and
Ar$_2$ and R$_1$ to R$_8$ are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or adjacent groups bond to each other to form a substituted or unsubstituted ring.

2. The compound of claim 1, wherein Chemical Formula 1 is represented by the following Chemical Formula 2 or Chemical Formula 3:

[Chemical Formula 2]

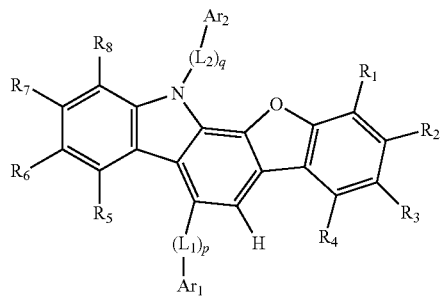

[Chemical Formula 3]

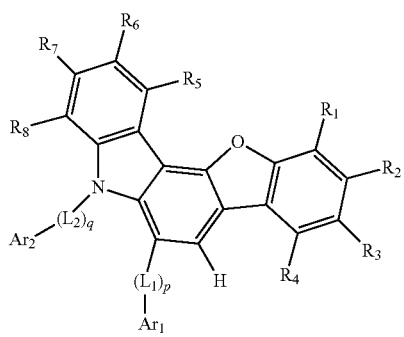

wherein, in Chemical Formula 2 and Chemical Formula 3, definitions of p, q, $L_1$, $L_2$, $Ar_1$, $Ar_2$ and $R_1$ to $R_8$ are the same as in Chemical Formula 1.

3. The compound of claim 1, wherein Chemical Formula 1 is represented by any one of the following Chemical Formula 4 to Chemical Formula 9:

[Chemical Formula 4]

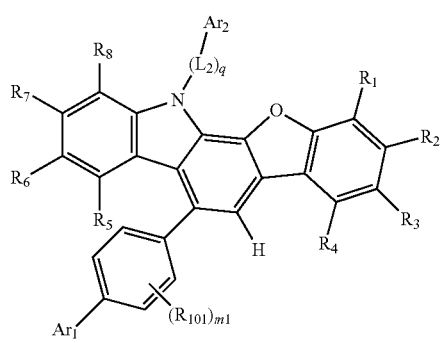

[Chemical Formula 5]

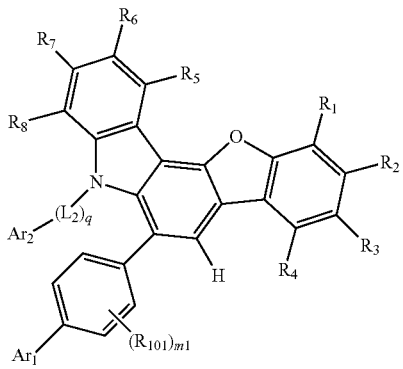

[Chemical Formula 6]

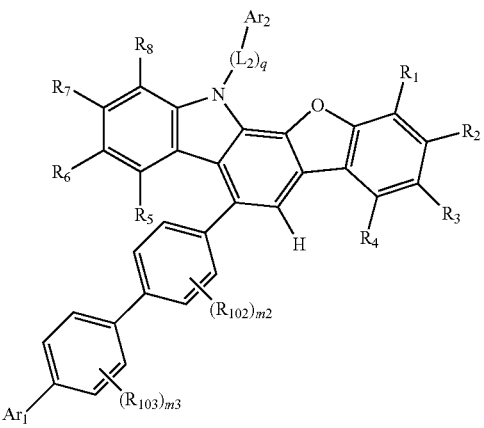

[Chemical Formula 7]

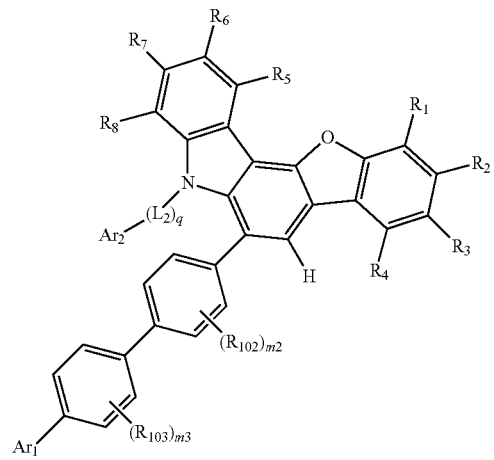

[Chemical Formula 8]

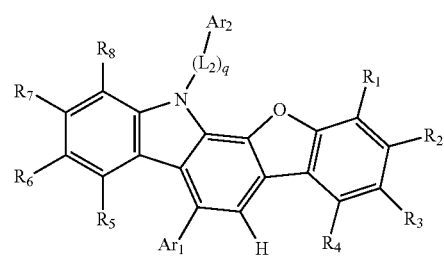

-continued

[Chemical Formula 9]

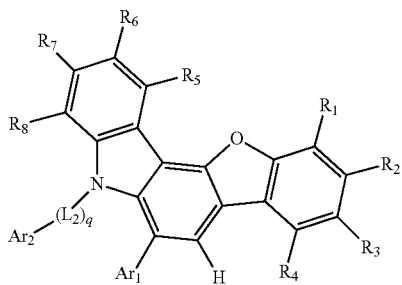

wherein, in Chemical Formula 4 to Chemical Formula 9,
definitions of q, $L_2$, $Ar_1$, $Ar_2$ and $R_1$ to $R_8$ are the same as in Chemical Formula 1;
m1 to m3 are each independently an integer of 0 to 4;
when m1 to m3 are 2 or greater, structures in the parentheses are the same as or different from each other; and
$R_{101}$ to $R_{103}$ are the same as or different from each other, and each independently have the same definitions as $R_1$ to $R_8$ in Chemical Formula 1.

4. The compound of claim 1, wherein Chemical Formula 1 is represented by the following Chemical Formula 10 or Chemical Formula 11:

[Chemical Formula 10]

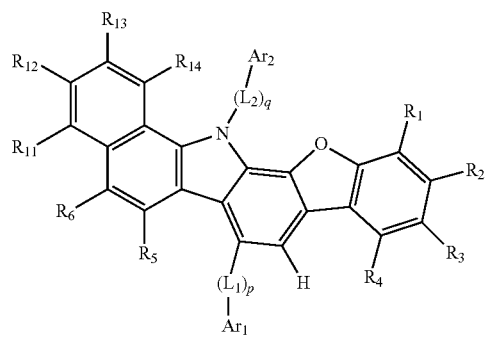

[Chemical Formula 11]

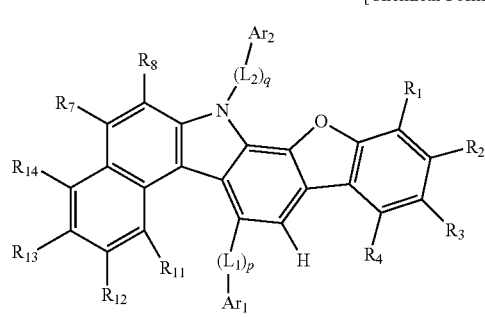

wherein, in Chemical Formula 10 and Chemical Formula 11,
definitions of p, q, $L_1$, $L_2$, $Ar_1$, $Ar_2$ and $R_1$ to $R_8$ are the same as in Chemical Formula 1; and
$R_{11}$ to $R_{14}$ are the same as or different from each other, and each independently have the same definitions as $R_1$ to $R_8$.

5. The compound of claim 1, wherein $L_1$ and $L_2$ are the same as or different from each other, and each independently one or more types selected from the group consisting of a direct bond; a substituted or unsubstituted phenylene group; a substituted or unsubstituted biphenylene group; a substituted or unsubstituted terphenylene group; a substituted or unsubstituted quaterphenylene group; a substituted or unsubstituted naphthylene group; a substituted or unsubstituted anthracenylene group; a substituted or unsubstituted fluorenylene group; a substituted or unsubstituted phenanthrenylene group; a substituted or unsubstituted pyrenylene group; a substituted or unsubstituted triphenylene group; a substituted or unsubstituted pyridinylene group; a substituted or unsubstituted pyrimidinylene group; a substituted or unsubstituted triazinylene group; a substituted or unsubstituted quinolinylene group; a substituted or unsubstituted quinazolinylene group; a substituted or unsubstituted carbazolylene group; a substituted or unsubstituted dibenzofuranylene group; and a substituted or unsubstituted divalent dibenzothiophene group.

6. The compound of claim 1, wherein $L_1$ and $L_2$ are the same as or different from each other, and each independently a direct bond or any one selected from among the following compounds:

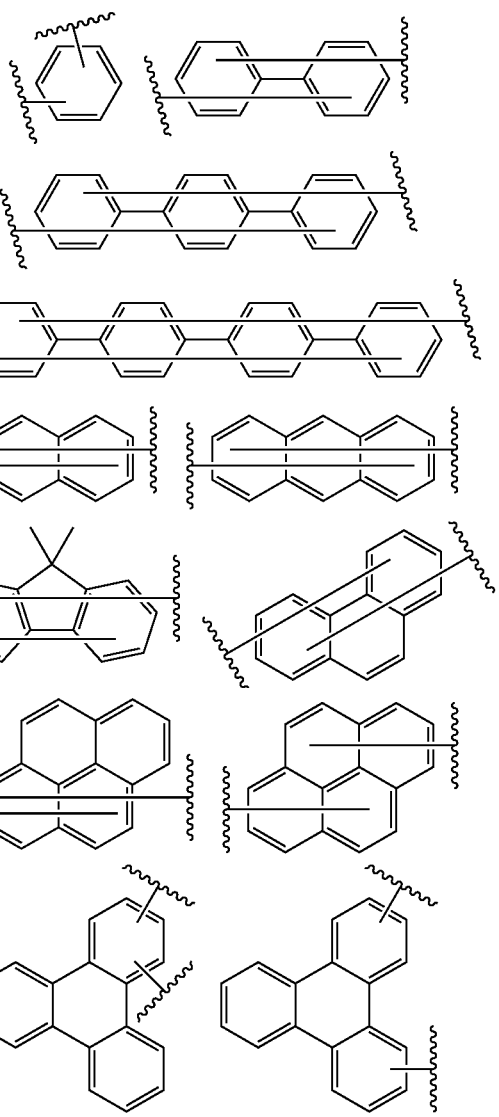

-continued

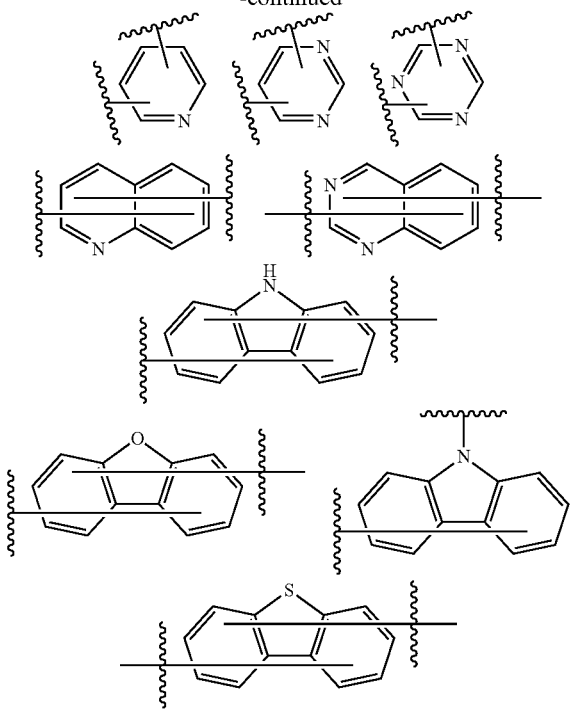

wherein, the structures are unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

7. The compound of claim 1, wherein $Ar_1$ is a substituted or unsubstituted biphenyl group; a substituted or unsubstituted terphenyl group; a substituted or unsubstituted quaterphenyl group; a substituted or unsubstituted multicyclic aryl group having 6 to 40 carbon atoms; an arylamine group having 6 to 40 carbon atoms; or a substituted or unsubstituted heterocyclic group having 2 to 40 carbon atoms; and $Ar_2$ is a substituted or unsubstituted aryl group having 6 to 40 carbon atoms; or a substituted or unsubstituted heterocyclic group having 2 to 40 carbon atoms.

8. The compound of claim 1, wherein -($L_1$)p-$Ar_1$ is any one selected from among the following structures:

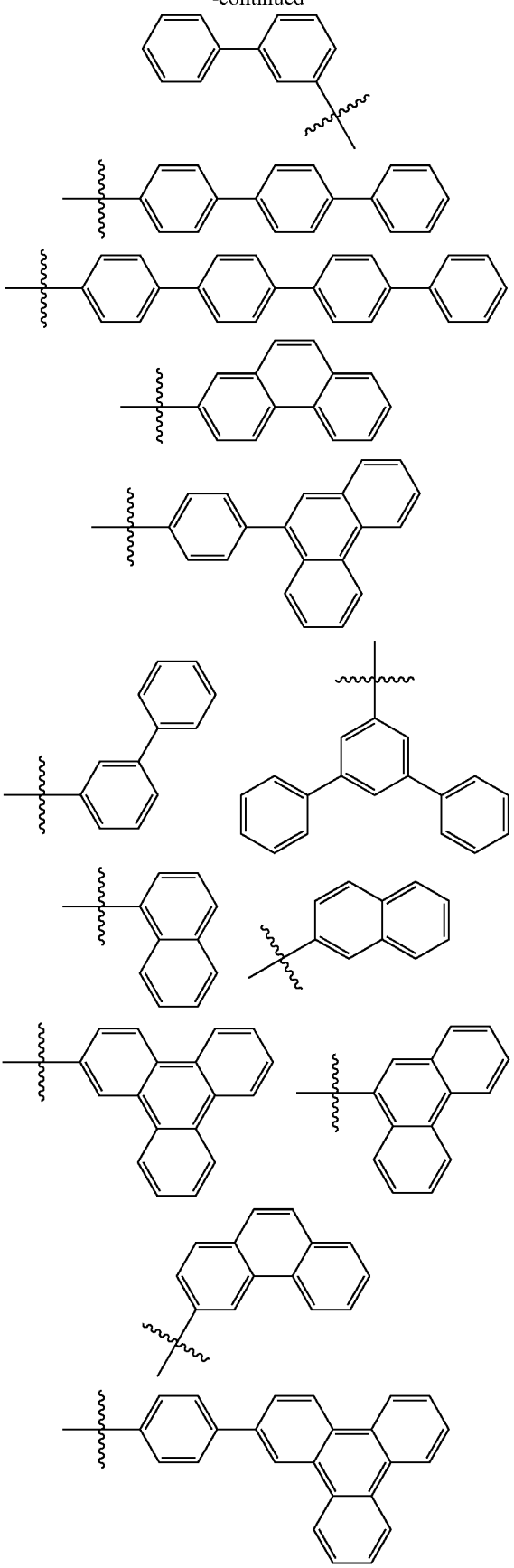

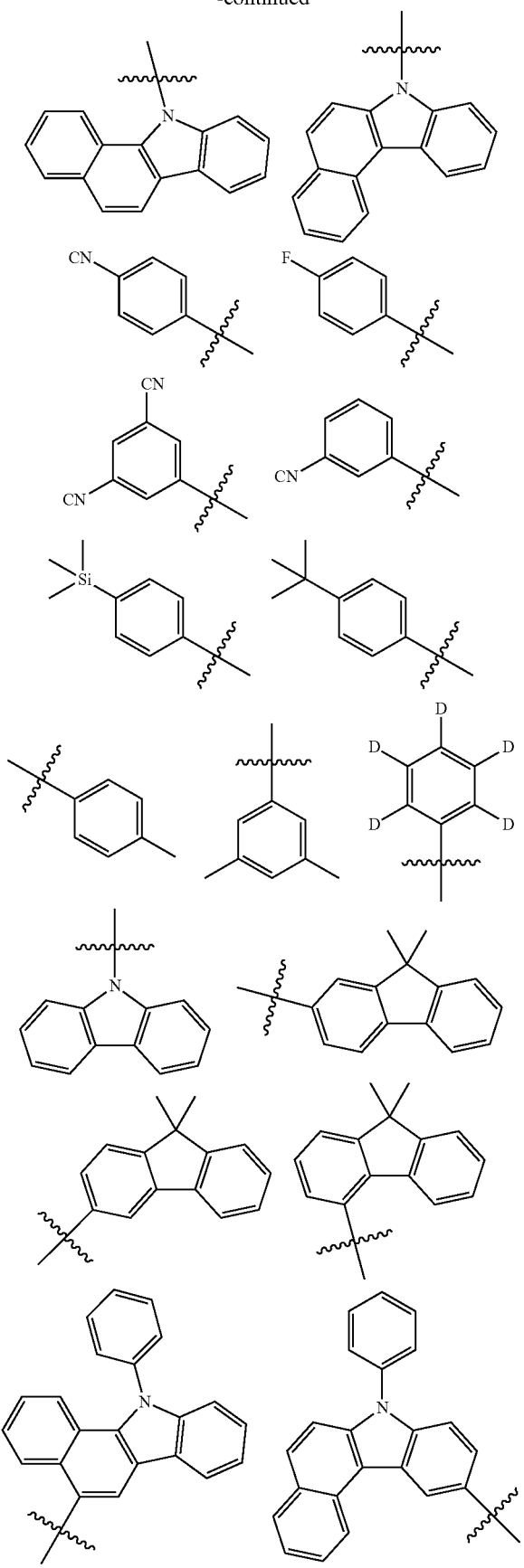
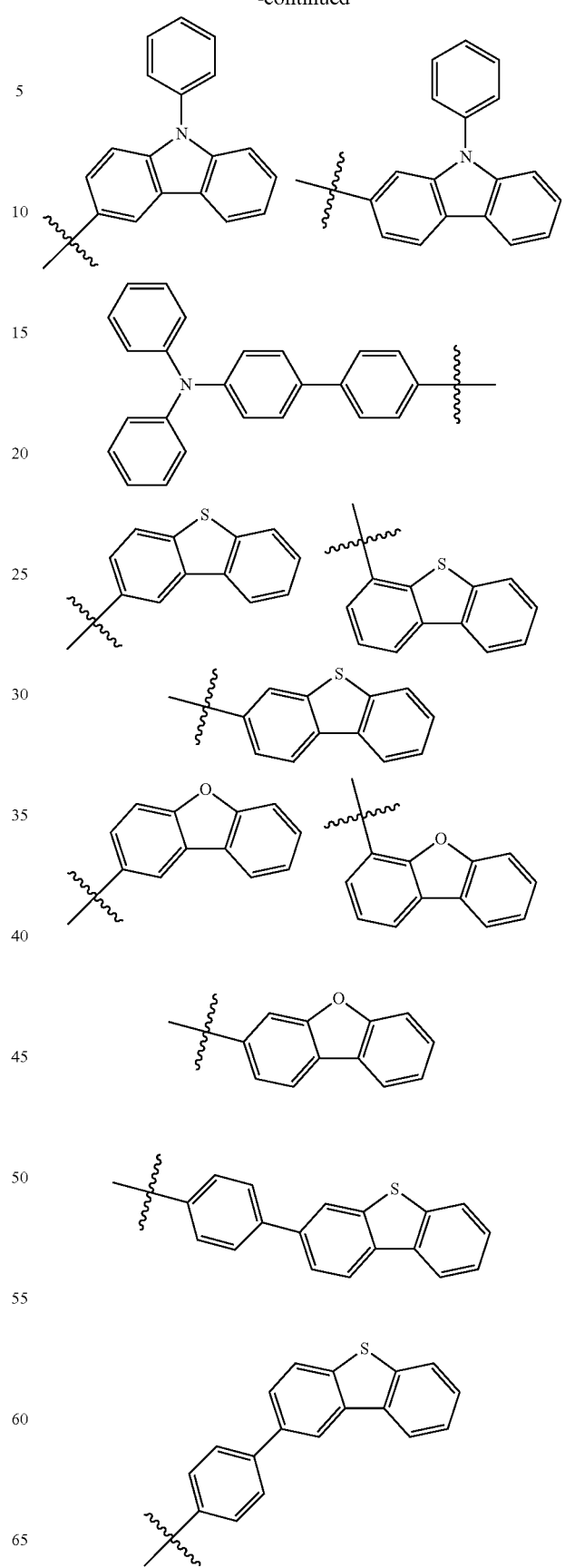

351
-continued
352
-continued
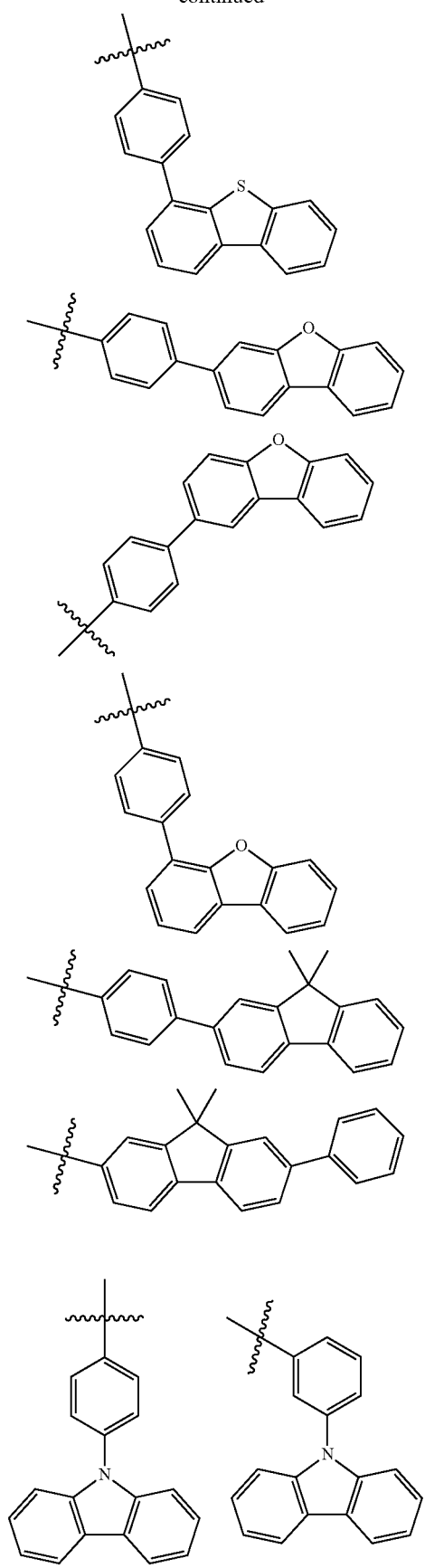
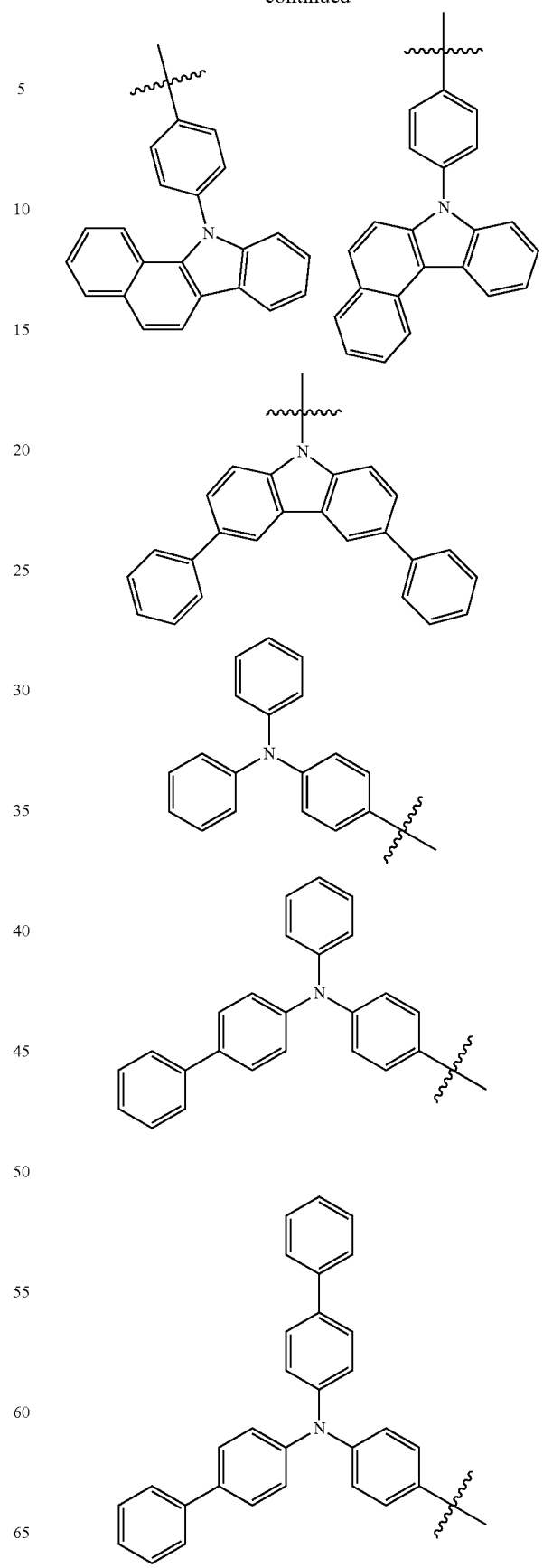

-continued
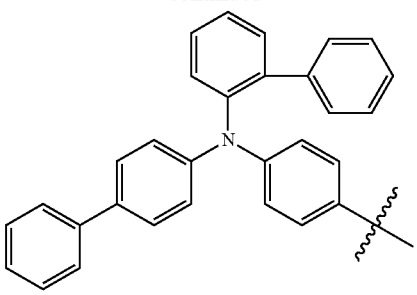
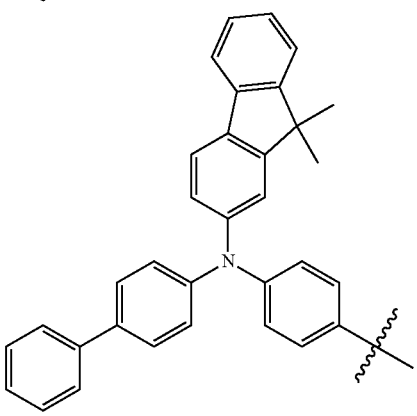
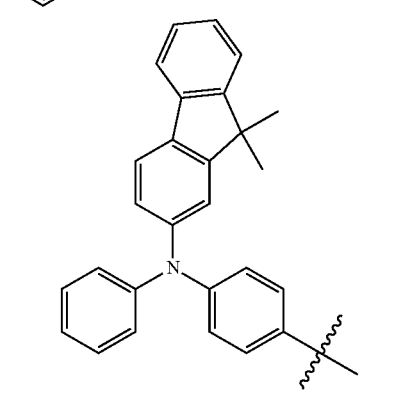
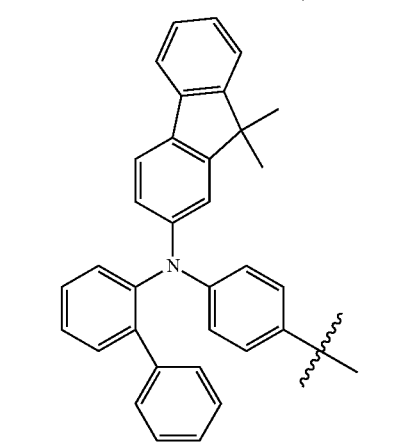
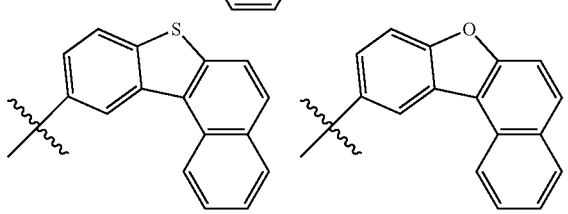
-continued
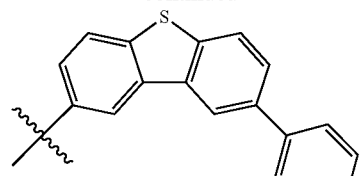
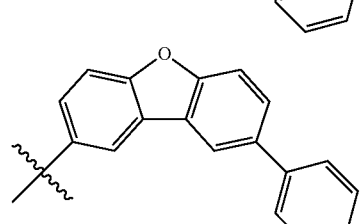
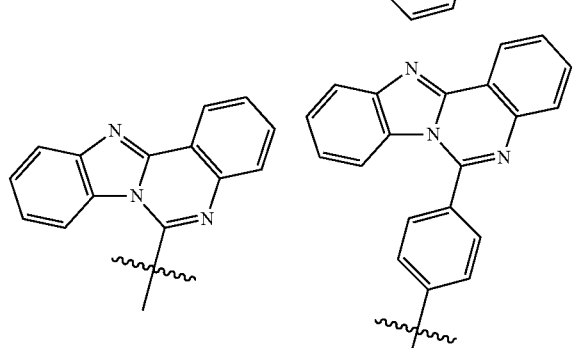
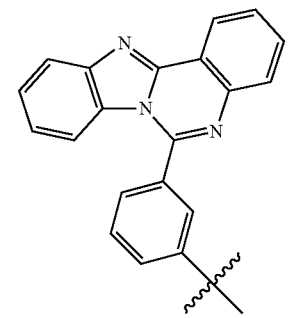
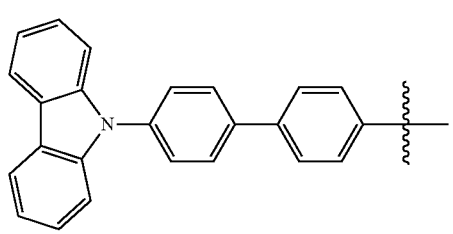
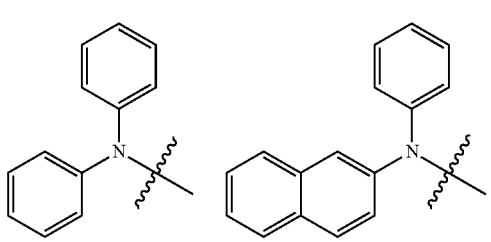

355
-continued
356
-continued
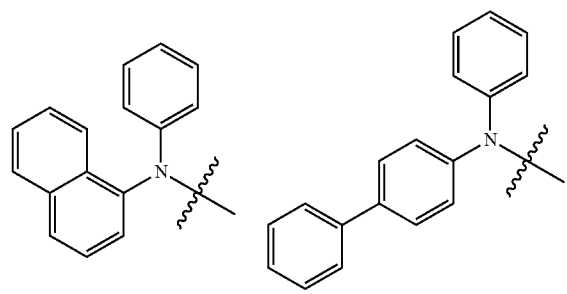
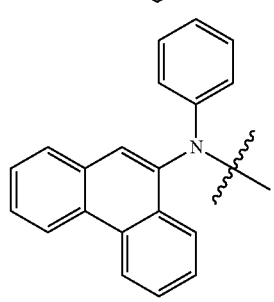
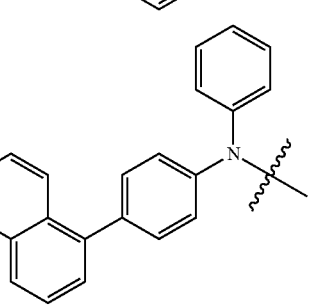

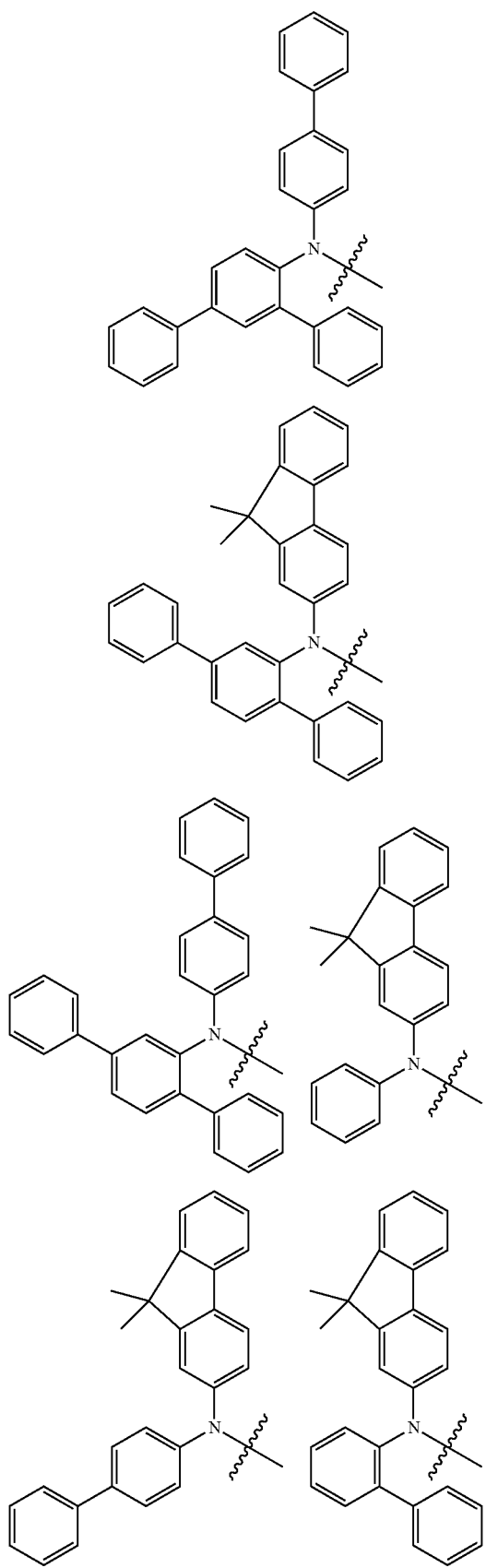
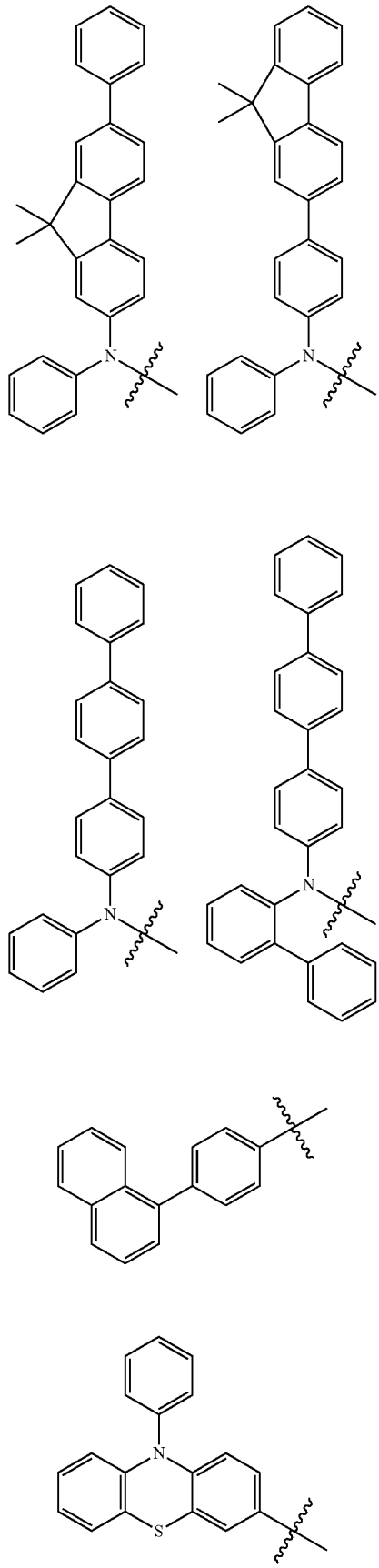

359
-continued
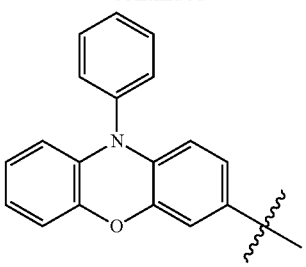
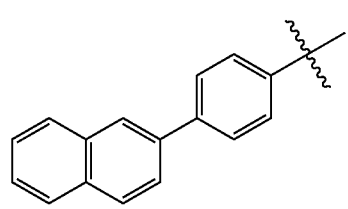
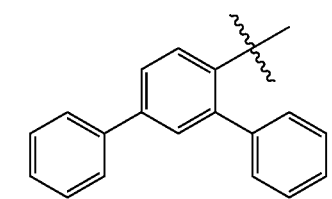
360
-continued
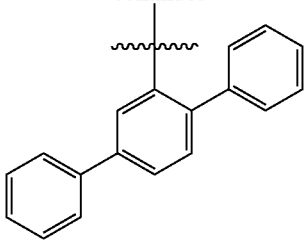
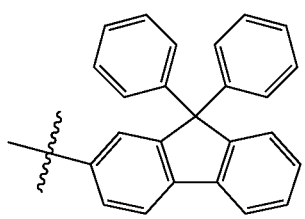
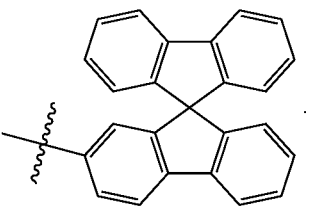
9. The compound of claim 1, wherein the compound of Chemical Formula 1 is any one selected from among the following structures:
1
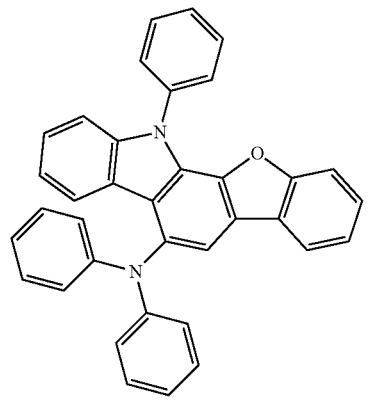
2
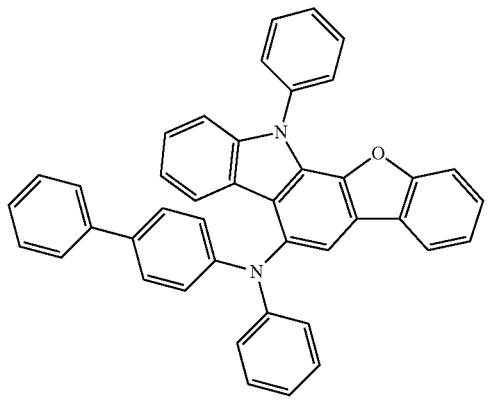

3
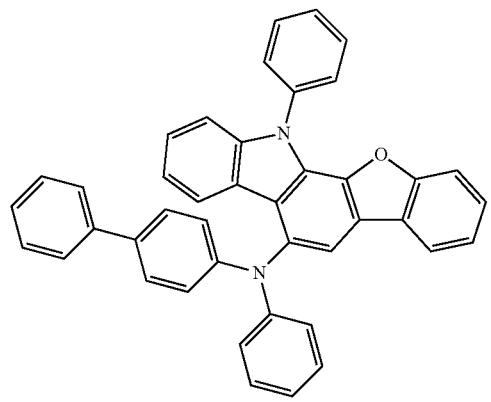
4
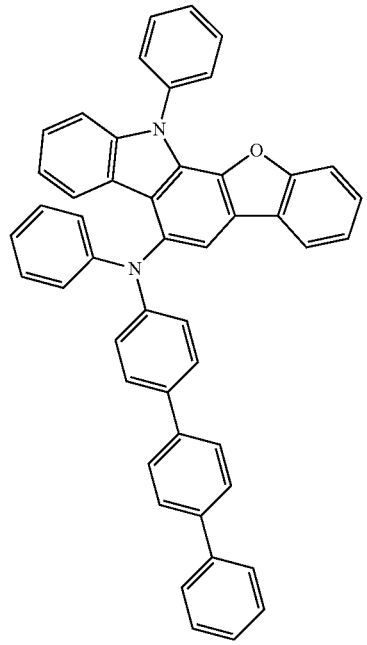
5
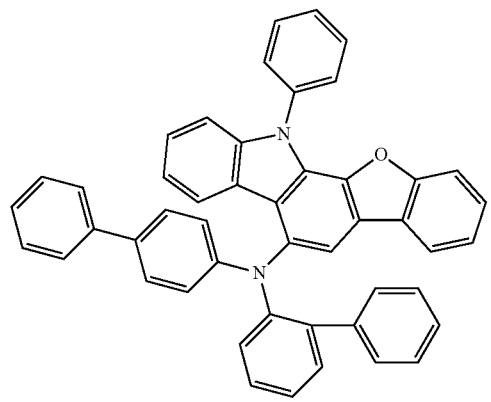
6
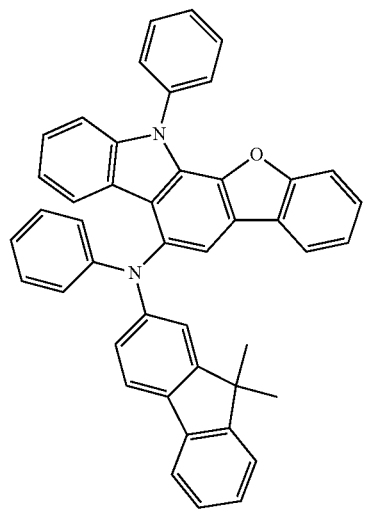
7
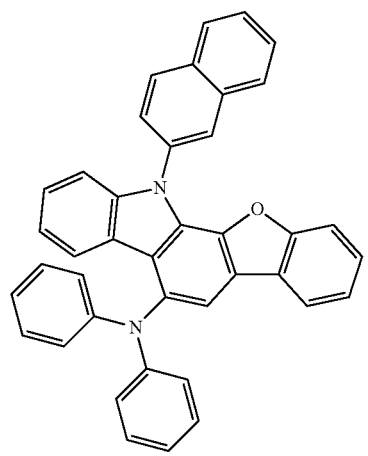
8
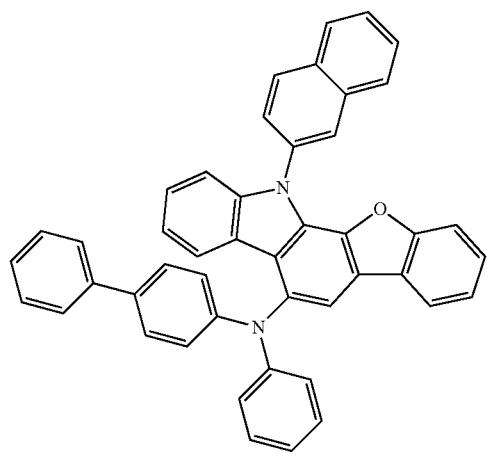

9
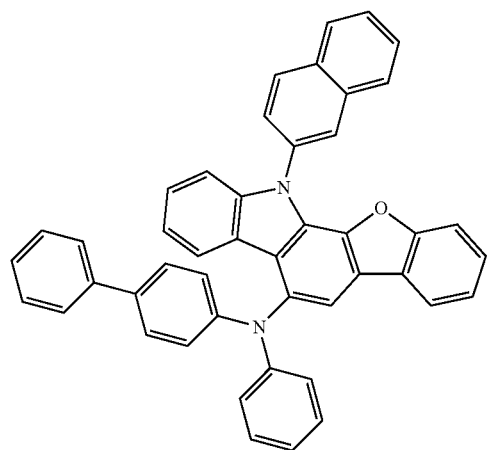
10
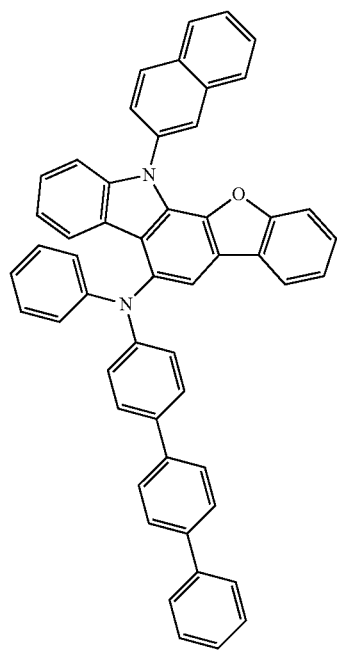
11
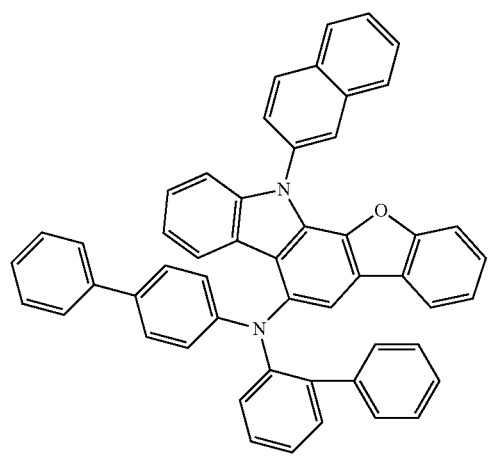
12
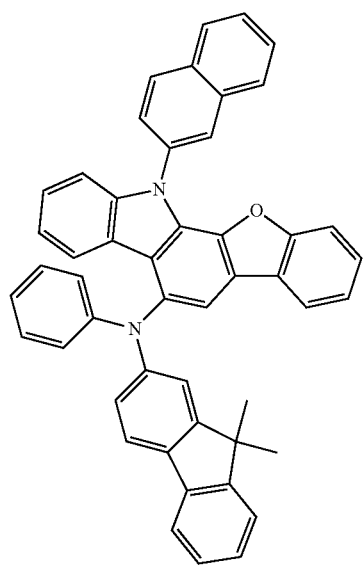

13
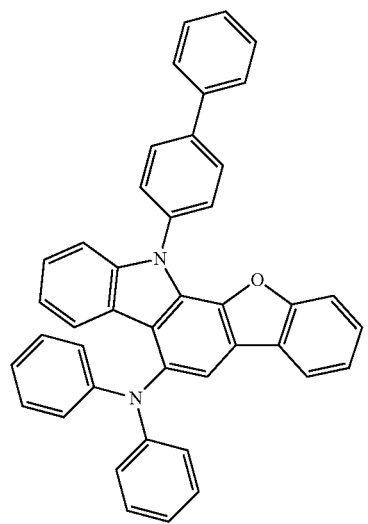
14
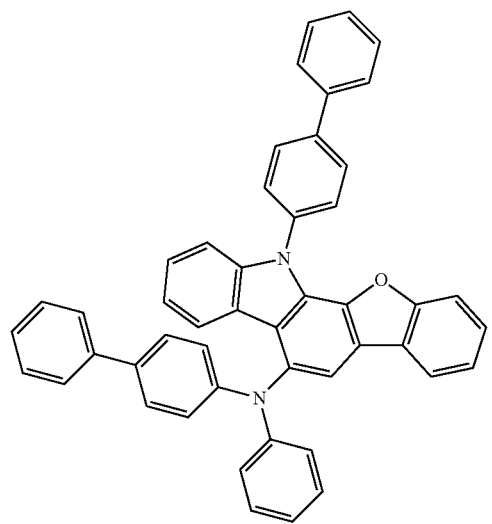
15
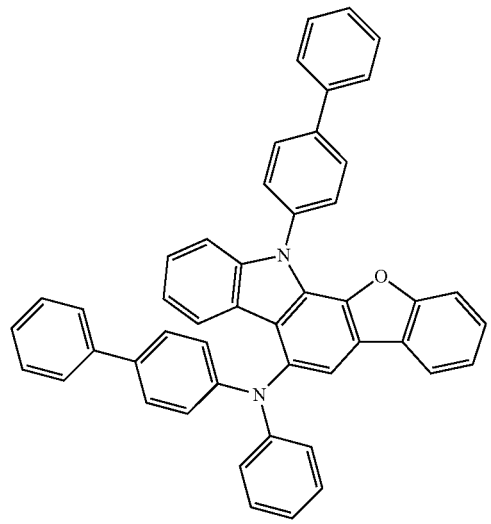
16
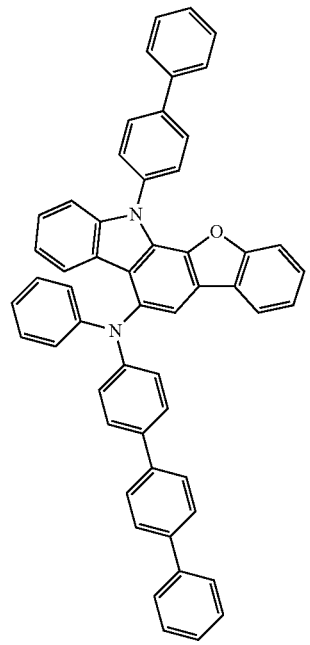

17
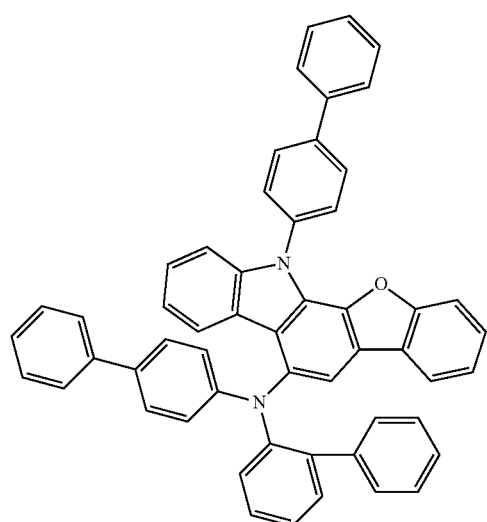
18
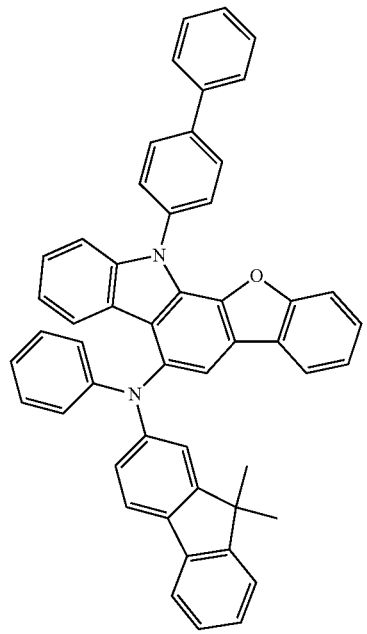
19
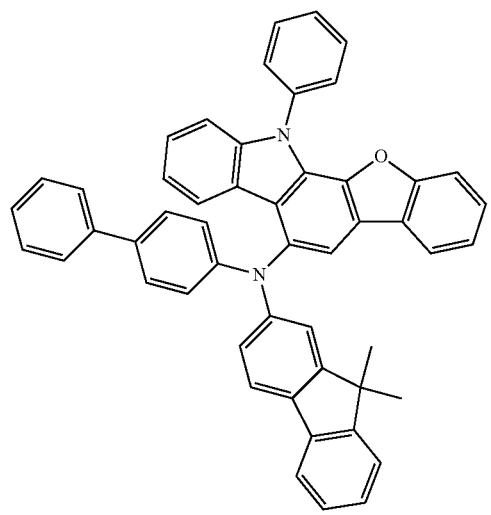
20
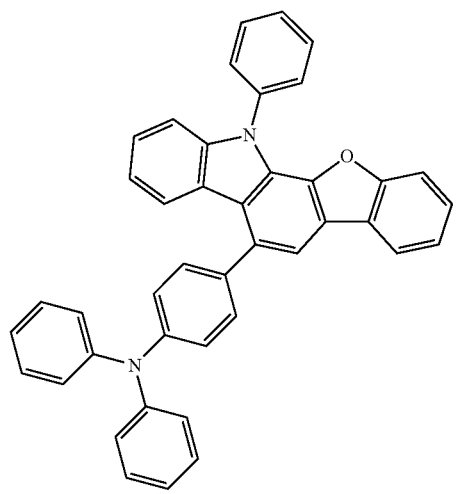

21
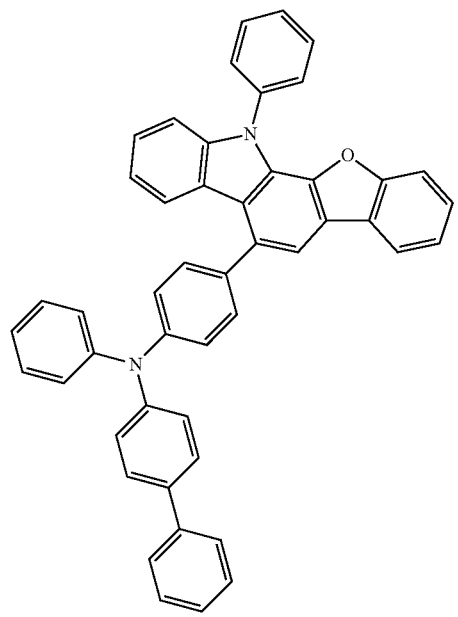
22
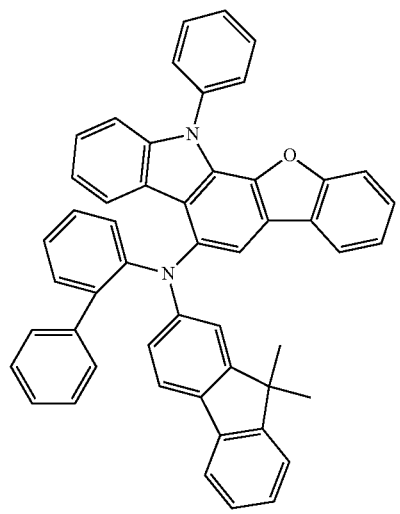
23
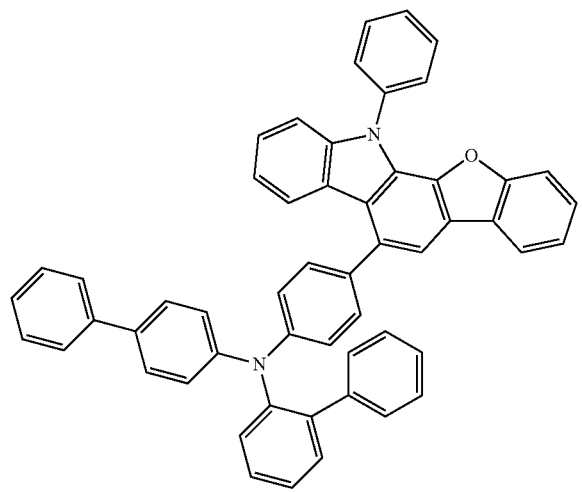
24
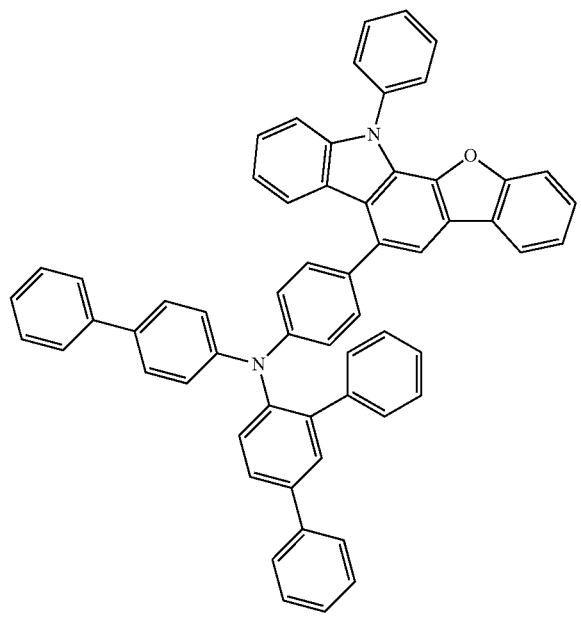

371
25
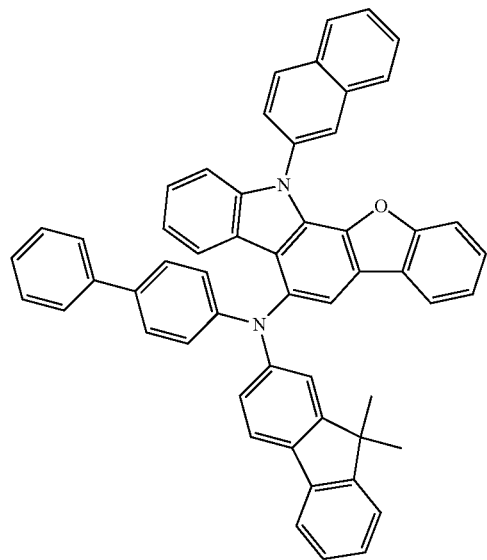
372
26
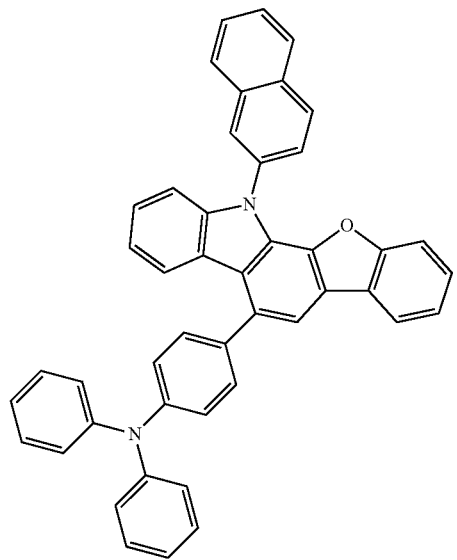
27
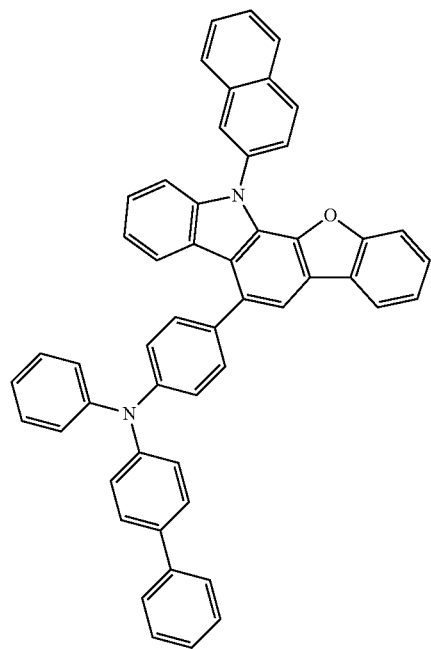
28

29
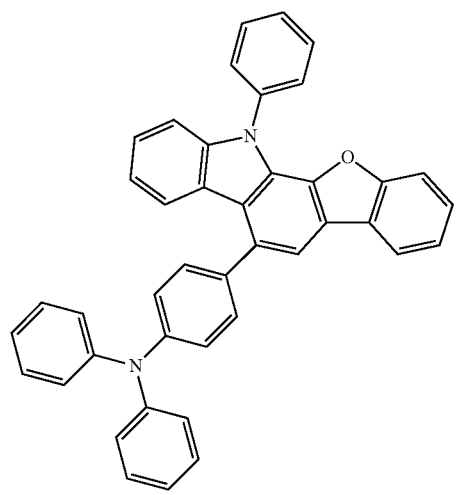
30
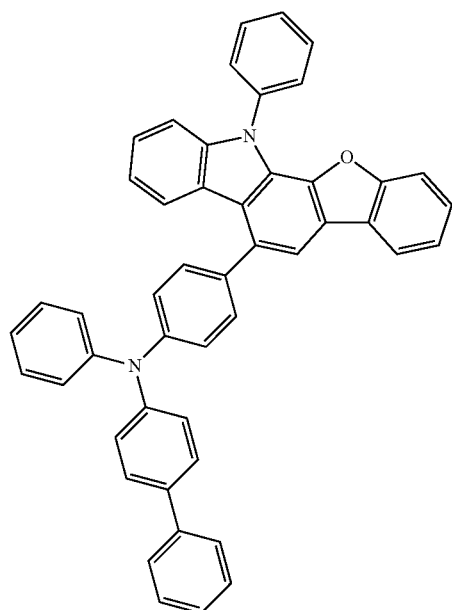
31
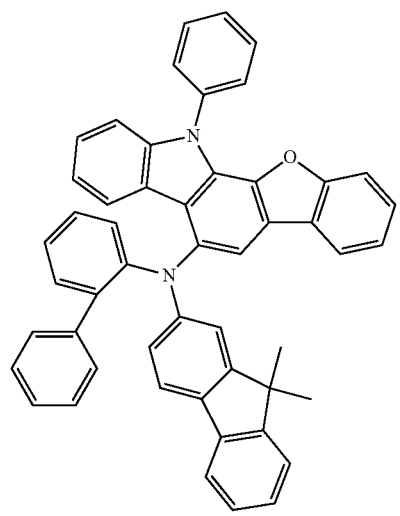
32
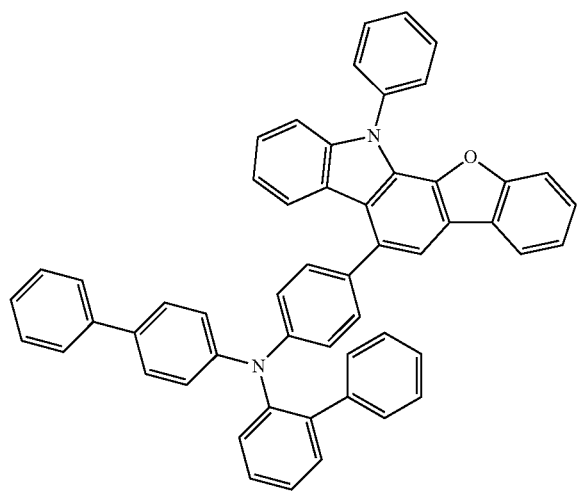

33
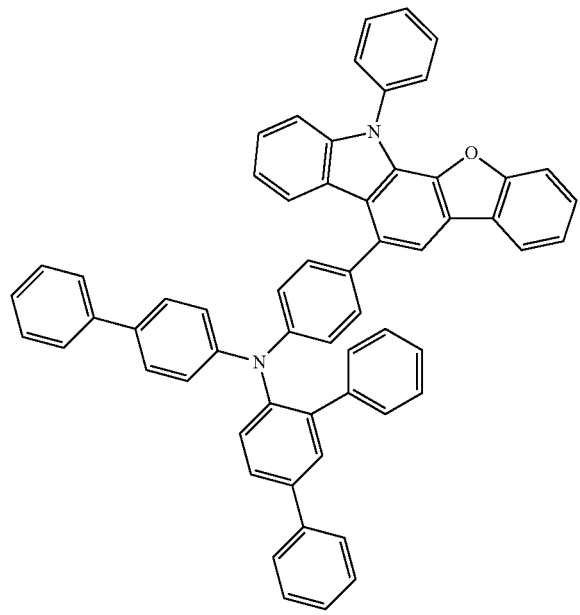
34
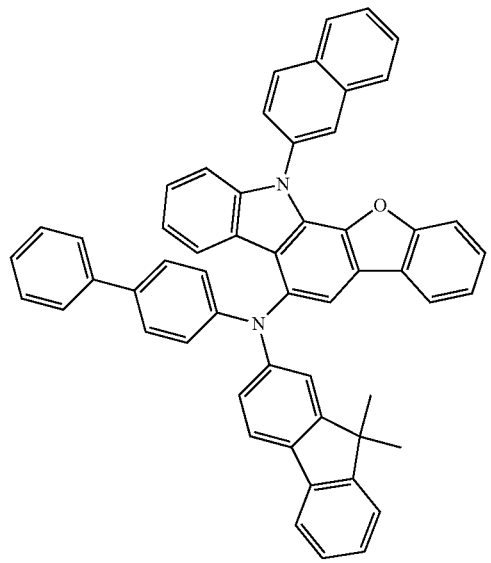
35
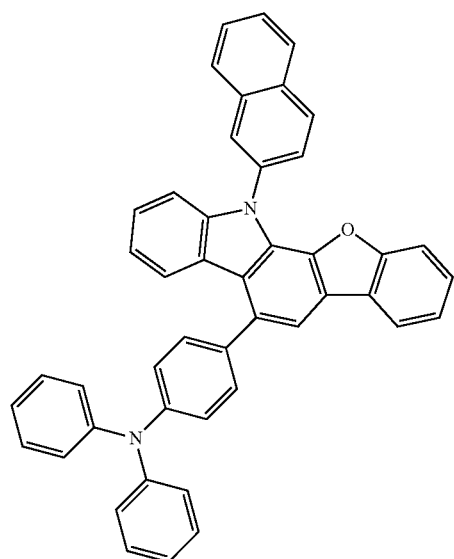
36
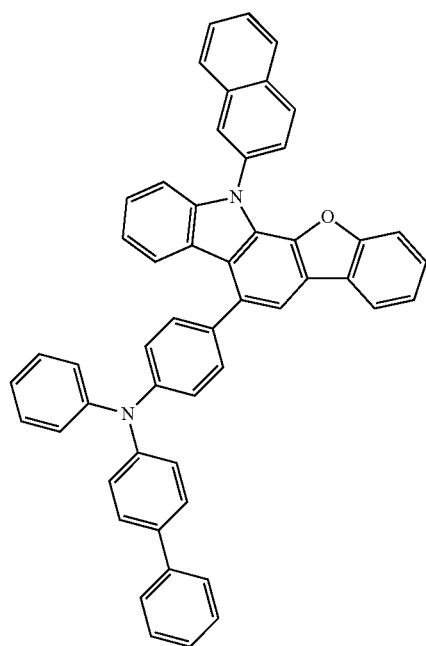

377
378
-continued
37
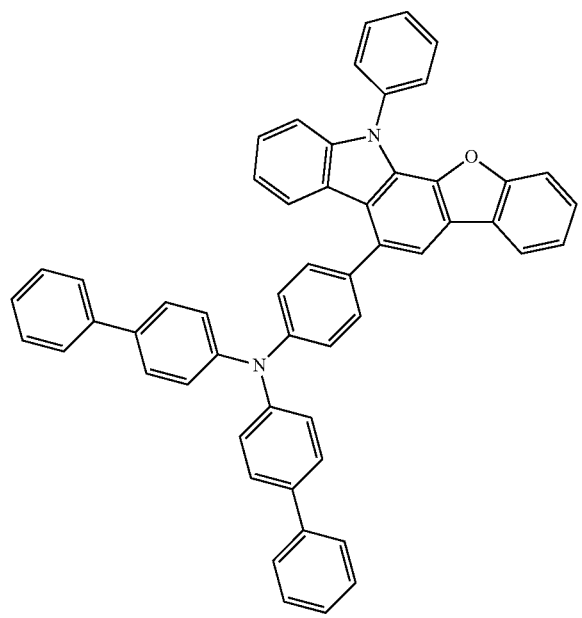
38
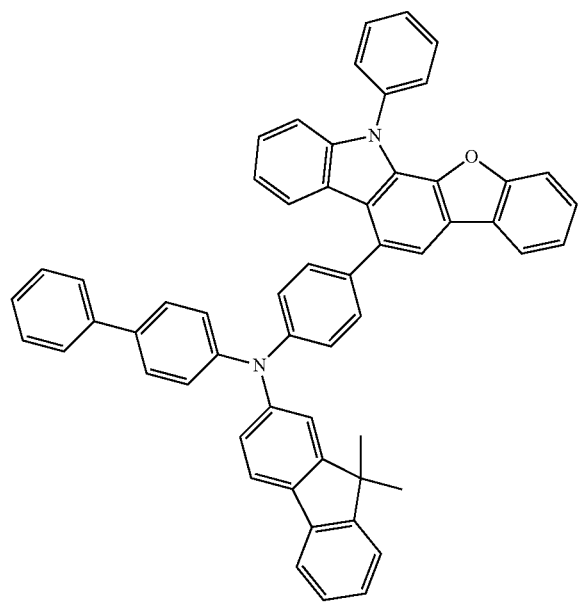
39
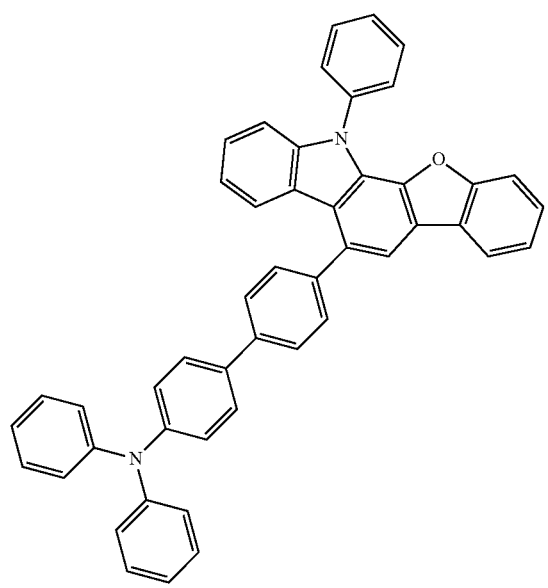
40
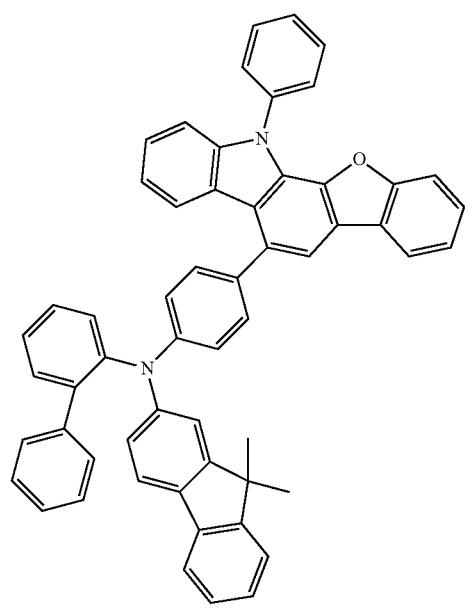

41
379
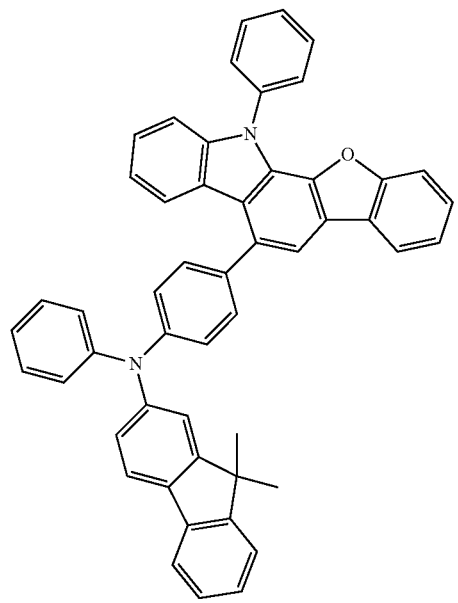
42
380
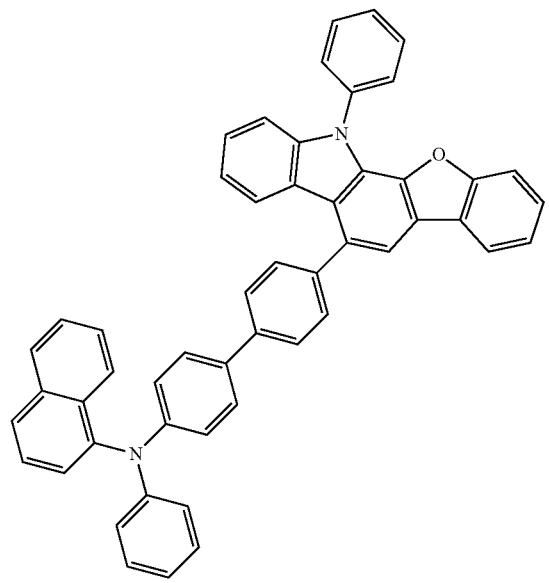
43
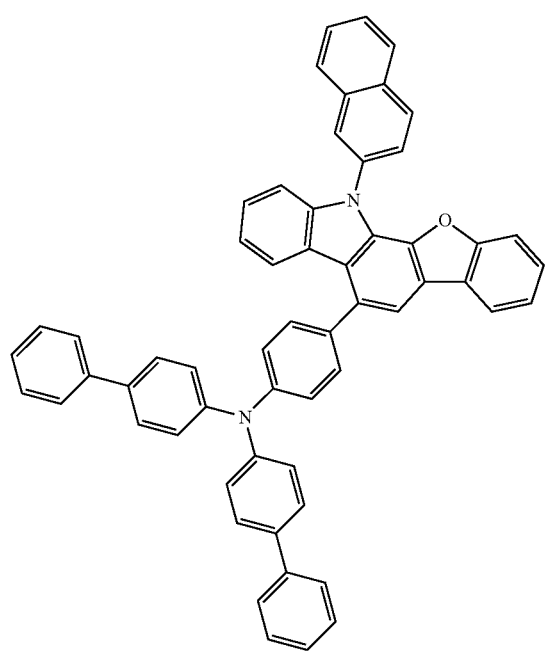
44
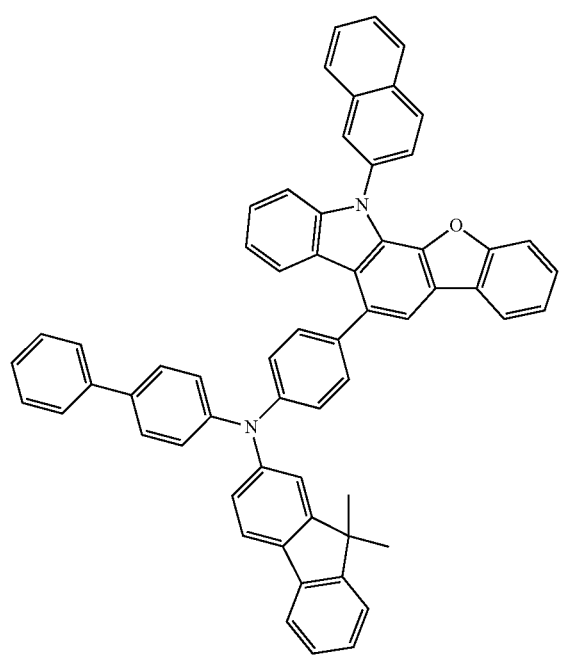

45
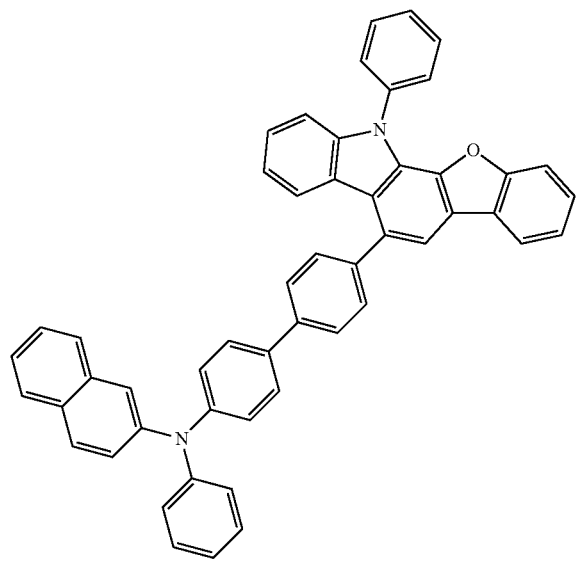
381
46
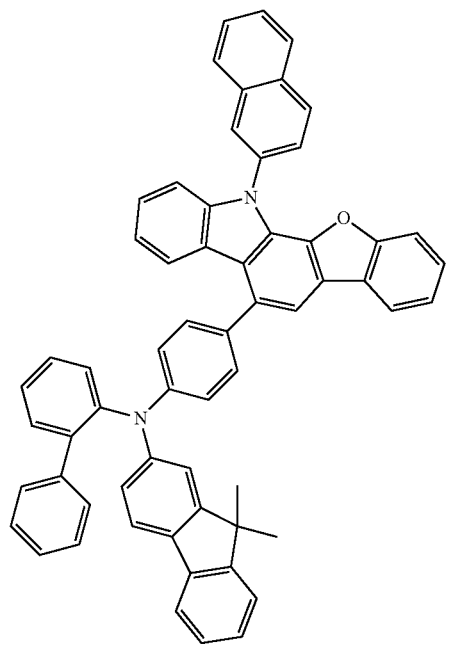
382
47
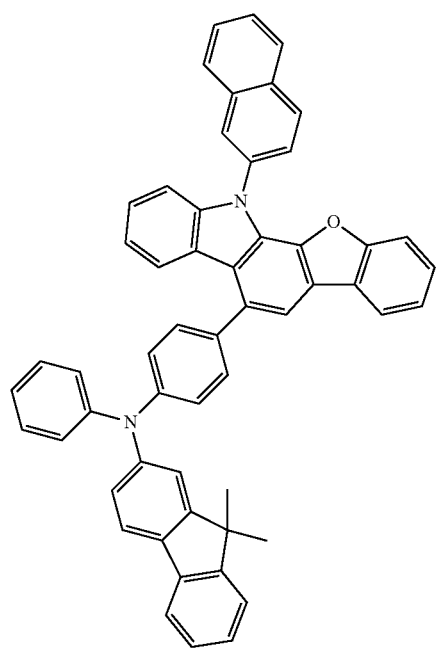
48
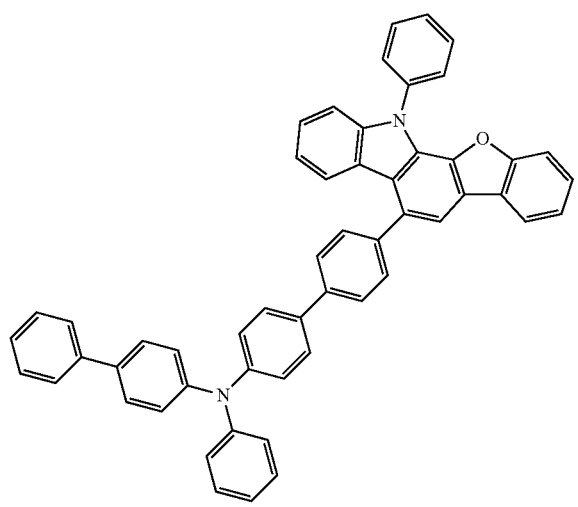

-continued
| 49 | 50 |
|---|---|
| 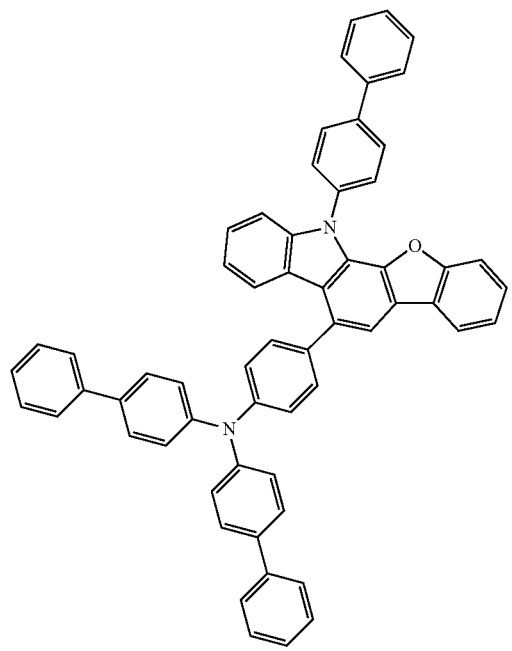 | 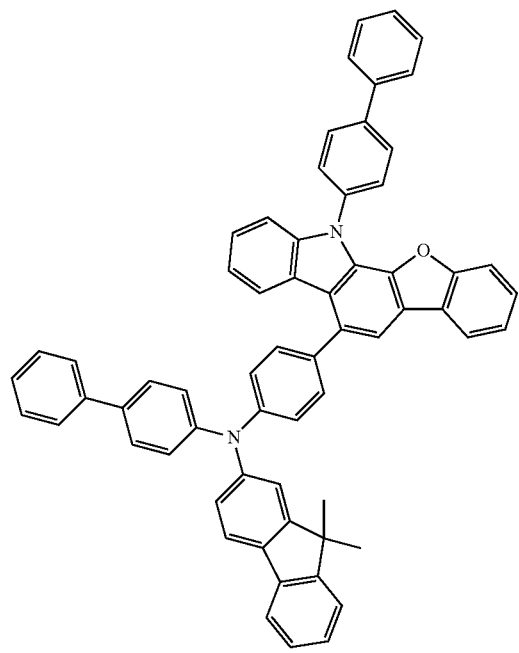 |
| 51 | 52 |
| 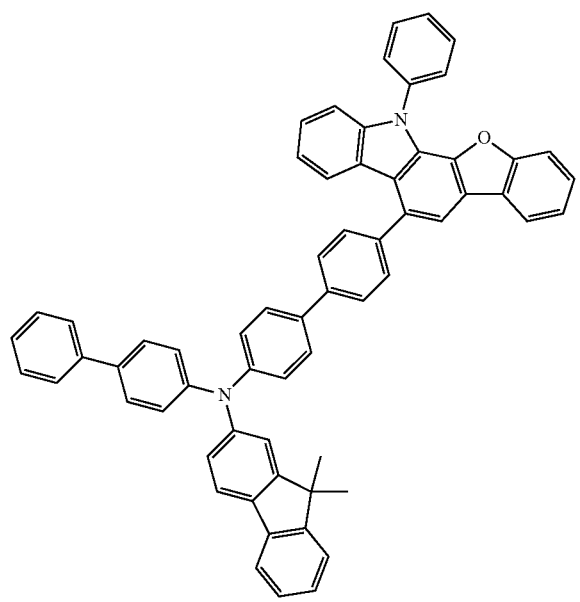 | 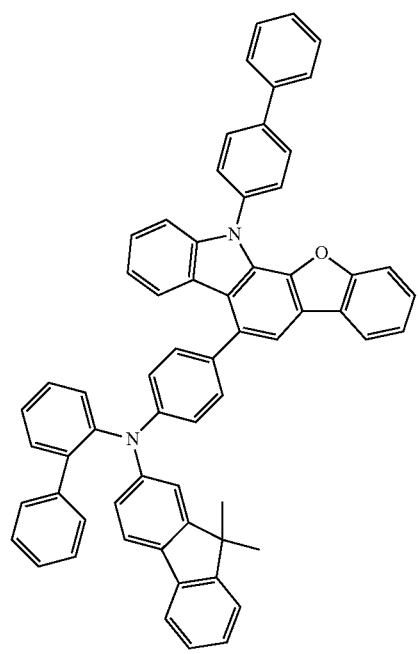 |

-continued
53
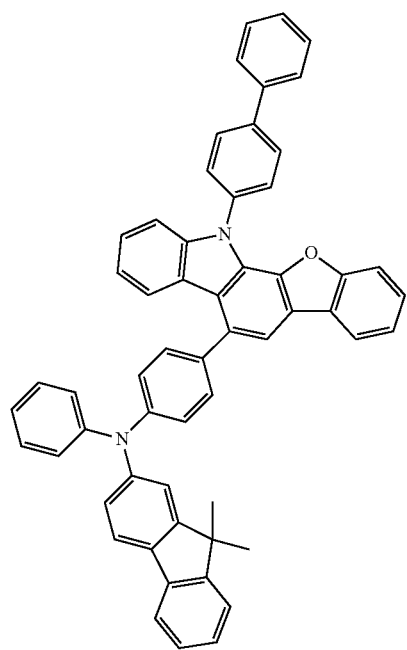
54
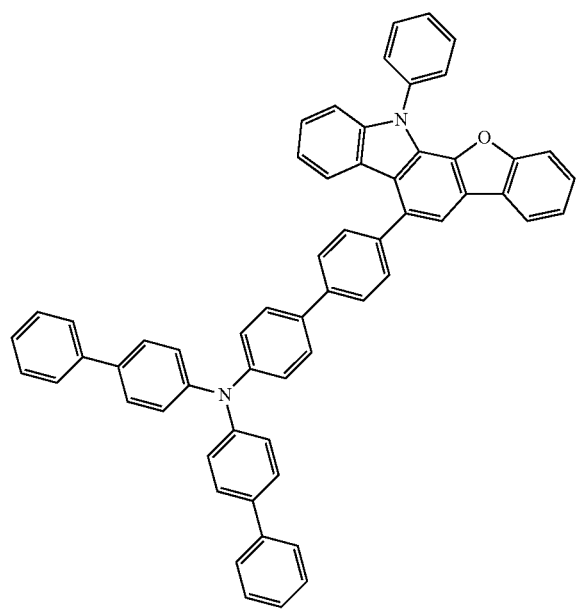
55
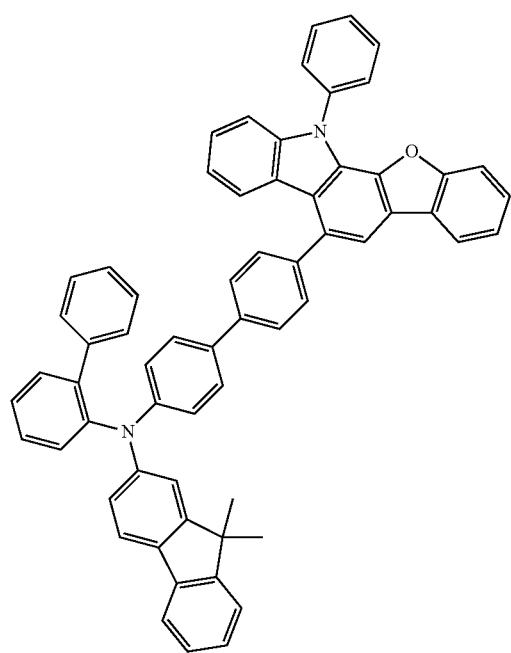
56
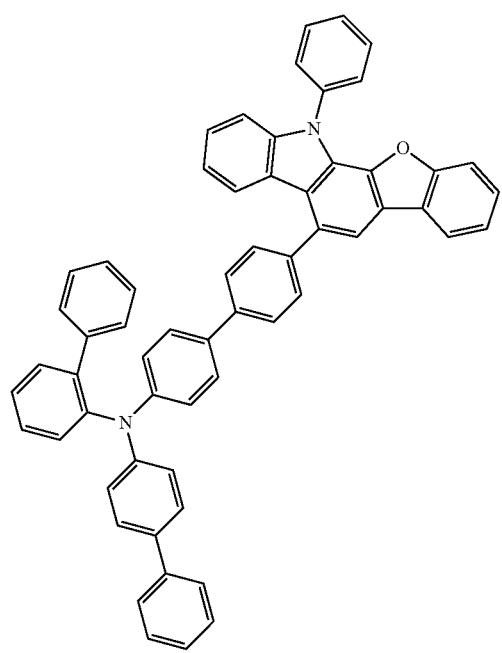

-continued
57
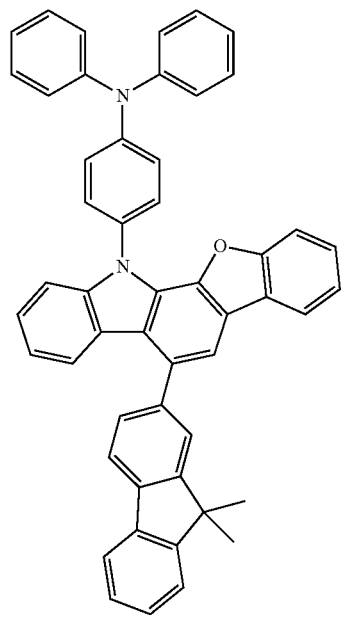
58
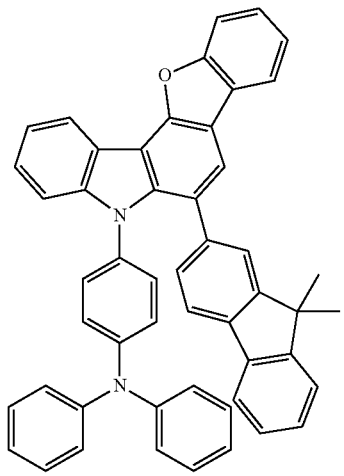
59
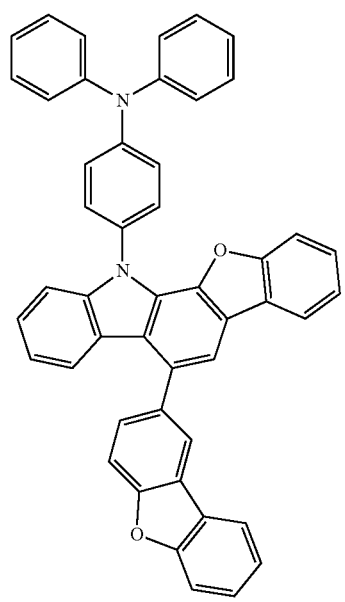
60
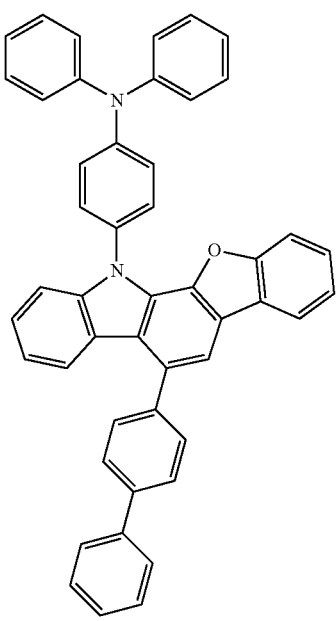

-continued
61
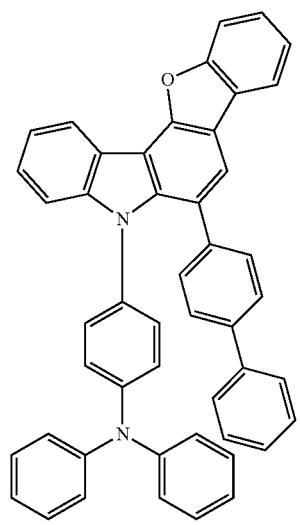
62
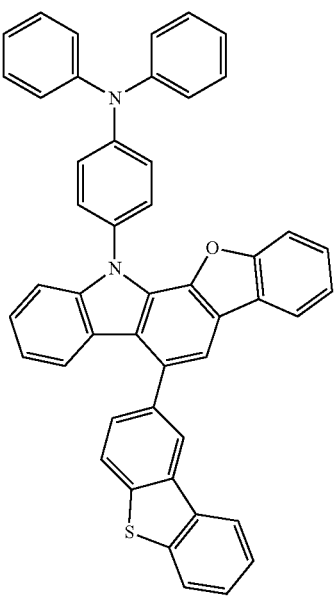
63
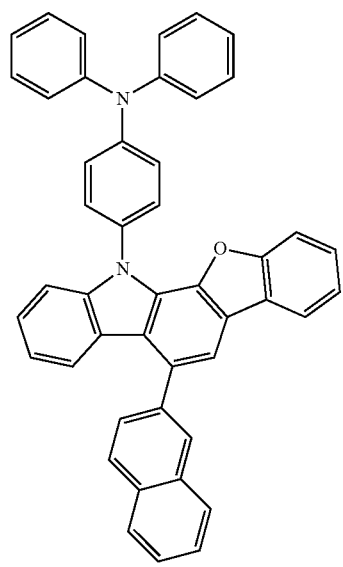
64
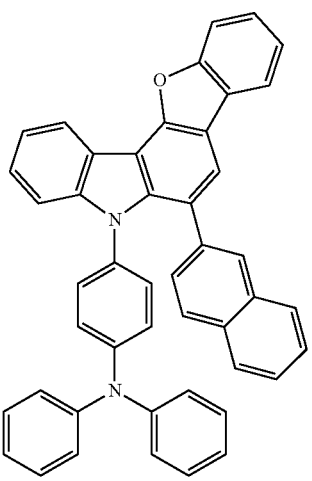

-continued
65
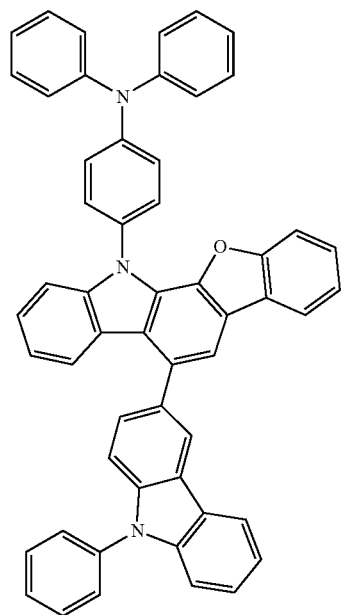
66
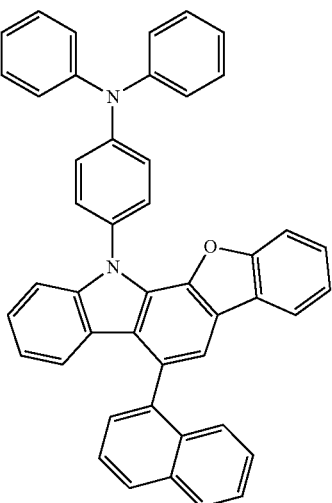
67
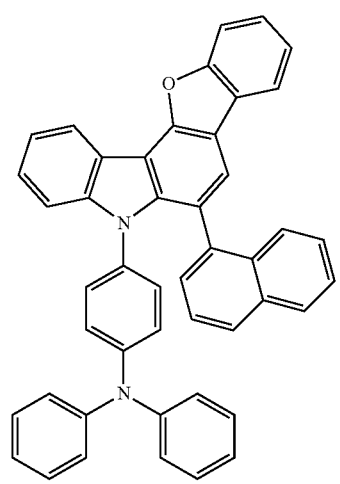
68
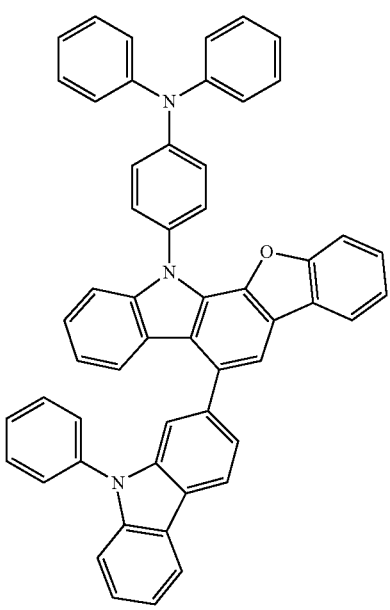

-continued
69
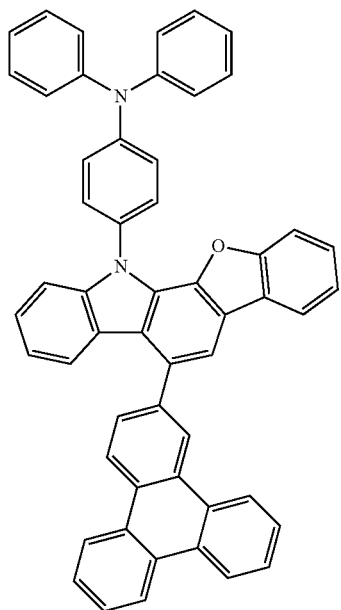
70
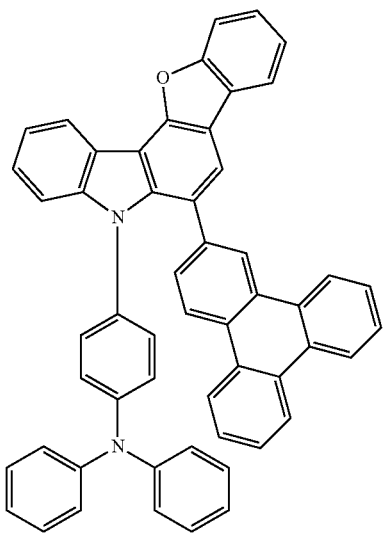
71
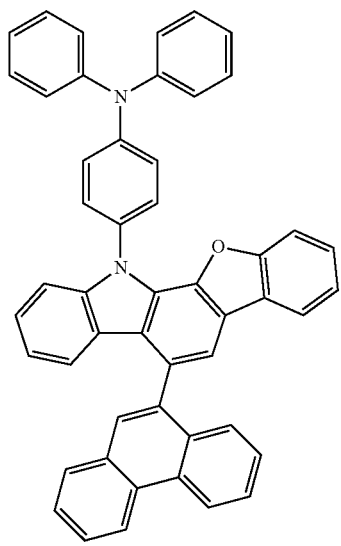
72
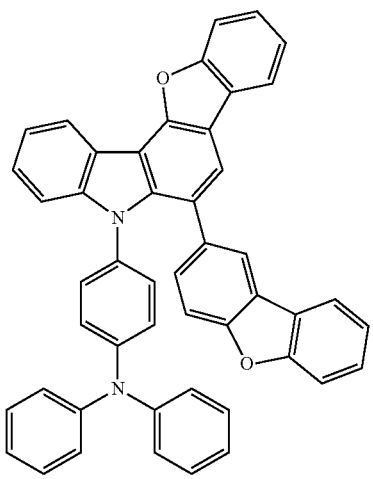
73
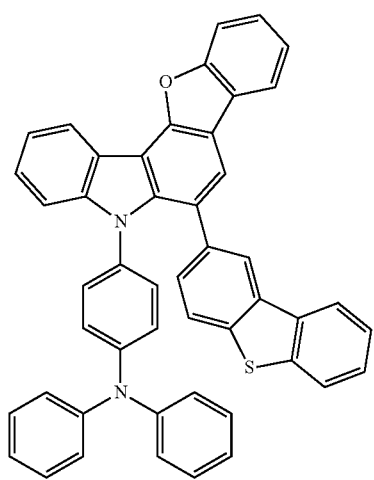
74
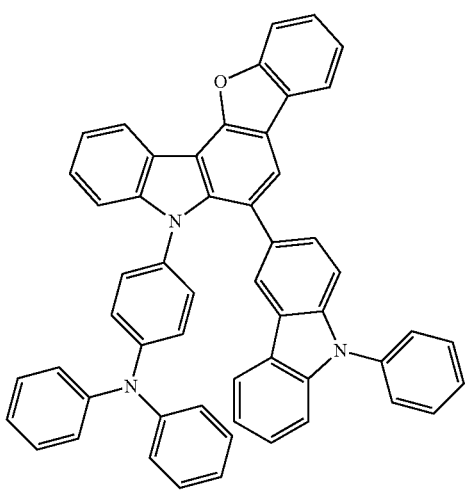

75
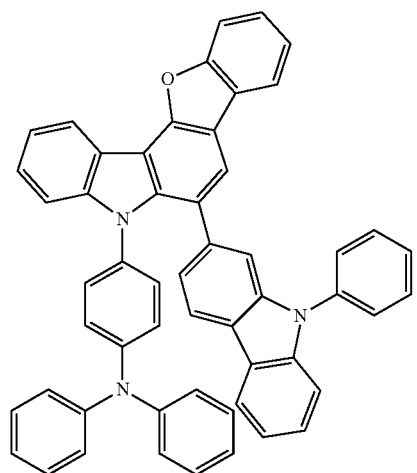
76
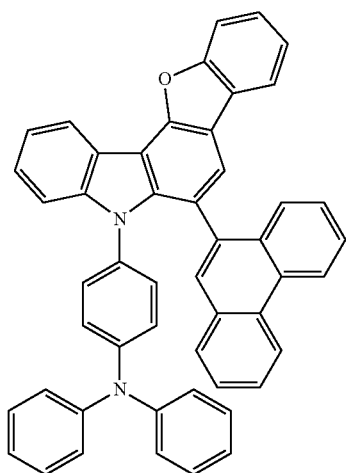
77
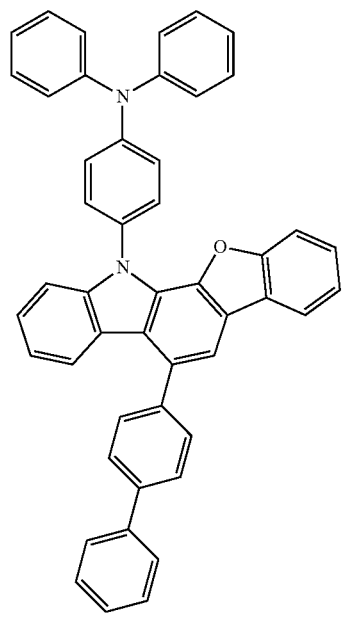
78
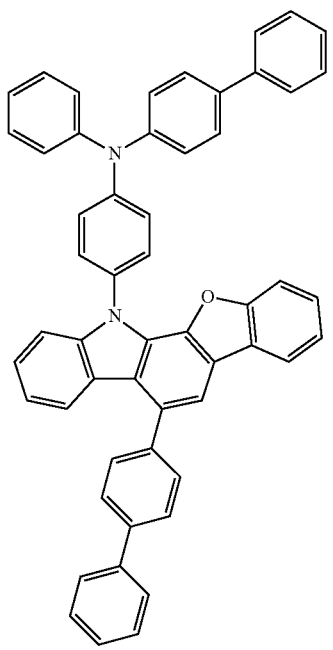

397 398
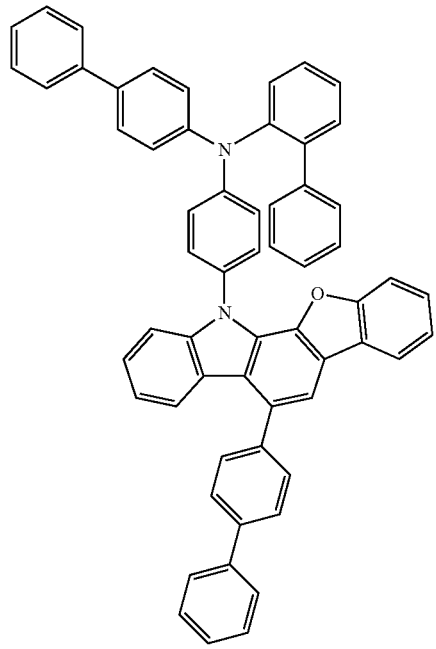
79
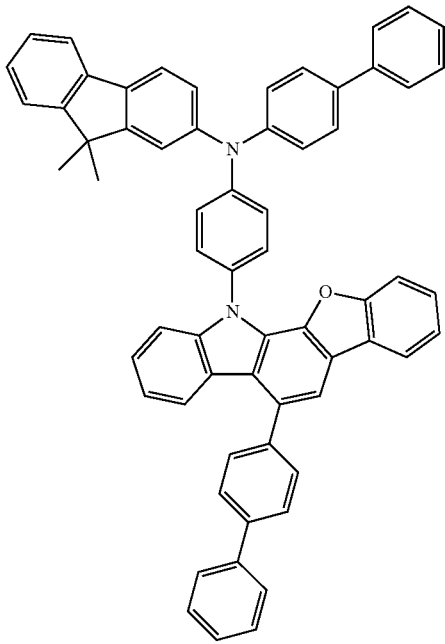
80
-continued
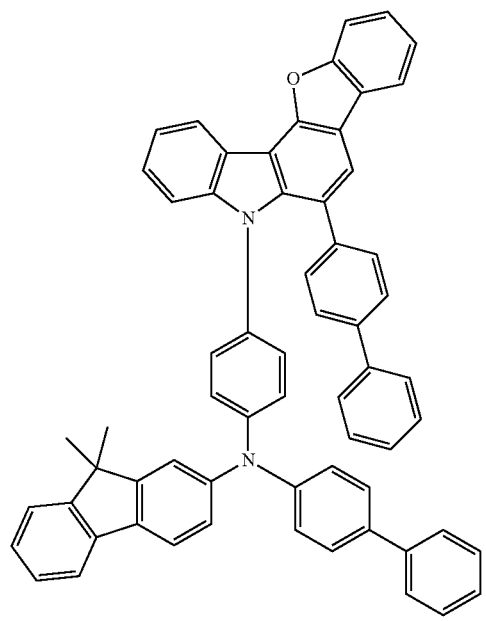
81
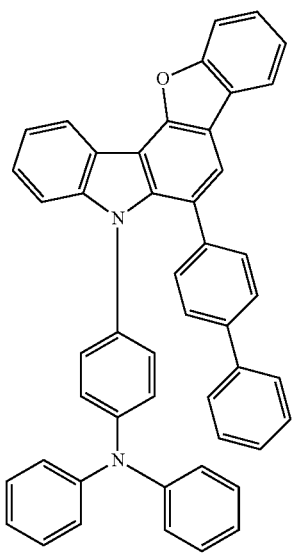
82

83
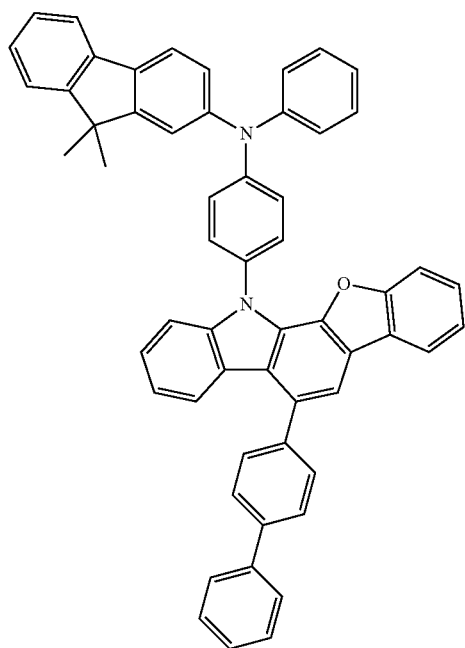
84
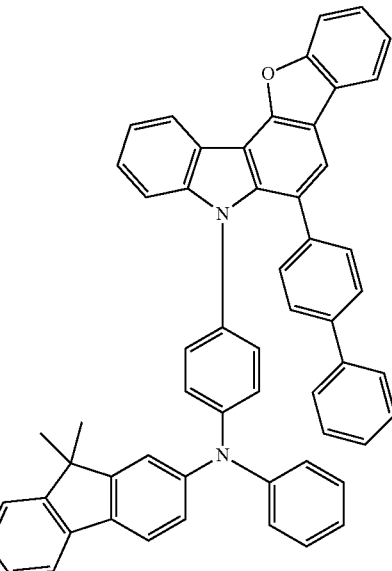
85
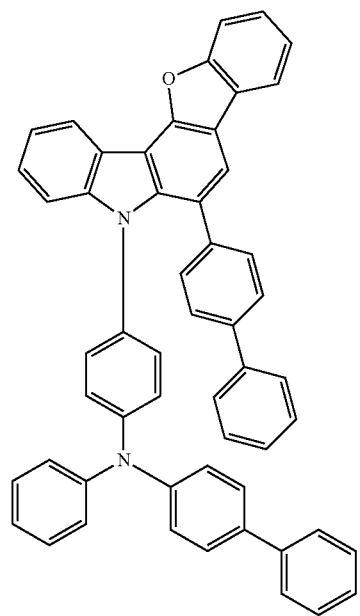
86
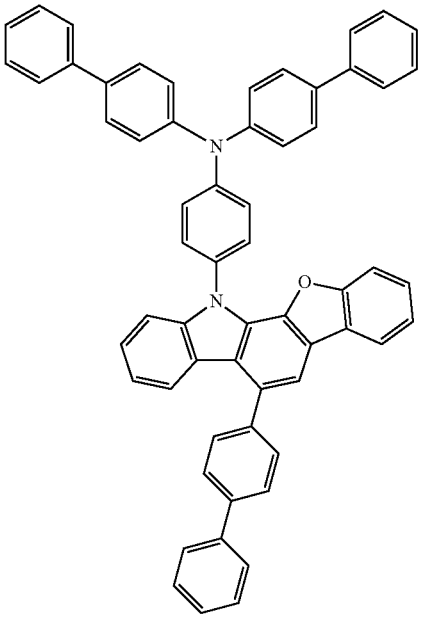

-continued
87
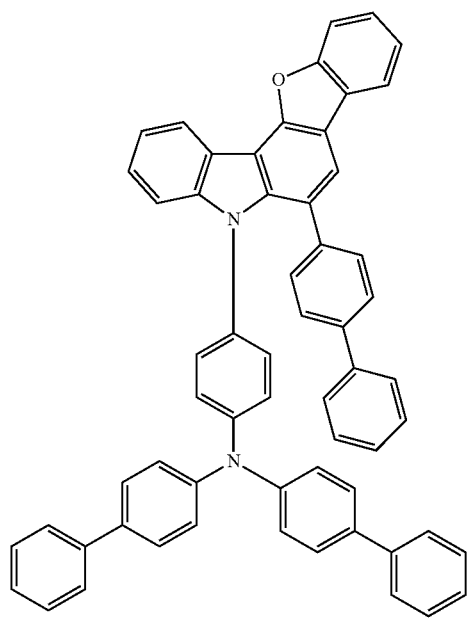
88
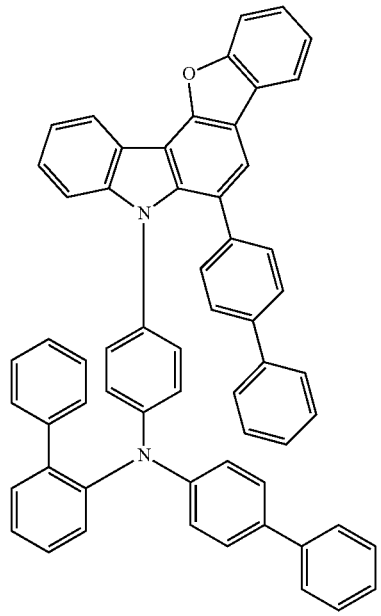
89
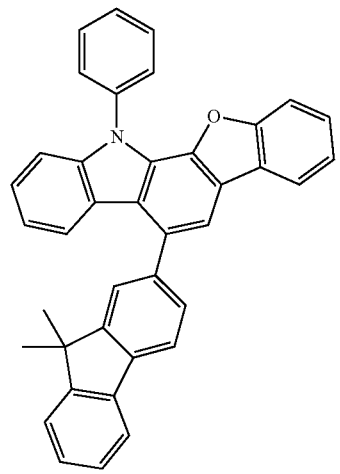
90
91
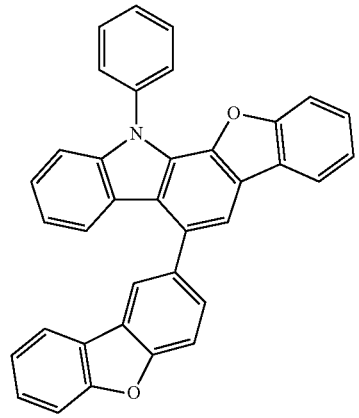
92
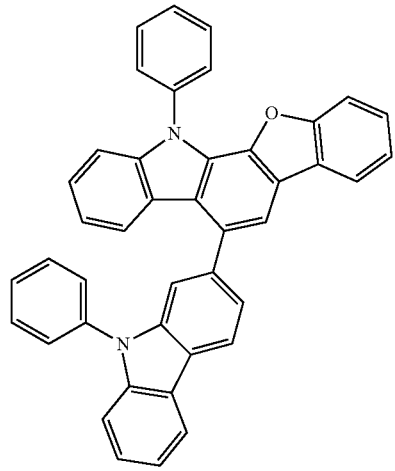

-continued
93
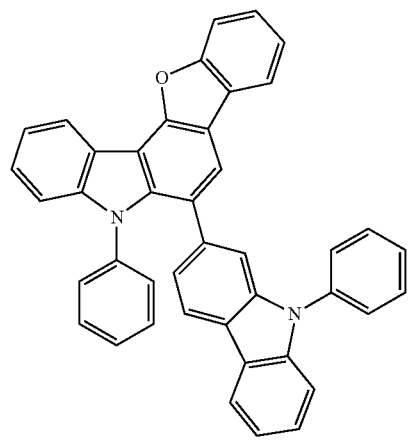
94
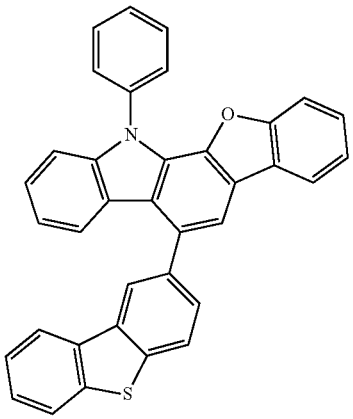
95
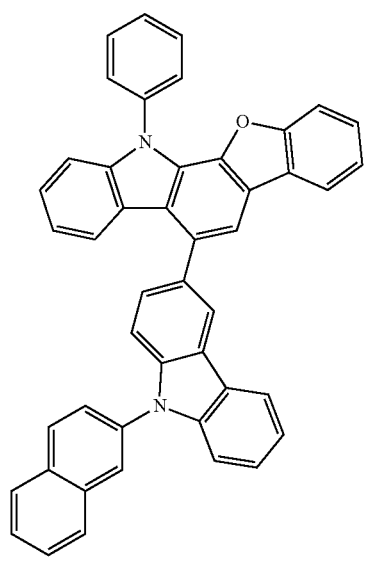
96
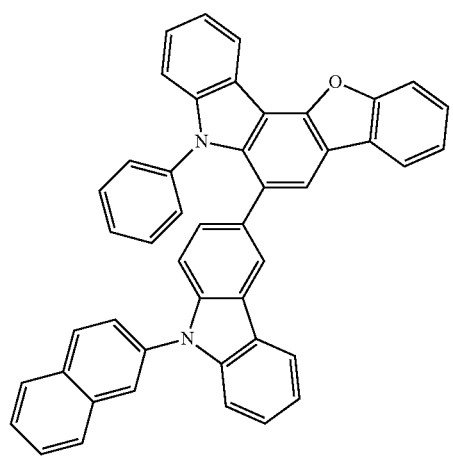
97
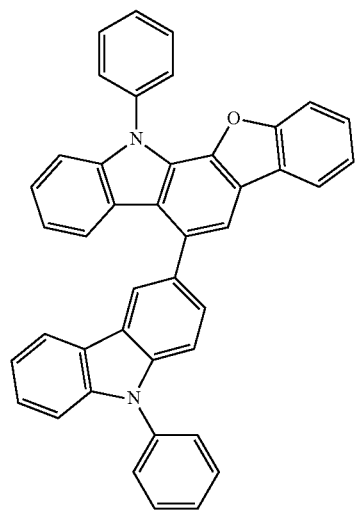
98
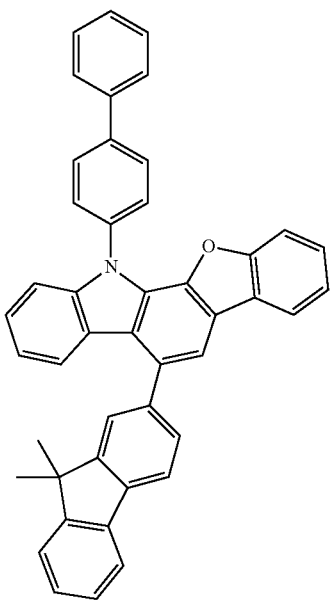

405
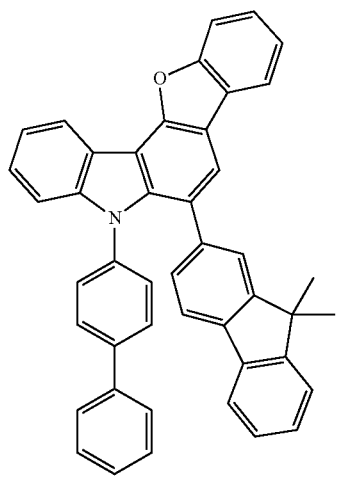
406
-continued
99
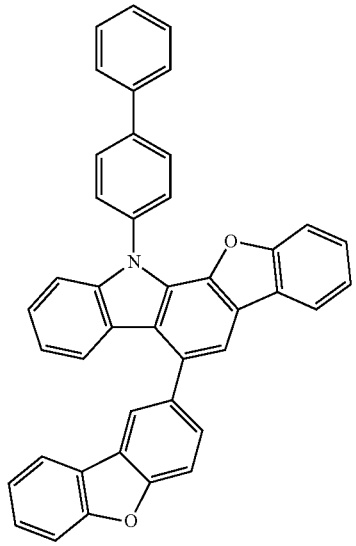
100
101
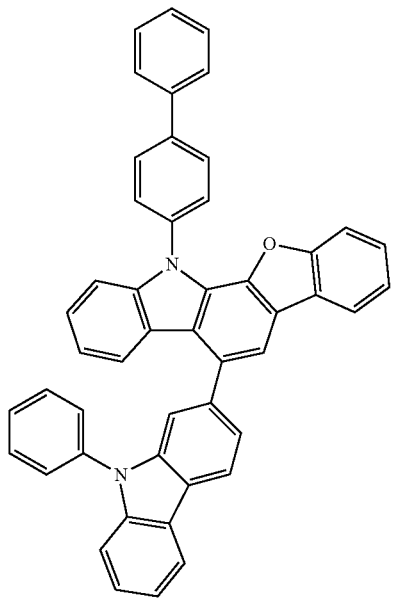
102
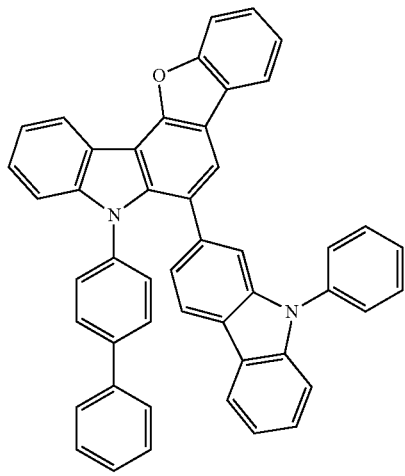

407
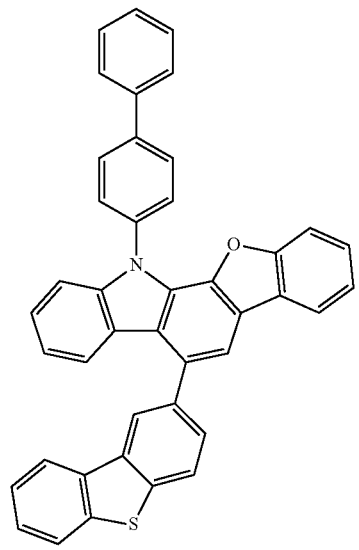
408
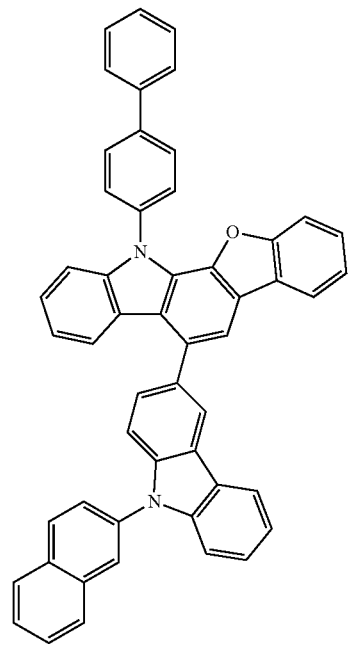
103
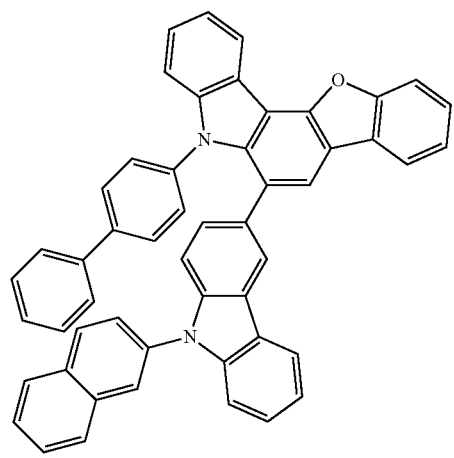
104
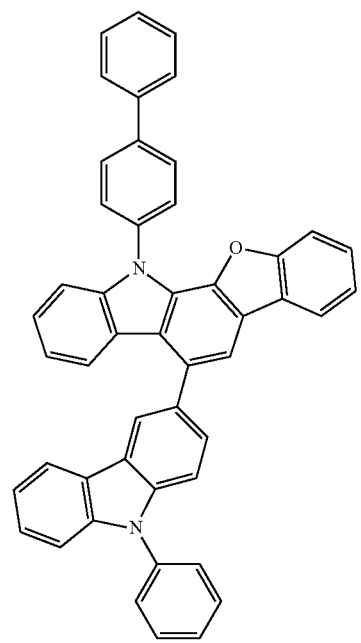
105
106

-continued
107
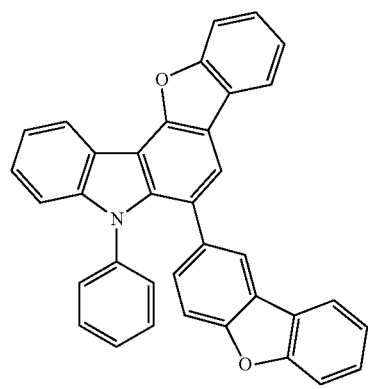
108
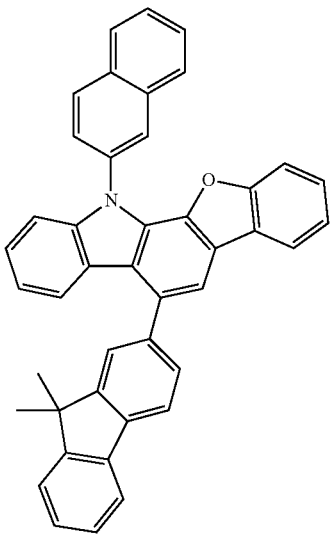
109
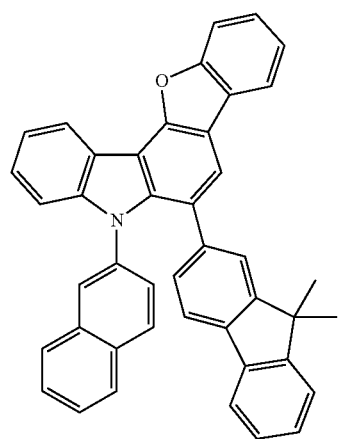
110
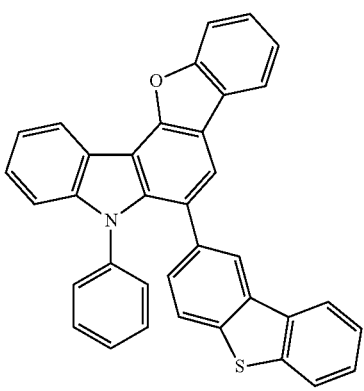
111
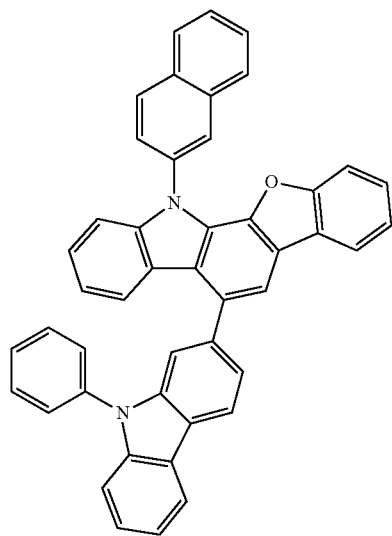
112
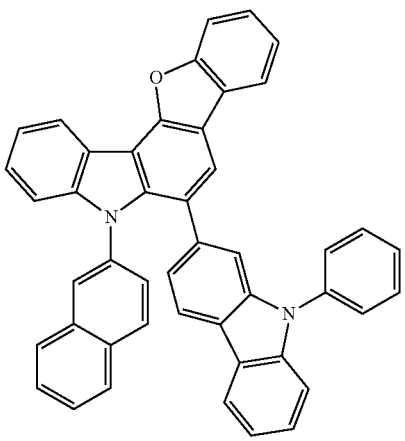

-continued
411
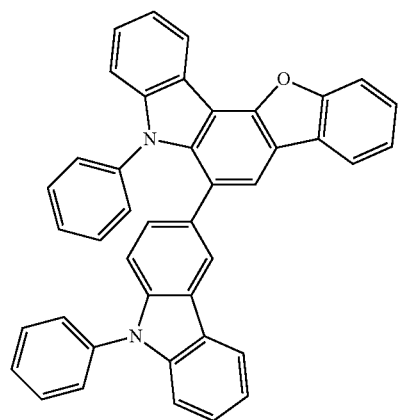
412
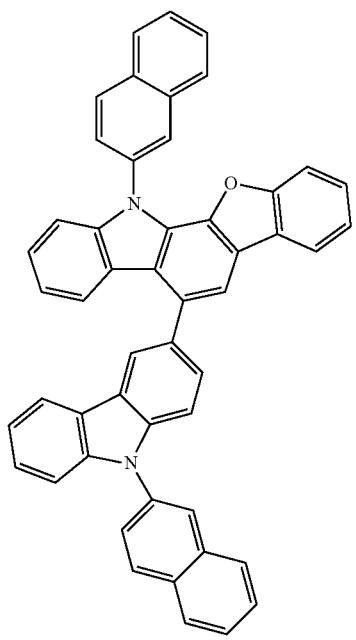
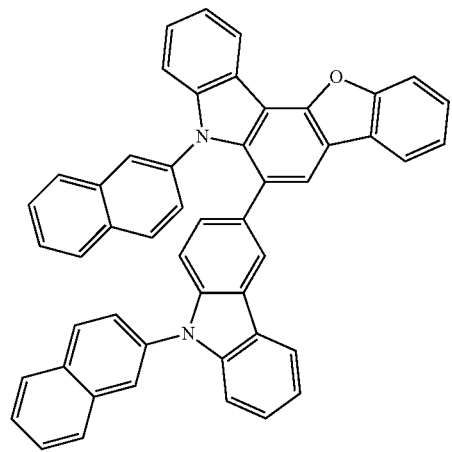
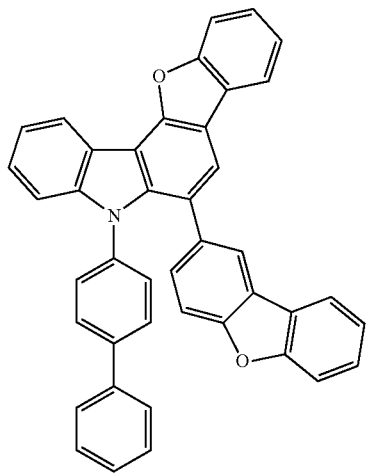

-continued
117
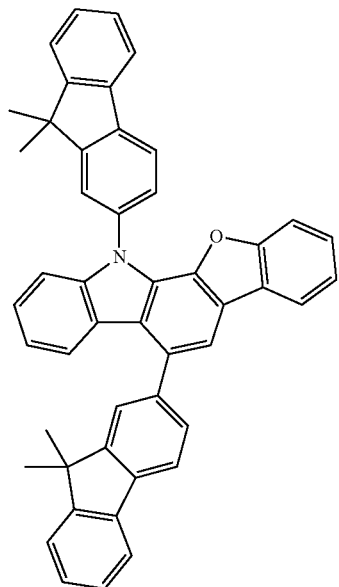
118
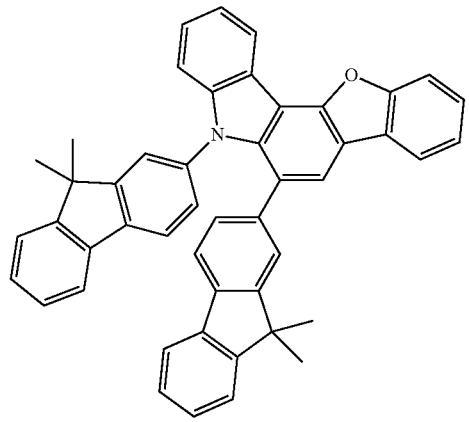
119
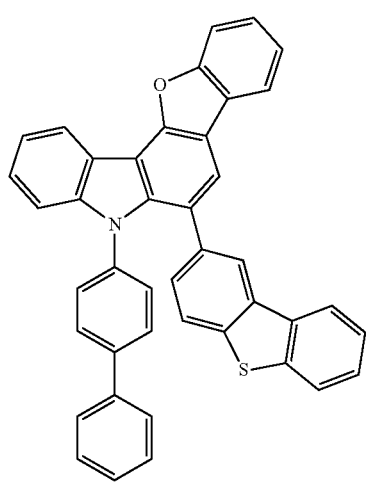
120
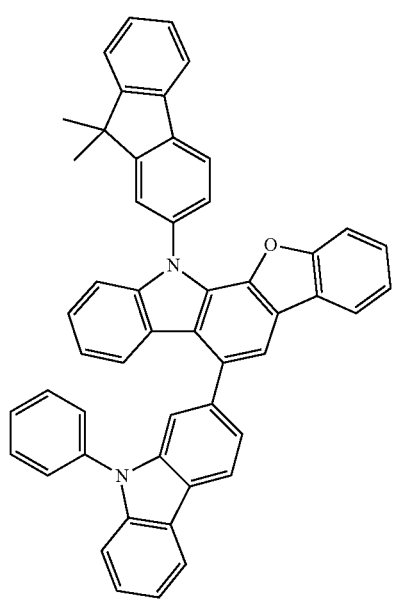
121
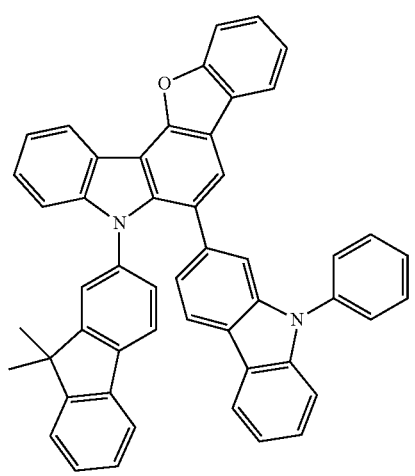
122
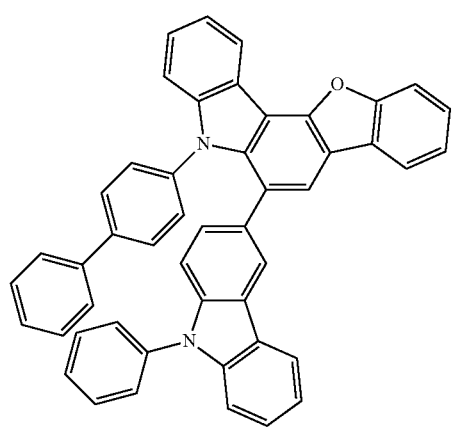

-continued
| 415 | 416 |
|---|---|
| 123 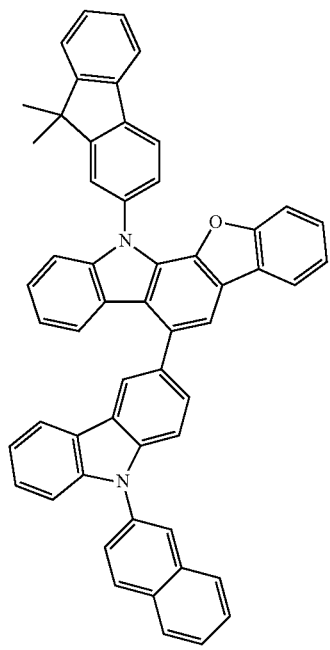 | 124 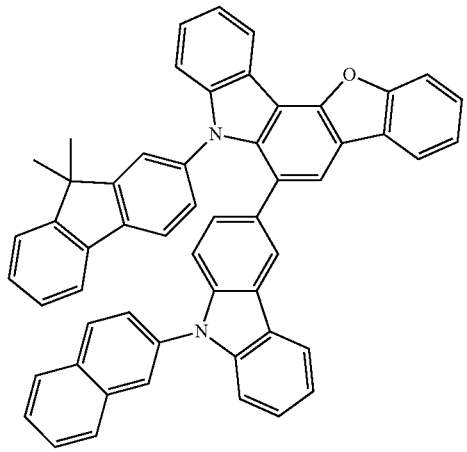 |
| 125 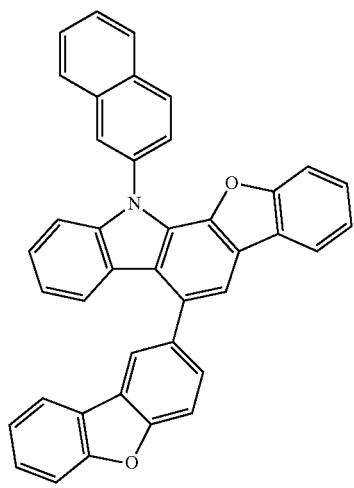 | 126 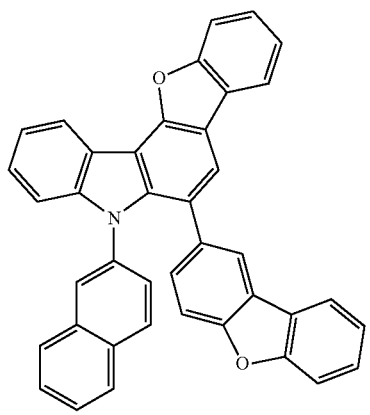 |
| 127 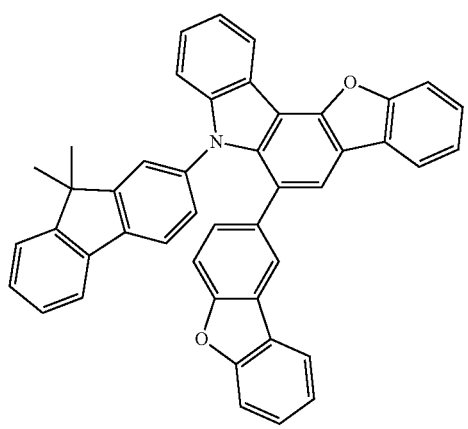 | 128 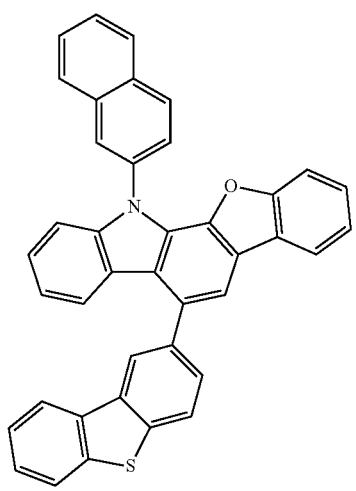 |

-continued
| 129 | 130 |
|---|---|
| 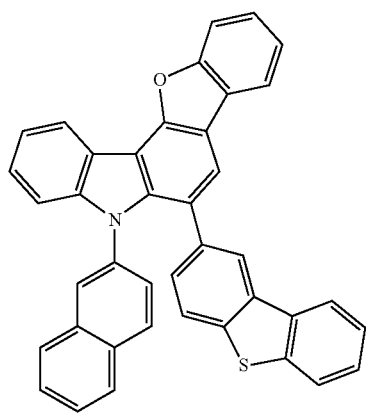 | 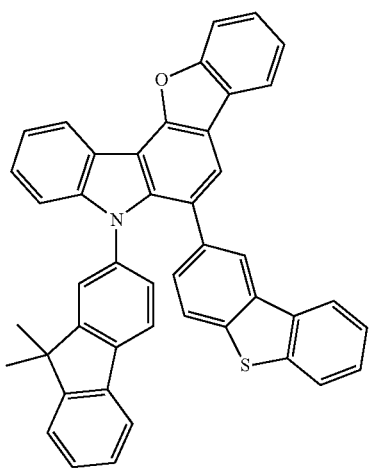 |
| 131 | 132 |
|---|---|
| 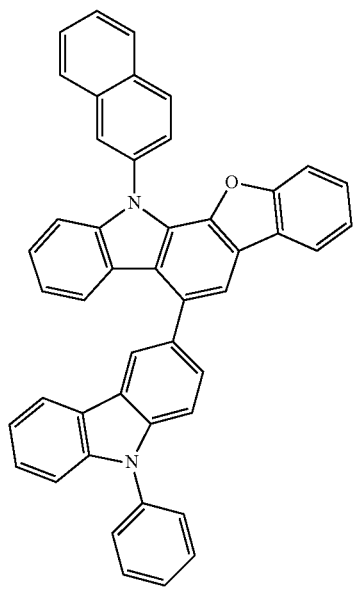 | |
| 133 | 134 |
|---|---|
| 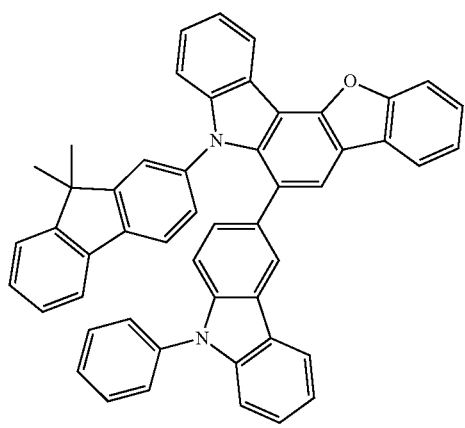 | 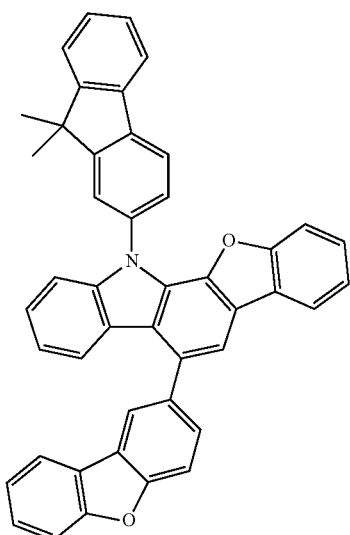 |

-continued
135
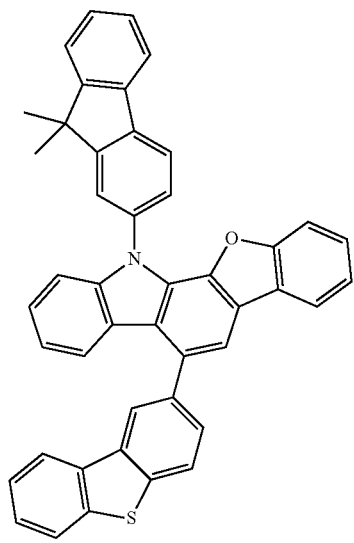
136
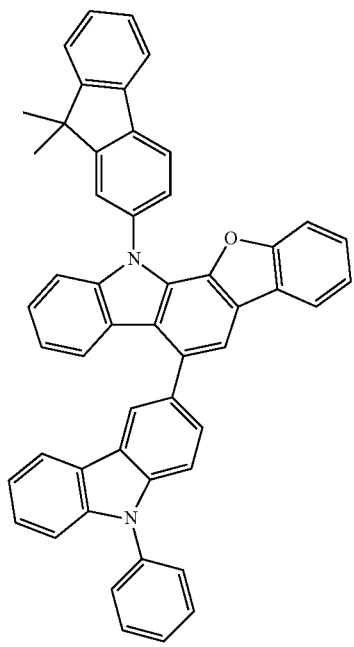
137
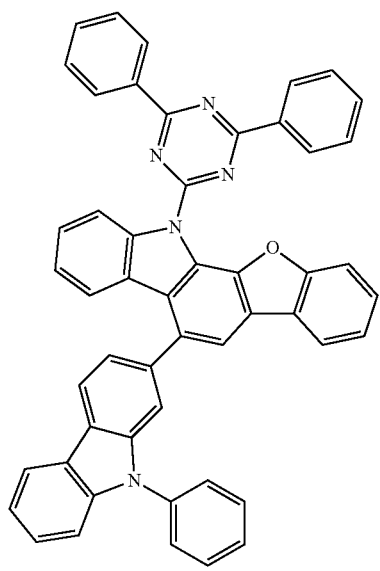
138
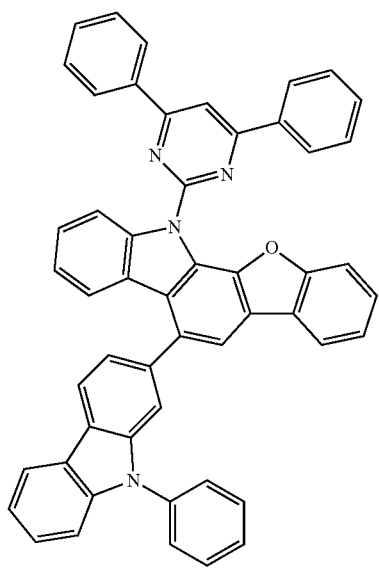

-continued
139
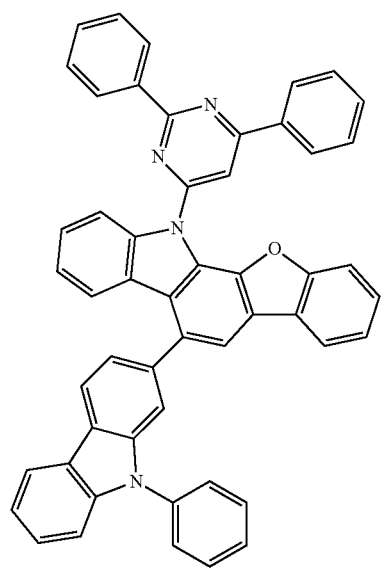
140
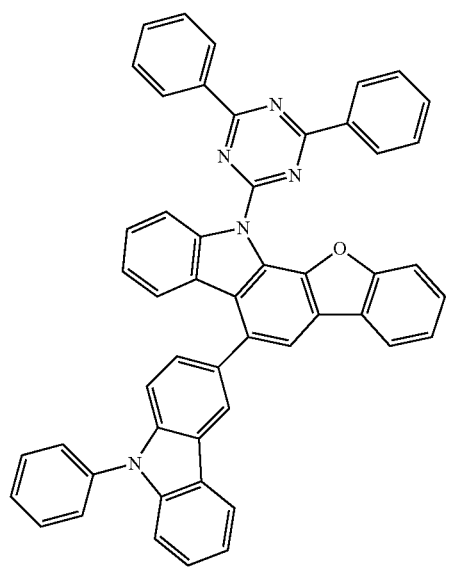
141
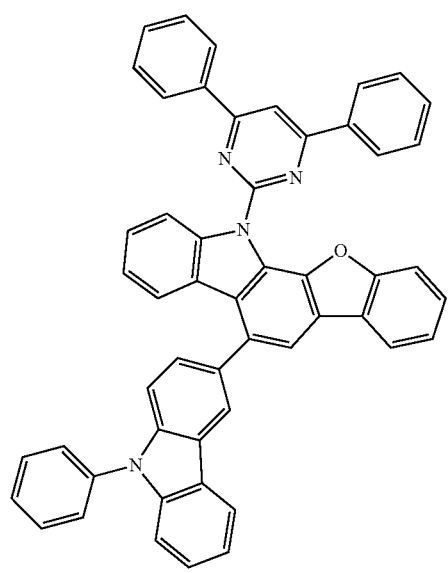
142
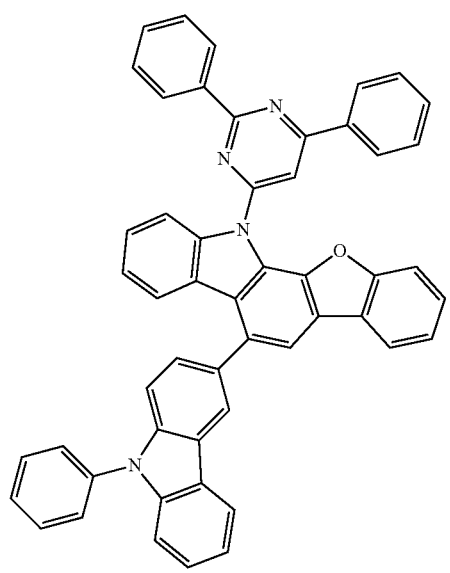

143
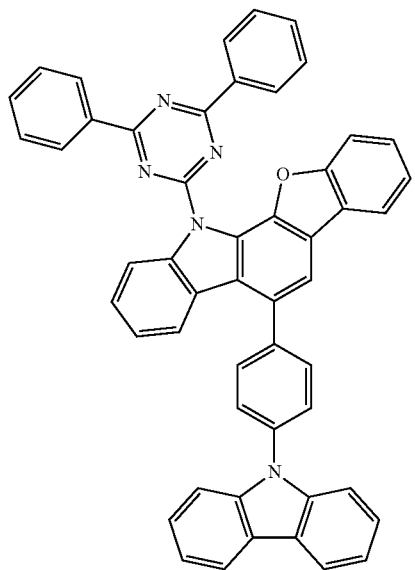
144
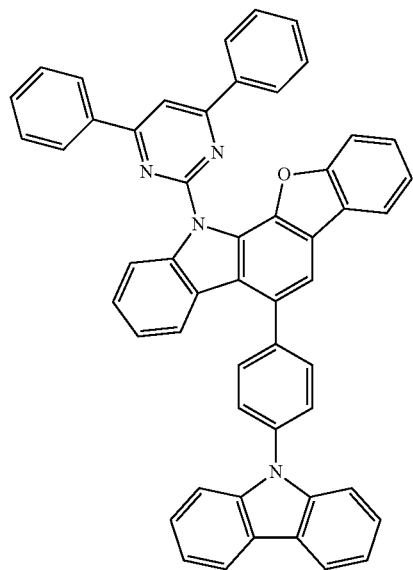
145
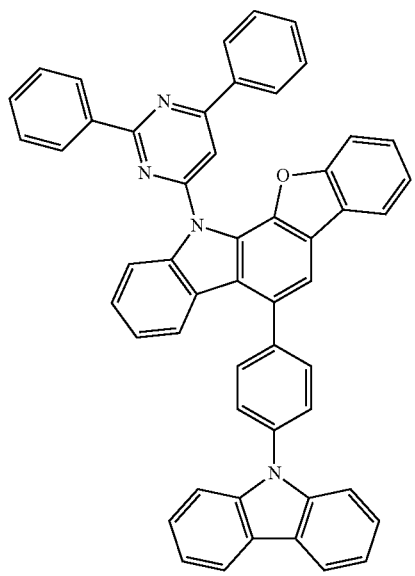
146
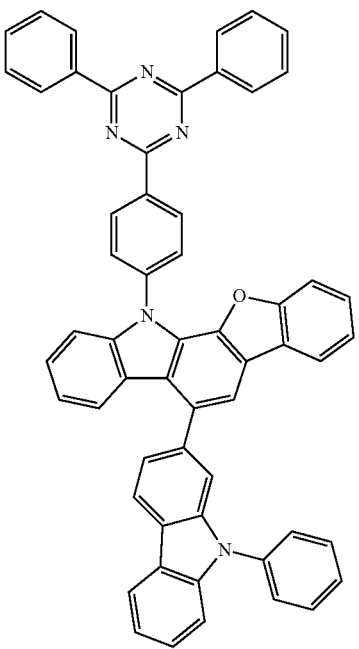

-continued
147
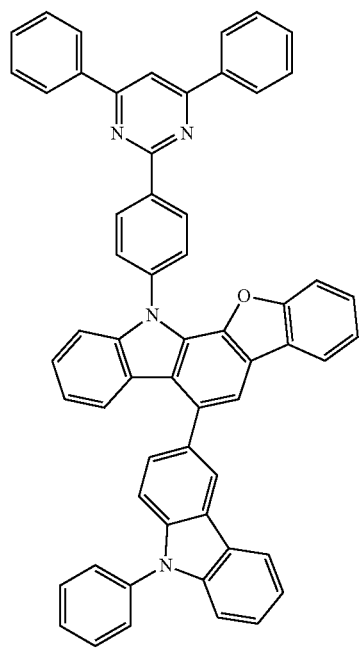
148
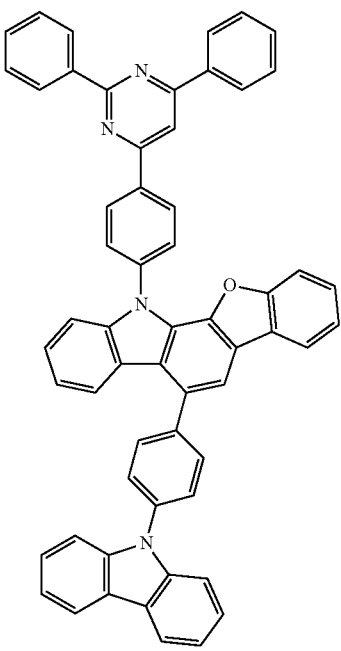
149
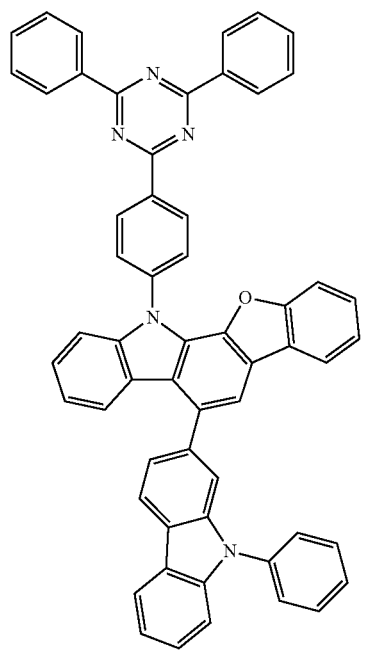
150
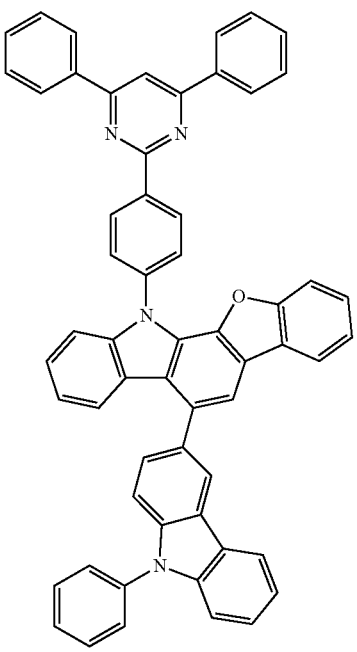

427                                   428
                    -continued
          151                             152
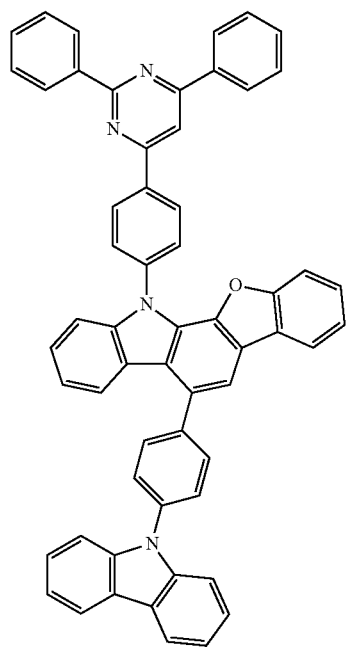          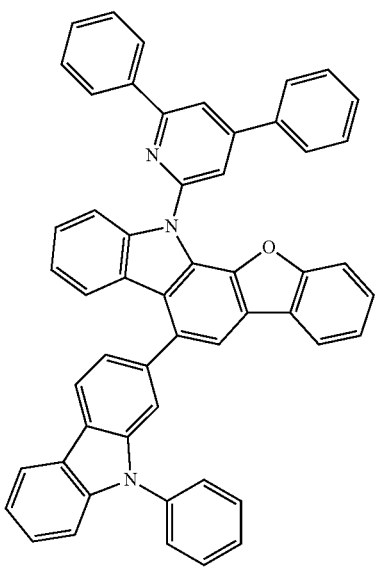
          153                             154
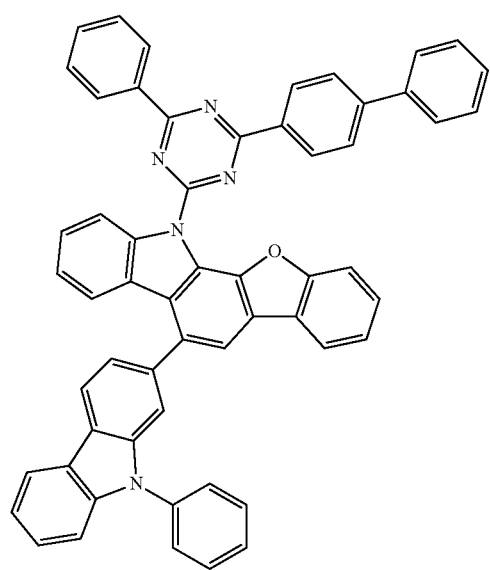          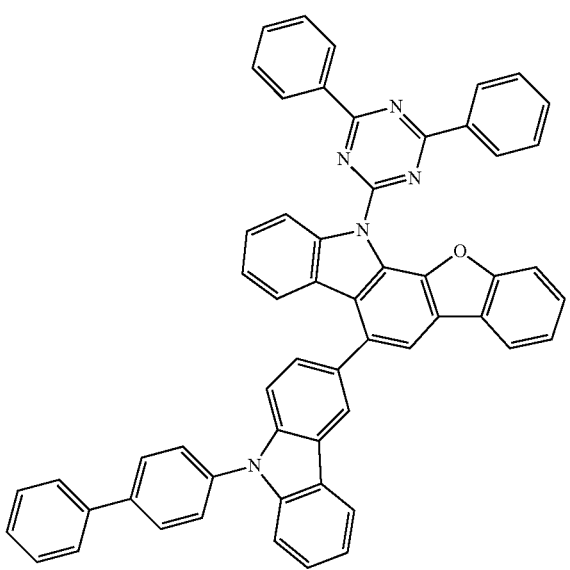

155
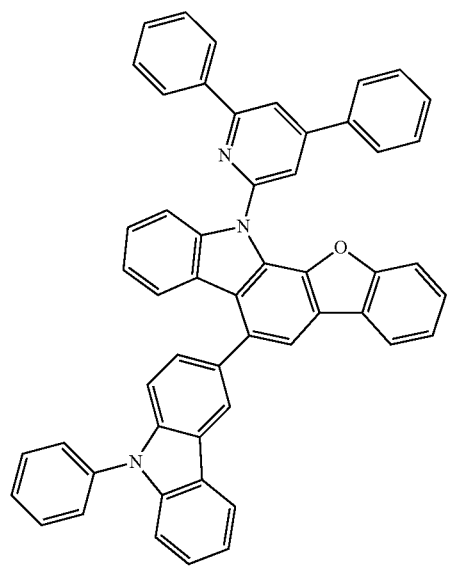
156
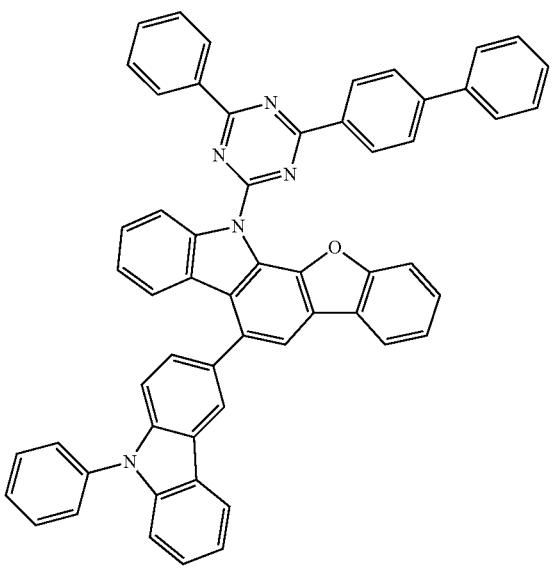
157
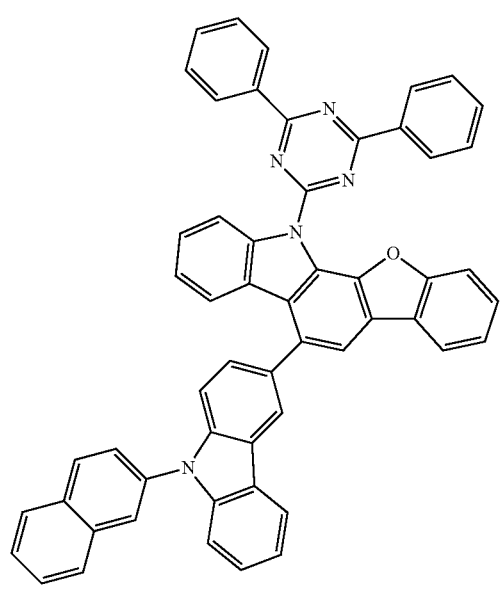
158
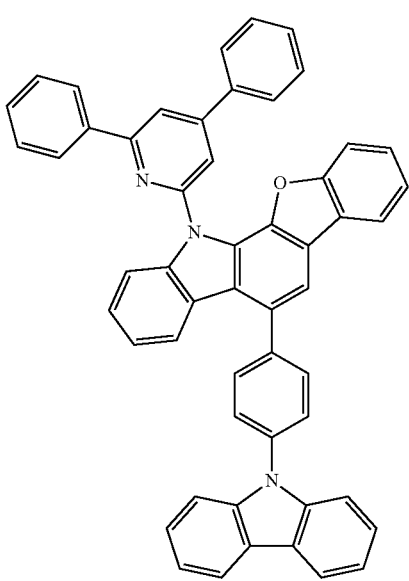

431
432
-continued
159
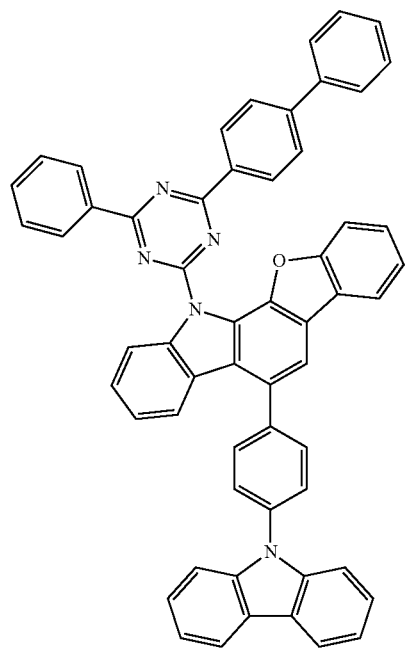
160
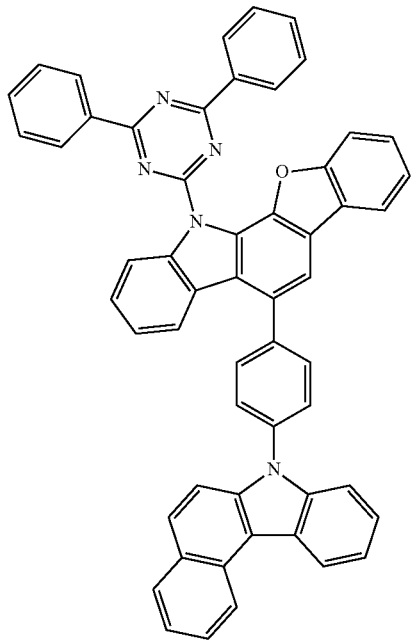
161
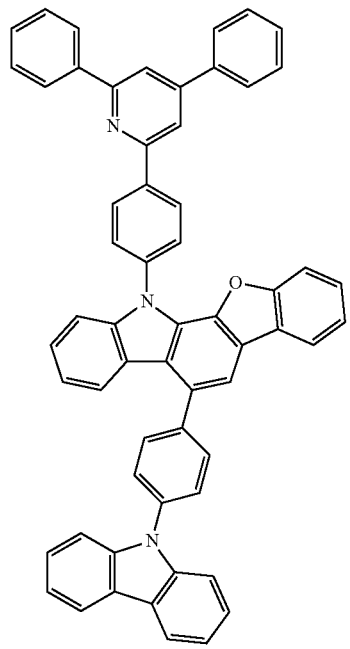
162
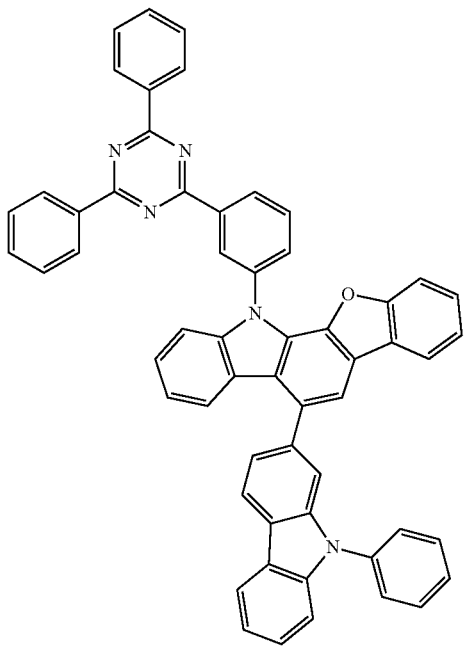

163
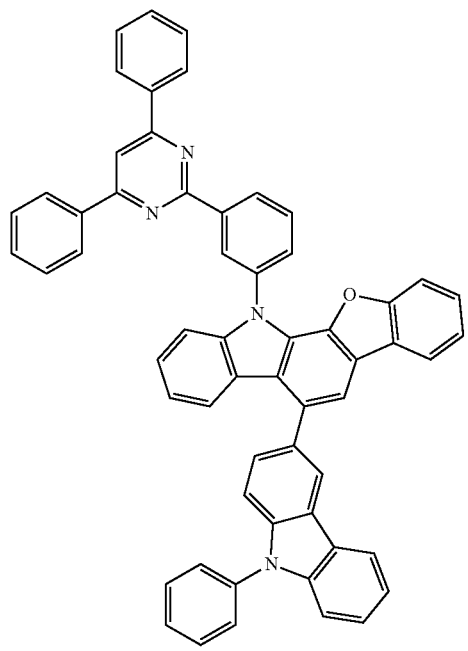
433
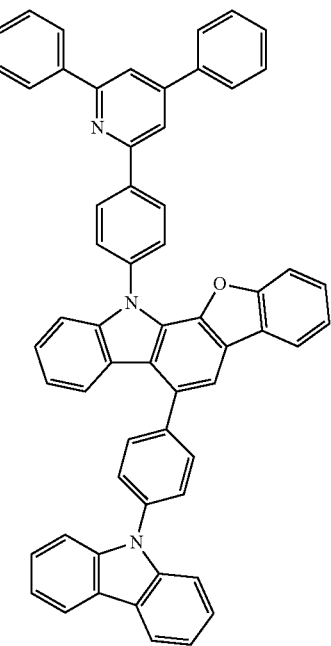
434
164
165
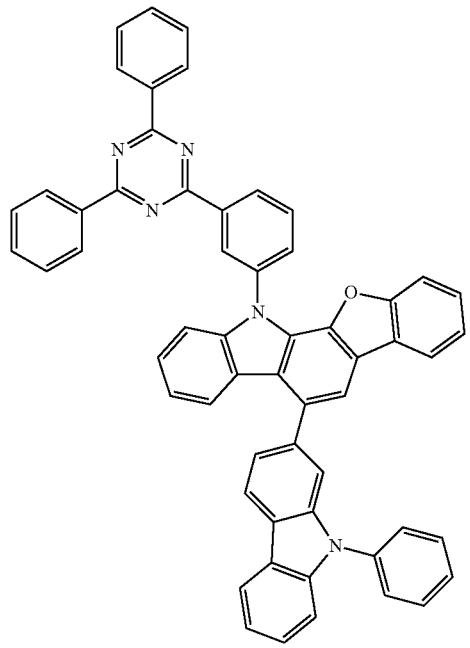
166
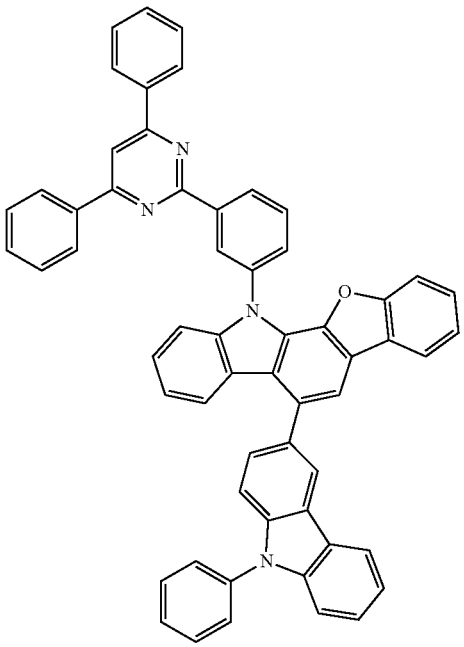

-continued
167
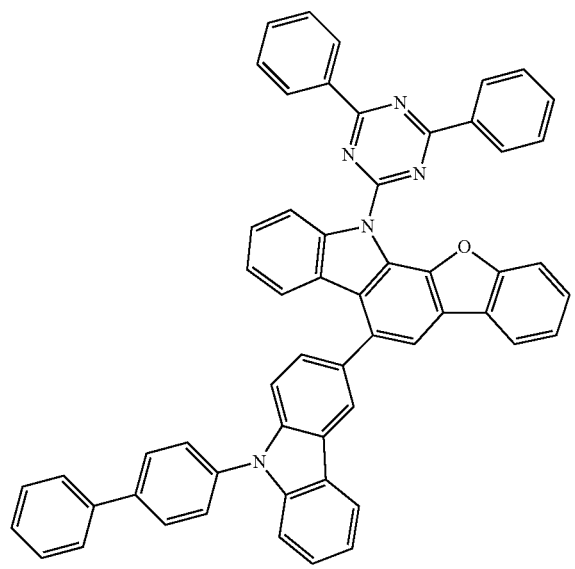
168
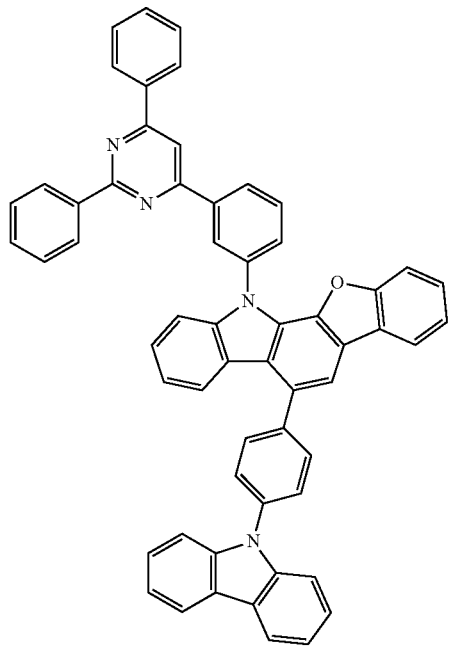
169
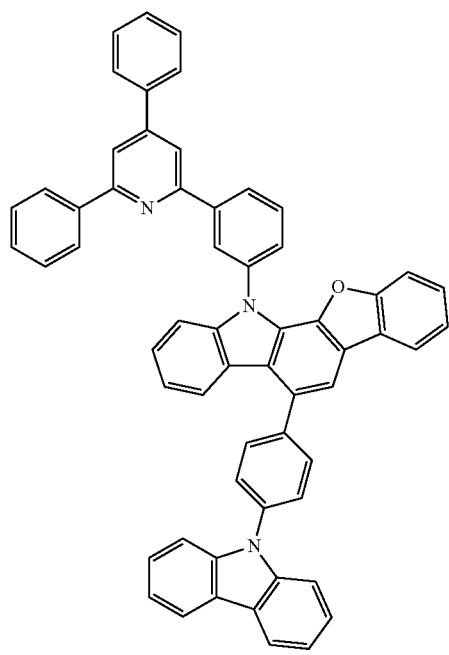
170
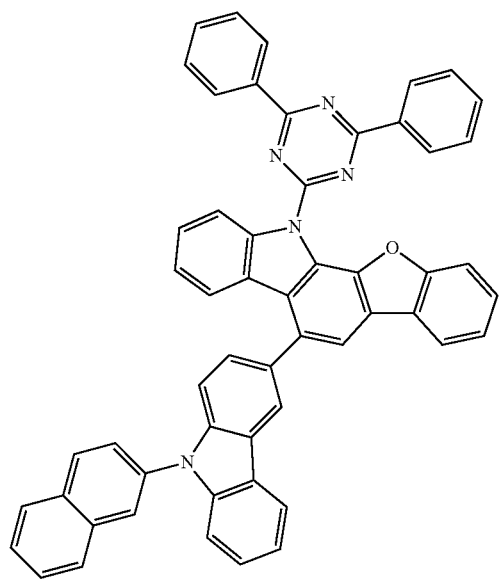

437                    438
171    172
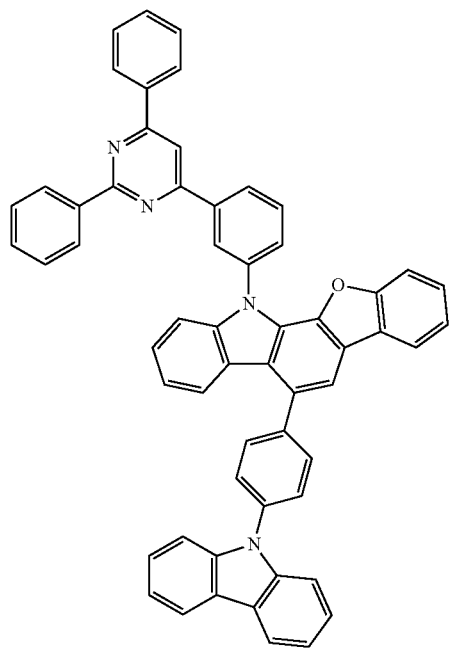 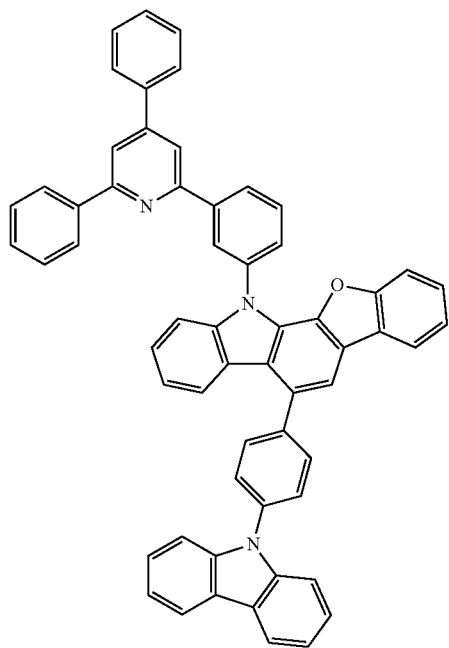
173    174
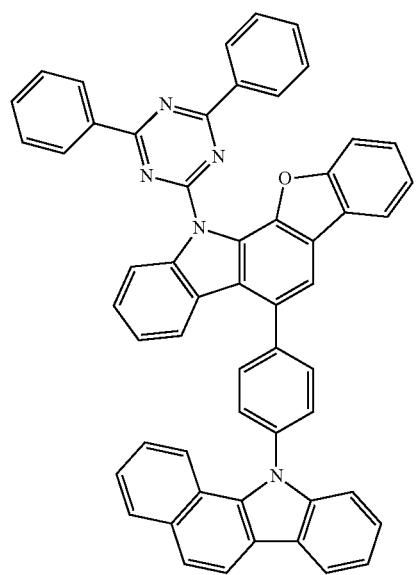 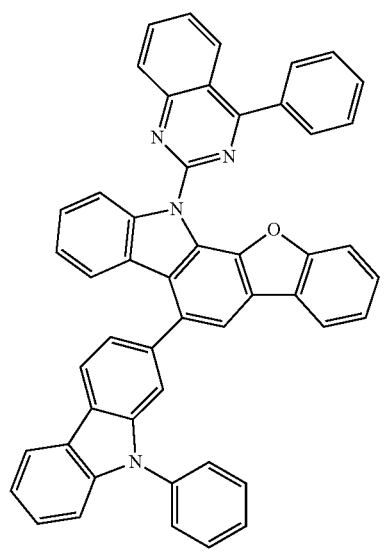

175
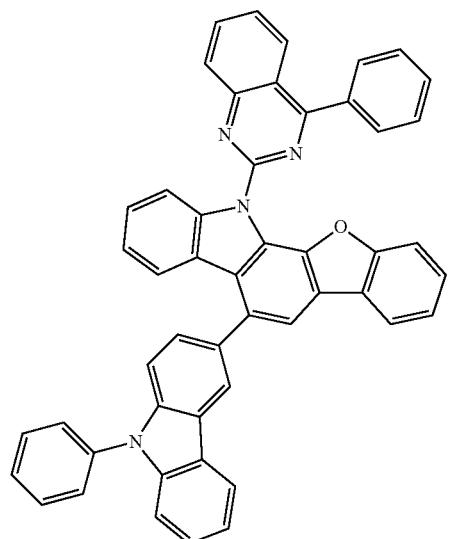
176
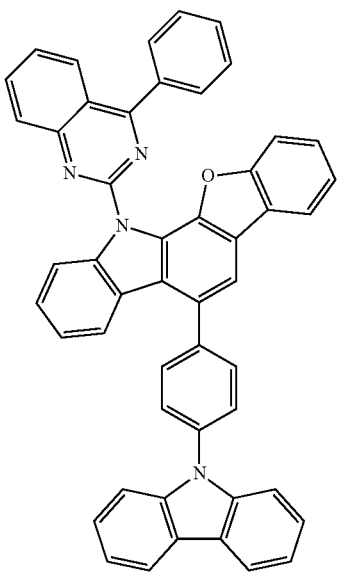
177
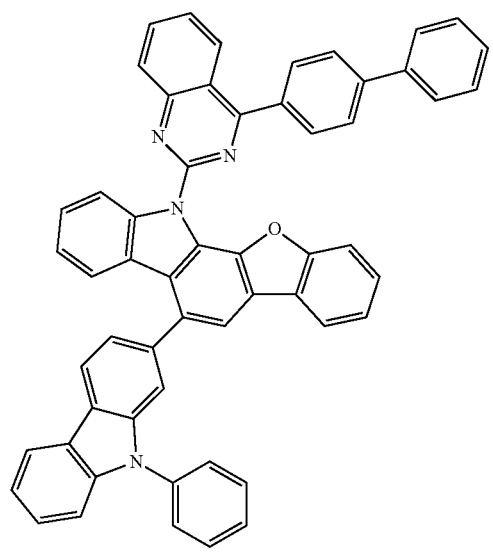
178
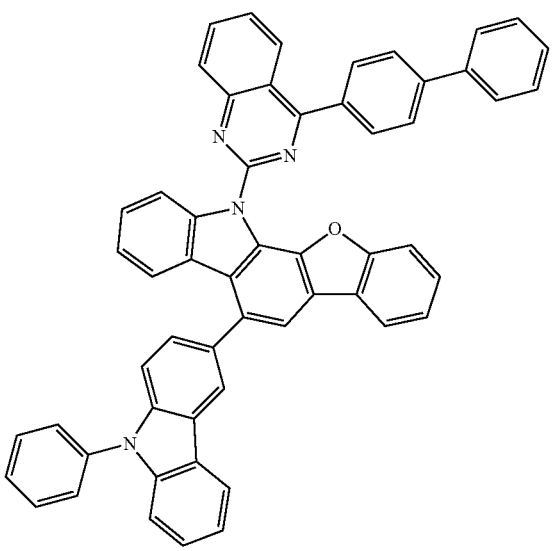

-continued
179
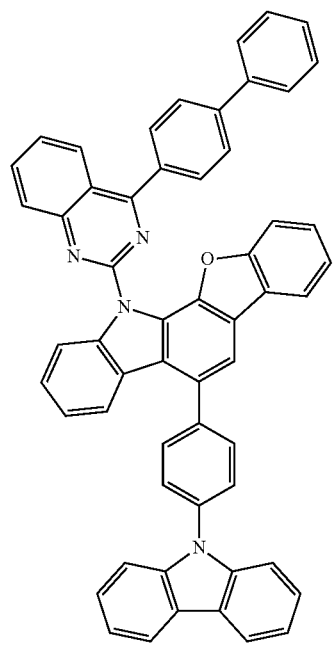
180
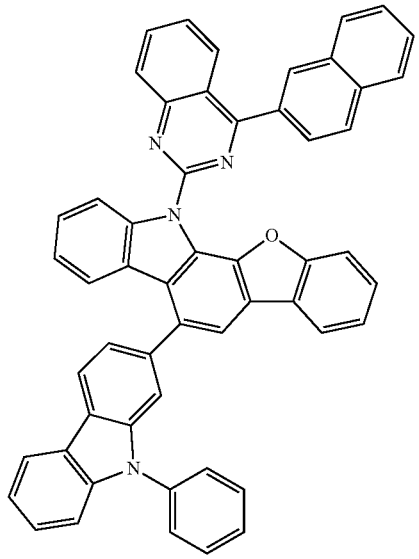
181
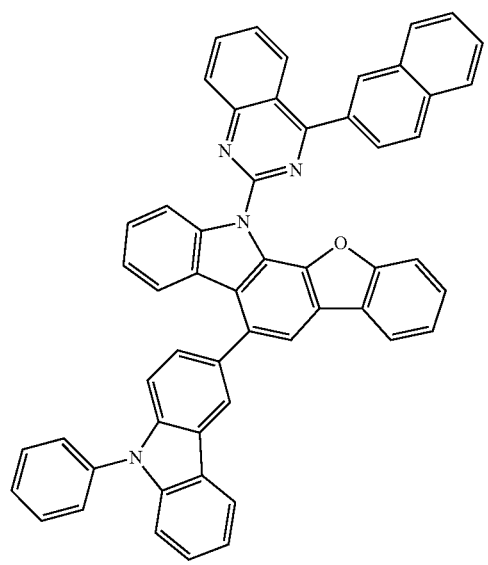
182
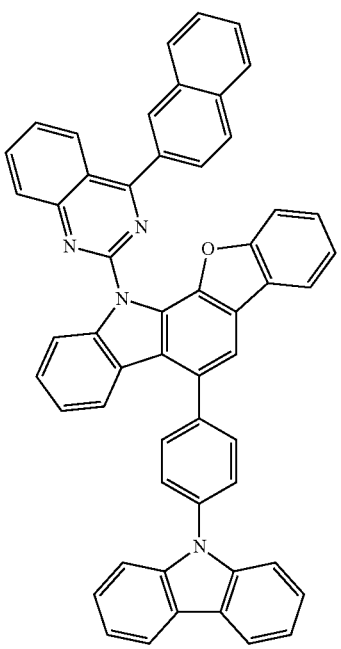

-continued
183 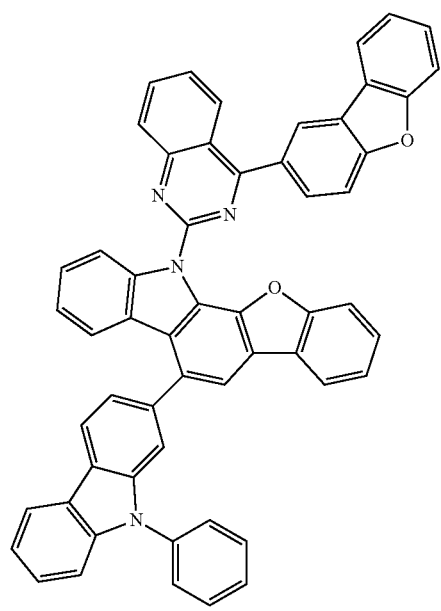
184 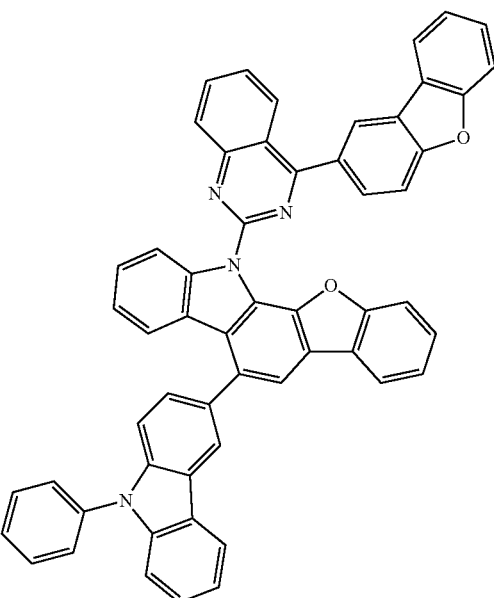
185 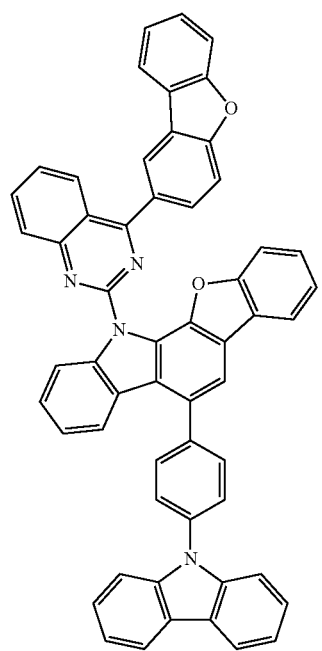
186 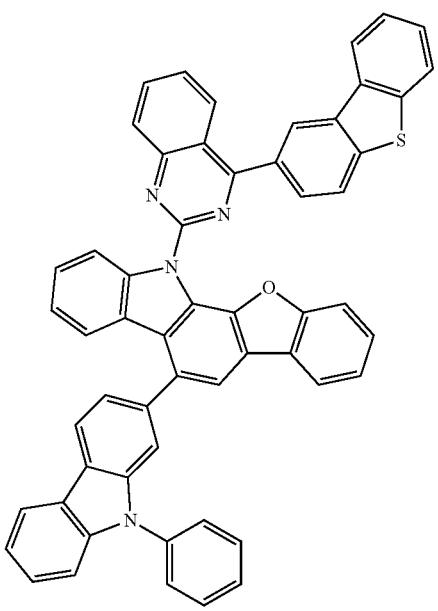

-continued
187
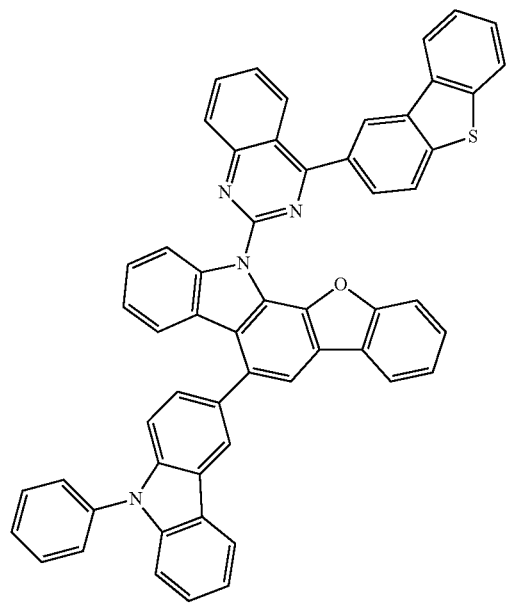
188
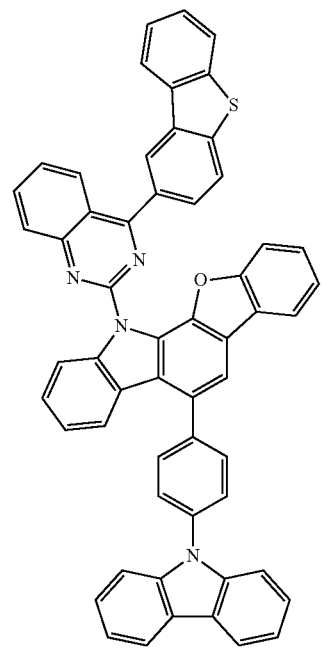
189
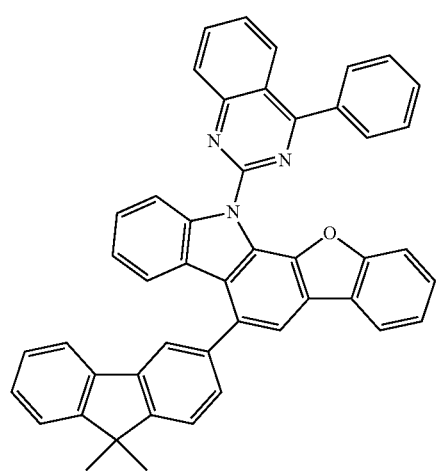
190
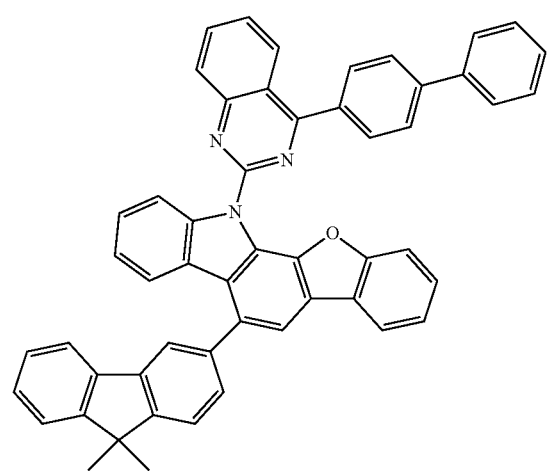
191
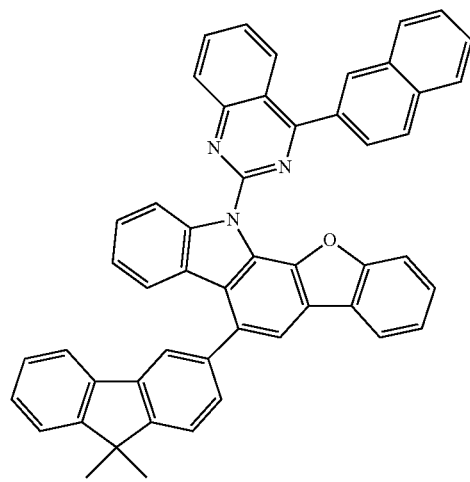
192
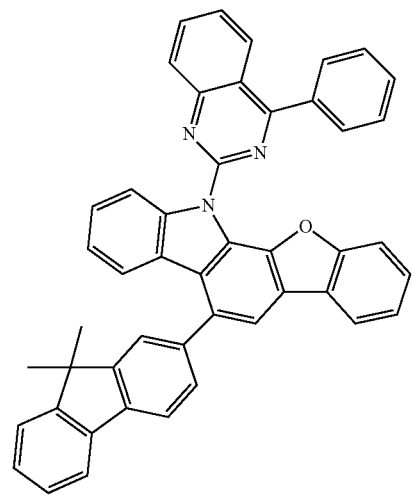

447 448
-continued
193
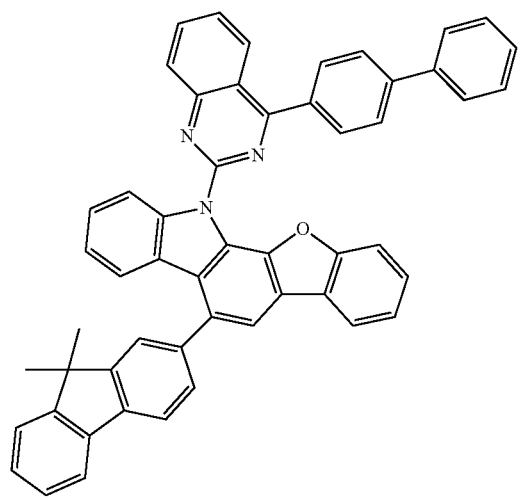
194
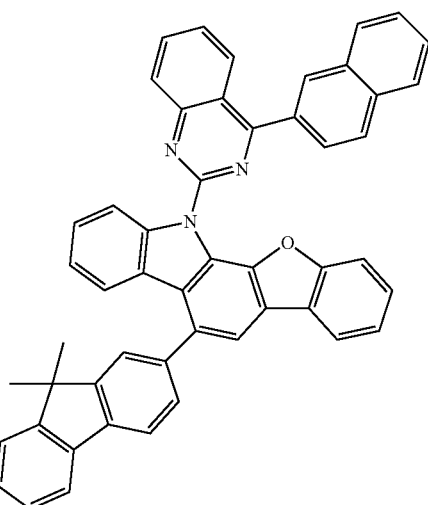
195
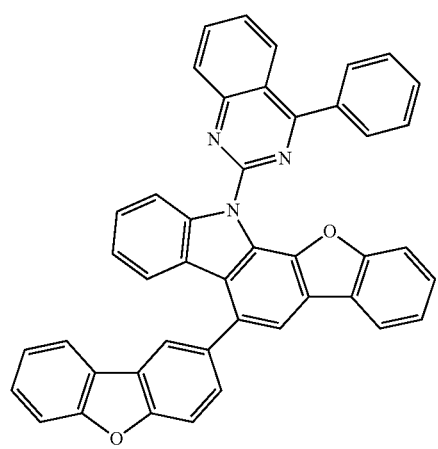
196
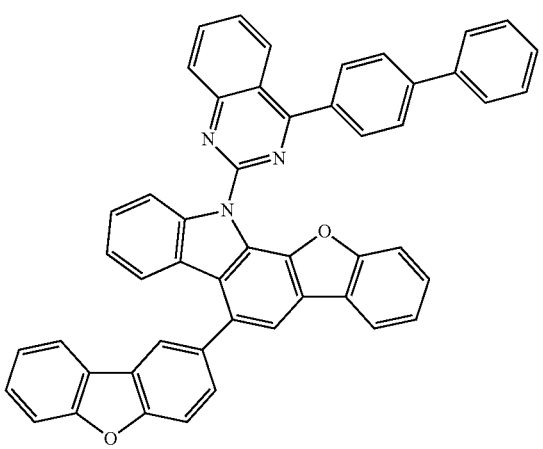
197
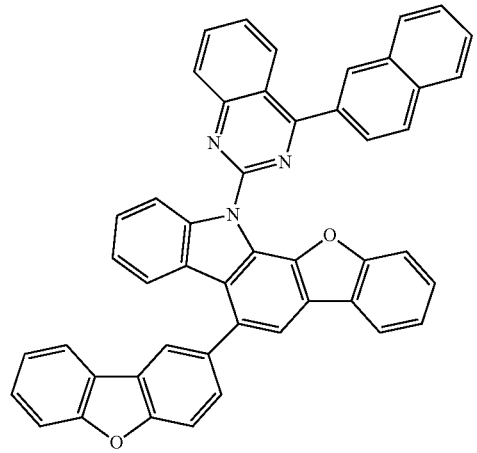
198
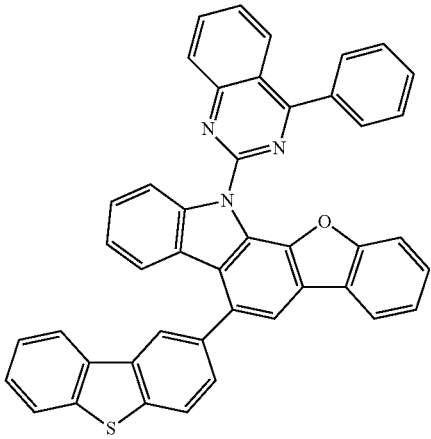

-continued
199
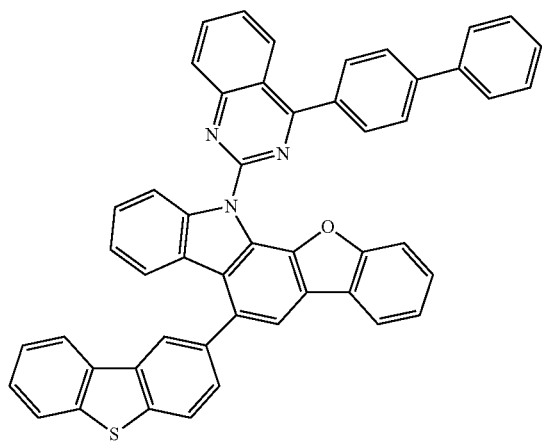
200
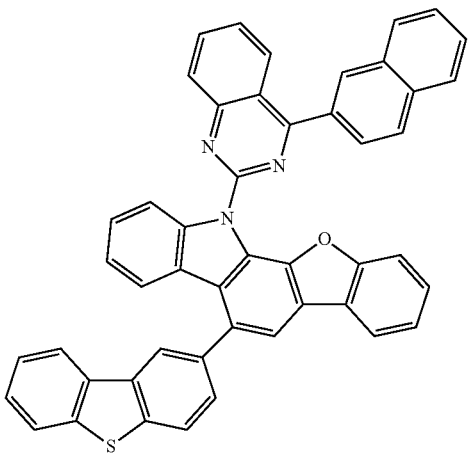
201
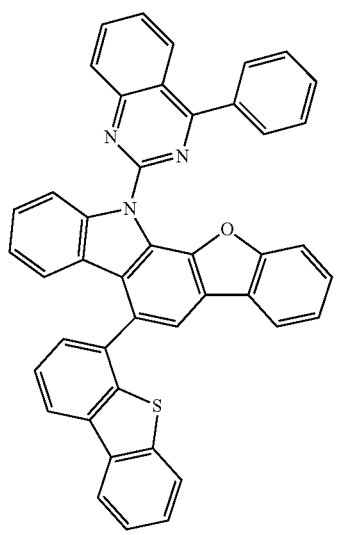
202
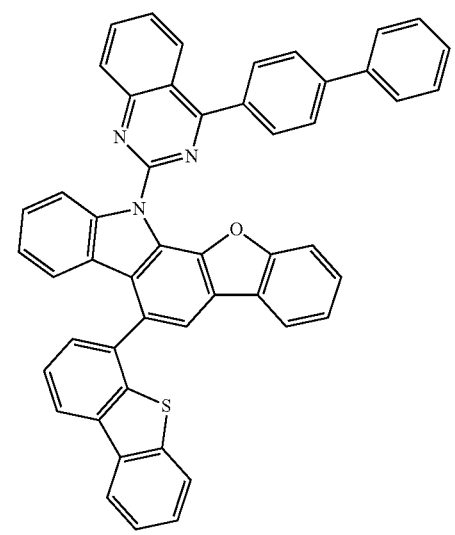
203
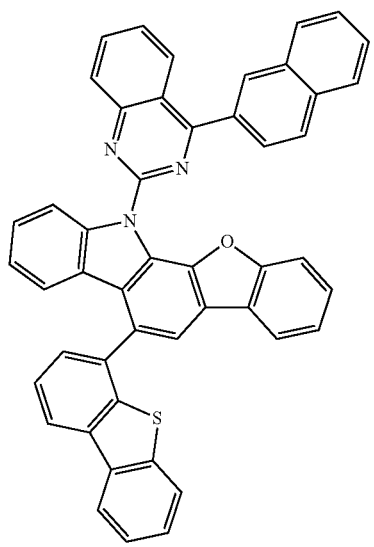
204
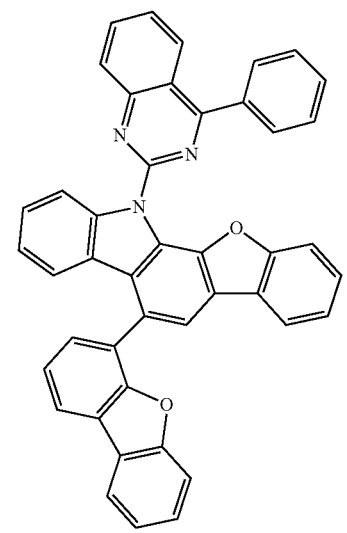

-continued
205
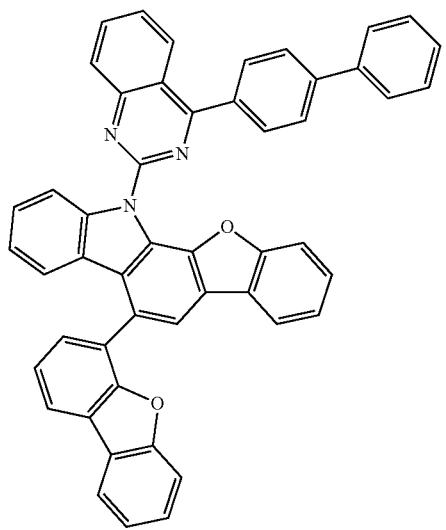
206
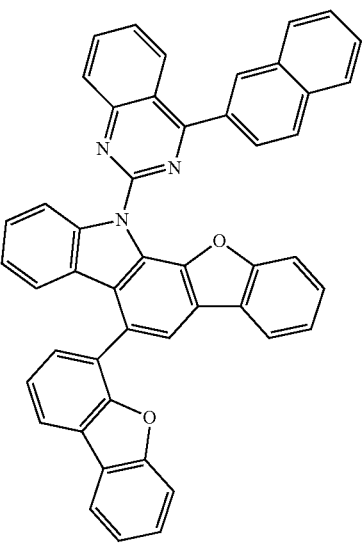
207
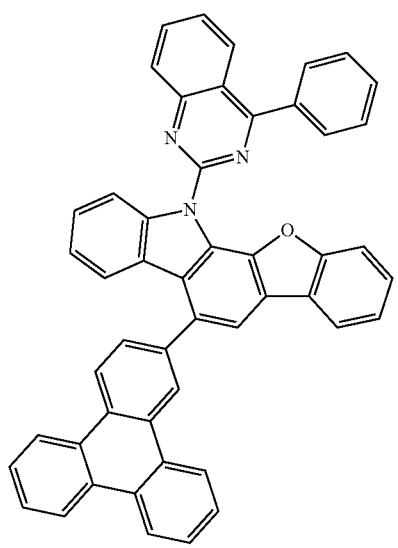
208
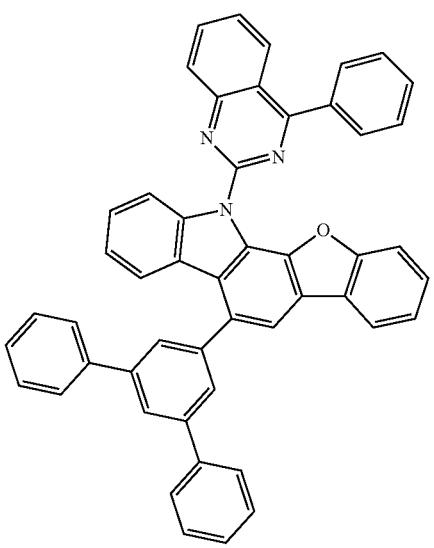
209
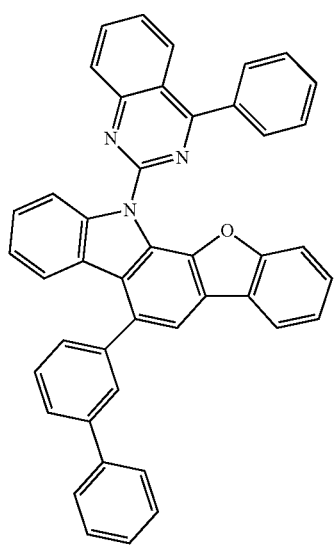
210
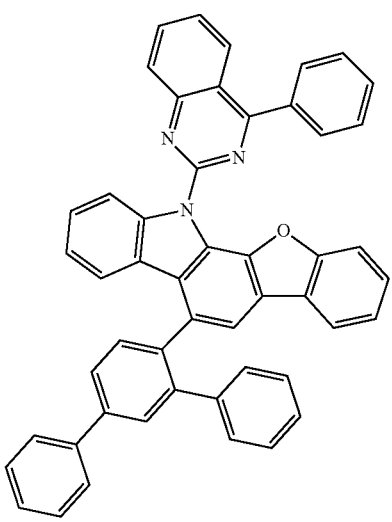

-continued
211
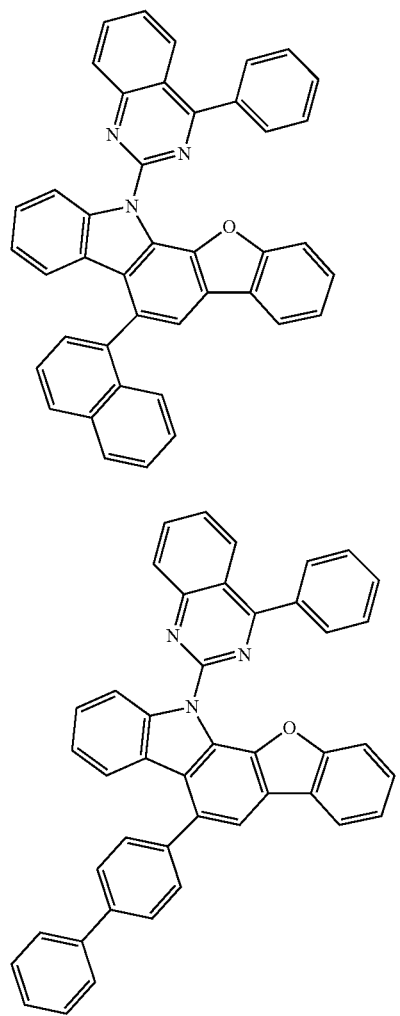
212
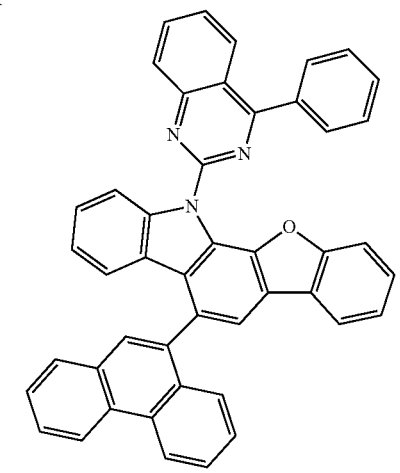
213
214
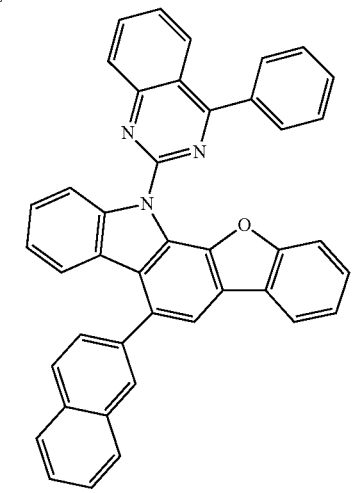
215
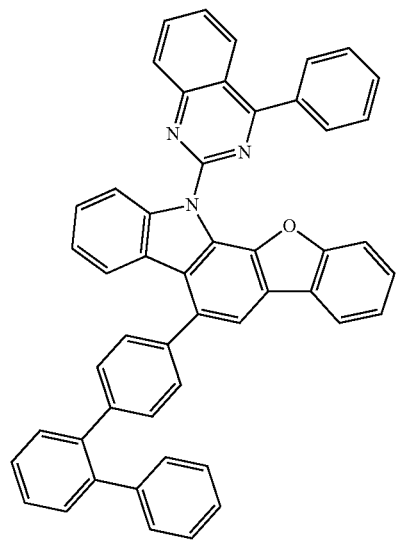
216
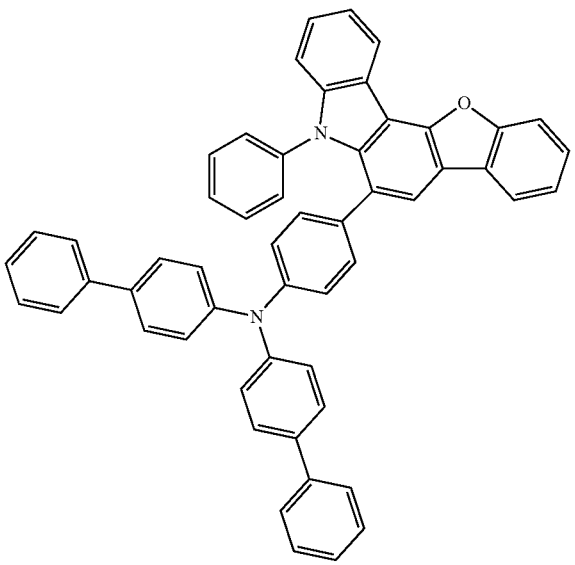

-continued
| 217 | 218 |
|---|---|
| 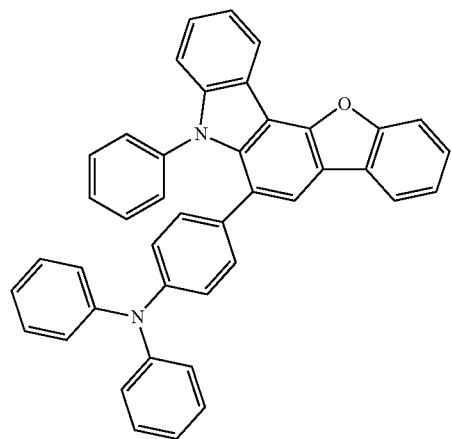 455 | 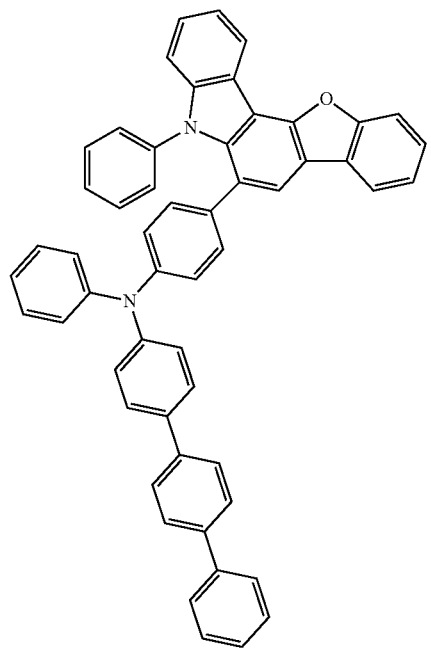 456 |
| 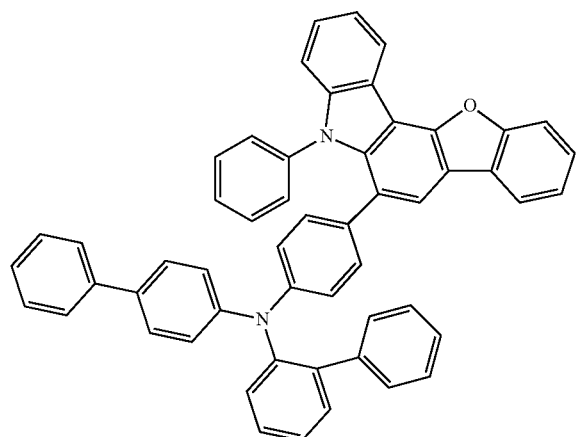 219 | 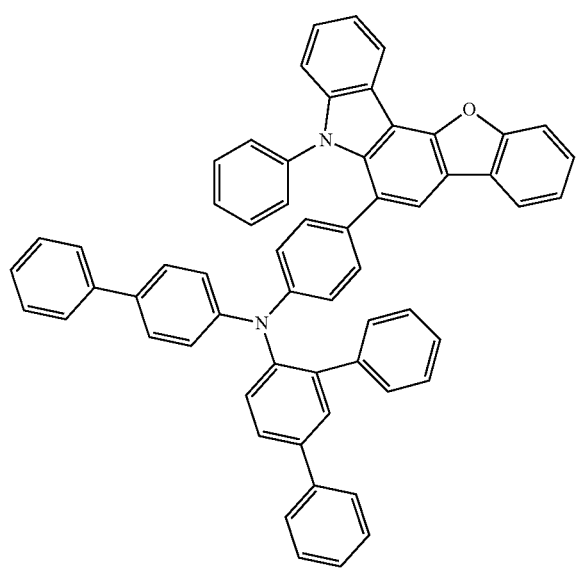 220 |

457
221
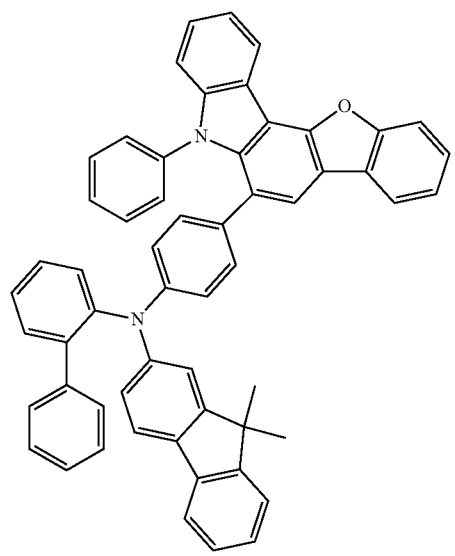
458
222
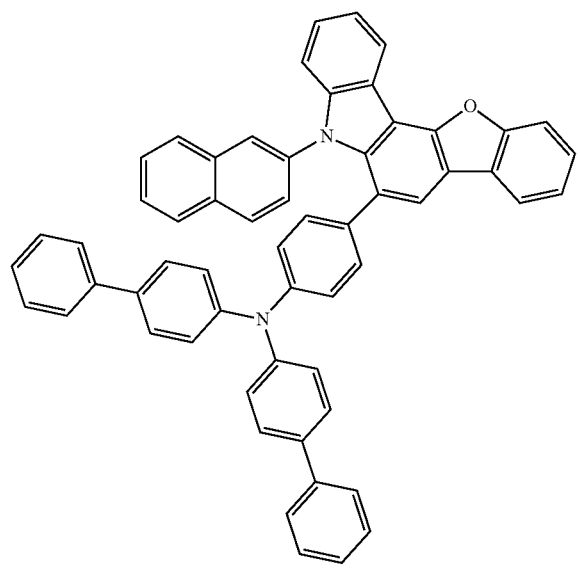
223
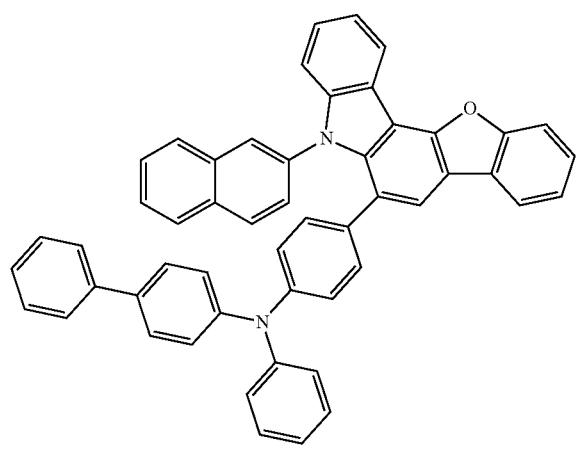
224
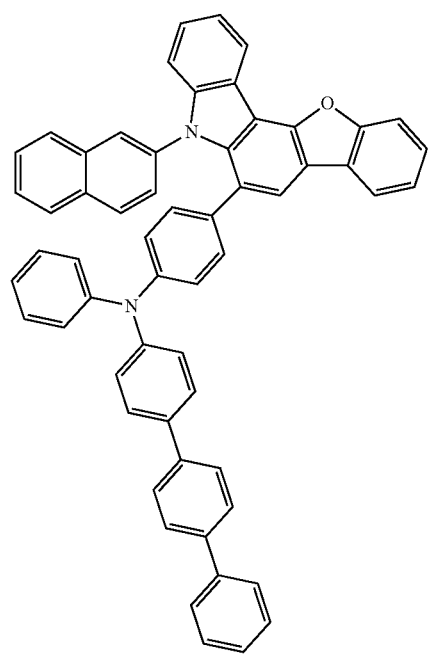

459 460
225
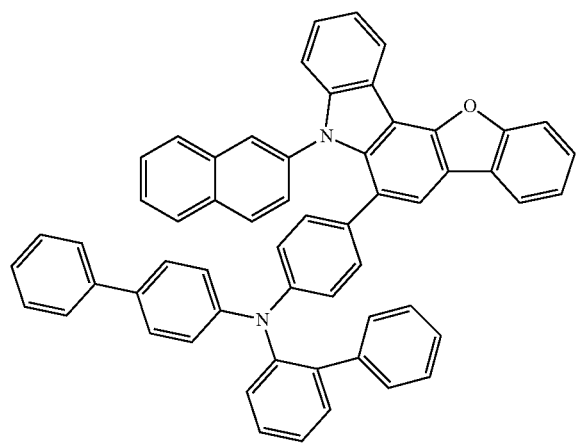
226
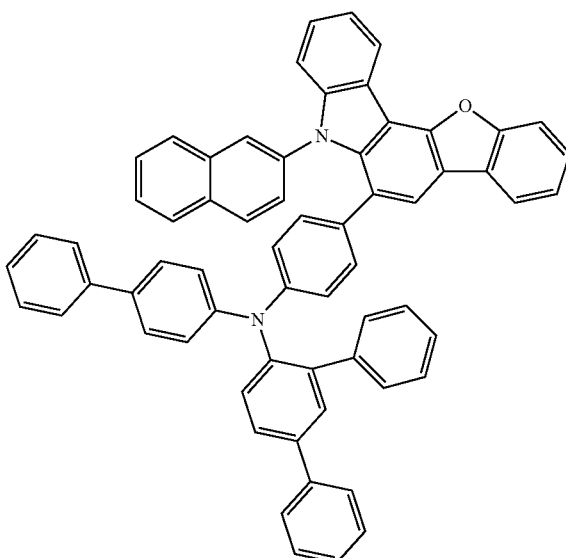
227
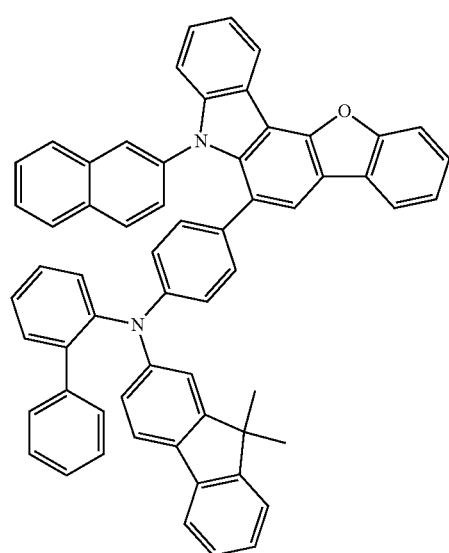
228
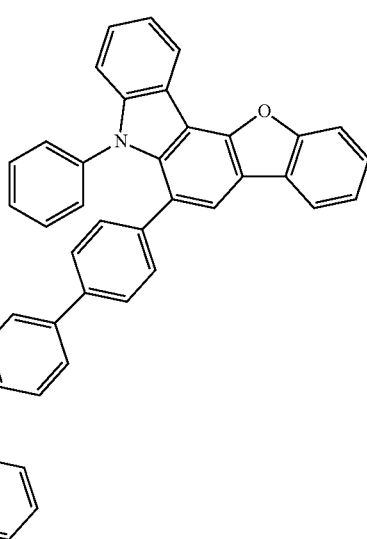
229
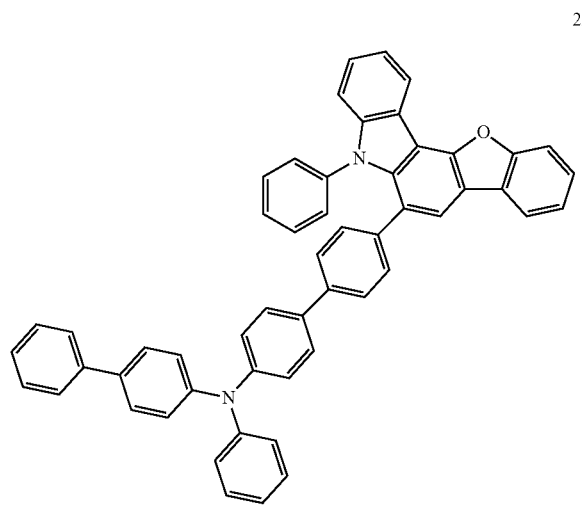
230
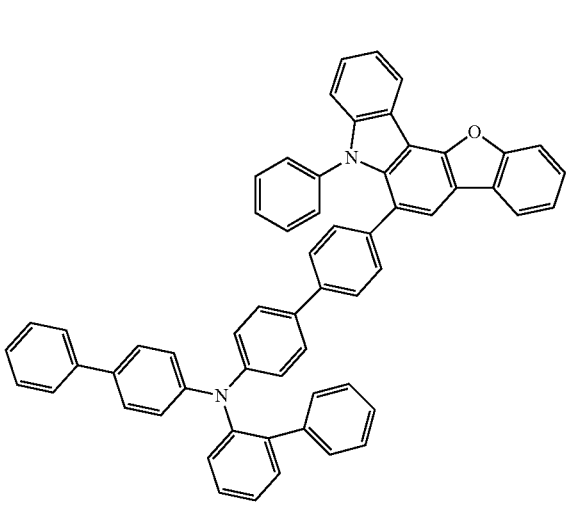

231
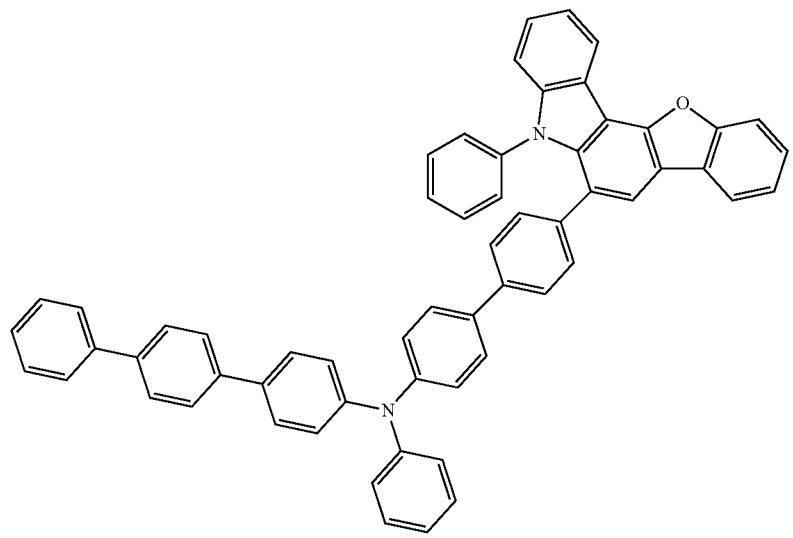
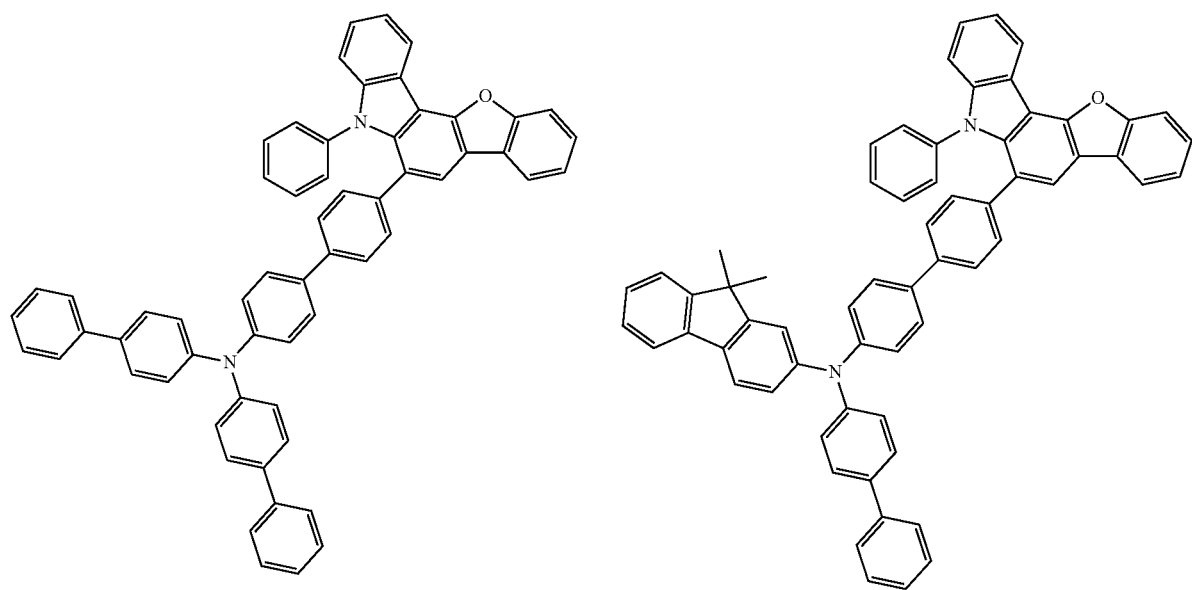

234
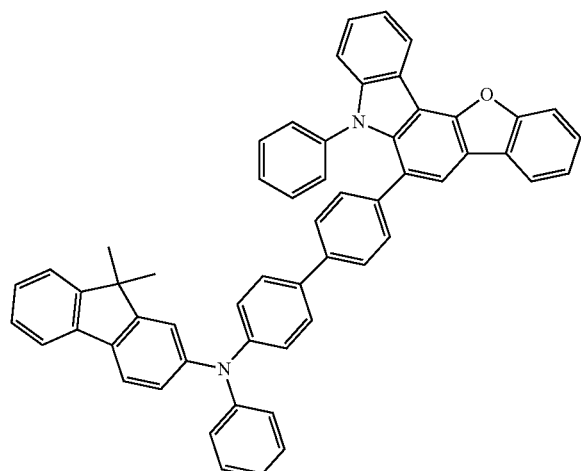
235
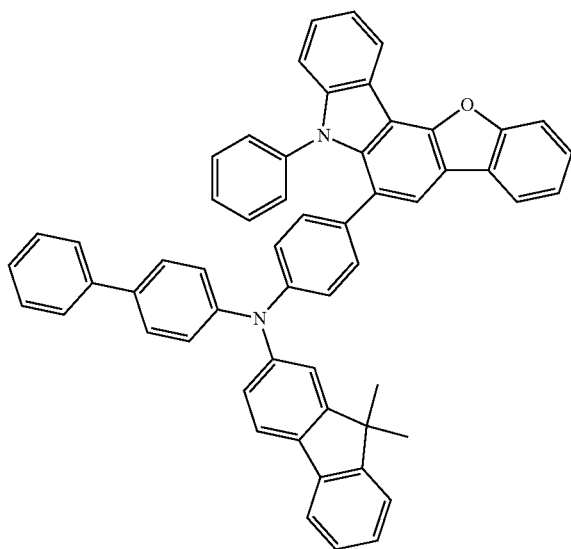
236
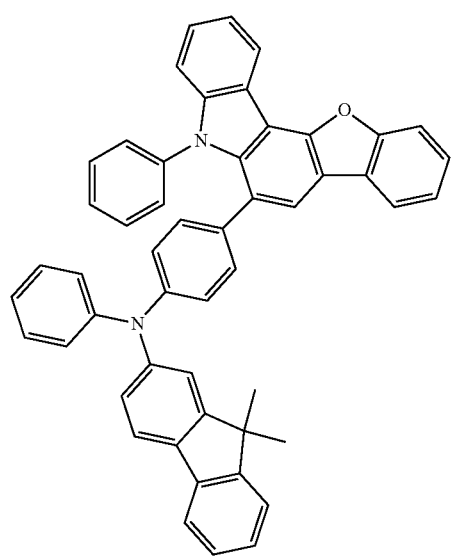
237
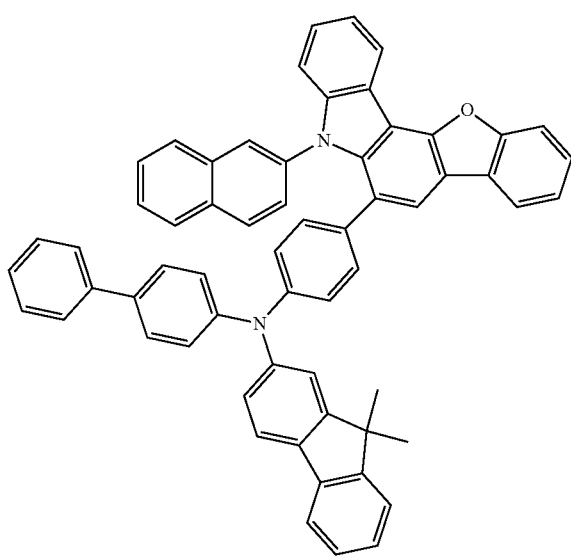

-continued
238
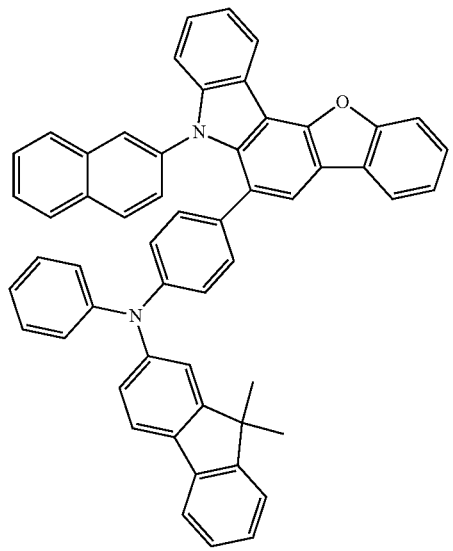
239
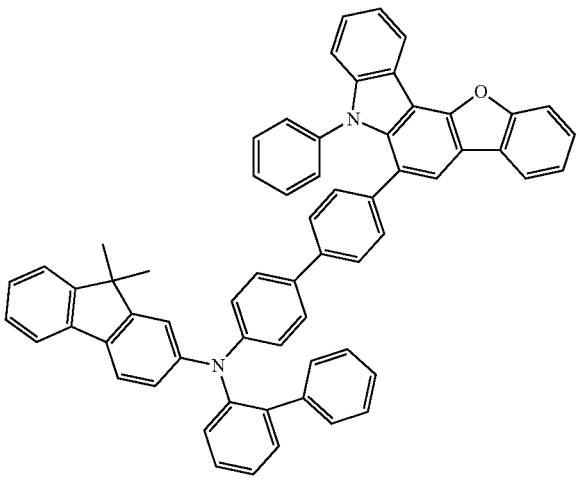
240
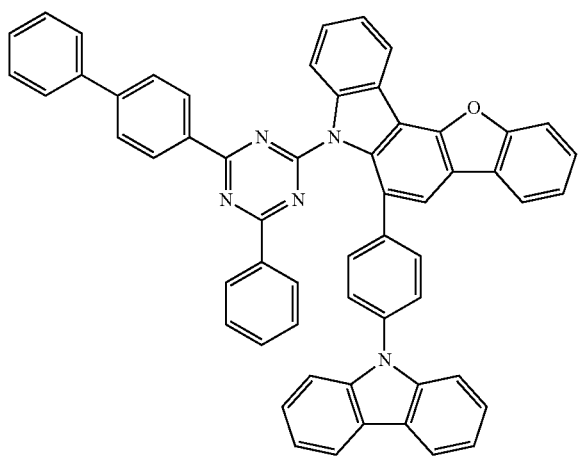
241
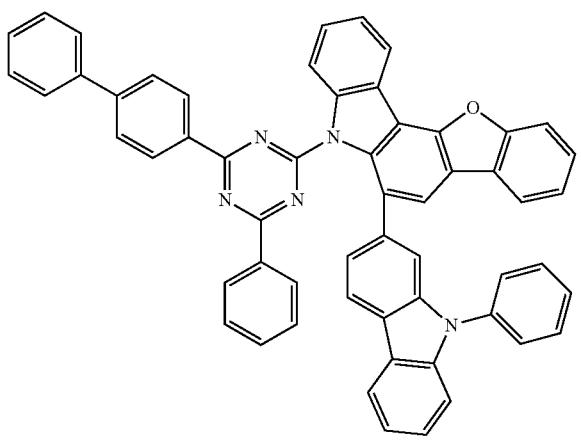
242
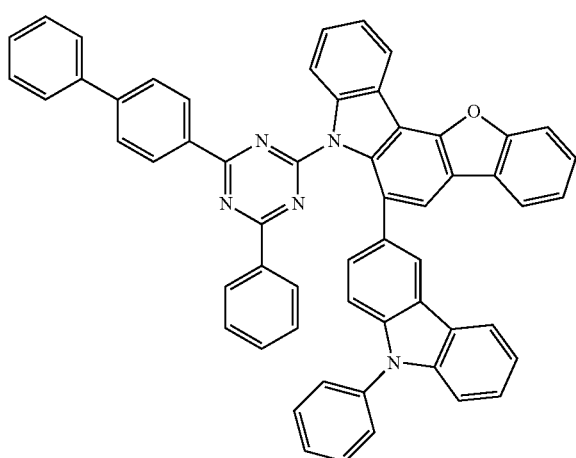
243
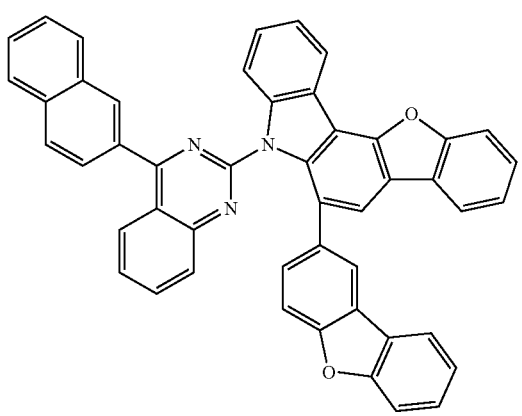

-continued
244
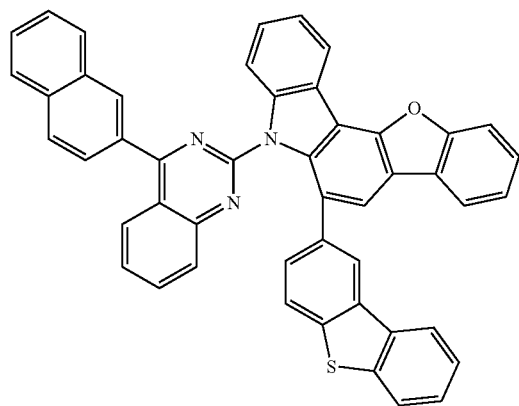
245
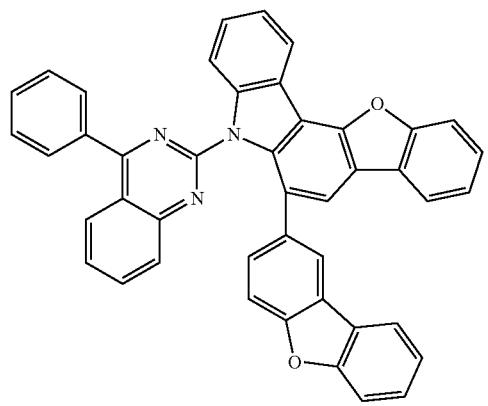
246
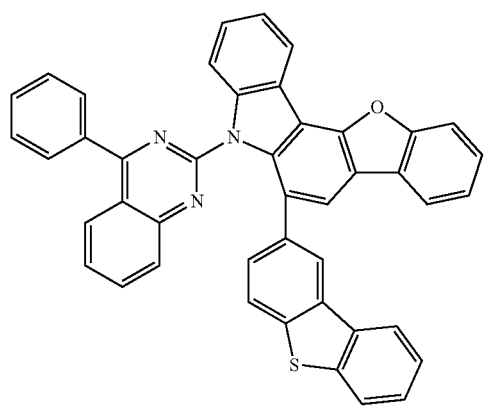
247
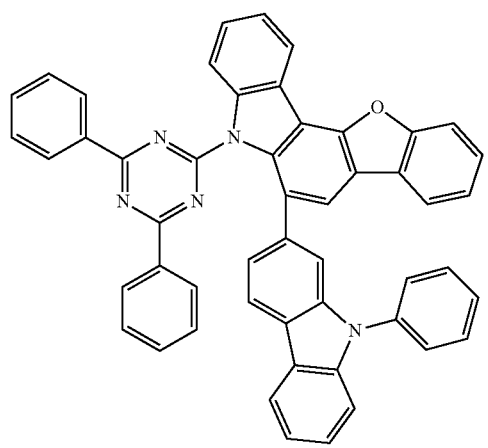
248
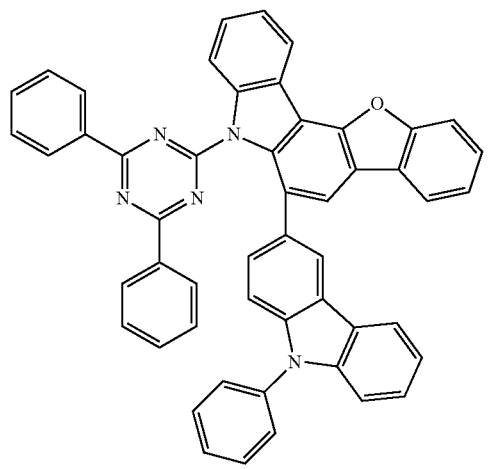
249
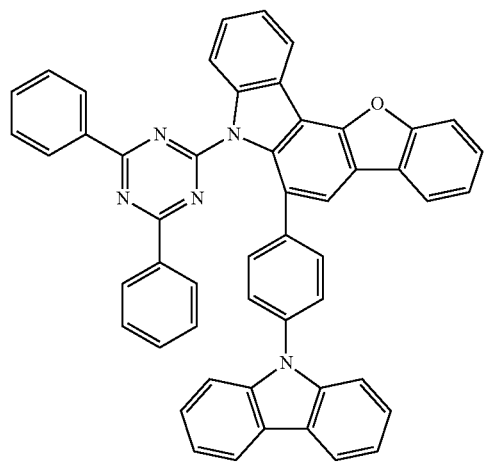

469
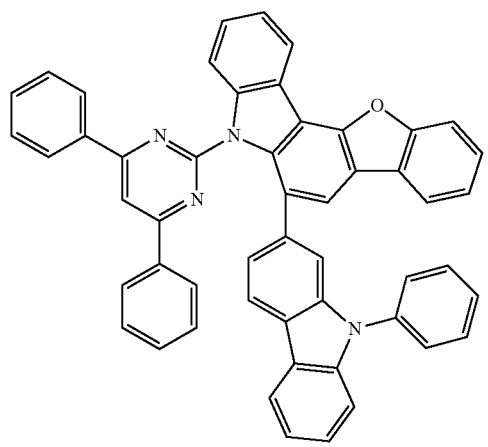
250
470
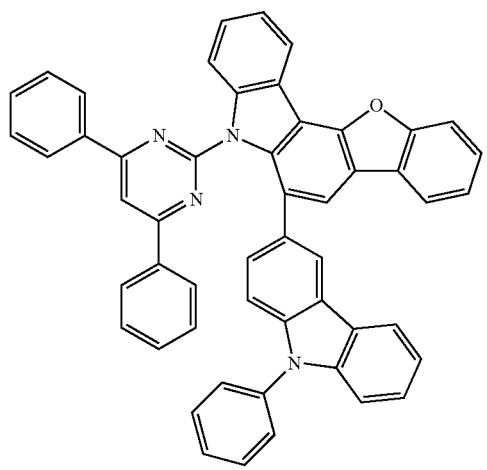
251
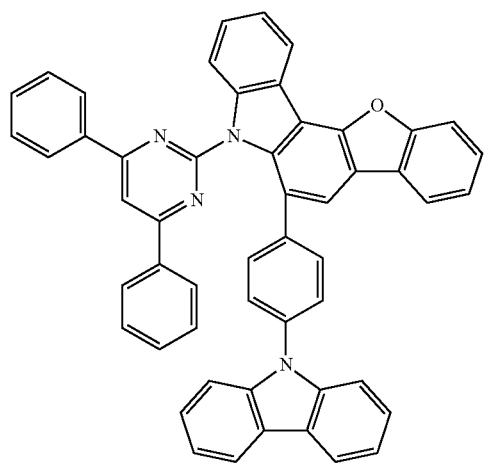
252
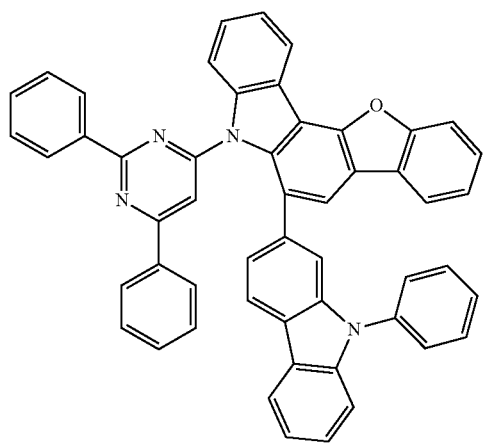
253
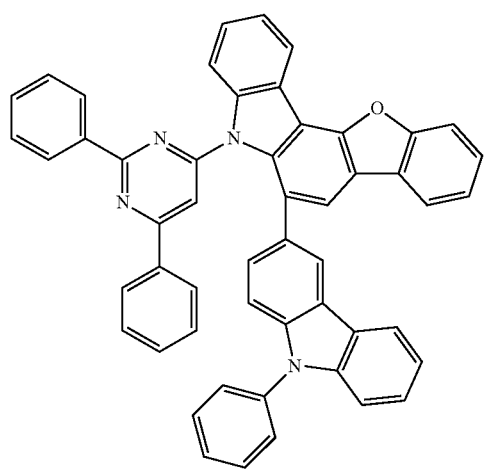
254
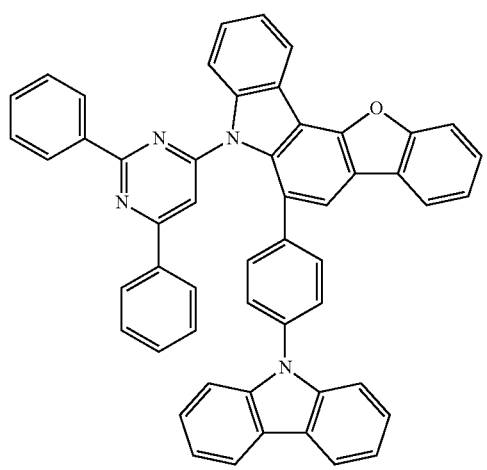
255

471
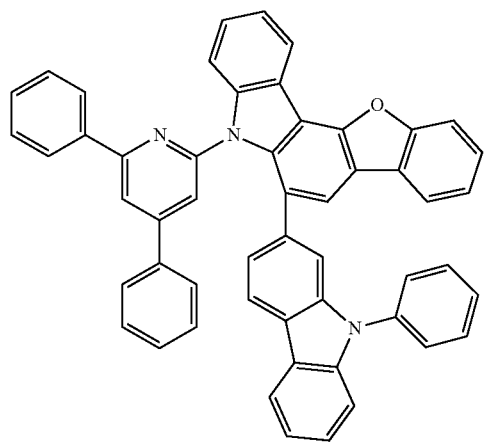
256
472
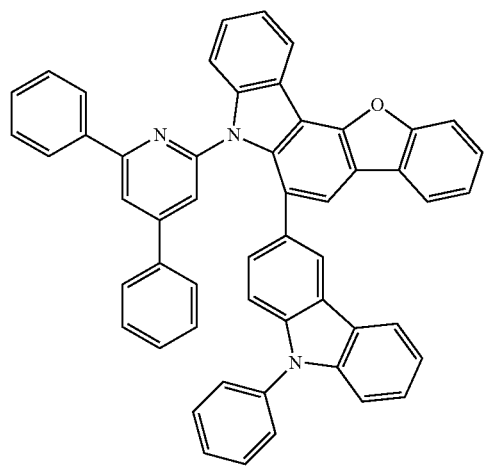
257
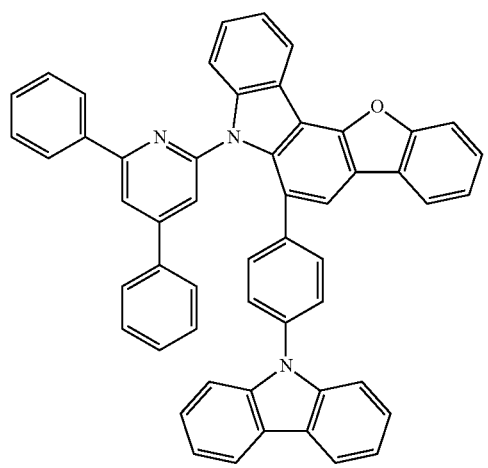
258
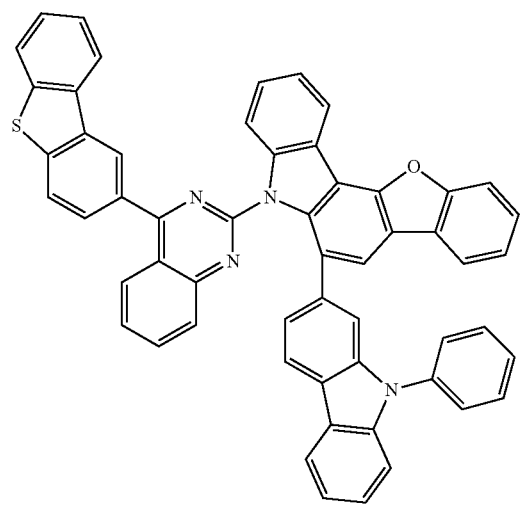
259
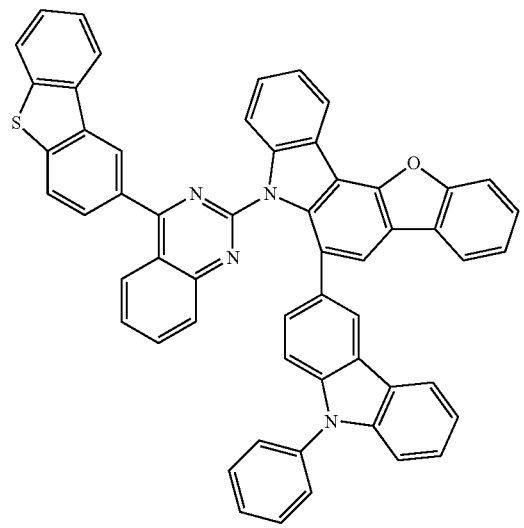
260
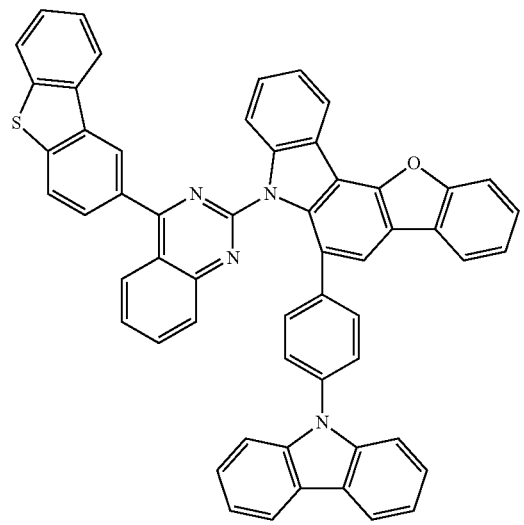
261
-continued -continued
262
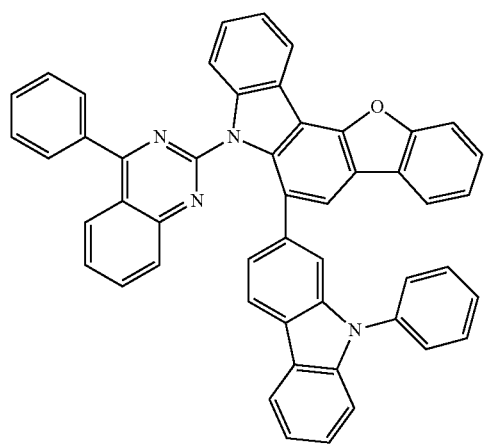
263
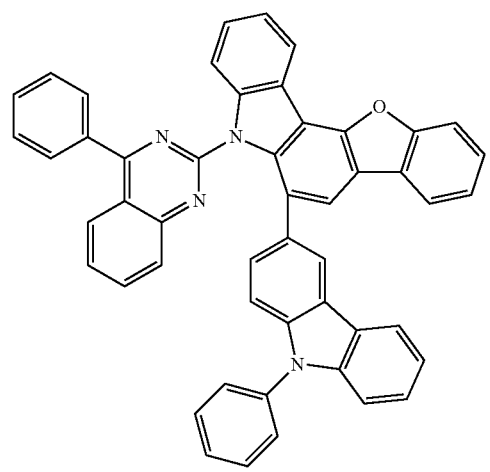
264
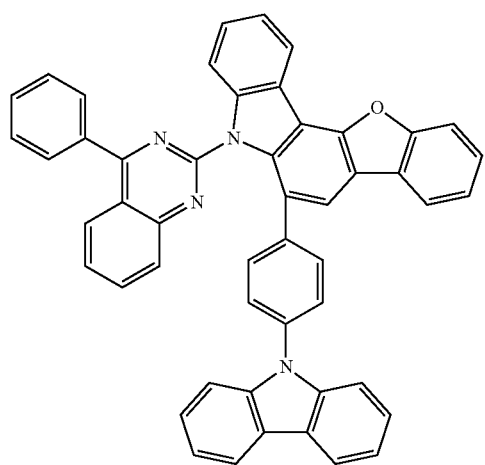
265
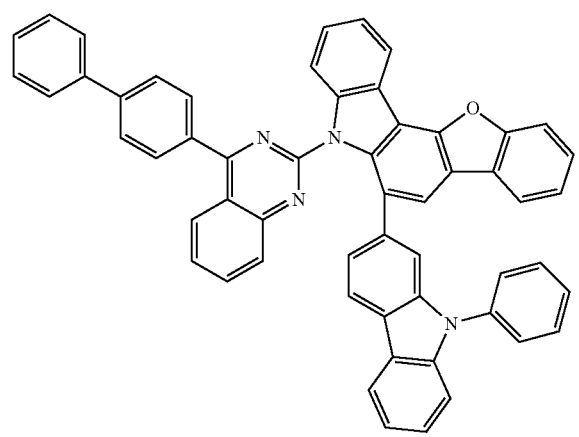
266
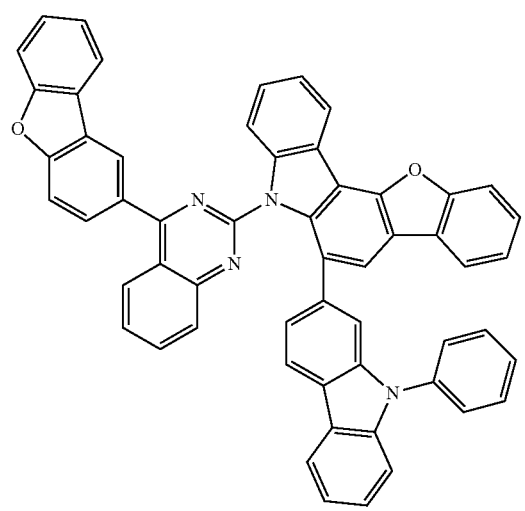
267
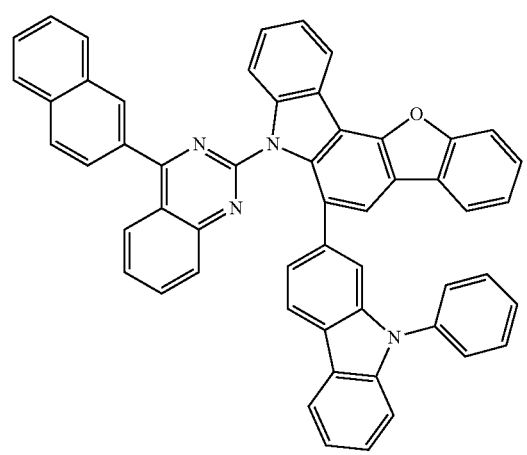

-continued
268
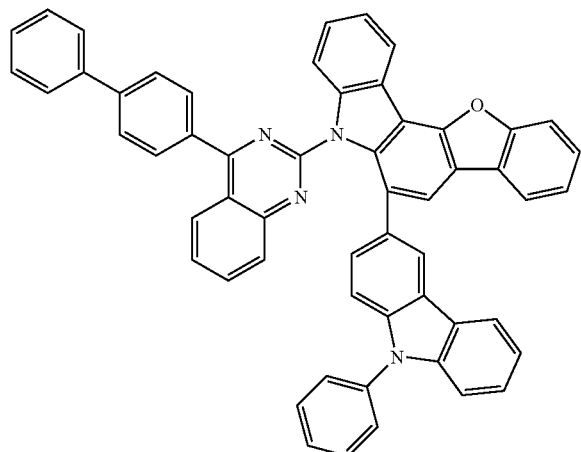
269
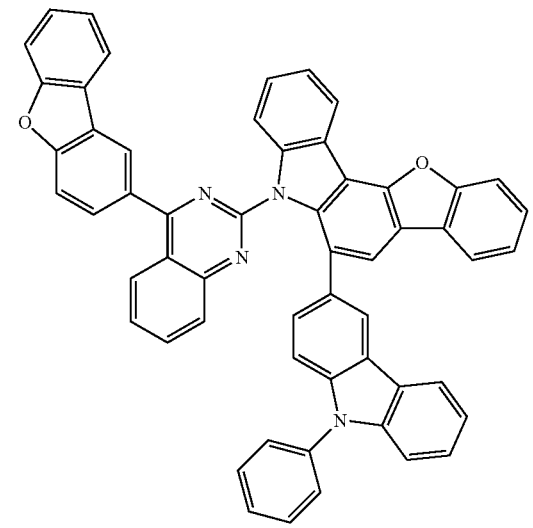
270
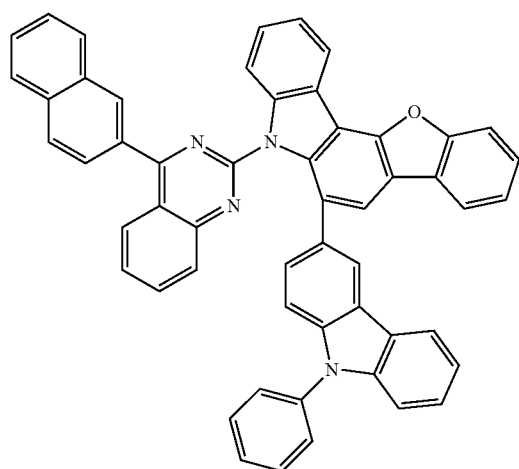
271
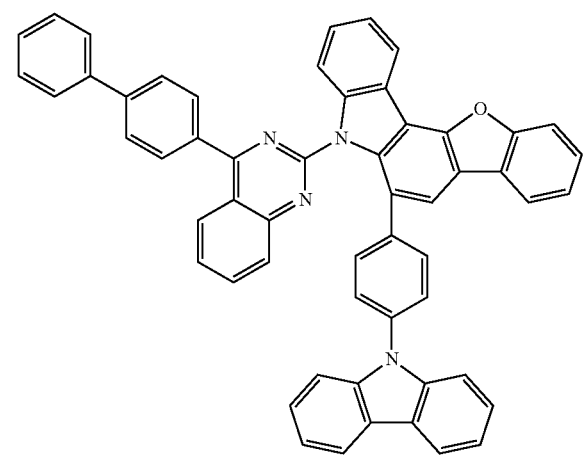
272
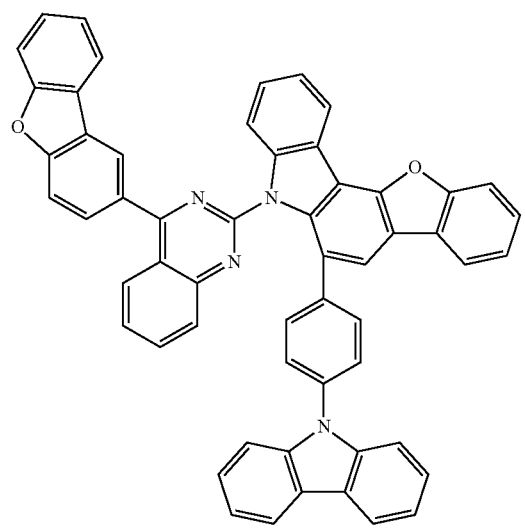
273
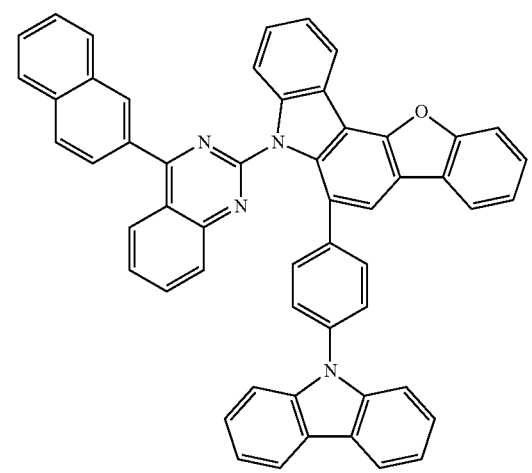

477
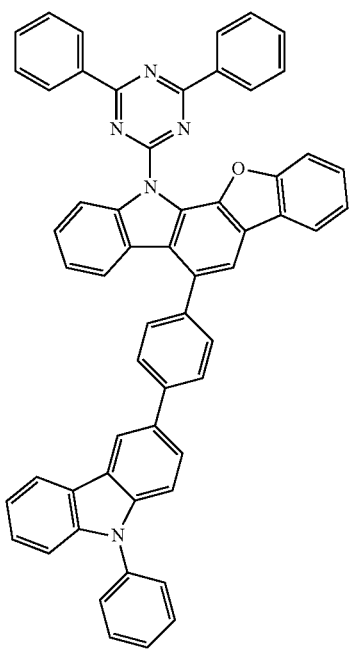
478
-continued
274
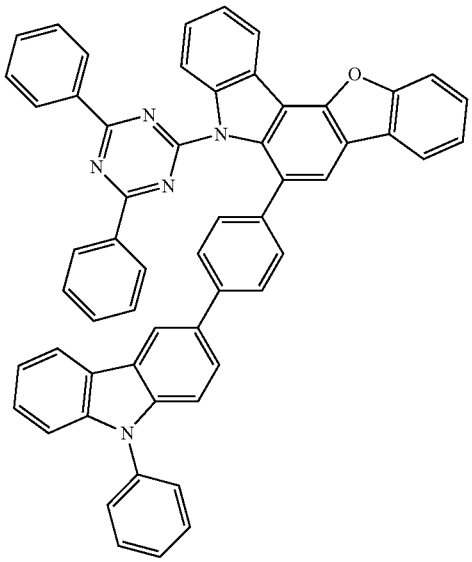
275
276
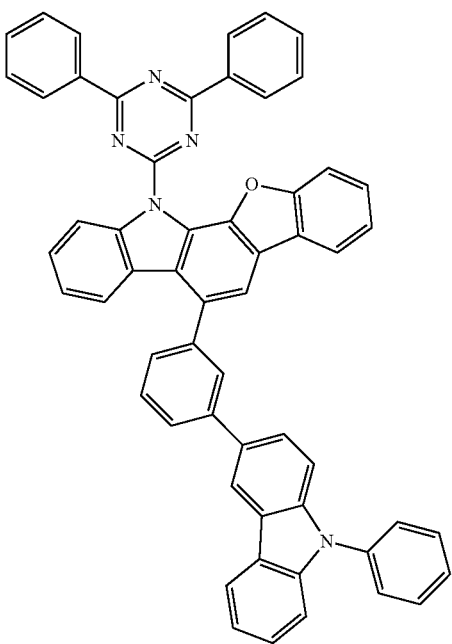
277
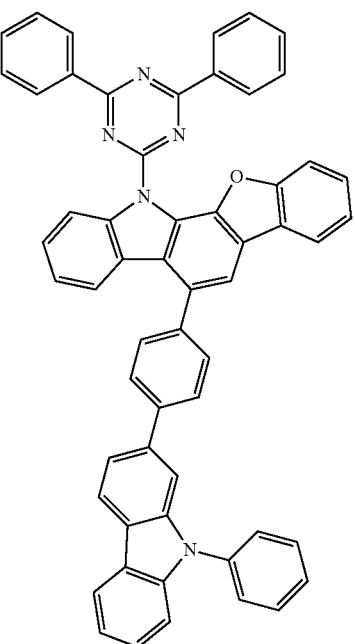

-continued
278 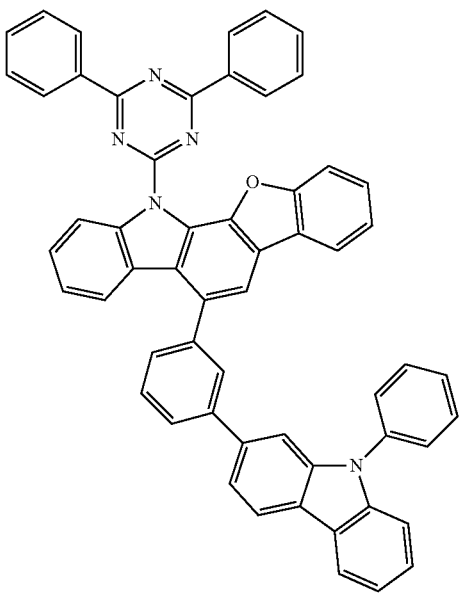
279 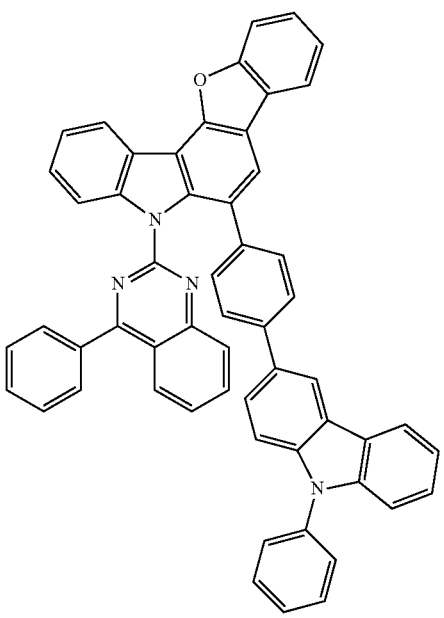
280 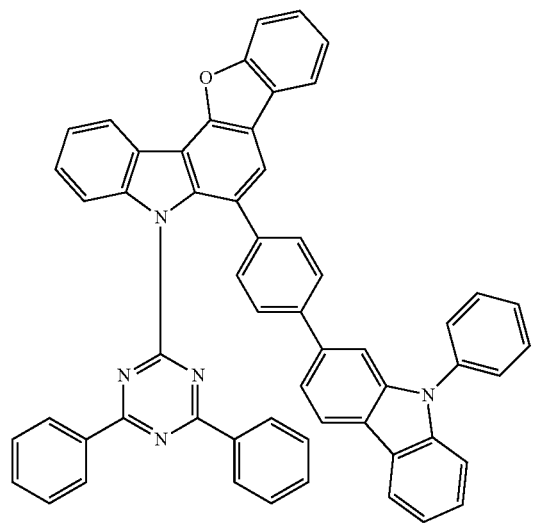
281 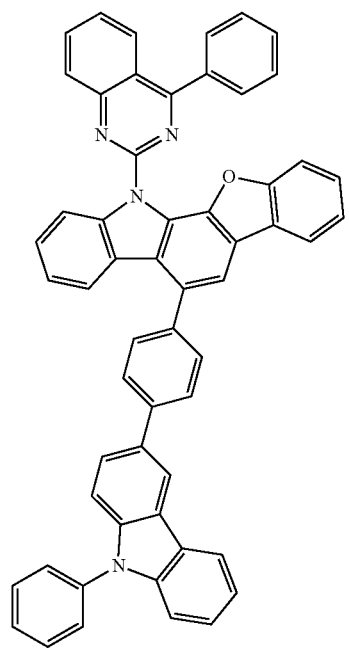

-continued
481
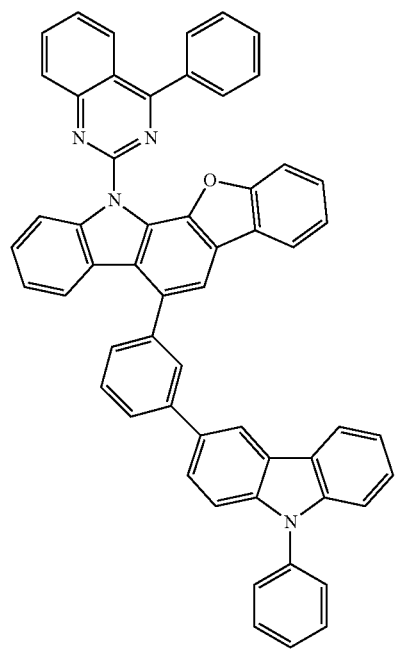
482
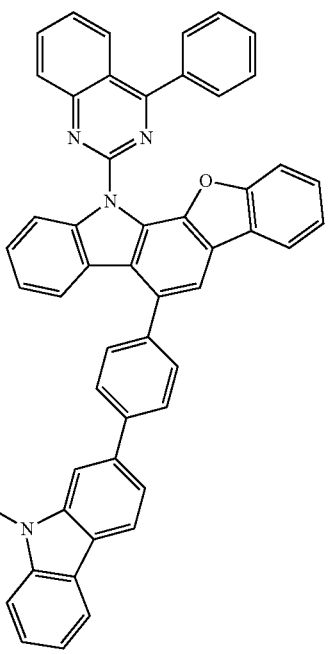
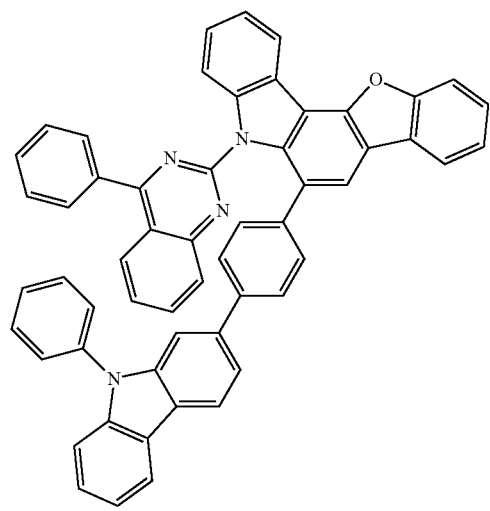
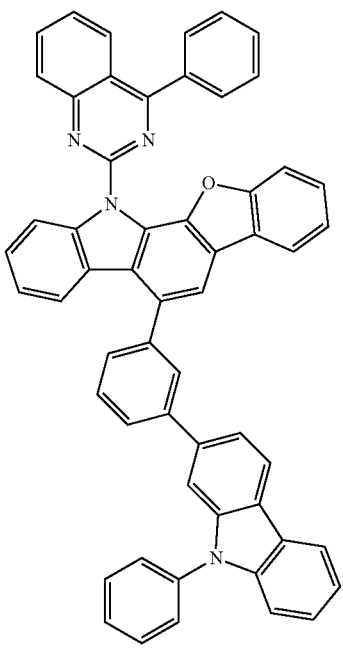

-continued
286 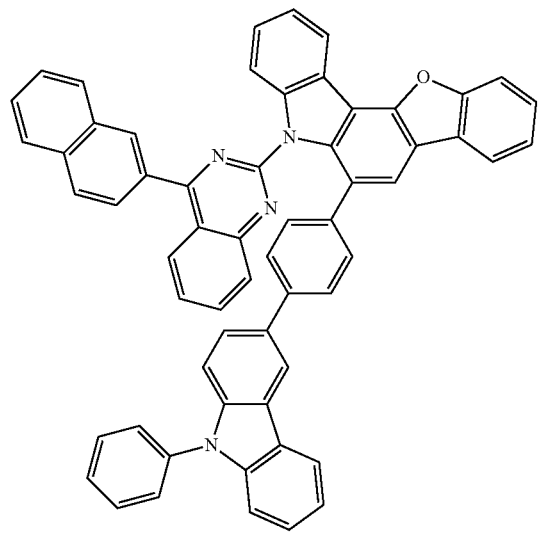
287 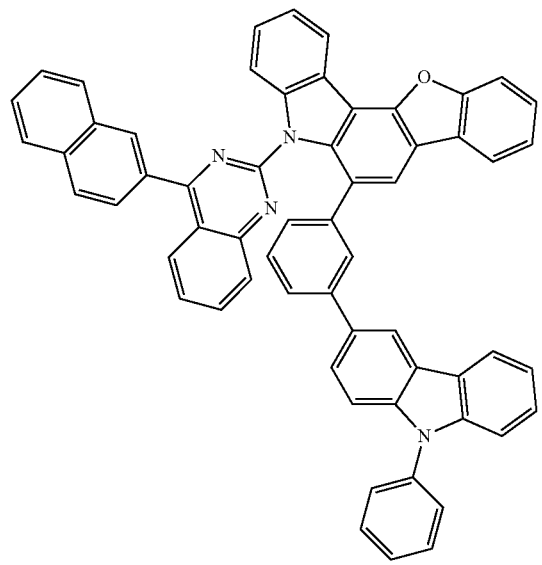
288 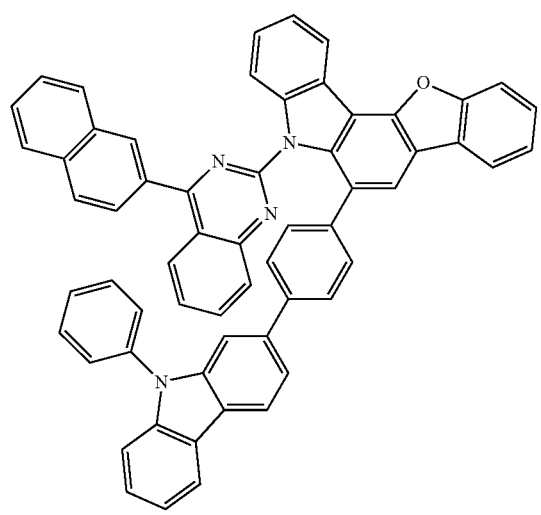
289 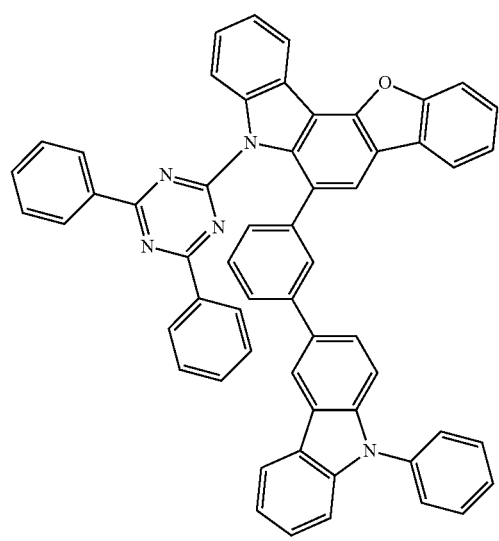
290 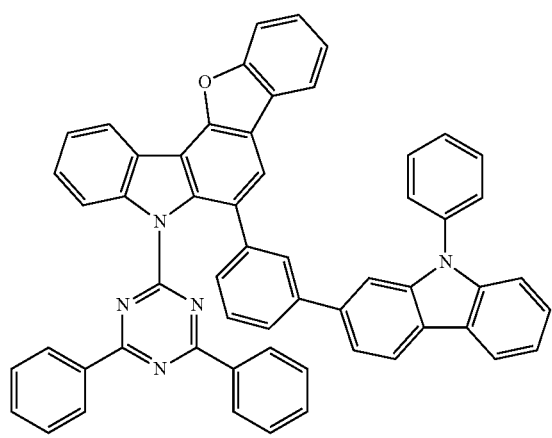
291 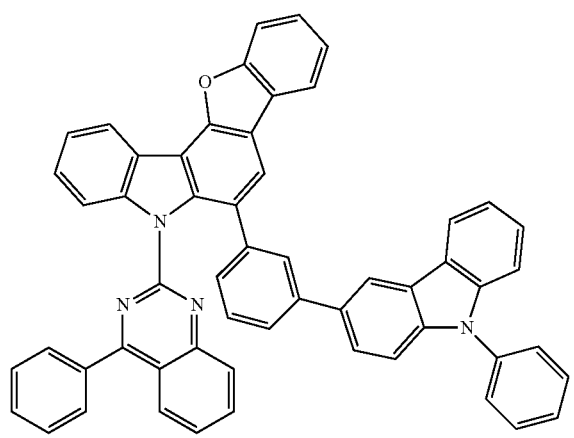

US 10,230,056 B2
485  486
-continued
292  293
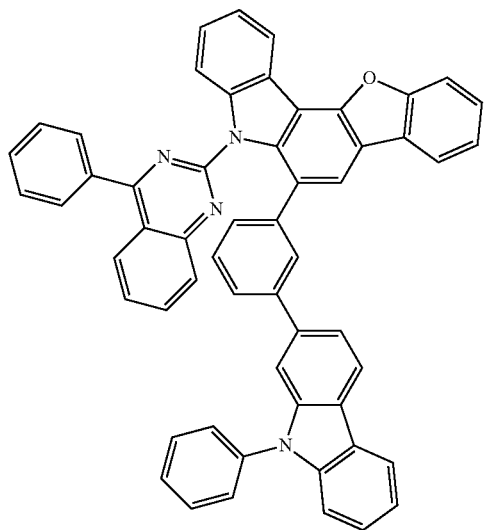 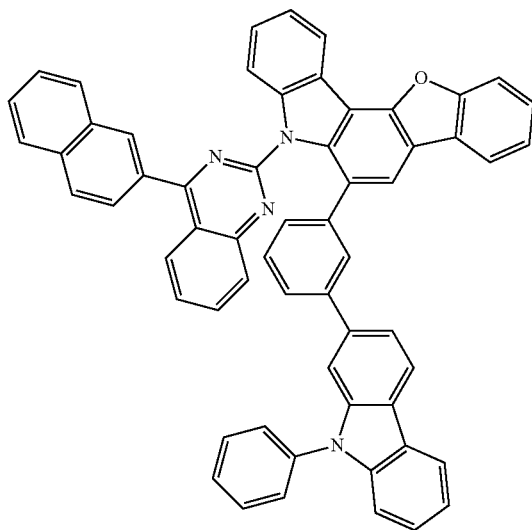
294  295
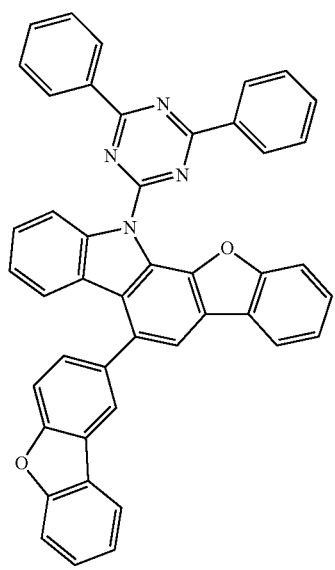 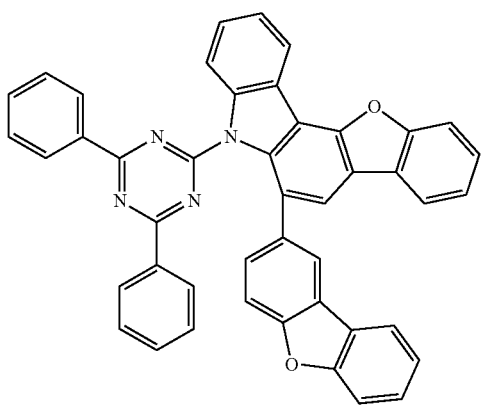
296  297
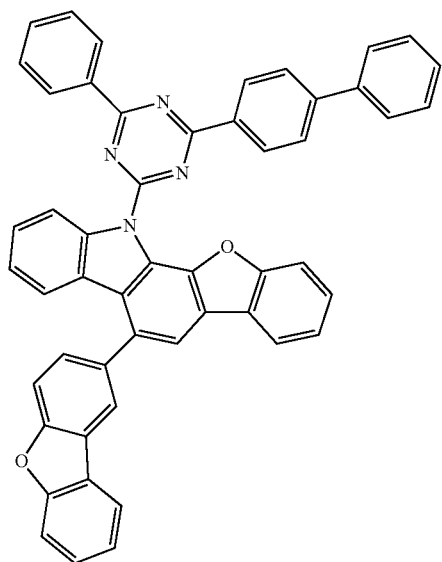 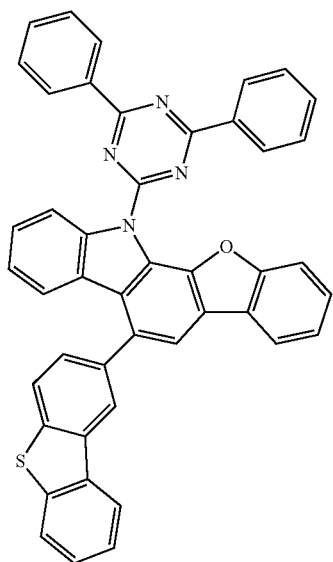

487 488
-continued
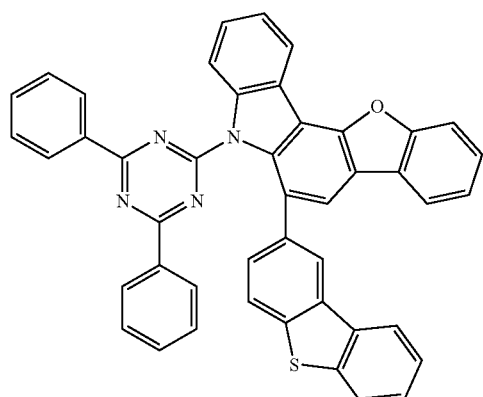
298
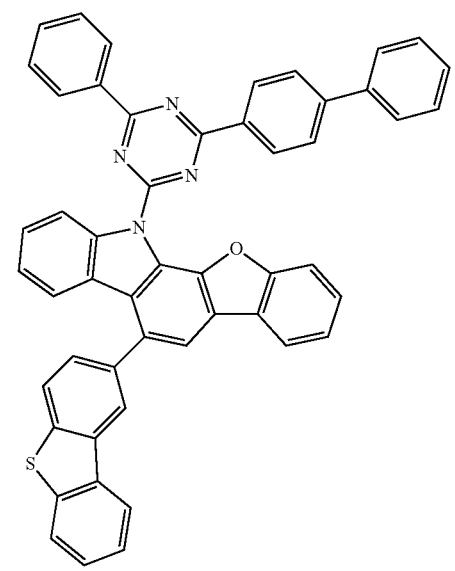
299
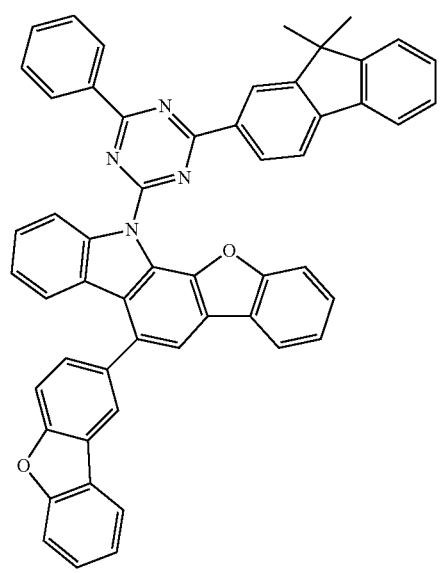
300
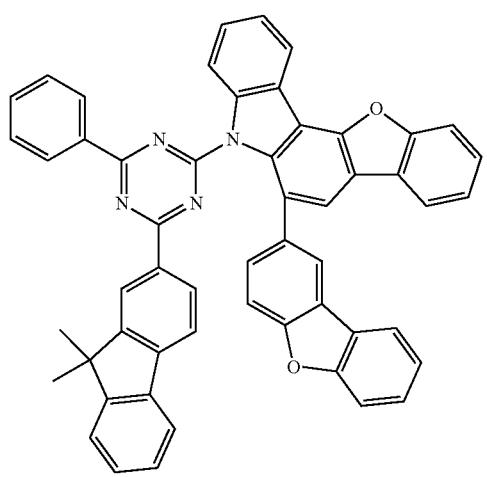
301

-continued
489
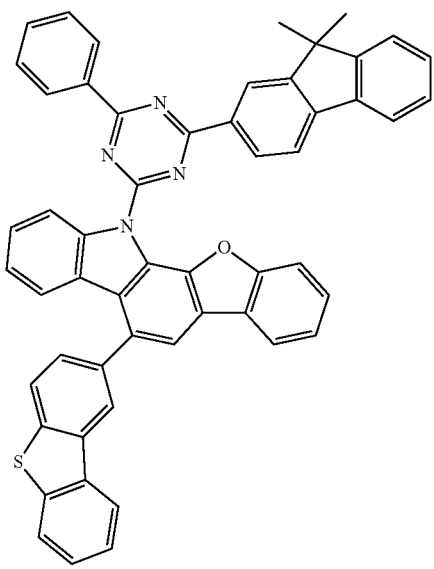
490
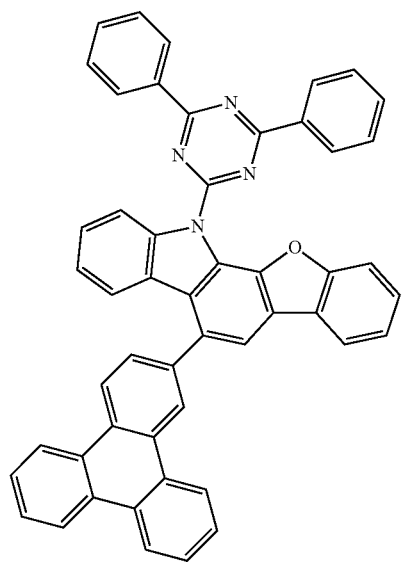
304
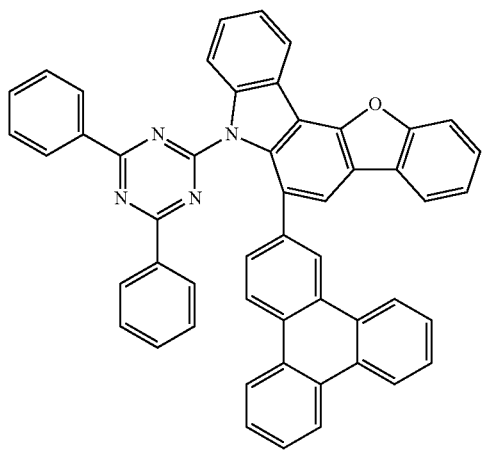
305
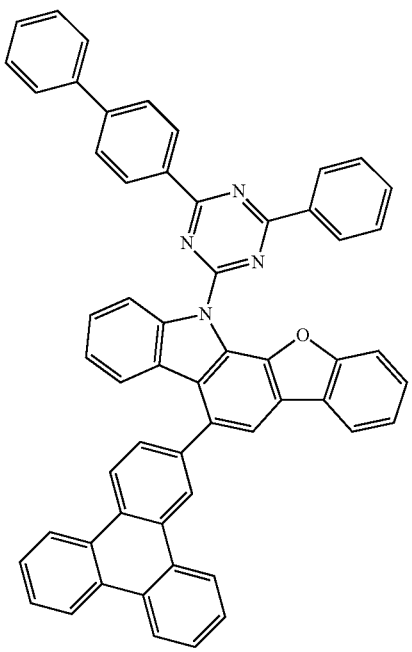

491
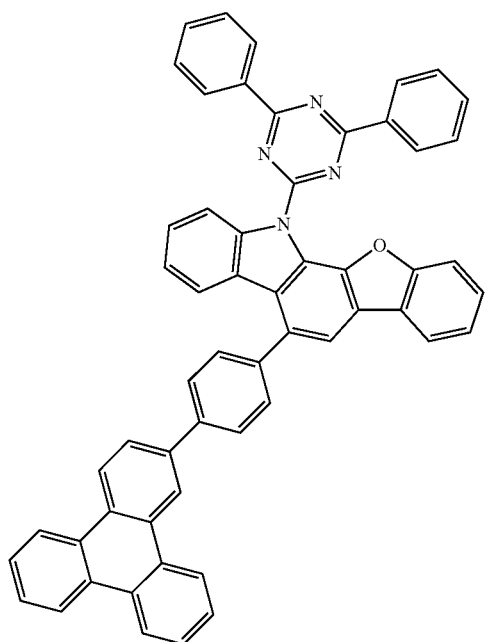
492
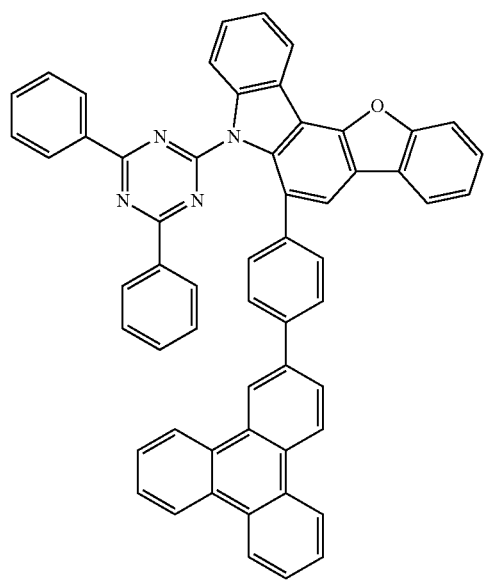
-continued
306
307
308
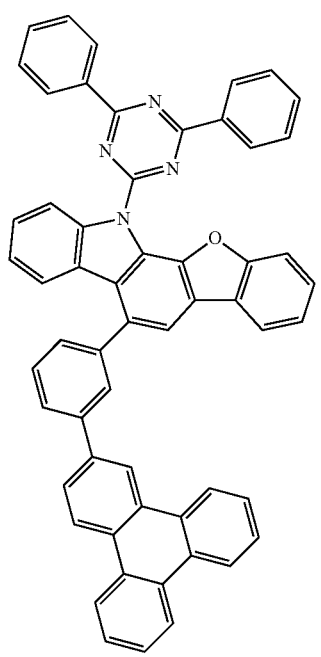
309

-continued
493
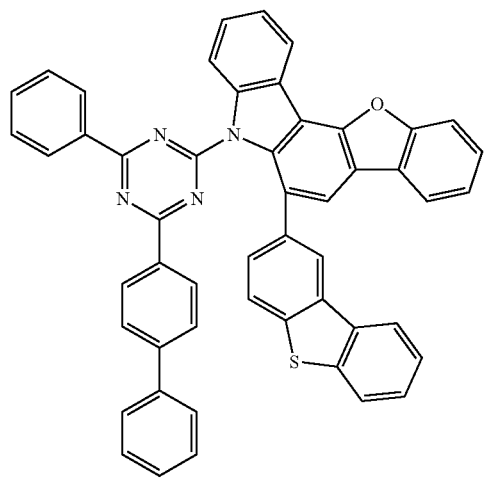
310
494
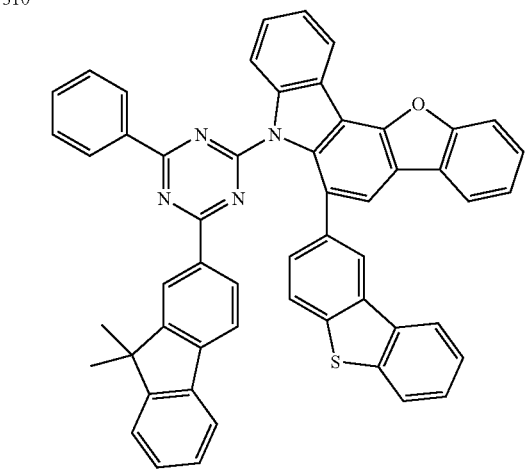
311
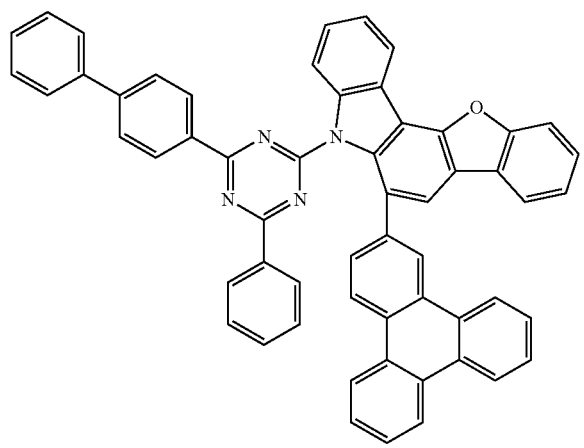
312
313
314
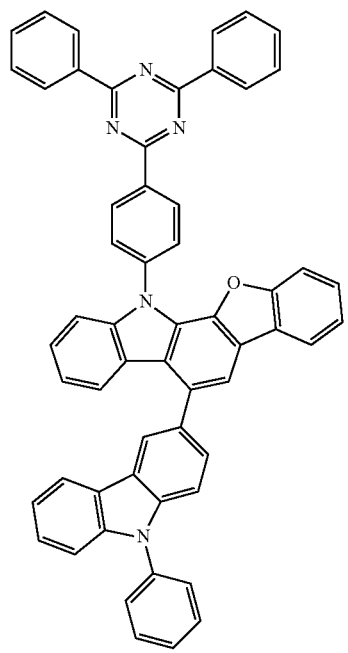
315
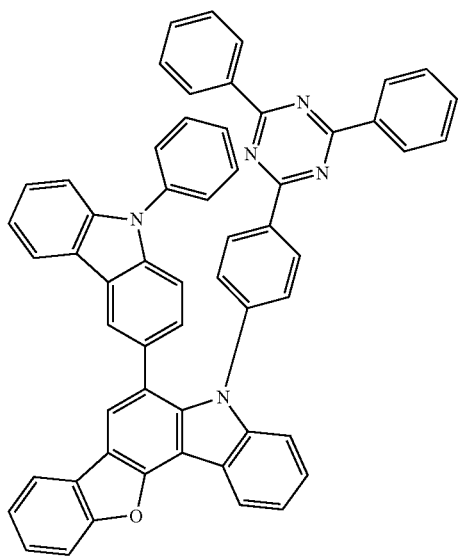

-continued
316
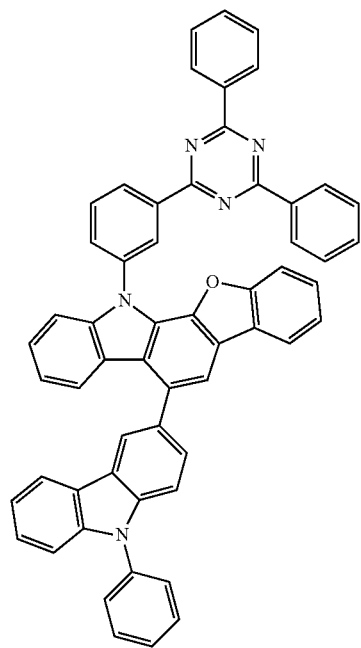
317
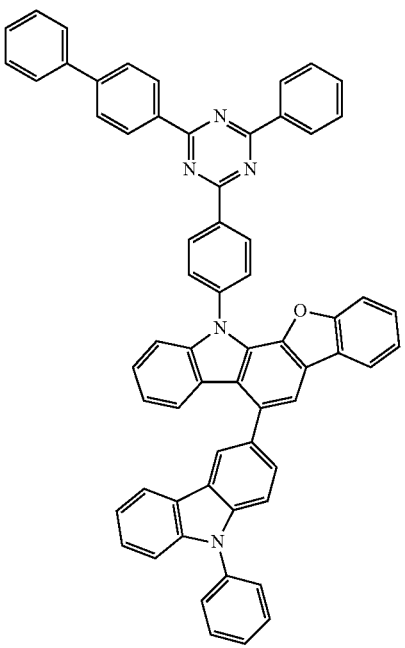
318
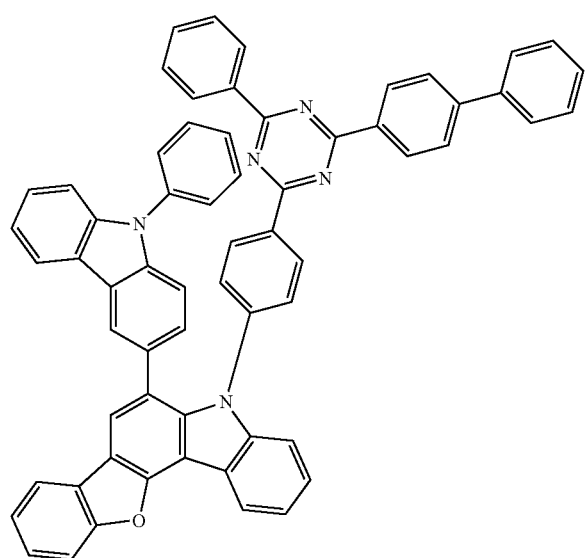
319
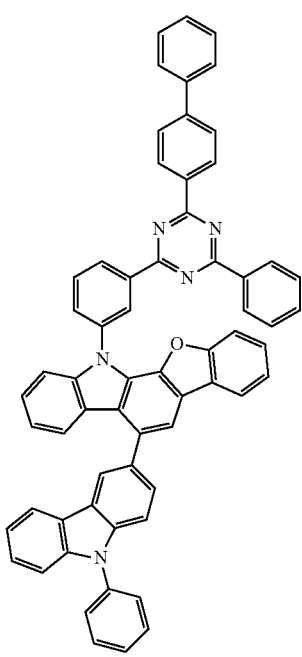

-continued
497
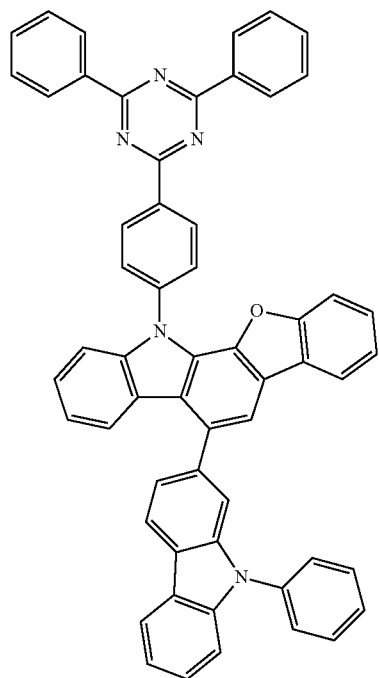
498
320
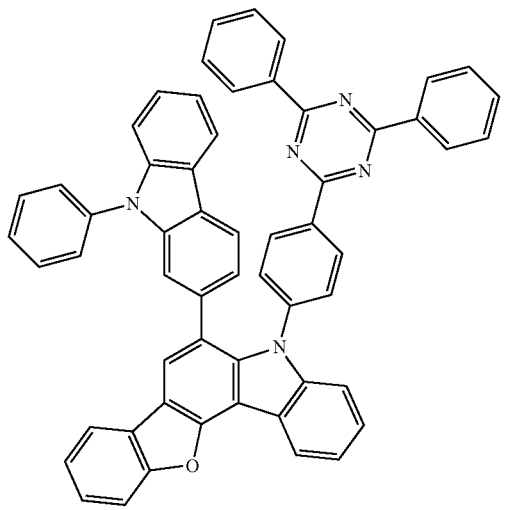
321
322
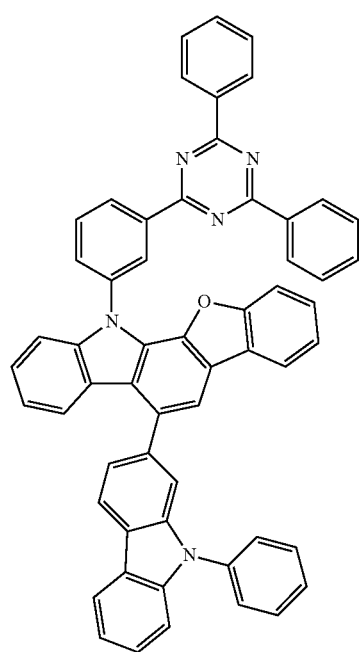
323
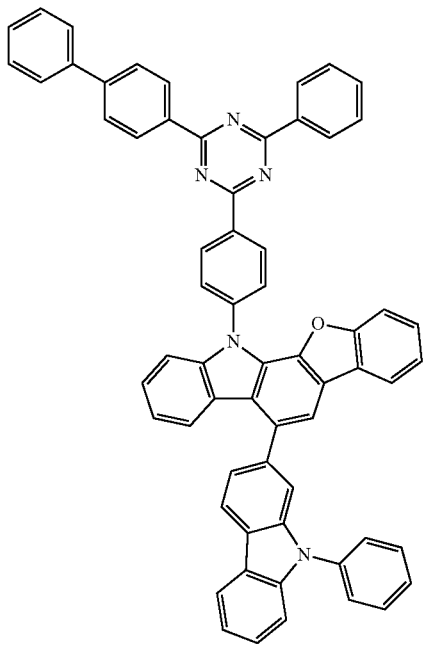

-continued
324
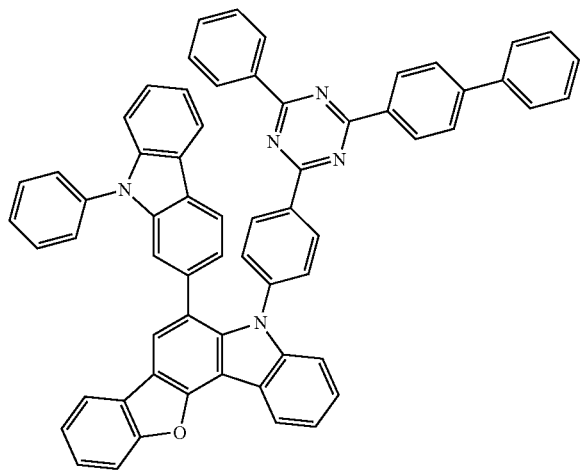
325
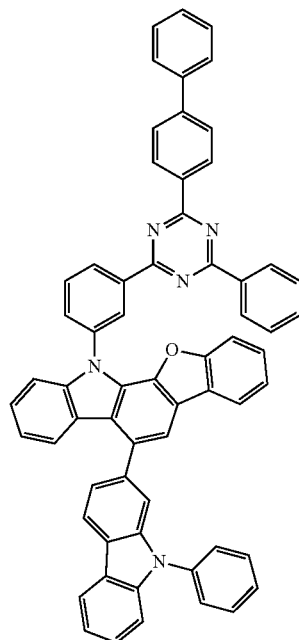
326
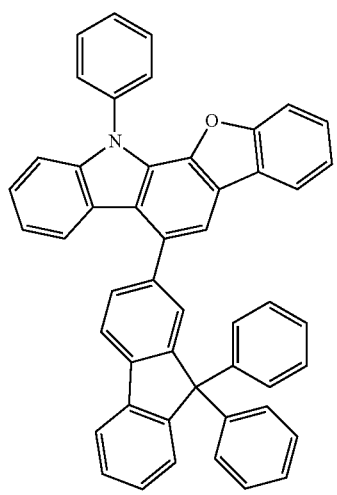
327
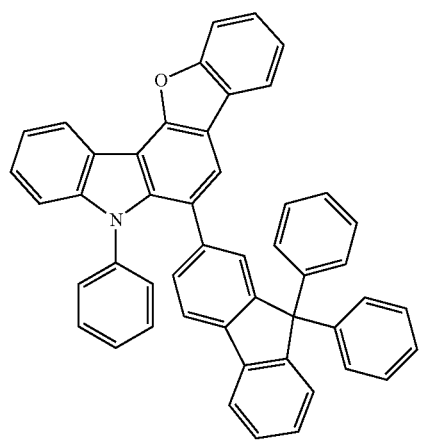

-continued
328
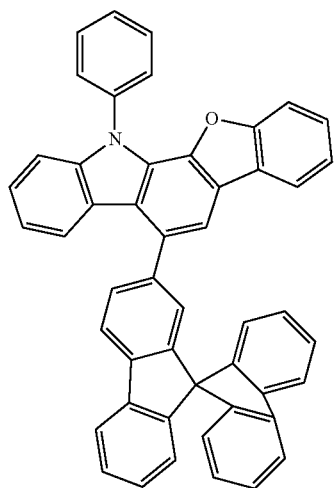
329
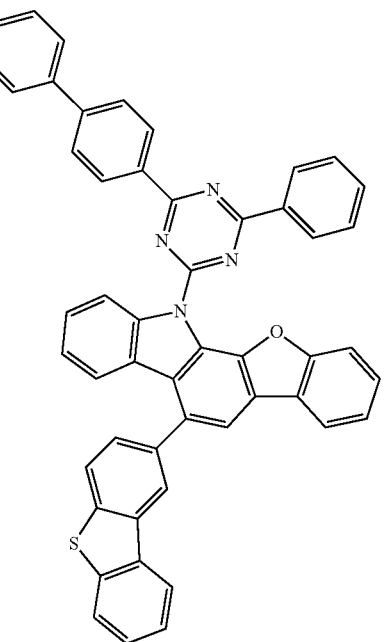
330
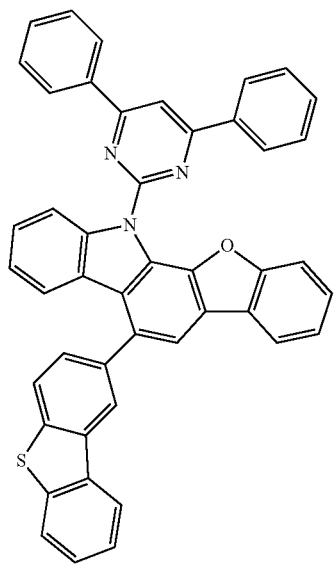
331
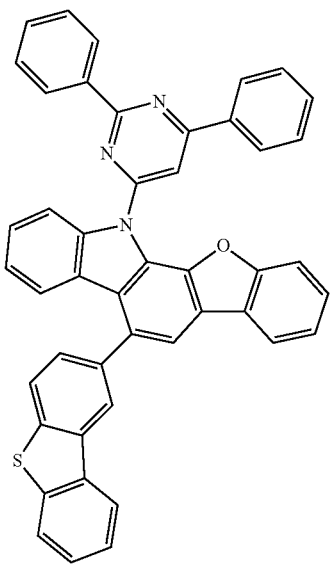

332
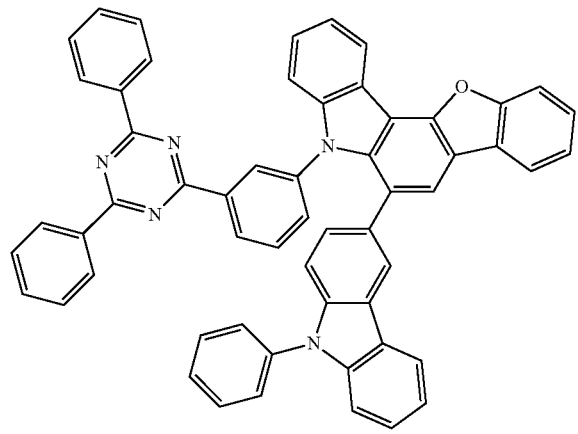
333
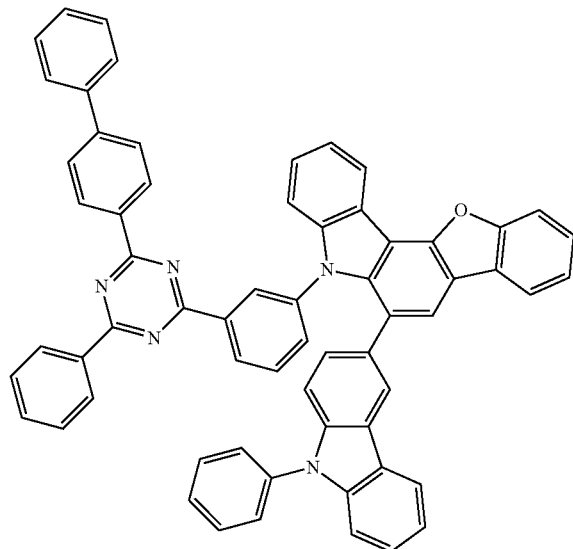
334
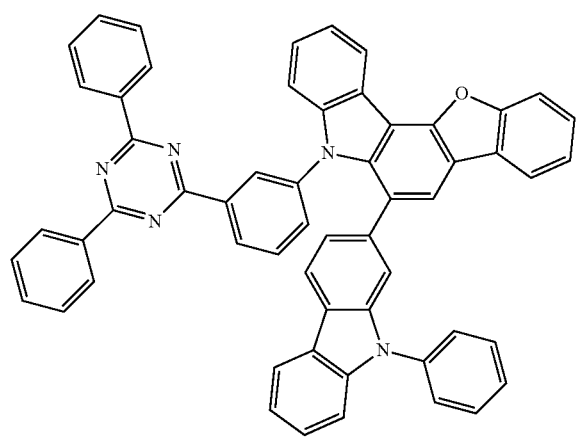
335
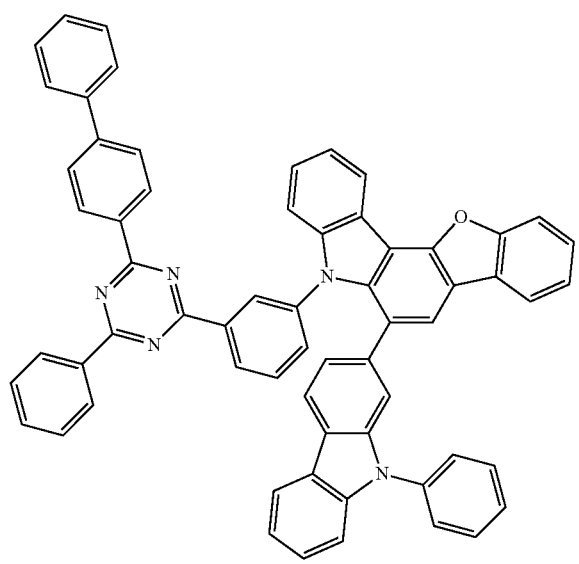

-continued
336
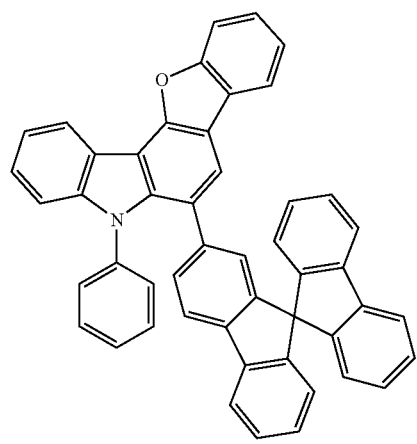
337
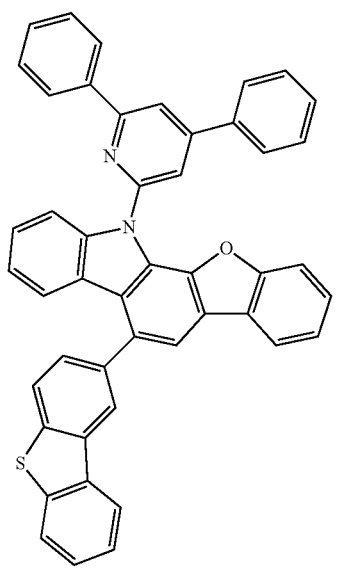
338
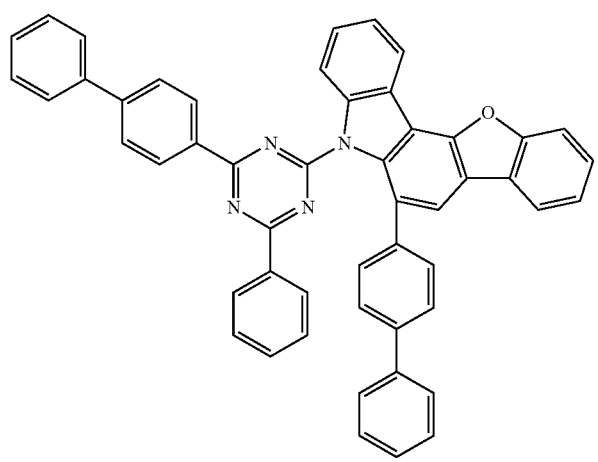
339
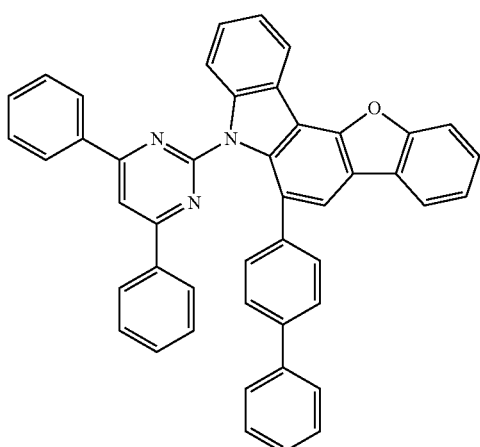
340
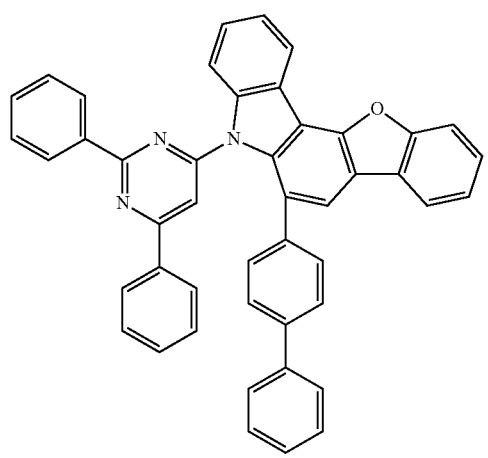
341
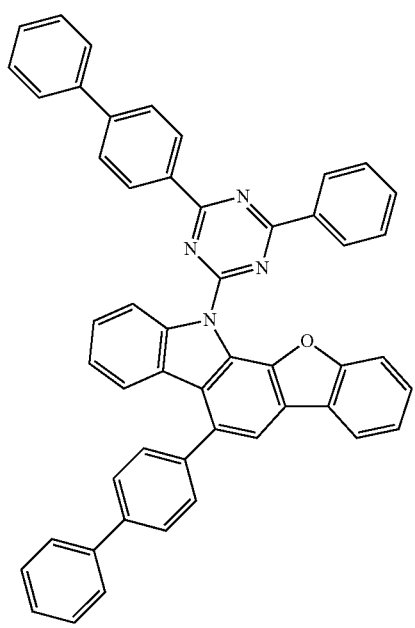

-continued
342
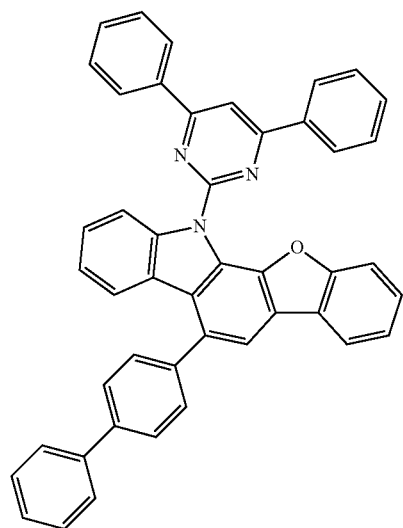
343
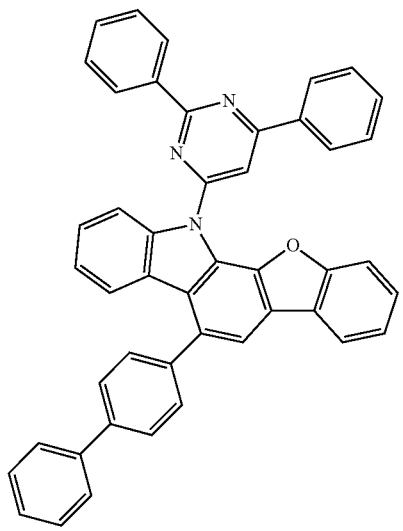
344
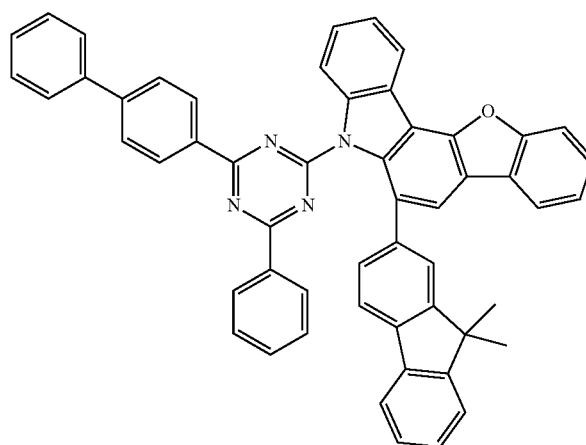
345
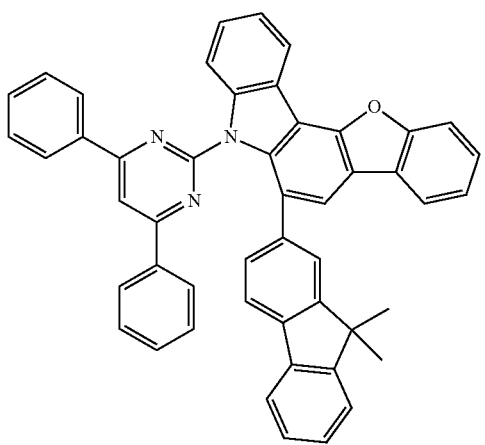
346
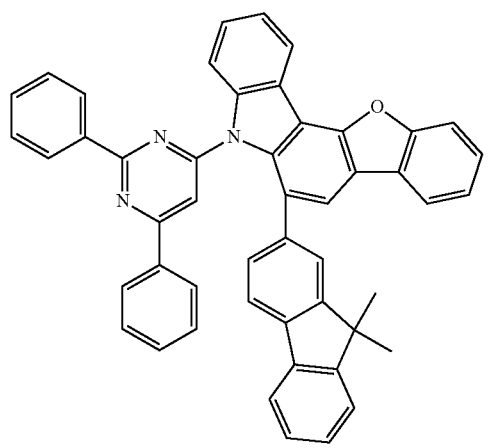
347
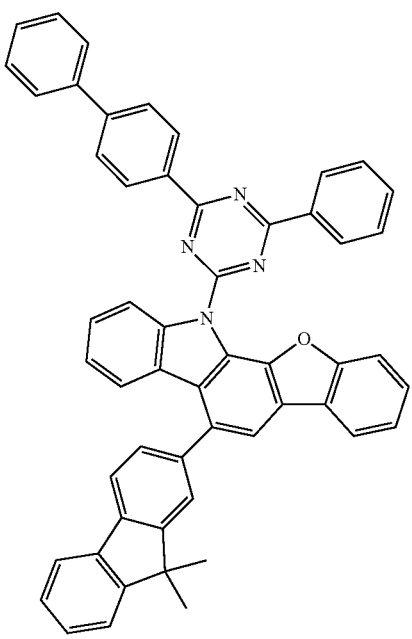

-continued
348
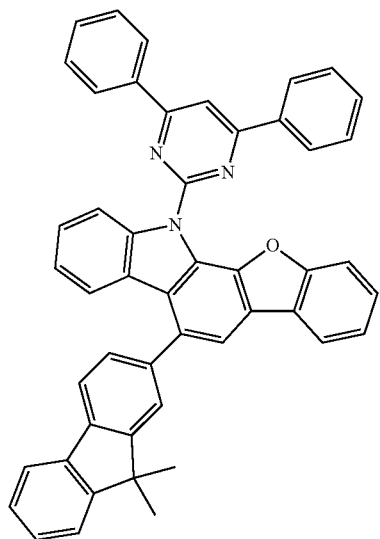
349
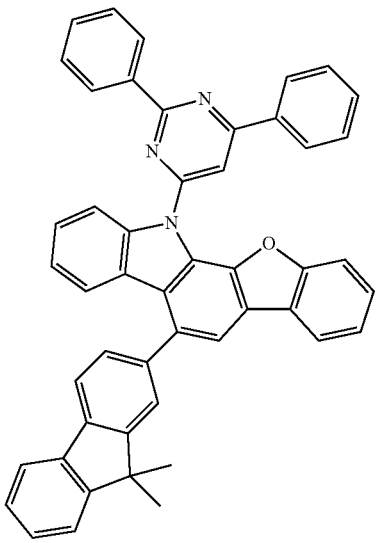
350
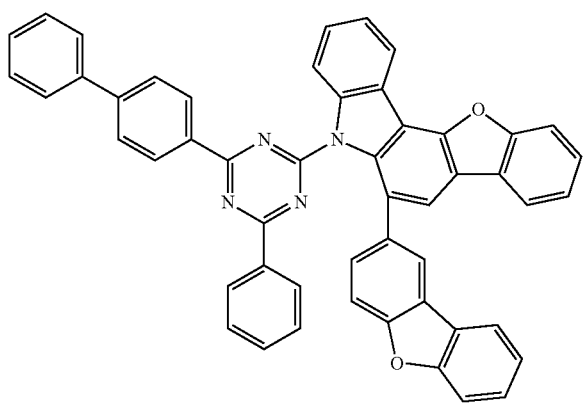
351
352
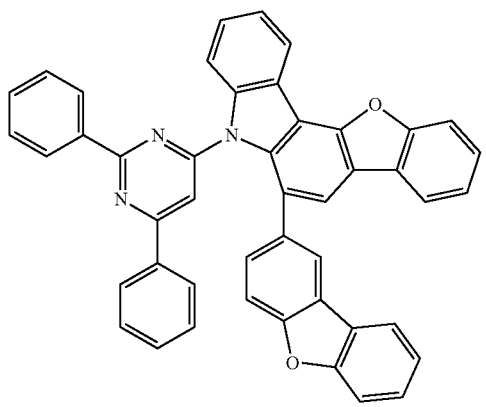
353
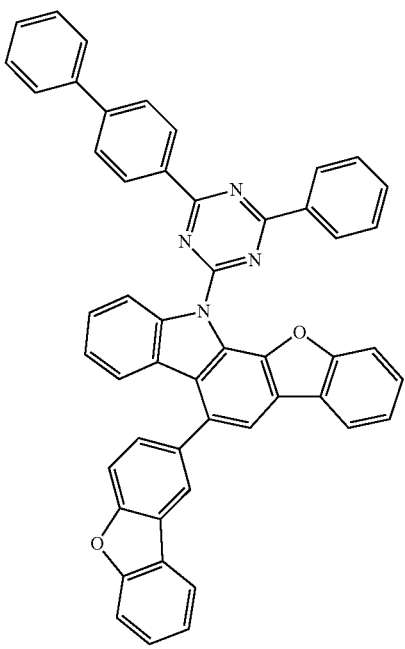

-continued
354
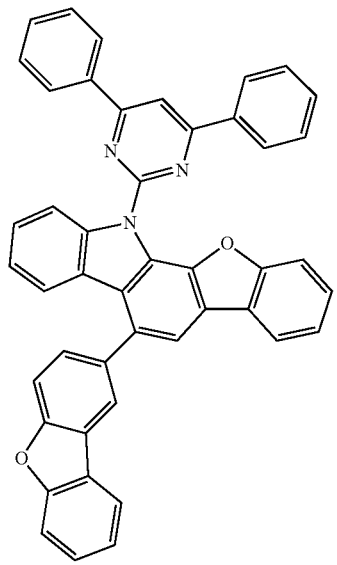
355
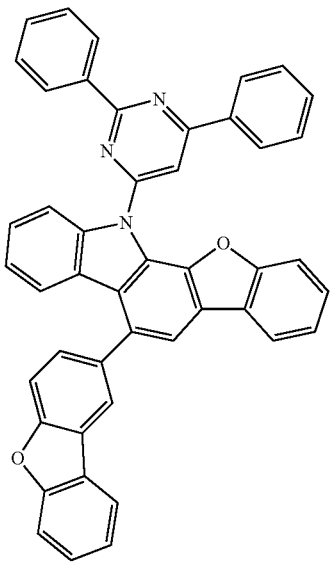
356
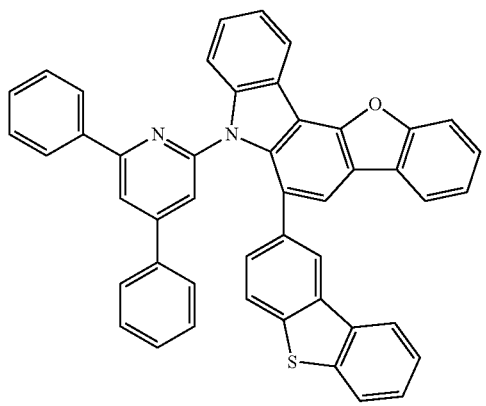
357
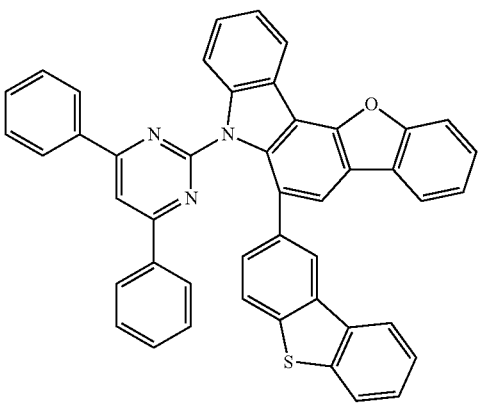
358
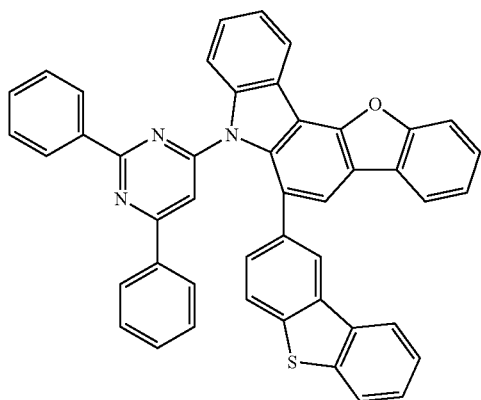
359
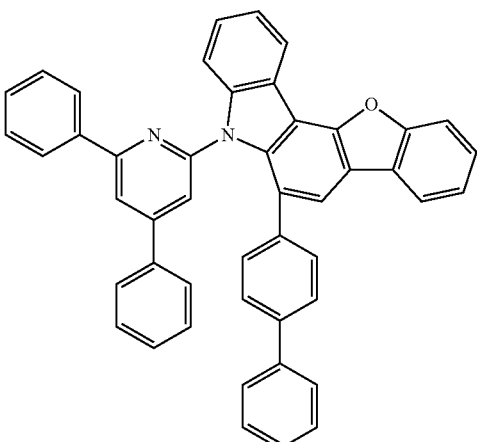

-continued
513
360
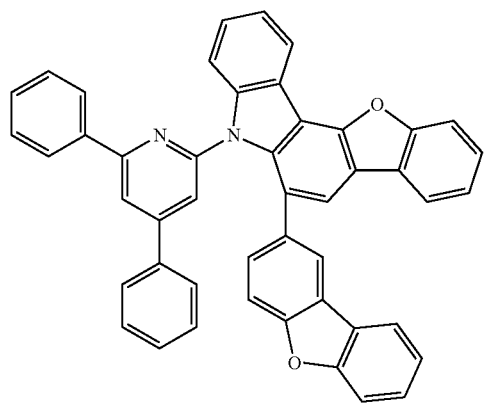
361
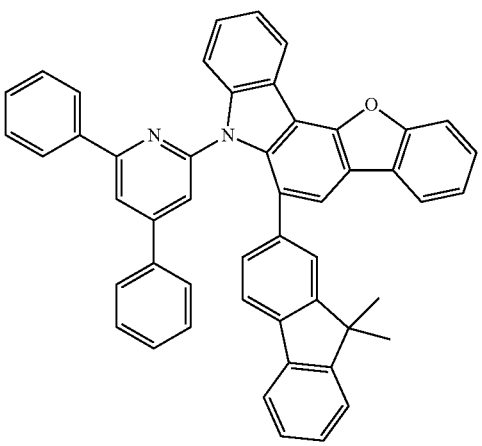
362
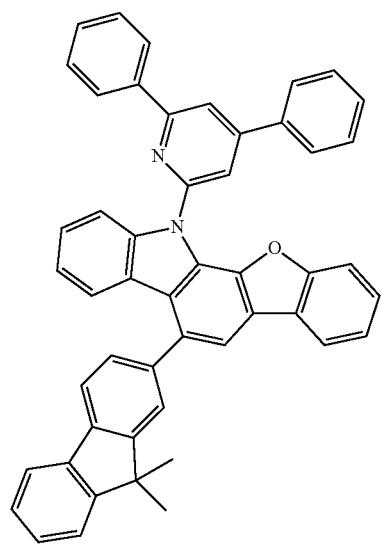
514
363
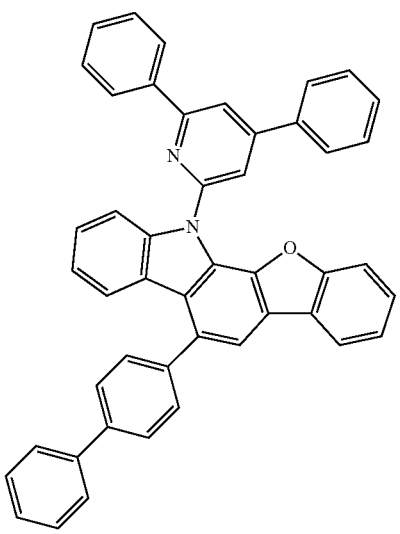
364
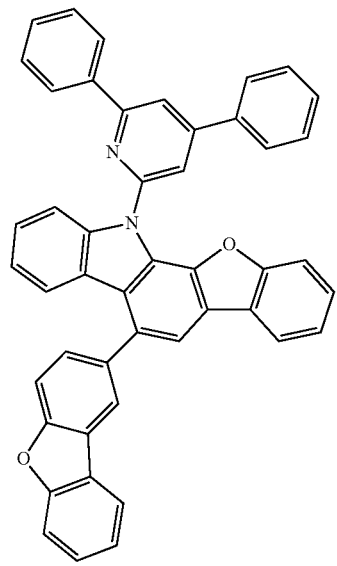
365
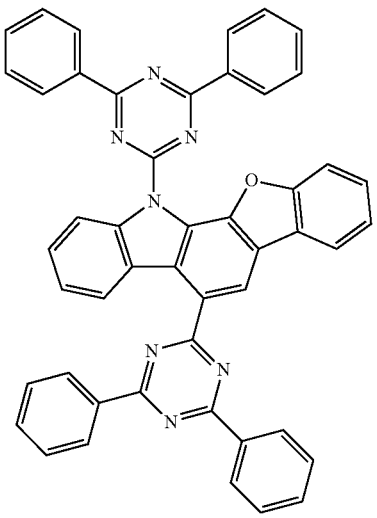

-continued
515
366
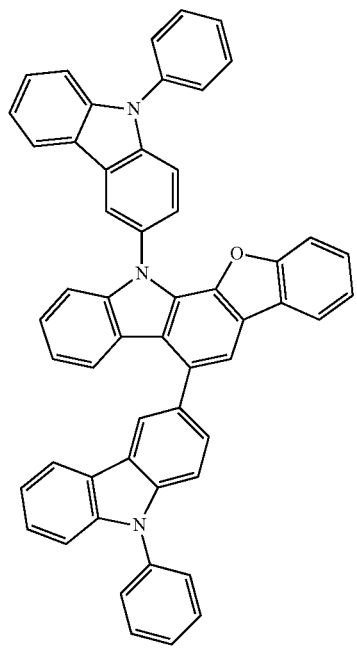
516
367
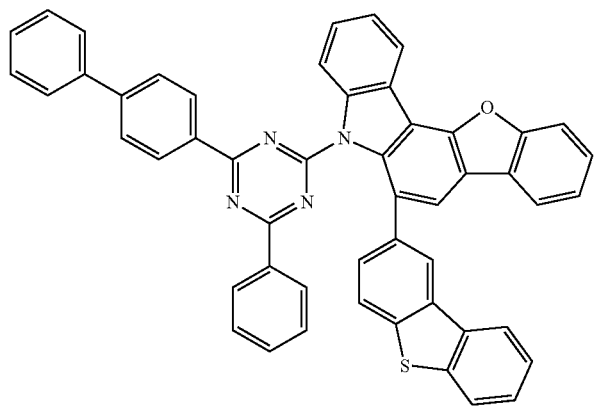
368
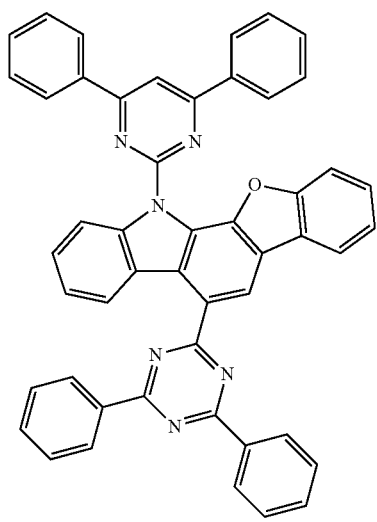
369
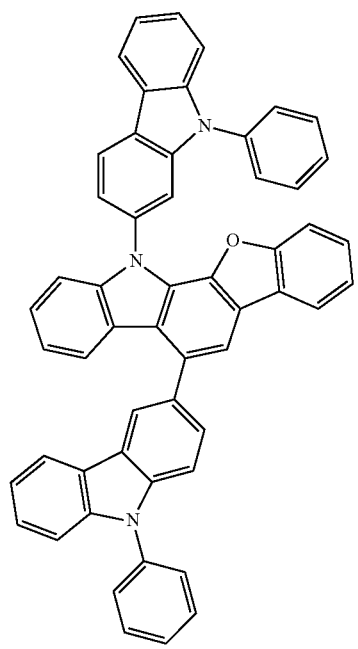

-continued
370
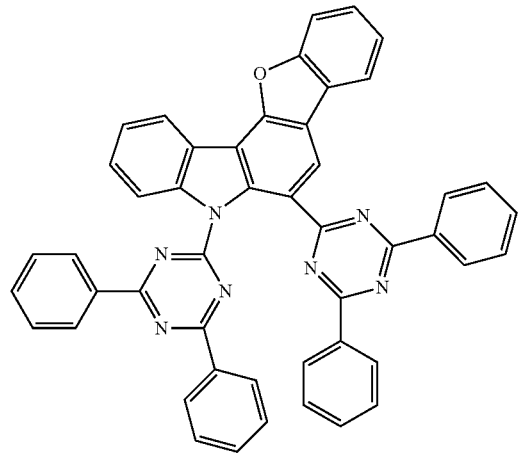
371
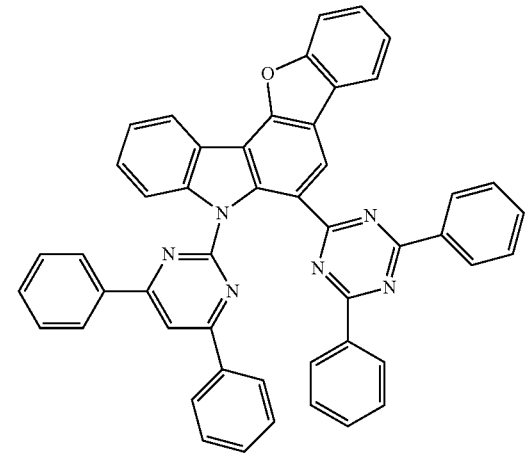
372
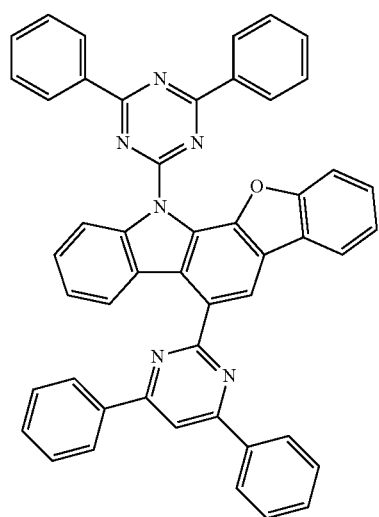
373
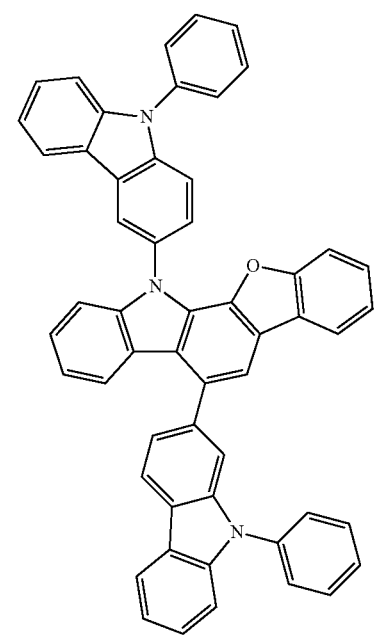
374
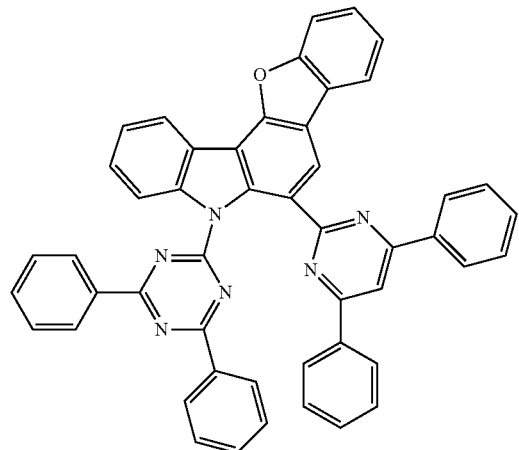
375
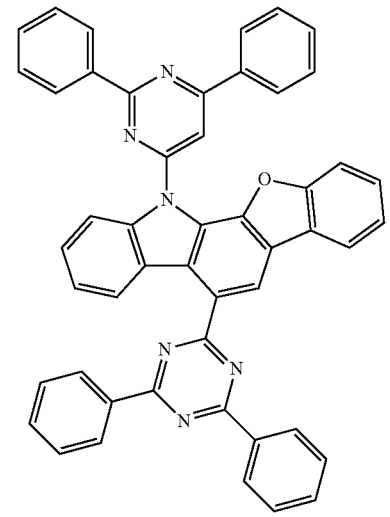

-continued
376
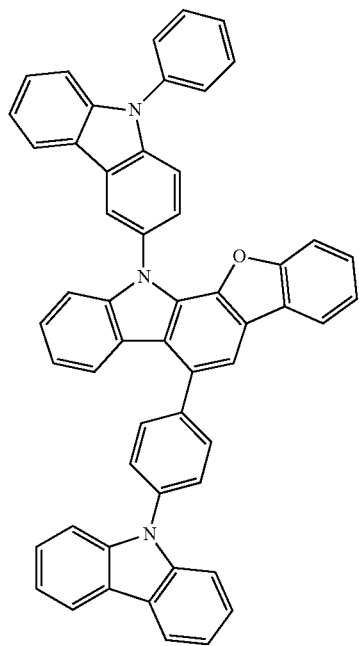
377
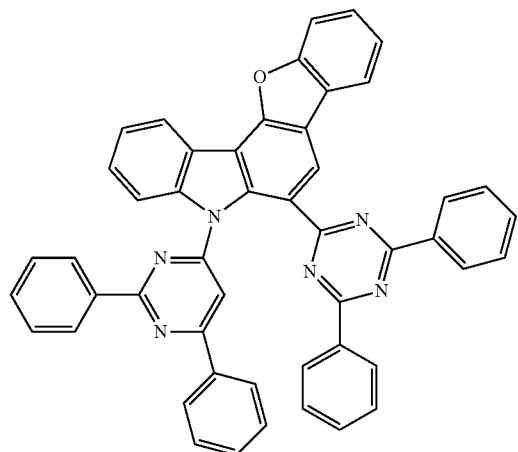
378
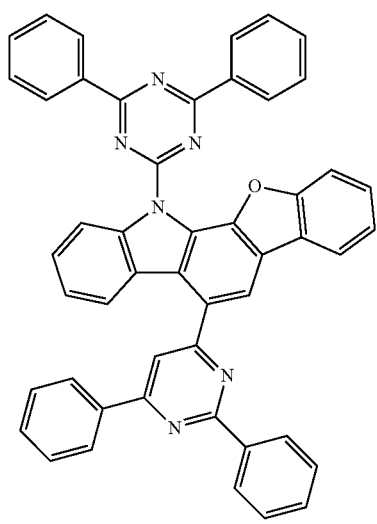
379
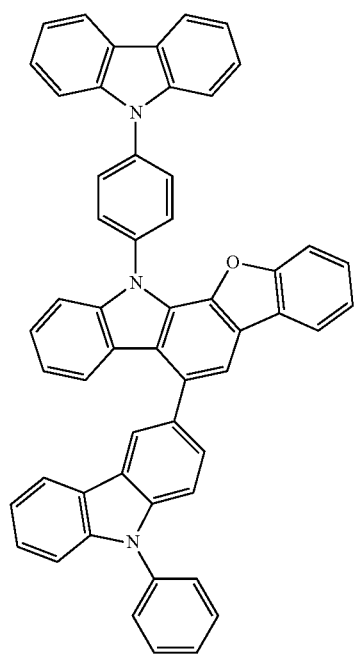

-continued
521
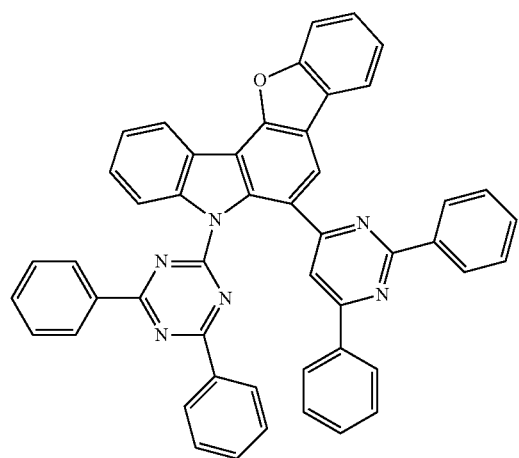
380
522
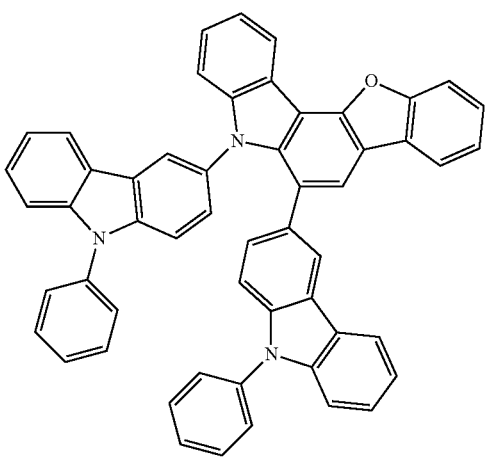
381
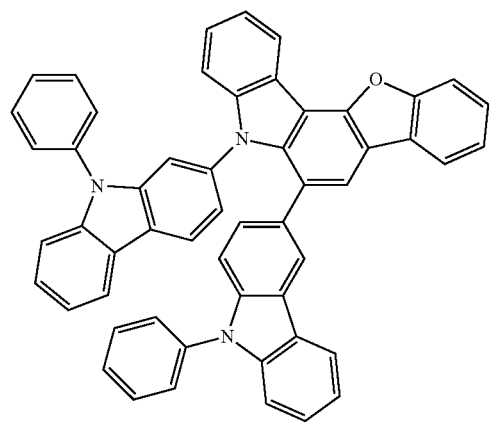
382
383
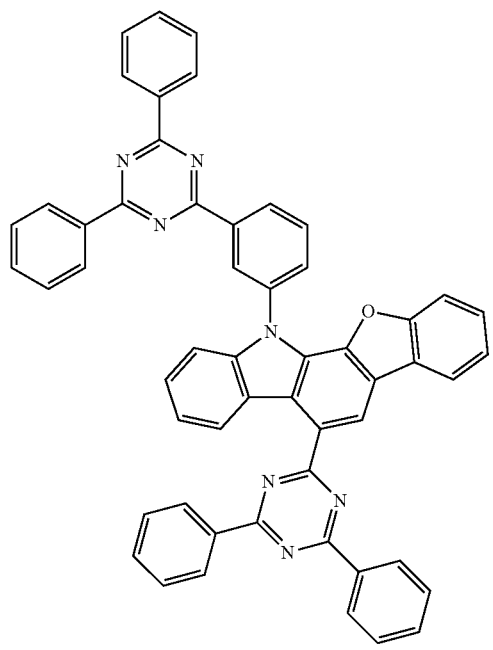
384
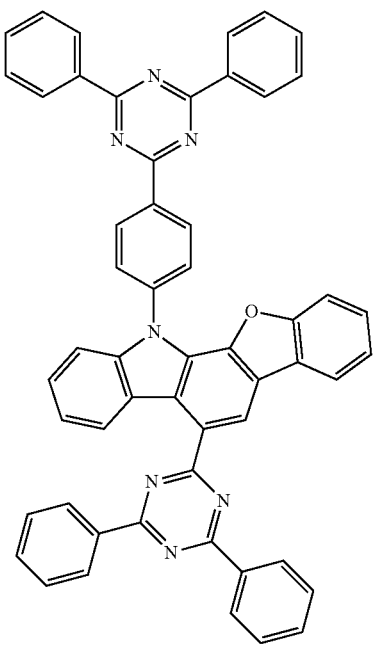
385

523
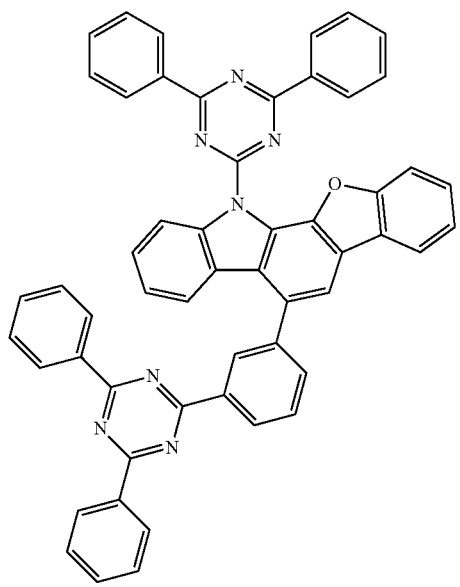
524
-continued
386
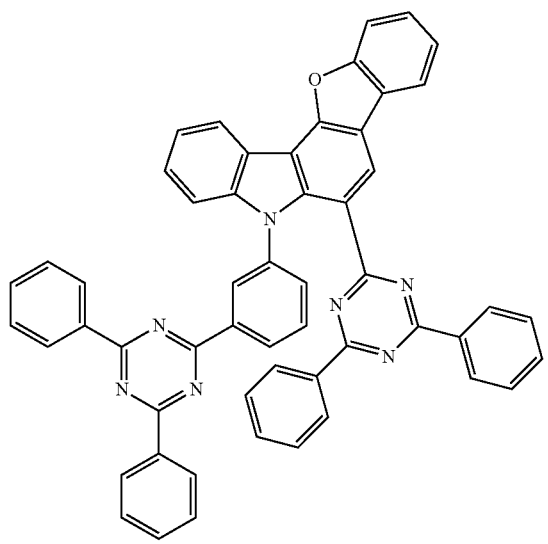
387
388
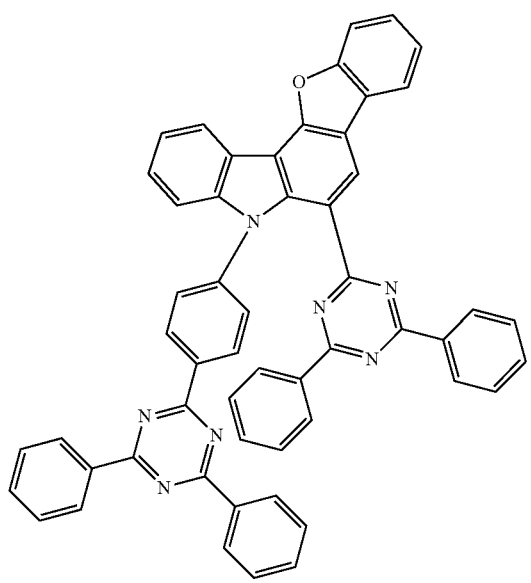
389
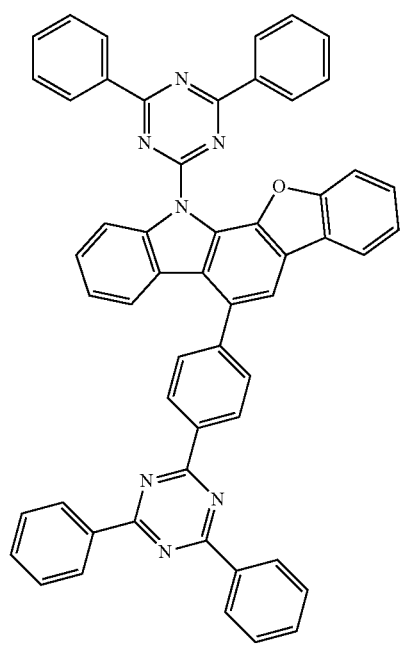

525
526
-continued
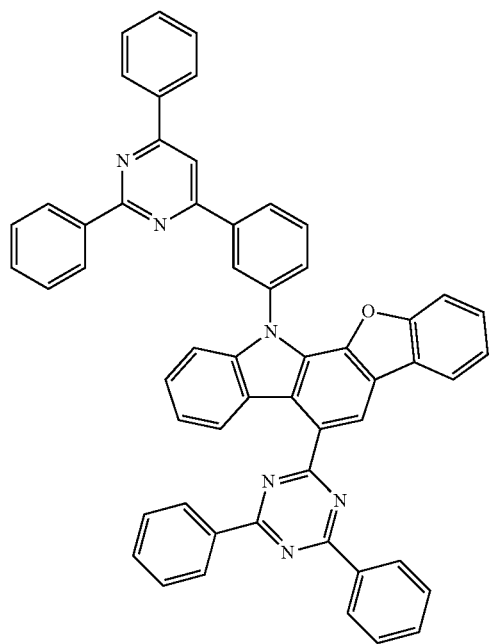
390
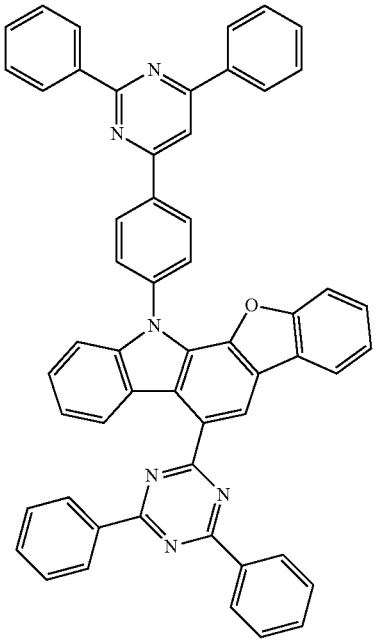
391
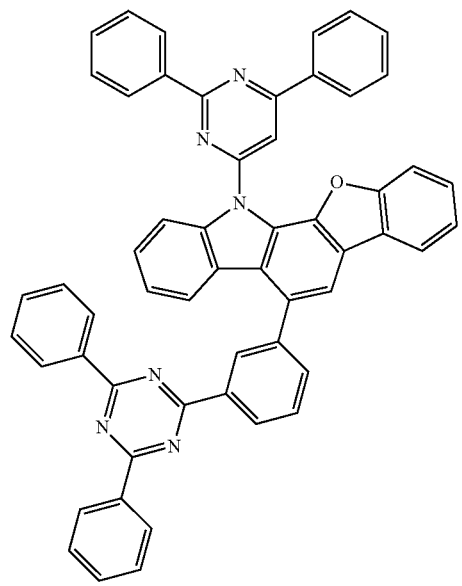
392
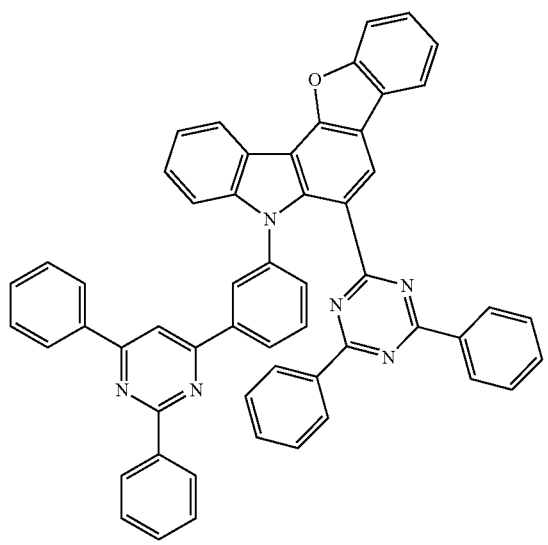
393

527 528
-continued
394 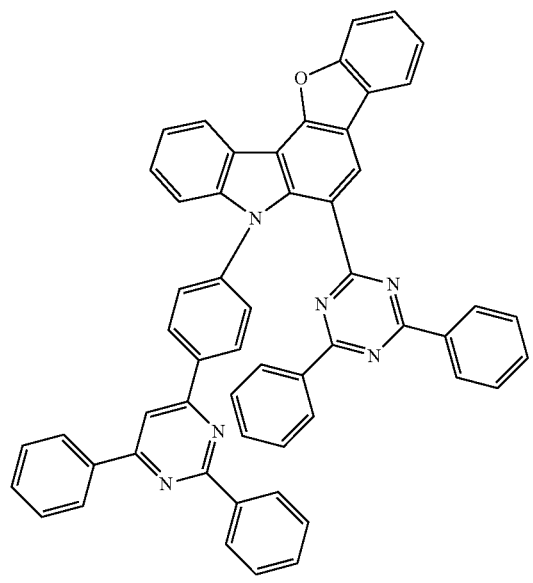 395 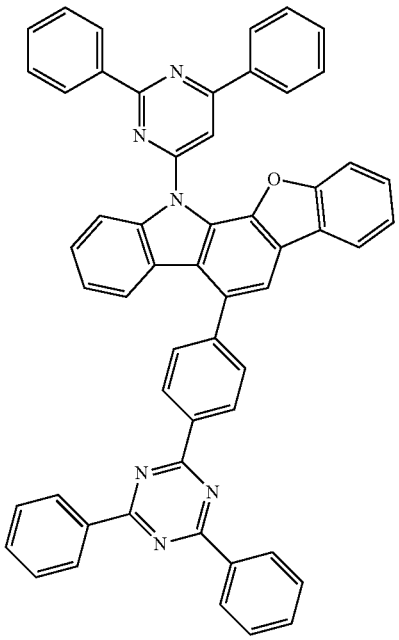
396 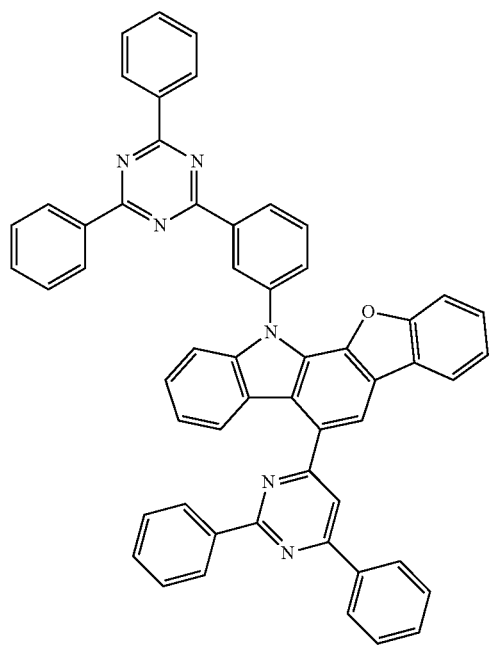 397 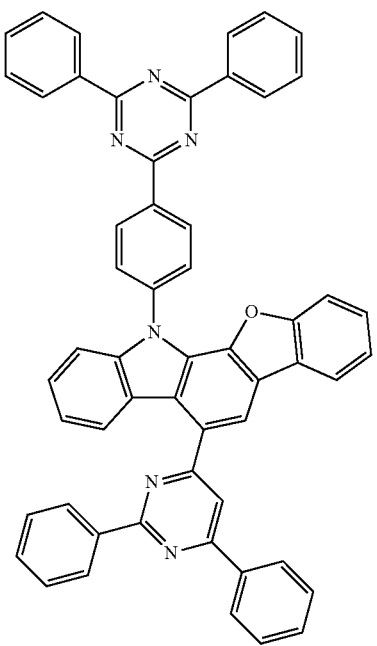

-continued
529
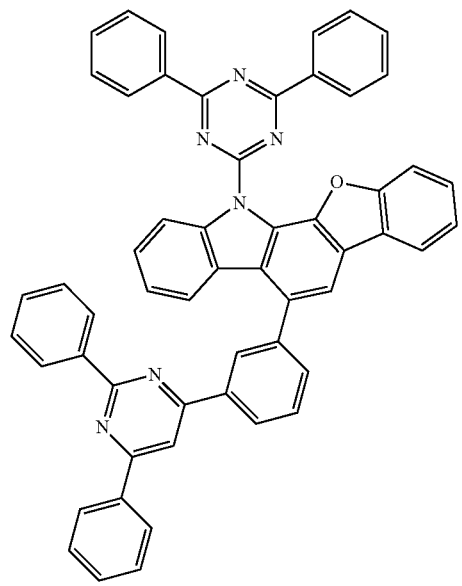
398
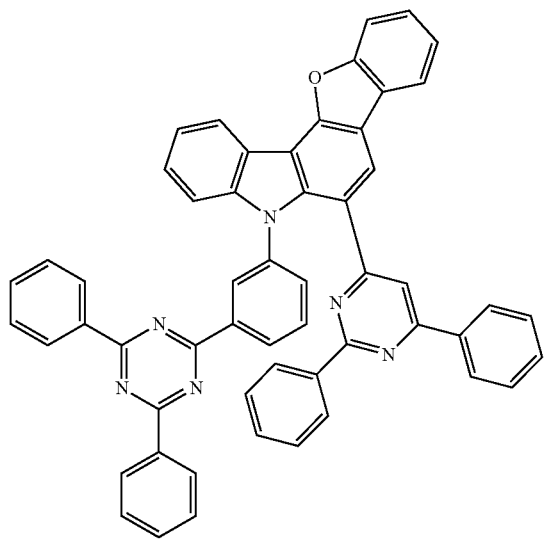
530
399
400
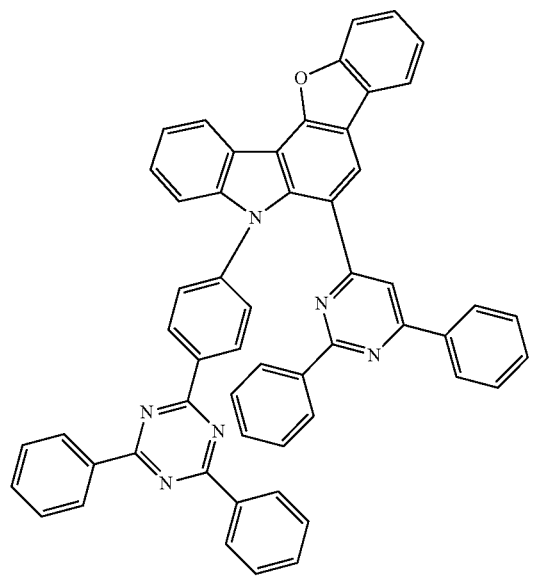
401
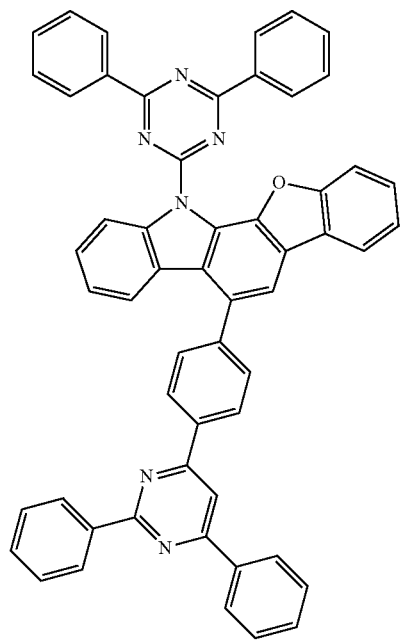

-continued
531
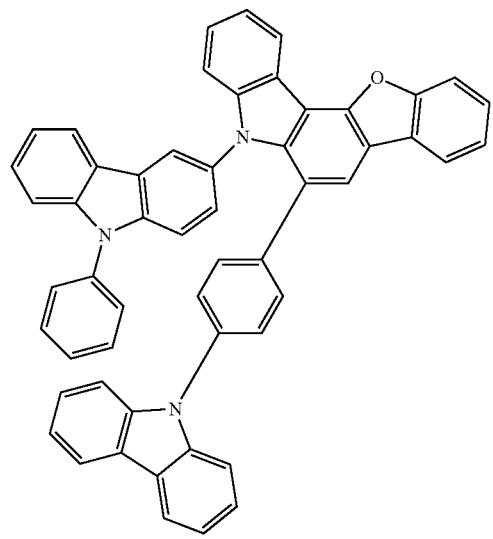
402
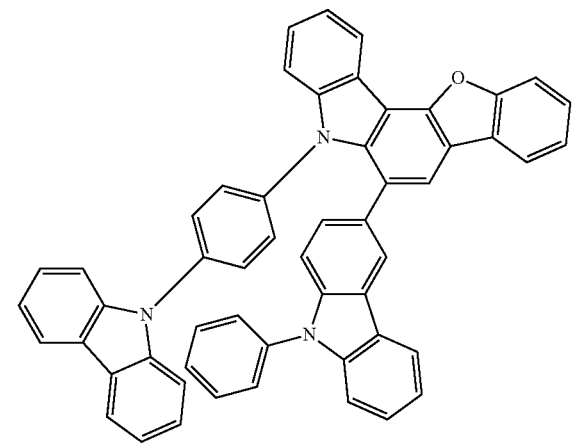
403
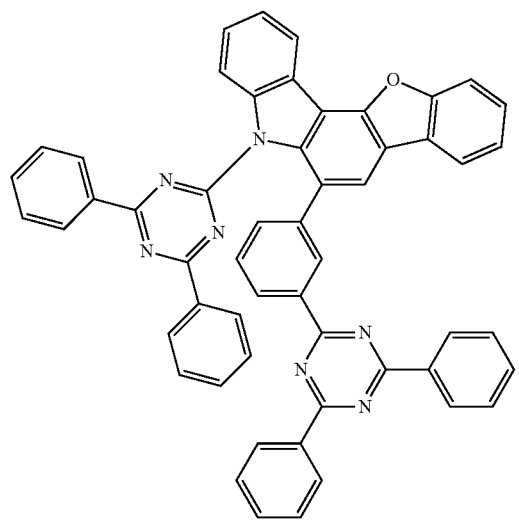
404
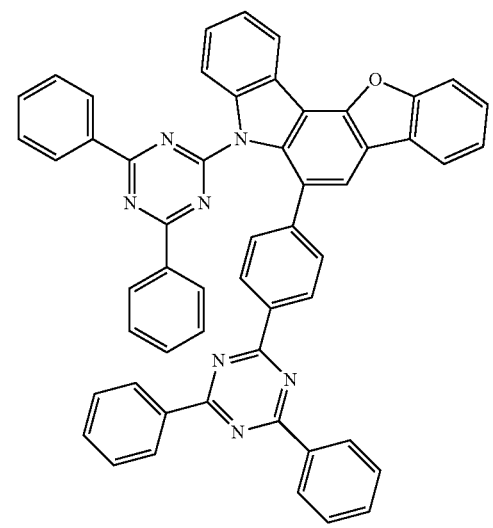
405
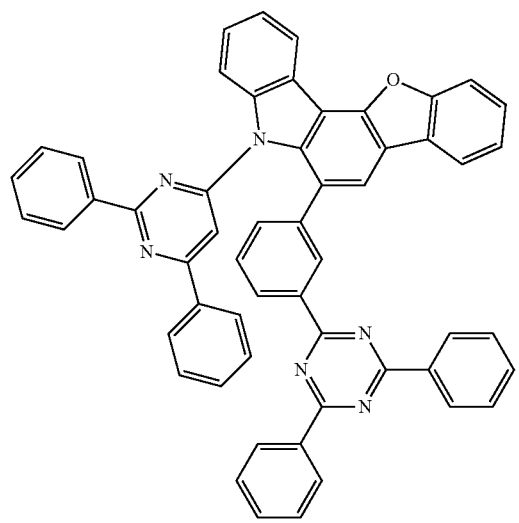
406
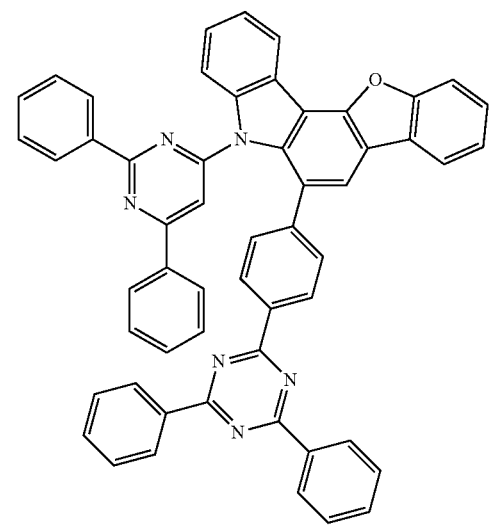
407
532

-continued
408
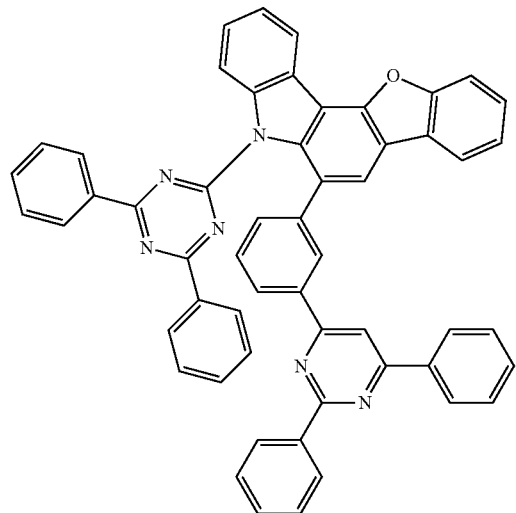
409
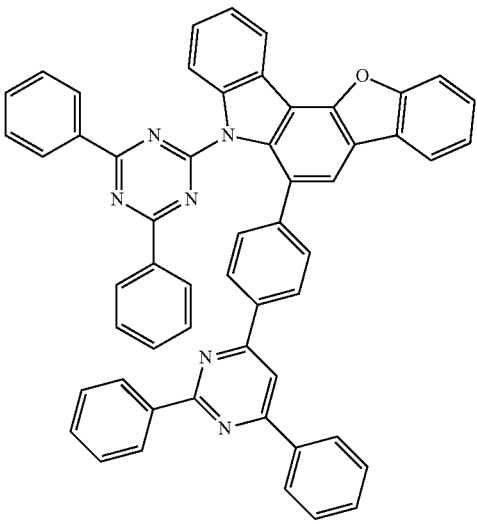
410
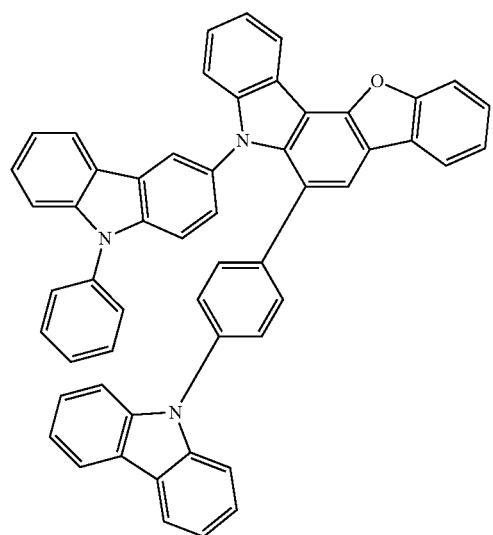
411
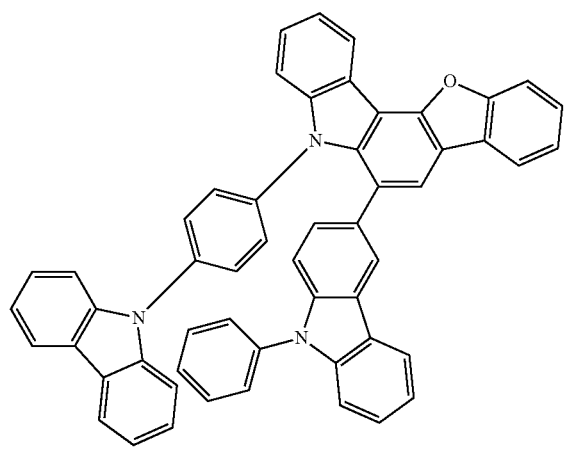
412
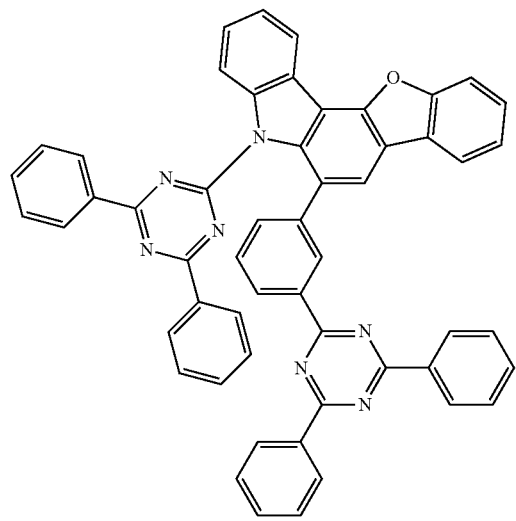
413
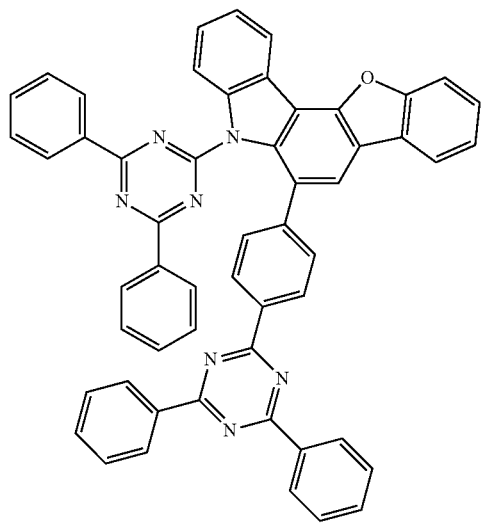

-continued
414
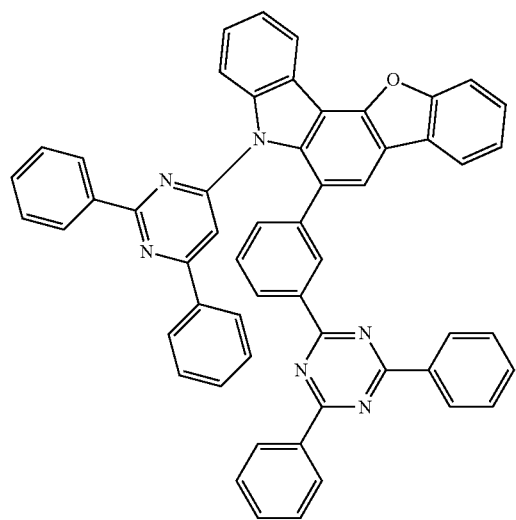
415
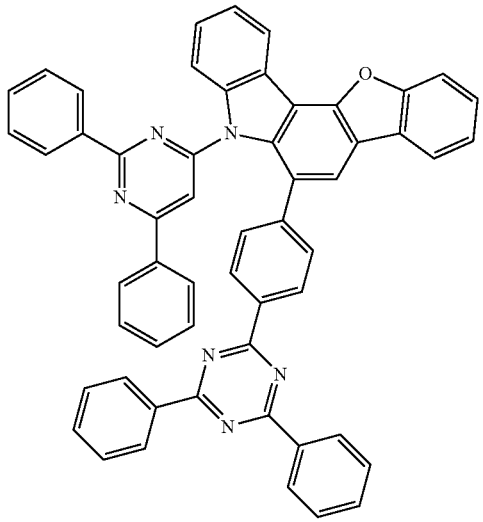
416
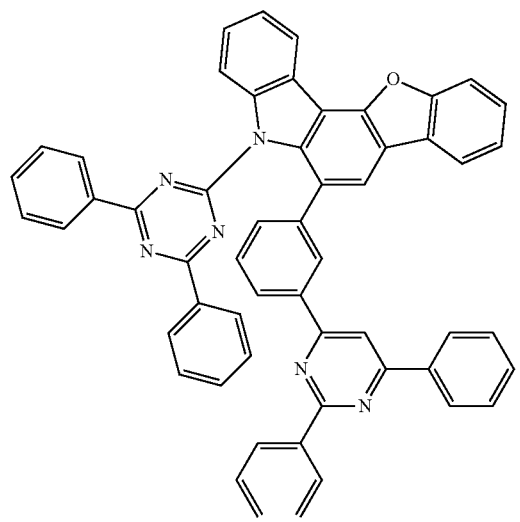
417
418
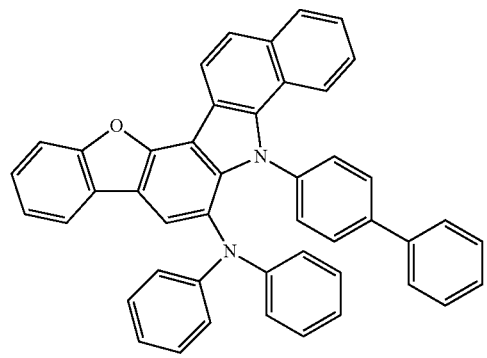
419
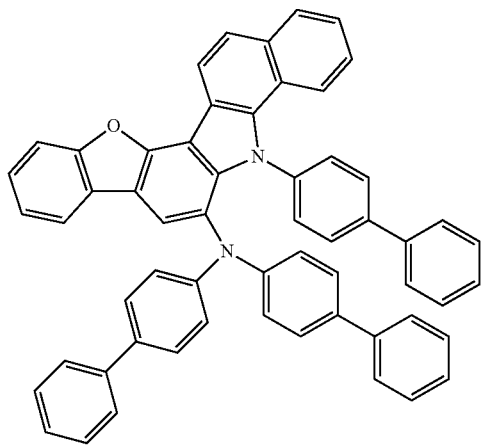

-continued
420
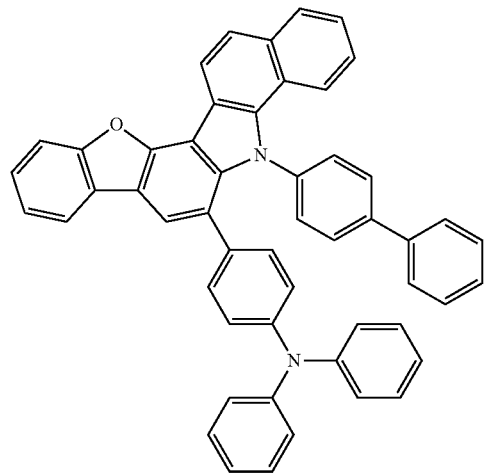
421
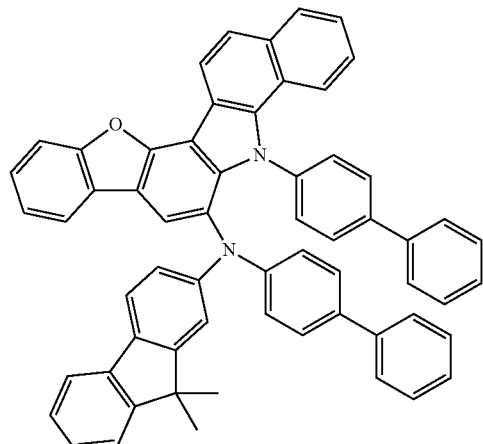
422
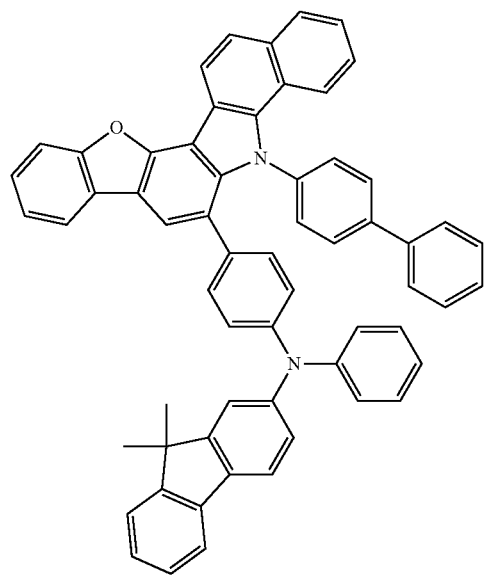
423
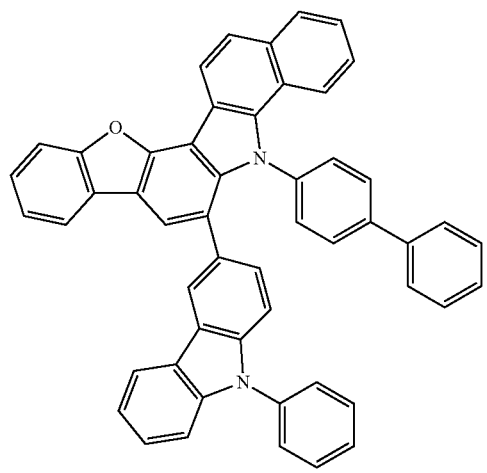
424
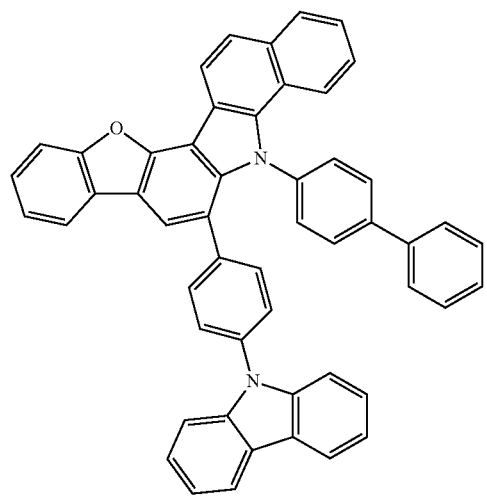
425
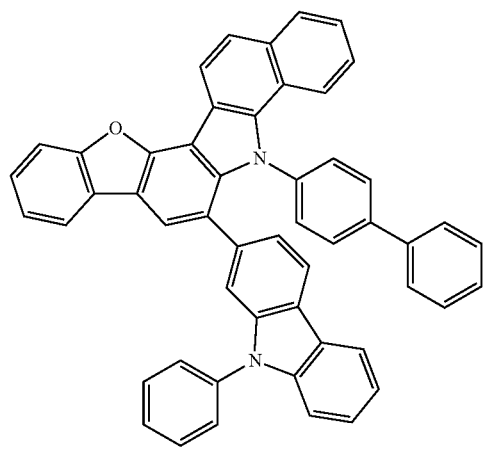

-continued
426
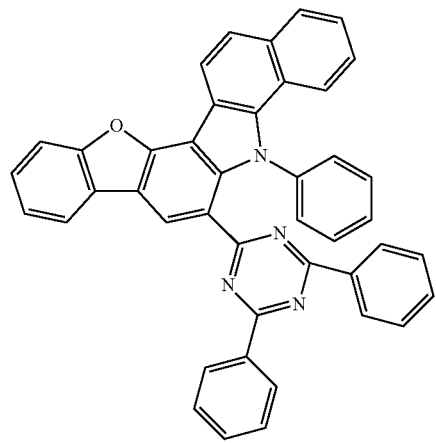
427
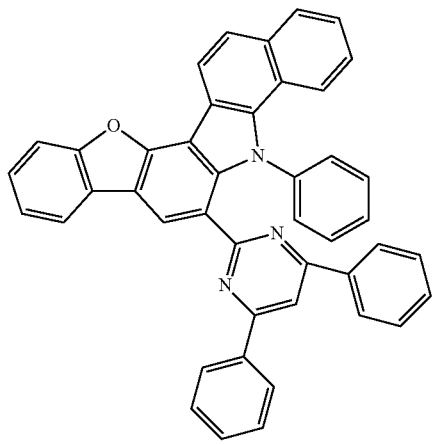
428
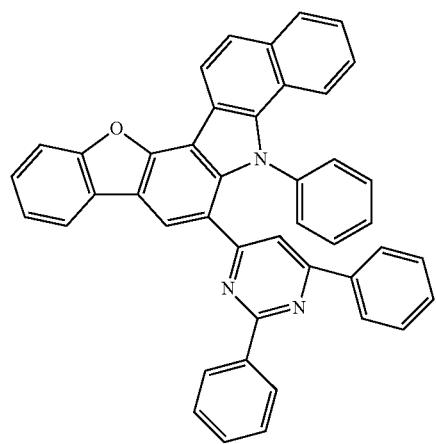
429
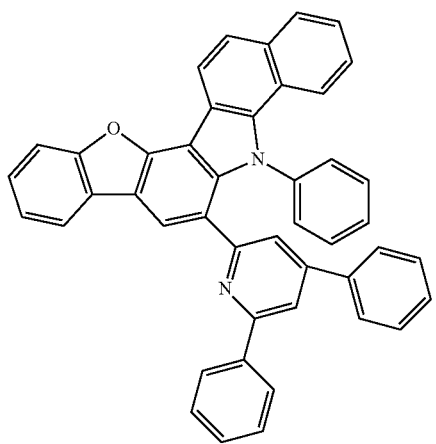
430
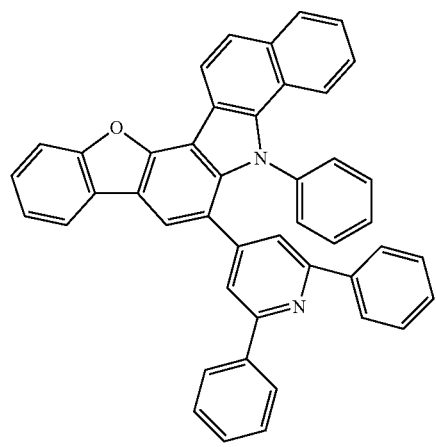
431
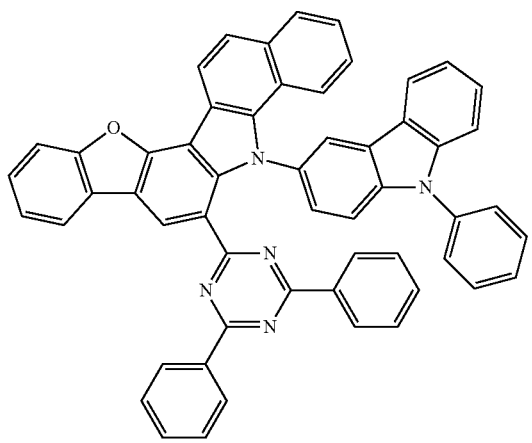

541 542
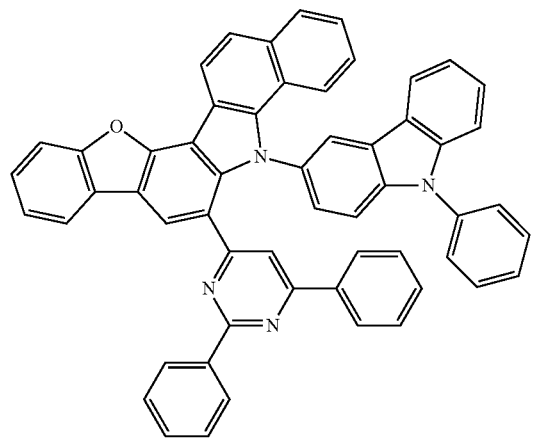
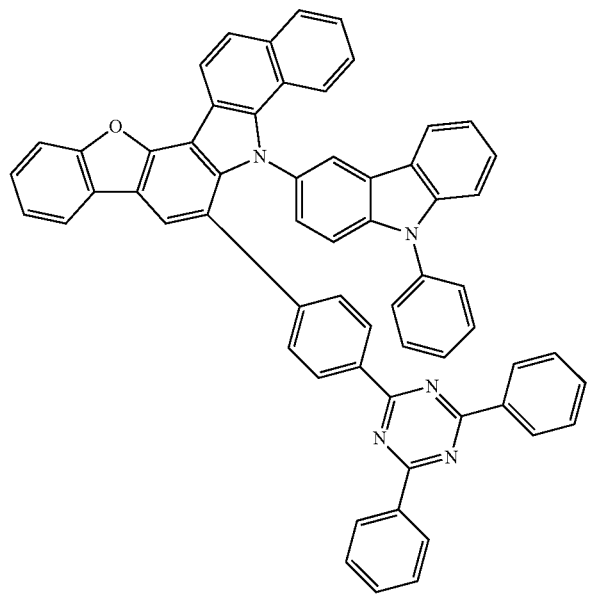
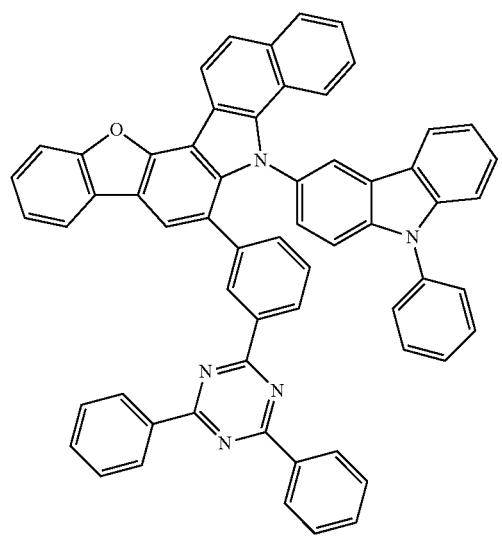
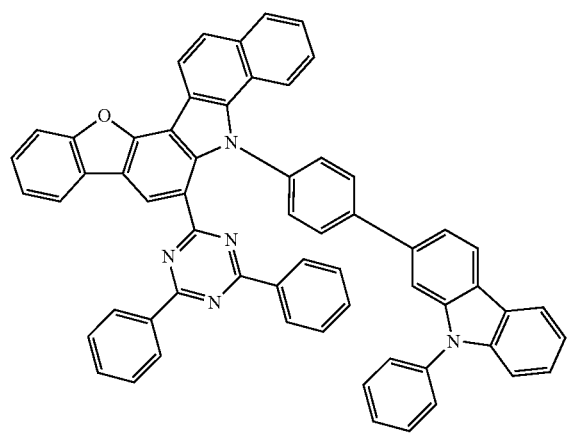
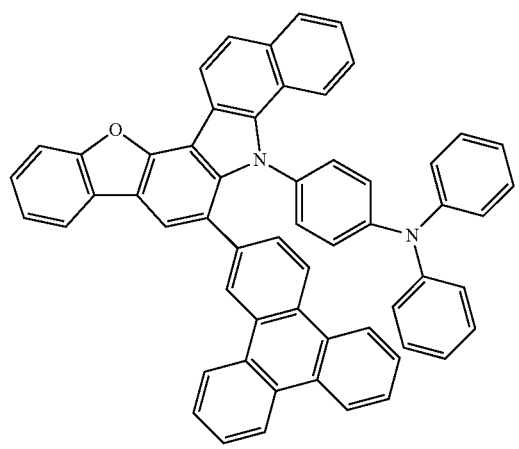

543 544
-continued
438 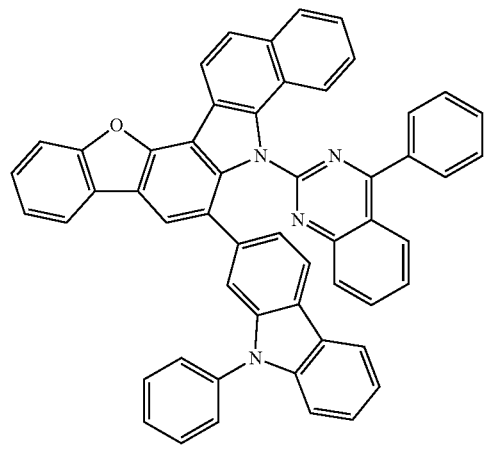 439 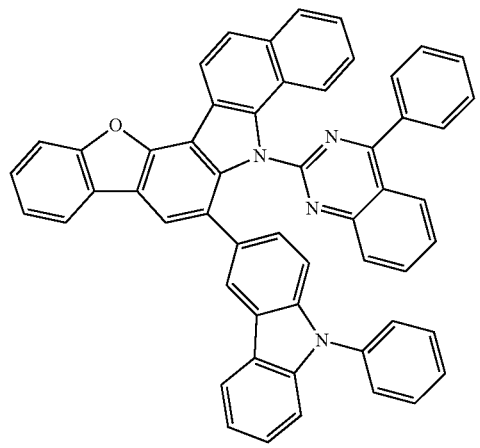
440 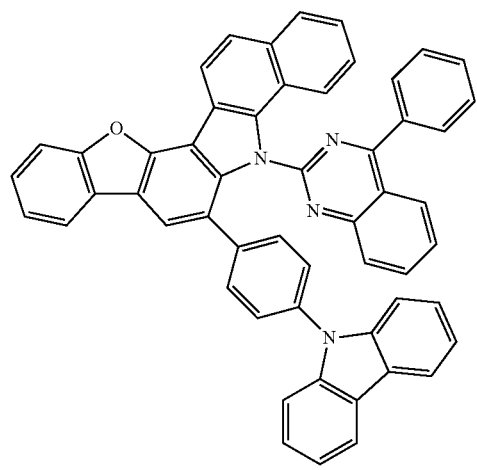 441 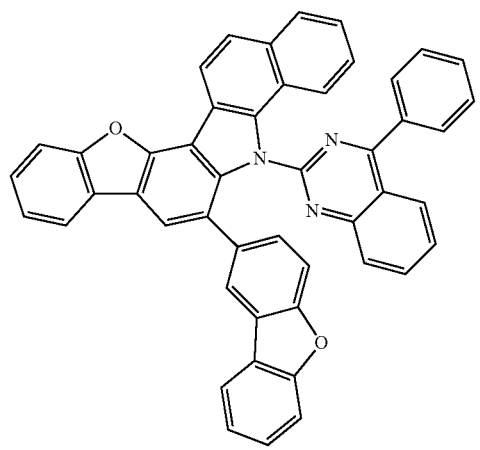
442 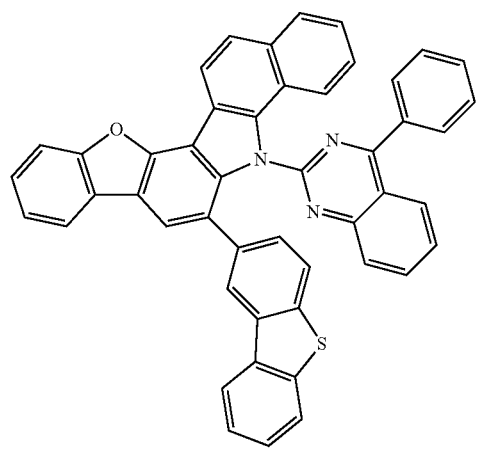 443 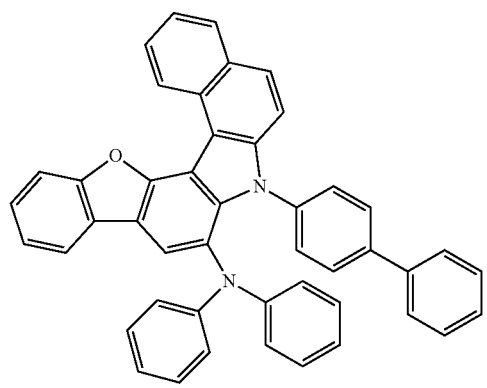

545 546
-continued
444
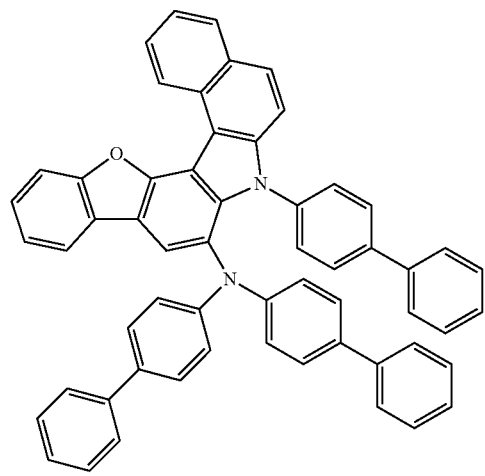
445
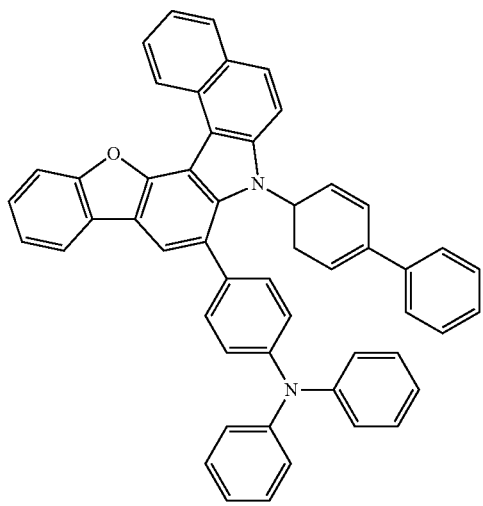
446
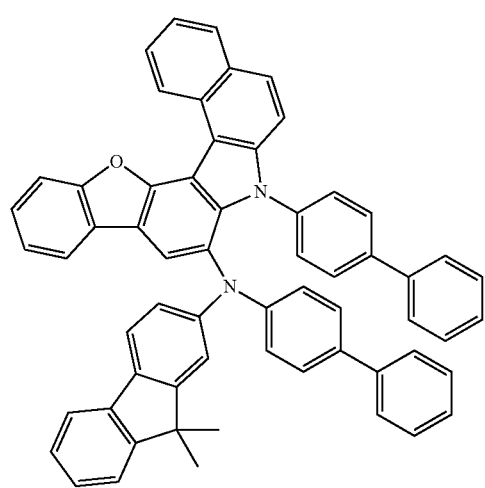
447
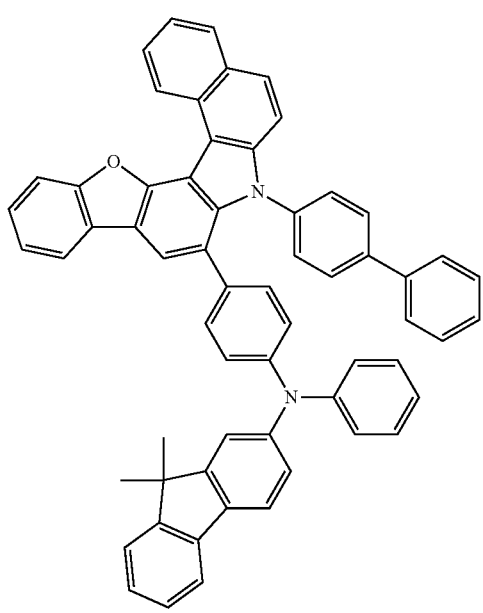
448
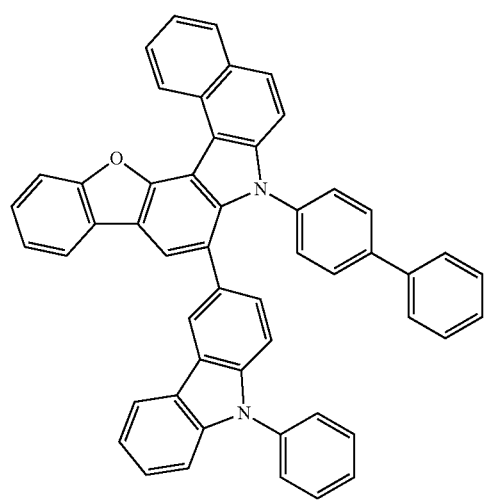
449
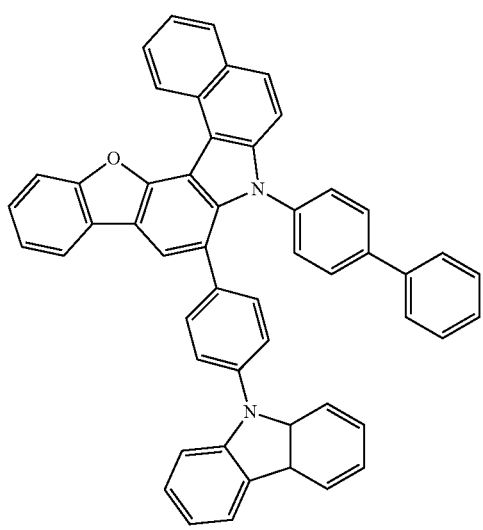

-continued
450
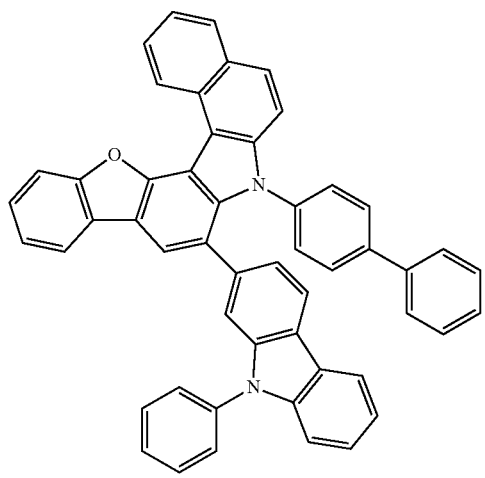
451
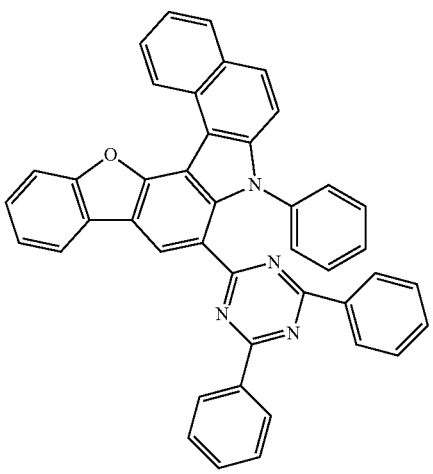
452
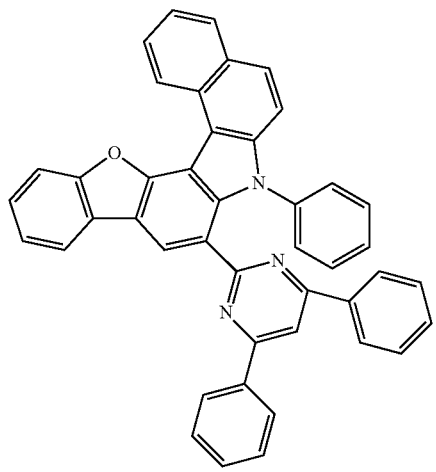
453
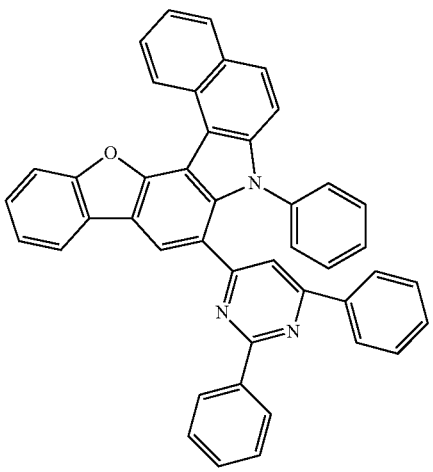
454
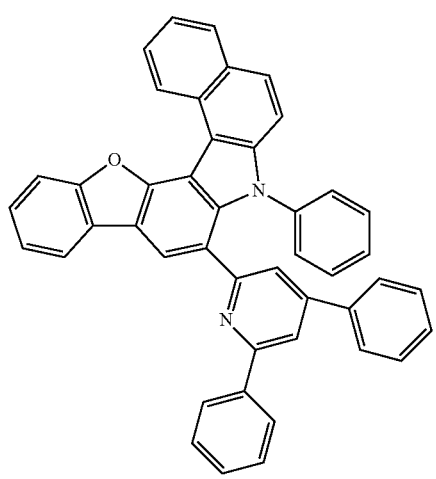
455
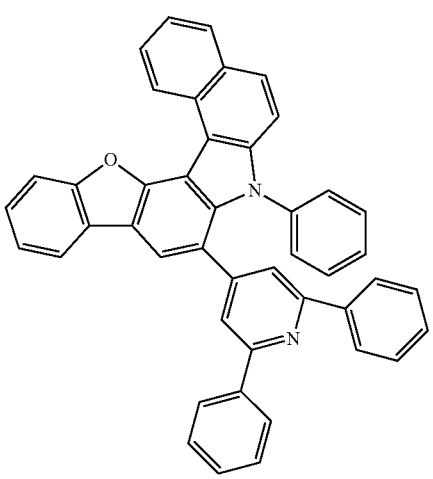

-continued
456
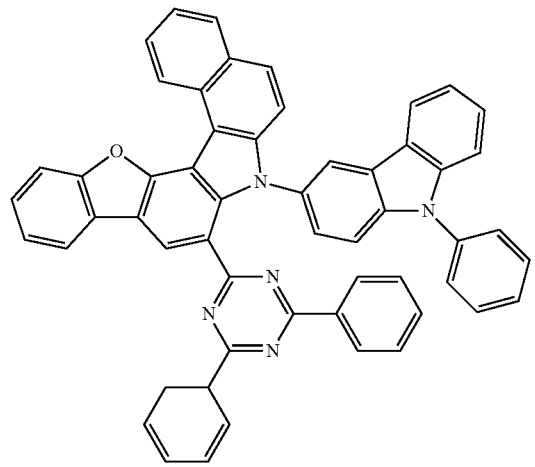
457
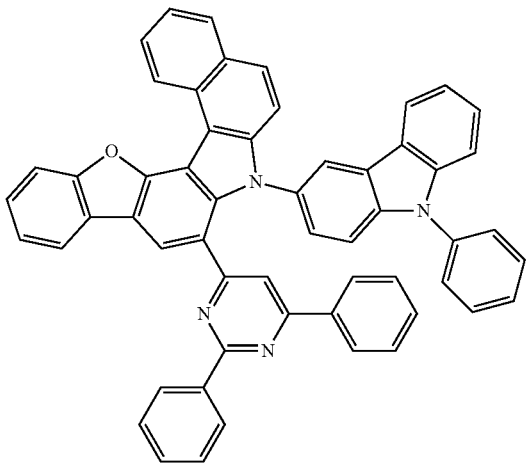
458
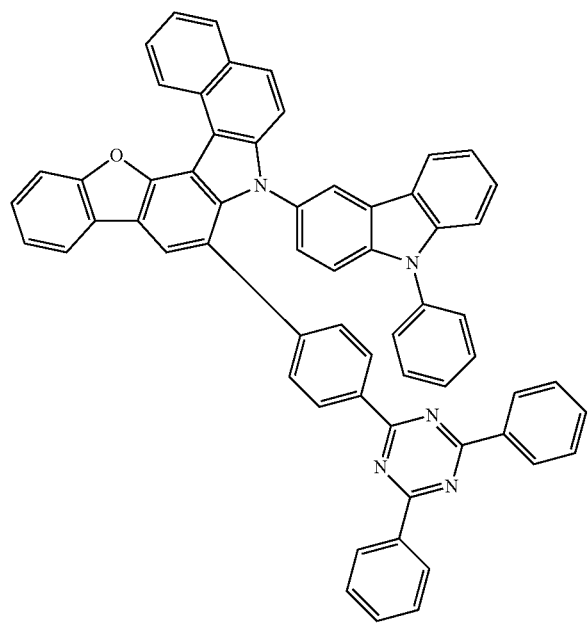
459
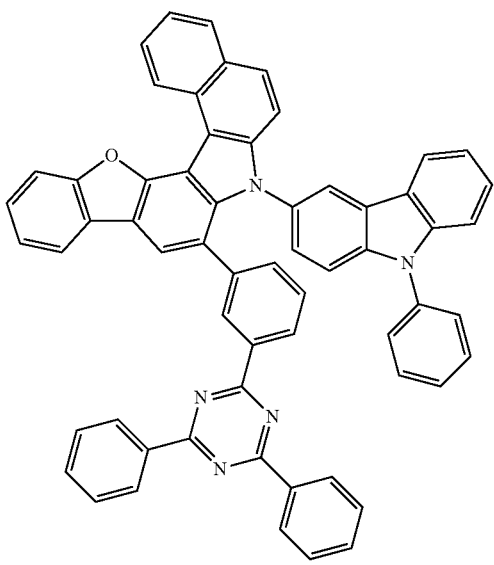
460
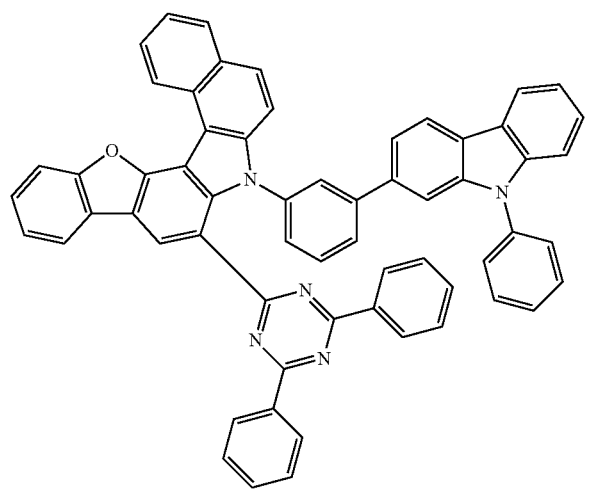

| 551 | 552 |
|---|---|
| 461 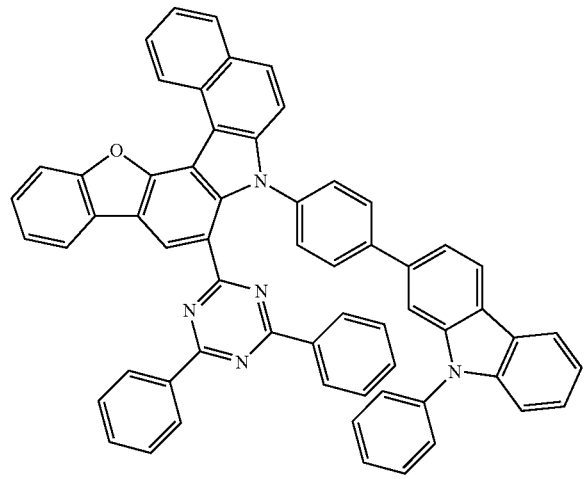 | 462 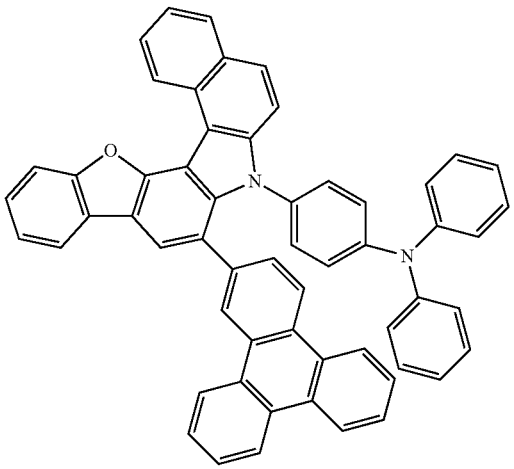 |
| 463 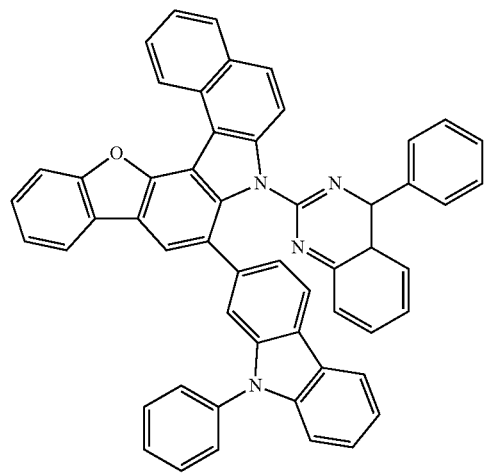 | 464 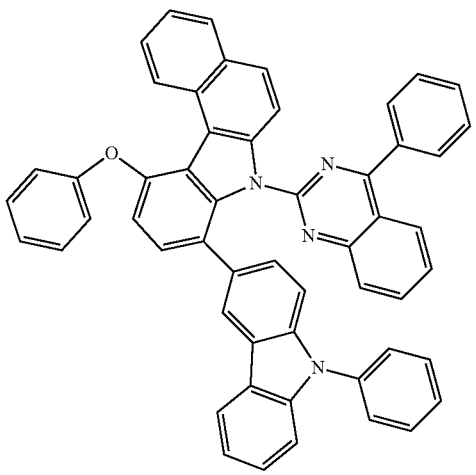 |
| 465 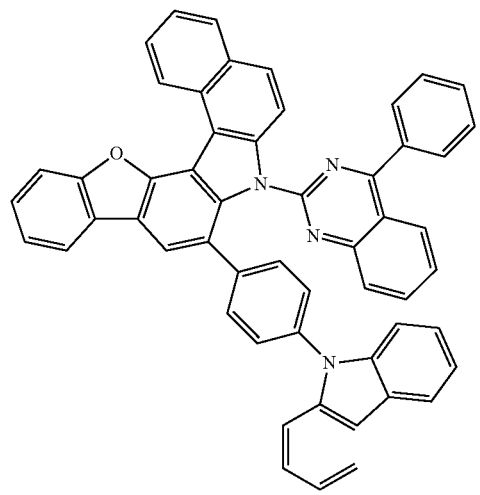 | 466 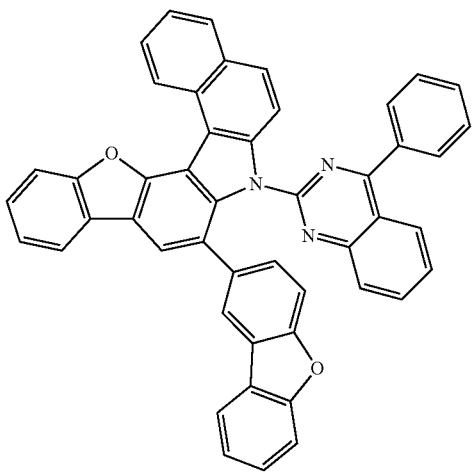 |

-continued

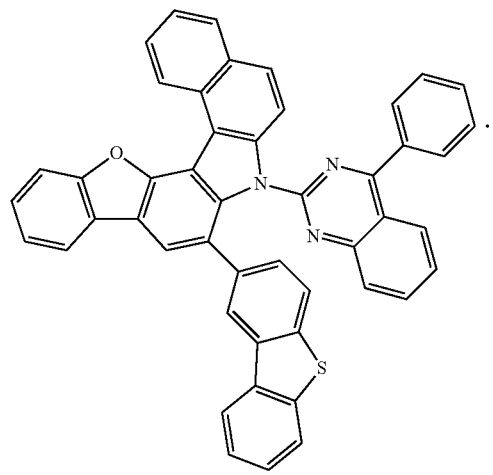

10. An organic light emitting device comprising:
a first electrode;
a second electrode; and
one or more organic material layers disposed between the first electrode and the second electrode,
wherein one or more layers of the organic material layers include the compound of claim 1.

11. The organic light emitting device of claim 10, wherein the organic material layer includes one or more layers of an electron transfer layer; an electron injection layer; and a layer carrying out electron transfer and electron injection at the same time, and one or more layers of the layers include the compound.

12. The organic light emitting device of claim 10, wherein the organic material layer includes a light emitting layer, and the light emitting layer includes the compound as a host of the light emitting layer.

13. The organic light emitting device of claim 10, wherein the organic material layer includes one or more layers of a hole injection layer; a hole transfer layer; and a layer carrying out hole injection and hole transfer at the same time, and one or more layers of the layers include the compound.

14. The organic light emitting device of claim 10, wherein the organic material layer includes one or more layers of a hole transfer layer; an electron blocking layer; and a hole transfer and electron blocking layer, and one or more layers of the layers include the compound.

15. The organic light emitting device of claim 10, wherein the organic material layer includes the compound as a host, and includes other organic compounds, metals or metal compounds as a dopant.

16. The organic light emitting device of claim 10, wherein the organic material layer includes a light emitting layer, and the light emitting layer includes a compound represented by the following Chemical Formula 1-A:

[Chemical Formula 1-A]

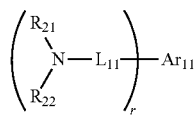

wherein, in Chemical Formula 1-A,
r is an integer of 1 or greater, and when r is 2 or greater, structures in the parentheses are the same as or different from each other;

$Ar_{11}$ is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group;

$L_{11}$ is a direct bond; a substituted or unsubstituted arylene group; or a substituted or unsubstituted heteroarylene group; and $R_{21}$ and $R_{22}$ are the same as or different from each other, and each independently a substituted or unsubstituted aryl group; a substituted or unsubstituted alkyl group; a substituted or unsubstituted silyl group; a substituted or unsubstituted arylalkyl group; or a substituted or unsubstituted heteroaryl group, or bond to each other to form a substituted or unsubstituted ring.

17. The organic light emitting device of claim 16, wherein r is 2, $Ar_{11}$ is a divalent pyrene group, $L_{11}$ is a direct bond, $R_{21}$ and $R_{22}$ are the same as or different from each other, and each independently an aryl group unsubstituted or substituted with an alkylgermanium group.

18. The organic light emitting device of claim 10, wherein the organic material layer includes a light emitting layer, and the light emitting layer includes a compound represented by the following Chemical Formula 1-B:

[Chemical Formula 1-B]

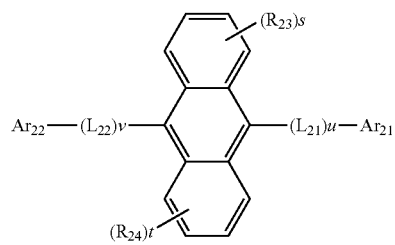

wherein, in Chemical Formula 1-B,
$Ar_{21}$ and $Ar_{22}$ are the same as or different from each other, and each independently a substituted or unsubstituted aryl group; or a substituted or unsubstituted heteroaryl group;

$L_{21}$ and $L_{22}$ are the same as or different from each other, and each independently a direct bond; a substituted or unsubstituted arylene group; or a substituted or unsubstituted heteroarylene group;

u and v are each independently an integer of 1 or 2, and when u and v are 2, substituents in the parentheses are the same as or different from each other;

$R_{23}$ and $R_{24}$ are the same as or different from each other, and each independently hydrogen; deuterium; a halogen group; a nitrile group; a hydroxyl group; a substituted or unsubstituted alkyl group; a substituted or unsubstituted silyl group; a substituted or unsubstituted cycloalkyl group; a substituted or unsubstituted alkoxy group; a substituted or unsubstituted aryloxy group; a substituted or unsubstituted amine group; a substituted or unsubstituted aryl group; or a substituted or unsubstituted heteroaryl group; and t and s are each an integer of 0 to 4, and when t and s are 2 or greater, substituents in the parentheses are the same as or different from each other.

19. The organic light emitting device of claim 18, wherein $Ar_{21}$ is a 2-naphthyl group, $Ar_{22}$ is a 1-naphthyl group, $L_{21}$ is a phenylene group, $L_{22}$ is a direct bond, u and v are each 1, and $R_{23}$ and $R_{24}$ are each hydrogen.

20. The organic light emitting device of claim 16, wherein the light emitting layer includes a compound represented by the following Chemical Formula 1-B:

[Chemical Formula 1-B]

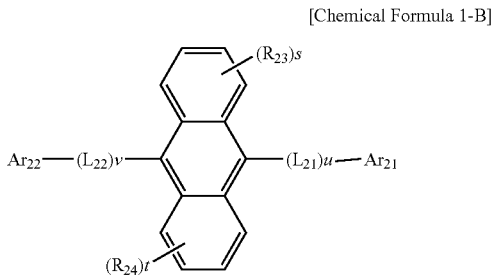

wherein, in Chemical Formula 1-B, $Ar_{21}$ and $Ar_{22}$ are the same as or different from each other, and each independently a substituted or unsubstituted aryl group; or a substituted or unsubstituted heteroaryl group;

$L_{21}$ and $L_{22}$ are the same as or different from each other, and each independently a direct bond; a substituted or unsubstituted arylene group; or a substituted or unsubstituted heteroarylene group;

u and v are each independently an integer of 1 or 2, and when u and v are 2, substituents in the parentheses are the same as or different from each other;

$R_{23}$ and $R_{24}$ are the same as or different from each other, and each independently hydrogen; deuterium; a halogen group; a nitrile group; a hydroxyl group; a substituted or unsubstituted alkyl group; a substituted or unsubstituted silyl group; a substituted or unsubstituted cycloalkyl group; a substituted or unsubstituted alkoxy group; a substituted or unsubstituted aryloxy group; a substituted or unsubstituted amine group; a substituted or unsubstituted aryl group; or a substituted or unsubstituted heteroaryl group; and t and s are each an integer of 0 to 4, and when t and s are 2 or greater, substituents in the parentheses are the same as or different from each other.

* * * * *